(12) United States Patent
Carulli et al.

(10) Patent No.: US 6,770,461 B1
(45) Date of Patent: Aug. 3, 2004

(54) HIGH BONE MASS GENE OF 11Q13.3

(75) Inventors: John P. Carulli, Southboro, MA (US); Randall D. Little, Newtonville, MA (US); Robert R. Recker, Omaha, NE (US); Mark L. Johnson, Omaha, NE (US)

(73) Assignees: Genome Therapeutics Corporation, Waltham, MA (US); Creighton University School of Medicine, Omaha, NE (US)

( * ) Notice: Subject to any disclaimer, the term of this patent is extended or adjusted under 35 U.S.C. 154(b) by 0 days.

(21) Appl. No.: 09/544,398

(22) Filed: Apr. 5, 2000

Related U.S. Application Data

(63) Continuation-in-part of application No. 09/229,319, filed on Jan. 13, 1999.
(60) Provisional application No. 60/105,511, filed on Oct. 23, 1998, and provisional application No. 60/071,449, filed on Jan. 13, 1998.

(51) Int. Cl.[7] .................... C12P 21/00; C12N 15/63; C12N 15/85; C12N 1/21
(52) U.S. Cl. ............... 435/70.1; 435/325; 435/252.3; 435/320.1; 435/71.1; 435/71.2
(58) Field of Search ............... 536/23.1, 24.1; 435/320.1; 514/14; 424/93.2

(56) References Cited

U.S. PATENT DOCUMENTS

| | | |
|---|---|---|
| 5,691,153 A | 11/1997 | Recker et al. |
| 6,545,137 B1 | 4/2003 | Todd et al. |
| 6,555,654 B1 | 4/2003 | Todd et al. |

FOREIGN PATENT DOCUMENTS

| | | |
|---|---|---|
| WO | WO 97/12903 | 4/1997 |
| WO | 9846743 | 10/1998 |
| WO | WO 99/09054 | 2/1999 |
| WO | WO 99/47529 | 9/1999 |

OTHER PUBLICATIONS

Bollag et al., Osteoblast–derived cells express functional glucose–dependent insulinotropic peptide receptors, 2000, ENDOCRINOLOGY, vol. 141, pp. 1228–1235.*
Ziegler et al., Glucocorticoid–induced osteoporosis: Prevention and treatment, 1998, STEROIDS, vol. 63, pp. 344–348.*
Kundu et al., Role of polypeptides in the treatment and diagnosis of osteoporosis, 1999, PEPTIDES, vol. 20, pp. 523–537.*
Rodan et al., Therapeutic approaches to bone diseases, 2000, SCIENCE, vol. 289, pp. 1508–1514.*
Kim et al., A new low density lipoprotein receptor related protein, LRP5, is expressed in hepatocytes and adrenal cortex, and recognizes apolipoprotein E, 1998, J. BIO-CHEM., vol. 124, pp. 1072–1076.*
Hey et al., Cloning of a novel member of the low–density lipoprotein receptor family, 1998, GENE, vol. 1, pp. 103–111.*
Verma et al., Gene therapy–promises, problems and prospects, 1997, NATURE, vol. 389, pp. 239–242.*
Anderson, Human gene therapy, 1998, NATURE, vol. 392, pp. 25–30.*
Walther et al., Viral vectors for gene transfer, 2000, DRUGS, vol. 60, pp. 249–271.*
Johnson et al., *Journal of Bone and Mineral Research*, 11(Supplement 1):S255, abstract S661, Aug. 1996.
Johnson et al., *American Journal of Human Genetics*, 60: 1326–32 (1997).
Nakagawa et al., *American Journal of Human Genetics*, 63: 547–56 (1998).
Hey et al., *Gene* 216: 103–11 (1998).
Dong et al., *Biochemical and Biophysical Research Communication*, 251: 784–90 (1998).
Kim et al., *Journal of Biochemistry* 124: 1072–76 (1998).
Koller et al., *Journal of Bone and Mineral Research*, 13(12): 1903–8 (1998).
Annex Form PCT/ISA/206 Communication Relating to the Results of the Partial International Search attached to Invitation to Pay Additional Fees dated May 7, 2001 in PCT/US00/16951 filed on Jun. 21, 2000.
A. Courseaux et al., "Homo Sapiens Chromosome 11 Clone BAC67–M–5 MAP 11q13, * Sequencing in Progress *, 3 Ordered Pieces", Database EM_HTG, E.B.I., Hinxton, U.K., Accession No.: AC024123, Mar. 2, 2000, XP002165276, Abstract.
D.L. Koller et al., "Linkage of a QTL Contributing to Normal Variation in Bone Mineral Density to Chromosome 11q12–13", J. Bone Miner. Res., vol. 13, No. 12, pp. 1903–1908, Dec. 1998, Blackwell Science, Inc., American Society for Bone and Mineral Research, USA.

(List continued on next page.)

Primary Examiner—Anne-Marie Falk
Assistant Examiner—Celine Qian
(74) Attorney, Agent, or Firm—Burns, Doane, Swecker & Mathis, L.L.P.

(57) ABSTRACT

The present invention relates to methods and materials used to isolate and detect a high bone mass gene and a corresponding wild-type gene, and mutants thereof. The present invention also relates to the high bone mass gene, the corresponding wild-type gene, and mutants thereof The genes identified in the present invention are implicated in bone development. The invention also provides nucleic acids, including coding sequences, oligonucleotide primers and probes, proteins, cloning vectors, expression vectors, transformed hosts, methods of developing pharmaceutical compositions, methods of identifying molecules involved in bone development, and methods of diagnosing and treating diseases involved in bone development. In preferred embodiments, the present invention is directed to methods for treating, diagnosing and preventing osteoporosis.

24 Claims, 32 Drawing Sheets

OTHER PUBLICATIONS

Michael P. Whyte, *"Searching for Gene Defects that Cause High Bone Mass"*, Am. J. Hum. Genet., vol. 60; No. 6, pp. 1309–1311, Jun. 1997, The American Society of Human Genetics, USA.

Marion Trommsdorff et al., *"Interaction of Cytosolic Adaptor Proteins with Neuronal Apolipoprotein E. Receptors and the Amyloid Precursor Protein"*, J. Biol. Chem., vol. 273, No. 50, pp. 33556–33560, Dec. 1998, The American Society for Biochemistry and Molecular Biology, Inc., USA.

G. Schneider et al., *"Formation of Focal Adhesions by Osteoblasts Adhering to Different Substrata"*, Experimental Cell Research, vol. 214, No. 1, pp. 264–269, Sep. 1994, Academic Press, Inc., USA.

Frederick M. Pavalko et al., *"Fluid Shear–Induced Mechanical Signaling in MC3T3–E1 Osteoblasts Requires Cytoskeleton–Integrin Interactions"*, Am. J. Physiol., vol. 275, No. 6 (Pt1), pp. C1591–1601, Dec. 1998, The American Physiological Society, USA.

Mark L. Johnson et al., *"Linkage of a Gene Causing High Bone Mass to Human Chromosome 11 (11q12–13)"*, Am. J. Hum. Genet., vol. 60, No. 6, pp. 1326–1332, Jun. 1997, The American Society of Human Genetics, USA.

Dong–Ho Kim et al., *"A New Low Density Lipoproten Receptor Related Protein, LRP5, is Expressed in Hepatocytes and Adrenal Cortex, and Recognizes Apolipoprotein E"*, J. Biochem., vol. 124, No. 6, pp. 1072–1076, Dec. 1998, The Japanese Biochemical Society, JAPAN.

\* cited by examiner

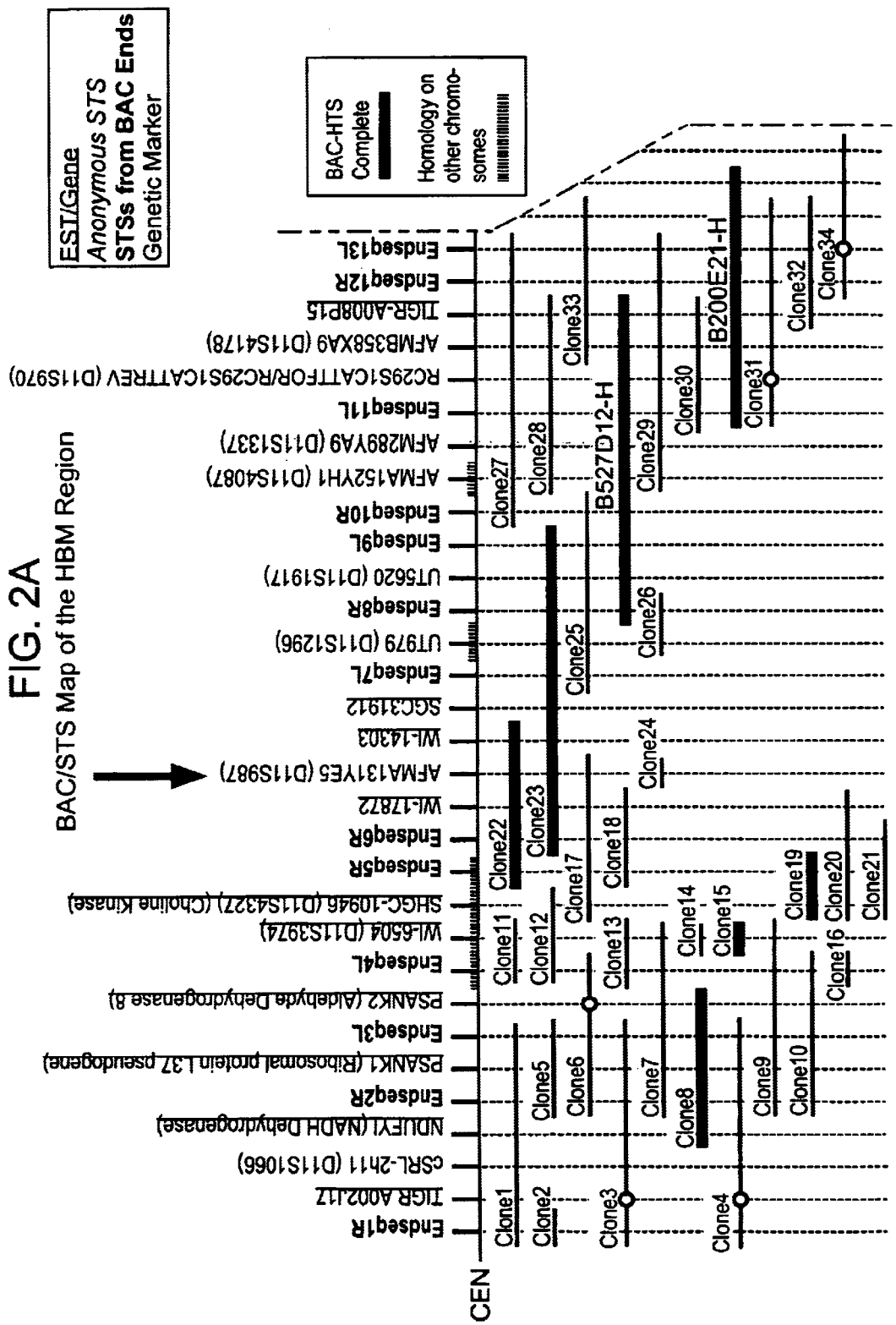
FIG. 2A BAC/STS Map of the HBM Region

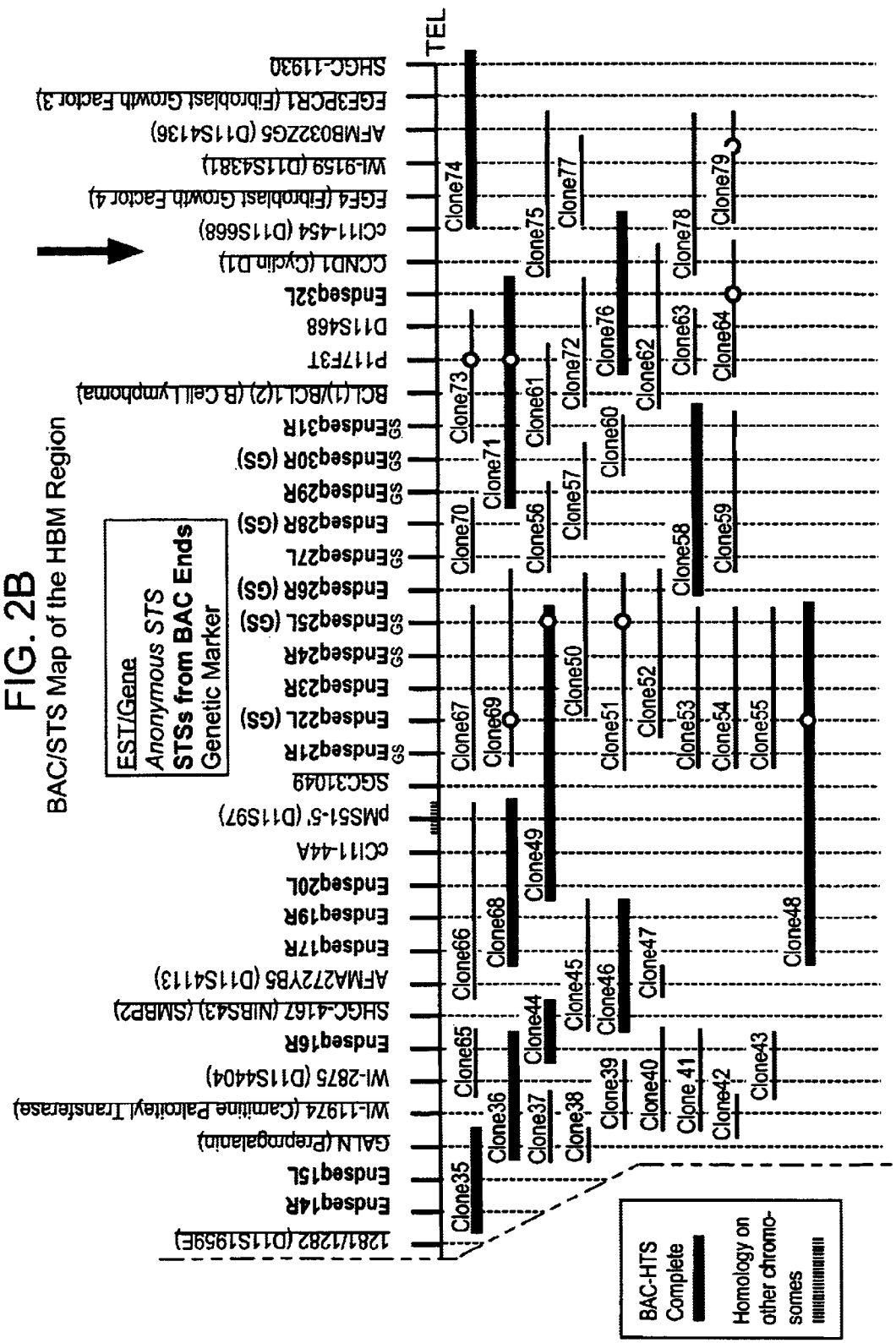

Exon 1
ACTAAAGCGCCGCCGCCGCGCCATGGAGCCCGAGTGAGCGCGGCGCG
GGCCCGTCCGGCCGCCGGACAACATGGAGGCAGCGCCGCCCGGGCCG
CCGTGGCCGCTGCTGCTGCTGCTGCTGCTGCTGGCGCTGTGCGGC
TGCCCGGCCCCCGCCGCGGCC

Exon 2 Coordinates: 527d12_Contig308G 30944-30549
gccccacagCCTCGCCGCTCCTGCTATTTGCCAACCGCCGGGACGTACGGC
TGGTGGACGCCGGCGGAGTCAAGCTGGAGTCCACCATCGTGGTCAGC
GGCCTGGAGGATGCGGCCGCAGTGGACTTCCAGTTTTCCAAGGGAGC
CGTGTACTGGACAGACGTGAGCGAGGAGGCCATCAAGCAGACCTACCT
GAACCAGACGGGGGCCGCCGTGCAGAACGTGGTCATCTCCGGCCTGG
TCTCTCCCGACGGCCTCGCCTGCGACTGGGTGGGCAAGAAGCTGTACT
GGACGGACTCAGAGACCAACCGCATCGAGGTGGCCAACCTCAATGGC
ACATCCCGGAAGGTGCTCTTCTGGCAGGACCTTGACCAGCCGAGGGCC
ATCGCCTTGGACCCCGCTCACGGtaaaccctgctg ... 9408 nt ...

Exon 3 Coordinates: 527d12_Contig308G 21141-20945
ccccgtcacagGTACATGTACTGGACAGACTGGGGTGAGACGCCCCGGATTG
AGCGGGCAGGGATGGATGGCAGCACCCGGAAGATCATTGTGGACTCG
GACATTTACTGGCCCAATGGACTGACCATCGACCTGGAGGAGCAGAAG
CTCTACTGGGCTGACGCCAAGCTCAGCTTCATCCACCGTGCCAACCTG
GACGGCTCGTTCCGgtaggtacccac ... 6094 nt ...

Exon 4 Coordinates: 527d12_Contig308G 15047-14850
tccctgactgcagGCAGAAGGTGGTGGAGGGCAGCCTGACGCACCCCTTCGCC
CTGACGCTCTCCGGGGACACTCTGTACTGGACAGACTGGCAGACCCGC
TCCATCCATGCCTGCAACAAGCGCACTGGGGGGAAGAGGAAGGAGAT
CCTGAGTGCCCTATACTCACCCATGGACATCCAGGTGCTGAGCCAGGA
GCGGCAGCCTTTCTgtgagtgccgg ... 1827 nt ...

Exon 5 Coordinates: 527d12_Contig308G 13220-13088
tttctcagTCCACACTCGCTGTGAGGAGGACAATGGCGGCTGCTCCCACCTG
TGCCTGCTGTCCCCAAGCGAGCCTTTCTACACATGCGCCTGCCCCACG
GGTGTGCAGCTGCAGGACAACGGCAGGACGTGTAAGGCAGgtgaggcggtgg
gacg

Exon 6 Coordinates: 527d12_Contig309G 7705-8100
ctccacagGAGCCGAGGAGGTGCTGCTGCTGGCCCGGCGGACGGACCTAC
GGAGGATCTCGCTGGACACGCCGGACTTCACCGACATCGTGCTGCAGG
TGGACGACATCCGGCACGCCATTGCCATCGACTACGACCCGCTAGAGG
GCTATGTCTACTGGACAGATGACGAGGTGCGGGCCATCCGCAGGGCG
TACCTGGACGGGTCTGGGGCGCAGACGCTGGTCAACACCGAGATCAA
CGACCCCGATGGCATCGCGGTCGACTGGGTGGCCCGAAACCTCTACTG
GACCGACACGGGCACGGACCGCATCGAGGTGACGCGCCTCAACGGCA
CCTCCCGCAAGATCCTGGTGTCGGAGGACCTGGACGAGCCCCGAGCC
ATCGCACTGCACCCCGTGATGGGgtaagacgggc ..... 3211 nt .....

Exon 7 Coordinates: 527d12_Contig309G 11311-11482
ttcttctccagCCTCATGTACTGGACAGACTGGGGAGAGAACCCTAAAATCGA
GTGTGCCAACTTGGATGGGCAGGAGCGGCGTGTGCTGGTCAATGCCTC
CCTCGGGTGGCCCAACGGCCTGGCCCTGGACCTGCAGGAGGGGAAGC
TCTACTGGGGAGACGCCAAGACAGACAAGATCGAGgtgaggctcctgtgg ...... 13445 nt .....

Exon 8 Coordinates: 527d12_Contig309G 24927-25143
ccgtcctgcagGTGATCAATGTTGATGGGACGAAGAGGCGGACCCTCCTGGA
GGACAAGCTCCCGCACATTTTCGGGTTCACGCTGCTGGGGGACTTCAT
CTACTGGACTGACTGGCAGCGCCGCAGCATCGAGCGGGTGCACAAGG
TCAAGGCCAGCCGGGACGTCATCATTGACCAGCTGCCCGACCTGATGG
GGCTCAAAGCTGTGAATGTGGCCAAGGTCGTCGgtgagtccgggggggtc ....2826 nt ......

Exon 9 Coordinates: 527d12_Contig309G 27969-28256
gttcgcttccagGAACCAACCCGTGTGCGGACAGGAACGGGGGGTGCAGCCA
CCTGTGCTTCTTCACACCCCACGCAACCCGGTGTGGCTGCCCCATCGG
CCTGGAGCTGCTGAGTGACATGAAGACCTGCATCGTGCCTGAGGCCTT
CTTGGTCTTCACCAGCAGAGCCGCCATCCACAGGATCTCCCTCGAGAC
CAATAACAACGACGTGGCCATCCCGCTCACGGGCGTCAAGGAGGCCTC
AGCCCTGGACTTTGATGTGTCCAACAACCACATCTACTGGACAGACGT
CAGCCTGAAGgtagcgtgggc

Exon 10 Coordinates: 527d12_Contig309G 31358-31582
cctgctgccagACCATCAGCCGCGCCTTCATGAACGGGAGCTCGGTGGAGCA
CGTGGTGGAGTTTGGCCTTGACTACCCCGAGGGCATGGCCGTTGACTG
GATGGGCAAGAACCTCTACTGGGCCGACACTGGGACCAACAGAATCGA
AGTGGCGCGGCTGGACGGGCAGTTCCGGCAAGTCCTCGTGTGGAGGG
ACTTGGACAACCCGAGGTCGCTGGCCCTGGATCCCACCAAGGGgtaagtgtt
tgcctgtc ......1297 nt......

Exon 11 Coordinates: 527d12_Contig309G 32879-33064
gtgccttccagCTACATCTACTGGACCGAGTGGGGCGGCAAGCCGAGGATCG
TGCGGGCCTTCATGGACGGGACCAACTGCATGACGCTGGTGGACAAG
GTGGGCCGGGCCAACGACCTCACCATTGACTACGCTGACCAGCGCCTC
TACTGGACCGACCTGGACACCAACATGATCGAGTCGTCCAACATGCTG
Ggtgagggccgggct .......2069 nt.....

Exon 12 Coordinates: 527d12_Contig309G 35133-35454
gtgttcatgcagGTCAGGAGCGGGTCGTGATTGCCGACGATCTCCCGCACCCG
TTCGGTCTGACGCAGTACAGCGATTATATCTACTGGACAGACTGGAAT
CTGCACAGCATTGAGCGGGCCGACAAGACTAGCGGCCGGAACCGCAC
CCTCATCCAGGGCCACCTGGACTTCGTGATGGACATCCTGGTGTTCCA
CTCCTCCCGCCAGGATGGCCTCAATGACTGTATGCACAACAACGGGCA
GTGTGGGCAGCTGTGCCTTGCCATCCCCGGCGGCCACCGCTGCGGCT
GCGCCTCACACTACACCCTGGACCCCAGCAGCCGCAACTGCAGCCgtaag
tgcctcatggt .......2006 nt......

Exon 13 Coordinates: 527d12_Contig309G 37460-37659
gcctcctctaCGCCCACCACCTTCTTGCTGTTCAGCCAGAAATCTGCCATCAG
TCGGATGATCCCGGACGACCAGCACAGCCCGGATCTCATCCTGCCCCT
GCATGGACTGAGGAACGTCAAAGCCATCGACTATGACCCACTGGACAA
GTTCATCTACTGGGTGGATGGGCGCCAGAACATCAAGCGAGCCAAGGA
CGACGGGACCCAGgcaggtgccctgtgg ......6965 nt......

FIG. 3C

Exon 14 Coordinates: 527d12_Contig309G 44624-44832
ctttgtcttacagCCCTTTGTTTTGACCTCTCTGAGCCAAGGCCAAAACCCAGAC
AGGCAGCCCCACGACCTCAGCATCGACATCTACAGCCGGACACTGTTC
TGGACGTGCGAGGCCACCAATACCATCAACGTCCACAGGCTGAGCGG
GGAAGCCATGGGGGTGGTGCTGCGTGGGGACCGCGACAAGCCCAGGG
CCATCGTCGTCAACGCGGAGCGAGGgtaggaggccaac ......1404 nt.....

Exon 15 Coordinates: 527d12_Contig309G 46236-46427
ccaccctcccgcagGTACCTGTACTTCACCAACATGCAGGACCGGGCAGCCAA
GATCGAACGCGCAGCCCTGGACGGCACCGAGCGCGAGGTCCTCTTCA
CCACCGGCCTCATCCGCCCTGTGGCCCTGGTGGTGGACAACACACTGG
GCAAGCTGTTCTGGGTGGACGCGGACCTGAAGCGCATTGAGAGCTGT
GACCTGTCAGgtacgcgccccgg .....686 nt.....

Exon 16 Coordinates: 527d12_Contig309G 47113-47322
ggctgcttgcagGGGCCAACCGCCTGACCCTGGAGGACGCCAACATCGTGCA
GCCTCTGGGCCTGACCATCCTTGGCAAGCATCTCTACTGGATCGACCG
CCAGCAGCAGATGATCGAGCGTGTGGAGAAGACCACCGGGGACAAGC
GGACTCGCATCCAGGGCCGTGTCGCCCACCTCACTGGCATCCATGCAG
TGGAGGAAGTCAGCCTGGAGGAGTTCTgtacgtgggggc .....3884 nt......

Exon 17 Coordinates: 527d12_Contig309G 51206-51331
ttgtctttgcagCAGCCCACCCATGTGCCCGTGACAATGGTGGCTGCTCCCACA
TCTGTATTGCCAAGGGTGATGGGACACCACGGTGCTCATGCCCAGTCC
ACCTCGTGCTCCTGCAGAACCTGCTGACCTGTGGAGgtaggtgtgacctaggtgc ....3905 nt.......

Exon 18 Coordinates: 527d12_Contig309G 55236-55472
gttctcctctgtccctcccccagAGCCGCCCACCTGCTCCCCGGACCAGTTTGCATGT
GCCACAGGGGAGATCGACTGTATCCCCGGGGCCTGGCGCTGTGACGG
CTTTCCCGAGTGCGATGACCAGAGCGACGAGGAGGGCTGCCCCGTGT
GCTCCGCCGCCCAGTTCCCCTGCGCGCGGGGTCAGTGTGTGGACCTGC
GCCTGCGCTGCGACGGCGAGGCAGACTGTCAGGACCGCTCAGACGAG
GTGGACTGTGACGgtgaggccctcc .......3052 nt.....

FIG. 3D

Exon 19 Coordinates: 527d12_Contig309G 58524-58634
tctccttgcagCCATCTGCCTGCCCAACCAGTTCCGGTGTGCGAGCGGCCAGT
GTGTCCTCATCAAACAGCAGTGCGACTCCTTCCCCGACTGTATCGACG
GCTCCGACGAGCTCATGTGTGgtgagccagctt ........1448 nt......

Exon 20 Coordinates: 527d12_Contig309G 60082-60319
gtttgtctctggcagAAATCACCAAGCCGCCCTCAGACGACAGCCCGGCCCACA
GCAGTGCCATCGGGCCCGTCATTGGCATCATCCTCTCTCTCTTCGTCAT
GGGTGGTGTCTATTTTGTGTGCCAGCGCGTGGTGTGCCAGCGCTATGC
GGGGGCCAACGGGCCCTTCCCGCACGAGTATGTCAGCGGGACCCCGC
ACGTGCCCCTCAATTTCATAGCCCCGGGCGGTTCCCAGCATGGCCCCT
TCACAGgtaaggagcctgagatatggaa ....1095 nt.....

Exon 21 Coordinates: 527d12_Contig309G 61414-61552
cttccctgccagGCATCGCATGCGGAAAGTCCATGATGAGCTCCGTGAGCCTG
ATGGGGGGCCGGGGCGGGGTGCCCCTCTACGACCGGAACCACGTCAC
AGGGGCCTCGTCCAGCAGCTCGTCCAGCACGAAGGCCACGCTGTACCC
GCCGgtgaggggcggg ......6513 nt......

Exon 22 Coordinates: 527d12_Contig309G 68065-68162
ttggctctcctcagATCCTGAACCCGCCGCCCTCCCCGGCCACGGACCCCTCCC
TGTACAACATGGACATGTTCTACTCTTCAAACATTCCGGCCACTGCGA
GACCGTACAGgtaggacatcccctgcag .......2273 nt.....

FIG. 3E

Exon 23 Coordinates: 527d12_Contig309G 70435-70901
tcaaacattccggccactgcgagaccgtacagGCCCTACATCATTCGAGGAATGGCGCCCC
CGACGACGCCCTGCAGCACCGACGTGTGTGACAGCGACTACAGCGCC
AGCCGCTGGAAGGCCAGCAAGTACTACCTGGATTTGAACTCGGACTCA
GACCCCTATCCACCCCCACCCACGCCCCACAGCCAGTACCTGTCGGCG
GAGGACAGCTGCCCGCCCTCGCCCGCCACCGAGAGGAGCTACTTCCAT
CTCTTCCCGCCCCCTCCGTCCCCCTGCACGGACTCATCC<u>TGACCTCGGC
CGGGCCACTCTGGCTTCTCTGTGCCCTGTAAATAGTTTTAAATATGAACAA
AGAAAAAAATATATTTTATGATTTAAAAAATAAATATAATTGGGATTTTAA
AAACATGAGAAATGTGAACTGTGATGGGGTGGGCAGGGCTGGGAGAACTT
TGTACAGTGGAGAAATATTTATAAACTTAATTTTGTAAAACA</u>

```
1    ACTAAAGCGCCGCCGCCGCGCCATGGAGCCCGAGTGAGCGCGGCGGCCCGTCCGCC          60
61   GCCGGACAACATGGAGGCAGCCGCCGCCGGTGCCCGGGCCCCGTGCTGCTGCTGCT         120
1           M  E  A  A  A  P  P  G  P  P  W  P  L  L  L  L  L         17

121  GCTGCTGCTGGCGCTGTGCGGCTGTGCGGCCCCGGCGCCTGCCGCTGCCTCTGCTATT       180
18    L  L  L  A  L  C  G  C  P  A  P  A  A  A  S  P  L  L  F         37

181  TGCCAACCGCCGGGACGTACGGCTGGTGGACGCCGGCGGAGTCAAGCTGGAGTCCACCAT    240
38    A  N  R  R  D  V  R  L  V  D  A  G  G  V  K  L  E  S  T  I     57

241  CGTGGTCAGCGGCCTGGAGGATGCGGCCGCAGTGGACTTCCAGTTTTCCAAGGGAGCCGT    300
58    V  V  S  G  L  E  D  A  A  A  V  D  F  Q  F  S  K  G  A  V     77

301  GTACTGACAGACGTGTCAGAGGAGGCCATCAAGCAGACCTACCTGAACCAGACGGGGGC     360
78    Y  W  T  D  V  S  E  E  A  I  K  Q  T  Y  L  N  Q  T  G  A     97

361  CGCCGTGCAGAACGTGGTCATCTCCGGTCTCTCCCGGTCTCTCCCGACGGCCTGCGACTG    420
98    A  V  Q  N  V  V  I  S  G  L  V  S  P  D  D  G  L  A  C  D  W  117

421  GGTGGGCAAGAAGCTGTACTGGACGGACTCAGAGACTAACCGCATCGAGGTGGCCAACCT    480
118   V  G  K  K  L  Y  W  T  D  S  E  T  N  R  I  E  V  A  N  L     137

481  CAATGGCACATCCCGGAAGTGCTCTTCTGGCAGGACCTTGACCTTGACCTTGACGACCCTGAGGGGCCATCGC 540
138   N  G  T  S  R  K  V  L  F  W  Q  D  L  D  Q  P  R  A  I  A     157

541  CTTGGACCCCGCTCACGGGTACATGTACTGGACAGACTGGGTGAGACGCCCGGATTGA      600
158   L  D  P  A  H  G  Y  M  Y  W  T  D  W  G  E  T  P  R  I  E     177
```

FIG. 6B

| | | |
|---|---|---|
| 601 | GCGGGCAGGGATGGATGGCAGCACCCGGAAGATCATTGTGGACTCGGACATTTACTGGCC | 660 |
| 178 | R   A   G   M   D   G   S   T   R   K   I   I   V   D   S   D   I   Y   W   P | 197 |
| 661 | CAATGGACTGACCATCGACCTGGAGGAGCAGAAGCTCTACTGGGCTGACGCCAAGCTCAG | 720 |
| 198 | N   G   L   T   I   D   L   E   E   Q   K   L   Y   W   A   D   A   K   L   S | 217 |
| 721 | CTTCATCCACCGTGCCAACCTGGACGGCTCGTTCCGGCAGAAGGTGGTGGAGGGCAGCCT | 780 |
| 218 | F   I   H   R   A   N   L   D   G   S   F   R   Q   K   V   V   E   G   S   L | 237 |
| 781 | GACGCACCCCTTCGCCCTGACGCTCTCCGGGGACACTCTGTACTGGACAGACTGGCAGAC | 840 |
| 238 | T   H   P   F   A   L   T   L   S   G   D   T   L   Y   W   T   D   W   Q   T | 257 |
| 841 | CCGGTCCATCCATGCCTGCAACAAGCGCACTGGGGGGAAGAGGAAGGAGATCCTGAGTGC | 900 |
| 258 | R   S   I   H   A   C   N   K   R   T   G   G   K   R   K   E   I   L   S   A | 277 |
| 901 | CCTCTACTCACCCATGGACATCCAGGTGCTGAGCCAGGAGCGGCAGCCTTTCTTCCACAC | 960 |
| 278 | L   Y   S   P   M   D   I   Q   V   L   S   Q   E   R   Q   P   F   F   H   T | 297 |
| 961 | TCGCTGTGAGGAGGACAATGGGGGCTGCTCCCACCTGTGCCTGCTCTCCCCAAGCGAGCC | 1020 |
| 298 | R   C   E   E   D   N   G   G   C   S   H   L   C   L   L   S   P   S   E   P | 317 |
| 1021 | TTTCTACACATGCGCCTGCCCTGGGGTGCAGCTGCAGGACAACGGCAGGACTGTGTAA | 1080 |
| 318 | F   Y   T   C   A   C   P   T   G   V   Q   L   Q   D   N   G   R   T   C   K | 337 |
| 1081 | GGCAGGAGCCGAGGAGGTGCTGCTGCCCGGCCGACTACGGAGGATCTCGCT | 1140 |
| 338 | A   G   A   E   E   V   L   L   L   A   R   R   T   D   L   R   R   I   S   L | 357 |

FIG. 6C

```
1141  GGACACGCCGGACTTCACCGACATCGTCTGCAGGTGGACGACATCCGGCACGCCATTGC  1200
 358   D  T  P  D  F  T  D  I  V  L  Q  V  D  D  I  R  H  A  I  A   377

1201  CATCGACTACGACCCGCTAGAGGGCTATGTCTACTGGACAGATGACGAGGTGCGGGCCAT  1260
 378   I  D  Y  D  P  L  E  G  Y  V  Y  W  T  D  D  E  V  R  A  I   397

1261  CCGCAGGGCGTACCTGGACGGGTCTGGGGCGCAGACGCTGGTCAACACCGAGATCAACGA  1320
 398   R  R  A  Y  L  D  G  S  G  A  Q  T  L  V  N  T  E  I  N  D   417

1321  CCCCGATGGCATCGCGGTCGACTGGGTGGCCCGAAACCTCTACTGGACCGACACGGGCAC  1380
 418   P  D  G  I  A  V  D  W  V  A  R  N  L  Y  W  T  D  T  G  T   437

1381  GGACCGCATCGAGGTGACGCGCCTCAACGGCACCTCCCGCAAGATCCTGGTGTCGGAGGA  1440
 438   D  R  I  E  V  T  R  L  N  G  T  S  R  K  I  L  V  S  E  D   457

1441  CCTGGACGAGCCCCGAGCCATCGCACTGCACCCCGTGATGGGCCTCATGTACTGGACAGA  1500
 458   L  D  E  P  R  A  I  A  L  H  P  V  M  G  L  M  Y  W  T  D   477

1501  CTGGGGAGAGAACCCTAAAATCGAGTGTGCCAACTTGGATGGGCAGGAGCGGCGTGTGCT  1560
 478   W  G  E  N  P  K  I  E  C  A  N  L  D  G  Q  E  R  R  V  L   497

1561  GGTCAATGCCTCCCTCGGGTGGCCCAACGGCCTGGCCCTGGACCTGCAGGAGGGAAGCT  1620
 498   V  N  A  S  L  G  W  P  N  G  L  A  L  D  L  Q  E  G  K  L   517

1621  CTACTGGGAGACGCCAAGACGCCAAGACAAGATCGAGGTGATCAATGTTGATGGGACGAAGAG  1680
 518   Y  W  G  D  A  K  T  D  K  I  E  V  I  N  V  D  G  T  K  R   537
```

FIG. 6D

```
1681  GCGGACCCTCCTGGAGGACAAGCTCCCGCACATTTTCGGGTTCACGCTGCTGGGGACTT   1740
 538   R  T  L  L  E  D  K  L  P  H  I  F  G  F  T  L  L  G  D  F    557

1741  CATCTACTGGACTGACTGGCAGCGCCGCAGCATCGAGCGGGTCACAAGGTCAAGGCCAG   1800
 558   I  Y  W  T  D  W  Q  R  R  S  I  E  R  V  H  K  V  K  A  S    577

1801  CCCGGGACGTCATCATTGACCAGCTGCCCGACCTGATGGGGCTCAAAGCTGTGAATGTGGC  1860
 578   R  D  V  I  I  D  Q  L  P  D  L  M  G  L  K  A  V  N  V  A    597

1861  CAAGGTCGTCGGAACCAACCCGTGTGCGGACAGGAACGGGGGTGCAGCCACCTGTGCTT   1920
 598   K  V  V  G  T  N  P  C  A  D  R  N  G  G  C  S  H  L  C  F    617

1921  CTTCACACCCCAGCAACCTGGTGTGCCTGCCCCATCGGCCTGGAGCTGCTGAGTGACAT   1980
 618   F  T  P  H  A  T  R  C  G  C  P  I  G  L  E  L  L  S  D  M    637

1981  GAAGACCTGCATCGTGCCTGAGGCCTTCTTGGTCTTCACCAGCAGACCGCCATCCACAG   2040
 638   K  T  C  I  V  P  E  A  F  L  V  F  T  S  R  A  A  I  H  R    657

2041  GATCTCCCTCGAGACCAATAACAACGACGTGGCCATCCCGCTCACGGGCGTCAAGGAGGC   2100
 658   I  S  L  E  T  N  N  N  D  V  A  I  P  L  T  G  V  K  E  A    677

2101  CTCAGCCCTGGACTTTGATGTGTCCAACAACCACATCTACTGGACAGACGTCAGCCTGAA   2160
 678   S  A  L  D  F  D  V  S  N  N  H  I  Y  W  T  D  V  S  L  K    697

2161  GACCATCAGCCGCGCCTTCATGAACGGGAGCTCGGTGGAGCACGTGGTGGAGTTTGGCCT   2220
 698   T  I  S  R  A  F  M  N  G  S  S  V  E  H  V  V  E  F  G  L    717
```

FIG. 6E

```
2221  TGACTACCCCGAGGGCATGGCCGTTGACTGGATGGGCAAGAACCTCTACTGGGCCGACAC  2280
718    D  Y  P  E  G  M  A  V  D  W  M  G  K  N  L  Y  W  A  D  T   737

2281  TGGGACCAACAGAATCGAAGTGGCGCGGCTGGACGGGCAGTTCCGGCAAGTCCTCGTGTG  2340
738    G  T  N  R  I  E  V  A  R  L  D  G  Q  F  R  Q  V  L  V  W   757

2341  GAGGGACTTGGACAACCCGAGTGTCGCTGGCCCTGGCCCTGGATCCCACCAAGGGCTACATCTACTG  2400
758    R  D  L  D  N  P  R  S  L  A  L  D  P  T  K  G  Y  I  Y  W   777

2401  GACCGAGTGGGGCGGCAAGCCGAGGATCGTGCGGGCCTTCATGGACGGACCAACTGCAT  2460
778    T  E  W  G  G  K  P  R  I  V  R  A  F  M  D  G  T  N  C  M   797

2461  GACGCTGGTGGACAAGGTGGGCCGGGCCAACGACCTCACCATTGACTACGCTGACCAGCG  2520
798    T  L  V  D  K  V  G  R  A  N  D  L  T  I  D  Y  A  D  Q  R   817

2521  CCTCTACTGGACCGACCTGGACACCAACATGATCGAGTCGTCAACATGCTGGGTCAGGA  2580
818    L  Y  W  T  D  L  D  T  N  M  I  E  S  S  N  M  L  G  Q  E   837

2581  GCGGGTCGTGATTGCCGACGATCTCCCGCACCCGTTCGGTCTGACGCAGTACAGCGATTA  2640
838    R  V  V  I  A  D  D  L  P  H  P  F  G  L  T  Q  Y  S  D  Y   857

2641  TATCTACTGGACAGACTGGAATCTGCACAGCATTGAGCGGGCCGACAAGACTAGCGGCCG  2700
858    I  Y  W  T  D  W  N  L  H  S  I  E  R  A  D  K  T  S  G  R   877

2701  GAACCGCACCCTCATCCAGGGCCACCTGGACTTCGTGATGGACATCCTGGTGTTCCACTC  2760
878    N  R  T  L  I  Q  G  H  L  D  F  V  M  D  I  L  V  F  H  S   897
```

FIG. 6F

```
2761  CTCCCGCCAGGATGGCCTCAATGACTGTATGCACAACGGCAGTGTGGCAGCTGTG  2820
 898   S  R  Q  D  G  L  N  D  C  M  H  N  N  G  Q  C  G  Q  L  C   917

2821  CCTTGCCATCCCCGGCGGCCACCGTGCGCCTCACACTACACCCTGACCCCAG     2880
 918   L  A  I  P  G  G  H  R  C  G  C  A  S  H  Y  T  L  D  P  S   937

2881  CAGCCGCAACTGCAGCCCGCCACCACCTTCTGCTGTTCAGCCAGAAATCTGCCATCAG  2940
 938   S  R  N  C  S  P  P  T  T  F  L  L  F  S  Q  K  S  A  I  S   957

2941  TCGGATGATCCCGGACGACCAGCACAGCCCGGATCTCATCCTGCCCCTGCATGGACTGAG  3000
 958   R  M  I  P  D  D  Q  H  S  P  D  L  I  L  P  L  H  G  L  R   977

3001  GAACGTCAAAGCCATCGACTATGACCCACTGGACAAGTTCATCTACTGGGTGGATGGGCG  3060
 978   N  V  K  A  I  D  Y  D  P  L  D  K  F  I  Y  W  V  D  G  R   997

3061  CCAGAACATCAAGCGAGCCAAGGACGACGGGACACCCAGCCTGTTTTTGACCTCTCTGAG  3120
 998   Q  N  I  K  R  A  K  D  D  G  T  Q  P  F  V  L  T  S  L  S   1017

3121  CCAAGGCCAAAACCCAGACAGGCAGCCCACGACCTCAGCATCGACATCTACAGCCGGAC  3180
1018   Q  G  Q  N  P  D  R  Q  P  H  D  L  S  I  D  I  Y  S  R  T   1037

3181  ACTGTTCTGGACGTGCGAGGCCACCAATACCATCAACGTCCACAGGCTGAGCGGGAAGC  3240
1038   L  F  W  T  C  E  A  T  N  T  I  N  V  H  R  L  S  G  E  A   1057

3241  CATGGGGTGGTGCTGCGCGGGGACCGCCGACAAGCCCAGGCCCATCGTCGTCAACGCGGA  3300
1058   M  G  V  V  L  R  G  D  R  D  K  P  R  A  I  V  V  N  A  E   1077
```

FIG. 6G

```
3301  GCGAGGGTACCTGTACTTCACCAACATGCAGGACCGGGCAGCCAAGATCGAACGCGCAGC  3360
1078   R  G  Y  L  Y  F  T  N  M  Q  D  R  A  A  K  I  E  R  A  A   1097

3361  CCTGGACGGCACCGAGCGCGAGGTCCTCTTCACCACCGGCCTCATCCGCCCTGTGGCCCT  3420
1098   L  D  G  T  E  R  E  V  L  F  T  T  G  L  I  R  P  V  A  L   1117

3421  GGTGGTGGACAACACACTGGGCAAGCTGTTCTGGGTGGACGCGGACCTGAAGCGCATTGA  3480
1118   V  V  D  N  T  L  G  K  L  F  W  V  D  A  D  L  K  R  I  E   1137

3481  GAGCTGTGACCTGTCAGGGGCCAACCGCCTGACCCTGGAGGACGCCAACATCGTGCAGCC  3540
1138   S  C  D  L  S  G  A  N  R  L  T  L  E  D  A  N  I  V  Q  P   1157

3541  TCTGGGCCTGACCATCCTTGGCAAGCATCTCTACTGGATCGACCGCCAGCAGCAGATGAT  3600
1158   L  G  L  T  I  L  G  K  H  L  Y  W  I  D  R  Q  Q  Q  M  I   1177

3601  CGAGCGTGTGGAGAAGACCACCGGGGACAAGCGGACTCGCATCCAGGGCCGTGTCGCCCA  3660
1178   E  R  V  E  K  T  T  G  D  K  R  T  R  I  Q  G  R  V  A  H   1197

3661  CCTCACTGGCATCCATGCAGTGGAGGAAGTCAGCCTGGAGGAGTTCTCAGCCCACCCATG  3720
1198   L  T  G  I  H  A  V  E  E  V  S  L  E  E  F  S  A  H  P  C   1217

3721  TGCCCGTGACAATGGTGGCTGCTCCCACATCTGTATTGCCAAGGGTGATGGACACCACG  3780
1218   A  R  D  N  G  G  C  S  H  I  C  I  A  K  G  D  G  T  P  R   1237

3781  GTGCTCATGCCCAGTCCACCTGTCTCCTGCAGAACCTGCTGACCTGTGGAGAGCCGCC  3840
1238   C  S  C  P  V  H  L  V  L  L  Q  N  L  L  T  C  G  E  P  P   1257
```

FIG. 6H

```
3841  CACCTGTGCTCCCCGGACCAGTTTGCATGTGCCACAGGGGAGATCGACTGTATCCCGGGGC   3900
1258   T   C   S   P   D   Q   F   A   C   A   T   G   E   I   D   C   I   P   G   A    1277

3901  CTGGCGCTGTGACGGCTTTCCGAGTGCGATGACCAGAGCGAGGAGGGCTGCCCCGT       3960
1278   W   R   C   D   G   F   P   E   C   D   D   Q   S   E   E   G   C   P   V        1297

3961  GTGCTCCGCCGCCCAGTTCCCCTGCGCGCGGGGTCAGTGTGTGGACCTGCGCCTGCGCTG  4020
1298   C   S   A   A   Q   F   P   C   A   R   G   Q   C   V   D   L   R   L   R   C    1317

4021  CGACGGCGAGGCAGACTGTCAGGACCGCTCAGACGAGGTGGACTGTGACGCCATCTGCCT  4080
1318   D   G   E   A   D   C   Q   D   R   S   D   E   V   D   C   D   A   I   C   L    1337

4081  GCCCAACCAGTTCCGGTGTGCGAGCGGCCAGTGTGTCCTCATCAAACAGCAGTGCGACTC  4140
1338   P   N   Q   F   R   C   A   S   G   Q   C   V   L   I   K   Q   Q   C   D   S    1357

4141  CTTCCCCGACTGTATCGACGGCTCCGACGAGCTCATGTGTGAAATCACCAAGCCGCCCTC  4200
1358   F   P   D   C   I   D   G   S   D   E   L   M   C   E   I   T   K   P   P   S    1377

4201  AGACGACAGCCCGGCCCACAGCAGTGCCATCGGGCCCGTCATTGGCATCATCCTCTCTCT  4260
1378   D   D   S   P   A   H   S   S   A   I   G   P   V   I   G   I   I   L   S   L    1397

4261  CTTCGTCATGGGTGGTGTGTCTATTTTGTGTGCCAGCGCGTGTGTGCCAGCGCTATGCGGG  4320
1398   F   V   M   G   G   V   Y   F   V   C   Q   R   V   C   Q   R   Y   A   G        1417

4321  GGCCAACGGCCCTTCCCCGACGAGTATGTCAGCGGGACCCCGCACGTGCCCCTCAATTT   4380
1418   A   N   G   P   F   P   H   E   Y   V   S   G   T   P   H   V   P   L   N   F    1437
```

FIG. 61

```
4381  CATAGCCCCGGGCGGTTCCCAGCATGCCCCTTCACAGGCATGCCATGCGGAAAGTCCAT  4440
1438    I  A  P  G  G  S  Q  H  G  P  F  T  G  I  A  C  G  K  S  M   1457

4441  GATGAGCTCCGTGAGCCTGATGGGGGGCCGGGGCGGGGTGCCCCTCTACGACCGGAACCA  4500
1458    M  S  S  V  S  L  M  G  G  R  G  G  V  P  L  Y  D  R  N  H   1477

4501  CGTCACAGGGGCCTCGTCCAGCAGTCTGTCCAGCACGAAGGCCACGCTGTACCCGCCGAT  4560
1478    V  T  G  A  S  S  S  S  S  S  T  K  A  T  L  Y  P  P  I   1497

4561  CCTGAACCCGCGCCCCTCCCCGGCCACGGACCCCTCCCTGTACAACATGGACATGTTCTA  4620
1498    L  N  P  P  P  S  P  A  T  D  P  S  L  Y  N  M  D  M  F  Y   1517

4621  CTCTTTCAAACATTCCGGCCACTGCGAGACCGTACAGGCCCTACATCATTCGAGGAATGGC  4680
1518    S  S  N  I  P  A  T  A  R  R  P  Y  R  P  Y  I  I  R  G  M  A   1537

4681  GCCCCCGACGACACCCCTGCCAGCGTGTGTGACAGCGACTACAGCGCCAGCCGCTG  4740
1538    P  P  T  T  P  C  S  T  D  V  C  D  S  D  Y  S  A  S  R  W   1557

4741  GAAGGCCAGCAAGTACTACCTGGATTTGAACTCGGACTCAGACCCCTATCCACCCCCACC  4800
1558    K  A  S  K  Y  Y  L  D  L  N  S  D  S  D  P  Y  P  P  P  P   1577

4801  CACGCCCCACAGCCAGTACCTGTCGGCGGAGGACAGCTGCCCGCCCTCGCCGCCACCGA  4860
1578    T  P  H  S  Q  Y  L  S  A  E  D  S  C  P  P  S  P  A  T  E   1597

4861  GAGGAGCTACTTCCATCTCTTCCCGCCCCCCTCCGCCCTGCACGGACTCATCCTGACC  4920
1598    R  S  Y  F  H  L  F  P  P  P  P  S  P  C  T  D  S  S   1615
```

FIG. 6J

```
4921 TCGGCCGGGCCACTCTGGCTTCTCTGTGCCCCTGTAAATAGTTTAAATATGAACAAAGA    4980
4981 AAAAAATATATTTATGATTTAAAATAAATATTGGATTTTAAAAACATGAGAAA           5040
5041 TGTGAACTGTGATGGGGTGGGCAGGGCTGGGAGAACTTTGTACAGTGGAGAAATATTTAT    5100
5101 AAACTTAATTTTGTAAAACA    5120
```

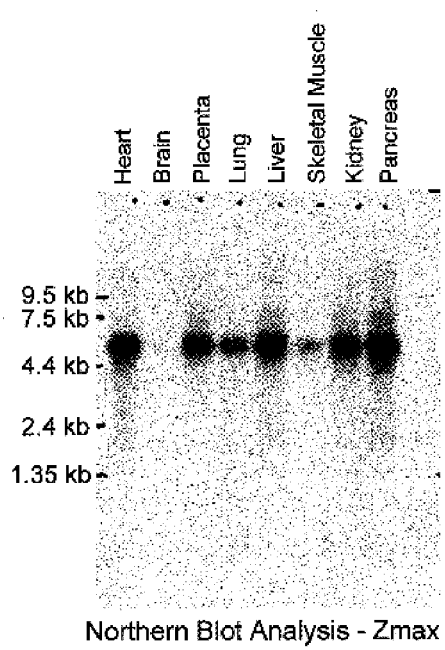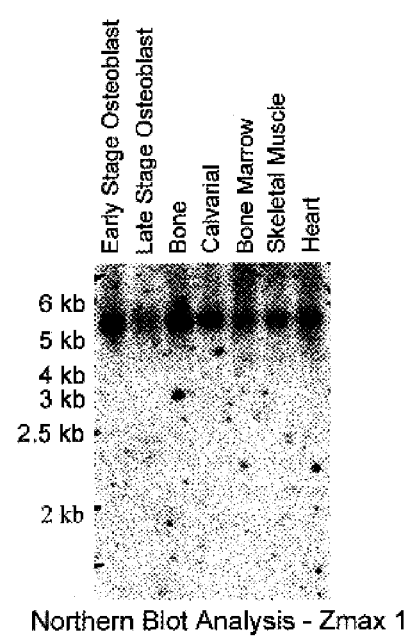
Northern Blot Analysis - Zmax 1
FIG. 7A
Northern Blot Analysis - Zmax 1
FIG. 7B Mouse Zmax1 In situ hybridization
100X Magnification Antisense probe Mouse Zmax1 In situ hybridization
100X Magnification Sense probe Mouse Zmax1 In situ hybridization
400X Magnification
Antisense probe Osteoblasts — Endosteum Mouse Zmax1 In situ hybridization
400X Magnification
Sense probe

SEQUENCE LISTING

<160> NUMBER OF SEQ ID NOS: 641

<210> SEQ ID NO 1
<211> LENGTH: 5120
<212> TYPE: DNA
<213> ORGANISM: Homo sapiens

<400> SEQUENCE: 1

```
actaaagcgc cgccgccgcg ccatggagcc cgagtgagcg cggcgcgggc ccgtccggcc      60
gccggacaac  atg gag gca gcg ccg ccc ggg ccg ccg tgg ccg ctg ctg       109
            Met Glu Ala Ala Pro Pro Gly Pro Pro Trp Pro Leu Leu
            1               5                   10 ctg ctg ctg ctg ctg ctg gcg ctg tgc ggc tgc ccg gcc ccc gcc             157
Leu Leu Leu Leu Leu Leu Ala Leu Cys Gly Cys Pro Ala Pro Ala
        15                  20                  25 gcg gcc tcg ccg ctc ctg cta ttt gcc aac cgc cgg gac gta cgg ctg         205
Ala Ala Ser Pro Leu Leu Leu Phe Ala Asn Arg Arg Asp Val Arg Leu
30                  35                  40                  45 gtg gac gcc ggc gga gtc aag ctg gag tcc acc atc gtg gtc agc ggc         253
Val Asp Ala Gly Gly Val Lys Leu Glu Ser Thr Ile Val Val Ser Gly
                50                  55                  60 ctg gag gat gcg gcc gca gtg gac ttc cag ttt tcc aag gga gcc gtg         301
Leu Glu Asp Ala Ala Ala Val Asp Phe Gln Phe Ser Lys Gly Ala Val
            65                  70                  75 tac tgg aca gac gtg agc gag gag gcc atc aag cag acc tac ctg aac         349
Tyr Trp Thr Asp Val Ser Glu Glu Ala Ile Lys Gln Thr Tyr Leu Asn
        80                  85                  90 cag acg ggg gcc gcc gtg cag aac gtg gtc atc tcc ggc ctg gtc tct         397
Gln Thr Gly Ala Ala Val Gln Asn Val Val Ile Ser Gly Leu Val Ser
    95                  100                 105 ccc gac ggc ctc gcc tgc gac tgg gtg ggc aag aag ctg tac tgg acg         445
Pro Asp Gly Leu Ala Cys Asp Trp Val Gly Lys Lys Leu Tyr Trp Thr
110                 115                 120                 125 gac tca gag acc aac cgc atc gag gtg gcc aac ctc aat ggc aca tcc         493
Asp Ser Glu Thr Asn Arg Ile Glu Val Ala Asn Leu Asn Gly Thr Ser
                130                 135                 140
```

-continued

| | |
|---|---|
| cgg aag gtg ctc ttc tgg cag gac ctt gac cag ccg agg gcc atc gcc<br>Arg Lys Val Leu Phe Trp Gln Asp Leu Asp Gln Pro Arg Ala Ile Ala<br>             145                     150                    155 | 541 |
| ttg gac ccc gct cac ggg tac atg tac tgg aca gac tgg ggt gag acg<br>Leu Asp Pro Ala His Gly Tyr Met Tyr Trp Thr Asp Trp Gly Glu Thr<br>160                     165                    170 | 589 |
| ccc cgg att gag cgg gca ggg atg gat ggc agc acc cgg aag atc att<br>Pro Arg Ile Glu Arg Ala Gly Met Asp Gly Ser Thr Arg Lys Ile Ile<br>             175                     180                    185 | 637 |
| gtg gac tcg gac att tac tgg ccc aat gga ctg acc atc gac ctg gag<br>Val Asp Ser Asp Ile Tyr Trp Pro Asn Gly Leu Thr Ile Asp Leu Glu<br>190                     195                    200                    205 | 685 |
| gag cag aag ctc tac tgg gct gac gcc aag ctc agc ttc atc cac cgt<br>Glu Gln Lys Leu Tyr Trp Ala Asp Ala Lys Leu Ser Phe Ile His Arg<br>             210                     215                    220 | 733 |
| gcc aac ctg gac ggc tcg ttc cgg cag aag gtg gtg gag ggc agc ctg<br>Ala Asn Leu Asp Gly Ser Phe Arg Gln Lys Val Val Glu Gly Ser Leu<br>225                     230                    235 | 781 |
| acg cac ccc ttc gcc ctg acg ctc tcc ggg gac act ctg tac tgg aca<br>Thr His Pro Phe Ala Leu Thr Leu Ser Gly Asp Thr Leu Tyr Trp Thr<br>             240                     245                    250 | 829 |
| gac tgg cag acc cgc tcc atc cat gcc tgc aac aag cgc act ggg ggg<br>Asp Trp Gln Thr Arg Ser Ile His Ala Cys Asn Lys Arg Thr Gly Gly<br>255                     260                    265 | 877 |
| aag agg aag gag atc ctg agt gcc ctc tac tca ccc atg gac atc cag<br>Lys Arg Lys Glu Ile Leu Ser Ala Leu Tyr Ser Pro Met Asp Ile Gln<br>270                     275                    280                    285 | 925 |
| gtg ctg agc cag gag cgg cag cct ttc ttc cac act cgc tgt gag gag<br>Val Leu Ser Gln Glu Arg Gln Pro Phe Phe His Thr Arg Cys Glu Glu<br>             290                     295                    300 | 973 |
| gac aat ggc ggc tgc tcc cac ctg tgc ctg ctg tcc cca agc gag cct<br>Asp Asn Gly Gly Cys Ser His Leu Cys Leu Leu Ser Pro Ser Glu Pro<br>                   305                     310                    315 | 1021 |
| ttc tac aca tgc gcc tgc ccc acg ggt gtg cag ctg cag gac aac ggc<br>Phe Tyr Thr Cys Ala Cys Pro Thr Gly Val Gln Leu Gln Asp Asn Gly<br>320                     325                    330 | 1069 |
| agg acg tgt aag gca gga gcc gag gag gtg ctg ctg ctg gcc cgg cgg<br>Arg Thr Cys Lys Ala Gly Ala Glu Glu Val Leu Leu Leu Ala Arg Arg<br>             335                     340                    345 | 1117 |
| acg gac cta cgg agg atc tcg ctg gac acg ccg gac ttc acc gac atc<br>Thr Asp Leu Arg Arg Ile Ser Leu Asp Thr Pro Asp Phe Thr Asp Ile<br>350                     355                    360                    365 | 1165 |
| gtg ctg cag gtg gac gac atc cgg cac gcc att gcc atc gac tac gac<br>Val Leu Gln Val Asp Asp Ile Arg His Ala Ile Ala Ile Asp Tyr Asp<br>             370                     375                    380 | 1213 |
| ccg cta gag ggc tat gtc tac tgg aca gat gac gag gtg cgg gcc atc<br>Pro Leu Glu Gly Tyr Val Tyr Trp Thr Asp Asp Glu Val Arg Ala Ile<br>                   385                     390                    395 | 1261 |
| cgc agg gcg tac ctg gac ggg tct ggg gcg cag acg ctg gtc aac acc<br>Arg Arg Ala Tyr Leu Asp Gly Ser Gly Ala Gln Thr Leu Val Asn Thr<br>             400                     405                    410 | 1309 |
| gag atc aac gac ccc gat ggc atc gcg gtc gac tgg gtg gcc cga aac<br>Glu Ile Asn Asp Pro Asp Gly Ile Ala Val Asp Trp Val Ala Arg Asn<br>415                     420                    425 | 1357 |
| ctc tac tgg acc gac acg ggc acg gac cgc atc gag gtg acg cgc ctc<br>Leu Tyr Trp Thr Asp Thr Gly Thr Asp Arg Ile Glu Val Thr Arg Leu<br>430                     435                    440                    445 | 1405 |
| aac ggc acc tcc cgc aag atc ctg gtg tcg gag gac ctg gac gag ccc<br>Asn Gly Thr Ser Arg Lys Ile Leu Val Ser Glu Asp Leu Asp Glu Pro<br>                   450                     455                    460 | 1453 |

-continued

```
cga gcc atc gca ctg cac ccc gtg atg ggc ctc atg tac tgg aca gac      1501
Arg Ala Ile Ala Leu His Pro Val Met Gly Leu Met Tyr Trp Thr Asp
            465                 470                 475 tgg gga gag aac cct aaa atc gag tgt gcc aac ttg gat ggg cag gag      1549
Trp Gly Glu Asn Pro Lys Ile Glu Cys Ala Asn Leu Asp Gly Gln Glu
        480                 485                 490 cgg cgt gtg ctg gtc aat gcc tcc ctc ggg tgg ccc aac ggc ctg gcc      1597
Arg Arg Val Leu Val Asn Ala Ser Leu Gly Trp Pro Asn Gly Leu Ala
    495                 500                 505 ctg gac ctg cag gag ggg aag ctc tac tgg gga gac gcc aag aca gac      1645
Leu Asp Leu Gln Glu Gly Lys Leu Tyr Trp Gly Asp Ala Lys Thr Asp
510                 515                 520                 525 aag atc gag gtg atc aat gtt gat ggg acg aag agg cgg acc ctc ctg      1693
Lys Ile Glu Val Ile Asn Val Asp Gly Thr Lys Arg Arg Thr Leu Leu
                530                 535                 540 gag gac aag ctc ccg cac att ttc ggg ttc acg ctg ctg ggg gac ttc      1741
Glu Asp Lys Leu Pro His Ile Phe Gly Phe Thr Leu Leu Gly Asp Phe
            545                 550                 555 atc tac tgg act gac tgg cag cgc cgc agc atc gag cgg gtg cac aag      1789
Ile Tyr Trp Thr Asp Trp Gln Arg Arg Ser Ile Glu Arg Val His Lys
        560                 565                 570 gtc aag gcc agc cgg gac gtc atc att gac cag ctg ccc gac ctg atg      1837
Val Lys Ala Ser Arg Asp Val Ile Ile Asp Gln Leu Pro Asp Leu Met
    575                 580                 585 ggg ctc aaa gct gtg aat gtg gcc aag gtc gtc gga acc aac ccg tgt      1885
Gly Leu Lys Ala Val Asn Val Ala Lys Val Val Gly Thr Asn Pro Cys
590                 595                 600                 605 gcg gac agg aac ggg ggg tgc agc cac ctg tgc ttc ttc aca ccc cac      1933
Ala Asp Arg Asn Gly Gly Cys Ser His Leu Cys Phe Phe Thr Pro His
                610                 615                 620 gca acc cgg tgt ggc tgc ccc atc ggc ctg gag ctg ctg agt gac atg      1981
Ala Thr Arg Cys Gly Cys Pro Ile Gly Leu Glu Leu Leu Ser Asp Met
            625                 630                 635 aag acc tgc atc gtg cct gag gcc ttc ttg gtc ttc acc agc aga gcc      2029
Lys Thr Cys Ile Val Pro Glu Ala Phe Leu Val Phe Thr Ser Arg Ala
        640                 645                 650 gcc atc cac agg atc tcc ctc gag acc aat aac aac gac gtg gcc atc      2077
Ala Ile His Arg Ile Ser Leu Glu Thr Asn Asn Asn Asp Val Ala Ile
    655                 660                 665 ccg ctc acg ggc gtc aag gag gcc tca gcc ctg gac ttt gat gtg tcc      2125
Pro Leu Thr Gly Val Lys Glu Ala Ser Ala Leu Asp Phe Asp Val Ser
670                 675                 680                 685 aac aac cac atc tac tgg aca gac gtc agc ctg aag acc atc agc cgc      2173
Asn Asn His Ile Tyr Trp Thr Asp Val Ser Leu Lys Thr Ile Ser Arg
                690                 695                 700 gcc ttc atg aac ggg agc tcg gtg gag cac gtg gtg gag ttt ggc ctt      2221
Ala Phe Met Asn Gly Ser Ser Val Glu His Val Val Glu Phe Gly Leu
            705                 710                 715 gac tac ccc gag ggc atg gcc gtt gac tgg atg ggc aag aac ctc tac      2269
Asp Tyr Pro Glu Gly Met Ala Val Asp Trp Met Gly Lys Asn Leu Tyr
        720                 725                 730 tgg gcc gac act ggg acc aac aga atc gaa gtg gcg cgg ctg gac ggg      2317
Trp Ala Asp Thr Gly Thr Asn Arg Ile Glu Val Ala Arg Leu Asp Gly
    735                 740                 745 cag ttc cgg caa gtc ctc gtg tgg agg gac ttg gac aac ccg agg tcg      2365
Gln Phe Arg Gln Val Leu Val Trp Arg Asp Leu Asp Asn Pro Arg Ser
750                 755                 760                 765 ctg gcc ctg gat ccc acc aag ggc tac atc tac tgg acc gag tgg ggc      2413
Leu Ala Leu Asp Pro Thr Lys Gly Tyr Ile Tyr Trp Thr Glu Trp Gly
```

-continued

|  |  |
|---|---|
| 770 775 780 | |
| ggc aag ccg agg atc gtg cgg gcc ttc atg gac ggg acc aac tgc atg<br>Gly Lys Pro Arg Ile Val Arg Ala Phe Met Asp Gly Thr Asn Cys Met<br>            785                  790                 795 | 2461 |
| acg ctg gtg gac aag gtg ggc cgg gcc aac gac ctc acc att gac tac<br>Thr Leu Val Asp Lys Val Gly Arg Ala Asn Asp Leu Thr Ile Asp Tyr<br>     800                  805                 810 | 2509 |
| gct gac cag cgc ctc tac tgg acc gac ctg gac acc aac atg atc gag<br>Ala Asp Gln Arg Leu Tyr Trp Thr Asp Leu Asp Thr Asn Met Ile Glu<br>815               820                 825 | 2557 |
| tcg tcc aac atg ctg ggt cag gag cgg gtc gtg att gcc gac gat ctc<br>Ser Ser Asn Met Leu Gly Gln Glu Arg Val Val Ile Ala Asp Asp Leu<br>830               835               840               845 | 2605 |
| ccg cac ccg ttc ggt ctg acg cag tac agc gat tat atc tac tgg aca<br>Pro His Pro Phe Gly Leu Thr Gln Tyr Ser Asp Tyr Ile Tyr Trp Thr<br>            850                  855               860 | 2653 |
| gac tgg aat ctg cac agc att gag cgg gcc gac aag act agc ggc cgg<br>Asp Trp Asn Leu His Ser Ile Glu Arg Ala Asp Lys Thr Ser Gly Arg<br>               865                870               875 | 2701 |
| aac cgc acc ctc atc cag ggc cac ctg gac ttc gtg atg gac atc ctg<br>Asn Arg Thr Leu Ile Gln Gly His Leu Asp Phe Val Met Asp Ile Leu<br>     880                  885                 890 | 2749 |
| gtg ttc cac tcc tcc cgc cag gat ggc ctc aat gac tgt atg cac aac<br>Val Phe His Ser Ser Arg Gln Asp Gly Leu Asn Asp Cys Met His Asn<br>895               900                 905 | 2797 |
| aac ggg cag tgt ggg cag ctg tgc ctt gcc atc ccc ggc ggc cac cgc<br>Asn Gly Gln Cys Gly Gln Leu Cys Leu Ala Ile Pro Gly Gly His Arg<br>910               915               920               925 | 2845 |
| tgc ggc tgc gcc tca cac tac acc ctg gac ccc agc agc cgc aac tgc<br>Cys Gly Cys Ala Ser His Tyr Thr Leu Asp Pro Ser Ser Arg Asn Cys<br>            930                  935               940 | 2893 |
| agc ccg ccc acc acc ttc ttg ctg ttc agc cag aaa tct gcc atc agt<br>Ser Pro Pro Thr Thr Phe Leu Leu Phe Ser Gln Lys Ser Ala Ile Ser<br>               945                950               955 | 2941 |
| cgg atg atc ccg gac gac cag cac agc ccg gat ctc atc ctg ccc ctg<br>Arg Met Ile Pro Asp Asp Gln His Ser Pro Asp Leu Ile Leu Pro Leu<br>     960                  965                 970 | 2989 |
| cat gga ctg agg aac gtc aaa gcc atc gac tat gac cca ctg gac aag<br>His Gly Leu Arg Asn Val Lys Ala Ile Asp Tyr Asp Pro Leu Asp Lys<br>975               980                 985 | 3037 |
| ttc atc tac tgg gtg gat ggg cgc cag aac atc aag cga gcc aag gac<br>Phe Ile Tyr Trp Val Asp Gly Arg Gln Asn Ile Lys Arg Ala Lys Asp<br>990               995              1000            1005 | 3085 |
| gac ggg acc cag ccc ttt gtt ttg acc tct ctg agc caa ggc caa aac<br>Asp Gly Thr Gln Pro Phe Val Leu Thr Ser Leu Ser Gln Gly Gln Asn<br>            1010               1015               1020 | 3133 |
| cca gac agg cag ccc cac gac ctc agc atc gac atc tac agc cgg aca<br>Pro Asp Arg Gln Pro His Asp Leu Ser Ile Asp Ile Tyr Ser Arg Thr<br>               1025               1030               1035 | 3181 |
| ctg ttc tgg acg tgc gag gcc acc aat acc atc aac gtc cac agg ctg<br>Leu Phe Trp Thr Cys Glu Ala Thr Asn Thr Ile Asn Val His Arg Leu<br>            1040               1045               1050 | 3229 |
| agc ggg gaa gcc atg ggg gtg gtg ctg cgt ggg gac cgc gac aag ccc<br>Ser Gly Glu Ala Met Gly Val Val Leu Arg Gly Asp Arg Asp Lys Pro<br>            1055               1060               1065 | 3277 |
| agg gcc atc gtc gtc aac gcg gag cga ggg tac ctg tac ttc acc aac<br>Arg Ala Ile Val Val Asn Ala Glu Arg Gly Tyr Leu Tyr Phe Thr Asn<br>1070               1075               1080               1085 | 3325 |
| atg cag gac cgg gca gcc aag atc gaa cgc gca gcc ctg gac ggc acc | 3373 |

```
                    Met Gln Asp Arg Ala Ala Lys Ile Glu Arg Ala Ala Leu Asp Gly Thr
                                1090                1095                1100 gag cgc gag gtc ctc ttc acc acc ggc ctc atc cgc cct gtg gcc ctg              3421
Glu Arg Glu Val Leu Phe Thr Thr Gly Leu Ile Arg Pro Val Ala Leu
        1105                1110                1115 gtg gtg gac aac aca ctg ggc aag ctg ttc tgg gtg gac gcg gac ctg              3469
Val Val Asp Asn Thr Leu Gly Lys Leu Phe Trp Val Asp Ala Asp Leu
        1120                1125                1130 aag cgc att gag agc tgt gac ctg tca ggg gcc aac cgc ctg acc ctg              3517
Lys Arg Ile Glu Ser Cys Asp Leu Ser Gly Ala Asn Arg Leu Thr Leu
        1135                1140                1145 gag gac gcc aac atc gtg cag cct ctg ggc ctg acc atc ctt ggc aag              3565
Glu Asp Ala Asn Ile Val Gln Pro Leu Gly Leu Thr Ile Leu Gly Lys
1150                1155                1160                1165 cat ctc tac tgg atc gac cgc cag cag cag atg atc gag cgt gtg gag              3613
His Leu Tyr Trp Ile Asp Arg Gln Gln Gln Met Ile Glu Arg Val Glu
        1170                1175                1180 aag acc acc ggg gac aag cgg act cgc atc cag ggc cgt gtc gcc cac              3661
Lys Thr Thr Gly Asp Lys Arg Thr Arg Ile Gln Gly Arg Val Ala His
        1185                1190                1195 ctc act ggc atc cat gca gtg gag gaa gtc agc ctg gag gag ttc tca              3709
Leu Thr Gly Ile His Ala Val Glu Glu Val Ser Leu Glu Glu Phe Ser
        1200                1205                1210 gcc cac cca tgt gcc cgt gac aat ggt ggc tgc tcc cac atc tgt att              3757
Ala His Pro Cys Ala Arg Asp Asn Gly Gly Cys Ser His Ile Cys Ile
        1215                1220                1225 gcc aag ggt gat ggg aca cca cgg tgc tca tgc cca gtc cac ctc gtg              3805
Ala Lys Gly Asp Gly Thr Pro Arg Cys Ser Cys Pro Val His Leu Val
1230                1235                1240                1245 ctc ctg cag aac ctg ctg acc tgt gga gag ccg ccc acc tgc tcc ccg              3853
Leu Leu Gln Asn Leu Leu Thr Cys Gly Glu Pro Pro Thr Cys Ser Pro
        1250                1255                1260 gac cag ttt gca tgt gcc aca ggg gag atc gac tgt atc ccc ggg gcc              3901
Asp Gln Phe Ala Cys Ala Thr Gly Glu Ile Asp Cys Ile Pro Gly Ala
        1265                1270                1275 tgg cgc tgt gac ggc ttt ccc gag tgc gat gac cag agc gac gag gag              3949
Trp Arg Cys Asp Gly Phe Pro Glu Cys Asp Asp Gln Ser Asp Glu Glu
        1280                1285                1290 ggc tgc ccc gtg tgc tcc gcc gcc cag ttc ccc tgc gcg cgg ggt cag              3997
Gly Cys Pro Val Cys Ser Ala Ala Gln Phe Pro Cys Ala Arg Gly Gln
        1295                1300                1305 tgt gtg gac ctg cgc ctg cgc tgc gac ggc gag gca gac tgt cag gac              4045
Cys Val Asp Leu Arg Leu Arg Cys Asp Gly Glu Ala Asp Cys Gln Asp
1310                1315                1320                1325 cgc tca gac gag gtg gac tgt gac gcc atc tgc ctg ccc aac cag ttc              4093
Arg Ser Asp Glu Val Asp Cys Asp Ala Ile Cys Leu Pro Asn Gln Phe
        1330                1335                1340 cgg tgt gcg agc ggc cag tgt gtc ctc atc aaa cag cag tgc gac tcc              4141
Arg Cys Ala Ser Gly Gln Cys Val Leu Ile Lys Gln Gln Cys Asp Ser
        1345                1350                1355 ttc ccc gac tgt atc gac ggc tcc gac gag ctc atg tgt gaa atc acc              4189
Phe Pro Asp Cys Ile Asp Gly Ser Asp Glu Leu Met Cys Glu Ile Thr
        1360                1365                1370 aag ccg ccc tca gac gac agc ccg gcc cac agc agt gcc atc ggg ccc              4237
Lys Pro Pro Ser Asp Asp Ser Pro Ala His Ser Ser Ala Ile Gly Pro
        1375                1380                1385 gtc att ggc atc atc ctc tct ctc ttc gtc atg ggt ggt gtc tat ttt              4285
Val Ile Gly Ile Ile Leu Ser Leu Phe Val Met Gly Gly Val Tyr Phe
1390                1395                1400                1405
```

| | |
|---|---|
| gtg tgc cag cgc gtg gtg tgc cag cgc tat gcg ggg gcc aac ggg ccc<br>Val Cys Gln Arg Val Val Cys Gln Arg Tyr Ala Gly Ala Asn Gly Pro<br>              1410                   1415                   1420 | 4333 |
| ttc ccg cac gag tat gtc agc ggg acc ccg cac gtg ccc ctc aat ttc<br>Phe Pro His Glu Tyr Val Ser Gly Thr Pro His Val Pro Leu Asn Phe<br>1425                   1430                   1435 | 4381 |
| ata gcc ccg ggc ggt tcc cag cat ggc ccc ttc aca ggc atc gca tgc<br>Ile Ala Pro Gly Gly Ser Gln His Gly Pro Phe Thr Gly Ile Ala Cys<br>              1440                   1445                   1450 | 4429 |
| gga aag tcc atg atg agc tcc gtg agc ctg atg ggg ggc cgg ggc ggg<br>Gly Lys Ser Met Met Ser Ser Val Ser Leu Met Gly Gly Arg Gly Gly<br>1455                   1460                   1465 | 4477 |
| gtg ccc ctc tac gac cgg aac cac gtc aca ggg gcc tcg tcc agc agc<br>Val Pro Leu Tyr Asp Arg Asn His Val Thr Gly Ala Ser Ser Ser Ser<br>1470                 1475                   1480                   1485 | 4525 |
| tcg tcc agc acg aag gcc acg ctg tac ccg ccg atc ctg aac ccg ccg<br>Ser Ser Ser Thr Lys Ala Thr Leu Tyr Pro Pro Ile Leu Asn Pro Pro<br>              1490                   1495                   1500 | 4573 |
| ccc tcc ccg gcc acg gac ccc tcc ctg tac aac atg gac atg ttc tac<br>Pro Ser Pro Ala Thr Asp Pro Ser Leu Tyr Asn Met Asp Met Phe Tyr<br>                   1505                   1510                   1515 | 4621 |
| tct tca aac att ccg gcc act gcg aga ccg tac agg ccc tac atc att<br>Ser Ser Asn Ile Pro Ala Thr Ala Arg Pro Tyr Arg Pro Tyr Ile Ile<br>              1520                   1525                   1530 | 4669 |
| cga gga atg gcg ccc ccg acg acg ccc tgc agc acc gac gtg tgt gac<br>Arg Gly Met Ala Pro Pro Thr Thr Pro Cys Ser Thr Asp Val Cys Asp<br>1535                 1540                   1545 | 4717 |
| agc gac tac agc gcc agc cgc tgg aag gcc agc aag tac tac ctg gat<br>Ser Asp Tyr Ser Ala Ser Arg Trp Lys Ala Ser Lys Tyr Tyr Leu Asp<br>1550                 1555                   1560                   1565 | 4765 |
| ttg aac tcg gac tca gac ccc tat cca ccc cca ccc acg ccc cac agc<br>Leu Asn Ser Asp Ser Asp Pro Tyr Pro Pro Pro Pro Thr Pro His Ser<br>                          1570                   1575                   1580 | 4813 |
| cag tac ctg tcg gcg gag gac agc tgc ccg ccc tcg ccc gcc acc gag<br>Gln Tyr Leu Ser Ala Glu Asp Ser Cys Pro Pro Ser Pro Ala Thr Glu<br>1585                 1590                   1595 | 4861 |
| agg agc tac ttc cat ctc ttc ccg ccc cct ccg tcc ccc tgc acg gac<br>Arg Ser Tyr Phe His Leu Phe Pro Pro Pro Pro Ser Pro Cys Thr Asp<br>              1600                   1605                   1610 | 4909 |
| tca tcc tgacctcggc cgggccactc tggcttctct gtgcccctgt aaatagtttt<br>Ser Ser<br>     1615 | 4965 |
| aaatatgaac aaagaaaaaa atatatttta tgatttaaaa aataaatata attgggattt | 5025 |
| taaaaacatg agaaatgtga actgtgatgg ggtgggcagg gctgggagaa ctttgtacag | 5085 |
| tggagaaata tttataaact taattttgta aaaca | 5120 |

<210> SEQ ID NO 2
<211> LENGTH: 5120
<212> TYPE: DNA
<213> ORGANISM: Homo sapiens

<400> SEQUENCE: 2

| | |
|---|---|
| actaaagcgc cgccgccgcg ccatggagcc cgagtgagcg cggcgcgggc ccgtccggcc | 60 |
| gccggacaac atg gag gca gcg ccg ccc ggg ccg ccg tgg ccg ctg ctg<br>                 Met Glu Ala Ala Pro Pro Gly Pro Pro Trp Pro Leu Leu<br>                  1              5                     10 | 109 |
| ctg ctg ctg ctg ctg ctg ctg gcg ctg tgc ggc tgc ccg gcc ccc gcc<br>Leu Leu Leu Leu Leu Leu Leu Ala Leu Cys Gly Cys Pro Ala Pro Ala<br> 15                  20                  25 | 157 |

-continued

| | | |
|---|---|---|
| gcg gcc tcg ccg ctc ctg cta ttt gcc aac cgc cgg gac gta cgg ctg<br>Ala Ala Ser Pro Leu Leu Leu Phe Ala Asn Arg Arg Asp Val Arg Leu<br>30                           35                    40                  45 | 205 |
| gtg gac gcc ggc gga gtc aag ctg gag tcc acc atc gtg gtc agc ggc<br>Val Asp Ala Gly Gly Val Lys Leu Glu Ser Thr Ile Val Val Ser Gly<br>              50                          55                       60 | 253 |
| ctg gag gat gcg gcc gca gtg gac ttc cag ttt tcc aag gga gcc gtg<br>Leu Glu Asp Ala Ala Ala Val Asp Phe Gln Phe Ser Lys Gly Ala Val<br>                  65                    70                    75 | 301 |
| tac tgg aca gac gtg agc gag gag gcc atc aag cag acc tac ctg aac<br>Tyr Trp Thr Asp Val Ser Glu Glu Ala Ile Lys Gln Thr Tyr Leu Asn<br>            80                        85                    90 | 349 |
| cag acg ggg gcc gcc gtg cag aac gtg gtc atc tcc ggc ctg gtc tct<br>Gln Thr Gly Ala Ala Val Gln Asn Val Val Ile Ser Gly Leu Val Ser<br>95                         100                      105 | 397 |
| ccc gac ggc ctc gcc tgc gac tgg gtg ggc aag aag ctg tac tgg acg<br>Pro Asp Gly Leu Ala Cys Asp Trp Val Gly Lys Lys Leu Tyr Trp Thr<br>110                       115                      120                    125 | 445 |
| gac tca gag acc aac cgc atc gag gtg gcc aac ctc aat ggc aca tcc<br>Asp Ser Glu Thr Asn Arg Ile Glu Val Ala Asn Leu Asn Gly Thr Ser<br>                  130                     135                   140 | 493 |
| cgg aag gtg ctc ttc tgg cag gac ctt gac cag ccg agg gcc atc gcc<br>Arg Lys Val Leu Phe Trp Gln Asp Leu Asp Gln Pro Arg Ala Ile Ala<br>                  145                     150                   155 | 541 |
| ttg gac ccc gct cac ggg tac atg tac tgg aca gac tgg gtt gag acg<br>Leu Asp Pro Ala His Gly Tyr Met Tyr Trp Thr Asp Trp Val Glu Thr<br>                  160                     165                   170 | 589 |
| ccc cgg att gag cgg gca ggg atg gat ggc agc acc cgg aag atc att<br>Pro Arg Ile Glu Arg Ala Gly Met Asp Gly Ser Thr Arg Lys Ile Ile<br>175                       180                      185 | 637 |
| gtg gac tcg gac att tac tgg ccc aat gga ctg acc atc gac ctg gag<br>Val Asp Ser Asp Ile Tyr Trp Pro Asn Gly Leu Thr Ile Asp Leu Glu<br>190                       195                      200                    205 | 685 |
| gag cag aag ctc tac tgg gct gac gcc aag ctc agc ttc atc cac cgt<br>Glu Gln Lys Leu Tyr Trp Ala Asp Ala Lys Leu Ser Phe Ile His Arg<br>                  210                     215                   220 | 733 |
| gcc aac ctg gac ggc tcg ttc cgg cag aag gtg gtg gag ggc agc ctg<br>Ala Asn Leu Asp Gly Ser Phe Arg Gln Lys Val Val Glu Gly Ser Leu<br>                  225                     230                   235 | 781 |
| acg cac ccc ttc gcc ctg acg ctc tcc ggg gac act ctg tac tgg aca<br>Thr His Pro Phe Ala Leu Thr Leu Ser Gly Asp Thr Leu Tyr Trp Thr<br>                  240                     245                   250 | 829 |
| gac tgg cag acc cgc tcc atc cat gcc tgc aac aag cgc act ggg ggg<br>Asp Trp Gln Thr Arg Ser Ile His Ala Cys Asn Lys Arg Thr Gly Gly<br>255                       260                      265 | 877 |
| aag agg aag gag atc ctg agt gcc ctc tac tca ccc atg gac atc cag<br>Lys Arg Lys Glu Ile Leu Ser Ala Leu Tyr Ser Pro Met Asp Ile Gln<br>270                       275                      280                    285 | 925 |
| gtg ctg agc cag gag cgg cag cct ttc ttc cac act cgc tgt gag gag<br>Val Leu Ser Gln Glu Arg Gln Pro Phe Phe His Thr Arg Cys Glu Glu<br>                  290                     295                   300 | 973 |
| gac aat ggc ggc tgc tcc cac ctg tgc ctg ctg tcc cca agc gag cct<br>Asp Asn Gly Gly Cys Ser His Leu Cys Leu Leu Ser Pro Ser Glu Pro<br>                  305                     310                   315 | 1021 |
| ttc tac aca tgc gcc tgc ccc acg ggt gtg cag ctg cag gac aac ggc<br>Phe Tyr Thr Cys Ala Cys Pro Thr Gly Val Gln Leu Gln Asp Asn Gly<br>                  320                     325                   330 | 1069 |
| agg acg tgt aag gca gga gcc gag gag gtg ctg ctg ctg gcc cgg cgg<br>Arg Thr Cys Lys Ala Gly Ala Glu Glu Val Leu Leu Leu Ala Arg Arg | 1117 |

-continued

```
        335                 340                 345
acg gac cta cgg agg atc tcg ctg gac acg ccg gac ttc acc gac atc       1165
Thr Asp Leu Arg Arg Ile Ser Leu Asp Thr Pro Asp Phe Thr Asp Ile
350                 355                 360                 365 gtg ctg cag gtg gac gac atc cgg cac gcc att gcc atc gac tac gac       1213
Val Leu Gln Val Asp Asp Ile Arg His Ala Ile Ala Ile Asp Tyr Asp
                370                 375                 380 ccg cta gag ggc tat gtc tac tgg aca gat gac gag gtg cgg gcc atc       1261
Pro Leu Glu Gly Tyr Val Tyr Trp Thr Asp Asp Glu Val Arg Ala Ile
            385                 390                 395 cgc agg gcg tac ctg gac ggg tct ggg gcg cag acg ctg gtc aac acc       1309
Arg Arg Ala Tyr Leu Asp Gly Ser Gly Ala Gln Thr Leu Val Asn Thr
        400                 405                 410 gag atc aac gac ccc gat ggc atc gcg gtc gac tgg gtg gcc cga aac       1357
Glu Ile Asn Asp Pro Asp Gly Ile Ala Val Asp Trp Val Ala Arg Asn
    415                 420                 425 ctc tac tgg acc gac acg ggc acg gac cgc atc gag gtg acg cgc ctc       1405
Leu Tyr Trp Thr Asp Thr Gly Thr Asp Arg Ile Glu Val Thr Arg Leu
430                 435                 440                 445 aac ggc acc tcc cgc aag atc ctg gtg tcg gag gac ctg gac gag ccc       1453
Asn Gly Thr Ser Arg Lys Ile Leu Val Ser Glu Asp Leu Asp Glu Pro
                450                 455                 460 cga gcc atc gca ctg cac ccc gtg atg ggc ctc atg tac tgg aca gac       1501
Arg Ala Ile Ala Leu His Pro Val Met Gly Leu Met Tyr Trp Thr Asp
                465                 470                 475 tgg gga gag aac cct aaa atc gag tgt gcc aac ttg gat ggg cag gag       1549
Trp Gly Glu Asn Pro Lys Ile Glu Cys Ala Asn Leu Asp Gly Gln Glu
            480                 485                 490 cgg cgt gtg ctg gtc aat gcc tcc ctc ggg tgg ccc aac ggc ctg gcc       1597
Arg Arg Val Leu Val Asn Ala Ser Leu Gly Trp Pro Asn Gly Leu Ala
495                 500                 505 ctg gac ctg cag gag ggg aag ctc tac tgg gga gac gcc aag aca gac       1645
Leu Asp Leu Gln Glu Gly Lys Leu Tyr Trp Gly Asp Ala Lys Thr Asp
510                 515                 520                 525 aag atc gag gtg atc aat gtt gat ggg acg aag agg cgg acc ctc ctg       1693
Lys Ile Glu Val Ile Asn Val Asp Gly Thr Lys Arg Arg Thr Leu Leu
                530                 535                 540 gag gac aag ctc ccg cac att ttc ggg ttc acg ctg ctg ggg gac ttc       1741
Glu Asp Lys Leu Pro His Ile Phe Gly Phe Thr Leu Leu Gly Asp Phe
            545                 550                 555 atc tac tgg act gac tgg cag cgc cgc agc atc gag cgg gtg cac aag       1789
Ile Tyr Trp Thr Asp Trp Gln Arg Arg Ser Ile Glu Arg Val His Lys
        560                 565                 570 gtc aag gcc agc cgg gac gtc atc att gac cag ctg ccc gac ctg atg       1837
Val Lys Ala Ser Arg Asp Val Ile Ile Asp Gln Leu Pro Asp Leu Met
575                 580                 585 ggg ctc aaa gct gtg aat gtg gcc aag gtc gtc gga acc aac ccg tgt       1885
Gly Leu Lys Ala Val Asn Val Ala Lys Val Val Gly Thr Asn Pro Cys
590                 595                 600                 605 gcg gac agg aac ggg ggg tgc agc cac ctg tgc ttc ttc aca ccc cac       1933
Ala Asp Arg Asn Gly Gly Cys Ser His Leu Cys Phe Phe Thr Pro His
                610                 615                 620 gca acc cgg tgt ggc tgc ccc atc ggc ctg gag ctg ctg agt gac atg       1981
Ala Thr Arg Cys Gly Cys Pro Ile Gly Leu Glu Leu Leu Ser Asp Met
                625                 630                 635 aag acc tgc atc gtg cct gag gcc ttc ttg gtc ttc acc agc aga gcc       2029
Lys Thr Cys Ile Val Pro Glu Ala Phe Leu Val Phe Thr Ser Arg Ala
                640                 645                 650 gcc atc cac agg atc tcc ctc gag acc aat aac aac gac gtg gcc atc       2077
```

```
Ala Ile His Arg Ile Ser Leu Glu Thr Asn Asn Asn Asp Val Ala Ile
        655                 660                 665 ccg ctc acg ggc gtc aag gag gcc tca gcc ctg gac ttt gat gtg tcc        2125
Pro Leu Thr Gly Val Lys Glu Ala Ser Ala Leu Asp Phe Asp Val Ser
670                 675                 680                 685 aac aac cac atc tac tgg aca gac gtc agc ctg aag acc atc agc cgc        2173
Asn Asn His Ile Tyr Trp Thr Asp Val Ser Leu Lys Thr Ile Ser Arg
            690                 695                 700 gcc ttc atg aac ggg agc tcg gtg gag cac gtg gtg gag ttt ggc ctt        2221
Ala Phe Met Asn Gly Ser Ser Val Glu His Val Val Glu Phe Gly Leu
        705                 710                 715 gac tac ccc gag ggc atg gcc gtt gac tgg atg ggc aag aac ctc tac        2269
Asp Tyr Pro Glu Gly Met Ala Val Asp Trp Met Gly Lys Asn Leu Tyr
    720                 725                 730 tgg gcc gac act ggg acc aac aga atc gaa gtg gcg cgg ctg gac ggg        2317
Trp Ala Asp Thr Gly Thr Asn Arg Ile Glu Val Ala Arg Leu Asp Gly
        735                 740                 745 cag ttc cgg caa gtc ctc gtg tgg agg gac ttg gac aac ccg agg tcg        2365
Gln Phe Arg Gln Val Leu Val Trp Arg Asp Leu Asp Asn Pro Arg Ser
750                 755                 760                 765 ctg gcc ctg gat ccc acc aag ggc tac atc tac tgg acc gag tgg ggc        2413
Leu Ala Leu Asp Pro Thr Lys Gly Tyr Ile Tyr Trp Thr Glu Trp Gly
            770                 775                 780 ggc aag ccg agg atc gtg cgg gcc ttc atg gac ggg acc aac tgc atg        2461
Gly Lys Pro Arg Ile Val Arg Ala Phe Met Asp Gly Thr Asn Cys Met
        785                 790                 795 acg ctg gtg gac aag gtg ggc cgg gcc aac gac ctc acc att gac tac        2509
Thr Leu Val Asp Lys Val Gly Arg Ala Asn Asp Leu Thr Ile Asp Tyr
    800                 805                 810 gct gac cag cgc ctc tac tgg acc gac ctg gac acc aac atg atc gag        2557
Ala Asp Gln Arg Leu Tyr Trp Thr Asp Leu Asp Thr Asn Met Ile Glu
815                 820                 825 tcg tcc aac atg ctg ggt cag gag cgg gtc gtg att gcc gac gat ctc        2605
Ser Ser Asn Met Leu Gly Gln Glu Arg Val Val Ile Ala Asp Asp Leu
830                 835                 840                 845 ccg cac ccg ttc ggt ctg acg cag tac agc gat tat atc tac tgg aca        2653
Pro His Pro Phe Gly Leu Thr Gln Tyr Ser Asp Tyr Ile Tyr Trp Thr
            850                 855                 860 gac tgg aat ctg cac agc att gag cgg gcc gac aag act agc ggc cgg        2701
Asp Trp Asn Leu His Ser Ile Glu Arg Ala Asp Lys Thr Ser Gly Arg
        865                 870                 875 aac cgc acc ctc atc cag ggc cac ctg gac ttc gtg atg gac atc ctg        2749
Asn Arg Thr Leu Ile Gln Gly His Leu Asp Phe Val Met Asp Ile Leu
    880                 885                 890 gtg ttc cac tcc tcc cgc cag gat ggc ctc aat gac tgt atg cac aac        2797
Val Phe His Ser Ser Arg Gln Asp Gly Leu Asn Asp Cys Met His Asn
895                 900                 905 aac ggg cag tgt ggg cag ctg tgc ctt gcc atc ccc ggc ggc cac cgc        2845
Asn Gly Gln Cys Gly Gln Leu Cys Leu Ala Ile Pro Gly Gly His Arg
910                 915                 920                 925 tgc ggc tgc gcc tca cac tac acc ctg gac ccc agc agc cgc aac tgc        2893
Cys Gly Cys Ala Ser His Tyr Thr Leu Asp Pro Ser Ser Arg Asn Cys
            930                 935                 940 agc ccc ccc acc acc ttc ttg ctg ttc agc cag aaa tct gcc atc agt        2941
Ser Pro Pro Thr Thr Phe Leu Leu Phe Ser Gln Lys Ser Ala Ile Ser
        945                 950                 955 cgg atg atc ccg gac gac cag cac agc ccg gat ctc atc ctg ccc ctg        2989
Arg Met Ile Pro Asp Asp Gln His Ser Pro Asp Leu Ile Leu Pro Leu
    960                 965                 970
```

| | | | | | | | | | | | | | | | |
|---|---|---|---|---|---|---|---|---|---|---|---|---|---|---|---|
| cat | gga | ctg | agg | aac | gtc | aaa | gcc | atc | gac | tat | gac | cca | ctg | gac | aag | 3037 |
| His | Gly | Leu | Arg | Asn | Val | Lys | Ala | Ile | Asp | Tyr | Asp | Pro | Leu | Asp | Lys |
| | | 975 | | | | 980 | | | | | 985 | | | | |

```
cat gga ctg agg aac gtc aaa gcc atc gac tat gac cca ctg gac aag      3037
His Gly Leu Arg Asn Val Lys Ala Ile Asp Tyr Asp Pro Leu Asp Lys
            975                 980                 985 ttc atc tac tgg gtg gat ggg cgc cag aac atc aag cga gcc aag gac      3085
Phe Ile Tyr Trp Val Asp Gly Arg Gln Asn Ile Lys Arg Ala Lys Asp
990                 995                 1000                1005 gac ggg acc cag ccc ttt gtt ttg acc tct ctg agc caa ggc caa aac      3133
Asp Gly Thr Gln Pro Phe Val Leu Thr Ser Leu Ser Gln Gly Gln Asn
                    1010                1015                1020 cca gac agg cag ccc cac gac ctc agc atc gac atc tac agc cgg aca      3181
Pro Asp Arg Gln Pro His Asp Leu Ser Ile Asp Ile Tyr Ser Arg Thr
            1025                1030                1035 ctg ttc tgg acg tgc gag gcc acc aat acc atc aac gtc cac agg ctg      3229
Leu Phe Trp Thr Cys Glu Ala Thr Asn Thr Ile Asn Val His Arg Leu
            1040                1045                1050 agc ggg gaa gcc atg ggg gtg gtg ctg cgt ggg gac cgc gac aag ccc      3277
Ser Gly Glu Ala Met Gly Val Val Leu Arg Gly Asp Arg Asp Lys Pro
            1055                1060                1065 agg gcc atc gtc gtc aac gcg gag cga ggg tac ctg tac ttc acc aac      3325
Arg Ala Ile Val Val Asn Ala Glu Arg Gly Tyr Leu Tyr Phe Thr Asn
1070                1075                1080                1085 atg cag gac cgg gca gcc aag atc gaa cgc gca gcc ctg gac ggc acc      3373
Met Gln Asp Arg Ala Ala Lys Ile Glu Arg Ala Ala Leu Asp Gly Thr
                    1090                1095                1100 gag cgc gag gtc ctc ttc acc acc ggc ctc atc cgc cct gtg gcc ctg      3421
Glu Arg Glu Val Leu Phe Thr Thr Gly Leu Ile Arg Pro Val Ala Leu
                    1105                1110                1115 gtg gtg gac aac aca ctg ggc aag ctg ttc tgg gtg gac gcg gac ctg      3469
Val Val Asp Asn Thr Leu Gly Lys Leu Phe Trp Val Asp Ala Asp Leu
                    1120                1125                1130 aag cgc att gag agc tgt gac ctg tca ggg gcc aac cgc ctg acc ctg      3517
Lys Arg Ile Glu Ser Cys Asp Leu Ser Gly Ala Asn Arg Leu Thr Leu
            1135                1140                1145 gag gac gcc aac atc gtg cag cct ctg ggc ctg acc atc ctt ggc aag      3565
Glu Asp Ala Asn Ile Val Gln Pro Leu Gly Leu Thr Ile Leu Gly Lys
1150                1155                1160                1165 cat ctc tac tgg atc gac cgc cag cag cag atg atc gag cgt gtg gag      3613
His Leu Tyr Trp Ile Asp Arg Gln Gln Gln Met Ile Glu Arg Val Glu
            1170                1175                1180 aag acc acc ggg gac aag cgg act cgc atc cag ggc cgt gtc gcc cac      3661
Lys Thr Thr Gly Asp Lys Arg Thr Arg Ile Gln Gly Arg Val Ala His
            1185                1190                1195 ctc act ggc atc cat gca gtg gag gaa gtc agc ctg gag gag ttc tca      3709
Leu Thr Gly Ile His Ala Val Glu Glu Val Ser Leu Glu Glu Phe Ser
                    1200                1205                1210 gcc cac cca tgt gcc cgt gac aat ggt ggc tgc tcc cac atc tgt att      3757
Ala His Pro Cys Ala Arg Asp Asn Gly Gly Cys Ser His Ile Cys Ile
            1215                1220                1225 gcc aag ggt gat ggg aca cca cgg tgc tca tgc cca gtc cac ctc gtg      3805
Ala Lys Gly Asp Gly Thr Pro Arg Cys Ser Cys Pro Val His Leu Val
1230                1235                1240                1245 ctc ctg cag aac ctg ctg acc tgt gga gag ccg ccc acc tgt tcc ccg      3853
Leu Leu Gln Asn Leu Leu Thr Cys Gly Glu Pro Pro Thr Cys Ser Pro
            1250                1255                1260 gac cag ttt gca tgt gcc aca ggg gag atc gac tgt atc ccc ggg gcc      3901
Asp Gln Phe Ala Cys Ala Thr Gly Glu Ile Asp Cys Ile Pro Gly Ala
            1265                1270                1275 tgg cgc tgt gac ggc ttt ccc gag tgc gat gac cag agc gac gag gag      3949
Trp Arg Cys Asp Gly Phe Pro Glu Cys Asp Asp Gln Ser Asp Glu Glu
            1280                1285                1290
```

-continued

| | |
|---|---|
| ggc tgc ccc gtg tgc tcc gcc gcc cag ttc ccc tgc gcg cgg ggt cag<br>Gly Cys Pro Val Cys Ser Ala Ala Gln Phe Pro Cys Ala Arg Gly Gln<br>1295                     1300                   1305 | 3997 |
| tgt gtg gac ctg cgc ctg cgc tgc gac ggc gag gca gac tgt cag gac<br>Cys Val Asp Leu Arg Leu Arg Cys Asp Gly Glu Ala Asp Cys Gln Asp<br>1310                  1315                 1320                 1325 | 4045 |
| cgc tca gac gag gtg gac tgt gac gcc atc tgc ctg ccc aac cag ttc<br>Arg Ser Asp Glu Val Asp Cys Asp Ala Ile Cys Leu Pro Asn Gln Phe<br>                  1330                 1335               1340 | 4093 |
| cgg tgt gcg agc ggc cag tgt gtc ctc atc aaa cag cag tgc gac tcc<br>Arg Cys Ala Ser Gly Gln Cys Val Leu Ile Lys Gln Gln Cys Asp Ser<br>1345                     1350                 1355 | 4141 |
| ttc ccc gac tgt atc gac ggc tcc gac gag ctc atg tgt gaa atc acc<br>Phe Pro Asp Cys Ile Asp Gly Ser Asp Glu Leu Met Cys Glu Ile Thr<br>1360                  1365                 1370 | 4189 |
| aag ccg ccc tca gac gac agc ccg gcc cac agc agt gcc atc ggg ccc<br>Lys Pro Pro Ser Asp Asp Ser Pro Ala His Ser Ser Ala Ile Gly Pro<br>1375                     1380                 1385 | 4237 |
| gtc att ggc atc atc ctc tct ctc ttc gtc atg ggt ggt gtc tat ttt<br>Val Ile Gly Ile Ile Leu Ser Leu Phe Val Met Gly Gly Val Tyr Phe<br>1390                  1395                 1400                 1405 | 4285 |
| gtg tgc cag cgc gtg gtg tgc cag cgc tat gcg ggg gcc aac ggg ccc<br>Val Cys Gln Arg Val Val Cys Gln Arg Tyr Ala Gly Ala Asn Gly Pro<br>                  1410                 1415               1420 | 4333 |
| ttc ccg cac gag tat gtc agc ggg acc ccg cac gtg ccc ctc aat ttc<br>Phe Pro His Glu Tyr Val Ser Gly Thr Pro His Val Pro Leu Asn Phe<br>1425                     1430                 1435 | 4381 |
| ata gcc ccg ggc ggt tcc cag cat ggc ccc ttc aca ggc atc gca tgc<br>Ile Ala Pro Gly Gly Ser Gln His Gly Pro Phe Thr Gly Ile Ala Cys<br>1440                  1445                 1450 | 4429 |
| gga aag tcc atg atg agc tcc gtg agc ctg atg ggg ggc cgg ggc ggg<br>Gly Lys Ser Met Met Ser Ser Val Ser Leu Met Gly Gly Arg Gly Gly<br>1455                     1460                 1465 | 4477 |
| gtg ccc ctc tac gac cgg aac cac gtc aca ggg gcc tcg tcc agc agc<br>Val Pro Leu Tyr Asp Arg Asn His Val Thr Gly Ala Ser Ser Ser Ser<br>1470                  1475                 1480                 1485 | 4525 |
| tcg tcc agc acg aag gcc acg ctg tac ccg ccg atc ctg aac ccg ccg<br>Ser Ser Ser Thr Lys Ala Thr Leu Tyr Pro Pro Ile Leu Asn Pro Pro<br>                  1490                 1495               1500 | 4573 |
| ccc tcc ccg gcc acg gac ccc tcc ctg tac aac atg gac atg ttc tac<br>Pro Ser Pro Ala Thr Asp Pro Ser Leu Tyr Asn Met Asp Met Phe Tyr<br>1505                     1510                 1515 | 4621 |
| tct tca aac att ccg gcc act gcg aga ccg tac agg ccc tac atc att<br>Ser Ser Asn Ile Pro Ala Thr Ala Arg Pro Tyr Arg Pro Tyr Ile Ile<br>1520                  1525                 1530 | 4669 |
| cga gga atg gcg ccc ccg acg acg ccc tgc agc acc gac gtg tgt gac<br>Arg Gly Met Ala Pro Pro Thr Thr Pro Cys Ser Thr Asp Val Cys Asp<br>1535                     1540                 1545 | 4717 |
| agc gac tac agc gcc agc cgc tgg aag gcc agc aag tac tac ctg gat<br>Ser Asp Tyr Ser Ala Ser Arg Trp Lys Ala Ser Lys Tyr Tyr Leu Asp<br>1550                     1555                 1560                 1565 | 4765 |
| ttg aac tcg gac tca gac ccc tat cca ccc cca ccc acg ccc cac agc<br>Leu Asn Ser Asp Ser Asp Pro Tyr Pro Pro Pro Pro Thr Pro His Ser<br>1570                  1575                 1580 | 4813 |
| cag tac ctg tcg gcg gag gac agc tgc ccg ccc tcg ccc gcc acc gag<br>Gln Tyr Leu Ser Ala Glu Asp Ser Cys Pro Pro Ser Pro Ala Thr Glu<br>1585                     1590                 1595 | 4861 |
| agg agc tac ttc cat ctc ttc ccg ccc cct ccg tcc ccc tgc acg gac<br>Arg Ser Tyr Phe His Leu Phe Pro Pro Pro Pro Ser Pro Cys Thr Asp | 4909 |

-continued

```
                   1600              1605                  1610
tca tcc tgacctcggc cgggccactc tggcttctct gtgcccctgt aaatagtttt    4965
Ser Ser
    1615 aaatatgaac aaagaaaaaa atatatttta tgatttaaaa ataaatata attgggattt    5025 taaaaacatg agaaatgtga actgtgatgg ggtgggcagg gctgggagaa ctttgtacag    5085 tggagaaata tttataaact taattttgta aaaca                              5120
```

<210> SEQ ID NO 3
<211> LENGTH: 1615
<212> TYPE: PRT
<213> ORGANISM: Homo sapiens

<400> SEQUENCE: 3

```
Met Glu Ala Ala Pro Gly Pro Pro Trp Pro Leu Leu Leu Leu
  1               5                  10                  15

Leu Leu Leu Leu Ala Leu Cys Gly Cys Pro Ala Pro Ala Ala Ala Ser
                 20                  25                  30

Pro Leu Leu Leu Phe Ala Asn Arg Arg Asp Val Arg Leu Val Asp Ala
                 35                  40                  45

Gly Gly Val Lys Leu Glu Ser Thr Ile Val Ser Gly Leu Glu Asp
 50                  55                  60

Ala Ala Ala Val Asp Phe Gln Phe Ser Lys Gly Ala Val Tyr Trp Thr
 65                  70                  75                  80

Asp Val Ser Glu Glu Ala Ile Lys Gln Thr Tyr Leu Asn Gln Thr Gly
                 85                  90                  95

Ala Ala Val Gln Asn Val Val Ile Ser Gly Leu Val Ser Pro Asp Gly
                100                 105                 110

Leu Ala Cys Asp Trp Val Gly Lys Lys Leu Tyr Trp Thr Asp Ser Glu
                115                 120                 125

Thr Asn Arg Ile Glu Val Ala Asn Leu Asn Gly Thr Ser Arg Lys Val
130                 135                 140

Leu Phe Trp Gln Asp Leu Asp Gln Pro Lys Ala Ile Ala Leu Asp Pro
145                 150                 155                 160

Ala His Gly Tyr Met Tyr Trp Thr Asp Trp Gly Glu Thr Pro Arg Ile
                165                 170                 175

Glu Arg Ala Gly Met Asp Gly Ser Thr Arg Lys Ile Ile Val Asp Ser
                180                 185                 190

Asp Ile Tyr Trp Pro Asn Gly Leu Thr Ile Asp Leu Glu Glu Gln Lys
                195                 200                 205

Leu Tyr Trp Ala Asp Ala Lys Leu Ser Phe Ile His Arg Ala Asn Leu
210                 215                 220

Asp Gly Ser Phe Arg Gln Lys Val Val Glu Gly Ser Leu Thr His Pro
225                 230                 235                 240

Phe Ala Leu Thr Leu Ser Gly Asp Thr Leu Tyr Trp Thr Asp Trp Gln
                245                 250                 255

Thr Arg Ser Ile His Ala Cys Asn Lys Arg Thr Gly Gly Lys Arg Lys
                260                 265                 270

Glu Ile Leu Ser Ala Leu Tyr Ser Pro Met Asp Ile Gln Val Leu Ser
                275                 280                 285

Gln Glu Arg Gln Pro Phe Phe His Thr Arg Cys Glu Glu Asp Asn Gly
                290                 295                 300

Gly Trp Ser His Leu Cys Leu Ser Pro Ser Glu Pro Phe Tyr Thr
305                 310                 315                 320
```

```
Cys Ala Cys Pro Thr Gly Val Gln Met Gln Asp Asn Gly Arg Thr Cys
            325                 330                 335

Lys Ala Gly Ala Glu Glu Val Leu Leu Leu Ala Arg Arg Thr Asp Leu
            340                 345                 350

Arg Arg Ile Ser Leu Asp Thr Pro Asp Phe Thr Asp Ile Val Leu Gln
            355                 360                 365

Val Asp Asp Ile Arg His Ala Ile Ala Ile Asp Tyr Asp Pro Leu Glu
    370                 375                 380

Gly Tyr Val Tyr Trp Thr Asp Asp Glu Val Arg Ala Ile Arg Arg Ala
385                 390                 395                 400

Tyr Leu Asp Gly Ser Gly Ala Gln Thr Leu Val Asn Thr Glu Ile Asn
                405                 410                 415

Asp Pro Asp Gly Ile Ala Val Asp Trp Val Ala Arg Asn Leu Tyr Trp
            420                 425                 430

Thr Asp Thr Gly Thr Asp Arg Ile Glu Val Thr Arg Leu Asn Gly Thr
            435                 440                 445

Ser Arg Lys Ile Leu Val Ser Glu Asp Leu Asp Glu Pro Arg Ala Ile
    450                 455                 460

Ala Leu His Pro Val Met Gly Leu Met Tyr Trp Thr Asp Trp Gly Glu
465                 470                 475                 480

Asn Pro Lys Ile Glu Cys Ala Asn Leu Asp Gly Gln Glu Arg Arg Val
                485                 490                 495

Leu Val Asn Ala Ser Leu Gly Trp Pro Asn Gly Leu Ala Leu Asp Leu
            500                 505                 510

Gln Glu Gly Lys Leu Tyr Trp Gly Asp Ala Lys Thr Asp Lys Ile Glu
            515                 520                 525

Val Ile Asn Val Asp Gly Thr Lys Arg Arg Thr Leu Leu Glu Asp Lys
    530                 535                 540

Leu Pro His Ile Phe Gly Phe Thr Leu Leu Gly Asp Phe Ile Tyr Trp
545                 550                 555                 560

Thr Asp Trp Gln Arg Arg Ser Ile Glu Arg Val His Lys Val Lys Ala
                565                 570                 575

Ser Arg Asp Val Ile Ile Asp Gln Leu Pro Asp Leu Met Gly Leu Lys
            580                 585                 590

Ala Val Asn Val Ala Lys Val Val Gly Thr Asn Pro Cys Ala Asp Arg
            595                 600                 605

Asn Gly Gly Cys Ser His Leu Cys Phe Phe Thr Pro His Ala Thr Arg
    610                 615                 620

Cys Gly Cys Pro Ile Gly Leu Glu Leu Leu Ser Asp Met Lys Thr Cys
625                 630                 635                 640

Ile Val Pro Glu Ala Phe Leu Val Phe Thr Ser Arg Ala Ala Ile His
                645                 650                 655

Arg Ile Ser Leu Glu Thr Asn Asn Asn Asp Val Ala Ile Pro Leu Thr
            660                 665                 670

Gly Val Lys Glu Ala Ser Ala Leu Asp Phe Asp Val Ser Asn Asn His
            675                 680                 685

Ile Tyr Trp Thr Asp Val Ser Leu Lys Asn Ile Ser Arg Ala Phe Met
    690                 695                 700

Asn Gly Ser Ser Val Glu His Val Val Glu Phe Gly Leu Asp Tyr Pro
705                 710                 715                 720

Glu Gly Met Ala Val Asp Trp Met Gly Lys Asn Leu Tyr Trp Ala Asp
                725                 730                 735
```

-continued

```
Thr Gly Thr Asn Arg Ile Glu Val Ala Arg Leu Asp Gly Gln Phe Arg
            740                 745                 750

Gln Val Leu Val Trp Arg Asp Leu Asp Asn Pro Arg Ser Leu Ala Leu
            755                 760                 765

Asp Pro Thr Lys Gly Tyr Ile Tyr Trp Thr Glu Trp Gly Gly Lys Pro
770                 775                 780

Arg Ile Val Arg Ala Phe Met Asp Gly Thr Asn Cys Met Thr Leu Val
785                 790                 795                 800

Asp Lys Val Gly Arg Ala Asn Asp Leu Thr Ile Asp Tyr Ala Asp Gln
            805                 810                 815

Arg Leu Tyr Trp Thr Asp Leu Asp Thr Asn Met Ile Glu Ser Ser Asn
            820                 825                 830

Met Leu Gly Gln Glu Arg Val Val Ile Ala Asp Asp Leu Pro His Pro
            835                 840                 845

Phe Gly Leu Thr Gln Tyr Ser Asp Tyr Ile Tyr Trp Thr Asp Trp Asn
850                 855                 860

Leu His Ser Ile Glu Arg Ala Asp Lys Thr Ser Gly Arg Asn Arg Thr
865                 870                 875                 880

Leu Ile Gln Gly His Leu Asp Phe Val Met Asp Ile Leu Val Phe His
            885                 890                 895

Ser Ser Arg Gln Asp Gly Leu Asn Asp Cys Met His Asn Asn Gly Gln
            900                 905                 910

Cys Gly Gln Leu Cys Leu Ala Ile Pro Gly Gly His Arg Cys Gly Cys
            915                 920                 925

Ala Ser His Tyr Thr Leu Asp Pro Ser Ser Arg Asn Cys Ser Pro Pro
            930                 935                 940

Thr Thr Phe Leu Leu Phe Ser Gln Lys Ser Ala Ile Ser Arg Met Ile
945                 950                 955                 960

Pro Asp Asp Gln His Ser Pro Asp Leu Ile Leu Pro Leu His Gly Leu
            965                 970                 975

Arg Asn Val Lys Ala Ile Asp Tyr Asp Pro Leu Asp Lys Phe Ile Tyr
            980                 985                 990

Trp Val Asp Gly Arg Gln Asn Ile Lys Arg Ala Lys Asp Asp Gly Thr
            995                 1000                1005

Gln Pro Phe Val Leu Thr Ser Leu Ser Gln Gly Gln Asn Pro Asp Arg
            1010                1015                1020

Gln Pro His Asp Leu Ser Ile Asp Ile Tyr Ser Arg Thr Leu Phe Trp
1025                1030                1035                1040

Thr Cys Glu Ala Thr Asn Thr Ile Asn Val His Arg Leu Ser Gly Glu
            1045                1050                1055

Ala Met Gly Val Val Leu Arg Gly Asp Arg Asp Lys Pro Arg Ala Ile
            1060                1065                1070

Val Val Asn Ala Glu Arg Gly Tyr Leu Tyr Phe Thr Asn Met Gln Asp
            1075                1080                1085

Arg Ala Ala Lys Ile Glu Arg Ala Ala Leu Asp Gly Thr Glu Arg Glu
            1090                1095                1100

Val Leu Phe Thr Thr Gly Leu Ile Arg Pro Val Ala Leu Val Val Asp
1105                1110                1115                1120

Asn Thr Leu Gly Lys Leu Phe Trp Val Asp Ala Asp Leu Lys Arg Ile
            1125                1130                1135

Glu Ser Cys Asp Leu Ser Gly Ala Asn Arg Leu Thr Leu Glu Asp Ala
            1140                1145                1150

Asn Ile Val Gln Pro Leu Gly Leu Thr Ile Leu Gly Lys His Leu Tyr
```

-continued

```
                1155                1160                1165
Trp Ile Asp Arg Gln Gln Gln Met Ile Glu Arg Val Glu Lys Thr Thr
    1170                1175                1180

Gly Asp Lys Arg Thr Arg Ile Gln Gly Arg Val Ala His Leu Thr Gly
1185                1190                1195                1200

Ile His Ala Val Glu Glu Val Ser Leu Glu Glu Phe Ser Ala His Pro
                1205                1210                1215

Cys Ala Arg Asp Asn Gly Gly Cys Ser His Ile Cys Ile Ala Lys Gly
                1220                1225                1230

Asp Gly Thr Pro Arg Cys Ser Cys Pro Val His Leu Val Leu Leu Gln
                1235                1240                1245

Asn Leu Leu Thr Cys Gly Glu Pro Pro Thr Cys Ser Pro Asp Gln Phe
                1250                1255                1260

Ala Cys Ala Thr Gly Glu Ile Asp Cys Ile Pro Gly Ala Trp Arg Cys
1265                1270                1275                1280

Asp Gly Phe Pro Glu Cys Asp Asp Gln Ser Asp Glu Glu Gly Cys Pro
                1285                1290                1295

Val Cys Ser Ala Ala Gln Phe Pro Cys Ala Arg Gly Gln Cys Val Asp
                1300                1305                1310

Leu Arg Leu Arg Cys Asp Gly Glu Ala Asp Cys Gln Asp Arg Ser Asp
                1315                1320                1325

Glu Val Asp Cys Asp Ala Ile Cys Leu Pro Asn Gln Phe Arg Cys Ala
                1330                1335                1340

Ser Gly Gln Cys Val Leu Ile Lys Gln Gln Cys Asp Ser Phe Pro Asp
1345                1350                1355                1360

Cys Ile Asp Gly Ser Asp Glu Leu Met Cys Glu Ile Thr Lys Pro Pro
                1365                1370                1375

Ser Asp Asp Ser Pro Ala His Ser Ser Ala Ile Gly Pro Val Ile Gly
                1380                1385                1390

Ile Ile Leu Ser Leu Phe Val Met Gly Gly Val Tyr Phe Val Cys Gln
                1395                1400                1405

Arg Val Val Cys Gln Arg Tyr Ala Gly Ala Asn Gly Pro Phe Pro His
                1410                1415                1420

Glu Tyr Val Ser Gly Thr Pro His Val Pro Leu Asn Phe Ile Ala Pro
1425                1430                1435                1440

Gly Gly Ser Gln His Gly Pro Phe Thr Gly Ile Ala Cys Gly Lys Ser
                1445                1450                1455

Met Met Ser Ser Val Ser Leu Met Gly Gly Arg Gly Gly Val Pro Leu
                1460                1465                1470

Tyr Asp Arg Asn His Val Thr Gly Ala Ser Ser Ser Ser Ser Ser Ser
                1475                1480                1485

Thr Lys Ala Thr Leu Tyr Pro Pro Ile Leu Asn Pro Pro Ser Pro
                1490                1495                1500

Ala Thr Asp Pro Ser Leu Tyr Asn Met Asp Met Phe Tyr Ser Ser Asn
1505                1510                1515                1520

Ile Pro Ala Thr Ala Arg Pro Tyr Arg Pro Tyr Ile Ile Arg Gly Met
                1525                1530                1535

Ala Pro Pro Thr Thr Pro Cys Ser Thr Asp Val Cys Asp Ser Asp Tyr
                1540                1545                1550

Ser Ala Ser Arg Trp Lys Ala Ser Lys Tyr Tyr Leu Asp Leu Asn Ser
                1555                1560                1565

Asp Ser Asp Pro Tyr Pro Pro Pro Thr Pro His Ser Gln Tyr Leu
                1570                1575                1580
```

-continued

```
Ser Ala Glu Asp Ser Cys Pro Pro Ser Pro Ala Thr Glu Arg Ser Tyr
1585                1590                1595                1600

Phe His Leu Phe Pro Pro Pro Ser Pro Cys Thr Asp Ser Ser
                1605                1610            1615

<210> SEQ ID NO 4
<211> LENGTH: 1615
<212> TYPE: PRT
<213> ORGANISM: Homo sapiens

<400> SEQUENCE: 4

Met Glu Ala Ala Pro Gly Pro Pro Trp Pro Leu Leu Leu Leu
1               5                   10                  15

Leu Leu Leu Leu Ala Leu Cys Gly Cys Pro Ala Pro Ala Ala Ser
            20                  25                  30

Pro Leu Leu Leu Phe Ala Asn Arg Arg Asp Val Arg Leu Val Asp Ala
            35                  40                  45

Gly Gly Val Lys Leu Glu Ser Thr Ile Val Val Ser Gly Leu Glu Asp
        50                  55                  60

Ala Ala Ala Val Asp Phe Gln Phe Ser Lys Gly Ala Val Tyr Trp Thr
65                  70                  75                  80

Asp Val Ser Glu Glu Ala Ile Lys Gln Thr Tyr Leu Asn Gln Thr Gly
                85                  90                  95

Ala Ala Val Gln Asn Val Val Ile Ser Gly Leu Val Ser Pro Asp Gly
            100                 105                 110

Leu Ala Cys Asp Trp Val Gly Lys Lys Leu Tyr Trp Thr Asp Ser Glu
        115                 120                 125

Thr Asn Arg Ile Glu Val Ala Asn Leu Asn Gly Thr Ser Arg Lys Val
    130                 135                 140

Leu Phe Trp Gln Asp Leu Asp Gln Pro Lys Ala Ile Ala Leu Asp Pro
145                 150                 155                 160

Ala His Gly Tyr Met Tyr Trp Thr Asp Trp Val Glu Thr Pro Arg Ile
                165                 170                 175

Glu Arg Ala Gly Met Asp Gly Ser Thr Arg Lys Ile Ile Val Asp Ser
            180                 185                 190

Asp Ile Tyr Trp Pro Asn Gly Leu Thr Ile Asp Leu Glu Glu Gln Lys
        195                 200                 205

Leu Tyr Trp Ala Asp Ala Lys Leu Ser Phe Ile His Arg Ala Asn Leu
    210                 215                 220

Asp Gly Ser Phe Arg Gln Lys Val Val Glu Gly Ser Leu Thr His Pro
225                 230                 235                 240

Phe Ala Leu Thr Leu Ser Gly Asp Thr Leu Tyr Trp Thr Asp Trp Gln
                245                 250                 255

Thr Arg Ser Ile His Ala Cys Asn Lys Arg Thr Gly Gly Lys Arg Lys
            260                 265                 270

Glu Ile Leu Ser Ala Leu Tyr Ser Pro Met Asp Ile Gln Val Leu Ser
        275                 280                 285

Gln Glu Arg Gln Pro Phe Phe His Thr Arg Cys Glu Glu Asp Asn Gly
    290                 295                 300

Gly Trp Ser His Leu Cys Leu Leu Ser Pro Ser Glu Pro Phe Tyr Thr
305                 310                 315                 320

Cys Ala Cys Pro Thr Gly Val Gln Met Gln Asp Asn Gly Arg Thr Cys
                325                 330                 335

Lys Ala Gly Ala Glu Glu Val Leu Leu Leu Ala Arg Arg Thr Asp Leu
```

-continued

```
               340                 345                 350
Arg Arg Ile Ser Leu Asp Thr Pro Asp Phe Thr Asp Ile Val Leu Gln
            355                 360                 365
Val Asp Asp Ile Arg His Ala Ile Ala Ile Asp Tyr Asp Pro Leu Glu
370                 375                 380
Gly Tyr Val Tyr Trp Thr Asp Glu Val Arg Ala Ile Arg Arg Ala
385                 390                 395                 400
Tyr Leu Asp Gly Ser Gly Ala Gln Thr Leu Val Asn Thr Glu Ile Asn
                405                 410                 415
Asp Pro Asp Gly Ile Ala Val Asp Trp Val Ala Arg Asn Leu Tyr Trp
            420                 425                 430
Thr Asp Thr Gly Thr Asp Arg Ile Glu Val Thr Arg Leu Asn Gly Thr
            435                 440                 445
Ser Arg Lys Ile Leu Val Ser Glu Asp Leu Asp Glu Pro Arg Ala Ile
    450                 455                 460
Ala Leu His Pro Val Met Gly Leu Met Tyr Trp Thr Asp Trp Gly Glu
465                 470                 475                 480
Asn Pro Lys Ile Glu Cys Ala Asn Leu Asp Gly Gln Glu Arg Arg Val
                485                 490                 495
Leu Val Asn Ala Ser Leu Gly Trp Pro Asn Gly Leu Ala Leu Asp Leu
            500                 505                 510
Gln Glu Gly Lys Leu Tyr Trp Gly Asp Ala Lys Thr Asp Lys Ile Glu
        515                 520                 525
Val Ile Asn Val Asp Gly Thr Lys Arg Arg Thr Leu Leu Glu Asp Lys
    530                 535                 540
Leu Pro His Ile Phe Gly Phe Thr Leu Leu Gly Asp Phe Ile Tyr Trp
545                 550                 555                 560
Thr Asp Trp Gln Arg Arg Ser Ile Glu Arg Val His Lys Val Lys Ala
                565                 570                 575
Ser Arg Asp Val Ile Ile Asp Gln Leu Pro Asp Leu Met Gly Leu Lys
            580                 585                 590
Ala Val Asn Val Ala Lys Val Val Gly Thr Asn Pro Cys Ala Asp Arg
        595                 600                 605
Asn Gly Gly Cys Ser His Leu Cys Phe Phe Thr Pro His Ala Thr Arg
    610                 615                 620
Cys Gly Cys Pro Ile Gly Leu Glu Leu Leu Ser Asp Met Lys Thr Cys
625                 630                 635                 640
Ile Val Pro Glu Ala Phe Leu Val Phe Thr Ser Arg Ala Ala Ile His
                645                 650                 655
Arg Ile Ser Leu Glu Thr Asn Asn Asp Val Ala Ile Pro Leu Thr
            660                 665                 670
Gly Val Lys Glu Ala Ser Ala Leu Asp Phe Asp Val Ser Asn Asn His
        675                 680                 685
Ile Tyr Trp Thr Asp Val Ser Leu Lys Asn Ile Ser Arg Ala Phe Met
    690                 695                 700
Asn Gly Ser Ser Val Glu His Val Val Glu Phe Gly Leu Asp Tyr Pro
705                 710                 715                 720
Glu Gly Met Ala Val Asp Trp Met Gly Lys Asn Leu Tyr Trp Ala Asp
                725                 730                 735
Thr Gly Thr Asn Arg Ile Glu Val Ala Arg Leu Asp Gly Gln Phe Arg
            740                 745                 750
Gln Val Leu Val Trp Arg Asp Leu Asp Asn Pro Arg Ser Leu Ala Leu
        755                 760                 765
```

```
Asp Pro Thr Lys Gly Tyr Ile Tyr Trp Thr Glu Trp Gly Lys Pro
    770             775             780

Arg Ile Val Arg Ala Phe Met Asp Gly Thr Asn Cys Met Thr Leu Val
785             790             795             800

Asp Lys Val Gly Arg Ala Asn Asp Leu Thr Ile Asp Tyr Ala Asp Gln
            805             810             815

Arg Leu Tyr Trp Thr Asp Leu Asp Thr Asn Met Ile Glu Ser Ser Asn
        820             825             830

Met Leu Gly Gln Glu Arg Val Val Ile Ala Asp Asp Leu Pro His Pro
        835             840             845

Phe Gly Leu Thr Gln Tyr Ser Asp Tyr Ile Tyr Trp Thr Asp Trp Asn
850             855             860

Leu His Ser Ile Glu Arg Ala Asp Lys Thr Ser Gly Arg Asn Arg Thr
865             870             875             880

Leu Ile Gln Gly His Leu Asp Phe Val Met Asp Ile Leu Val Phe His
            885             890             895

Ser Ser Arg Gln Asp Gly Leu Asn Asp Cys Met His Asn Asn Gly Gln
        900             905             910

Cys Gly Gln Leu Cys Leu Ala Ile Pro Gly Gly His Arg Cys Gly Cys
        915             920             925

Ala Ser His Tyr Thr Leu Asp Pro Ser Ser Arg Asn Cys Ser Pro Pro
    930             935             940

Thr Thr Phe Leu Leu Phe Ser Gln Lys Ser Ala Ile Ser Arg Met Ile
945             950             955             960

Pro Asp Asp Gln His Ser Pro Asp Leu Ile Leu Pro Leu His Gly Leu
            965             970             975

Arg Asn Val Lys Ala Ile Asp Tyr Asp Pro Leu Asp Lys Phe Ile Tyr
            980             985             990

Trp Val Asp Gly Arg Gln Asn Ile Lys Arg Ala Lys Asp Asp Gly Thr
        995             1000            1005

Gln Pro Phe Val Leu Thr Ser Leu Ser Gln Gly Gln Asn Pro Asp Arg
    1010            1015            1020

Gln Pro His Asp Leu Ser Ile Asp Ile Tyr Ser Arg Thr Leu Phe Trp
1025            1030            1035            1040

Thr Cys Glu Ala Thr Asn Thr Ile Asn Val His Arg Leu Ser Gly Glu
            1045            1050            1055

Ala Met Gly Val Val Leu Arg Gly Asp Arg Asp Lys Pro Arg Ala Ile
            1060            1065            1070

Val Val Asn Ala Glu Arg Gly Tyr Leu Tyr Phe Thr Asn Met Gln Asp
    1075            1080            1085

Arg Ala Ala Lys Ile Glu Arg Ala Ala Leu Asp Gly Thr Glu Arg Glu
    1090            1095            1100

Val Leu Phe Thr Thr Gly Leu Ile Arg Pro Val Ala Leu Val Val Asp
1105            1110            1115            1120

Asn Thr Leu Gly Lys Leu Phe Trp Val Asp Ala Asp Leu Lys Arg Ile
            1125            1130            1135

Glu Ser Cys Asp Leu Ser Gly Ala Asn Arg Leu Thr Leu Glu Asp Ala
            1140            1145            1150

Asn Ile Val Gln Pro Leu Gly Leu Thr Ile Leu Gly Lys His Leu Tyr
    1155            1160            1165

Trp Ile Asp Arg Gln Gln Gln Met Ile Glu Arg Val Glu Lys Thr Thr
    1170            1175            1180
```

-continued

Gly Asp Lys Arg Thr Arg Ile Gln Gly Arg Val Ala His Leu Thr Gly
1185                1190                1195                1200

Ile His Ala Val Glu Glu Val Ser Leu Glu Glu Phe Ser Ala His Pro
            1205                1210                1215

Cys Ala Arg Asp Asn Gly Gly Cys Ser His Ile Cys Ile Ala Lys Gly
        1220                1225                1230

Asp Gly Thr Pro Arg Cys Ser Cys Pro Val His Leu Val Leu Leu Gln
    1235                1240                1245

Asn Leu Leu Thr Cys Gly Glu Pro Pro Thr Cys Ser Pro Asp Gln Phe
1250                1255                1260

Ala Cys Ala Thr Gly Glu Ile Asp Cys Ile Pro Gly Ala Trp Arg Cys
1265                1270                1275                1280

Asp Gly Phe Pro Glu Cys Asp Asp Gln Ser Asp Glu Glu Gly Cys Pro
            1285                1290                1295

Val Cys Ser Ala Ala Gln Phe Pro Cys Ala Arg Gly Gln Cys Val Asp
        1300                1305                1310

Leu Arg Leu Arg Cys Asp Gly Glu Ala Asp Cys Gln Asp Arg Ser Asp
    1315                1320                1325

Glu Val Asp Cys Asp Ala Ile Cys Leu Pro Asn Gln Phe Arg Cys Ala
1330                1335                1340

Ser Gly Gln Cys Val Leu Ile Lys Gln Gln Cys Asp Ser Phe Pro Asp
1345                1350                1355                1360

Cys Ile Asp Gly Ser Asp Glu Leu Met Cys Glu Ile Thr Lys Pro Pro
            1365                1370                1375

Ser Asp Asp Ser Pro Ala His Ser Ser Ala Ile Gly Pro Val Ile Gly
        1380                1385                1390

Ile Ile Leu Ser Leu Phe Val Met Gly Gly Val Tyr Phe Val Cys Gln
    1395                1400                1405

Arg Val Val Cys Gln Arg Tyr Ala Gly Ala Asn Gly Pro Phe Pro His
    1410                1415                1420

Glu Tyr Val Ser Gly Thr Pro His Val Pro Leu Asn Phe Ile Ala Pro
1425                1430                1435                1440

Gly Gly Ser Gln His Gly Pro Phe Thr Gly Ile Ala Cys Gly Lys Ser
            1445                1450                1455

Met Met Ser Ser Val Ser Leu Met Gly Gly Arg Gly Gly Val Pro Leu
        1460                1465                1470

Tyr Asp Arg Asn His Val Thr Gly Ala Ser Ser Ser Ser Ser Ser Ser
    1475                1480                1485

Thr Lys Ala Thr Leu Tyr Pro Pro Ile Leu Asn Pro Pro Pro Ser Pro
1490                1495                1500

Ala Thr Asp Pro Ser Leu Tyr Asn Met Asp Met Phe Tyr Ser Ser Asn
1505                1510                1515                1520

Ile Pro Ala Thr Ala Arg Pro Tyr Arg Pro Tyr Ile Ile Arg Gly Met
            1525                1530                1535

Ala Pro Pro Thr Thr Pro Cys Ser Thr Asp Val Cys Asp Ser Asp Tyr
        1540                1545                1550

Ser Ala Ser Arg Trp Lys Ala Ser Lys Tyr Tyr Leu Asp Leu Asn Ser
    1555                1560                1565

Asp Ser Asp Pro Tyr Pro Pro Pro Thr Pro His Ser Gln Tyr Leu
    1570                1575                1580

Ser Ala Glu Asp Ser Cys Pro Pro Ser Pro Ala Thr Glu Arg Ser Tyr
1585                1590                1595                1600

Phe His Leu Phe Pro Pro Pro Pro Ser Pro Cys Thr Asp Ser Ser

<210> SEQ ID NO 5
<211> LENGTH: 3096
<212> TYPE: DNA
<213> ORGANISM: Homo sapiens

<400> SEQUENCE: 5

| | | | | | | |
|---|---|---|---|---|---|---|
| catcttctca | cacgatctct | cgcttcgcac | tccttccttt | gattggtttt | caccatttac | 60 |
| tcagacgacg | gtccttcttc | gatctttgca | cattcttcta | tcatctacta | ccttcatacc | 120 |
| cagctccgtc | ccctaatatt | catgcgcgga | tgggcccatc | cgtggtgaaa | attcccttct | 180 |
| actctgctaa | tctgctgttc | tctctcccctc | ccgtcgggtt | ctgctcctgc | cacgttctcc | 240 |
| cctctcccca | ccaaaggctg | gttttctttt | gtcaggagctc | cttttcccctt | tggaagaagg | 300 |
| gggggctgtat | ggccttggtg | cgaggccctc | cagtgacagg | atccccccatc | acccagagtt | 360 |
| ccacaggccc | tggtagggag | gagggggagc | agaagaggag | gtgccatctt | tgcctgctgg | 420 |
| ggaagggcag | gggccaccca | cacagagctc | tcccatttgc | tgtggaccct | ggggccactg | 480 |
| cccagttcct | tccaaaggaa | agccagctcc | caggtggtg | ggagagtgat | atggcttcct | 540 |
| cttaaactta | gggaattgag | tgtgtggttg | cttctaagtg | ccttagaagc | cgggagcggc | 600 |
| tcctggaaag | agcctgcctg | ccacagcggg | ccttaccctg | gctgtgccca | cagatgtccc | 660 |
| tggggcctgc | cgctcctgcc | cggctctcct | ggcctccccc | ggtgtgggtt | gggaaaagca | 720 |
| cagcaaatta | aaaacacct | ccatctctgg | cctttgaaga | atgcatctga | acagccgaga | 780 |
| gtgtaaaccg | tggtgaaatg | tggtcttttcc | agtttgggga | gaagcagggc | agagctgggg | 840 |
| cttttgtacc | cagggtttcc | aagagctcct | gcctccctcg | gctgggctgg | ccagggcccc | 900 |
| ccgctgggac | ctccagctgt | aatagggaag | gttttactgg | gttgctggcc | actgtggact | 960 |
| gcccctaagg | gcaggtatgc | ctgccttttac | ccgggttccc | ctcctgcctg | gaagatacag | 1020 |
| cccatgggag | gcctgttgtc | tgtgggatcc | tccagcatca | gagacactgg | ggccagcgtc | 1080 |
| tgcctggtga | ggtgcaggcc | tggcaggcc | ggtcccccac | ctgcttgagc | acccacggtg | 1140 |
| gtgggggctc | gctgcctccc | gagacaatct | atgtcattgt | tgtccaagga | agctaattta | 1200 |
| gagtagaaag | ttccgtgtcc | agtcccactc | tgtgcgtgtg | ttagcagggg | actctcgggc | 1260 |
| cggagctggg | tccaccctgg | tagggggact | tcatggggcc | tgggcgacag | cactgtgtat | 1320 |
| ttgtgtgtgt | gtgtgtttgt | gtgtgtgtgt | gtctgaggag | gtggaccagt | ttctcaaaag | 1380 |
| gcctgtgacc | ccaagaacca | aggaatttca | gcctgggtgg | atcacacctt | cactggtgag | 1440 |
| tgggacaagc | tgggggccct | cgccacagga | gcagccaggg | catgggcac | agttggcctc | 1500 |
| attcacaaaa | tgggagtata | agtgatccct | gctctggcgg | ccaggacgat | gagtgggaac | 1560 |
| acaccgtgtg | ggggctgcct | ggcctgggtg | tgccgcgggt | gtccttgttg | gtgatggttc | 1620 |
| cacctgcttg | tgccaccagt | gccctctggg | tctcacacac | aactctcttc | ccagcgaagg | 1680 |
| cccctcctgc | cctcaggcct | cagtgctgct | tccgtctcgg | aaggccccag | gagctcctgc | 1740 |
| atcctgggcg | tgattcctgt | gtgcctgcag | acccccctcgc | ggctgccatc | tcatcctttg | 1800 |
| gtgcacctgt | tggccagacc | tcctggtagc | gggtgctgca | ctcccctgaa | tgtgccgggg | 1860 |
| cctgggggca | gggacctggg | ctcctccctc | actgagtgga | gggaactcag | tgtcttggag | 1920 |
| ttggggtgcc | tgcaggctgg | gtggtgcagg | tgaaatgcag | acctctcagc | tggtgttcca | 1980 |
| gagcagctgc | cttccccccgc | ccgagggact | tcacccgcag | cccagtcagg | ggtggcgcct | 2040 |
| gggtgcatcg | cccgcaggct | gggtaggggt | ggagcctggg | tggccctgcc | tgtgagctgc | 2100 |

```
atagttgtcg cctttgaccc tgagttttct tcgttatctg tttggacctg tttggggcag    2160 gcagggatg agatctgaag ataaatgcct tagctgtgac catctccttt tgtgagaggt     2220
caatgtccag ttccgctgca gttataacat cccatttttt gatttctttt tattttttcc    2280
tttttctttt tgagatggag tctcgctctg tcacccaggc tggagtgcaa tggggtgacc    2340
tcagctcact gcaacctcca cttctcgggt tcaagtgatt ctcctgcctc agcctcctga    2400
ctagcagggg ttacaggcgt gagccaccac gcccagctaa ttttgtatt tttagtagag     2460 gcaaggtttc gtcatgttgg ccaggctggt ctcaaactcc tggccttaag tgatctgccc    2520
gcctcggcct cccaaagtgc tgagatgaca ggtgtgagcc accgtgcccg gcccagaact    2580
ctttaattcc cacctgaaac ttgccgcctt aagcaggtcc ccagtctccc tcccctagtc    2640
cctggtccca ccattctgct ttctgtctca atgaatttgc ctaccgtaag tacctcatat    2700
aaattgaatc ataagtatt tgtcttttta tatctggctt atttcactta gcataacatt     2760
cttaagtttc atccatgttg tagcatgtgt cagaatctct ctcttttttt tttttttttt    2820
tttttttttt ttttgcagac agagtctcgc tctgtcatct agactggagt tcagtggcac    2880
gatctcggtt cactgcaaca tctgcctcct gggtccaagc aattctcctg cctcagcctc    2940
cttagcagct ggaactacag gcgcgtgcca ccatgccttg ctaattttg tatttttatg     3000 tggaggcagg gtttcaccat cttggccagg ctggtctcga attcctggtc ttcaccacgg    3060
gggcccgaag gacccgggca aagcgtggag gggagg                              3096
```

<210> SEQ ID NO 6
<211> LENGTH: 26928
<212> TYPE: DNA
<213> ORGANISM: Homo sapiens
<220> FEATURE:
<221> NAME/KEY: unsure
<222> LOCATION: (12044),(12489),(26433),(26434),(26435),(26436),(26439),
      (26441)
<223> OTHER INFORMATION: Identity of nucleotide sequences at the above
      locations are unknown.

<400> SEQUENCE: 6

```
gaagaccaag ggcacacagc gaggcagttt cagggcgggc agcctggggc cccacggggc    60
ggccccggac acttgttctc acctgtggag ggcagagaag ggaacaggga gagaagtggc    120
cggctgggag tggaggtggg tttgaggttt tactgtaaac taaatgtgta ccctctacct    180
tagttatgaa ttatgagaca cgaagactgc gaaacagaca cactcctcta aaagtgcctc    240
taggctgaca gggagaaagt cccgccaggc tcccagacgc cacctttgag tccttcaaca    300
agcccgccag ggcctcttgc ccaccggtgt cagctcagcc actgaaccct ccaggaagaa    360
gacgtgctgg taggagaaga atctcaccca ggcacagcct ggaaggggca cagaagggc     420 tccggaacca gcaagcccaa gttggaactc ccagtctgct actttctaga acgactgtgc    480
ccttggcggg tctaagtaga acctctccgc gcactctttc ctcctttgta aagtggggac    540
agcaatggcc accttgcagg ttcagagagg gcttgcagta cctcacagaa ctgagtgccc    600
gtgaacgtgt gtgttcctcc agatttgtga cagctttgcc aggctggagt caggctgaac    660
gcctctgccc tcatggggtt tatattctag gaagaccaac aaaaacaaga agacggaaaa    720
ttaaaacaac aaaagcccca ttgacaggcc gtgaagaatg ccatgaaaaa tgaatggcgt    780
tgtgctgcag tctttgggga aacgggctta cggaaagaag gacacttgag ctgctaccaa    840
tgagcagccg tccggtggga gggcagttca ggaagagcag acatccactg aggaggcgct    900
```

-continued

```
ggggcagagg gcagcctggt cgctggattc gggggaggaa ccacatcagg ccatgagctg      960
gagctggtgg tagaatgtac aggagaggcc agccagggcc agctcatgtc agacctcaag     1020
cggggaagat gaatcgagaa tgcacnccac gagcaatggg aagccagtct acgatttaag     1080
cagcaaaaat attttcccTt cttccaccct gcatccagct ctaccagcac agcctggggt     1140
tctattttca agatagaata gacccagact cccagctctt cttacacttc tactactgcc     1200
acctgtcacc cactcatgcg tccccacttg cagcctcgac cccctTccac ctgatctcat     1260
ggcagccagg gaagctccag ggctcgtgag ggctgccatc tcaggaaaga agcaaaagcc     1320
ttcggcacct gcagggcctg ctccaaccac acttcttcct tgacctctca gcttccttag     1380
ccactccctt cccacatctc accctgctcc agccacagtg gtgtctctgt gggttctcaa     1440
acacaccagg tgcactcctg cctcaggggcc tttgtgcttg ctgttctctg ctgggactct     1500
ttttttTtTt tttTtTtttg agacagggTc tcactctgtg gcccaggctg gagtgtagtg     1560
gTgtgatcgt agctcattgc aacctcaaac tcctgggctc aagcaatcct cccacctcag     1620
cctctcaagt agttagcttt tgttgttttg ttTtgagatg ggatctcact ctgttgccca     1680
ggctggagtg cagtggggca atcttggctc accacaacct ctgcctccca ggctcaagca     1740
attctcctgc ctcagcctcc caagtagctg ggattacagg catgtgccac cacgcccagc     1800
ttatttttgt attttagta gagacagggt ttcaccatgt tggtctggct ggtcttgaac     1860
tcctggcctc agatgatcca cctgcctcgg cctcccaaag tgctgggatg acaggcatga     1920
gcctgtctct agtagTtagg actacagaga ggggccatca tgcctggtga tcctcccacc     1980
ttttctgctc caactctttc accccactta gcctcgtggc tcactctctt acctcttcag     2040
ctcctcagtc aggcctgagg acccctgTtg aaaattgcaa accacacccc ccaccaccac     2100
cacccactat tgccagcact ttctactcca tttctctgct ttacttttct cctttgtact     2160
catcaccacc tgactcatta catgtttacg tatctttctt ctctccacta gcatggaagc     2220
tccaggagag cagagagtgt agtttTtattc cctgatgtgt ttcctgtgcc cgtaccaggg     2280
cctagcacac agtaggtgct cagtaaatgt gtgttggatg aacaaataca gtgaaaggat     2340
ctgatctaca tttataaaga aggcactctg gctgctgagt ggggatgaga ctgtcaggag     2400
gaaagaggcc cctgtggggg cctggccagc agtgggtac aatggtagca gccaggagag     2460
agggcctctt ggactcaagt ggatggggcc tgctcagggc tccggccaca ggaacaaagg     2520
gaaggggggcc caggatggcc tgtcatagag gacacattac aactggccca agttcaagt     2580
caggTtTcta aatttgggaa gggatacaga aaaactaaag actctactgg acagtcagtt     2640
attgaaatga ttacatagaa aatgtaccaa gaattaaaaa aaaaaaaaa aagcattatg     2700
aaggggccac cagagactcc cagagaggaa agggactatg ggctggatgc ggtgactcac     2760
acctataatc ccagcacttt gggaggccga ggagggtgga tcacgaggTc aggagttcaa     2820
aaccagccta ggcaacatgg taaaaccccc gtttctacta aaaatacaaa aattagctg      2880
ggcatggcag catgtgcctg taatcccagc tactcgggag gctgaggcag gagagTtgct     2940
agaacccagg aggcagaggt tgcagtgagc cgagattgag ccactatgct ccagcttggg     3000
cgacagagca agactccgtc tctaaaaaaa agaaaaaaaa ggccagatga ggtggctcat     3060
gcctgtaatc ccagcacttt gggaggccga ggtgggtgga tcacgaggTc aggagatcga     3120
gaccatcctg gctaacatgg tgaaactcca tctctactta aaatacaaaa aattagccgg     3180
gcgtggtggc gggcacctgt agtcccagct acttgggagg ctgaggcagg agaatggcgt     3240
gaacctggga ggcggagctt gcagtgagcc gagattgcgc cactgcactc catccagcct     3300
```

-continued

```
gggcgacaga gttagactcc gtctcaaaaa aaaaaaaaaa aaaaaaatta gctgattagt    3360
tgggcttggt ggcgggcgcc tgtaatccca actactcggg aggctgaggc gggagaatca    3420
cttgaacccg ggaggcagag gttgcaatga gccgatatca cgccactaca ctccagcctg    3480
ggcgacagag caagactcca tctcaaaaaa gaaaaaaaaa aagaaagggg ctgtgctgtg    3540
gcctgggacc caaagcacac tactgcaagg tcccaggtg cctgactcca accggagcct    3600
tgagaacatt catttgcaaa gaatgaatta aaattcagca ctattttatt ctgcaggatt    3660
ccagcacccc aaggacagtc attttagac ccttcagtaa cgtaataagt aaccggagga    3720
tgtgctgagc ttccacttcc ccagacggtt gcctgtcaca gctcatcagg ccaacaaact    3780
tttcttaggc ctcaaatttg gaaatgttca ctctcagttc gttccttaga tgcaagtcca    3840
tcccaatgaa gtaacagggg ctcagcacct gtccaatctc attgcttccg gggacagggg    3900
cccatgagga tgtcgtttca gcccggtgac acttgggcaa agtgccttt ggtttccctc      3960 ccaggctgga acgtgctggc tctgtgaagt tacgctgggc acaagagccc cccccaaccc    4020
ggcaggactg actgctgtgg tcagaggcgc ccctggggct ttgggagcca cagaatcttc    4080
ctgagggcag cgccggagga ggccccagtg agagtgccca ctgccaggct cattcctcag    4140
gctgccgcag gcctctcccc aaaacaggca atgcttctca gcaacctgcc ccaggagcag    4200
gccagggaag gccgccatcg gcctacagtg ctgggctctg gagggcttgg ttggtaacag    4260
gccatggttt ctatgagcca gctgggggtgt gaaggacaca ggctggattc acctctctgg    4320
gcctcagttt ctgcattcaa aaagtgggaa tcatgatatc tgctctattt cttatctctc    4380
agtgctgatg tgaacctcca ataagacttt taaaaatact cttctacct tactttatt      4440 tttcattat ttaagataa tgtctagctg tctcacccag gctggagtgc agtggtgtga      4500
ttacggctca ctacagcctt aacctcccag gctcaagtga tcctcctacc acagcctccc    4560
aagtagctgg aactacaggc atgcaccacc gcacctggat aatttttct tttgagacaa     4620 ggtttcactc tgttgcccag gctggagtgc agtggtgcac tcttggctca ctgcagcctc    4680
aacctccctg gcttaggtg atcctcacac ttcagtctcc caagtagctg ggactacagg     4740
tatgtgccag tacacccagc taatattttt gaaggatggg gtttcactat attgcccagg    4800
ctggtcttga actccaggt ttaagcaatc taccttcctc agcctgccaa agtgctagga     4860
ttataggtat gagccacccc ccggcctata atcctaccac tttaaaaag cctgtaattt     4920 tagcactta aaaatttt ctaaatttt tatagagatg ggggacagct gtggtctcac        4980
tgtgttgccc aggctggtct tgaactccta ggatcaagcc atcctcctgg cctggcctcc    5040
caaagtgttg ggattataag cataagcctt accttacctt tttttttga gttgcagttt     5100 tgttcttgtt gctcaggctg gagtgcaatg gcaagatctt ggctcactgc aacctccacc    5160
tcccgggttc aagcaattct cctgcctcag cctcccgagt agctgggatt acaggcatgc    5220
gccaccacac ccagctaatt ttgtattttt agtagagatg gggttctct atatacctta     5280 attttaaagc actgcattca tgtaaattgt gattaacatg gattcaagag agggagtgag    5340
gatgaatgag ccaggcagtc acctcggctg tcaccctcca cttctctcct ccttctgaca    5400
gtcatcgtcc atccgtttct gcagctgttt gtttgactct cctgatcatt ttgcttgcca    5460
cataacttgc ctcctgggaa agaatgccct gggcaggccc acatgagtag tgaaaaataa    5520
tctgcagtga aaaataaaac taagtagtct ggtccacaga gcagtcttat ttttcactg     5580 cagatgaagg agttgacatt caggcttcat tctcatttat aagtgtttta aagacacata    5640
```

```
cagtggattg aacagtggcc ttcaaaaaga tgtatctaca tcctaatccc tgggacctgt   5700
gaatgttaac caagttagga aaagggtctt cccgggtgtc attaagttag agatcttgag   5760
atgaggagct catcgtggat tatccaggtg gaccctgcat ccaaggacaa atggtcctta   5820
gaaaagaaaa gcagaggctg gcacagtggc tcaagcctg taatcccagc actttgagag   5880
gccgaggtgg gtggatcacc taaggtcatg agttcgagag cagcctggcc aacatgatga   5940
aatcccatct ctactaaaaa tacaaaaatt agcaaggcat ggtggcgggt gcctataatc   6000
ccagctactc aggaagctga ggcaggagaa tggcttgcac ctgggaggcg gaggttgcag   6060
tgagccaaga tcgcgccact gcactccagc ctgagggaga aaagtgaaac tctgtctcat   6120
aaaagaaaag aaaagcagac agagatctga gacagaagag gagagtgaag gaaaaaaggc   6180
catgtgaaga tgaggcagag gttggagcca tgcagccaca agccaaggaa tacctggagc   6240
cccagaagtt gcaagaggta ggaagaagcc tccctagag cctccagacg gagcacagcc   6300
ctgccaacac ctccacctca gacttctggc ctccagcact gtgagataat caactgctgt   6360
tgttttaagc caccagattt gtggtaattt gttatggcag ccacaggaaa ctaatacagt   6420
acctaatctt cacaaaccca tcttacagaa aaggaaactg aagtcagaga ggtagtggct   6480
tgtgcagtgt gttaggccat tcttgtatta ctataaagaa ataacctgagg ccgggcatgg   6540 tggctcacgc ctgtaatccc agcactttgg gaggccaagg tgagtggatc acttgaggtc   6600
aggagttcaa gaccagcctg gacaacatgg tgaaacccca tttctactga aaatatgaaa   6660
attagccagg catggtggcg tgcatctgta gtcccagcta ctcaggaggc tgaggcagga   6720
gaatcacttg cgcccgggag gaggaggttg tagtgagcca agattgtgcc actgcactcc   6780
agcctgggag acaagagaga aaccctgtct caaaataaat aaaaaacaaa taaacacctg   6840
agactgggta gtttataaag aaaggggtta actggctccc ggttctgcag gctgtacaag   6900
catggtgccg gcatctgctt ggttgctggg aaggcttcag ggagttttac tcatcgtgga   6960
aggcagagcc agagcaggtg catcacacag caaaagcagg agcgagagag agagagagca   7020
gggaggtgtg cacacttttta aatgagcaga tctcacgaga actcaccatt gcaaggacag   7080
caccaagcca cgagggggtct gcccccatga cccaaacctc ccactaggcc ccaccccaa   7140 cattgggaat tacagttcaa catgaggttt gggggggacaa atatccaaac tatatcattc   7200 caccccctggc ccccagatc tcatgttctt ctcacattgc aaaatatagt catgccttcc   7260
cagtagcccc ccaaagtctt aactcatccc agcattaact caaaaatccc attcccaagt   7320
ccaacgtctc atctgaagat gagttccttt cacctacaag actgtaaaaa tgaaaacagt   7380
tatttactgc tgagatacaa tgggggcata ggcattaggt aaacattcct gttccaaaag   7440
ggagaaatcg gtcaaaagaa aggggctata ggccccaagc aagtccaaaa cccagcagag   7500
caatcattca atcttaaagc tccaaaataa cctccttaaa ctccatgtcc catagccagg   7560
gcacactggt gcaaggggca ggctcccaag gccttgggca gctctattcc tgcggctttg   7620
cagaattcag tccccatggc tgctcttaca gattggagat gagggcctgc ggcttttcca   7680
ggtgcagggt gcaagctgct ggtgatctac cattctgggg tgtggatggt ggcggccccg   7740
tcccgcagct ccactaggca ttgtcccagt ggggactcta tgtggggcct ccaaccccac   7800
atttcccctc caatgggaag ctctgccccc tgcagcagcc ttcttcctgg ctcccaggc   7860 tttctcatac atcctctgac atctaggtgg atggtgtcaa gcttccttca ctcttgcact   7920
ctgcacacct acaggcttaa caccacatgg aagctgccaa ggtgtatggc tggaaccctc   7980
tgaagcagca gcctgagctg tgactatggc cctttgagcc aaggctggag ctggaacagt   8040
```

-continued

```
ctagatgcag gcagggagca gtgtcctgag gctgtgcaga gcagcagggc cctgtgcctg    8100
gacaatgaaa ccattctttc ctcctcatcc tctgggcctg tgatgggagg gttgtggaag    8160
atctctgaaa tgcctttgag gccttttgc ctctgaggcc tatttcctat tgtctcagtt     8220
attggcagtc ggctcctttt tagttatgca aatcctctag caagaggtta ctccactgcc    8280
ggcttgaact cctctcctga aaaagctttt tctttctttg tcacatggcc aggctgcaaa    8340
ttttccaaac ttttatgctc tgttttacct ttaaatataa cttctaactt taattcattt    8400
atttgctcct gcatttgagc atagggaatt caaagaagct gggccacatc ttgaatgctt    8460
tgctgcttca aaatttatgg ccacgcttgg tggctcacac ctgtaatccc agcactttgg    8520
gaggcctagg tgggcagatc acgagatcag gagatcgaga ccatcctggt caacatggtg    8580
aaacccatct ctactaaaaa tacaaaaaaa ttagcttggt gtggtggcgc agacctgtag    8640
tcccagctac tggagaggct gaggcaggag aattacttga acctgggagg cagaggttgc    8700
agtgagccca gatcatgcca ctgcactcca gcctggtgac agaataagat tgatctcga    8760
aaggaaggaa ggaaggagga agggaagaaa tgtcttcccc ccagatgtcc tgggtcatcc    8820
ctcttatgtt caaacttcaa cagatcccta gggcatgaaa ataatacagc caaattattt    8880
gctaaggcat aacgaaagtg acctttgctc cagttcccaa taagttcctc atttccatct    8940
gagactcatc accctggcct tggcttgtcc atatcactgt cagcattttg gtcacaatca    9000
tttaaccagc taatcgggag gctgaggcaa gaggatcact tgaacccagg aggttgaggc    9060
tgcagtgagc tgtgatcaca tcactgcagt ccagcttggg caacagagca agatcctgtc    9120
tcaataaata aataaataaa tacataaata acttaagttt atttaaagct gcatctttgc    9180
caccatggag aaaggccagg ccagctcctt ctctctttct gcacgtgttc ctcccacctc    9240
agctgcctct gctcctcaag gaggaacaga gggagtagga aaggccatcc caggaggccc    9300
agcaccccat gacctggctc tggggccttg tgggtttatg gattcccagt gctgagtcat    9360
ccctcacagg ctcttgtggg caccttggac attggtcaga agcatgtggt ccccgggaac    9420
acaccttttc ctgatcatct gggaagggca gcttgtgcca gcgaggccac ctgttcagcg    9480
ccacggcccg ccagacagct gcagccacag ccttgccttt gatcagagca aacaccagac    9540
atgtgtgtca tgcccccaac ccatctccag gggacacatg tcctttcttg ccaggcctga    9600
gatgaacaag agagggacaa gtccccaagc ctctctctcc ttcctgcctc acccactccg    9660
ctgttagatt ctcaaggtgg atggtgggct aactagggca accgaccatc ctggtttacc    9720
tagaactgag ggggcatttt caggaataaa actgcaaaag tctggagcaa acaggagcaa    9780
gttggtcact ctggggctgg tggagtcagg tttccttctg caggcccct ccccgcaagc     9840
atgggtggaa cccaggacag gaacacagag caggccccag gaccgggctt gtcacttaca    9900
agtcttttttt tttttttttt ttttgagatg gagtcttgct ctgtcatcag gctggagtca    9960
cagtggtgcc atcttagctc actgcaacct ctgccttctg ggttcaagtg atcccctgc    10020
ctcagcctcc tgagtagctg ggactacagg tggcaccacc acgccagct aatttttttgt    10080
atttctagta gagatgagat ggccaggctg gtcttgaact cctgacctca gtgatctgc    10140
ccgccttggc ctcccaaagt gctgggatta caggtgtgag ccactgtgcc tggccccact    10200
cacaagtctt aaaccatgcc tcagcacatc aatgccattt acaaaaggt agagggattt     10260
tccaggcaaa aatagatgaa agacatagga tgattgatca tgtcctgctt aaacataggt    10320
ctgatgctat taagaattga gggctgggag cggtggctca cgcctgtaat cccagcactt    10380
```

```
tgggaggccg aggcgggcgg atcacgaggt caggagatcg agaccatcct ggctaacacg    10440
gtgaaacccc atctctacta aaaatacaaa aaatggccgc gcgcggtgac tcacgcctgt    10500
aatcccagca ctttgggagg ccaaggcggg cggatcacga ggtcaggaga tcgagaccat    10560
cctggctaac acagtgaagc cccgtctcta ctaaaaaata caaaaaaaat tagccaggca    10620
tggtggcggg cgcctgtagt cccagcaact gggaggctg aggcaggaga agaatggtgt    10680
gaacctggga ggtggagctt ccagtgagcc gagatcacac cactgcactc cagcctgggc    10740
gacagagtga aactccatct caaaaaaaaa ataaataaat aaataagaat tgttagtatt    10800
ttgcaggtgt gacaaatgat tctgtttctg tggcagaatg ttctcaggag atctcttttg    10860
aactctcatg gaaagcatca tgctgttggc aacatcacat ttatttttat ttatttatta    10920
tttttagag acaggtctt gctctgttgc ccaggctgga gtgcagtggc acaatcacag    10980
ctcactgcag cctcaacctc ctgggctcaa gcaatcctcc tgcctcagcc tcccaaagta    11040
gctgggacca caggcgtgag ccactgcact cagcccaatg taccttcaat atttacattt    11100
ctggcaaagg tagcaaaacc ttaacaaatt ttgaatctag ataataaaat tatgaggctg    11160
ggtgcagtgg ccctgacagg gatggctcac atctgtaatc tcaacatttt gggaggccaa    11220
ggtaggcgga tcacctgagg ccaggagttt gagaccagcc tggccaacat ggtgtaaccc    11280
tgtctctaac aaaaatacaa aaaattagc cagacgtggt ggtgcacgtc tgtcatccca    11340
gctactaggg aggctgaggc aggagaattg cttgaacccg agaggcagag gttgtgatga    11400
gccgagatcg cgtcattgca ctccagcctg ggcaaaagca agagcgaaac tctctctcca    11460
aaaaataaaa aaaaataaa ttaatgaatt aattaaaata aaataaaata atggatagtc    11520
actgtaaaga aaaaataaat gtatatatca gccaacaagt gatggaatag agcaccccat    11580
ctccctggct ggacagatac atcccacaac acctggaagg cggctccatg tagaactttc    11640
tggactgctt gaggtgctgt gctggagcac ggtgacagag gagctggacc atggacctcc    11700
cccggcccc accaagggcg aggtcccct gtggtgggtc tgagggaggc atccgtatgg    11760
cctctgcggc ttgggcaggg aatttggggt ccaagtactt ggtgcaaagc ctggaaagag    11820
ggtttgggtg ctgagggcat atcccctggg ccacatgggg gcagaagtgg ggccccctga    11880
agcttggagt cctgggcagg ggcatctatt ttgctgtctg aggccttcag tacttgaagc    11940
aaaatggagg cagaatgtcc caccttaatg ccctgattc ctccaaacca attccagaga    12000
cagcaagggc cagaacaggg atggccctgc ccagggtcat gcancgagga agtggccagg    12060
ctgggatctg aacccaggct aatcccctcc cttgtcctcc tccaggccct cacccctgca    12120
tagagccctc cagctcactc atcctcggcc agctccatct cctcagcttg taaaccccc    12180
cgggattttc ctttcttaaa aaacaaaggc ttggccaggc acggtggctc acgcctgtac    12240
tttgggggtg ctcccagca ctttgggagg ccaaggtggg cggatcatga ggtcaagaga    12300
ttgagaccat tctggccagc atggtgaaac cctgtattta ctaaaaaaaa aaaattaac    12360
tgggcatggt ggctagctac ttaggaggct gaggcaggag aatcgcttga acctgggaga    12420
aagaggttgc agtgagccaa gatcgcgcca ctccacttta acctggcaac agaacaagat    12480
tccgtttcna aaacaaaca aacaaacaaa taaacaaaaa aaggcggagc gcgatggctc    12540
gcgcctgcaa tccagcacact ttgggaggct gaggcgggcg gatcacttga ggttaggagt    12600
ttgagaccag cttggccaac atggtgaaac cccatttcca ctaaaagtac aaaaatcagc    12660
caggtgtggt ggtgggtgcc tgtaatccca gctactcagg aggctgaggc aggagaatcg    12720
cttgaaccca tgacctggag gctacagtga gctgagattg cgccactgta ctccagcttg    12780
```

-continued

```
ggcaacaaga tttgtttctc taaaaaaaaa aaaaaaaaga ctggcccttc cccttcagct    12840
cttcctcagg gtccctgagc actctacacc cccgtctaca ctgagcactc caccctgctg    12900
tctacactga gcactccacc ctgccatcta cactgaggac tccacccac tgtctacact     12960 ggctgcctcc cgccctcacc tcctgctaag gccattcccc gctgcatctg tcttctagat    13020
tctgcagcct tcagcacgct gggcccctcc tttgtcccct tgagccacct ccagcctccc    13080
cctgagctgc tactcctctc ccagcagcct ccacccaagc ccctccagtc cccaagctgt    13140
cccttgcatc cagcactgcc cttccacgtg ccccttccct ccagcttcac agcagggtgg    13200
ggcctccagg ccctgcccac tgtgcccatc acaagttgt ggtgggagct ccgaggggag     13260 gcagggtgt gcatggactt gggacgtcca agtctgggac caggggcagc tggttggtgg     13320
agtgtggagg gggataggga ctttcaggta gagaggctgt aggggcaaga tcgggacggc    13380
ggatgtccct aaggagggct ctgacctggg aaatattgtg cagcttcctc tttgccattc    13440
ctggagctca gacactggcc ggctctcacc ccgcccttcc tgcaggacac agctccatcc    13500
cagtgagttc ctagtgtaga catctccagc agcacggatg ggaaaggaag tcatcaaagg    13560
tgcccaggac cggaggcttt ttctggaggt ggcagaggag ggtgtgggtc tcagggctct    13620
ggctgagggc aagcgtggga ggtcttaggt ctgcaccagc cccgtgaagg ccctcctgc    13680 tccctggtgg agtcctagag ggaacagcag cccctaggct ctagcaggag tgggtagggg    13740
cttttctggc ttcctactgt gccagcagga tagctgggcc tggcactgag cccaaagatc    13800
acatgccggg gcattggcgc agtgaggaac agacccttgc caaagctggc aaagaagacc    13860
ccatggggtg cagctggtga agctgagagc tcaatgtttg ggggagcctg gcaaaagggg    13920
tcctcccctc cctctgcagg ccaggatcgc aggttttccc tacatgttgg taattctcaa    13980
acaatcccat ggccactgga gcaaagatca cagtgggcgg cggcctcggg agcagtggac    14040
agggcacgca gtgcctttga tgccagagcc ctcgccccaa agtcaacaaa ctctgcagcg    14100
gactttgcac ccggactttg ttttcaccat acaaggaaag ggacagatca caggccctct    14160
cgctgccctc gctgagccgg aagctgcagc gtgagctctc tcaagcccca tttctaggtt    14220
ccccaggcgc acccctgagc ccctactcgc ctattaagtt ctcctaatag cccttcaagg    14280
tcttaatgta tgtccattag acagagggga aaactgaggc gagggcaagt gacttgaccg    14340
aggttcctcg gcgagcaggg cgtggagctg agaacctcgt tattactgct ccccacacaa    14400
ccctctggcc gttcttggaa gaaggctgag ccccggggg gccagagtga cccaaacacc    14460
atgggccgcc tgcggtaaca cgtgcggcca cgaagggca gcagtttccc gcccggccgg     14520
gctctctccg gcgctcagta tccgtcccag gccaagaaga agaaactcgg ggaggagggc    14580
ggagggggct gcgtgggagg gcgtggaaga tggacgtggc caggggagtg gcagctgcac    14640
acagtggatg ctgttaagat gaagggaaag aacgtgggct ccgagatcac tggacacggt    14700 tccaccttc ttcccgctca ctgcatggcc ctgggcgggt tgttgaaccc ttggaaacct     14760 gttttttcctt ttttcctttt tttttgagac agggtcttgc tctgtggccc agactggagt    14820
gccgtggcac gatcttggct cactgctgcc tcccaggttc aagtgatcct cccagctcag    14880
cctcctgcgt agctgggacc ccaggtatgt gtcaccacag ccggctaatt tttgtatttt    14940
tttgtagaga cgggatttcg ccgtattgcc caggctggtc tcaaactcct gagttcaccg    15000
gatcttcctg cctcagcctc ccaaagtgct gggattactg gcatgagcca ccgcacccag    15060 cagagaccctc agttttctaa cctgtgccag caggaataat gatagctgcc tagcttggct    15120
```

```
gtgctgggaa ttaagtaaga tgaccgggta gcaaatatga agtattactg gacacagagg    15180
gccccaggct gggttagcag cggtggtcag ggctgctgct tcctggcctg agctcgaagg    15240
agggccctca ttaccacctg ggtgagtcct cgtccaagcc tggcactgct gcgtgggaat    15300
aacttctgcc acccaagttg gcagattgtg tgcaaagtta agtcctgact ctgtggggtg    15360
gacttcgagg cctcttcatc ggacctgctt ccggtgactg cattcgcacc tcctcctgtt    15420
cctggtttaa cacagcccag ctttcctcct gctgagccct ccctgggcct gctgtcaccc    15480
tcgtgccgct gtgcctcgca gtgccactcc ctgtaccctg aatactttgc cctgcctctc    15540
cacccagctg agagtcaggg cccctgtgag gctctgccca gcccgtcctc cgggtttctg    15600
cctctgctga gcacttccct gcatgattgc ttctgagagt cccccagcc tgtgagcttc     15660 tcaggactgg gacagcttct caggaccgag gcttcctggt ctgcttgcaa ttttacaggg    15720
gggcacattt tcccttggcc aacatcagag actggacatc tgcagatctg tgctagccac    15780
tgagcaccca ggcaccccag caggtagctc tgtaaccaac ccattctgta aagctgaggc    15840
tcagagaggt gaagcgcctg gcctggggcc acagcctgcg tcagctgcag agccaggagc    15900
tgagatatgc acctgcggct ctgctcacag ggtcctgcac agactgctgc tggagccacc    15960
tatgtagagt caagagagtt catgttaact ccctctcaca tccctcagcc agggtggggg    16020
ctgacgatag acactcaggg atggcctacc ctccccaaca accccgtca ggtttgccgg      16080 atctccttgg aagaaaagtt ctgggcagaa ttccaccgtt ggcctggcct acactctcct    16140
tagtggctta ggaccctcag cggtggataa gttgtgggca gaagagatgc aatcaggatt    16200
ctcacccact cacccttgc cagccccaat aagctcaata agctgggctc ggtctgagga     16260
agtgtccagg aaatgtgcaa atggcctggg acagccctgt gttcctttca gtaaggttgc    16320
tgaaggtgag gctgaaagtt ggagaaacag aagccagtgc ttatggtttt aattaagata    16380
atggaatgta tgtatgtatg tatgtatgta tgtatgtatt tatgtattta tctttagaga    16440
tagagtctca ctctgttgcc caggctggaa tgcggtgaca caatcatagc tccttgcagc    16500
ctcgacttcc tatgcccaaa tgatcctcct acctcagcct cctgagtagc tgggactaca    16560
gacacacgcc aactatgcct agctaatttt tatttctatt ttttgtggag actgggttct    16620
cactttgttg cccaggctgg tcttgaaccc ctagcttcaa gcaatcctcc tgcctcagcc    16680
tcccaaagtg gagggattac aggtgtgagc caccacacct ggcctggaat ttatttgtat    16740 tctgccttata aaattaatac attcttattg cagaaaagtt tgaaaataaa agaaaggaca    16800
aagaacaaaa agcgtatata atttcacagc tcagatctca ctgctattaa catttttatt    16860
tactttcagg cttttttctt tctaggtaca tatgcagaga ttattttatt ttatttattt    16920
tattttatat tttattttat attttttatt tcattatttt attttatttt attttattat    16980
ttttagagac agggcctcac tctgtcaccc aggctggagt acaatggagt gatcatagct    17040
cactgcagcc tcaaacacct gggctcaagc aatcccccca ctcagccttc tgagtagttg    17100
ggactaaagt gtgagtctgg ctaattttt ttactttttg tattgacaga ggtctcacta      17160
tgttgcccag gctgatctca aactcctggg ttcaagcgat cctcccacct ggactccca     17220 aagtgctggg attacaggca tgagccacca tgcctggcct aaaatgccac tttttgtcat    17280
ttactaaaat cccatggaca ctttgacatg tctgtattct atgctattga tctgactgtt    17340
ggcatctaca tcattatggc catctatcat ctatcataat ccattttaac attaaaattg    17400
tgctgctgct tagattttc tggcctgtct cctatttgta ttcttccaga taaatttag      17460 aatcattta tcaaattccc cttgcagaaa aagcccctatt ggatttggt tgaaaaatac      17520
```

```
tgaatttta cattaactta ggaaagggct gggcacggtg gctcacgcct gtaatccta     17580 cacttttcga ggccaaggca ggtggatcac ttgaggttgg gagtttgaga ccagcctggc   17640
caacatggtg aaactcggtc tttactaaaa atacaaaaat tgccaggcgc attggctcac   17700
ctgtaatccc agcactttgg gaggccgagg tgggtggatc acgaggtcag gagatagaga   17760
ccatcctggc taacacggtg caaccccgtc tctcctaaaa atacaaaaaa ttagccaggc   17820
gtggtggtgg gcgcctgtgg tctcagctac ttaggaggct gaggcaggag aatggtgtga   17880
acccaggagg cggagcttgc agtgagccaa gatcgcgcca ctgcactcca gcctgggcga   17940
cagagtgaga ctccatctca aaaaaaaata ataataataa tacaaaaatt agccgggggt   18000
cgtggcgtgc acctataatc ccagttactg gggaggctga gcaggagaa tcgcttgaat    18060 ccaggaggtg gaggttgcaa tgagcagaga tcgtgccact gtactccagc ctgggtgaca   18120
gagtgacact ctgtgaaaaa aaaaaaaaaa ttctgaagga ttgagactct tagactctta   18180
ggtcttccta tccaagagca caatatagct tttcatgtat tcaagccttt ttcaatgcat   18240
caacagaatt ttacagtttt tttcatgata tcctgctatt tcttataaaa tgtattccta   18300
gatattctgc atgttttccg gttgtttgtt aataaatatt tttcatttgt cattatttcc   18360
taattggctg ttatttgtat atgacatc tgttgaattt tttgattact ttgaaaatgg     18420
ccattctttt gtgtttttt ttaactttct atttgagat aatttgact tacagaagat      18480 ttgcaaaaat agtacagaga gttcctgttt cccccttatg ttaacccagt ttctccttat   18540
gttaacatct tacataacta cagaacaatt gtcaaatcta agaatcaacc tgggcacaat   18600
gctattaact aaactgcaga agctgttcag atctcaccag ttcttctact gctccccttt   18660
tctcttccag tgttcaatcc ggaatcctac attatattta gttgtcattt ctctttggtg   18720
tcttccaatc tgtgacagtt cctcagtctt tctttgtctt tcatgacttt catttttta    18780 tacttttgaa aaatactggc cggttgtttt gtagaacgcc ctcagtttgg gtttgcctga   18840 agtttttttgt gattagatcg aggtcatgca ttattggaga gggtgccacc gcctcgatgt   18900
gcaagctcaa tgcatcatat cagagggttt gtaatgtcag tttataccgc cggagaccct   18960
aacctggagc atttcgtgaa ggtgctgtct gccaggattc tccactagaa agttactatt   19020
tttccctttt taattactga atgtctgagg ggaaatactt tgagactatg caaatatcct   19080
gtttctgctt taacttcggc tcactaagtt tagcattcat ctatggatct cgcttatagc   19140
aagtattact gtggagttct aatggtaatt ttctgtttct ctcattcctt caacctttat   19200
taatatgctt cttcctcact tattcatttt gtttcagttg tttataccaa catggatttg   19260
tggatattgg ttttattctt tgggttgcaa ttgaatccta tcattatttt gttagtcagt   19320
tgttccatcc gaccttggtc attaggagcc cttgaaattt ggctcccatg ccttttttt   19380 ttttttttgag accgagtctc actctgtcac ccaggtttga gtgcagtggc atgatcttgg   19440
cttcctgcaa cctccgcctc ccaggttcaa gcaattctcc tgcctcagcc tcctgagtag   19500
ctggtattat aggcgctcca ccaccttgcc cggctaattt tttgtatttt tagtagagat   19560
ggggttttat tatgttggcc aggctggtct caaactcctg acctcaggtg atctgcccgc   19620
ctcggcctcc caaagtgctg ggactacagg cgtgagccac cacacctggc ctcctatgcc   19680
attttaacat gcccgtcttt tcttttttct tcctactttc tgtgactgta agaagctcca   19740
ggatacattt ttgctgccct agacttagcc tcaatcagtt ctcagaaaag ctctggttct   19800
ttttatggga tacttagaaa actagctctg tatggcctgg cgcggtggct cacgcctgta   19860
```

-continued

```
atcccagtac tttgggaggc cgaggtgggc agatcacaga tcacgaagtc aggagatcaa   19920
gaccatcctg gctaacatgg tgaaactctg tctctactaa acatacaaaa aattagtcca   19980
ggcgcggtgg cgggcgcctg tagtcccagc tactcaggag gctgaggcag gagaacggca   20040
tgaacccggg aggcggagct tgcagtgagc cgagatcggc agccactgca ctccagcctg   20100
ggccacagag cgagactccg tctcaaaaaa aaaaaagga aaaagaaaaa agaaaactag   20160
ctctgtatgc tagtttttt tttaagacag gtctctctt gccccagctg gagtgtagca   20220
gcacgatcac agctcactgt agcctcaacc ttctgggctc aagcaatcct cctgcctcag   20280
tctcctaagt agctgggtct acaggcatgc accaccgtac gtggcaattt ttaaaaactg   20340
tttgtagaga tggagtctcc ctatgttgcc tggtctggaa ctcctggcct caagtgatcc   20400
tcctgcctcg gcctcccaaa gtgctgagat tacaggcatg agccactgta cctggcctgg   20460
ccaaggtctg tcttttttta aagaagttg ttgtatagtt gttttttttt ttatttttt   20520
ttctgagacg gagtctcgct ctgtcgccca ggctggagtg cagtggtgcg atctcggctc   20580
actgcaagct ccgcctccca ggttcacgcc attctcctgc ctcagcctcc cgagtagctg   20640
ggcctacagg cgcccgctac cacgcccggc taatttttg cattttagt agagacgggg   20700
tttcaccgtg ttagccagga tggtctcgat ctcctgacct cgtgatccgc ccgcctcggc   20760
ctcccaaagt gctgggatta caggcgtgag ccaccgcgcc cggcctgttg tatagttttt   20820
atctcgagtt ttctagcgat ttaatcatat tggttacaaa aaaggatgat tttactacct   20880
cctttccaat gtttctacat atttttcat tttatctaac tgcattttaa aataaacttt   20940
taattttaga atggtttcat atttacagaa aatgtgcaaa gatagtacag agagttcctg   21000
tgtactccac acccggtttc cttattatta tcttaacgtg atacacaatt aataaaccag   21060
taacattatt attcactgaa gtccacactt tcttttttt ttttctgag acggagtcta   21120
cttctgtcac ccaggctgga gtgcagtggc gcaatctcgg ctcactgcaa cctccacctc   21180
ctgggttcag gcaattctgt ggctcagcat cccaagtagc tgggaataca ggtgcccgcc   21240
accacgcccg gctaattttt tgtattttta gtagagatgg ggtttcacca tgttagccag   21300
gatggtcttg aactcctgac ctcgtgatct gcctgcctca gcctcccaaa gtgctgggat   21360
tacaggcgtg agccaccgcg cccggcgtcc atactttctt tagatatcct tcctttttac   21420
ctaacgtcct tcttctggtt caggatccca tccagaaagc aacattaccc ctcgccatca   21480
cgtcttcaca ggctcccctt gacgggaaga gttcctcaga cttccttgt ttttgttgac   21540
cttgacagtt ttgaggagga ctggtatctt agtctgtttt gtgctgctat cacagactag   21600
ctgagaccga tacatgatac atgaaaaaaa atgtattctt acagttgtgg aggctgggaa   21660
gttcaagacg aagttgctgg ttggtttggt tctggtttc aagatggcgc cttgctgctg   21720
catcctctgg agaagaagaa tgcggtgtcc tctcactgca gaagatggaa gcgctaaaag   21780
gaatgaactc cctttgccaa gccattttat aatgggcatt aatccacaaa ggatgaaacc   21840
ctgagaaaca tcaagcttta aagcactggt tctcaacctt tttggtctca ggagcccttt   21900
atactcttaa aacgttttga ggatcccaaa aaaggcttc tacaggttcc atctttaat   21960
atttaccata tcaaaaatta aactgaaaaa attttaaatt atttattcat ttaaaataac   22020
aaggataaac ccattacatg ctaacataaa tcatgtattt tatgaaaaat agctatattt   22080
atcaaaacaa aaattagtga gaagagtggc atgtataatt ttttttgttt attttttgtt   22140
tttagatgga atcttattct gtcgcccagg ctggagtgca gtggtgtgat ctcggctcac   22200
tgcaagctct gcctcccagg ttcacaccat tctcctgcct cagcctcctg agtagctggg   22260
```

-continued

```
actgcaggtg cctgccacca cgcccggcta atttttgta tttttagtag agatggagtt    22320
tcaccgtgtt agccaggatg gtcttgatct cctgaccttg tgatccaccc gcctcagcct    22380
cccaaagtgc tgggattaca ggcttgagcc actgcgtctg gcctaaattt ttgtgaatgt    22440
ctttaatgcc tgccttctca tatttgtttc tgcattcaag ttattgcaaa atgttgtgtt    22500
ggttgaagtt tgtaaagaaa atgtggcctc atacagttgt gtagttggaa aggcaagagt    22560
attttgattc tctcttcaaa caactatgga caacctgctg ttacaaaacc agaatgcaaa    22620
aagttgtagt aaatacaggt taggtgtagt gtggaatctg aaagcatgtg aatgaacttt    22680
ctgagttttg taacattaaa gtccagttgc gttaagctac tgtgatagca tatagcattg    22740
tcctaatact ggaattagta tcagaagtgg ggtgctactg ttaataaata aaagaaata    22800 aataaatcat gtgatactgg ctcagaagtc aggcagtagg ctgtgtggaa cctgacatca    22860
cgccatgtaa tacattggca accatttgat ccagctgtct gtcatgatga cttggaaagt    22920
caaccacata cttacagagc ctgtagacat agggggaaaat agtataaaac agaatactaa    22980
cagtggacct tggttcttgc cagttgcatt tagccaaata ttaaacaaaa gagatattct    23040
tgggcagcaa ctggaccatc ttcaagtaaa agtgaaaggt aataaacaga gtccagacat    23100
ttgtgcccat gcgggttaag aaaaatccag ttgcttctag acaccgtata tgaaaacaac    23160
gctgaaaaca agcctttgag tggtaaaggc cgattaacac tcagcgcggt aacaaagacc    23220
aggtgggcta acccgaaatg aaatgagaag cctgtggtga tgaggaggca gagaagtaaa    23280
atcaagtttg agcatttcgt ttaggagagt ttgggctctg attacttgca catgcaaacg    23340
aactggaaac aaacagatca gatgtctacc acttcttcga gggaattgca ttgccaaaga    23400
agtcatgaaa gcagactcta tactgattag gcattaaaac aaaaacaatc tttaggcccc    23460
taaacttgca tgggcaggaa gtgggctgtc aaagctgttc atcctctaag gtggacctag    23520
ttcctagtcc ccagtataca cttcagatgt ggccctggag gacactggac atggaggacc    23580
tcccagagga tgaggctagg gcttcatttc tccaatgacc tcagctgcct ctatttcccc    23640
ttcttcctct ggaagtccta tcatcgttat tattattatt atcatcattt ttattttgag    23700
ataaggtctc gctctgttgc ccaggctgga gtgcagtgac atgatcatgg ctcactgcag    23760
ccctcccagg ctcaagtgat cctcctgcct cagcctcctg agtagctggg agtacaggca    23820
catgccacca tgcttggcta tttttttttt cagtagagat agggctctca ctatgttgcc    23880
agggctgatc tcaacctcct gggttcaaga gatcctccta cctcagctcc tgagtagctg    23940
ggattcgggt gcacaccacc atgccaacta atttttaatt ttttttgta tggacaggat    24000 gtacagtgtt agaaatggat tgcttgcaga ggcaggagga tcacttgagc ccaggagttt    24060
gatcacactg tgaaccatga tcgcacccct gcactccaat ctgggcaaca gagtgagacc    24120
ttgtctcaaa aaaaaaaaa aagagagaga gagagagact caaagatagg caaaaaagtg    24180
ggaaagcttt atagtggaca aaaaggaacg ctctaagtct gccctattgg catggtgctg    24240
aaggtgggct aactagagat aggggggtact atgtggttga ctatgggtgc atctttggct    24300
ttccctgggt gatcctaagt tggaagcagg gacaaaaatt agggaagctg ttagttattc    24360
atcacgttct ggcagtagtg gactggttgt gatagaagtt attgttttgg ccaggtgcgg    24420
tggctcatgc ctgtaatcct agcccttttca gagttcaacg tgggtggatc aggaaggagg    24480
gaggatttgg gaggtcagga gttagcctgg ctaacctggc gaaatcccat ctctactaaa    24540
aatacaaaaa ttagctgggc gtggtggtgc atgcctataa tcccagctac tcgggacgct    24600
```

-continued

```
gaggcaggag aatcagttga acctggggag gcggaggttg cagtgagcca agatcgtgcc    24660
caatttcatc tcaaaaaaaa aaaaaagtt atcgtttagc ttcctcgatt gttactggac     24720
gtagtaatct ggcttcctgc aagtctaact ttcagcagac tggctacatg ggctgtgtac    24780
tgtagataag gcagtaagta aagcaaaaat tgatagagca tcaaggataa atagaaaatc    24840
cgtaatcaag cagaagattt gaacacttca ctttcagtaa ctgataaaac aagtagacaa    24900
aaaaaatcag taaggatgta gaagatttga acaacgtaat taacaaactt gacttgattt    24960
acacgtctag aaccctgcag aacacacact ttttcaagca tactcagaac atttatataa    25020
agtgaccata tggtggacca taaagcagtt tcaacaaatc tcacaggagt aaaataacag    25080
accgtgtttt ctgaccgtaa gtacagttaa cctagaaatt gaaaacaaaa agctagaaaa    25140
accccatgta tctggaaatt ttaatataca ctttgaaata acaaatggat cagagattaa    25200
ttcaaatagg aatttagaaa taccttgaac tgaaaaataa tgagaatact ataccccaaa    25260
actgtggggt gcagctgaac agtatataga cgaaaagtat actcatatgt gcataccttta   25320 aggagcgggg aggattgaaa gttaatggga ggcaaaagca ggtggatcac ttgaggttag    25380
gagttcaaga tcagcctggc taacaggtg aaaccccatc tctactaaaa atacaaaaaa     25440
ttatccaggc gtagtgaggc tgaggcaaga gaatcgttgg aacccaggag gcagaggttg    25500
cagtgagccg cgattgcgcc actgcacccc agcctgggag acagagcgag actccatctc    25560
aagaaagaaa aaaaaaaaag aaaaggccag gcgcggtggc tcatgcctgt aatcccagca    25620
ttttgggagg ccgaggtggg cggatcacga ggtcaggaga tcgagactat cctggctagc    25680
acggtgaaac cccgcctcta ctaaaaatac aaaaaaatta gccaggcgtg gtggcgggtg    25740
cctgtagtcc cagctactca ggaggctgag gcaggagaat gtcatgaacc caggaggcag    25800
agcttgcagt gagccgagat cgcgccactg tactccagcc tgggcaacag agagagactc    25860
tgtctcaaaa aaaaaaaaaa gttaatggga taaacatcca tctcaagaag ttagaaagga    25920
atgacaaata aaccaaaaaa aaaaaaatca aaagaagaaa atcataaggt caagactata    25980
aagagagtgg ctgggtgcag tggctcaggc ctgtaatctc agcattttgg gaagcagagg    26040
tgggcagatc acttgagccc aggagttcaa gaccagcctg agtaacatag agagacctca    26100
tctttgctga aaataaaaat aaaaaattag ccaggcatgg tggtactgag gtgggaggat    26160
cacttgagcc taggaggttg aggctgcagt aagccatgat tgtgccactg cacttcagcc    26220
tgggtgacag agtgggaccc tgtctctaaa aaactaaaat aaggctgggc gcggtggctc    26280
aaatctgtaa tcccaccact ttgggaggcc aaggctgagg tcagcagttt gagaacagct    26340
tggccaacaa gatgaaacct catctctact aaaaatacaa aaaattagtt gggtgtggtg    26400
gcatgtgcct gtaatcccag ctacttagga ggnnnnctnt ngattatatt ttctccttcc    26460
tacgtcgtta ttggactgaa ttcagaatga tgactctcat tggagctctt cctgtctcct    26520
aactacagtg gcttccgacc ccactctggt tttcacttca cccctctgct gctcatacga    26580
gtagatactt ccttccttct ttctcacttg ttgctcttcc tcaaccccc ccgttggtgt     26640 ccctcctct ttatctttt ctcgcgacac ctgcgttctc ttgccctctt atcatcccctt     26700 tctcgaggcg gtcctttcct ttatccagct taaataccctt ctcctctgtt tatttggggg   26760
ttgggttttt atctctcacc ctccctctaa tttctttcct cttccgcac ccatcaagcc     26820 tctcgtggtt tctcttcctc tactctcggg tccccccct ctcccttct ttttttcttc      26880 accccccaa gcgctttgcc ttttttttct ttgcccttta ttccccccc                 26928
```

```
<210> SEQ ID NO 7
<211> LENGTH: 29430
<212> TYPE: DNA
<213> ORGANISM: Homo sapiens
<220> FEATURE:
<221> NAME/KEY: unsure
<222> LOCATION: (4336),(4345),(4349),(4392),(4447),(4490)
<223> OTHER INFORMATION: Identity of nucleotide sequences at the above
      locations are unknown.

<400> SEQUENCE: 7
```

| | | | | | |
|---|---|---|---|---|---|
| aggggaaggg | ccggctccgt | agctcacacc | tataatccca | gcactttccg | aggagagagg | 60 |
| atcatctcag | gccaggagtt | caagaccagc | ctgggcaaca | cagcaagacc | gcatctctac | 120 |
| aaaaacttct | tttaaagctt | aaaaaaaaaa | aaaaagcaa | agaggacagt | tcaggagaaa | 180 |
| agcctgtaga | ggcagcacac | taaggaggag | acgcagccca | ggcaccagga | ggggctggcc | 240 |
| atgggcactc | actcctccag | caggcgagtg | cccagcacca | gctggcccac | ccagacaccc | 300 |
| aggacacggc | ctgaatggct | ccgtattcac | gtgggtggta | ataaacaagc | aatcacata | 360 |
| gccaataagg | acaccttagt | aatgttacat | cataaacgct | gcagatcagg | gaaatggtgc | 420 |
| agggtgaagt | gggttggggg | gctgcatgct | acatgagaag | tgggtcgggg | ggctgcatgc | 480 |
| tacctgagac | agagcaggcc | ttgctgggaa | agaaggagcc | ggcaggcctg | ggcaaaggtc | 540 |
| ctggggtggg | agcacactgg | agcagagtgt | ggggtagca | tggcgggtgc | tggtcctctg | 600 |
| ggcgccttcc | caccacgtca | tgtgcccatg | tgcccaaggt | ctctcgtttc | acagcccct | 660 |
| gaagctcagg | ggtcacagct | acacagcccc | cagatacctt | ggcctgcccc | aggtcattcc | 720 |
| atccagtgat | ggacctgctg | acctctagcc | tgacctctgg | gcagcgtaat | ttgagaagga | 780 |
| ggagaaggga | gggcaacaga | cctggggcga | tgagggatgc | acagggtggc | agacacctga | 840 |
| ggctgcacct | tggagcctca | gttctgggtg | tgggtggggg | atggacaggc | tgagggctga | 900 |
| agcagctggg | cccggccacc | atcacacccc | aggacccacc | agatcaccat | gaaaaaccga | 960 |
| atgtcaactg | gcagcccaga | gtgcagaaca | aacctttcag | aaacacggtg | gtgactgccg | 1020 |
| catcatgaac | ataaaataat | tacgccctct | ccccagggat | caccctgca | ggagtttgtc | 1080 |
| ccaagaaaca | ccagaaagaa | ggaaaacgtc | tgagtcacaa | tatttgctga | ggccttattt | 1140 |
| gtaatagcaa | aaaaaaaaaa | aaaaaagaa | caatctccag | cggcaggggt | aactagacta | 1200 |
| ttgtctccgt | ggaaaggtag | caccaattaa | ctagtaacaa | aatgactgcg | gtaacaacaa | 1260 |
| aacgttcgac | atgtcaacac | caaaaccac | acacccagca | taaccgtgaa | ccatgatttc | 1320 |
| tactagaatg | aatggcagtt | atgagaaagc | accagcggag | acaaagattg | aaaaagtaaa | 1380 |
| ggtggcctca | ttagggagac | aagtctctgg | gtaatatatt | gtaatactgg | taaatatata | 1440 |
| gtttttaata | tattttttaa | ttccaaattc | catatatgtt | cctatgaagc | tatttctgca | 1500 |
| aatatttttt | tcaggaccgt | acatcacaaa | ggcaaaggg | ccaggtcagc | tctccagctg | 1560 |
| agagtgacca | cttcagagca | gacggcagac | tccagggtta | gcaagcctgg | ctgagacctg | 1620 |
| gcccatgaca | atcactcaac | ccctctgacc | tcaacatcct | gtctgtgaaa | tggggataat | 1680 |
| tactgcaccc | ccacatcaca | gagtgcgagg | cttaaacagg | atgcttcata | gaaaagcgct | 1740 |
| caagaggtaa | cagccgggag | ggggtagtgg | ttttcattaa | ttaaatgttg | ccttcatcca | 1800 |
| gccctgggcc | agctccaaca | caaagcacac | accatccact | cagactcagt | tgcctggatt | 1860 |
| caaagcccgg | cctggcctcc | agctgtgaga | ttccgggcag | gatttcccat | ctcccagagc | 1920 |
| ctcagtttcc | tcattcatga | aacaggaagt | gatcattcct | tttattttta | tttttatttt | 1980 |
| tatttgaga | cggagtttca | ctctagttgc | ccaggctgga | gtatgatggc | gcaatctcag | 2040 |

-continued

```
ctcactgcaa cctcggcctc ccagtttcaa gcgattctcc cacctcagtc tcctgagtag   2100
ctgggattac aggcacacgc caccacgccc agctaatttt gtatttttag tagagacggg   2160
gttttgccat gttggtcagg ctggtctcga actcctgacc tcaggtgatc cgcccgcctt   2220
ggcatcccaa agtgctggga ttacaggtgt gagccaccaa gcccagttga caactgcttt   2280
taaagacacc tctggctgct gtggaaaaca gcctggtagt gcctcaaaaa gttacacata   2340
gaatgatcct atgaccagta attccactcc tacatatata cccaaaagaa ctgaacccct   2400
ctactcatgt atgtacacat acaggtacac gcatgttaac agcagtgttc acaaagccaa   2460
aacatggaaa cagctcaaat gtccataacc gatgaacgga taaatgaaac gtagtctatt   2520
caccacctga cggaggtgag agggggccata aaaaggaatg atgcataaaa acgaatatta   2580
tggccaggta tggtggctca cgcctgtaat cccaggactt gggaggctg aggcgggcgg   2640 atcacgaggt aaggagttcg agaccagcct ggccaacacg gtgaaacccc atctctacta   2700
aaaatacaca aattagctgg gcatggtgga gggcgcctgt aataccagct actccggagg   2760
ctgaggcaag agaatccctt gaacctggga acagaggtt gcagtgagct gagattgcac   2820
cactgcactc cagcctgggc gacagaccaa aactccgttt cggaaaaaaa agaaaaaatt   2880
agccaggtgt ggtggcgggt gggtccctgt aatcccagct ctacttggga tactgaggca   2940
ggagaaccac ttgaacccgg gaggtggagg tagcggtgag ctgagattgt gccactgcgc   3000
tccagcctgt gtgacagaag gagactctgt ctctaaaaaa caaaaacaaa aaaggcccga   3060
cgcggtgtct tacacctgta atgccaacac tttgggaagc caaggcaggc agatcatctg   3120
aggtcaggag tttgagagca gcctgggcaa cacggtgaaa ccccatctct actaaaaata   3180
cagaaattag ccaggtgtgg tggcacatgc ctgtaatccc agctactcgg gaggctgagg   3240
caggagaatc gcttgaaccc aggaagcgga ggttgcagtg agccgacatt gcaccattat   3300
actccagcct gggtgacaga gtgagattct gtctcaaaaa aaaaaaaaaa aaaaaaaaa   3360 ctaaacaaaa gcaaaaaaac caatgagtaa tgttgtcaag tgaacttcat cccaatggga   3420
atgcagataa tttgtttaaa aggcaccatg cacactgggc aggctggctt ccctgggaa   3480 cgtcttcttt tgcctggatt cccagttggt ttaatcgggc gtagaacact ttcttcaatc   3540
cgggattcag gcacccctgc tcagcacaaa ctcagtacac cccgcactct gctgtgggtt   3600
cttggcacta ttaggagaat gtgagggggt gattcagatc tatctctagt gggtgcatgt   3660
ctgccactcc caggaacgcc cacttctggc aagtcagtgt cagagaaagg ccagctcgtg   3720
gcccctcctg ccttgagtcc caggacccgt gatcagtcct acccggagca gaatcaggag   3780
tttgaaaacc caagtgccaa caatctcatt ttaacccatg taagcatatc caatatttat   3840
atatagaatt cataacagat gtctgggctt ccattccaat agcctatatt ttacactgtt   3900
tatttacatg gttacaccaa acaagactca attcaaggta acccaatcct ttgctactat   3960
accaaaataa gcaacatttt cagtccatgc cttatatata ttccaccaagc attacactag   4020 gcctccaact gctcatcgga gcaagctgca gcctggacac aagctagaga ttaatcagtc   4080
aggaatgatc ctgcgtccag tgccagcatg atggaagaga cagagaaaca gaagacatca   4140
gggctccaga gtcaaggagc ctgcaggtta gttgggcagg atatacacac atacacacac   4200
acacgcacac acaaaaccac ccaagaagaa aaggtgggat gaatgcatgg acaggtaatg   4260
cctggagcct ggggatggat aagctgactg caggtggccc aggcaggctt cctggaggaa   4320
gaagacctgg ctgtangtgg ggtangcang cttctctaaat ggggaaaatc tggctgtggg   4380
```

```
tggagttggc angtttccga aaagaagaaa agctgactat gggtacacct ggctgttggt   4440
ggaacangca ggcttcttgg aagaagaaaa tctggctgtg ggtggatcan gcaagcttct   4500
tggaagaagt aaacctgact atgggtggac caggcaggct tcctagagga agaagaccgg   4560
ctgtgggtga accaggcagg cttcctagac agaggaagat ctggctgcgg ttagagtggg   4620
caggcttcta agaagaggaa gggctgactg tgggtagacc tggctgtggg tagactgggc   4680
aggcttcctg gaggaggaag agctggagca ttgaaaaaca acatgactt ggtgaatgtt   4740 gagcatgccc aggcctgatc cccagaggca attacgcact caagttactt aattctactc   4800
acaatgcctc acaaacaact tctctgacac ctaacacagc tctgggcacc ttctagcttc   4860
agctcctcaa agcagttatt cacgctacta ccctgcacac ctcctcacac cccaacccca   4920
gggacaggag ttctgccaga tgccaaagct cctgatgcca agcctgggt ctgcttccgg   4980 gctcctcttg gtctaactgt ccaccccgca tcggcatgat gtgcaaaaac aaggctttgc   5040
aatctgccct gatgcctggc ggagcgagtc cctcccgatt cgtctccttc agaaacacct   5100
gggctgccct ggtcctgtta tacccccaac acattctaca gtcagctccg caagttccac   5160
aaagatcaac gctggcgttt ttatggcatt ttatttacag tttttacaat ataaaaaagg   5220
aaggatgcca cagctcagcc agcaggacag acagagatct atgatgcttc tgctgcacca   5280
ttgtttgtgg tcaagaaagt ctgttttcaa tgatttatta aattgtggtg ggagatggat   5340
ggtggcagtg gttaccagca acatgaatgt tcttaatgcc actgaacttc acacttacaa   5400
atggttacga cgataagtgt tatatgtatt ttaccacaat taaaaacagg taaatgcagg   5460
ccgggcacgg tggctcacga ctgtaatctc agcactttgg gaggccaagg caggcagatc   5520
acctgaggtc aggggttcga gaccagtctc gccaacacgg tgaaactctg tctctattaa   5580
aaatacaaaa attagccaga tgtggtggtg catgcctgta atcccagctt ctcaggaggc   5640
tgaggcagga aaatagcttg aaaccgggag gcagaggttg ccatgagctg agattgtacc   5700
attgcactcc agcctgggtg acaaaagcaa aactctgtct caaaaaaata aaataaaata   5760
aaaataggta aatgcaaaca tatggtatag taatattatg ggctattatg agctacaaaa   5820
aagaatgact tgggactaca gttacagccc tcattcagga atttgttta aatgtgggtt   5880 ggtcgctaag gcatgtacac aacattttga cgttcaaata ttcctagatt tggacagtga   5940
gcacccctct aagctggctc ttctgtccca gaggtcccca ccagtcctcc agaacttctt   6000
tgctttctta cacaataaga tgccccatgc tcggcttgta cctttccttg ccccagccct   6060
agaaccagct tcttcgtgga caagctctga ctcctttggg tggagaatgg tattcagaaa   6120
cccagacctg ggctctggtg tgctcactgc tacttgggt cattgcttct aggcctctct   6180
gctgatggag gtaggatata cacgtacagt cttccctctt cccagattcc gtacttgagc   6240
tcgcctactt gctaacattt atttatatcc cccaaattaa acctcacagc acttctgcaa   6300
tcactcactg acttgcagag tgtgaaaaaa ctgagtcacc atcacacgtt ccaaactgag   6360
gtcaactgag gccacaacgc cccatcttct tgctccggct gtcgagatgt aagcaagtgt   6420
ccttctctcg gtctagctag tgccatgctt tccacatcac tgtgcttttt gtgggcaatt   6480
ttgctgtata aaatgtcccc tgcacatatg ctgctgtgta gtgctcctag gtgcatgagg   6540
ctgccccacg ccttacagag agaatatgca tgagaggctt tattcaggta tgagtttatag   6600 cgtagttggc catgaattca atgttaatga atcaacaata tacagtaaat aaggtgcttt   6660
ttagagacag ggtctcactc tgtcacccag gctttagagt ccagtggtgt gaccttggct   6720
cactgccgcc tcaacctcct gggctcaagt gatcctccca cctcagcctc ccaaactgtt   6780
```

-continued

| | |
|---|---|
| gggattacag gcgtgagcta ctgcactcag cctaaataag gtgtcttaga aacacacata | 6840 |
| agacaaggtt atgggctgag tgcggtggct catgcctgta atcccaacac tttgggaggc | 6900 |
| caaggtggga ggttcacttg aggccagaag tttgagacta gcctgggcaa catggcaaga | 6960 |
| cctcatctgt atatttttt aaatcagaca ggtgtggtgg tgcatgccta tagtcccagc | 7020 |
| tactggagag gctgaggcag gaaaatggcc tgagcccagg aggtcaaggc tgcagtgacc | 7080 |
| catgattgta ccactgcatt ccagcctggg gtgacacagc aagacgctgt cttaaaaaaa | 7140 |
| aaaaaaaaaa aagccaggtc aggtatcgaa cagttggcaa aaacgttgtg acctgaggct | 7200 |
| cacaggaacc tagcccgatg tttcccctag gagcaatggt tcagtattca ataattcagg | 7260 |
| gttcccagtg actttatgga gcataacttt caagaataac aagaaccaac tgtacgtgtg | 7320 |
| tatgtatact cacactttta ttttatttta ttttatttt tgagacagag tctcactctg | 7380 |
| tcacccaggc tggagtaaaa tggcgtgatc tcgactcact gcaacctccg cctcccaggt | 7440 |
| tcaagtgatt ctcagcctcc caagtagctg ggattacagg tgtgccccca caaccggcta | 7500 |
| atttctgtat ttttagtaga gacggagttt cgccacattg gccacgctgg tctcaaactc | 7560 |
| ctaacctcaa gtgatccacc cacctcagcc tcccaaagtg ctggaattac aggcatgagc | 7620 |
| tgccgtgcct agcctacata cactttata cacacatgca tctatgacta tttctctatt | 7680 |
| tctgtgcatg tgtgcgtggc agtacctaca gtttcagcta tgtgtctggg tactgtctcg | 7740 |
| tccaagtttg taagcacctt ctccaaagtg caaagcctgg cttgtgttac tatccatatg | 7800 |
| tttacttatt tgctcaatca atttacttat tagctccata accagcttcc catctgctcc | 7860 |
| agtagcctct gctgtcagtc acctctgcac cctaccccac cttgcttccg gatgctggat | 7920 |
| gccaatcacc cccgacacct ctacatagca ccaccctcga catgctgctt ctttatttct | 7980 |
| tattttatttg tttgagatgg agtcttactc tgttgcccag gctggagtgc agtggcacga | 8040 |
| tccaggctca ctgcaacgtc cgcctcctgg gttcaagtga ttctcctgcc tcagcttctc | 8100 |
| aaatagctgg gattacaggt gcccaccacc acgcccagct aattttttgta tttttagtag | 8160 |
| agatggggtt tcaccatgtt ggccaggctg gtctcgaact cctgacctca agtgatccac | 8220 |
| cttggcctct caaagtgctg ggattacagg tgtgagccac cgcgcctggt ctgcttcttt | 8280 |
| aaatgccagg caccaacatt tgtgcaatgg ggtgggagga agaacaggg aggagagcac | 8340 |
| actgccggcc cctgcactga atccactgat caatctgggg gcaactgcca tctccatctc | 8400 |
| ctgtcttcct atccgtgaac atctactgca gtcctctcca atgtccttct gtaaagttgt | 8460 |
| attatgtttt gcatacaggc cttgcatatt agttctcaga tataatccat atactttata | 8520 |
| taaaattcaa accacattta aaaaaataaa actagcatga ctataacgga gtctgcaaca | 8580 |
| ttctcacaga ctttatgata aaacatgaaa cttcaaagat acttagggtg gggcagggac | 8640 |
| aatgtttaag gctgcctgga agcctcccca tccctgagcc agaaagtcct atctcccctt | 8700 |
| caaggggaaa tgcttgaaaa agcactgatc aggctaaaat gacagggatc agggagtaat | 8760 |
| caaagtacaa gtgagctggt ctcctccatt ctgagcacag caaagttcag tctctccaag | 8820 |
| tccaagaatc atacacctgt ttgccaagaa tgaagttcag gtgtctacaa gtggctgaaa | 8880 |
| atattcattg ctgggccatt aacaacattc ttggcaaaac catacctag cttctcgtgg | 8940 |
| aaatttctta aggtagaaga aacaggaaac acccaggctc gcttttatgt agacagttcc | 9000 |
| atgaagccag ggaccttccc cacatccacg tttcaattac ctgcacgcag ctcacagtgt | 9060 |
| attcaacatc tacgcgtctc tcctactggg gtggcggtgg ccactcaaac cctcatgcag | 9120 |

```
ctacgatgac cgcaattttg gcaacataat ttcatgtttt tccttgggct tttacccaag    9180
tcagtgacac aattctgcag ttgtctaaag attcaaaatg agggacttga catttacaac    9240
aataataaaa tcttgggttt cctttaacca agcacatgtt ctgcctttta gagaaagctc    9300
tgcaaactca agctggagtg ggatacttgc tgacatcttc aagcacccca ggaatagctc    9360
tactccccca tttccacctt ggctgaacca tctatatccc accaattccc ccaacatccc    9420
tccatccgtc catccatcca cccaaggacc tgctaagcca ggaggtctct cccatctacc    9480
ccacagcctg gcctcagccc acaagggctc tctctacatg aatcccaccg caccagagta    9540
gaccaagtct cccgtagact ccaccctgac cacctccatg cctccagcca ttcccacccc    9600
taaaaaccct ccctggtctc tacacccagc tgatgaatac ttggctgaat gtgacctggc    9660
ctcctggacc caggtgaagc ccacgtcctc cgtaagcccg ccagctcacc ctgcctctgc    9720
accttcactg gagagagccc gcacttcacc tcctcagggc aggcatggct gatgccaccc    9780
agtggaatct ggtgcaaagc agggcccggt gcagagcagg gctgcctgca gagcaaggcc    9840
ctggtgctgg ggccgagcac ctccaatgct ggccgtggaa ccatccctcc cattccaggt    9900
gctgtctcca tcaagaatga gcgagctgct gacatttgca tgacaataat gaataaaatac    9960 catattttgc ttcaaatcca gaatagatgt ggccagggtt ggcatatgac tgttgggaaa    10020
ggacagtttg cctcttccca aaccaacttg gattataaaa agcttttctt aacgaccaca    10080
agagcggagg agctcagggg cagacaaaag gaaggctggc tgcagaaggc gggagagtgg    10140
ggccttcagg ggcgggtggg gagagagaaa gcctggagct gcacccccaa ggtctgtgta    10200
catcaggtgc tacagaataa caccacctct tccagcttgg cccccacctg ccctctccca    10260
gcccagtcac ccagacagca ccccactccc cacacacacc tcacatctgc ccgcctcaca    10320
ctcaccagct tcggctctca atgcaacctg gaacctgccc ttggcctctc agctcagcca    10380
cccccattcc tgttggcccc tggcccccca tcgaattctc tctaatccta atgcacacac    10440
ttgcacactc aaacacacac acacacacac acacacacag cccagaggaa aaccataatt    10500
gactgaggtc caggcaagtt ccccgagcag ggaccacatt tcaaaggtca gggaagcagg    10560
cgaacaggaa acatacaggg ggcacgtttg ggggtggagc aggaaataag aaatcacttg    10620
caaaagataa aaagaaaatg aggtagctgg tttcagacac ctcggagcac acagaacagg    10680
acaggcgcct ccgggtcttc cctcaacagg gagatgggcc aggcaggtcc ctgctgctcc    10740
accgcagagc tgggggctat ggccctgaca ccaaggccct ggggcaggcg gggaggcagc    10800
tgttctcctg cctgtgctcc cgggcagggc ctggccccac aagggaactg gccgaaggct    10860
ctgcttggct actccggaaa gtcctgggag acaagcaaag gacttgctag gtcactccaa    10920
acggcccaga tgtgacaact gtgaagaagc cacaccaaag caaggtgaca gaacaatgtt    10980
ggtgacgtca ggttatcagc ttacgctcaa ctccacttac ccggactcac ccgtaacctg    11040
ccgtctcttc ccaaccagta aaggatgcct aggtagaggg gcacaaggcc tggagcataa    11100
ttaccatttt aaaggctctg agaagtcctg cggtgaggaa gcctagttca ctttctctcc    11160
cctaggattt cccaactgcg cctgatcaca gaacattttt tcatttccac tcaggaaaca    11220
tattttgaaa aacactggcc tagaggcaga agtgaaatgg aaaacacaaa agtaaaactg    11280
aacaggaggc actgggcaga gaacggtcag aggcgcctg aatcctggac cggtggagat    11340
ccccagcttg gcatgctccc ctccctgggc ccagaccgcc tccccccatt tcctggataa    11400
gaaggctaat gcgcatcagg gtgaagggct tgcctgggct acacccccag gctcgcccca    11460
caccaatcgc gctcctgcga gagccagtga ctttcttgat ttggctactg tggaattgtt    11520
```

-continued

```
tgcaactaac cacccagat acagatacaa atgacaggat gatcagatgt aaaggaccca    11580
caggtctctg tgatacggct tcatgcagcc agcatggcta gtgccgtgca gaatgagaat    11640
gaccccaggc aagtccttgc ctcccagacc cagaacccca tggagcccac cagggctggt    11700
tcacaagcac tgtctgggtc gggcagagat tccagcaaga ggagggaaca tccatgcacc    11760
ggagccagtt accagaagca aatcgcctct tccaaaaccc aggctattaa tggagtccac    11820
tgttgagtgg agctggggtc tagctatgga atactgcaca gcagagatct tcctgagaga    11880
aagcagtttt ccctgaaagc catgtgtcct ccactaactg tgttttaatt gggcgaacgt    11940
ctgtatctca ttgcagtggc cgcgcatgtg ctgacaaggg gctgggggcg gggtggggag    12000
cagaagctca ggggcctggg agggaaggaa acaggccacc agggctcccc agaaggcatg    12060
tatctctctc acaaacacac gcatgcacac acacgtgcac acatactctg caagccctga    12120
gttagcaact gtggaatgtg accagctcag tgatcccagg acaagctgct agggaatatg    12180
acatttgatt gatgtctgca aatgtgcgtt ttcactaatt agaaggttta gggcagagca    12240
gagaaaaata tgtatttcag agtcccagtt tgacctgcca gaaaccagcc cattactaac    12300
attcttattt tcaacaaaat atagcattct gattacatac catcttggtt ccacgcctcc    12360
tgccttgcca gcccccggga gcggcccaa ggccatggca aatagtgaga gaaacagttc    12420
cagggtggag actgactcag gggtgtcagt cagtggggcg ctgatggccg gtgggaggcc    12480
agcagtcatc accctctcct tgggacagtt gagtagctct cccccagggt catgtggcca    12540
ctcaggttca tatgggaggc gagaggagtg gcagagtcca ggagagtggc tccgaagtca    12600
ctgttccctc caggcctcag tgtcttcatc cattaaatgg gtaggctgag gtctgggatg    12660
acaaggaggg cttgcactta ctgaaaccca tgggaggctg ttcgccgatt tcttttattg    12720
atggaagaaa acactcgtat aattcaagta ccaattaaaa ggcaggcact ggaaccaccg    12780
tctgccaatt cctagttttg cctataccaa atttgagcaa gttaattgac ctctcccagc    12840
ctcagtttct tcgtctgtaa aatgagggta gggatggccc ccagcccaca gggcagctgg    12900
aaggattaaa gaaatcaaac atctcttaga gcccacctgg cacactgtga tacacaacaa    12960
atgttagcta tttttgtcta tgaagtctag attttatatc ttgggtgttc taaagcagga    13020
tacatttatt taaaaacaag gattttcatt aaacacgtac cccacagaca gcaacccat    13080
ggagactgct cttaattcag gccagtatcg aaacgactct aactacaagc tttatacagg    13140
tctcttggct gtccttcaaa tccaactaag gtggtacttc tgaagcactg tgcacatgtg    13200
tgtgtgcatg cacacgtgtg ggaagggcgg gctcacggat ccctcaggta ccccacccac    13260
gcagtctcaa gtcacaaagc gacagagcag ccgaggaagg tctgtgcccc actgaccct    13320
cgtgaagcca ccaactctac ctctgcgccg tgtcctgcag actgggctac cctttgggtg    13380
gggaccagca tttgatgcaa gaaaggcaga cagaaaagga aaagggcaag ttcgactcca    13440
gataacacag acagtaccaa gccccagggt ccataaatgc cacgcagatg gaagcattta    13500
ctgcgaggcc acacagcaaa cgcacggatc cagggacgga ggtgcagact gcggtgccc    13560
tgagccatga ccctgcaaat taccaccatg ggaaaggagg ctgccaaacc ccccgacagt    13620
cggctgggct ggcacagact cgtggttttcc atcgaggtgg gaggaggtgg gacgtccag    13680
ccctcccc atgcccactg cagagggaag cggccgtttc ccctgtgtgg ttacaaaggt    13740
ctcattgttc ttcctcacag ggaggaaact ggaggaccga gctcagaacg catttttagaa    13800
ctggcagaaa agaacatctg gggaaggaaa cacatttcag aaacaaacat accttttgtac    13860
```

```
cagcttttat tttctttaag tgttgaaaaa ataataataa taaagacatg ccaaatttat   13920
catcgctcta caaaatccct ttattgagca aaacgtggca gctctacttt caaatgatta   13980
ctgttcctgg aaaattgcag caacgtggat gccaaggccc gaaggccgcc atcagcagcc   14040
aaacaaaaga tgccacctcg ggctccgcga cactgtacca tgccagggaa ctggacagat   14100
ttggggaatg ccacggtttg cctttaaccc cttgcctcct ggtctcctga tgcatctcag   14160
aggctaacat tctttgagga actggcattt cttagttgta aatatgcatg tgggtttggg   14220
agctgcctgc aaagtccagt gttgacgatc agctttgatt ccttggaat  caagtttacg   14280 tgtcgagtct ggaagttaag aagaatttgg agaagctgag cactatggtg ttgcaggccc   14340
tgggtgaact cttccaccaa gcattcattg tggactgaca gcgtgcgagg ggctctgcag   14400
gcaggtgcac aggacgaaac acattccgtc cgggggaaac ctgcaggaaa gctccctctt   14460
cttcctaagg tgccgggcct agcttcatgg gtccctaccc tccacgcctg tcacactttc   14520
tgagtctcat gtgggagctg cttctggttc ctgacttcac tcagtcctca taggaggtgg   14580
aactactgtc accccatttt acagatgggg agactgggca caaggggacc aagaaaccaa   14640
tgcaaagtca cacttgtggg atcagtgaca ggggagatca attcccaggt tctttctgca   14700
agagttaaat tgttttcatg ctgcctaagg gggggcaact gaaagaccac tgcatatctt   14760
tgccaaaagg gtcaagcaca ggagccgcag ccagtgggtc agatccgcag aggcgctggg   14820
gtgaccctcc ccatacctgg agggatgctt gtcccctcct ggccttcact gggtcccctc   14880
atgaccgtgg cctcccagga cctcagcaca atcccggtcc tgtgctccag acaagccct   14940 ccgtccccaa gactgtgagg aaatggaacg aagagggct  cgctgcagcc cagcacccac   15000 actgccctt  tcaggggca  agaaccgtcc tggaggactt ggctttggag ggggagcctg   15060
ggaggccagt aagtcaacaa gcctctactg ctcatggtg  ggatcccacc gcaggcccc    15120 acctgctggg gcgggcaggg acgggcggca cagcttggcc agggcagata ccccccacct   15180
tggccagggc gaaggcagga cacgtgggct ccagcctggc cccaccatcc ctgcacaaca   15240
ctgggcaaag tccacgtttt cctcaactgg gtgttgacat ctgcaggaca ggggcatgga   15300
ggtacagagc gctgaagcca cacagcaacc taggagcgag actccatgcc tccccgggga   15360
cccctcccca ccatgaggac catgaaggct tcccatgtgc cgcaaggact ctggtgtgga   15420
gacacacgtc tcctacacag ccaggcctaa cgctcttgta actgggtggt cccacctggg   15480
ctcacagctg gagggccagg agctcaaggc ttcgcagggt ctgctctcat cccagaggcg   15540
atggggagcc acagcaggct gcaggagaga gggtgggccc cctccacttc agaggcccca   15600
tctggcccac agactggaga gcacatctct cagcaaccac ggagcgccaa ctgcgcacag   15660
ggcctggtcg tcagagcggg gcaaaggcac tgaccgtcac ggccagggcg agggaagacg   15720
ggtgggcagg gaccttgggc agaggggaa  gaacctggtg cccaggctgg ccctgccttc   15780
agcagtgaag ctgagtgggg aggcgctgat gcaggggggcc agaaagggct gctggtcagc   15840
cgggaggagc cccccacaga ggaagcagcc agcccagacg cagatggcag ggtcccctca   15900
acaatgtcct ctgaaaagga gaggcgggga ctgctctggt gacacctaca aatagatagt   15960
cagccctcag ccccctgcca tacttctgac aaagcagagg ccccaggggg aggcgcaccc   16020
gaaggtaccg gcacctgtcc cccagactcc tagagcccac ctgaccccat cccaccaggg   16080
ctccagctac aaaataaatg ccgaggccag ctaggcaagg acgcacactc ggtaccgact   16140
gaataggctc cacgttgtca tgagcgcaac ccacaggcca ccaggccaca ctatgcagag   16200
ctgagatggt ttcggccaag cagcctctca gctgagctga acaagtccag agtccccggg   16260
```

-continued

```
gggtcgtcac tatggagtaa caattgcgat gcgatggtaa ccctaacagc taaccgtcac    16320
tgagccaggc cctgagctag gtacttttca acgctgcctc tctgcagcct caggacgagc    16380
ctgtgggagc ataaagatca ttccctatca cggatgggga aactgagctc tgaagcagtt    16440
aacgtgcttg tcccagaccg cagagctagg agcaggacac aacagcaggt caggcaggaa    16500
cgggtgaggg gggcctgcat gggcttctct ggaggctgcg catacacgca accccccagga   16560 ccccgaccct gcacctgcag ctcgctactg cccccctcagt gactccagca aacctcgggg   16620
taggggaagg aggctgggaa tacctcgggt gtccgaaaca gcagcttctg cttggaggcc    16680
actgctgcat aatggttgct gcccagcaca ccccaagcca cctgtgccac ctgtggtgac    16740
cttccagcat gccttggtga ccaagctggc cttaggtgct gtgggcagcc aagaatagaa    16800
cagggcccac ccctcctctt cacactaaca caaagcaaga ggcgggcact tcgactgagt    16860
gcatccctct agctcaaggg cctcacggat cacaggggtc agggcaagat cccaattctg    16920
cattcccgtc tgcctttcat cctgctctgc caacaacagc cagtgaggct ggggacatcc    16980
ctgaacctgt ttctcacctg aaacacatca taccattgga ccccagccct ccgggagagg    17040
ccctaatccc tgactgtggt gagatcagat cactggttaa gtacccagaa gggccttggt    17100
caggggctcc aggggtgggg ggtgatgggc gtggtggtat cccgctctgg gctatagtcc    17160
accctgatgg aggaggtctg tggtcagaac cgggctgtgc agggcacagg agcccagagg    17220
gacccccaga gctcacctgg tggtctctga gcagggctcc ctcaaccctc agagaaaagc    17280
acagcaagga ggccgcccag agcccagcgc ctagcaccca gtggcgtgcc agacctgcct    17340
ggatcctgga gatctctcat caccctccaa gtcagtcatg cccaacccag ggacccacag    17400
cccacggggc cgtgaaggtg tgctgagtcc aagaaggcct tcgacactgg gaagccaagt    17460
ggcacctcct ggtgtggagc aggcggaatc ccaccagcct ctgctctgcc agtgggcaca    17520 gctgacgat gagcagaagg ggctgttgct taataaacgt catttcctta agaggataaa     17580 accttcaaa acagatggaa attttttttt aattaaaact ggtggccaaa gagatggaaa     17640
gcacccctTg tgcctccctc ccatcgtgac ccatcctctg cacacctcaa gctgttcgct    17700
gcccaggtgt ctcctgaggc actggggcg ggtgagaatc cgtgagccct cggccagccg     17760
tggctctctg gagctctgcc ccaggccatc agggcacacg ccgggcaccc tgggggccac    17820
acagggcaga gcccagctgg gtcagcacac agggccacac tgggcacaca agtctctgag    17880
cctcccctgt ggacgcagct ctcactatcc caccccacta ggtcccgggg atctgtccca    17940
cagggtgata tgctgtcaca gaccactacc agagccatgg cctgctgttc cgcccgcagc    18000
caggtagtca cttgctccac agggacaggc aacgccgcac ttgggggctg ctctgcggca    18060
ggactagagc tccagcagct cagccctcct gagaaggaga actccatgct ctaagaggca    18120
gacgcagcgg acggcaccaa agccaccaca agcccacggg gccctgcatg gcaggtcagg    18180
agtccctgac cactcgctct ttgtaaccag agctgcagtg gagtctacga ggcaaggact    18240
gtgggcggca gtggcacag caaatgaatg agtgtcccaa gggagcaggc ggctgcgggg     18300
aggcacagcc gggacccagg agtcctccgg cactgcagca aactccctgg gcccctgag    18360 cagcgaccag gtggcaagtg catgaactcc cggggcata acctgggagg gtgacactct     18420
cttcgtgttc aaattcttga gaacgcatta aaaatatcac tcagtcacct actctatagt    18480
tttaactcaa aagtaccaaa gtagccaggc gcggtggctc acgcctataa tcccagtact    18540
ttgggaagct gaggcaagag gatcacttaa gcccaggagt tccaaatgaa cctgggcaac    18600
```

```
atggagggac cccatttcta caaaaaaagt gttttaaaaa attacctggg cctggtggtg  18660
tgtgcctgta gtcccagcta ctcaggaggc tgaggcggga gaaccacatg aacccagggg  18720
aggtagaggc tgcagtaggc tgtgatggca ccactgcact ccagcctggg taacagagtc  18780
agactctatc tcaaaataaa tttaaaaagc accaagccag gcttggtggc tcacacctgt  18840
aatcccagca ctcagggagg ctgaggcaag tggatcacct gagtcagaag ttcgagacca  18900
gcccagccaa catggtgaaa ctccatctcc actaaaaata caaaaattac ccaggcgtgg  18960
tggcgggtgc ctgtaatccc agctactcag gaagctgagg caggagaact gcttgaaccc  19020
aggaggcaga ggttgcagtg agccaagact gtgctactgc actcaagcct gggagacaga  19080
acgagactcc atctcaaaaa ataaataaat caatcaaaac caccaagact ttttaatata  19140
aacatttatt attccataat tcctttttg catgattaaa aatgtttata taagtttcc  19200
tgaaaatggt aagaatgcca agtgaaggct gcaaatgccc aagccccac cgtggcatct  19260
cacgagtct gggccctagg aggctggtgg gtaccacgtg gacccgagac ttcacagtca  19320
agtcccttg gggtacactg ggtttcccac accccagaaa tatgggctct tactgcagga  19380
ccatgggggt cctcacactt ggcccagaag ctgtcacata gccagacagg tgttctacaa  19440
cctaggctag agggagctca tgctccagca gaattcgagc cagaggaggt aaaagatggg  19500
taagatctgc tccctggaca gatgaggcct tggcctcaga acagttactg atcatctacc  19560
agacatcaca ctagaggcag aggggcgcag acgaagacag cccctgtcct caaggccctc  19620
ccaggttggg tggaccatgg aaggttccag acagatctgg caagagaagt gcccacacca  19680
ggggcagaag atgggcaggt ctgctcaggg cggcacggcc tgccaggcca aaaagttcca  19740
acttcagatg ctggagaatg ggcacgactg tctgagaaag ggaaggatgt gatgaaaact  19800
acttggagaa aaattaatct ggccagagca taagataaat gggcaaaggg gaggttccag  19860
aaagcaagga gaccaagtaa aagctgatgt cattggctct gaatctaggc tttcactgaa  19920
tatgcaccgc agggcctgta ggtaaagcct cagagcccag ggagtctgag tggaggagag  19980
ggcaggggac agagctgggg cctgtgtcta cagtgctcag gaggaatagg catgacgtc  20040
agctcggagg ctccagctga agtgaggagg cggccagggc agcacggcca cgcccggatc  20100
cagactcctt ttgggaagca agttcgctct gggggaaagt ttggagaaat ggcctttacc  20160
cgcagaagca agccccagaa catatcttgc tccaaaacta tctcgtacag tgaggacgtt  20220
aagcttcagg tcccctagag gagacagtct gctccttcct ggggcagaac ccaaggtggc  20280
cagagcctgg aaggcaccca gcacccaggc tggtgtgttc cagcccaggc cacacgctca  20340
gatagctatt aatgccccgt tgagcaattt cctgagagct ttgccaggca ggtaccgcct  20400
ccccatctga actaatacag gggtacatcc caaggaagaa atgaaaggtg cccacatttt  20460
gctctgggat taactaggga ggggagtgat aattaactca gtaattatat ttgccatcgg  20520
gctaatgcta aaattagtgt gcattagaat ttctttcctg agcagacacc ggagtgagtt  20580
gggcagcagg agtggctcgg gcaagtcggc acaagggca cctccagagc cttccacaaa  20640
tgtcagcaaa acccacaaat gtcaaggccg gctccactgc acccagcaga tgaattcact  20700
tccacagcct gagaccgcca gctcatcgga ggccatttaa aatccagccc tctgacacct  20760
gctggatatc accatttacc gtccccagat caagagatca aagggtggaa cctgatagga  20820
cggctctgaa gttcaccaca aaagcataaa cgtgcaagca gagccaatac gtcttttgaa  20880
aaggacaatg aggtgggaat ttacataact gatcttaaaa tatgttctga tgcttcagag  20940
atggagacag cagcattccg gtacacaaag acactcacag gcagtggagc acagtgaagg  21000
```

```
gtctggaatc aggacccagg tgtctgtgga cactacacat aaaagagcag catttacaat   21060
gaatggatag gatggaccat cccaccaagg tgttggacaa ctccctattc actggccaga   21120
cccctacctc ataccatata caaaaaaaaa aaaaaaaaa aaacccagac agaataatgt    21180
ctgaatgtaa aacataaaac agtaacagtc ctggaagaaa ataatggagg atatatttat   21240
aatctggaga tggagtaaca agggatagga aaaaagccat agggaaaaag tagagttatg   21300
attatatgaa gcttcttaat atctttatga taatgtacca ccagaaacaa ggatgaagga   21360
ctagctacag accagcagtg aaacctgaaa caaacagaac aaagaattaa agtccatacc   21420
aaataaagac ctcccacaaa tctataagaa aaagataaac aggctggcac cgtggcttat   21480
gtctgtaatc ccagcacttt gggaggcgga gatgggtagg tcacttgagg tcaggagttc   21540
gagaccagcc tggccaacat ggtgaaaccc tgtctctacc aaaaatacaa aaattagcca   21600
ggcgtggtgg cgcatgcctg tagtcccagc tacttgggag gctgagccag gagaacagct   21660
ggaacccggg aggcagaggt tgcagtgaac caagatggca atcgcgccac tgcactccag   21720
cctggaggac acagcgagac tctgtctcaa aaaaaaaaa aaagaagaa gaagaaaaaa    21780 gaaaagaaaa agacaacaga aaaatgggcc aaggataagt gtaggcaatt tgcagaaaag   21840
taaataccaa taaaccagaa atgagggttg tgcaaatcaa aaggtgttat aattttaac    21900 caaactggac caaagaaaac accaaaaacc aaatcttgt aattgccagc atcagagagg    21960 ataggaaa gtgtgtgttc tcgtagatgc ttgcaggtat gaactgctac agccttttag    22020
gagttatgta tgtatgtatg cttgtatgta tgtatttgag acagggtctc gctctgttgc   22080
ccaggctaga tctgttgcag tgctgtgatc atggcttact gcagccttga cctcctgagc   22140
tcaatagatt ttcccacctc agcctttcaa gtagctgaga ctacaggagt gtgcaatcat   22200
actcagctaa ttttttaaat tttttgtaga catgggggt ctcccaattt tgcccaggct    22260
ggtctcgaac tcctggactc aagtgatcct cctgcctcaa cctcccaaag tgctgggatt   22320
acctggatga gccactgtgc ccggcctcaa tatctttaaa aacagaaatg gacacactct   22380
ttgactagga atgtatccta taaaaacact tatacacatg cagagacaca cgagcaagca   22440
tgctttgtaa tagcaatgaa ggctggaaaa actcctcaat caggtaaatg ctgtcaagtg   22500
cacctgtgta ctatgaaatg gcacttggct tttaacaaga gcaaagacag aaaagcaaaa   22560
gtacaaagta gggtgtgatg gcacatgcct gcagtcccag ctactcagga ggctgaggca   22620
ggaagatcct ttgagcccag gagttggagg ccaggagctg ggcaatagtg agaaaaaata   22680
aaattaaata ataataataa taaaataggc tgggcacagc ggctcatgcc tgtaatccca   22740
acactttggg aggctgaggt gggaggatcg cttgatccca ggagttcaag gccagcctgg   22800
gcagcaaagc aagacaccca tctcaacgac aaattttaaa aaatcagcca ggcaggctgg   22860
gcatggtggc tcacgcctgt aatcccagca ctttgggagg ccgaggcagg cagatcactt   22920
gaggtcagga gttcgagacc agcctggcca acgtggcaaa accctgtctc tactaaaaat   22980
acaaaaatta gctgggcatg gtggcagatg cctgtagtcc cagctactga ggcacaagaa   23040
tcgcttgaac cagggtggca gaagttacag tgagccgaga tcgtgccacc gcactccatc   23100
ctgggcgtga gtgagactcc tgtctcaaaa aaaaaaaaa aaaaaaaaca aggagccagg    23160
cacggtgggg tgagggaggg cacagaagca gcgcctcttc tgggggcacc cccaatctct   23220
agcgatccag aggcctcagg atcctgaagg gagaaaaac gtgaagctcc gtgctagaag    23280
agaccataga gattggaatc agctggttct attttacaaa aaaaggaaac tgaggccctc   23340
```

```
agaaggtgag tgcctctcaa tgccccacag ggaggcaggg agagggctct gagccctgca    23400
gggccctgga ttcttgcaat ggggtggagt ggagcctgtg ccgccccac caggcacctt    23460 ctcaggagag gagccgttgt catatccttg aagggtcct tgagcccctc aaaaggctaa    23520
aaaccacttt cctccttgag tgaaccttca cctcagttta accacaagaa aaactacatt    23580
aaggcccagc gcagtggctc atgtctgtaa tcccagcact ttgggaggct gaggtgggtg    23640
gatcgcttga gcccaggagt tcaagaccag cctgggcaac atagtgaaac cctgtctcta    23700
caaaaaacaa caaatcagc tgggcgtggt ggtgcacacc tgaggtccca actacttgcg    23760
ggctgaggtg agaggattgc ttcagcccag gaggtagagg ctgcagtaag cggtgactga    23820
atcactgcac tccagcctca gcaacagagc aagactcaaa aaaaaaaaa aaagcaggcc    23880 gggtgtggtg gctcacgcct gtaatcccag caccttggga ggccgagcgg gaggatcagg    23940
agatggagac catcctggct aacacggtga accccgtctc tactaaaaa tgcaaaaaat    24000 tagccgggcg tggtggcggg tgcctgtagt tccagctact caggaggctg aggcaggaga    24060
aaggcgtgac cctgggaggt ggagcttgca gtgagctgag atcacaccgc tgcactccag    24120
cctgggcgac agagcaagac tccatctcaa aaaaaaaaa attaaatctc aaaaaaatt    24180 acattaaggc aaactaaaag atgtttaaaa tatatatatt aaattaaata cactccaata    24240
gagcaaatac gaaataccc agaaaacaca atccccgcac ccccaggaca acctcccagg    24300
gggtccacag caagagaccc caagcacgag agacagagaa cagtgtccct gtggcggaac    24360
ctctggccca tcaggctcta ttagaaaata aggctcttgc cactgagaga aagaggcaca    24420
gtcgcccagc agccacgggc tctggcacac cacgagtcag gccagcaaag tgtcaactgc    24480
cccctacaag gtgacaaact aggacaaact ggaaaccaga ggctggacct ggagcacagg    24540
gaccaccaca tggggctggg gaatgggcag ggacctcaga gcgccaccca catgcctaag    24600
agcagcgcgt atgcgcatgc ctctgcatgg cttaggggaca cagggagctc ccccaccc    24660 caacccagga aggcagcccc cactacccag gtagggaacg gataggacca gcaccccgtt    24720
ctgctcgtaa ctcagggctc caggcccct cggggggcaac cagcacagag ctcagacccc    24780
aaatatcttc acccacctcc tggtccccat ctggacaagg gtgctgggga ctggctctca    24840
gtcacaccct cggggtactc ttcaaaggac agctggatgc cccagggcag gagcttttgg    24900
cccccagctc cctcacccca gacaccagct cttgggaccc caccagcatg ggcaaggtgg    24960
acaccatcgt cccgattttg cagatgagga aactgaggct gagggctggc acacggctct    25020
ccagagctga agagaatgca gagagcagcc ggagccagcc ggtgggtccc tgaggccggc    25080
tcgtagcaag ccacagctgc ctccgcccat cacacttgga cctcactggc cccaggacag    25140
ccctccaggg cggcctggca cagagcccac accctgctgc ttcctgaaca aataagtgaa    25200
caaggccacc aagccgagga cctggatgta gccccggctc ccgccagggc ctccccaaca    25260
gactccccat ttggagagcg cattaagtgt ttccaaagcc tcacaaacca cagatgtccg    25320
gctgtctcac ggcttctgta acctgaactt ggccctcact ctgccctccc agcactcctc    25380
tcagggccca ggcccctcct ctgagatgcc agcactgact ccccaacttg tccccatcac    25440
ctggctcgtt cctgaacctc ggcaggagag tctcaggcca gatcctccca ccagccacct    25500
ccaccaggat gcaggaggca tgagacctgc tcgtgccggc tggagatgc aaccaaccaa    25560 gatcaatcca atcagcggat gaactgacaa atataatgtg gtccctccac acaatggaat    25620
attattcagc cacaaaaagg gctgaaatag gccgggcgtg atggctcaca cctgtaatcc    25680
cagcactttg ggaggccgag gccggcagct cacttgaggt caggagttca agaccagcct    25740
```

```
ggccaacatg gtgaaatccc gtctctacta aaaatacaaa aattagctgg gcgtggtggc   25800
gggcacctgt aatgcaagct acttgggagc ctgaggcagg agaatcactt aaacccagga   25860
ggcagaagtt gcagtgagcc aagatcgcac caccgcactc caacctgggc aacagagcaa   25920
gactccattt caaaaaaaaa ataaaaggct gaaacaccca tacgtggtac tacttggatg   25980
actcctgaaa acgttacagt aaccaaggaa gtcagccacg aagacgcatt gtaagattcc   26040
cttcatgcaa aatgcccaga acaggcagaa ccacagaggc agaaagtcga ctggtgttca   26100
ccaggggatc cggggagagg gaacgggaag tcaccgtgta atgggtatgg gttttatttt   26160
ggggtgatgg aaatctctta aacttgata gaagagaggg ttgtaaacac tgtgaatgta   26220
ccaaatgcct gccttctata ctttaatatt ttatattata taagtttcac ctcaatttaa   26280
aaaaaaaaca actcgacacc tttcacctag gaaagatctg gctttagctt gcatttcctg   26340
taactcctgc ctaaagcctt ccagaagctt ccgctgcctt gtggatcaca accagactcc   26400
acaccatgat ctggcctcta agggcctctc gcaggacacc ccgagggtga aggagcaccc   26460
gtgggcccac ctctgcatag ctgcaaagct tctttccctg tcctcccctc tacatgggaa   26520
gctctgcccg caggggcggg gccttatctg ccattctatc gcactcaacc ctagcacttc   26580
actcggtagc agacaccaaa gcaaacagc aacagcatta taccgggcca ggtgcacgtt   26640
aactcactga attcatggta ggaaggattc tattcccatt ttacaggtga gaaaactgag   26700
gcacacaaag gtagcatcag cttcctaagc ctcccagcac aggaagcggc caggctggaa   26760
tcagaccctg ggcgcagggg ctctgtccac agtgctaact aactactcct gcccccgagg   26820
gctgcagcgg tgagtgagtg agtttgtcag tggactggat gtccaaggtc atacaggaaa   26880
aatccagact attgtaataa cagcctctag accggctggg gccagaaaga tcgaggacgc   26940
tgacacacaa ctgcgctcac tgcagctctg ccagggatgg ggctaaaggt ctcacacagg   27000
gcagttaggg ctccccatag cctgggagag gaacggggtg agataacaga aactaggtat   27060
ggtgcccgaa gtcaaacagc cactgagcat gtaaacccag gtgggtctga ccccaaaccc   27120
ctccaccccc atcagccctg caacccgtcg ctgcaaggga gaaagcaact cagaggcctc   27180
acctgcctac atcccccacc cgtgtgtgtg agttctacta aatgcctgag cagtgacaca   27240
gcacggctga aattaaacgg gttccaaaaa cgacaggaag cacgaagtga atctccccag   27300
gaaagtgctg aacaaatgct ggatcgggtt caccggcgaa tttcttggaa ctgaagaggg   27360
gagctaaaca cacggggccc tgctttggag gggactctct cagggtgctc cacacagcac   27420
ttggttaacc ccactcagcc cttctgggct ctcccagagg gcccggcctt ggccttgggc   27480
atctacagga ggaacctcca gggggagagg gggtgcctgg acaggccggc cctggaacaa   27540
gcacttgggc cccgaggaga gaggactagg gcttgggagc tggggaagtt ctcagcactg   27600
ggaccactag aacaaagcca tttccgtgcg ttcacagctt ccaattgcaa caggaagcaa   27660
tcaggaaaaa taattagcgg cccacttact ggcttcgctg aggtccgagg catgtatttc   27720
acacagtaaa accagggata taacatcaaa accgttctgc agaaagattc ctccctttcc   27780
ttccatttta ggcctggatc accacattca ctggggctcc caggccttgc tgcctaatgt   27840
taaaataatc aactctattt ttgcctcaca cacaactgaa ctctacagct ataattcttt   27900
ctcctcaggg gctcgaacca catggacgac aggcatttga ctccagcaac atcacccaa   27960
aacgtgcaca aaacccaaaa ctgcaatgag gtgaaaggca acgcggtcgg cctagaaacc   28020
ccccctttaa aacaaacagt ttccccaaaa cccctttgc ctccttgacc caggcatttc   28080
```

-continued

```
cggaaaaagg agcggcgctg gcctgtactc cccagatact gtcgctgttt tgtcttcacc    28140
ttgttttgct agctccagac aaggccccac aatgtaaaca cgctcctgaa agaggcagat    28200
ttggggtgaa actgtccata gaatctctag gcttgggtca gaggcaggag gacgtgaaac    28260
aaactccaag ctcctcctgt tccccgctgt cccccacacc tccaagcaga ggctgcagcc    28320
tgggggatct gactacaggg ccaccccgct gcaccattca cactggaaat attcagggag    28380
acagctgttt gccttaagga ggcccagaca aaggggcccg aggtcctccc cgctaaactg    28440
ccacaaacag aacaggagcc gcggcgtgca caggcacttg cggccgtgcc acttggccag    28500
ccatactcca gaaaaacaaa acacgcacat ccgaagagaa tgatttaggt agcaagaggc    28560
ttgcttgaaa aaccacatgg caatctccaa attaaaagaa catgtgtagc gtttcacgac    28620
tgcttaagtt tcctgagtcc tcctgacctc aactccaccc cctgggaaac accaaaagtt    28680
ggatgagaaa gttccccgc cctacctctc cccacgggag tgtacaactg aggcacaagc    28740
ctgcctcccc cactgccccg cgatctggga ccacgtctcc tccgcgtagc cgacccgggg    28800
atggacacta tctggggacc cggcggccac acggggcatt cgggtcgccc gggcacctgg    28860
caggtgtcag tccgcttgga aacccacagc cacgcggctc acaggagcag cgccaccggc    28920
taggccgccc cgcgcccggg ctcagaactt tctcgctgcc acttcagccc gtcctcggag    28980
cacgcggggc ggccgcgcgg ccgctggaaa caggcttgcg aaccggctcc ccgggccagg    29040
cccgcctccg cgccccaagt cccgctcgg tgcccggccc gggccacacg ggcccagcgc    29100
gggctcggct cggctcccgg cttccgcgcg gctcgggcag gtgaggaccc gcccgcgccg    29160
cacctggcgg agcgggcgcc ctcctcgcca gcccgggacg cagcgtcccc ggggagggcc    29220
cgggtgggga gacaaagggc ccgcgcgtgg cggggacgcc ggggacggca gggggatccc    29280
gggcgcgcgc cccaactcgc tcccaactcg ccaagtcgct tccgagacgg cggcggcgcc    29340
cgcgcacttg gccgcggggc cgcccggggcc attgtccgag caacccgcgg cccgtcttac    29400
acgccgggcg cgggaaggta tcgaatcagg                                     29430
```

<210> SEQ ID NO 8
<211> LENGTH: 33769
<212> TYPE: DNA
<213> ORGANISM: Homo sapiens
<220> FEATURE:
<221> NAME/KEY: unsure
<222> LOCATION: (33739),(33749),(33758)
<223> OTHER INFORMATION: Identity of nucleotide sequences at the above
      locations are unknown.

<400> SEQUENCE: 8

```
cttcccctta cactggtcct tcgacccgcc tcggatgaaa actgaatggg tttagcctta     60
gaggctctcg gtctctaagg gaggtgggtc aggatgccgg ggacagggtc ctcttcctgg    120
ggcaacgtgg gggaacgagc cacctacccc tccactgaat tgccctgggg tgtgggtacc    180
gacggctcat tcggtgtcca gggtctgaga tgtgttgaca ggaagaatga aagggggatgg   240 gagggatggg gcgaaagaag ccacctgcag ccccaggaac tatctggcca gcacaccgtc    300
acccagcggc ctgagccacc cctgccagag ccaggaggag accctgccaa tgggtcacca    360
gtgtgcagga actcagaagg tcatcacagt taataccctc catgccccaa tgtgggaaaa    420
caggtttttt cacaacaaac aagataattt ttgttatttt ggcaaaagga ggcagggcag    480
ccccggacac ctccatccca cctcatcacc cagccgcagg gccccggcca tccctgcaga    540
cagagtggat gtcacaacct ccctgcaccg aaccaagtgc agctcccagg ccacaggcca    600
```

-continued

```
cccaggaaag gtccagtggc ccccggaggc tcccaccgca ggcctcccac cacagccggc      660
accaacccag gatagctgtg ttctcctggc ttctttttcac acgggtagca gaaagctgag     720
atccggggaa agctgagatc cagggaaagc tgagaatcgg cctctgctgc ccggacgccc     780 accccccagct ctgctcccag ctccagggcc tccttctcag gtgcccttac aggaggcaga    840
gggcttgagc cacctcctgg gcctgggca cgcaggatga acgggtcac ggtgcaggcc       900 actgtccact gcgcagatcc caaggccata acagcctgg ccacagtggc ttcccagctg      960
gcaggcggcc agattatttt tgttgtttag caattgatta agtttctccg ctgcccccag    1020
gggtaagtgg tggggcaaat gccgcaaccg cagcatttga cccgggatcc tgtgccaagt    1080
gaccataggg tcacaaagca caagggaagt ggctgggccc gatgctggct ctgctggaac    1140
ctgaggccgg ccactgtcac ctgcacggtg cctgggacct tccagcaagc acagagaagc    1200
tatggccctc caggagcagc tggcaggcac cttggcctgc agtcaggggc tctgtctgct    1260
cagctctaaa acaggaaagt cgctgctctg cctggggtca gggcagccag agagtgacca    1320
agtcagtgcc ggcctcagga agggacctgc aggcgggtcc cttcctctcc catccctcgg    1380
tgccagccag cccctcctgt ggcccccac tgcctgcctc tgcccccatg ccccaccaca    1440
acctcaggcc catggctgca tggccactcc ccaggcaggc agtggggatg ggatttcacc    1500
atgttggcca ggctggtctc gaactcctga cctcaggtga ggagttccta aagtgctggg    1560
attacaggcg tgagccaccg cgccagccct ccctgtggta ctaaacactc acccccctt    1620 gctggggacc ctggtgaggg aacacagcct cacaagtgaa gtgtggtttt gttgagcaaa    1680
tgacgcctgg gcagccctct catctttgcc taaaactgaa gaatttaggg gcgtggatgt    1740
ataaaacagt tggtgactta aatgaaaaag aaggccacac tccccccttt aggcaggcgg    1800
cctaattctt taaaagccag cacagggtgc ctttctgaac ccaggcacac agtaggtgtt    1860
caatggacag cagcggttac ttgtactgct catgacaccc tgtctgtggc ctctgcagct    1920
ggctccagcc tgacgcatgg ctgcgcccct ccgcaaggcc accccggtat acatggaaac    1980
tctgtggaga aggccttggg ggccggccag gacgccaggc ccagatccca tctgcgccct    2040
tcctccatag acctcagcga gctctcggca ccatgtgcct caggcccatt taagaagtag    2100
ggccggccag gcatggtggc tcatgcctgt aatcccagca ctttgggagg cccaaggtgg    2160
gtggatcacg agatggtcag gagatcgaga ccatcctggc taacacggtg aaaccccatc    2220
tctactaaaa atacaaaaaa taagccgagt gtggtggcgg gtgcctatag tccaagctac    2280
tcgggaggct gaggcaggat aatcgcttga gctcagcagg cagaggttgc agttagcgga    2340
gatcgcgcca ttgcactcca gcctaggtga cagagagaga ctctgtctca attaaaaaaa    2400
aaaaaaataa aaaaagaag cagggccagc cacgacgca ccctcacaca gctcccagga     2460
cgcgtgcctg ggtatagggc tcaggaccat gaccgctgca gtggccccca agaaacgtta    2520
cttttgtcac ccaccccgcc tcagtggcag tagccaaaat aacggattag aatgaaccca    2580
tgtgacaatg ccactgcccc aactgacaga agatggctat cagcagttca cgcggcccca    2640
cctatcacaa gtgcagggca ctctacaact tatgcatcct tccccagaca ccgtcctttc    2700
gaccctccca ggtcagcaag gcacacaggg cctacatttc acagccacac agcagagggc    2760
tgaggctgga actcggatgc tctgatttcc gttcaatcac atcccagag gtggcacaga     2820 gacgggggc ttctcttgac aaagtcaaga aagtcactgc cagctccact gaagaccaaa     2880
gaacctcagc tctcaaaccc tcttgaaggt gttaccgaac tctcccagcc tgtttcctgg    2940
gtcccgatgt tggtcccgtg ggacacagga agaggaagaa gctccctaga gcagagcctg    3000
```

-continued

```
gtgcacctgc cacactctca gagggctgcg cacgggcgga ggagccgtgt gcaggagtgg    3060
ggtctggatg gaggggcgct gtggccgggg gcaggggggca ggggaagggt gctccaggtg   3120
gtgggcacag cacgagcagg ggcagggagg tccacactca gatgtgcaca gggagaaaca   3180
aatcgtgcat ttccattgga ataggcggta aaggtagaa aaacagagtg ggggccagga    3240
agggagtcgg agccttctag tgtctctctg caggtgagcg gcagcccgag gtgtcagctc   3300
agcagacttg gggtccaggg gccgtgtctt ctatcactga ccccagggca cacggaactg   3360
gggaggggaga gcagaggcac agggcacggt cagtgaaacg aaacaaggag tcatcaccaa  3420
atgcggaaag ggcaaggagt gcccgcagcc gcacaagggt tctgtctggg caacgtgggc   3480
gtccccaccag gccccgcacc ctgcaagcgc aaagctcgcc actgaagata aagggaagct  3540
gttggagctg cggagctggt ctggggtccg catggagctg ggcttatgct gcagtcacaa   3600
ggggggacatg gaagaggctg caggggacaa aaccagtgac cacagtctaa ctctgagcct  3660
gtggaaaggc gcccacagca ttcacccatc ccagagatgc cattccccct gtgccccgc    3720
tccacggtga cagcgttctc caggaatatg atgcgcccct ctcctcttgc atcagccctg   3780
acagtgagta ttcaggccaa aaagcagaag agcacagctg cgtggttcca tttccatgta   3840
gttctggaac aggcaacgct aatccaaggt gatagaagtc aggagagtgg tggaggggc   3900
gggggttgag gatggcaaag gggcaccggg aactttccca gtggtagaaa tgttctctgt  3960
ctggaccgtg tggtagttat gcagacatat gcagctgtca aagttaatcc aaatgtacac  4020
gttaaaatgt gtcgttta ttgcctgcaa gttatacctc aattaaaaaa ataaagttag    4080
cactcaggct tcttccacaa cttcctgaac cgtgtgagct gatttttcttg ctattaaaaa  4140
ttcacgtcc atggctgaga acagcagctg ccttctgttt gcaaagtcaa cgccaatcac   4200
tgcccggccg cggcagactc ggccccacag gacctccttt ctttttttccc tttgacctac 4260
ttccctgata agtgacaaga cagccagact ctgggaacaa acgcccgtta ttcggccccg  4320
agctgagcgg gccctgcttc ctgagctaat ccgcccggac agacggaggg acgtgagggg  4380
cttttgccgtc ggctccagct gtcagtctgc ccgtcagact cgacagtggc cccctctgtt  4440
cctcccgctg ccccccactcc atccccgact tcttttttgtt tcctgtccct gacagacgaa 4500
catctgttaa aactctgtct gggtgagctg tggccagcgg cccacaaatc cccaagccgc  4560
accccagcct catctgggcg ctgccgggag cactgcctgg ccaccctctg gacatagctc  4620
tgagagccac cggccagggc acgtgtggcc cgagtggcat ggtgcacgcc gctaagccca  4680
ctgcccaaag gccccaagc aggagggatg tgcaggagac aaaagtcaaa agaacagggg   4740
cacgttccac agaggatggg gctggagggg tggcagtgag gaacagcagc ttccgaggat  4800
ggcggtggca actcccaaat aaggcctcac tcctgctgtt tttagctcat tccacataat   4860
tggaaaaaca tggcagaaac cgaagccagc tgctgccttg gtcctggggc tgtgtggagg  4920
gggtggggag gccggaggcc caggctctgc actcgactgc tggggatgag agtgactctg   4980
agctgcagag agcagcatcg cagccgccat ggtcccattg agccccggcc acgctgggcg  5040
gcagaggctc gtgggatata cctgccctgt ctcatggggg tcacttcagg aggggcgggg   5100
gagccaggac acagcccagg gctagcggtc accctgcagc tcaggggcca cgtaaatagt  5160
gccaccttga aggcacacag cagtgcgggg cccccccccgc caccaacgca tccctacctc  5220
taggaggccg cctgtgtgcc cctgggaacg ctgctccctg tcccttgggg tcctggtgtg  5280
accaccctct cagccccttc cttggggaag gcacctgact ccctacaccc agctggcttt   5340
```

```
catttgctca aaatcaggaa aaagcagaat tcaagacatc acagaaatgt cttcgcctgt    5400
aactccatga agataaacg gtcagacacc caggagggag tcccagggac ccttgagtct    5460
cacctgaggc tctggcttca aacctcgaga tgtttccagc catgctagcg ccgcccccca    5520
caacctgccc cacacagtcc tcccttggga actcacagat ttggccccca cctgcccgt     5580 ttcttctggt ggagtgggtg cgttgggttg gggtggggct ggggactctg gatgtgtctt    5640
aagagtctga gtgattctga cacagccagg ccctgcccc  ctcctgacct tcgcccaca    5700 ggaaagggag ccacacgcct gaagcgccca gcacaccccc ctccgtcctc cccaggtcac    5760
ccgctggccg tgtgagccgt gctccccact gccccttcac ccaccccagc tcctcctggc    5820
agcacccagc cttggaagct acttctgatt acaaccgccg aaggaagact cgctccctcg    5880
gcactgaccc agacagcctg caccatcacg ctgctcagca aacccacac  agccttcctc    5940 caaacccat  ggagcgggga gtataatcac cccctttcta ccaacggaca aactgaagca    6000
cagagaggtt aagtcacttt cctaagctcc caacacgatg acaaaaaata gaaggtcagc    6060
ccgcaagtgg aactaggtgc tccaagtccc cggtctgcct gacactgcac ctcctcgccg    6120
ccacggtccc gggtccgcct gacactgcac ctcctcgccg ccacggtccc gggtccgcct    6180
gacactgcac ctcctcgccg ccacggtccc gggtccgcct gacactgcac ctcctcgccg    6240
ccacggtccc gggtccgcct gacactgcac ctcctcgccg ccacggtccc gggtccgcct    6300
gacactgcac ctcctcgccg ccacggtccc gggtccgcct gacactgcac ctcctcgccg    6360
ccacggtccc gggtctgcct gacactgcac ctcctcaaca ccaccacggt cccgggtctg    6420
cctgacactg cacctcctca ccaccaccac agtcccgggt ctgcctgaca ctgcatttcc    6480
tcatcaccac agtcccgggt ctgcctgaca ctgcatttcc tcatcaccac ggtcccgggt    6540
ctgcctgaca ctgcacctcc tcaccgccac ggtcccgggt ctgcctgaca ctgcactttc    6600
tcaacaccac tccttggccg gctcccaact acaaaccaag ccatgtcttc catcctgaat    6660
cctcttggcc taaacatcac tcacaatgcc tccctcggga acaggcacaa gtcccaccag    6720
cacagcctcc ttcgttacct gcgtttccgc tagcccaggg ccagtccag  agccctcacc    6780 acagagcctc tatccttcac ccccggacac tggacctcac caacccatag cctggaggag    6840
atccctgtgt gaccccaggg cctcctctgc ccgactctga atttcactgc caacgtgac     6900 acctcggaag gctctctggg cactggcagc cctccatggg caccgctcct tctggccagc    6960
tctgacatcc cggctggtga ggtgccctgc acgaggcctc tgcccactgg gacctcacag    7020
ccgtgctgtc agctgcaaca agcgacagaa tttcacgttt tcttcacgtt gcccctgggt    7080
gagcagctcc aggtagtttt cagtcgaggc gaggcgtccc gtcagcagcc aggcggcaca    7140
gctaattcat gcccgccggg cgcacggccg caataccaat gggcacctgc agcctggaaa    7200
gccacagagg aaccgagaac agcgactgtg ctcaggtgac aggactgtgg tcttttaaca    7260
aaacattttc ctttaacgtg atattttacg gcaaggaatg aaacctggag ggcaggacat    7320
ttggatacta aagccccagg ctgccgcgtg gtctgctttg tgaagtctga agcccgcgcc    7380
ccattctggc cccgctcaca ggtccggctc tgactcacca gcttcaatgc taggccgtgc    7440
ctgtcctcca accagaacat gacttcctta aggacaaagc cgtttctcgc ccatccccat    7500
ctccctctgg attaagaaat atgggaagat cttctagaac cacctcaaat ttgcagagag    7560
ccatcctggt gacaaaccct tgaaatgctt ctaagaagag tttaggtttc ttctcaactc    7620
taaaacctct agaaaactct atttccacac cagctgcccc tggaacactt cagcttcaaa    7680
agggcccagg gcagggagac ggaggagcca gcatccacac cgagcaccag cctgttaatt    7740
```

-continued

```
aacgggaagc gggtggggcc catctccagg cagctctgag gtcagactgg ggaaccatgc    7800
ttacaaaaaa aagtgaactg aaacgctcac gtcctcatgc aaaaccagac tcccagttgc    7860
atctttctgt ctcattgagg agcttttcc tcccttgac agaacaccct acacacggca      7920
tctggaacca aagcagaaag attcaggctc agagtaaaac agtccccaca ctggctgcat    7980
gtggacgttc ccggcccaga gtctcgccca agcagggcct ataaatgaca caaaatgttt    8040
ttctcctgcg tgccagtcat gctccaactg agttatgtgt aaaagtgcct ctcacggctg    8100
agggcaaaaa cagttcccac aagactagag aaaggtgacc cctgacggct gagtctctag    8160
ggagcgtgga gctgcgtgct cagccctgcg gccctgacgg ctctggaatg aaaagctat     8220
ccaactggaa gggcagggct cgctgctagt ccagcggtcc aaccccacag gtgtctgtgg    8280
tgtcagctcc atgccacaga gcccagggct ggggccagag ccaccaggcc cctgccagc     8340
ctgcaggggc ctcctcctct gggtagccta accaccccct gtgagcgcag gcagcctcct    8400
ctaatcacca cagggcctgt cccccctct ccccgcttg caggaaaatg agccctgagg      8460
actccccagg gctgctctgg gcctggacat ggagactggg aattacattt gcagaaggag    8520
cgcaatgccc ttgaagggct cagccacgag cagccagtcc ccagggctca gaaggcccag    8580
ctgttagaac cctgggagcc agcaaagagc caggggctcc acctaagtct atagcccctg    8640
cctcttctgg ttgggaaaga atcaacgcc ccttactgg ctcccactga cagcccactc      8700
ccccaggtat gggaggattc tgggacgatg caggcaaacc tggaccctga gtgaacctgc    8760
cccagctctc acgggcctgg caccagccac agcacctaag gcgccggtca tggtgacaac    8820
atgaaggtga taagggcatg gacagtggac atggcagctg gacactgggc acccactgga    8880
tgccaggcac ccagcacggc tccgtcaccc ctggatgagc agtggccctt gcaagccag     8940
ggtagcctgg gcaagttatt tggggggtctc caagcttgtc cagctgtgcg acttcactga   9000
gccatgagtc tgggattttta tcagggccca cacccgttcc tggaactctg atacgtgagg   9060
gagccacaca gggacccta acaaaagctc ccagggcaac atgttctctt gcctcagtct     9120
cccaaatagc tgggattaca ggcgcacgac taccgcccgg ctaatttttg tattttagt    9180
agagacaggg tttcaccatg ttggccaggc tggtcttgaa cccctgacct caaatgatcc    9240
ttccactgtt agggcaaggc acctgacagg cacgactgca cgatctgctt gttggggct     9300
gtgtccattc cccactcctt cgacaaatgt ccacacccag ccttgctttg acacccaag    9360
aacagagatg gtgacacctg cttcctacat gccattgct ctcccaaggc agacatcccc    9420
agcagatgca acacagtgtt taggcagaca tcaccaatcg atggtggcaa cagacaccag    9480
gccctgctcc ctctaactcc agtggccagg ccccaagcca gctctcacct gcccactccc    9540
aacccacagc agcaagactc agaaatggca aaaacacaaa gagaacagaa acgcccata    9600
gcggaggat gactaaaaga catgtcttga taagatattg ttcaggcata ggccaggcac    9660
agtggctcat gcctgtgatc ctagaacttt aggaggctga ggtaggtgga tcacctgagg    9720
ttaggagttc aagaccagcc tagccaacat ggtgaaaccc catctctact aaacatacaa    9780
aaattagcca gacatagtag cgggcgcctg taatcccagc tgcttgggag gctgaggcag    9840
gagaattgct tgaacctggg aggtggaagc tgctgtgagc cactgtactc caacctggac    9900
aacagagcaa gactctgtct caaaaaaaaa aaaaaaaaaa gatatccttc actaaaactc    9960
atgtctttga tacatatttta cctcctgcaa tcgcaaatgc ttctgcagtg cataaagtga   10020
aataaatagc aggaagcctt acggttcgat cacccacaca gacacacagt cacatacagg    10080
```

```
aaaaacgcag ggagggctgg ggaacaaaaa aacagaagat aaaatgtgga gacagacaca   10140
ccaagagagt aagagaccac ctccagacct cccttcagct tctcaaacac acgagccggg   10200
cccgttacag aatttgcggg gaccgctgca aaatggaagt gcagacagcc ccttactcaa   10260
aaggtaggaa tttcaggtca acaacagagc tcacctcata tgactacaca ggtcacacag   10320
cccgtgaagt cggtcccaac accagcatgc tcctgcctca aagccgctgc acgtgctgtt   10380
ccttctcgcc tttccctctt ttagtccttc agatctcagg cctcctgaga gagacctctg   10440
acctgccggc tcaggcggcc acaccccag tacaggagtc tccggctcag cccctgctgt   10500
gttccgtacc cgatccaggt ctgtcctatg tccatctgtg tgccggcttg cttcctgaca   10560
tggcccccac cacacgtgtg cctcggggca ggggaacagg cccgtctcat taactgcttt   10620
cttctcagat attttctgga atatttgtgg atattgggca acatatatgc tccacctttt   10680
tcagactagc caggacgagc tgcattttt tttttttttt tttgagacag gtctcactc   10740 tgttgcccag gctggagtat agcggcatga tcttggctca gtgcaacctc cgcctcctag   10800
gctcaagcaa ttctcctgcc tcagtctccc aagtagctgg gattacaggc ccgtgccact   10860
actgcccagc taattttat attttagta gagatggagt ttcaccatgt tggccaggct   10920
ggtcttgaac tcctgacctc aaatgatcca cctgccttgg actcccaaat tgttgggatt   10980
acaggcgtga gccactgcgc ccggcccgag ctgcctgttt tacacctttg ccatattccg   11040
gtgattctct ctcccctccg tcccccggcc ctgactgtgg tggccactcc ctgccgtcat   11100
gagcccgtat gtcctcactc tttcccttc cgccaggact tcaaccaaca ctgcagagcg   11160
cagggtccag ctccagcact gagttcagcc tcttctcacc aacagacagg caggaaagaa   11220
aacaaactct gagaaggcca aggttcccgg gcagccagca agccaagcat ccttctccgc   11280
tgaggcttgt gcagccgagg cacccctcc tccagggagc aggcagcgtc ctgggcagt   11340 ctgcgaggga gaccagggcc cttgctccac cagggcccca ggtatggggg cagcagcaaa   11400
ctcatggctc tgggagccag accccacctg ctagaaccta ctatgccacc tgctgtgggc   11460
aaccccaggc tggtgacttg ccctggcctc tctgtaaac aaagggctca tccaacctgg   11520
tcaaaccact cctccccttc aagggtctat aatcctccct taacctgctt ggtccaaacc   11580
cctggtgtcg ccaggtcact caggaggcag ctcatctgga ctccttccct gggtccagtt   11640
tctctctcaa cattgccttt gaggccgagg tgaacggtca acagcgaagg gccccagagg   11700
tgatggagga gcgggtgtcc aagacactca cctttctaa tgcactgact ccctcgtgga   11760
ctcacttgtg ccgtctcccc cacccaccca gccccagagc ccagagtgcg agcgccgag   11820 gcccgggatt ctgtctgcac cgcggggtcc ccagtgcctc ggagcaatgc cagcacccgg   11880
caagtgttcg acaaatgcct gctgaatgag caaatggatg gatgaacgaa tgaatgagca   11940
agcagatgaa tgaatgggt gctgtccaga gccgtgagga ctaggccgcc caagtcccca   12000
tttctcaaat tctccttctc ccgacttggg aaacaagatg cttggtcggg gaggctctcc   12060
aaccatcccc tgcagcagcc ggcacagcgg acagacccctt tgatgtaaca gccatgtctt   12120
cattaaagat gccctgctct cagaaagaga aagacaaata caaacctgga aaatcctcac   12180
caaacgcagg acccctgcca gggagcagag aaaagaccca cacgccacgg gcgccacgac   12240
cacacacaca ccccagccgc tgcacacaaa cacagaccct agccagcaag aacaggggga   12300
ccaggaaact gttcctaaag tcaggacccc catgtgctca gacagcagtg agagcaagga   12360
cacttctcca tccaccggat gccaggagag tccttttagg gggccccaca ccagagactct   12420 gcccttagga ctgttcctga gtgtggaagc cagcccactt ggaagccccc tgccctcccg   12480
```

-continued

```
agtgggacac cggcacagga agcaggccct gtcccccacc actttctgca agctgggccc    12540
catcacgcta cagaaacggg gaggactggt cccagggatg gcgctttcct gacacctctc    12600
gttacccccT cgcttgccag gccccagggt cagcccagA ggccagactg gctatcccag    12660
gcccgggagc atcccCGAAg gcgagctgca tcctgaacgt gtgtgatttc ccgaagggcc    12720
cgccccgaac cgacacctgg aaagaaagat cctcagccgg tgccccagag gagaagagcc    12780
atgcctcact gcaacacagt cccaggaagc accaagtgcc tgaggaccaa ggcggagagt    12840
aaaaaagtgg aaaatatctg gggcaaaaat aaaacaaaac aaaacaggat tgacctcctg    12900
ggctcaagca atcctcccaa ctcagcttcc cgagtagctg ggaccacaga cttgaatcac    12960
cacacccgcc aagtggatca tttcgaacgg gtttgccgag gttccttctg ggcaccccc    13020 ggcggccgca acccattccc gccaggcccc gccccgcccg cccgcccgt cccgtcccac    13080 cgcctcacct gccttacacg tcctgccgtt gtcctgcagc tgcacacccg tggggcaggc    13140
gcatgtgtag aaaggctcgc ttggggacag caggcacagg tgggagcagc cgccattgtc    13200
ctcctcacag cgagtgtgga ctgagaaaac caggacagac tgagagaagg ttccagaaga    13260
ggaccgtcac ttgtttctga atgagtcaca tcctgcctcg tcccccgtga cagcctccag    13320
tgtgtccctc tgcccaaaca tcggcctcaa gtggcatcag ggacctcccc gcgggcacca    13380
ttccacctgc ctcatcgctg gccccgtcca catgggcccc tcagcctggc cagacggcct    13440
gcaatttccc caaaaccagc cgtgaccttc ctggccaccc tcacacccag atgtgacctg    13500
cccatggagt gacatcctcc ccatctgctt cctcccacca agctcctatg actagaacac    13560
cctccccagc tcctcggagc ccccaaagga caccctctg caaaggctgc ccccacgct    13620 ccaatgccg gggtcaggac ctgcctgtgt ggtagtgacg ggaaccccag agacaatggg    13680
ctcctgggca aaaggcttgt cttgtctttg tgctatgtgt ggacccagca gcttccatag    13740
gaacactgtc cttcttgctg ggatggccaa gcttgtcact ctcccaagcc ctcctatgac    13800
caacagcaat tgaacggaac tcgataaatg cttccagcac ctcattcaaa ccaggggaaa    13860
gctgggtgta gcagcccaa aatacggata taactggaac aacaaactca tcaaaatgaa    13920
cctctccctc cctcatgctg ccccaagtgt agatgggttt tgtgaccacg actttctcac    13980
caggaaacag ctccagagag ccccaccctc ctgtgtcctg ctctgggaac agctggcacc    14040
cctaggcccc acatttcaat tcaaagtcca aaccttccat aatggcctgg ccagaaatct    14100
ccatccctgg tccctgtggg agtgggccac tgtcccaga gccgcagccc cactgtcaca    14160
gaagctggtg catttcccca tcagggacct ctgtcacaac ccagcgtggc ccccaggctg    14220
agaactgctg attctgggca gattattcat tgataaatac gcgacttgca gggcaagca    14280 tggtggctca tacctgtgac cccagcactt tgggaagtca aggtgtgagg atcactggag    14340
cccacgagtt tgagacaagc ctgggcaacg tggcaaaatc tctcatctct attaaaaata    14400
catacacaca cacacacaca cacacacaca cacatatata tgtatatata aataaccata    14460
tatatatata cacacatacg tgtatgtgta tataaataca tatacacaca cacacagaca    14520
acttcttctg ggccttgaaa acgaggcaac cttccttgga aatccccttg ccactgctga    14580
gcctgaaata gccccatga gctctgcaga ggggtcctct gcaggccgt gtcccccagc    14640 cagccacaca cctccctcca ttgcagcagg taccccttta gagaggggc ccccagagc    14700 atgggcttct gcagggaggg gtcacctgcc cccacccc acccacgccc gcgcacccc    14760 acgcccccgc atcctcccac tcccctgccc cgcgcccccg ctccccccag cccccctcacc    14820
```

```
ctctccccg tgccccaacc ggcactcaca aaaaggctgc cgctcctggc tcagcacctg   14880
gatgtccatg ggtgagtata gggcactcag gatctccttc ctcttccccc cagtgcgctt   14940
gttgcaggca tggatggagc gggtctgcca gtctgtccag tacagagtgt ccccggagag   15000
cgtcagggcg aagggtgcg tcaggctgcc ctccaccacc ttctgcctgc agtcagggaa    15060
gcggggtgga ggagccatca ggagggtccc ccgacagtca ttgctgctga cccaattaat   15120
ttcttttttt tttttgaga tggagtctcg gtctgtcgcc caggctggag tgcagtgatg    15180
taatctcagc tcactgcaac ctccgcctcc cgggttcaag caattatcct gcctcagcct   15240
cccgagtagc tgggatcact gatgcccacc actacgccca gatgattttt gtattttag    15300
tagagacagg gtttcatcat gttggcaagg ctggtctcga actcctgacc tcaggtgatc   15360
cacccacctc agcctctcaa agcgctggga ttacaggcgt gcgccaccat gccaggcttc   15420
ccatttgctt tcaaccagac aagtgaggcc aggtcaagag ccccaggagc tggcgccctc   15480
gtacatttct cccggcgtgc acagggcacc tcccaaacac agcctgtgat ggtgacacac   15540
gggctccccc aggtcaagtg gcaaagtctc cccagggaa gaaaggagga agccatgcct    15600
ggcaaaaagc acacctctcc tgcccaacgc tttaacctct gtatacaaat caggccatgt   15660
gcactcgctc cttcttacaa tgctcataat ttatactttc agagtaaatg aaacttggca   15720
tcaacccgag aaacagctat tcttttctag atgcttacag tgcccagcaa atgaggactc   15780
gggtgtaatg agattatgga cactggaaac aggatcataa tgtgacgtgg tcggtaatgt   15840
gcagttttat ttgcttaatg accctcgccc cgtgacaggc tccctgaggg tgggcctggg   15900
ggcagaggtc cccgccacgt ccccagccct cagcacagtt gccaggagag ggtgacactc   15960
atgaagtggc acaggaaga tgggagctgt gggctctgca gatccaccac ctcttctgtt    16020
cattttgtt gatgctgttt tttaagaaaa ttattgaagt aaaattcaca ggacatacgt     16080
ttactttttt tttttttttt ggagatgggg tctcactctg tcacccaggt tggagtgcag   16140
tggtgtgatc tcagctcact gcaacctctg cctcccaggt tcaagcgatt ctcccacctc   16200
cgcctccaga gtagctggga ccacaggcgt gcaccaccac acccagctaa tttttggggg   16260
gtatcttttt ggtagagaca gggtttcgcc atgttgccca aggctggtct tgaagccctg   16320
agctcaggcg atccaccgc cttggcctct caaagtgctg ggattacagg cataagccac    16380
tgcacccagc ctaaatttac cactttaaag tgaatagtgt tacctagtgc attcgcaagg   16440
cggtgcagcc tccacttctg tctagttcca aagcacttcc attgccccac aggcaaaccc   16500
cacacccggc agcagtcatg ccccagtccc cgcccccagc cccggcaaac acttttgatg   16560
gacttaacta cacacattct caacatctca tataaacgga atcacaatat acagcctctg   16620
atgtctgtct tctttgactt ggcaccatgt tttcgaggtt catccaggct gtagcatgtc   16680
agtgcttcat cccgttttag gggtgaacca tattccagtg tgcagacaga aaccaatctg   16740
tgcatccatt cacccactgg gggacctttg tgtcatttcc accctcggct gttgtgcaca   16800
gtgctgctac ggacattact gtccattcac attttgtgtg aagacctgtt ttcgattctt    16860
aagagtatac agctaggagc ggaattgctg ggtcatacgt aaatcaatgt ttacgtctca   16920
aggaatcaac aaactgtttt ccacaatgtt gtctttttg tttgttttct gagacagggt     16980
cttgctctgt cacccaggct ggagtgcggt ggtgtgatca tggctcactg cagcctcaat    17040
ctcctaagct caatccatcc tcctgcctca gcctcctgag tagctgggaa cacaggtatg   17100
taccaccatg gccagctaat tttctaattt tattttttt tgtttttgtt ttttgagac      17160
agagtctcgc tctgtcgccc aggctggagt gcagtggtgc catctcagct cactgcaagc   17220
```

```
tctgcctccc gggttcacac cattctcctg cctcagcctc ccgagtggct gggactatag   17280
tcaccggcca ccacgcctgg ctaattttt tgtatttta gtagagatgg ggtttcaccg    17340
tgttacccag gatggtctcg atctcctaac ttcatgatcc acctgccttg gcctcccaaa   17400
gttctgggat tacaggcgtg agccaccacg cccgaccttac ctttaatttt tttaatttta   17460
ttattttatt ttattttttt ttttttgag acagagtctc gctctgtagc ccaggctgga    17520
gtgcagtggc gggatctcag ctcactgcaa gctccacctc ccaggttcac gccattctcc    17580
tgcctcagcc tcccgagtag ctgggactac aggtgcccac cacgatgccc ggctaatttt   17640 ttgtatttt agtagagaca gggtttcact gtgttagcca ggatgatctc aatctcctga    17700
cctcgtgatc cgcccgtctc agcctcccaa agtgctggga ttacaggcgt gagccaccgc    17760
gcccagcctt tttttttttt tttttttt tttttgagata gagtcttgct ctgtcgccca    17820
ggctggagtg cagtggcggg atctcagctc actgcaagct ccgcctccca ggttcacgcc    17880
attctcctgc ctcagcctcc cgagtagctg ggactacagg cacccaccac cacacctggc    17940
taatgttttg tattttagt agagacgagg tttcaccgtg ttagccagga tggtctcgat    18000
ctcctgacct cgtaatccgc cgcctcggc ctcccaaagt gctgggatta cacgcgtaag    18060
ccatggcgcc cagcccatgt ggccattttt cagtgagaga agccagaggc ccatcactct    18120
cggttgctcc ctgggccatg ctctgcctca gccagaagca ctgagggaag gtcagcctcg    18180
gcccttgccc cagccacagt cacagataaa ggggcctgca caggtctgtg tggctccaga    18240
gctcgtcacc caacacacga cgcttccatg tgaatagccc caggtgcatc atgaagagcg    18300
atggccgctg cagaggcaga agaatcccgc ggggaagcag gtgggagaga ggctgagaac    18360
agaccagacc ctggagctac agaccctatg ttccaaccct ggctgggact agctgtgtgg    18420
ctctgggcaa attcacatgc ttctctgtgc acaggggatc aaaatagcaa acacaggcta    18480
ggcacagtgg ttcacaccta taatcccagt gctttgagag gccgaggtgg acacatggct    18540
taagctcagg agtttgagac cagcctgggc aacatggtga acctcgtct ctacaaaaaa    18600 ataccaaat aaattagcca ggcgtggtgg tacgtgcctg tggtctcagc tacttggaag    18660
gctgaggcgg gaggaacact tgagcccaag aagtcaaggc tgtggccgcg tgtggtggct    18720
cacgcctgta atcccagcac tttgagaggc tcaggtgggt ggatcacttg tgatcaggag    18780
ttcaagacca gcctggccaa catggtgaaa ccccgtccct actaaaaaaa tacaacaatt    18840
tgccaggcgt ggtggcgggc acctgtaatc ccagctactt gggaggctga ggcaggagaa    18900
tagttagaac ttgggaggtg gaggttgtag ttagccaaga tggtgccgct gcactccagc    18960
cagggggaca gagcaagact ccatcccaaa aaaaaaaaa acaaacaaac aaacaaaaaa    19020
agaggtcaag gctgcagtga accatgattg tgccaatgca ctccagcctg ggtgacaaag    19080
tgagaccctg cctcaaaaca ataaaaatat aaataaaaat aaaacataat agcaaacgtt    19140
tcatagaggt ggtatgagca ttaaatgaac tgataaacgt ccctggaaaa cagtaagtgc    19200
tatggaagga ttcgctgccg ccaccgccac caccattagc atgtttcaac ctccatcacc    19260
ctcactgtcc cctgtcacca tcctttgacc agggcactcc cagctgcagc ctttctatcc    19320
tcttgtccac ccttcataac tgtaagatca ctcagctccc aagaaccaca gtctacaggg    19380
taaccacatt tccaaatctc aaaccagacc cgctggtctg cacttccagg acaacagga    19440 tattttcaaa ccagcccaaa agagatgtgt ggctcagcat aagaggaaca ggagaaactg    19500
aggcctcttg ccctgagaat gagcttggaa gtggatgtcc cggcctcact caaaccttca    19560
```

```
gatgactgag gcccagccag gagcttgagt gtaccctcag gtcataccct gagccagaag    19620
cacccagcta atccactcct catcactgac tccctcccca taaaaaacct gtttgctgtt    19680
tcaggctgtt aagttgtggg ctgttttgtt acacagcaat ggataactaa cacacgaggc    19740
ctggcaagtg tggagcaaag ctgcccaagc cctcaagtct gttcatgtgg gtgttggcct    19800
gtgtttgcag aaatccagcc actgagtcct cccatgcagt cactactgcc ctctgcacag    19860
acacctgcca catccctgcc tgggccagga gctccactag tgcaggaatg gggtctgccg    19920
tcccaggagg atccctgaca cctagcacag ggctagcagc aggcagcact tggttagtga    19980
ataaactgcc cttcacctgt acacagaagg gatgtttcta taagggtaa ttaagtacag    20040 agctgggaag ctatgctgac cagaaggctc taaaagcaat taaccaacga ggggaaaacc    20100
cttcctactc attctcggcc cattttattg agcactgacc atgtggaagg cccctggtg    20160 agactgggga atgcaccaat aactgagaca gcttccggct gttgccctca ggatgcctga    20220
gctgggatag ggccagggtg ggggtggtgc gtgtgacagg gttactgttc acaaccctgc    20280
cgggccataa gccctcccca acaattccaa atccaaaac gctctgaaga tggaaagctt    20340
ttgttgctca tctggtgaca aaacctcatt tggtgcatgg gccgggtgcg gtggctcacg    20400
cctgtaatcc cagcactctg ggagccgagg ggaaggatcc cttgagctta ggagtttgag    20460
accagcctga gcaacatgtg agaccccgtc tctaccaaaa atacaaaaat tagccaggtg    20520
tggtggcgca ctcctgtagt cccagctact cgggaggctg aggcgggagg atcgcttgag    20580
cctgggaggt gggggctgca gtgagctgag attatgacat tgcactccag cctgggtgaa    20640
agagtgagac tctgtctcaa aaaacaaag ttaaaaaaa aaaactgtg catgggtgtg    20700 ggctacagat agtcttttct gccctactta gaatgaacgt gccacatttg ctatagaaat    20760
attcaagggc tggtggcaaa tgccacacag accctgacgc tgttccaagt tctgagaagt    20820
cctgcattcc tcagggcccc agagtttcag agaagagtct gtaggcctga gttaagaagg    20880
aacgccttca aaagccctgg ggacaaaggg gaaagggtg ccccaggact gcgtgggtac    20940
ctaccggaac gagccgtcca ggttggcacg gtggatgaag ctgagcttgg cgtcagccca    21000
gtagagcttc tgctcctcca ggtcgatggt cagtccattg ggccagtaaa tgtccgagtc    21060
cacaatgatc ttccgggtgc tgccatccat ccctgcccgc tcaatccggg gcgtctcacc    21120
ccagtctgtc cagtacatgt acctgtgacg ggggcagggc aagagaagca gctaacacag    21180
atctgttttt tgttttgtc tgcatagatg cagacatgaa acaacagaca gtgaacttgc    21240
cctaaaatct cacccatcgg aaataaccaa caggtatggt ttcaggtatt cctgccttaa    21300
gctgggcaat caaaatatac tatttccaac ttgttctcag ttaacagtaa attctgggca    21360
ccttcccttc ttgtggatag aaagattcct tgttcttttg atgattgcct agtgtactct    21420
gctgtaagtt ttttaaagaa cttcaggtta tttctgattt ttttgctacc atgaaaatgc    21480
tgtaaatgaa cctctaaaag gcaattcaaa acactcagga tggaatatta tttagtggta    21540
taaagaaatg agctatcggc tgggcccagt ggctcacacc tctaatccca gcactttggg    21600
aggccaaggc gggtggatca cgaggtcggg agatcaagac catcctggct aacacagtga    21660
aaccccgtcc ctactaaaaa tacaaaacat tagccaggcg tggtagtgag cacctgtagt    21720
cccagctact taggaggctg aggcaggaga atcatttgaa cccgggaggg ggaggttgca    21780
gtgagcagaa atcgcaccat tgcactccat cctgggcgac agagcgagac tccatctcaa    21840 aaaaaaaaa aagaaaagaa aagaaatgat ctatcaagcc atgaaagac atggaggaaa    21900 cttaaatgca tgttagtagg tgaaagagcc aatctgtatg agtccagttc taaacactct    21960
```

-continued

```
ggaaaaagca aatacacaga gacagtaaag catcagtggt tgccaggagt tggagaggag   22020
agggatgaat gagtggagca cagaaaatca gggcagtgga actatcctgt atgacatgga   22080
atggtgggtg catgtcctta ctcatctgtc taaaccaaga atgtacaaat caagggcgaa   22140
ccctcgtgta aacgtggatt ttgggtgatg gtgcgtcagc cagctttcat cagttgtaac   22200
aaatgtacca ccctgcacag gatgctgaca gttgggaagg ctgtgtgggt gtgaggacag   22260
ggatgtatag gaactcagta cctgctgctc atcaattttg ctgtgaacct acaactgttt   22320
gaaaaaatta agtctattta aaaacaacaa aacatggcca ggcacgatgg cttgcacctg   22380
taattccagt acttcgggag gctgaggtgg gtgggtcact tgagccaccc tgggcaacat   22440
ggcaaaatcc cacctctaca aaaataaaa attaaaaaaa agttagctgg gcatggtggc   22500
acactcttgt agtcccagct acttgggagg ctgacgtggg aggatccctt cagccctggg   22560
aggtcgaggc tgcagtgagc tgtgactgta ccactgcact ccagcctgga tgacagagtg   22620
agaccctgcc taaaaaaaaa aaaaaaaagg ctgggtgcgg tggctcatgc ctgtaattcc   22680
agcgctttgg gaggccgaga tgggcggatc acgaggtcag gagatcgaga ccatcctggc   22740
taacacggtg aaaccccgtc tctactaaaa gtacaaaaaa aaaattagc cgggcatggt   22800 ggcggacacc tgtagtcaca gctactcggg aggctgaggc aggagaatgg cgtgaacccg   22860
ggaggcggag cttgcagtga gccaagatca caccactgca ctctcagcct gggagacagc   22920
aacactccgt ctcaaaaaaa aaagaataaa acccatggct gggatggacc ctgaacctgc   22980
agctgcagct gttcctgggt aggtctgtgg gcgacgtggc tttgcttctc catgttccca   23040
agagacaagc atcacccatc catgagaaac aagcacatcc tcagggcgcc cttacgtgat   23100
ctctggccaa tgaaccaaga caaagtgagc agacaccagg tctgggatgg caggtcccac   23160
ccccaccagt gcccagtgtg ccctgtttgg aggtgaccac agggtgtgtg cccagaggct   23220
gggcgtgact ctcagcggag accagagggg aaccacacca gcttggagga ctcagttccc   23280
atcccagcca gctgggatga gccacaggac acaagggctg gcagacctat tgtgttttgt   23340
ccacccttca cagcagagaa aggggacagt gcccagaatg tcctctgagg agcctcctcc   23400
cactcttggt ccttgtaaaa tggtgctgac tcccttgctc ccttcttcct ggggtgggcg   23460
gcaaacccca ttcccctcag ccttagcaag tgatttagaa acaggcagct cgcccaagcc   23520
aggcatgaga gtgatcccgg gacacaggga gaacaagccc cgctttgccc tctggggtc    23580 tccattcagc agaagaggca aatgacagac acacagccgc ctcctccccc accatggtgc   23640
tctgcagcct caggagcctc aggtgcacca agggccaccc catccagggg gccatgcttc   23700
cttgagtggt atcgttcctg agcgagtacc atctccacct tccagagggg ctgtgacaag   23760
atcaacaaga atgagggcat aggagcctcg aaccaaacat gccctcttcc ctgcagaggc   23820
tgactgcgcc cagctgctat caccaagccc ctgctcctcc ggcccgtggg gacagggta    23880 agagggtgt cacatggaac agctctccaa acagtccctc tcaagctgct gtctcctgtg    23940
catctagtga gaacccaacc aacaaaggga aggtgggaat tgctattccc attaggcaga   24000
tgagaaaact gaggccccga aaggctggcc tgttccaggt tacaggcgct gagcggctgc   24060
tctgggaaca cacttggtgt ctgctgaggg cccgagcccg gccatcatat gactcaccct   24120
tcgccagcaa agcccgggtg tgggtgaact tttcctggca gcctgggact ccaaggtgct   24180
ggcagccagc ccagggaagg ctcccgcgtg cctgcggcag acgccttgct ttacctgcac   24240
gtccccaccc ctaggagcct ggacagagcc cagaccctcc gccacctcct gagaaggtat   24300
```

```
cagggcatc agtctggact tgggggggaa tccacacagg ccttccccaa atgctccacc    24360
gtggcccatg gaaaaggctg gaaaacgtgc aggagcagga gcctccgcat ggagcataat    24420
tcacattcct tccccgagtt tcataacaga ggcctgctgg tttccttaaa tgggaatttt    24480
gcgagccagt cggtgaccag agactggttg gcgtggacgt gctcttgcag agtctcaaac    24540
gctaccacaa gcccagccaa attcacggga ggaaaatcga cttccgaaga aaagagctgc    24600
agcatggcct tcgtgcagag ccagctgcgg ttgtggttgt gtgttatttt agggaagggc    24660
cattttgcat tttaaagagg gggttgggtt tcaccctggc tttaatttga gacccggggg    24720
ccactgcagc cccttgtcag gctggtacag gccggggact cctcccatgc taagccagtg    24780
tctttctggc cccagatcct caggggccag agggtcatcc ccagagcccg ctctgccacc    24840
cacatgggta ccctgggcct gggagggatg tgccttccct caaccctgcc tggatgtccg    24900
cacgggcca cctgcattgc tgaaactgca acgaagtcga gtctcaggag ggcccccct    24960
ggctgcaggg ctcttgatcc ttttggccac gtgcacactg aggtggacgc tcggaccccag   25020
agaccccctt catgatgatg gccggggcag gaaccccctc ctctgaggaa ggaccctggt    25080
gggggacagc actgcaggag ggcacaggag atgacggggg ctctagcagg gccgggagga    25140
aggccaagat gctcctcgca accgtgtgcc tgtggccagg acagaggaca aacccacctt    25200
ccactgtccc cactctcagg acagcagtcc tgccccagga ctcagcgccc acacttatgc    25260
ctgaggacca ctattcaagt cagtatttgg cgagcagggg ttgctgccgc gggcgctgtg    25320
acaggctgga atcctctccc tctccctctc cctctccgga gacatggagc ctacagggac    25380
agagtcagca cctcagggta ggaccatggc tggcgtcatc agcatcactg gatctgatga    25440
gtgggagccg gcatctcact gttttcactc tctcattcaa atgactggag caaagggaag    25500
gtgtgggag aggcccagga atcaacacta aggtcaactt tgccccagg ggcaggggtg     25560
ggagtgaaca gccacaggtg tgatcctggg gagggcttct gggagagaat tcagaggcaa    25620
gcatgtagag gaaccatttc aaatagttaa gaaaagccag agccaaacag ggacagttgg    25680
ctcgcagaga tgatgcaggc aaagccagct cagatctgag catgggaaag actactccca    25740
accaagggcc cagcatctcc caaccaagca ccaagtacct cccaaccaaa tgccaagcac    25800
ctcccaatca aataccctcc aaccaagcac ctagcacctc tcaactggac accaactact    25860
cccaaccagg caccaagtac ctcccaacca agtgccaagc acctcccaac caagtaccaa    25920
ttacctccca accaagcgcc tagcacctcc caactgagca tcatgcacct cccaacagag    25980
catctagcac ctcccaactg atcacctccc aacctagcac cgagcacctc ccaaccaagt    26040
gcagagcacc tcccaaccaa gtgccaagca cctcccaatc aaatacctcc caaccaagca    26100
cctagcacct ctcaactgga caccaacaac tcccaaccaa cgccaagca cctcctaaca     26160
aagtaccaat caccttccaa ccgagcacct agcacctccc aactgagcat catgcacctc    26220
ccaacaaatc acctagcacc tcccgactga tcacctccca acctagcact gagcacttcc    26280
caaccaacat agcaaaagcc ataaagaagt aaaaagacaa aaccacgtag gcatggagac    26340
tggacttctg gtggcgagga aagggcattt ttattataac gacagctaac atttgttgaa    26400
ctcacaaact gttcttggtg ttttcctcat gacatgcagc atggtcacgc tctgtacag    26460
acaaggatac tgaggcacag agtggcaccg tgccaacctt gtctcatctt tttatcgaac    26520
ctacatgcag agtgccagca aatccagctg tctttctct tcagaacaga tcccaaatct     26580
cgccactcct tacccccaca agtgaggtgt cccgctgct gctttctgtc gccaggatcc     26640
cggtaataac cgtggagagg gctcctgccc ccacgccacc caccccacag ctcactctcg    26700
```

```
ctccagccac cagggatgc cttccagcac gagtcagagc tggcacctcc tctgctcgag     26760
acctcatgtg tcctctcctc acaccttggg ccctgtttcc ctacattctg ctacagcccc     26820
tcaaacaggc cccgccccaa accagcccag ggcctttgca ctggctgatc cctctgcctg     26880
gaccgcgctg cccccagaca gccacacggt tctcagcctc atctgcttcc agtctcgact     26940
caaaagtcac caagaggcct tcccagcacc tgagctccga cggaagcccc tcgccacagc     27000
acccaagcac tgctttatcc ccctacgcac acgtcccttt caaatactat tcatttacca     27060
tctcctccca ctcactgaaa gggccagaga ctgggctata cccgctgcgt ggggagcagg     27120
accaggcgca agggctcaca aatgcagtgg atgcctggtt gggaggtgag ggagctgcag     27180
cgacccacgc tgggagggaa cgcaatgaca ggaggagcgc aggtcctggc gacacgatgg     27240
ccatggcagc cgctggtgag caaccgcagg ccggccctgg gagagggctt ctagcaagct     27300
gctatcttca gcctctccga ctactgcaga tgcccctcc tagccagaga cactgctaca     27360
ccagccgacc cttccaaaaa gaaggtcagt aaccccgcga ctcctggagc cacagtgcag     27420 gggagaggg ctgagagggc aacagttcac caagcggaac agaggctgcc ccggaggtca     27480
gctggctccc cggcagctgc aggggtggct agcccactcg gagggcagcg agggcatacg     27540
aggggctcca gggatgagtg gttgcccagc acagcacccc tgggaggccg ggggcacttc     27600
tcaggtagtg ggggcacgag gctgctctgg cctgacctca gggactcaaa atactttggc     27660
gataaattcc accgtgtccc acccctgctg gtaccccata cttacacaca gactggttca     27720
gatgcagaca ctctcgcgca catactcgct cacacgggca catacgcgtg cacacacagt     27780
cacatgcgca cactcataca cacacaaata tccactcaca cgcatgcatg cacacacacg     27840
gacacacaca ggctcacacg tatgcacgca tatgcgtgca cacgcacaca cacacacaca     27900
cgctcacatc ctcccactcc cacactcagt tgctcagaca cacacacgcc tggctctcac     27960
acaaacctgt tgggctctga aaggctccag cccttcccat gctcgtcaga agccagtcaa     28020
tggcttccta agtcaccaca cagatcaaag aggtgaactt ggccacatgg cactctgctt     28080
cctgagctcc caaacaccag ccttggtgag gacagaccct caccccacac cctcattccc     28140
actaccctgg gcaggcccag aggaggggca tctgcaggat ctggcaacca gcccctcccg     28200
cccggctcct gcagccggca ccatgggagt caggggagg tcactgcaaa gggcaacagc     28260
aagttggtgg ccccaggact agagcccagg ggtcttcagt cctactccag agcttggaca     28320
ctgtcccaca gggcatggcc aagggaaggg cttccagagc cctgacttca gggaggaggg     28380
caggcgggct cctgtggcag gcctggatgc atggccgccc actcctggga ctttctaacc     28440
tagaatatct aggtcaggct gggtgcagtg gctcacgcct gcaatcccaa cactttggga     28500
ggccgaggag ggtggatcac ttgaggttag gagtttgaga ccagcctggc caacatggcg     28560
aaaccctgtg tctactaaaa atacaaaaacc tagccaggtg tggtagtgca cgcctgtaat     28620
cacagctact caggaggctg aggcaggaga atcacttgaa ctcgggaggt ggaggttgca     28680
gtgagctgag atcgtgccat tgcgcaaaga agatctaggc cggcccctca accggtgagg     28740
tccaggctgg gagtgctgag agactgtggt gacactgaat gaactaacag gcaaagggct     28800
tccaactgag cctgggggtg gtgggaaatg gctcttgtgt tctagtcaag acctctgcca     28860
accagttctg acactgaccc agcacagaac ctgacaggtc agcaagggcc agggcttagc     28920
acagcccagg taagggtgtg tgtacggccc ccagagtcac tcccaggctg caagaaaagg     28980
gacaaaggag ggacaagggg tggccaagca aactgttccc tctgctcggg agtctgggt      29040
```

```
gacctggcct agctggccag tggagctggg ccacctcccc ttaaactctc caccccggac    29100
ttcgactcca aagctttcct gccacccacg ctctccccac ctgggatcac ggccaggccc    29160
tgagccttca agggcccagg tgaactcagc cagactagga gctgaggagg acacagggca    29220
gcttccagaa cggacccgag aaccactccc agcaggttct gcttccagac aaggagctgc    29280
acttttcag ccaatgcaat tagaaagcca ggagaaggtg caaattccac ctgcctgagc     29340
gtccgcactt cccaggccgc ccaccataca cacagcaaag atgtgtttaa ccattcaaac    29400
ccatggccaa ccacatcggt tgcctcagac atgcaagttt taaaaggaa cataactatg     29460
ggccaggcac ggtggttcac gtctgtaatc ccagcacttt gggaggccga ggtgggtgga    29520
tcacctgagg tcaggagttc gagaccagcc tagacaccat ggtgaaaccc catctgtacc    29580
aaaactacaa aaattagctg gcgtggtgg tgggcgcctg taatcccagc tacttgggaa     29640
gctgaggcag gagaatcact tgaacccggg aggcgaaggt tgcagtgagc cgagattgtg    29700
ccactgcact ccagcctggg caacaaggga gactccatct caattaaaaa aaaaaaaaa     29760
aaaaaggaac ataactatgg agtctcaagg ggaagtaatt ccttcaacaa taacaaatct    29820
tgaaagctga gctctttttt ttttttgaga caggatctcc tcactttgtc gcccaggctg    29880
gagtgcagtg gtgggatcac agctcactgc agcctcgatc tcccaggctc aaatgatcct    29940
cctacctcag cctcccaaga agctgggatt acaggtgcat accatcacac ccgattcatt    30000
tttgtatact ttgaagagat ggggtctcac catgttgccc agtgtggtct tgaattcctg    30060
gactcaggtg atctgcccgc cttggcctcc cagagtgctg ggattacagg cctgagccaa    30120
caccccacg ggttcatttt cagagtcgca ccgagtgctg gggttacagg cctgagccaa     30180
ccccccacg ggttcatttt aagagtgaca ccgagtgctg gggttacagg cctgaaccaa     30240
ccccccacg agttcatttt cagagtcgca ccgagtgctg gggttacagg cctgagccaa     30300
ccccccacg ggttcatttt aagagtgaca ccgagtgctg gggttacagg cctgagccaa     30360
caccccacg ggttcatttt cagagtcaca ccgagtgctg gggttacagg cctgagccaa     30420
ccccccacg ggttcatttt cagagtcaca cccttttttct gaaaacaac ttgggctcat     30480
gcaaattcga gagagagatg gtgacactcc ccgcccctg gacccaggtg gagtcgcagc     30540
agggtttacc cgtgagcggg gtccaaggcg atggccctcg gctggtcaag gtcctgccag    30600
aagagcacct tccgggatgt gccattgagg ttggccacct cgatgcggtt ggtctctgag    30660
tccgtccagt acagcttctt gcccacccag tcgcaggcga ggccgtcggg agagaccagg    30720
ccggagatga ccacgttctg cacggcggcc cccgtctggt tcaggtaggt ctgcttgatg    30780
gcctcctcgc tcacgtctgt ccagtacacg gctcccttgg aaaactggaa gtccactgcg    30840
gccgcatcct ccaggccgct gaccacgatg gtggactcca gcttgactcc gccggcgtcc    30900
accagccgta cgtcccggcg gttggcaaat agcaggagcg gcgaggctgt ggggcagaag    30960
caaaccgtga gggccactgg ctaagccagc aagatacaca gccctgggat ggagcactat    31020
gcccagagca ctcctggtac tgccctgccc atgcccaaga cctccagttc cttcctccca    31080
cccctaaggc gttgtcagga agttgcctgg gcagccccgg cccgcatcat tcagaggctc    31140
ctgcagcgca gcaaacagcc ttcttcccac attcggtgac agcacctgtt tgtttaccaa    31200
ctgttacgtc tgttccccca gatatgggtg acccttcctg ccatgcccaa aacctccac     31260
atcgtcctcc agaggctaca ggggccctgt cctgttctgc agagaagcca catccccttt    31320
gttggcctga cacaggggat ggggacatgc aggcacagca ctggccatgc tgctcgctac    31380
agacccagcc acagggccac atttttttgag gggttcagag cccaggccag acagagcctc    31440
```

```
aagattccct tacaagtctt tgaccactgt ccaagctcag gcccgtttcc ttggccgtgg    31500
catcagcttc ccatccaccc ctgtattcca tgtttctccc accctgcttc tggacattcc    31560
tacatttaaa gggtcactct ggaatgccac cccttggctc agacaccttc cacagctccc    31620
tgtgccagtg ccatgcagaa caaggtcaga cccccctagcc tggcctccaa ggccttggcc   31680
tctggcctca cctacacttc tctccaccac cccaccccaa gcattcctga tctgcctgcg    31740
gccaggctgg ctccctcacc tccctgtgca ccgcagccct cagccccttc tgcctgtgca    31800
agaagcctca tctcacagac aacggtctca ttcccacaac gggctcaatg agaaatcagg    31860
agaggccttc agaccatcac cccaccagac acctcagacg tcggaccagg agggtccagc    31920
aacccccaac acagactcag agggactaag aagccacatg aggagtgaac acaagatgtg    31980
gacaggagga ggttaagggc ctccagggag ctccatcagt ccgtgttctg ctgtcagcag    32040
ggttaggctg ggctggccac aaacaccccc aaaaaacatc tgaagccttg gcttgaaaca    32100
gctgacattc ctcatgaaaa ctgcagaccc ctgggtcctc ctgcgcagat gggggagccc    32160
agccaacccc acactcccac cttccaccaag aaagagaaag ccaaaacaaa ctcaactcag    32220
ccaatgacaa tcacagaact gaatcctgta gttagttcag ttggtttcat ttcagcaggg    32280
gaaagatttg cagcctctat gagggtagct gggaacacaa agggccagag catggcccag    32340 gagacccccag cgcagtgggg tagatggttc cgagcacagg cctccctgcc aagacaagca    32400
ctggctcaaa tcctggcccc tcccattccc aggagacatg ctccacagga tgggaggaca    32460
cacagaggac ctgaggccag gaaaatgaca gcggcgcctc cgccgcccca cccgtgctgt    32520
catcatctta ggtctacagt tctttgtggc aacgagggac actgtgaaag tcaaacaaca    32580
ggaaggcata ggccacaaat aaagacaaac gggacttcat gggaagctaa agattttgtg    32640
catcaaaaga cactatcgag agagtaaaaa ggcaacccac agaatgagag aaaatatttc    32700
caaatcatag atctactaag agattaatat ccatgaaata cagagaactc ctaaaactca    32760
acaatgagaa aacaactaag ccaactcaaa aatgggcaaa caacttgaac agacatttct    32820
ccaaagatga catataaatg gccaataaac acatcaaaac aggcttaata tatccctaat    32880
catcagggaa atgcaaatca aaactacaat aagataccat cttgcaccaa ttaggacggc    32940
tactatcaaa aaaacaaaat agcaagtgtt ggtgaggatc tggagcaact ggaacccttg    33000
tgcaccactg gcaaaaatgt gaaatggtgc agctactatg gaaaacagca tggcagttcc    33060
ccaaaaactt aaacacagaa ttaccatatg acccagcaat ttcgctttgg gttatatacc    33120
caaaagaact gaaaacaggg acacaatcag atatgcatac accttggatc acagcagcat    33180
ccttcccaac agctaaaaca tggaggcagc aggcatggt ggctcacgcc tgtaatccca     33240
gcactttggg aggctgaggc gggtggatca cctgaggtca ggagttcgag accagcctgg    33300
ccaacatggt gaaacccgt ctctactaaa atacaaaaat tagctgggcg tagtgacggg     33360
cacctgtaat cccagctact cacaagtctg aggcaggaga atcacttgaa ccctggaagt    33420
ggacgttgca gtgagccaag attgcgccac tgcattccag cctgggtgac acagcgagac    33480
tctgtctcaa aaacagcaa aacaaaaaca aaaaacaaa caaacatgga agcaacccaa      33540
gcgtccctct actgagggat gaatagcggg gcaaaatctg ctccatccac acaatggagt    33600
actattcagt ctcaaaaagg aaaaagattc tggtcaggca cggtggctca tgcctgtaat    33660
cccagcactt ggggaggctg aggcgggtgg atcacctgaa gtcaggaatt caaggcccgc    33720
ctggccaaga ctggcaccna gctacacana agtatangg ccccggaaa                 33769
```

-continued

<210> SEQ ID NO 9
<211> LENGTH: 72049
<212> TYPE: DNA
<213> ORGANISM: Homo sapiens
<220> FEATURE:
<221> NAME/KEY: unsure
<222> LOCATION: (8356),(8385),(38585)
<223> OTHER INFORMATION: Identity of nucleotide sequences at the above
      locations are unknown.

<400> SEQUENCE: 9

| | | | | | |
|---|---|---|---|---|---|
| tataccttgc | gcggaccttc | ggctcctgtg | gtgaagacaa | tatgaagaaa | atagaaatta | 60 |
| cccataattt | tgccacacag | acttagttgt | gtccatgtat | cttgtgcacc | tttttctgt | 120 |
| ttacggatca | aaatcgactt | ttagggtcag | gcgcggtggc | tcacacctgt | aatcccaaca | 180 |
| ctttgggagg | ctggagttgg | ggttgggggg | tggatcactg | aagatcagga | gtttgagacc | 240 |
| agcctggcca | acatggcgaa | actccatctc | tactaaaaat | aaaagattag | ccaggcgtgg | 300 |
| tggtgggtgc | ctctaatccc | agctactccg | gaggctgagg | caggagaatc | gcttgaaccc | 360 |
| aggagacaga | ggttgcagtg | agccaggatc | acgccactgc | actccagcct | ggcaacagag | 420 |
| cgagactctg | tctcaaaaaa | aaaaataaaa | ataaaataaa | taaatacata | aattgacttt | 480 |
| taggagattg | gttcaaacaa | tgtgtgtaat | gttgtgtctg | agtgtttttc | atttatcgtt | 540 |
| catgcaaatt | ccgacatcat | tcactcttct | ccagagtgtg | ctgttttcct | gcctgtgtca | 600 |
| tcacccgtca | ccttgaatgc | cctcgtttag | gtaaaataag | tacattttat | tcaaaaatat | 660 |
| ttgaggacat | ttgggttgtc | tccaggttct | tggtcttgag | ttttgctgtt | cttgtggagc | 720 |
| catggtggtg | tctggttgca | ggaacctcca | tgcgttccag | ctgctgcttc | tgcctgtgtt | 780 |
| cttagagagg | aaatgctggg | gtccgcggtt | cccgggctgc | tgaccaggaa | gcctgcggtg | 840 |
| ctttacggcc | cttccagaag | cgggagatgc | ccccacttaa | gtgtcagaca | ggcctttcca | 900 |
| cctcactggc | agctctgagc | ggctcccttc | tatttgcaga | tgactgagaa | gttaccaatt | 960 |
| tccacgttta | ctgactgctg | tttctcctgt | taatttgtat | ttatagtctt | cgctaattta | 1020 |
| ttgctagggt | tttggtgttg | tccctattga | cttgtatgcc | ttttaatttt | ttaaacaaca | 1080 |
| ttaatatact | tcattttttt | agagcagttt | taagtttaca | ggaaaattaa | gggacaagta | 1140 |
| cagagagttc | cttccacctg | ctgtcctcct | ctcctcctcc | ccaccttccc | tccttcccct | 1200 |
| attgtaactt | tctttctgat | attataaaag | tcactcatgg | ctgggcgtgg | tggctcacgc | 1260 |
| ctgtaatccc | agcacgttgg | gaggcagagg | caggcagatc | acctgaggtc | aggagttcca | 1320 |
| gaccagcctg | gccaacatgg | tgaaacccg | tctctactaa | aaacacaaaa | agttagccag | 1380 |
| gcgtggtggc | gggcacctgt | aatcccagct | actcaggagg | ctgaggcagg | agaatggcgt | 1440 |
| gaacctggga | ggcagaggtt | acagtgagtc | gagatcgcgc | cactgcactc | cagcctgggc | 1500 |
| aataagagtg | aagcttcgtc | tcaaaaacaa | agtcacacac | gcttcttgta | cgagggtcat | 1560 |
| ttggccgagg | ggccagatgg | ctcaccatct | agttgggaca | ggccatgagc | tcggaatgct | 1620 |
| ttttacatat | ttcatggtt | gagaagaaaa | tcaggagaat | aatgtttgg | gacatgggaa | 1680 |
| aatgacatgg | aatttgcatt | ttagtgtcca | taaatgaagt | tttgtttgct | cccagctgtg | 1740 |
| ttgactgagg | caggctggct | tcctacagct | gcggcagagc | tgaggaggcg | ggaaggagac | 1800 |
| cgtgcaggcc | gcagcaccga | aaatatttgc | tctctggccc | ttcccagagt | gcttgccgac | 1860 |
| ctctgtccga | cagctagaag | gaaggatagg | accgtccga | cgataaccac | tgttgacatt | 1920 |
| tgagcgcgtt | tccttcccgg | cttttgtgtg | agagtggcag | tctgtttgct | tttgtggtcg | 1980 |

```
ggatctgctg cacgcacggc gggctgtttg catgaggctt cctggaggat agggctgggc    2040
tcggagctgc acgcagtggg gcgtgtcctg catgcagtgg ggcctcagaa gagagctgtg    2100
gtgggcgggg cagtgccaac gctggtgggt gccaggcctc cacgctcaga tcagccccgg    2160
cgacaggttt gggccaccct ctctctggcc tctgtgcagt ggcccaggcc gtctgctctg    2220
cctggcacac ttgcctctgt ccttccactg aagcgctcct cttaccctct gctcccggct    2280
gggtacgttg aattgtgtcc ctcaaggaga tatgctaaag gtctaacccc aggaacctgt    2340
gtatgtgatc taatttggaa acagggtctt ggctgatgta atcaagcgag gatgaggtca    2400
ccctagagta gggggcctat atccacggtg ctggtgtcct catgagagca ggtgagcaga    2460
cactgacact caggggtgaa ggctgcatgg agtcagaaca gggcttagtg cgatggcggc    2520
cacaagccaa ggaactccaa gtatttcctg caacaccaga agctggaaga tgccaggaag    2580
gatcctgccc tggagccttc ggagggagtc tgtccctgca gacgtcttga cttttgattg    2640
cagggatgca tgtcttaggg tgtgtggggg ggtgcatttc tgatgttaga agccacctgg    2700
ttggtggcga tgtgtcacgg gagccctctg caggttctgc gtgtccatgt ggtcggggac    2760
agaggtgggc agggacggac ggtgtcgagc tggacatgtc catgacgtcg gccatcccctt   2820 gggatggctt ttttgttttg aggataaggc tgcctgccag gaagctgtgc cctgcctggc    2880
ccttgcccca gcccctggc ctgtgcttgg cctcgcggaa gggatgtcgc ccttctctcc     2940
tgcatgcgtg cagggaggaa gggagagggt cagcagcccg cctggaggag gctcgggcga    3000
ggggaaggtt tcactttcag gcaatgttgt ggggctgttt aaacaacccc aaagaaaacc    3060
atttggccaa actgttagtt ccaaacatt ttacttcctt ggtgtttaaa taaattccta     3120
ccaagactct gtagctggtc ccagggaagg agttggcctc tcttctttat agcccggcac    3180
agtcagtccc ctgcacctgc cctcccaac cccaggcctg cttcccgtg gccatggctg      3240 ctgcccggac ctctctacac acagaacctc ctggaggcca gctgtgggca ccagccttgg    3300
cagggctgtg gcggagccca ggctgctggt actctctctg cagctgctcc ctgctggcct    3360
ggctggacag cgtcccccacc accactgggg tcacctctgt gctggtcaca gctcactcag   3420
accttcaggc aaatgggttg gatcctgcct ctctcccagg tgtctcagtc tctgcaaaac    3480
tcaaaaacct cagaggcctt gcagcctgag gggtgtcaga gacacctcct tcgaatcagt    3540
aaacacctac agattcaccc cagcagtgaa aggactgctt cgccacagag gtttgattta    3600
ctcctaagta attggaaggg atgccgagaa taggttcctc atggtgggac tagaggccct    3660
ctgctgacct agttaacaga gggctagggc tgggtgtgct cagcccctga aggttctagg    3720
cccatttggg acaccccgcc agaacctgcc acaacctgcc atgtggtgac agctacctaa    3780
atcccagagg ctcttgagct ggagagcaga cctctcaatc tcagcaggcc ccccacacag    3840
accccataac cctagtctgc cttcacagta cagttcgtgg ctatgtgttc acggatggtg    3900
ttgttcacct aaggtctctg ccctgtgacc ccaagggcgt cctgagggca gattccaagt    3960
ctgtttcgtc caccctcct tccctagcag cgggtccagg gcctggcctg aactagcttc     4020
ccacagagat actggtggga tgatgaaggc agccaggcgg caagtgaaaa acgcacttcc    4080
tgcatgtgct ggctcctggg attgaagtgt ttgaggaagc aaagtgaagt gagctttcct    4140
cttgcggctg tgtgtccttg ggccgggagc ctaccctctc tgagcgttgg ggtccttgtc    4200
agtagaatgg ggcatcctca tagctcaagg ggtggtgtgt gaaaattgtg ctattgtgtt    4260
actttaatga tttttttttt ttcgagacaa agtctcaccc caacgcgcag gctggagtgc    4320
agtggcgcga tctcagctca ttgcaacctc tgcctcctgg gttcaagtga ttctcctgcc    4380
```

-continued

```
tcagcctccc aagtagctgg aattacagga gtgcgccacc aggcccggca tattttttcta     4440
tttttagtag agagggggtt ttaccatgtt ggctaggctg gtcttgaact cctgacctca     4500
ggtgatccac ctgcctcggc ctcccaaagt gctgggatta caagcatgag ccaccgcgcc     4560
cggcctactt tagtgatttc ttaggaggac agagggaacg ggctggcaag acaggcttgg     4620
aatgtgtttt gggatcaagt gccggttttct gtctggcact ggcgttctct gtggggccat     4680
gatggacaca ctgctgaggt caagcgtgat tcgtcttgcg ctgtgcctgg cagtctcatt     4740
ggaaagttct gtagacatcg tgtggatggg gctcttcccg gccaagccct tggggacctt     4800
ccaggactgt gatctcccca cagtggctgt taagcaggga cctttcgtga agtggagtct     4860
ctggtcccct ccaagtcata gctagacagg gactcgggca tcgccaagcc tggctgatta     4920
ttcactggat gaggagacag gcccagagag gggcaggaac ctgcccgagg tcacccagca     4980
ggccccagag gtttcggtct cggattctcc ctgctcatcc ctggatgtag tgctgctgtg     5040
gatgtggttc tgtgctgggg gctgtggaga gcaggggct tgtgccagga ccccagtgag     5100
ggtggcgccc tcgccatgag gccgactgtt ggtatgggc ggccatccac tggggtgtgg     5160
ggaggaacag cttttcctgag gaggaggtgg cgggaggaac agcttccctg aggaggaggt     5220
ggcggtgctg tgtgacctgg gccttgaagg acaggtccat tgtcaacaga acatttggg     5280
agtggagcct agagggagaa aatttgttga aattcagatt cccctccccc taccaataca     5340
caccaaatca gatgccctg accagatcta aatttggctc tcagagattt ccattgtagc     5400
tgggcacttg gggaaccttc taagtgctgc ctctgcctct cccagcctg cctgcctcag     5460
tttccccagc cctgggcccg tgtcgctgtt gccatcacgt gggcgccctc tagtggagga     5520
atcagattat gcactccggg gcttggagca ggagtcagga ggggctcctg tctttccttg     5580
aaacgttgga tgccgggatc ctggaacagt ctctgcattc ctcctggcga gaaccagagc     5640
ctgggcacag gggaccatct gttgtttgaa ggctgcagcc tggcagggca ctcaggagat     5700
ctggcagttg gctgcagggc caggtctagg ggccagggca tcaggaggc tctgggctgg     5760
ttcagccccg ggccccttg cagattgtga cctgggcccc tgtgcagggg catgccaca     5820
ggatgctggg aggggtctct gaccctgacc ttcttggctc tgtgcatcct tgagaccaga     5880
aaggtctgga acaaatgagt agacgatgcc ctaacctggg gagggagcca catcctgatc     5940
ccagcaacct cgggaaggat ctgtcaggat tatggggcac cctgggggcc ccaagtctgc     6000
atgggtctcc acttgcaatt tctgtaggaa gctctgataa atccaaactg ggggtcctag     6060
gacacagtca gaaatgctga taccgttgtg tgtggagcct cgggccctgg gggtcaggag     6120
catgtggagg gtgggccacg gggttcaga agagaatcct gtaaccccc acccccaaa     6180
ctgaagccca cttgagggcc atggctgaaa ggttgggggg tctccgtgcg tcctgtggag     6240
tgggtggtga ggagtccttg ggtttgcacg cctctgggcc tgagcggcgg accccgtcc     6300
acagcggatc cctgggccct gttgctcaga tgctctcaga gtgttgctgt ggccacggag     6360
ggagcctgag ttaagcttct cttgtgccgg ttgtacgctg tcaggtcaca ctggtgagtt     6420
aggcagggca cagatgccca gagcagaggg aactttcctt ggggattcaa cacgtgcaag     6480
tcttagggc tggcaaatcc tgccctcagc tagagaggg gctttttattt gagaccagaa     6540
tcacctgagc atcctcctgt ccccagctgt gtccagcctg tctgcaggga catcctgaga     6600
ggaccaggct ctcccctcat ccacctgcct aagtgccact ctgaaccctg tccacctgtg     6660
ccgtggaggg gcgtgacctc aagctgctca gccagcagca ggcttggccc tgggggcag     6720
```

```
cagagaccca ggtggctgtg gggtgggtgc ttcgtggcgt ggttctgaaa cttcgttgga   6780
agtgtgtgga cagtgccttg cctgttctct gtgggaccct atttagaaac gaggtctgag   6840 ttactgggggg tcatcactgt gttctgatgg cccagctgtg tggaggccgc ggtgcagccc   6900
catccaagga gccagggccc tgggtctagc cgtgaccaga atgcatgccc cggaggtgtt   6960
tctcatctcg cacctgtgtt gcctggtgtg tcaagtggtc gtgaaactct gtgttagctc   7020
ttggtgttcc tgaaagtgcc cccgggtctc aggcctcaga accaggggttt cccttcatct   7080 cggtggcctg ggagcatctg ggcagttgag caaagagggc gattcacttg aaggatgtgt   7140
ctggccctgc ctaggagccc cccggcacgg tgctggggcc tgaagctgcc ctcgggtggt   7200
ggagaggagg gagcgatgaa gtggcgtcga gctgggcagg aagggtgagc ccctgcaagg   7260
tgggcatgct ggggacgctg agcagcatgg ccagcagctg ggtctgcagc ctggtacccg   7320
gcgggacttg tggttggggc tggtttgtgg ccaggagagg ggctggcagg agacaagggg   7380
gactgtgagg cagctcccac ccagcagctg aagcccaatg gcctggctgt gtggctctca   7440
gctgcgtgca taacctctca gtgcttcagt tctctcattt gtaaaatgag gaaacaaaca   7500
gtgccagcct cccagaggtg tcatgaggat gaacgagtga ccatgtagca tgggctgggt   7560
gcgtgtcacc taacatcacc agcctttgca aggagagccc tgggggcctg gctgagtatt   7620
tcccttgccc ggcccacccc aggcctagac ttgtgcctgc tgcaggccct tgaccccctga  7680 ccccattgca cctgtctcca caggagccga ggaggtgctg ctgctggccc ggcggacgga   7740
cctacggagg atctcgctgg acacgccgga cttcaccgac atcgtgctgc aggtggacga   7800
catccggcac gccattgcca tcgactacga cccgctagag ggctatgtct actggacaga   7860
tgacgaggtg cgggccatcc gcagggcgta cctggacggg tctggggcgc agacgctggt   7920
caacaccgag atcaacgacc ccgatggcat cgcggtcgac tgggtggccc gaaacctcta   7980
ctggaccgac acgggcacgg accgcatcga ggtgacgcgc ctcaacggca cctcccgcaa   8040
gatcctggtg tcggaggacc tggacgagcc ccgagccatc gcactgcacc ccgtgatggg   8100
gtaagacggg cggggggctgg ggcctggagc cagggccagg ccaagcacag gcgagaggga   8160
gattgacctg gacctgtcat tctgggacac tgtcttgcat cagaacccgg aggagggctt   8220
gttaaaacac cggcagctgg gccccacccc cagagcggtg attcaggagc tccagggcgg   8280
ggctgaagac ttgggtttct aacaagcacc ccagtggtcc ggtgctgctg ctgggtccat   8340
gcgtagaaag ccctgnaaac tggagggagc cctttgtccc cctgncttca gtttcctcat   8400
ctgtagaatg gaacggtcca tctgggtgat ttccaggatg acagtagtga cagtaagggc   8460
agcctctgtg acactgacca cagtacaggc caggcctctt ttttctttt ttttttttgag   8520 atggagtctc actctgtcgc ccaggctgga gtgcagtggt gtgatctcag ctcactacaa   8580
cctctgcctc ctgggctcaa gtgattctcc tgcctcagcc tcctgagtag ctgggattac   8640
aggtgcctgc cactgtgctt ggctaatgtt tgtattttttg gtagagatgg ggtttcaccg   8700
tcttggccag gctggtcgca aactcctgac ctcaggtgat ccacctgcct cagcctccca   8760
aagtgctggg attacaggca tgagccacca cgcccggtca ggccaggcct cttttgaaca   8820 cttttgcacac catgggtctt ttcatccagg ggggtaggta cagttgtaca gttgaggaca   8880
ctgaagccca gagaggctca gggacttgcc caggggtcaca cagcaggatg tgcaggtgt   8940 ggggctgggc ctggcagcgt ggctccagct ttccagcata gaaatctgtg aaagcagata   9000
gtttgtcggt cggtaggggga gactttctga gacccgcccc agcggctcag agggtagtag   9060 ccagggggcct tcctgggggc tcataaccca gaacactgaa tgggaaaacc ctgatggagg   9120
```

-continued

```
aggcgcagtg gagctgtggg tgccgatggg aagtcccaga ggagctggga ggtcagtagc    9180
ggtgctgccc tctgtggagc acttagtggg caccaggtgt gtttccaggt tcatggccct    9240
gggacctgaa gctcagaagg tgaagtaact tgcccaggge acccgtcggg cagcggcggg    9300
cagaggattt gtgggctgtg gagcctgtgc tcgtggccca gccctggggg ttgtgagtgt    9360
gctggccggg gagcttttcc tgcaagtgga ctggtgtcta ggagccagca tgtcaggcag    9420
caggcagcgg gagtgcagca ggcagcggga gcacagcagg cagagggcgg ggctcgagca    9480
gccatccgtg gaccctgggg cacggaggca tgtgggagag ggctgctcca tggcagtggc    9540
tgaagggctg ggttgtgccc cgaggagggt ggatgagggt aagaagtggg gtccccaggg    9600
gctttagcaa gaggaggccc aggaactggt tgccagctac agtgaaggga acacggccct    9660
gaggtcagga gcttggtcaa gtcactgtct acatgggcct cggtgtcctc atctgtgaaa    9720
aaggaaggga tggggaagct gactccaagg cccctcctag ccctggtttc atgagtctga    9780
ggatcccagg gacatgggct tggcagtctg acctgtgagg tcgtggggtc cagggagggg    9840
caccgagctg gaagcgggag gcagaggggc tggccggctg ggtcagacac agctgaagca    9900
gaggctgtga cttgggcct cagaaccttc accctgagc tgccacccca ggatctgggt     9960
tccctccttg gggggcccca gggaacaagt cacctgtcct ttgcataggg gagcccttca   10020
gctatgtgca gaaggttctg ctctgcccct tcctccctct aggtgctcag ctcctccagc   10080
ccactagtca gatgtgaggc tgccccagac cctgggcagg gtcatttctg tccactgacc   10140
tttgggatgg gagatgagct cttggcccct gagagtccaa gggctggtgt ggtgaaaccc   10200
gcacagggtg gaagtgggca tccctgtccc aggggagccc ccagggactc tggtcactgg   10260
gcttgccgct ggcatgctca gtcctccagc acttactgac accagcatct actgacacca   10320
acatttacaa acaccgacat tgaccgacac cgacatttac cgacactgac atttaccaac   10380
actgtttacc aacactgaca tctactgaca ctggcatcta ccaacactga catttaccga   10440
cactgacatt taccaacact atttaccaac actgacatct actgacattg catctacca   10500
acaccaacat ttaccgacac caacatttac caacactgaa atttaccgac accgacattt   10560
accgacaccg tttaccaaca ccgacgttta ccgacaccga catttaccga cactgatatt   10620
taccaacact gacatctact gacgctggca tctactgaca ccgatgccag catctaccaa   10680
caccgacatt taccaacact gacatttacc aacactgaca tttaccgaca ttgacattta   10740
ctgacactga catctactga cactggcatc tactgacact gacgtttacc gacactagca   10800
tctactgaca ctgacatttta ccaacaccag catctaccaa caccgacatt taccaacact   10860
gacatttact gacactgata tctactgaca ctggcatcta ctgacaccaa catttaccaa   10920
caccagcatc taccaacacc gacatttacc aacaccagca tttaccaaca ccgatgttta   10980
ccaacgccga cgtttaccga cgccagcatc taccaacact gacatttacc gacaccgaca   11040
tttaccgaca ctgacatttta ctgacactga catctactga tactggcatc taccgacact   11100
gatatttacc aacgccagca tctactgaca ctgatgttta ccaacaccga catttacgag   11160
caccgacatt tactgacacc aatatttact gacatcaaca tttagccatg tgatggggc    11220
cggcttgggg gcaggccttg ctcttggcac tggggatgct gcagagacca gacagactca   11280
tggggtcatg gacttctgct tcttctccag cctcatgtac tggacagact ggggagagaa   11340
ccctaaaatc gagtgtgcca acttggatgg gcaggagcgg cgtgtgctgg tcaatgcctc   11400
cctcgggtgg cccaacggcc tggccctgga cctgcaggag gggaagctct actggggaga   11460
```

```
cgccaagaca gacaagatcg aggtgaggct cctgtggaca tgtttgatcc aggaggccag    11520
gcccagccac cccctgcagc cagatgtacg tattggcgag gcaccgatgg gtgcctgtgc    11580
tctgctattt ggccacatgg aatgcttgag aaaatagtta caatactttc tgacaaaaac    11640
gccttgagag ggtagcgcta tacaacgtcc tgtggttacg taagatgtta tcattcggcc    11700
aggtgcctgt agacacagct acttggagac tgaggtggga ggatcgctgg agtccaagag    11760
tttgaggcca gcccgggcaa aggggacaca ggaatcctct gcactgcttt tgccacttac    11820
tgtgagattt aaattatttc acaatacaaa attaagacaa aaagttaatc acatatccac    11880
tgccctgctt aagacagaaa acatgggtgt tgttgaagcc agaggcagct gctggcctga    11940
gtttggtgat tggttcctaa gcagttgaag gcagttttgt ttttccatag atgtctgttc    12000 tcccttctgct gggtgcagcc tcgccctgct gctgtggtcg ggtttcagtg gcctcgtccc    12060
gtggacgcag cctcgccctg ccgctgtggt cgggtttcag tggcctcgtc cgtggacgc    12120 agcctcgccc tgccgctgtg gtcgggtttc agtggcctcg tcccgtggac gcagcctcgc    12180
cctgccgctg tggtcgggtt tcagtggcct cgtcccgtgg acgcagcctc gccctgccgc    12240
tgtggtcggg tttcagtggc ctcgtcctgt ggacgcagcc tcgccctgcc gctgtggtcg    12300
ggtttcagtg gcctcgtccc atgggcgtgc tttggcagct ttttgctcac ctgtggagcc    12360
tctcttgagc ttttttgttt gttgtttgtt tttgtttgat tttgtttgat tgtttgtttt    12420
tgttgtcgtt gttgttgccc aggctggagt gcagtggcgc gatctcagct cactgaaacc    12480
tctgcctcct tgggttcatg ccattctcct gcctcagcct cccacatagc tgggattaca    12540
agtgcccgcc accacgcctg gctaaatttt gtattttag tagacagggg gtttcaccat    12600
gttggtcagg ctggtctgga actcctggtc tcacatgatc cacctgcctc ggcctcccaa    12660
agtgttggga ttacaggcgt gagccaccgc gcccagccct ctgttgagca tattttgagg    12720
ttctcttggt gccagtgata tgtacatgtg tccccatcgc accatcgtca cccattgagg    12780
tgacattggt gcctctcctc ggggtggatg cctccctctg tttccagcaa cttctgaagg    12840
attttcctga gctgcatcag tccttgttga cgtcaccatc ggggtcacct ttgctctcct    12900
cagggctccc aggggaggcc cgaatcaggc agcttgcagg gcagggcagg atggagaaca    12960
cgagtgtgtg tctgtgttgc aggatttcag accctgcttc tgagcgggag gagtttcagc    13020
accttcaggg tggggaaccc agggatgggg gaggctgagt ggacgccctt ccacgaaaa    13080 ccctaggagc tgcaggtgtg gccatttcct gctggagctc cttgtaaatg ttttgttttt    13140
ggcaaggccc atgtttgcgg gccgctgagg atgatttgcc ttcacgcatc cccgctaccc    13200
gtgggagcag gtcagggact cgcgtgtctg tggcacacca ggcctgtgac aggcgttgtt    13260
ccatgtactg tctcagcagt ggttttcttg agacagggtc tcgctcgctc acccaggcga    13320
gagtgcagtg gcgcaatcac ggctcgctgt agcctcaatc tccctgggct caggtgatcc    13380
tcctgcctca ccctctgagt agctgggact acagacacat accaccacac ccagctagtt    13440
tttgtgtatt ttttgtgggg ggagatgggg tttcgctgtg gtgcccaagc tgatctcaaa    13500
ctcctgaggc acaagcgatc cacctgcctc ggcctcccaa agtgctggga tgacaggcat    13560
cagccgtcac acgcagctca atgattttat tgtggtaaaa taaacatagc acaaaattga    13620 tgatttaac catttttaaag tgaacagttc aggctgggcg tggtggctta tgcttgtaat    13680
cccagtactt tgagaggctg aggtgggcag atcacctgag gtcaggagtt tgagaccagc    13740
ctggccaaca tgatgaaatc cagtctctac taaaaataca aaattagcc gggcatggtg    13800 gcaggtgcct gtaatcccag ctactcggga ggctgaggca ggagaatcgc ttgagcccgg    13860
```

```
gaggtggagg ttgcagtgat ctgagatcat gccactgcac tccaatctgt gtgacagagc   13920
aagactctgt cttgaaaaat aaataaataa aaaaattttt aaaaagtgaa caattcaggg   13980
catttagtat gaggacaatg tggtgcaggt atctctgcta ctatctactt ctagaacact   14040
ttcttctgcc ctgaaggaaa ccccatgccc accggcactc acgccattc tccctctct   14100 cccagcctct gtcaaccact aatctacttt ctgtctctgg gggttcactt cttctggacg   14160
ttttgtgtga ctggaatcct gcaatatgtg gtccctgcgt gtggcttctt tccatagcat   14220
tgtgttttcc agattcaccc acacattgtc gcacgttatc agaatctcat tcctgactgg   14280
gtgcagtggg ttaggcctgt aatcctaaca ttctgggagg ccaaggcggg acgatcactt   14340
gaggcaggag tttgagacca gcctggccag cctagcaaga ccccagctac caaaaaattt   14400
taaaagttaa ctgaacgtgg tggtggtggg cacttgtggt tcccagctac ctgggaggct   14460
gaggttggag gatcgcttaa gcccaggagg tcaaggctgc agtgagctat gatcgcacca   14520
ctgcactcca gcctggacaa cagagcaaga ccctgtctga aaaaaaaaac aaaaaaaaaa   14580
gttcctttct ttttgtggct ggatgacatc ccattgtatg gccacagcac attttgtttg   14640
tctgtttatc gggtggtggg cagtggtttc cacctttgt ctcctgtgaa taatgctgct   14700
gtgaacattt gaattcaagt ttttgtttga acacctgttg tgaattattt ggatatatgt   14760
gtaggggtag gattgctgag tcctatggta atgttaggtt tgacttactg aggaaccatt   14820
aaactgtttt caacagtggc tgcgccgttc tgcatcccca ccggcagtgt gtgagggttc   14880
tgactttacc tcctcacaaa cgcttctttt ccatttaaaa aaatattcag ccaggtgctc   14940
tggctcacgc ctgtaatccc agcactttgg gaggccgtgg cgggcggatc acctgaggtc   15000
aggagttcga gacgagcctg gccaacatgg tgtaaccca tctctaccaa aaatataaaa   15060
attagccggg tgtggcagcg ggcgcctgta atcccagcta cttgggaggc tgaggcagga   15120
gaatcacttg aacccgggag gcagaggttg cagtgagcca agatcgcgcc actacactcc   15180
agcctgggtg acaagagtga aactccatct aaaataaaac aaaaataaaa ataaatcaaaa   15240 atttattaaa acattcatca cagccagcct agtgggtgtc ccatgtggct ttgcctcgca   15300
tttccctgat aactaggatg ctgagcgtct tgtcccaggc ttgccacacc tcagcacttt   15360
gagatacgtc gcacagtccc catttgcgaa cgagaaatga ggtttaggga acagcagctg   15420
tgtcatgtca cacagcgagc agggggtctc tgagccgtct gaccccacag ccgaccaagc   15480
tccaatcctt accgcctcct agtgttgtgg atgtagccca gggtgctccc acattttca   15540 gatgagaaca ccgaagctca aaacaggagc gttttgtcca cattggatac acgatgtctg   15600
tggtttggtc ctgaagtcac tttatatctc agtggtccag actggagtag acaggggt   15660 tctggggaat ggggaaggtg tctcaggtga aggaaggaa ttccagattc tccatactgt   15720
ccttgggaag ttagaagact cagagggtct ggcaaagtca gacaaagcaa gagaaatgca   15780
gtcaggagga agcggagctg tccaggaaca gggggtcgc aggagctcac ccccaggaac   15840
tacacttgct ggggccttcg tgtcacaatg acgtgagcac tgcgtgttga ttacccactt   15900
tttttttttt tttgaggtgg agtctcgctc tcttgcccag tctggagtgc agtggcacga   15960
tctcggctca ctgcaagctc tgcctcccgg gttcatgcca ttctcctgcc tcagcctccc   16020
gcgtagctgg gactacaggc gcctgccacc gcgcccggct aattttttgta tttttagtag   16080 agatgggatt tcactacatt agccaggatg gtctcgatct cctgacctca tgatccgccc   16140
gtctcggcct cccaaagtgc tgggattaca ggcgtgagcc accgcgcccg gcccgatttc   16200
```

-continued

```
ccactttaag aatctgtctg tacatcctca aagccctata cacagtgctg ggttgctata   16260
gggaatatga ggcttacagg ccatggtgct ggacacacag aagggacgga ggtcaggagg   16320
tagaagggcg gagagaggga acaggcggag gtcacatcct ggctttcaa aatgggccag    16380
ggagagacac cctctgagca tggtaggaca ggaaagcaag attggaacac attgagagca   16440
accgaggtgg ctgggcgtgg tggcttacgc ctgtaatccc aacactttgg aaagctgagg   16500
tgggtggatt gcttgaggcc aggagttcaa gaccagcctg gccaacatgg tgagaccccg   16560
tctctactaa atatacaaaa attagccagg cgtgatggtg catacctgta atcccagctg   16620
cttgggaggc tgaggcagga gaattgctta aacctgggag gcggaggttg cagtgagccg   16680
agatcccgcc actgcactcc agcctgggcc acagagtgag actccatctc aaaaaaaaaa   16740
aaaaaaaga taaaaagacc aaccgaggaa ttgaagtggg ggggcgtcac agtagcagaa   16800
gggggatcgt ggagcaggcc accctgtggt catgcactgg aagctcatta cctgacgatt   16860
tggagctcat cactggggc ctaaggagaa tagatactga aggatgagga gtgatggcgc    16920
ggggcacggg tgtctttggt ggccagaact tggggactgc tggggtgcct cactgcaggc   16980
cttctcagcg ccctttatat gcttacacag gctgtttcta agaggggat acattgcata    17040
agcgttttca gactacctca tcatgggtcc cttttctttac cctctgtggc cctggtggcg   17100
cactctctgg gaaggtgcag gtggatgcc agacccgccc tgccatccac ctgcacgtcc    17160
agagctgact tagcctcgag attgctgctg gcacctcctg ccccgggaca cctcggatgt   17220
gcccgtggag atgctggctc tgtgttttct gctggagttt ggtgcgtctt ttcctcctgc   17280
aagtggccac cgctcttggg tatgtcctca ggcttctgcg agtcatggct gcttctcagg   17340
tccttgccca cgccaggag caaaccctcc tggcactttg ttcaggggtg gatgcgccag     17400
tgttcctgct gtggaccgcc atctcacatg agggtcttgg gcctgcaggc tcgttcagga   17460
aacacccgct gagtatgcag tgtgtgccag ctgtgtccca ggcaatggcg gggacagtgg   17520
ctgctgctgg ggttgtggtg gcttctgggg actctgggga cagctgaggt gcaaggagcc   17580
acggctcctt gaggatgcag ttggactcca ggtggaaggg atggttgggg gaggtataaa   17640
tggggtcagg gaggagacac atttggaaca atgggaacat ttttaagatg ctatgtcggg   17700
aggcaacaag gtggccaacc caggtgctga ggagcccaca ccagccctgg acgtgttttg   17760
ccgctcacct ttgctgggga gtggtgggag agaggattcc gttccacgtg gtggtgtgcg   17820
cagctgggct gtgtggagct gggcgctagg aggaaggtgc tttctgcggg gctagccggg   17880
ctctgccttt gaacacaatc aggctccagg ttttcagcat ccagtgcatg agaggacttc   17940
acgggcagct gtggctgatc ccttgatgaa ttgggagaag aacaaaggtc tatgaaatga   18000
ggtttcatgt agatggcatt agagacgccc acaacagatt tacagagtgg agcggagacg   18060
gcggatgggt ctgggaggcc cctcctgctg gccttgactg tgacagctgt cctgggaatc   18120
agcttccagg ccgccccagc agcctgactg acacacacag gggttttagc cccatcctgc   18180
gaccagctgt tgccatcatc agtgacagct gggagtggcg gtggttccag ccctgggcac   18240
cctccccacc tgctgggggcc cacccagggc agtcctgaca cctacaggtt gcttggagcc   18300
gcatccgagt cctgccccac cacgtgtgaa gcccgagtgg tcgtgggctg aggtcccctg   18360
attgcatccc cacttccctt ctgcttcaca tagctgcctc ttctcaccgt ttttccagcc   18420
tcctgggcta ggaattccag tgttgtgctg gctttgcccc aggacacctc cttagccctc   18480
ttcctgagtc tagagccccg ggggttggaa gtcctggccc ctgggacacc tgcagccaca   18540
ctcagcttct cctgtgagcc tccagcatgt cccctcagga ccaagccctc acgttcttgc   18600
```

```
ctccccgccc acctgggctc agccagggga aggcctggct gggagcgtct ccctctgcc      18660 ctgcccttct ccctcctac cctgcccttc tctcctctgc ccgccatgg cttttatatc       18720 ctgtgccaca agacatggct gtgtgtgaaa gtggcagggt ctggcatctc tgtgggtctc     18780
tgaggcccac gctccagtgc cactcttccc acccgctggc cgtgccctca tgctggaggg    18840
acagcccagc cctctcccga accccagccc catgtgccca gctgccccg ccctctccc      18900 ctggaagccg gggtcactcc agccgtatgc catggtgggg acatcctgct tccttggcct    18960
tccagggaag gtcctctttc caaatggcga cacctggtcc ctgcctggag ctgaagct     19020 gtggcccttg tatgcccctc cagggtctgt gcgctcggtt ggcccgagtt cccatcaccg    19080
tcatcatcac catcatcatt gtcatttcgc ttgtctgtga gccggcctgg tctcccagag    19140
cagagaccct ctgaggtcca gcctgagttg gggtctccgt gctgaccct gacggggact    19200 caggacgtac caggtctggg tcaggagtga cccccaaacc tcgtgccctt tgacaggcac    19260
ccctgacttt tgctaagtgg gtggaggtga catcacttac agcgggagtg atgggacagg    19320
gtctgttggc tgcactgtgc tcccagggat ctggggagag gctatatccc tgggcttttgg   19380 cactgcagag ctgtgtgtgt ttgtgtgtgt gtgtgtgtgt gtgtgtgtgt gtgtgtgtgt    19440
gtgtgtgttt gcgtgcgcgc acatgtgtat aagatctttt tttattacat gaagcaagat    19500
aactgttgct gtttccttt gggttttgtg ttcaacagag tggggtactt cttccctcag     19560
acaacagaac tctcccctt aaacacgtgc tgtcagaggg tgggtcttgg gctcatgtct     19620
gtttgcacag ccgagtcaga ggaaacacag ggttcttcat aaaaacactg cacagcaggc    19680
gactgtccag agtcagcctg caggacggca gcagccctgc ccctcagagc acagctaggg    19740
tgggctgctt tgggatctcc cgtcattccc tccagctgg cagccggcgg ccggcccatt     19800
ccttggtgtg ctggtcaggg gggcgtgcgc ctgctctgct caccctgga atgggacaga    19860 agctggcagc tcggagagga cagggctgga cccttgggtg gcctctggct ggaccatctc    19920
attgtcctca gacacagcct ctcgggtcta gtttcatttc ctgaaaaaca agtgcacaga    19980
actagagcag gagtcgagag ctacggcccc cgggccagat ccagccctgc cacctgtttt    20040
cacaccatgc tcaagctgag tgggttttac attttttaat tacttgaaaa aaaaaaagcc    20100
aaaggaggtt tcatgaccca tgaaaattat atggaattca aaaaaaaaaa attatatgga    20160
attcaaattt cagtgtccat aaataatttc ttgagacagg gtctcgctct gtcacccagg    20220
ctggagtgca gtgctatggc atggctcgct gtacccttga cctccaggc tcaagcgatc    20280 ctcctgtctc agcctcctga gtagctggga ctacgggtgt gtgccaccaa gcccggctaa    20340
ttttttttta atttagtaa agacagggtc tttctatgtt gcccaggctt ttctggaact    20400
ccatcttggc ctcccaaagt gctgggatta caggctcgag ccacggagcc cagcctgttt    20460
ttgttttttc actgataaag ttttgccggg tgtggtagtg tgtgcctcta gcgatttggg    20520
aggctgaggt gggaggatcg cttaagccca ggagtttgag gctgggctca agtgatcagg    20580
aggtgaacta tgatcatgtc attgcattcc agcctgggtg acagagcaag aacctatctc    20640
ttaaaaatat atatttaaaa agtattgggt gtggtggctc acgcctgtgg tcccagctac    20700
ttaggcatct gaggtgggag gatggcttga gcccaggagt ttgaggttgc agcgagccaa    20760
gatcgtgtca ctacactcta gcctgggtga cagagcccag accctgcctc tttaaaaaaa    20820 aaaccaaaa aacatgtatt ggaacacagc catgcctgtt cagtcacgtg ctctccatgc    20880
tgctttctgc tccagagacc cttatggcct gaaagctgaa aatattttct atcctttaca    20940
```

```
aaaaagtttg ctgacctctg tcctggaaaa ttcatctccc aagttctctt ccggcactgg   21000
cgttcctggg tgtcctaaat ttggcccctg ttatttctga actctgtttt ggctctgttc   21060
cctcccagga gccaggacag gcacgttctc tgcatcttgt ccccctgacgc ccagaggctt   21120
ggctcggctc aggcattctt ggaaatatct ggctccagga aggcagagg cctcctgagt    21180
cggcccagag ggaacctgcc ccaggtctgg gggaggcctg acccagcaga gtggcttttg   21240
ccgatgggtt gggccggtca agatgtgctg aaagttgtcc tcagaaggcc actttgggat   21300
tccttcctcc agtattagag caactgagag ctgctcattg caagcctgat gttttcccag   21360
ttggccgggt ccaccgggtg ccctgggatt ctgggatctg ggtggaaagt aggggcttg    21420
ggggagtgtc ctgggttctg gaatccaggt ggcaagtggt gaggttcagg gagtggcttc   21480
tgagccacca taggggtctc tgtgggaggc tctgcccatc caggagattc cgcaggccct   21540
gccggcccag agccagcgtc ttgcgcttgc cgaggctaca gccagcccca gccgggtgga   21600
acagcccgtc gcctcctctc actttgtttt ggggccacct gggagtgtgg agcaagggta   21660
gagagggagg aagtggctgc cggccgctgc ccagcaccct tgtttgcctt gggccctctg   21720
tgggctcctt tttattgctc ttcaatgaag ccagggaaat ggacttcctt gcctcacttc   21780
agttcaacat gtctggaagt ttggtattaa aattaagaaa gtgtggaaat agagcaagaa   21840
gagaaaaatc tctccaagag ataatagtga cctctgagct gggcgcggtg gctcacgcct   21900
gtaaatccca gtactttggg aggctgaggc gggcagatca cctgaggtcg ggagtttgtg   21960
accggcctga ccaagatgga gaaacccgt ctctactaaa aataaataaa taaataaata    22020
aataaataca aaattagcca ggcatggtgg cgcctgccta atcccagc taaggcagga     22080
gaatcgcttg aacctgggag gcaaaggttg cagtgagcca agatcacgcc attgcactct   22140
agtctgggca acaagagtga aactccgtct caaaaaaaat aaataaataa aaaataaaaa   22200
tagtgacctc tggccaggtg tggcagctca tacccgtaat cccagcactt tggaaggaag   22260
gccgagatgg gcagattgct ttagcacagg agtttgagac cagcctggcc aacatggtgg   22320
aaccccatct ctacaaaaat agaataaaat ttaagaggta atagtgacct tttggtagat   22380
cgaaacctgg attgctttct ttttctaaat gctgattctt ttctttgtgg tgtttgtgtt   22440
ctgtgccgat gtccctcccc cagccctgtt attgtgagtg gaagaagggg aaagggttcg   22500
cccgctactg tgagcccctc ctctcacgct gggtgtcctt ggagaagcct gcacttcttc   22560
attgtacgcc agggctgggt ccctccctgg agtggtctg tgctgctggg atggggccaa    22620
cccctcagat gttttctgag tgtcacacac aggtgtgtgc attcatggcc tttgcgtgtc   22680
ttcctgttgt ggaggcaaaa atgtgaagaa ccctagatga ttttgggacc agggctccat   22740
cacctgctgt tcattgcaca ccggagcatc caggcatggg tggagagctc agacttccag   22800
gcacggtcgc aggggctggt ctaaccatgt tcccgcccgc ctgctcgtca gaaccgcctg   22860
ttgggagctg ttatcatgat accataccctg ggccctgggc tatccgattc tgacttaatt  22920
gctccaggtt ggggccaggc cgttgtttgc tgttttgttg tttcttctgt gacgttagcc   22980
actgggctaa tctgagcccc tcagttacag gtggagaaac tgagacccat ggggtgcaa    23040
ggacttgccg aggacccaga gccccttggg ggcagagctg aggcggggcc tggctttggg   23100
tcccagagct tccagtcccc ttcccgctct cctaacagct ttttttttg agacaagatc    23160
tcacccctgtc acccaggctg gagtgcaatg gcatgatctc ggctcactgc aatcttcgct  23220
agctgcgttc cagcgattct cctgcctcag cctcccgagc agctgggatt acaggtgtgt   23280
gccgccatgc ccagctcgtt ttttttttgta cttttagtag agatagggtt tcaccatgtt  23340
```

-continued

```
ggccaggctg atctcgaact cctgacctca aatgatccgc ctgcctcggc ctcccaaagt   23400
gctaggatta caggctggga tcacactgtg cctggcccta gcagctttgt cctgtgccat   23460
ccaacaacag atgaccgaag tctttgtttc ttaacatgca ttccatctgc cttacagttt   23520
tgccacctgc aaaacagagg acttgtcgct tttctggtaa gctggaaatg taatctggta   23580
gcaggaggcc tgtggaagct tgcctttaat ggccttgtgt ctctttcatc ctgtcctgag   23640
agccggagaa cttggatgtt gcacctaact caaccttcct gttaacatac agttctgcag   23700
gctcatggat catcagaacc acgtcctatc tcacgcggct gtatgcttcc gttggttcag   23760
gtgttttttac cttgacagta ttttctcctc ggtggctttt gcggtggttg cttttaatca   23820
gcattgactc ttcaagaaaa atatttagct gctacatctc agaggagaca gggtggaaag   23880
catctgagac ctgcaggctc agacttagaa ccagaagtgc cctcagagtt catccggccc   23940
tgacccagcg ggaaatgagt tcacagaaa gcgggagaac tttgcccag gccctgccgt    24000
tgctcataac tgccccaggt ccttacattt gctccaggtc ctgccccagg ccctgcagtt   24060
gctcataact gccccaggtc cttatatttg ctccaggtcc tgccccaggt cctgcagttg   24120
ctctgtgtgg tgggtgtgat ctggagccct ccgcccattg ctgcacctgg ggcaggcatt   24180
gctaattgat cccaggactc cttcctgcgg agcacgccct ggttctccag gcagccgctg   24240
cctgtcagcc tgcagtggtt cgggagagga cacctgcttg cctggtctgt tccaaatctt   24300
gcttctcatc ccagcacagg tagggggtgc tatgggaaag ggatcctcag ttggccctgt   24360
cactgctcta tcagctgggg acgtggcatc ctagtgaaaa catcatggcc gggcgcggtg   24420
gctcacgcct ggaatcccag cactttggga ggctgaggag ggtggatcac ttgaggtcag   24480
aagttcgaga ccagcctggt caacatggtg aaacccatct ctactaaaaa tacaaaaatt   24540
cgccaggtgt ggtggcgggt acctgtaatc cgagctactc gggaggctga ggcaggagaa   24600
tcgcttgaac ctgggaggtg gagcttgcag tgagccgaga tcttgccact gcactccagc   24660
ctgggcaaca gagtgagacg ctgtctcaaa atctcaaaca acaaacaaa caaaaaacaa    24720
acaaacaaag cgtcatttat ccagcacccc tggggaacca tgctacctgg tgttttatgg   24780
tacctggcaa ggtgcaggtg aagttgctgc tcttgggcat tgaacccgtc ttgtttgggg   24840
cagctcaggc cccaggcagg gtccgggttg gctctcgttg gtgtggccct ggcccatcca   24900
gacctatatt tctgccgtcc tgcaggtgat caatgttgat gggacgaaga ggcggaccct   24960
cctggaggac aagctcccgc acattttcgg gttcacgctg ctgggggact tcatctactg   25020
gactgactgg cagcgccgca gcatcgagcg ggtgcacaag gtcaaggcca gccgggacgt   25080
catcattgac cagctgcccg acctgatggg gctcaaagct gtgaatgtgg ccaaggtcgt   25140
cggtgagtcc ggggggtccc aagccatggc tcagccatgc agacttgcat gaggaggaag   25200
tgacgggtcc atgcctgggc ataagtgttg agctcaggtg ccccgacctg ggaagggca    25260
ggacaggaaa ggtgacagta tctggccaag acagatggg aagggaccaa gggagctgat    25320
tagggagtgg ttatgctcta ggaatgtcgg taacaatggt tagaaagtga ctaacatttg   25380
ttgagcacct gctgtgtgcc cggccctggc cgggagcctt cgtgcccaca gtgacccgt    25440
ctgcaaatgt agttccttgc cctactcgca ctggggagca ggacgcagag ccgtgcaact   25500
cacaggtgcc aagctcagga ctccctcctg gtctgcctg ggctgggctg tgcttgttgc    25560
ccctgtggcc cacgcatgtg caccttccac ctgaaagcca ggatcttcag gacgctcccc   25620
gaggaggtcg ttgtctggca caatgatttg tctcttcctg aaaaggtgac agagttacac   25680
```

```
tggagagagc agcatccagg tgcggcaggg acaggcctgg ggctcgcggg cagggactct  25740
gtgtcctgcc ggggtcccac actgcacctg cttgtcagag gcactcagtc aatctttgct  25800
gatgaaggat gagaggacag aggacgtgat gcttgctgct gcattgcctg cagtcctggg  25860
tgagatgccc gggttgactc tgctgcccgt cgggtggatg tgatgtcaga tccccggctt  25920
taaaatacga gggagctggg aattgaggga gcaggttggg gcagaaagca cagccccgtg  25980
gaagcctgga gctgaggcag tgtgggcgac ccctggagca gtgagtgctt ccttcatggc  26040
cttcatcgca ccctgcagtc ctcatgtagg ggatgccatc catgaattta gttttcccag  26100
cctcctttaa aaacgcgttc atgctgggc cggggcagtg cagtggctca catctgaaat  26160
cccaccactt tgggaggccg aggcgggtgg atcatgaggt caggagatcg agaccatcct  26220
ggctaacaag gtgaaacccc gtctctacta aaaatacaaa aaattagccg ggtgcggtgg  26280
cgggcgcctg tagtcccagc tactcgggag gctgaggcag gagaatggcg tgaacccggg  26340
aagcggagct tgcagtgagc cgagattgcg ccactgcagt ccgcagtccg gcctgggcga  26400
cagagcgaga ctccgtctca aaaaaaaaa aaaagtaca aaaaaaaaa aattagtctg  26460
ggtgtggtat cacgcgccta taatctcact actcgagagg ctgaggcgga gaattgcttg  26520
aacccaggag gtagaggttg tagtgagccc gtatcgtacc actgccctcc acctgggcaa  26580
tagagcgaga ctctgtctca aaagaaaaa aaaaaaga acatttatgc caggtgtggt  26640
ggctcatgcc tgaaatccca gactttgga agactgaggc aggaggatca cttgagccca  26700
gaaatttgag agtgtcttcc ctgggcaaca tagagagacc tcatctctac cagaaaaaaa  26760
aaaattagcc cggcatggtg gcatatccct gtggtcccag ctacttaggg ggctgacgtg  26820
gcaggatcac ctgagtctgg aggcagaggt tgaagtgagc tgagatcatg ccactgcact  26880
ccagcctggg tgacagacag agaccctgtc tcaaaaaaaa aaaaaaaaa aagcatttac  26940
tatccaccat ggaaggtgag actgacctgt gagtgattgt tcaaagaaca aaaaataaac  27000
cccagagata agacaaaagg gtgcctccat gggggtgtga tttaaagctg agaaattggg  27060
cttcttcccc ctcccctctc accccgtggt ttgctaaagg agatgggaaa aaggattctt  27120
ttttttggctg aaatatttaa cactaaatta aagccaattt taacagcact ttggttgatg  27180
agtgaaatta acagactggc caaaaataaa cgaacggtct gtactatgtg aaaaagaggc  27240
agctttggcc atgctgggcc aatgtgagtt ttcagggttg ctgggaatgt ctgtgaatcg  27300
gaggaagggc ctagctggga ctctcaggag ccaaggccct gagggcaac ttgcctggtc  27360
cctgccctga ggcgttcact gctttcttcc tgggccagat cacaggcccg gaggctggac  27420
cactgggctg gcactcttgc cgagctgctc cctgacttcc tgaccatgct cctttcagca  27480
gccttgctgc actttagttt ccttgaatga aaaatgggga tgagaatagc tcctacctcc  27540
aaggtgaatg gagtgagttc ggacaggtga ctccctggga ccagtgcctg gcgcctgaca  27600
aggtccagtc agagcccgca ctgctgttac tgataccctt ggctgtacca ggggagaact  27660
tggttgccat tgccaggtgt ctcccacca ccccactac tgtccctgtt tgatgtgtgg  27720
cgggaataaa gctgtgcaca ttggagcttt tggcacatcc tggctttcag gtgaaaggtg  27780
cgtgtgtgtt tgagggttta gcctggccaa cccagccatg aggtcggacc tgacctgggg  27840
gtgagtcctg agctcggcac ccctgagctg tgtggctcac ggcagcattc attgtgtggc  27900
ttgggccgca cccctttccc tgctgggctg ttgatgttta gactggagcc tctgtgttcg  27960
cttccaggaa ccaacccgtg tgcggacagg aacgggggt gcagccacct gtgcttctgc  28020
acaccccacg caacccggtg tggctgcccc atcggcctgg agctgctgag tgacatgaag  28080
```

```
acctgcatcg tgcctgaggc cttcttggtc ttcaccagca gagccgccat ccacaggatc    28140
tccctcgaga ccaataacaa cgacgtggcc atcccgctca cgggcgtcaa ggaggcctca    28200
gccctggact tgatgtgtc caacaaccac atctactgga cagacgtcag cctgaaggta     28260
gcgtgggcca gaacgtgcac acaggcagcc tttatgggaa aaccttgcct ctgttcctgc    28320
ctcaaaggct tcagacactt ttcttaaagc actatcgtat ttattgtaac gcagttcaag    28380
ctaatcaaat atgagcaagc ctatttaaaa aaaaaaaga tgattataat gagcaagtcc     28440
ggtagacaca cataagggct tttgtgaaat gcttgtgtga atgtgaaata tttgttgtcc    28500
gttgagcttg acttcagaca ccccacccac tcccttgtcg gtgcccgttt gctcagcaga    28560
ctctttcttc atttatagtg caaatgtaaa catccaggac aaatacagga agactttttt    28620
tttttttttt tgagacagag tcttactctg ttgcccaggc tggagtaccg tagcgtgagc    28680
tcagctcact gcaacctccg cctcccaggt tcaagcgatt cttctgcctc agcctcctga    28740
gtagctggga ctacagacat gcaccaccac acccagctaa ttttttttat attttttagta   28800 gagacagggt ttcatcatgt tggccaggct ggtcttgaac tcctgacctc agggaacag     28860 acggggttgg cctcccaaag ggcggaaata acaggggtga gccaccgttc ccggcctagg    28920 aaaactttt gccttctaaa gaagagtta gcaaactagt ctgtgggctg gccttctgat      28980
tctgtaaaga aagtttgatt ggtggctggg tgcggtggct cacacctgta atcccagcac    29040
tttgggaggc cgaggtgggc agatcacctg aggtcgggag ttcgagacca gcctcaccaa    29100
cgtggagaaa ccccgtctct actaaaaata caaaaaaaa attaaccggg catggcggcg     29160
cctgcctgta atcgcagcta ctcaggaggc tgaagcagga gaattgcttg aacctgggag    29220
gcggaggttg tggtgagctg agatggcacc attgcactcc agcctgggca acaaaagtga    29280
aactccgtct cagaaaaaaa aaagtttgat tggtgtaacc aaagcgcatt tgtttatgga    29340
ttgtctgtgg cagcttttgt tctgccgaga tgagttgtga cagatctgta tgggctctaa    29400
agcctaaaac atgtgccatc cgcccctta cagaaaaagt gtgctgacct ctgttctaaa     29460
gtattggaca actacaatgt ttgctcattt attattctat gatttgtttt ctgctttttg    29520
ttgttgttgt tgttgttgag atagggtttc cctctgtcac tcaggctgga gtgcagtggt    29580
gtaatttcag ctcactgcag cctcgacctc ctgggctcta gtgatcctct catctcagcc    29640
tccctagtag ctgggactac aggcacacac caccactcct ggctgatttt ttttttttt    29700 tttttttt gtggagacag ggtttccgca tgttgcccag gctggtttca aactcctagg     29760
ctcaaacacc cacctcagcc tcccaaagtg ctgggattac aggcgtgagc caccatgccc    29820
agcctattct actgtttgta ttacatagct ttaaaagatt ttttatgact ttaagtcaca    29880
agggttcttt gtagaaaaaa atatatatat aggaaagtat aaaaagaaag taaaaattgt    29940
ccataacctc tccagccaga gacgaccgtt gctgacacct cagcatattg cctttaagtc    30000 tttttctct aagatagcat ttctcttcat cacagtcata tgctacgcag aattctgtat     30060
cctgattttt tcacttgaca ttacaacagg tatttgatgg cgctgtgaca aactctttgg    30120
cacaatcttt taaatgtatg aaatactcca ctgcacagat gtttgctttt aggcttaact    30180 gttctttat tttgcgtgtg ctggttacag ccgggcacag tggctcatgc ctgtaatcac     30240
aacactttga gagggtgagg caggaggatc acttgagccc agaagtttga gaccggcctg    30300
ggcaacatag tgagacccca tctctacaaa aaactttttt aataagtcgg gcgtagtggt    30360
gcatagctgt agtcccagcc accaaggagg ctgagttggg aggattgctt gagccccagg    30420
```

```
aggttgatgc tgcagtgacc tgagattact ccactgtact ccaacctgag cgacagagca    30480
agacttgtct ggggaaaaaa aaaaaaaaaa tatatatata tatatatata tatatacata    30540
tatacataca cgcacacaca cataaataaa aatatatat ttataaatat ataatatata     30600 ataaaaaat atatatttat aaataaaatt tataaattat atttataagt aaatatataa     30660
tatataatat aaaaatatat attatataat atataataaa atatataata taaaaatata    30720
tatttataaa taatatataa tacatactta taagtatata tttaaaatat atgtaatgta    30780
tattttttaa tgtatgatat ataatataca tttataaata cacatttata ttatttata    30840 taaaatatat ataaaatctc caagttgctt tttccaaaaa ggtgtcttgc tgcatttcaa    30900
acattcattt aaaaacttga atgctggtga tctggtccag aatgtgttca gtagctgctg    30960
ccagtggcca agcatctcgg gagatgtcta caaaacacgc tggttctggc ctggcgtggt    31020
ggctcacgcc tgtaatctca gcactttggg aggctgaggc aggtggatca actgaggtct    31080
ggatttcgag accagcctg ccagcttggt gaaacccat ctctactaat aatacaaaaa     31140
aattagccag gcgtggtggc atgtgcctgt aatcccacct acttgggagg ctaaggctgg    31200
agaatcgctt gaacccaggg ggcagaggtt gcagtgagcc gagatcgcac cattgcactc    31260
caggctgggc aagaagagcg aaactccgtc tcaaaaaaaa aaaaaagat gctggttcct     31320 aaaatgtggc cctttttcctc ctcacctgct gccagaccat cagccgcgcc ttcatgaacg    31380
ggagctcggt ggagcacgtg gtggagtttg gccttgacta ccccgagggc atggccgttg    31440
actggatggg caagaacctc tactgggccg acactgggac caacagaatc gaagtggcgc    31500
ggctggacgg gcagttccgg caagtcctcg tgtggaggga cttggacaac ccgaggtcgc    31560
tggccctgga tcccaccaag gggtaagtgt ttgcctgtcc cgtgcgtcct tgtgttcacc    31620
tcgtatgaga cagtgcgggg gtgccaactg gcaaggtgg caggctgtcc gtgtggccct     31680
cagtgattag agctgtactg atgtcattag ccttgatggt ggccaggact ggtagggccc    31740
tcagaggtca tggagttcct tcgtggagcg ggtgctgagg ctgtatcagg cacagtgctg    31800
gctgctttca cctgggccgt ctcaccgaag tgtccatgga gcctgcgtag ggtgggtatc    31860
tgtgtcgatt ttacagatgc agaaacaggc tcagagaaac cgagtgactt ccctaaggtc    31920
acatacccag ttagagcaga gctgggccag gaagtgctgt ctcaggctcc tgaccaggtc    31980
tccttgcttt gcactcttgc caaaaccatg atccagaact gactttgagg tccccggacc    32040
tcaggctcct ccgaaatggc ctcttggagg ctgctgagcc acagcttagg acccacctcg    32100
agaggcaaat gtgctttgag ctgccaggcg tcctgggggc cctgccttgg gcacggggtt    32160
cagacaggcc ccagatgtgt ggggcgtctt tctggacttg agttttcttt tctgtgtggt    32220
ggacacagtg ctcaccccctt aaagcacctg tgatgtgtgc agcagcccaa tccctgcctg    32280
tcgcctgttc tgctagggaa ggaaggaata cttcaggatg gcaggacaac agaaagaggt    32340
ccaggtttta gagcaaggc aggtcaaact tagaaaattc tggaatgagg atgtgcattt      32400
cctcttctgg atctgctaaa agaagaggga aggaggggct gctgggggag gagcccagag    32460
ccgagtttac atccggatcc cgcaaggcct cccctgccct gaggtcttgt tttgtgatgt    32520
gcttgtgtcc atcctggttt ctgccgtgtc cccaacatcc ggccaagctt aggtggatgt    32580
tccagcacac actcaccctg tctgtgcacc tgttttttgtg tccgtaagtg ggtatttact    32640
caccttacga gtgagccact gtgggaattc agggaggtgg cgcagtgacc accccctggag    32700 ggatatgtgt gtgcagggg tcgagggtct cgcccttccc tgcttcctgc gcgtggcttt     32760
ctccaggacg gggagggctg agctgaagag gtggggacag ttgcgtcccc ccgccaccca    32820
```

```
ctgtcctgcg gtgagagcag actcactgag cctgcccttc tcccttgtgc cttccagcta   32880
catctactgg accgagtggg gcggcaagcc gaggatcgtg cgggccttca tggacgggac   32940
caactgcatg acgctggtgg acaaggtggg ccgggccaac gacctcacca ttgactacgc   33000
tgaccagcgc ctctactgga ccgacctgga caccaacatg atcgagtcgt ccaacatgct   33060
gggtgagggc cgggctgggg ccttctggtc atggagggcg gggcagccgg gcgttggcca   33120
cctcccagcc tcgccgcacg taccctgtgg cctgcaagtt ccccaacctg gcaggagctg   33180
tggccacacc cacgactgcc cagcagcctc accctctgct gtgggagttg tccccgtcca   33240
cccctgggtg cctttgctgc agttatgtcg ggagaggctc tggtgacagc tgtttcctgt   33300
gcacctgctg ggcactaggt cccagctaat ccctgtgcca ggactctaat ttcaccctaa   33360
cacacatggt ggttttcatt gctggggaag ctgaggcctg agcacatgac ttgccttagg   33420
tcacatagct ggtgagttca ggatccccca gagataccag ggccagcact cgatccccac   33480
ccagccctga accccaccat gtgctgggat tgtgctggga gtgtccacac gcctgggacc   33540
ccagggctgg tgctctcatc tccttttttcc agatcatgag aatgaggctc agggaagttt   33600
gaaaaaaacc tatcccaagt cacacagcaa caggagcagg atttgaaccc agaaaagggg   33660
accgcacact ctgttctgct agagtagtta gctgtcctgg gtgatatggc aggtgacagg   33720
ggcaactgtg cttaacaaag gaaccccccat ccccctgcc aagttgggag actagaaggt   33780
caggggcaga agctctgaag ggccaggtgc agtggctgac acctctaatc ccagcacttt   33840
gtgaggccaa ggcgggcaga tgatttgagc ccaggagttc aagatcagcc tgggtaatgt   33900
agtgagacgc catctctaca aaaaatttt ttaaaaatta gctgggcatg gtggttcatg   33960
cctgtagtcc aagctacttg ggaggctcag gtgggaggat tgcttgagcc caggaggttg   34020
aggttgtggt gagctgtgat catgccactg cactccagcc tgggcaatag agtgagaccg   34080
tctccaaaaa aaaaaaaaga agaagaaaaa gaagctctga ggctccaagt ccccaggcac   34140
cccttggctt gagggcagac aagggaggag agggtcacct gggcagccct gacttttgtc   34200
ccctggcaaa gggaccttca gtgaccttgg ccctaggaga gcctctgagc acgtcagcca   34260
tgtcgaaccg ctcaggaagg gcagcaagaa tttggcttct gacctctgcc tctcctactc   34320
gccatctgca ctgggtgtgg ttgtgcccat tttacagatg aggaggctgg ggcatcgacc   34380
agctgaatgc cttgtcccag gtactgcgta ggcagagctg gcagttgaac cccgtgtcct   34440
ggttgtcgct gggggtgggc tgcacccctga cttgtgaggc cagtagcaag gtttgcacgt   34500
gacttcgtga ccgtcaccca gctctgcagc acatcccgtg acccagctca tccaggccgc   34560
atgcaaacct gttgccaggc gagaaaccag tcaccgcaca gctgtggttg cctgaaatga   34620
ttaagctcat taatcacccc ggagtgagga cagactcaga tgaaaaccag caaaagccct   34680
ggaaactcat gtgaccctgc caatgagggc ggccatgtgc attgcagcct ggccgtcact   34740
cctcggtacg tgttttggac ttaaacgctc cggatgttta ctgagtgctt gattaataac   34800
atggaaggcc tggtctcatt gctgtgggag tgaaggatgc acagccaggc ctgcatgat   34860 gagaacaaga acctggagtc tcgctgcctg ggtggtaatc ctggccctgc cacttagcaa   34920
ctgtgtgact gtagccaggt cacttaattt tgctagatcc tgcctgcgct tcagtggatc   34980
ttgctggttt tccaaggtgg ccaaacactt taaggcattc atgtggtcgc taggctgcag   35040
ggttgaaccc tggctcaccc cgcagggcgc cgtgtgctct gtggcctggc tgtgcctttg   35100
ctgacaccgt gcccgtgtgt gttcatgcag gtcaggagcg ggtcgtgatt gccgacgatc   35160
```

```
tcccgcaccc gttcggtctg acgcagtaca gcgattatat ctactggaca gactggaatc   35220
tgcacagcat tgagcgggcc gacaagacta gcggccggaa ccgcaccctc atccagggcc   35280
acctggactt cgtgatggac atcctggtgt tccactcctc ccgccaggat ggcctcaatg   35340
actgtatgca caacaacggg cagtgtgggc agctgtgcct tgccatcccc ggcggccacc   35400
gctgcggctg cgcctcacac tacaccctgg accccagcag ccgcaactgc agccgtaagt   35460
gcctcatggt cccccgcacc tcactccctc gttagatcag gctggttctg ggagctgacg   35520
ctgaaaggag cttctcatct ggggttcctg ggtgtacata gatggttggg taggttgtgc   35580
actgcacaag ctgcatgatg ctacctgggg gtccaggtcc aggctggatg gacttgttgc   35640
ttcatcagga catagataaa tggccaaaac tcctcagctg aaggtcctg ggcaggatct    35700 ttgggtgtga aaccagtca caggggaagg gtgcttgctc atactgccag cacagtgctg     35760
agtgctttcc atagcgctcg tttactcctc aagcctggag ggtggggagt agcatggtcc    35820
catttcacgt acaaggaacc cgatgcacag agaggtgtgg caacccatcc aaggccatac    35880
aactggggtg ggttgagccg gggttgactg tggcaggctg gctcaagagt ccctgctcct    35940
gaacccttgc caggcagcct ggcatcagct cggggaattt ttgccctgac ccttggaagc    36000
aagtgggcct ctttgttctc atgtcagtga tgagaagagt gactttccta tggcccctct   36060
ggagtacagg tgtttcctgt tggcgggctc ttcccccatg acatcagcag cgagctggtt   36120
atgattccct acgcagaact tgatagttta taaagctctt tgtcatccag gcccgttgg    36180 agtctcacgc agacctggtc gcaggcgggg ctggtcttgc ctgtcccagc tgcatggatg   36240
gggaacttga ggcttgcaaa ggttaagggg ctgttcgagg cccacgctgg caggagatgg   36300
gcctgggcca gagtctggga cttcccatgc ctgggctgtc tttggtcctg ttgctcacca   36360
tccctccctg gggccatgac cttagagagc caaatggagg tgcaggtaac ccacggcaag   36420
gaggggttgc catgactcag agtccccgtc ctgtggccgg cagtacctgg tgcaacgact   36480
tggatttcag accagccact gtagcccgct gacggtgcgc tcgaagtgcc acagcttctg   36540
aagccaggca ggactcaggc caggagactc tgttagctgt tgagagggag aggccaacgg   36600
atgttctggt tctgctagag agctggttct tcggatcctg gtaccagtgc actgagagga   36660
ggcccagctt gattctgggg ctgccttgtg gtggcatgtg ctgctcactg acaccctcga   36720
ggagtgtctt ctctcgggct tgttgactgt gcccggtttt ccgcagttca ctggtgcaca   36780
cataggcaca tagcaaaccg cacacacagt cgtgggtatg agtttcacta cattccacca   36840
ccagtgttca ctaccattac ctgccttccg tcttaagtgt tcatcattta aaataaatt    36900 tattgggctg gacgcggtgg ctcatgactg ttatcccagc actttgggag gctgaggcgg   36960
gcagatcacc tgaggtcagg agttcaagac cagcctggcc aatatggtga aactccatct   37020
ctactaaaaa tacaaaatta gctgggcatg gtggggcatg cctataatcc cagctactca   37080
ggaggctgag gcaggagaat ggcgtgaacc cgagaggcag agcttacagt gagcccgat    37140 agcaccactg cagtccagcg tgggcaacag tgcgagactc catctcaaaa aaaaaataaa   37200
taaataaaag aaaaataaat ttatgatcta tttcaaaaat aacacatgta ctttgaaaca   37260
gcagagacac atatgacacg gagaatgaaa ttccccatag cgcacccca agagacagcc    37320 ctggtccccc cgtcttttccc gtggacctcc agcggggcag atgctgagcc gcctgttgtc   37380
gagtggcatg ctatcccgtc ctccagctcc tctgtggctt acagacaccc acctgcagcc   37440
ctgtctttgc ctcctctagc gcccaccacc ttcttgctgt tcagccagaa atctgccatc   37500
agtcggatga tcccggacga ccagcacagc ccggatctca tcctgcccct gcatggactg   37560
```

```
aggaacgtca aagccatcga ctatgaccca ctggacaagt tcatctactg ggtggatggg    37620
cgccagaaca tcaagcgagc caaggacgac gggacccagg caggtgccct gtgggaaggg    37680 tgcgggggtgt gcttcccaag gcgctcctct tgctggtttc caggctgctg ccctgtcct    37740 tagcagaggg aggaaacaga ggatggctct gggtgaatga tgacttgggc ttcgattatg    37800
tagtcacagg gtatgaccct gagatgcgtg aaccccgag actgtgatta tatgtagaaa    37860
ctgggtttcc ccgttgttta agtagtcatg gtggggtcag accccacagg acttttgtct    37920
tttcaagaaa gaaatggtc gtgtgtcatg caggggtagt tggtactggt taatccaggt    37980
ttatccttta ttttgtggga actgtacagt catttctgct acaatgctgt atatgctctt    38040
ctgaaagaca cctatgcaaa atcgcacagt aaaaatgaca caactcatag ggaaagcggg    38100
gccagggcac agccctcaaa atctccatca atgacatgta agaaaagaga ggaacctggg    38160
aaatagcaaa gtgccttttg cacattaaat ggttagctat atcccacaat actgtgcatt    38220
cgtaaacgtt aatgctgcaa taaatacggc acttcacctt gggaagatct ggagttggct    38280
tatgagtgtg gaagggtgta gcgcatgagt ttttgtgaaa cactggaagg aggattgtgg    38340
gaaatcaaat ggaaagttct caccccaggc gtggagaaga gtgggtcatg gccccagcag    38400
tgagcccagg gaggtcagag acggaggtgt gtgtgtgggt gtgaccctgc gcagttccct    38460
gccggctgta gttttttgca ttcgcttaat gtttctcgtg gaggaaattg tgcatgagca    38520
aatgtgaaac cgtgctgtgc tcaaattgtc ctaatacatc attgcattgg aacagattgg    38580
cttttntttt tttttttttt tttttttttt tttgaaatgg agtctcactc tgtcaccagc    38640
ctggagtgca gtggcatgat cttggctcac tgcaaccttt gcctcctatg ttcaagtgat    38700
tttcctgcct cagcctcctg agtaactggg attacagggc atgagccacc gcggccggcc    38760
agatttgcat ttttgaaaca actgctaggc tgggcgcggt ggctcacacc tgtaatccca    38820
gcactgtggg aggccgaggc aggtggatca cctgaggtca ggggttcgag accagcctgg    38880
ccaacatggt gaaaccccgt ctctactgaa tatacaaaaa tcagctgggt gtggtggcgg    38940
gtgcctgtaa tcccagctac tcaggaggct gaggcaggag aattgcttga acccaggagg    39000
cagaggttgc ggtgagccga gatcacacca ttgcactcca gcctgggcaa caagagcaaa    39060
actccatctc aaaaaataaa aaatagaaaa acaagtgctg tagcggaagt gagcactttg    39120
cggagtcagg cttgtgtggc ctgttccaca aatgatgtgc tcacggtggc ctcaggccca    39180
cctggagtct gcagcatggg gcacaacagg ttcattagtg tagaattcca ggacaggcct    39240
ggctcctaag cagccttctt ttacaaaaac tgcagagccc gcctgtatcg tagcactttg    39300
ggaggccgaa gtgggtggat cacgaggtca ggagttcaag accagcctgg ccaacatggt    39360
gaaaccccat ctctactaaa tatcgaaaaa ttagctgggt gtggtggcac gcgcctgtag    39420
tcccagctac tcgggaggct gaggcagaat tgcttgaacc tgggaggtgg aggttgcagg    39480
gatctgagac catgtcattg cactccagcc tgggcaacag agcgagacgc catctcaaaa    39540
aaaaaaaacc tacagagcca cacggcctct ttctccaccg agtgttggtg tgggagcttg    39600
tgttattgtg gtgaaatctt ggtactttct tgaggcagag agaggctgag cgcctggaga    39660
gactttcaca tgggtcgcca tgtccgccgt cggtttcgct gttgtgctcc ccatctgaag    39720
gctggtgccg tccagacagg ctggacgccc ctttccacca gatccttcct cccgcagcag    39780
tttctagtta cgttgtactg tgaggtctgt gtccttggtt gatggcaaaa gtcagccgaa    39840
ttgaaattca gagccatgcc tggctccctg gagcttctct cctgggcagc tgtgatcatt    39900
```

```
gcctctgctg tggtgtgggt ggtggaaatg gattcctttc atcttgcttg ctacaggtga    39960
ctgtcacgtg gagtcctttg gagagaggga cgtgttaatt gatggatgtg gctcccatgc    40020
tgagaaagct cctgggcgta cattgcctta gagtttcatt ggagctgcgt tcttttatgg    40080
tgtctgctag gcagaagtga tgaagacttg gaagaaaacc cagaaggttt tccacttaat    40140
ttggaaaatg tgcttttccc ctcctgtgtc ttttgctaag gtccagcctc ctgcagcctc    40200
cccgctctgt ggactctggc tttgattctt tattaggagt cccctgctc ccccaaaaga    40260
tggtgtctaa attatcatcc aattggccga ggttttgttt tctattaatt gttttattt    40320
tttattgtgg taaatttata taacataaaa tttgccattt taattgtttt gttattgttg    40380
tttttgagac agggtctcac cccagtgccc aggctggagt gcagtggtgc gatcatggct    40440
cactgcagcc tcagcctcca gggctccagt gatcctctca cctcagcctc tctagtagcc    40500
gggactacag gcatacacta ccacatctgg ctgattttt gtattttttt tttattgtag    40560
agacccgcta tgttgcccag gctggtctca actcctggac tcaagccatc ctcccacctc    40620
accctcccaa agtgctggga ttacaggcat gagccacaac acccagccat tttaattttt    40680
ttttttttt tgagatgga gtctcactct atcgcccagg ctggagtgca gtggcgtggt    40740
atcaactcac tgcaacctct gcctcccagg ttcaagcgac tctcctgcct cagcctcctc    40800
ccgagtagct gggattacag gtgcccatca ctatgcctgg ctaatttttg tatttttag    40860
cagagacggg gtttcaccat gttggccagg ctggtcttga actcctaacc tggtgatccg    40920
cccgcctcgg cctcccaaaa tgctgagatt acaggtgtga gccaccgtgc ccggcctttt    40980
tttgttttg agacagggtc ttgccctgtc acccagactg gagtgcaatg gtgggctctt    41040
ggctcactgc agcctccgcc tcccaggctc aagttgtgca cctccacacc tggctaactg    41100
tattttatgt agagacagat ttcaccatgt tgcccaggct gggcttgaaa tggactcaag    41160
cagtccaccc acctcagcct cccaaagtgc tgagattaca ggcgcgagcc accgcaccca    41220
gcccattta cctattctgc agttgacagt tcagtggcat tcagtcagtt cacgaggtaa    41280
ccatcactgc cattcatctc cagactactt caccttctcg gcagatgtcc gaaactgtcc    41340
gcattgaaca cactcctcat ctccctctga cagccaccat tctactttgt atctctctct    41400
gccttctcta ggtacctcat gtaagtggaa ttataccaat atttgccctt gtgtgactgg    41460
cttctttcat gtgacatggt gtcctcaagg ttcatctgtg ttatagcctg tgtcagaatt    41520
tccttcctta aagcctgaat aataacccgt tgtaaaggct gggcgcggtg gctcacaccc    41580
tctaatccca gcattttggg agtccgaggt gggcagatca cttgaggtca ggagtttgag    41640
accagcctgg ccaacatagt gaaaccctgg ctctactaaa agtacaaaat tagctgggtg    41700
tggtggcgcg cacctgtaat cccagttact caggaggctg aggcaggaga atcgcttgta    41760
cccgggaggc agaggttgca atgaaccaag attgtgcctc tgcagtccag cctgggtaac    41820
agagtgagac ttcctgtctc aaaaaaaaaa aaaatcatcg gatggatgga cggaccactt    41880
cttgttattt atccatccac gggtgctagg tttcttccac ctttggttgt cgtgaataag    41940
gccactatga acatttcctt ccgtggtgaa ggttttgtac tagtgaggaa aaggcgtgtt    42000
tgtggtgttg cataggattc tggtaagaaa gtttgcacta accataagta tttgtactac    42060
attaaaatga aagctcaggg gccgggcgcg gtggctcacg cctgtaatcc cagcactttg    42120
ggaggccagg gcgggcggat catgaggtca ggagatcaag accatcctgg ccaacatggt    42180
gaaacccc gt ctctactaaa aataccaaaa aactagccag gtgtggtggc gggcacctgt    42240
agtcccagct acttgggagg ctgaggcagg agaatggcgt gaacccggga ggcggagctt    42300
```

-continued

```
gcggtgagcc gagatcgctt cactgcactc gagcctgggc aacagagcaa gactccgtct   42360
cacgcaaaac tctgtctcac gcaagactcc gtctcaaaaa aaaaaagagt tcagggttta   42420
tgaaactggc cagccgcgta aagtttgctg tgttgttttt gtgcccggga ggagtgtggc   42480
cagggtgtca cgtcacacag tacacgtttc tcagatggtg gttctccaga ctgctgtccc   42540
aaagtctgtt tttgcatctg gttcccacag acccaccctc cacggtgagc ctgattttgg   42600
ccagggtagc tggaatcttg cttgtctttc agcccggcag ctgtaccagt ccagggtcca   42660
cagctagtgg ctttttaggaa ggaatttgtt cagttggctt tgacacatgg cccctaggg   42720 tccacagctc tgtagtgatg tggatgttgt tatctacaaa gacacatgat ccttcgtgtc   42780
cagatgaaag tgatgatgtc tttgcagctg cccagcaagg ctgtgtgtgt gtgtgtgtgt   42840
gtgtgtgtgt gtgtgtgtgg tgtgtgtgtg gtgtgtgtgt gtgtatgggg gagggaggca   42900
ccctttccat ctgggggtgt gtgtgtgtgg ggtgtgtgtg tgtgtgtgcg cgtgtgtgtg   42960
gtgtgtggtg tgtgtgtgtg tatggggggag gcacccttc catctgggtc caagagactg   43020
ggcctgggga agacgcttct ttttatctac ttagagactt tgttttattt gtatttttt    43080 gagacagggt ctcactctgt cacccaggct ggggtatggt gatatgagca tagctcactg   43140
cagcctcggc ctcccaggct gaagcgatcc tcccacctca gccttctgaa tagctgggac   43200
tgtaggcgtg cgtcaccata ctgagctatt gttttttttg tttggttggt ttaattttt    43260 ttgatacaga tggagtcttg ctatgttgcc cagactagtc tcaaactcct gaactcaagt   43320
gattctccca cctcagtttc ccgacattct gggatcacag gtgtgagcca ctgctgtctc   43380
cctgttttat taactgctga aagacctaga taaagaaagt ctgaaaagac ttactatcag   43440
agcaccatcc taagatgatt ccctctgact caatggagag ggaggggagc ttttccttca   43500
ggcctgggtg gcaggagccc aggtgctcca ggccccattt gccccaggcc aaatcactcg   43560
ggaacttgga tgcagctgtc tttcagggta acccaaagga accagatccc cgcaggcagt   43620
aggcttctgg gctgtcctct cctcctacgt cagctcagta agagcccttc gaagggatgc   43680
tgtgtcggag gccccaaaag cccaggctca tccctgagat gcacagggtg ggctgggctt   43740
aggcagcgct cgagcatctc ctggacggtg accccagaga gtgtggagac ggagagtcct   43800
tgagagtcac tgagagacgt ggctgccctg ccttcccaag aggggctctg agtcattccc   43860
cacactcacc tgcccctacc caccctcacc tggcccccag cctcacctac ccccacatct   43920
gtaccgatcc ctttacccgc accttcccta cccacccctca cctcccctgt accttcacct   43980
cccccactca cccgcccctg caccctcacc tgtccccac cttcacctaa cccccaccct    44040
cacctgccct cccctcacct ggcctccttc cgttggggaa ggggttgtaa ggggcggccc   44100
ccaaactgtc tgtcctggtg ccctgcagag aaaacagtac gtgagggccg cagtccaaaa   44160
gcttgagtcc tggaaggtgg aggagacagg gatgtgttgg gaaggccccc atggtcttgg   44220
atcccttctc gactgtcaat ggggccttca tgggagcgcc agtctagtga tgcacagctg   44280
ggtgcccggc gggtggctga ggaggcctaa agtccgaggc ggcaagagct cttccagagg   44340
ctgttgtcct aatcgctctg gcatactcag gcgggcacgt agttaggagc tgattggaga   44400
ggagagaccc ccacaccaat actgggattt gactttcagg ctaaacttga gaagtgtggc   44460
ctctgctgtc ctgccagagc tctccagcca gtgcccaggc ctctccagcc agtgcccggg   44520
ggtctccacc agtgcccggg ggtctccgcc agtgccaggg gtctccgcca gtgcccaggg   44580
gtctccgcca gtgctcagga gtcttggttt ctttgtctta cagcccttg ttttgacctc    44640
```

```
tctgagccaa ggccaaaacc cagacaggca gccccacgac ctcagcatcg acatctacag   44700
ccggacactg ttctggacgt gcgaggccac caataccatc aacgtccaca ggctgagcgg   44760
ggaagccatg ggggtggtgc tgcgtgggga ccgcgacaag cccagggcca tcgtcgtcaa   44820
cgcggagcga gggtaggagg ccaacggggtg ggtgggggtg ctgcccgtcc aggcgtgccc   44880
gccgtgtctt ctgccgaatg ccagcctctc acaggctggg gagactttcc accctgggga   44940
tccaatgggt ggctttccag ggtcccaaaa gcaaacacag gctctttcac agcccctcca   45000
ggaaagcaga aagcccccaag ggctggaagg gaaggggggag ctctgctgag aggttacaag   45060
gcagcgctgg ccgacgggag ttgcagttga taggttttgt atcatccttg ttaaacttga   45120
accctgtgca gaaatccctt ccacggcatg ggggctgcct gttgactcgc tcctgttcca   45180
ccacagggag ctcctgggct tcttcctccc agaggccccc gacgctccca cctgttggtc   45240
gtcagagctt ctggttggtg ggaaggcacc caggaccttg aggtctccag agagaaaagc   45300
cagggaaaga gggagaccga aacccatgtg acatgaaact caggctccaa actgagcacg   45360
ggaacgtttg gggacaggag cgcgatggcc ttcctcagat agctgggggg ctggcatgaa   45420
gacgggagct acagccagca caggtcctgg gccgggagcc cagagattga gccctgactc   45480
tgtcacttac tggccacgtg accttgggcg ggtggcatag cctcttggag actcagtttc   45540
ctcattggta ggagtgacgg ccacagtggt gcggcctctg cagcacacgg ggggctcggt   45600
gggcggaagc cccgggtcta taaggcggct gtgcaggagc cagccgagct ggtctcccaa   45660
cagccagggc tccggggtcc ttagcagctg tggggggcct gcacctgttt cccatggctg   45720
ctgtcagaaa ttaccagaag ccaggtggct gagagtaatg gacacttgtt ctctcacagt   45780
tcctgagggc tgaagcccga gatcgaggtg tgggcagggc cctgcgccct ctgaaggctc   45840
tgagggaacc tttgggcttc tggtggctcc aggcacccct tgacttgtgg tcctgtcact   45900
ccagtctctc tgtctggctg cacatggcgt ggcctcttct gtaccattga aggacacttc   45960
agttggattt agggcctacc ctcacccatt gtggtcgtat cttgatcctt catgacattt   46020
gtaaagaccc tgcttccaaa taagctcaca ttctgaggtt ctggggtgag cgggaatttg   46080
gagagcattg ttcaactagt atagaatgtg acctgtcagc ctcgggcagc cctgagaggc   46140
aggggctttc cacagcccag ctgggtgccc tgggctccgt gctgtccgag gagacgccat   46200
ccccacaccc gtccttcacc cgccaccctc ccgcaggtac ctgtacttca ccaacatgca   46260
ggaccgggca gccaagatcg aacgcgcagc cctggacggc accgagcgcg aggtcctctt   46320
caccaccggc ctcatccgcc ctgtggccct ggtggtggac aacacactgg gcaagctgtt   46380
ctgggtggac gcggacctga gcgcattga gagctgtgac ctgtcaggta cgcgccccgg   46440
ggcctgccct aaccgcagac acccggcctt cattgtcagt aatggcagca gctgccacat   46500
tgtccgagac ctgccgtgag cccagtgccg cgccagggggc tttgtgtgta gcgtgttttg   46560
tcctcacact gacagctgta ggctggggtt ctgagtgagc cccacagggc agaggcagaa   46620
aatgagtctc agagagggtg agcgagctgc ttggggcccc acagcaggag atggagcagg   46680
actgcagcct agcctctgcc cccagcacct gcgcaagaag ctgctctgct ctggactgtg   46740
ttaggctgcg agggctggag agaaatgaga gttggtgctt agagaggggg cgcaggtccc   46800
catggctttt cctcttatga tgaggtagat gggtgaaggg aggggccatg cttgcagggg   46860
ccagtgaccg aggcccgccg ttggaactga tggccttcat cccgagccca gcccaggtgg   46920
gagcagggct ttccgagggc ttgtcttggg tcggcctgct tccagggact ctgctgcagc   46980 tcccaccccct gtccaaagca tggaatcccc caggctccct ggcagtcctg tcaacctctg   47040
```

```
tcctcccaag ctgagtgtgg ggcaagttct ggaggtcagc actgctcagg ggggcccacg    47100
ggctgcttgc aggggccaac cgcctgaccc tggaggacgc caacatcgtg cagcctctgg    47160
gcctgaccat ccttggcaag catctctact ggatcgaccg ccagcagcag atgatcgagc    47220
gtgtggagaa gaccaccggg gacaagcgga ctcgcatcca gggccgtgtc gcccacctca    47280
ctggcatcca tgcagtggag gaagtcagcc tggaggagtt ctgtacgtgg gggctggcag    47340
tggggtgggc agggtggcct ctaaacccga cccctggagg aggctggagg ccagtgcaag    47400
atcctgtgtg gcctcagcca ggcggtggtc tctgccagat gccaactgtt gcccgctggg    47460
gttcagcgac atgtccgaat gtcccgaggc ctctgaggtt gttttctttt gccgcagaac    47520
aaatcaccac gaacagcgtt ttaagacaac accaactctt tttttttttt tttttttga    47580
gtcaggatct tgctctgttg cccaggctgg ggtgccctgg tgcaaacaca gttcactgca    47640
gcctcgacct ctgggcttaa ttaagtgaac accttgcctc agcctcccag gtagctggga    47700
ctacaggtgg gcaccaccac acctggctaa tttttttttg tagagacggg gtttccccat    47760
gttgcccagg ctggtctgca actcctgggc acaagctatc tgcctgctgt ggcctcccaa    47820
agtgctagga ttataggtgt gagccactgg cctgacaaca cccacggatt gtctctcagt    47880
tctgtaaggc aaagtccagg cacagcgtgg ctcacctggg ttctctgctc agggtctcac    47940
ggggccagaa tcaaggtgtc aggaacgctg ggccctcagc ggaggctctg tggagaaatt    48000
agcttccttg ctcactcagc aggtagcagt tgtgggatcg aggttctgtt ttctctctgg    48060
ttattggtcg gggaccactc tcagctccta gaggccaccc caggtccttg ccccgtggcc    48120
ctctctgcct cagcagtggg ggctccctgc gtcagtccct cccgcacctt gagtctctct    48180
gatttgcttc taaagggccc tgtgattcgg ctcagccacc tttagattag gttagcctcc    48240
cctttgatag actccaagtc ggctgattaa taaccttact cacatctgca gaatcccttc    48300
tgccacataa ggtcatgacg ccgtgctggg gactggggtg ggaaattacg gggtcattta    48360
ggattctgcc tgccactgcc ttgctgtgtc ccagggcttg ggggaggggc ctccacagct    48420
gggaccacag tccttcctcc cctccatggt aaccatctga ggattacttg agaccagcct    48480
ggcaacatg gtgagaaccc atccctacaa aaaatacaaa caaaaaggga ccaggctggg    48540
cttggtggct catgcctata atcccagcac tttgggagac caaggtgggc tgatcacttg    48600
aggttgggag ttcgagacca gcctgcccaa catagtgaaa tcccgtctct actaaaaata    48660
caaaaattag ctgggtgtgg tggcaggcgc ctgtattccc agctactggg gaggctgagg    48720
tgggagaatt acttgaacct gggaggcgga agttgcagtg agccaaaatt acgccactgc    48780
actccagcct aggcaataga gtgagactcc gtctcaaaaa aaaaaagggg ccaggggtgg    48840
tagtgacaaa gagaccctat cccaaaaaaa ccgaacactg aatccttgag actgagtaag    48900
gacactgtga aattttctg ggtggggcag ggaacagagc gtcttctgtc atttcttcca    48960
cctgggtgtg gtcagctctc cctccaagct gcctcctctt cttctcattg tccgggtgtt    49020
ggacacattt ggttaactgg atagaataac gcgagttccc agggacttgg tccatttgct    49080
atttttatttt attttatttt attttatttt atttatttat ttatttattt atttatttat    49140
tgagatggag tttcgttttt gtcgcccagg ctggagtgca gtggcgcgat ctcggttcac    49200
tgcaacctct gcctcccagg ttcaagtgat tctcctacct cagccttcca gtaactggg    49260
attacaggca cccaccacca taccaggcta atttttttgt attttagta gagacggggtt    49320
ttcgccattt tgcccaggct ggtcttcaac tcctagcctc aggtgatcca cgcacctcgg    49380
```

```
cctcccaaag tgctgggatt acaggcatga gccaccacgc ctggcaccat ttgctatttt    49440
aattcccatg tgtattagtg tcccacggct gctgtaacaa atgaccacaa actggatggc    49500
ttaaagcaac agaaatggat tcccccaatg tgctggagac cagaagcctg cgaccaaact    49560
gttgggaggg ctgtgcttcc tctgggggct ccagggagga tctatttgtt ggcccttcca    49620
gtgctgtggg tgccagcgtt ccacacttgt ggatgcgccg cctcaacctc tgcccatctt    49680
catgtgtcca tctcctttgt gtctgcgtct ttacctcttc ttcttgtctg tgttgcctct    49740
tataaggacg tttgtcattg ggtttagggc ccacccaaat catccgagat gacctcgtct    49800
tgagatcctt aacctgcaaa gacccttttt ccaaaaaaag gttatgctca cagattctag    49860
gccttaagac atgggtgtat ctttctgggg ggcactatcc aaccccttat acaatgaaag    49920
acgggaagag ggccaggtgt ggtagttcac gcctgtaatc tcagcacttt aggaagctga    49980
agcgggagga tcacttgagc ccaggagttt acaagtagct aggcaacatg atgagacccc    50040
atttctacaa aaagtaaaaa aaaaaaaaaa aaaaaaaag ccaggtgtgg tggctcacac    50100
ctgtaatccc agcactttgg gaggctgagg caggcagatc acgaggtcag gagattgaga    50160
ccatcctggc taacacggtg aaaccccgtc tctactaaaa atacaaaaaa ttatggccgg    50220
gcgcagtggc tcccgcctgt aatcccagca cttgggagg ccgaggtggg tgaattacaa    50280
ggtcaagaga tcgagaccat cttggctaac acggtgaaac cccatcaaga tcacaaggtc    50340
aagagatgga gaccatcctg ctaacacgg tgaaaccccg tctctactaa aaatacaaaa    50400
aattagccgg gcatggtagc gggcgcctgt agtcccagct gctcgggagg ctgaggcagg    50460
agaatggcgt gaacccggga ggcggagctt gcggtgagcc gagatcgctc catgccattg    50520
cactccagcc tgggtgacag agtgagactc cgtctcaaaa aaaaaaaaaa aaagaaaatt    50580
agccaggcac agtggcaggt gcctattgtc ccagctactt gggaggctaa ggcaggagaa    50640
tggcatgaac ccgggaggtg gagtttgcag tgagccgaga tcatgccact gcgctccagc    50700
ctgggcgata gagcaagact ctgtctcaaa aaaaaagcc aggcatggtg gtgcatgcct    50760
gtagtcccag ctactcaaga ggctgaggca ggagggttgt tcgacccacg gagatcaagg    50820
ctacagtgag ccatgatcgc accactgccc tccagcctgg gtgacagagt gtgaccctgt    50880
ctcaaagtaa gtaaatagga ggagagacaa gtgggcagtt cagactgatg gtatgggcac    50940
agtagagact ggtgcagaca ggctggcctg tgatgtcaag caacttctgt aactgtttcc    51000
ggcatccatt tgtgtgtcaa tttccgtgtc agtaggaaga ctctgtaggc tgccaagagg    51060
aataagtggg aggatcctcc cagagaggcc gggcctgcag gagggccagt tctcatgagt    51120
tcttatttgg cccctacccct ccaggctgtg gttctgaggt gggagacaga gcctgacctc    51180
tgtttgtctt gttttgtctt tgcagcagcc cacccatgtg cccgtgacaa tggtggctgc    51240
tcccacatct gtattgccaa gggtgatggg acaccacggt gctcatgccc agtccacctc    51300
gtgctcctgc agaacctgct gacctgtgga ggtaggtgtg acctaggtgc tcctttgggg    51360
tgatggacag gtacctgatt ctctgcctgc taggctgctg cctggcatcc ttttaaaatc    51420
acagtccctg tggcatccag tttccaaagc tgattgtgtc ttcctttgcc ctcctttctt    51480
ttctactatg tgcattcggt gctatgaatt ttcctctaag tactgcgttt cctgcatctc    51540
acaaattttg ttcattttc attttcaggt agtttgaata tttttacact tctcctgaga    51600
tgacatcttt ggctcatgtg ttatttagaa gtgttgctta gtttctaaag agttggggct    51660
tttccagctg tctctctgca actgatttct aatttaattc tactgtagtc tgagagctta    51720 tttttatatga tttctgttat tttaaatgtg ttgggtgtgg tgttttttgtt gttattgttt    51780
```

```
ttgtgtcttt ttgttttgtt ttgcttcgtt tgttttgttt ttgagacagt gtcttgctct   51840
gtcactcagg ctggagtgca atggcgcgat ctcagctcac cgcaacctct gcctcccggg   51900
ttcaagtgat cctcttgcct cagcctcctg agtagctggg attacaggtg cacgccacca   51960
tacccagcta attttttgtat ttttagtaga cggggtttt caccatgttg gtcaggctgg   52020
tctcgaactc ctgacctcgt gatccgccca cctcggcctc ccaaagtgct gggattatag   52080
gcgtgagcca ctgtgcctgg ccattaggtg tgttttatca cccagcatca tgcagtttat   52140
cttggtgaat gttctgtgta ctcttgaaaa gaatgtggat tctgctgttg ttgggtggag   52200
tgttccagaa acatcaatta gatccagttg gttaatagtg ctcatcaggt tgtctctatc   52260
cttccttcct gactgcctgc ttgagctgtc agttattgac agggtgtgg agtctccaac   52320
tctaatggtg gatttgttta tttctcctag tagttctatc ttttctctc cttctacccct  52380
tgatcctctt ctcccctag gcttcctgg tgttggtggt gggagagtgg ggtagtgaag    52440
aacctggact ttagggccaa agaggccagg gttcaaatcc tggctctgtc acttcccagt   52500
tgagtgaccc tggctggtgc ctgaatctct gtgagcctcc acttcctcct ctgtgaaatt   52560
gagagcactt acctggcagg ctgtcatggg catcaagtaa cagggcactc cacctggacc   52620
ctgacacgtg atgcacagga atgccagctg ctatgccatg ggtgtggcag tagtaataaa   52680
gtgaccatct gtatcctcac cacagtgaag cctgtccagg gctttctctc ctatgccccc   52740
atgcctccag gtggccttgg atcctgttgg ttctgtgctc tgctcagcga cctttctccc   52800
gtgggagttc ctgggggttc agcttcatcc tacagacagc agcacacact ggctgtgcac   52860
ccttttttttt tttttttttt tttttttga gatggagtct cgcttttttc gcgcaggctg   52920
aagtgcagtg gtgtgatctt ggctcactgc aacctctacc tcctgggttc aagtgatttt   52980
cctgcctcac cctcccaagt agctgggatt acaggctccc accaccacgc ccggctaatt   53040
tttgtatttt cagtagagat ggtgtttcac catgttggcc aggatggtct tgaactcctg   53100
acctcaggtg atccgcccac ctcagcctcc caaagtgcag ggattacagg cgtgagccac   53160
cacacccgga gtgccggttg ttttagcag tttgtcttgt tcctggagag actggctcct   53220
gcccaggagc tcggggagta gggccgcggg gtgctgcctc acacctcgag tttggccgta   53280
agcagagggg acattttgtg actgtccccc tcctgagctt cccagcagct tttctccaag   53340
ttacagccca aaagctcagg tggatttgca acccaacggt gtctgtgcac ctcccactga   53400
tgcccgaact gccctggcca agaaacgggg ccgtcagaac gctgcactaa ctgcagcctt   53460
gggcctccat gccagaggcc atgcccttcc atccaccacc ccctggcctg gcccctggcc   53520
ctcctggctc gggaactcca ggccccttcc tcacggatcg agagacgtgt atttaccgca   53580
caggtgcttg tcattctctt gtggcctctt ctccagggag atcacagaag acagggcct   53640
cactgaggtc tcggacatgg acccttttgat agtggcagga gccaggctgg gcaagaggcg   53700
gccacagtca cctcagcagt gccatcacca ccgccattca gcccttccct gagccgggcg   53760
cgcccctggc tctggcccca gtgtcccagt tacagctcac aggagcttgt ggtgcccagc   53820
ggctgcttct gattgagagt cgaggtcgga ggctttggga ggctgagagg ctgctcggtt   53880
tcacaactgc tgagggagac ttgggctcca tctcaggtct gccccatgtc gccctcaacc   53940
tccagccacc ggtcctccgt gtcccccatg gccaggcacg gcttgcagac atctgtcgtt   54000
ggctcctctc agccgtcgtg ggctgaccct ggcacgtcct cctgtggctg agcccagtgg   54060
ggacagctgc ttcctttttat tacccctagaa ctctcgtctt tgatcaggcc ccctcccta   54120
```

-continued

```
tgccacacag tccctgtcac tcgggtgagc ccagtagtca tggggaaggc ctgcgggttc    54180
caaacatcca aaggcttgcg tgcagcatga cagcttgaaa ccgatgtttt ttaccttgat    54240
cagatttcag cttggcgggg gctttgctca gctttcagtg aggcctgggc cgatttccca    54300
gcatcccctc ctgaggccag cctctgtttc ctgtgatttt ctgcacaaag tgggagggag    54360
gagtcttagg aaatgggggg ccacctcgaa acctaggcct cctctggctt ctctgtgcca    54420
gtgcccccac gctttgtgtc tgtgtcccca gcccatggga ctgtgttatt ccctgagtgc    54480
tgccgcatgc ccagcccgca ctgaggacgt ggagccccga ggggcaggat ggcctccatg    54540
gtcacacgta ggaagtggcc tccacctcc gatgatcctc tcccccctc cctttcagcg    54600 ccttccccgg gggtgtcatc agccctcctg cctgtgcttt gtcccgtctt ctgcaggcgc    54660
atgggacgtg ctgacaggtc ctctgccggg ttcctgcctt gctatgcgca cgctggtcac    54720
cacagaggcc tggcccttct tctgtagcag tcccacaccc gcaacaggtg tggctgctga    54780
ccacctgctt tctgccctc tggtcctgag gagggcgcag tgggcactca ggcgtggctg    54840
agcagatgtg tgttgccggg aggaggaagg actgctccag tcagggctga atttcccacc    54900
cggagcattt ctgctgtatt tggtgtagcg cctgctgctt aaagtctga ttcccagttg     54960 gcacccttc ccttctgcat tgaaaaacat acggatgcat gtcttcttgc agtgaatgtg    55020
tattctccca gcctctcttc tgggttgggg ctggaggtgg agcggcacac aggagccgca    55080
gcgatggagg atgtgcgggt gcagcacccc gtacagcagg gatgccaaac ccgcgctgag    55140
tccctctcaa cttctgcttt gaagcccagt cacgccattg cctgggtttt gctgggcggg    55200
gctgcatgtg atgttctcct ctgtccctcc cccagagccg cccacctgct ccccggacca    55260
gtttgcatgt gccacagggg agatcgactg tatccccggg gcctggcgct gtgacggctt    55320
tcccgagtgc gatgaccaga gcgacgagga gggctgcccc gtgtgctccg ccgcccagtt    55380
cccctgcgcg cggggtcagt gtgtggacct cgcctgcgc tgcgacggcg aggcagactg    55440
tcaggaccgc tcagacgagg tggactgtga cggtgaggcc ctccccgtca aggctctgcc    55500
aagaccctgg ccctgccctc cgggatacga gcttggggct gcctccggcc tcacaggagt    55560
aggggctctg aaaacctttg cttgcaggga gattgccaag tctgtctttt aggcccaaca    55620
aggaaaactc tgcagttcca cccatcctgt cccaccaggt agtgtggctt gaaggcagac    55680
tgtgagggtc tatctcacct tcctgcatta ggtcaggagt ttcacagaaa cctgaggcac    55740 attcagggt gggctgcaga ggtccatggc tcacaccctg gaaaatccgc ccccaaaaga    55800
cagtgctgtc tccactgacc agtctgtggg atagtgctta agcctgagtg gtttctatca    55860
acatgtagaa tcaggaggta taaagagatt tgctcaggca tcctgggccc tctctgacca    55920
gcaggatctt cctttagatc ttgacagtga aacacatctc ttctgtgccc cctgtgagtt    55980
ttctttcatt cattcattca ttcattcatt cattcattca ttcgagacag agtcttgctc    56040
tgtcacccag gctggagtgc cctggtgtaa tctcggctca ctgcaacctc tgcctccagg    56100
gttcaatcga ttctcctgcc tcagcctccc gagtagctgg gatgacaggt gcgcaccacc    56160
atgcctggct aatttttgta tttttagtag agacagggtt tcaccatgtt ggccaggctg    56220
gtctcgaact cctgacctca ggtgatccgc ccgcctcagc ctcccaaagt gctgggatta    56280
caggcatgag ccaccgcgcc cggcctgagt tttccttta tgaaggacct gcttggttgg    56340
ttgcctgcca catgttgtca gcaccatggg cccaggactg ctgaggagct gttgatgccc    56400
tcgctctccc agagccaccg gctctgttag ataattcaca tgcagtctgg ccactgtcct    56460
acgtcctcat tcacaaagag cagacatttc gtagaagatg agggcctggg agtaacctcc    56520
```

-continued

```
ctgcatgttt ttctataaag gcatagtggt taagtccttc cagctcattg accattggag    56580
aattttatgg aggctgtaga ctaggggctg gtaaactaag ggcccagggg ccaaatccag    56640
cctgccacct acttttgtaa ataaagtttt cttggtgcac agccatgccc attcattcat    56700
ttgcacaatg tctgtggctg ctttcatgcc aaaagcagga gaactgagtg gttatgctgg    56760
agacctacgg ccttcaaagc cccagacctc acgtctggcc cttgacagac agagcttccc    56820
cagccctgct gcgcatcctg gcccagcatg tgctgtgtgt gtgatttcag cttgcaggag    56880
ccgtggttag gaattgtccc tgtgttggtc cattttgcat tgctatgaag gagcacctga    56940
ggccgggtag attatgaagg aaagaggtct gtctggctca tggttctgta ggcagcacca    57000
gtatggcacc cgcatctgct cagcttctag tgaggtctca ggaagctttg actcatggtg    57060
gaagtcgaag cgggagcagg tgcatcacat ggtgagagag ggagcaacgg agagagagag    57120
agagagagag agagcgcctc tccctcttgc cctcaccttg agaggagatg ccaggctcct    57180
ttaagtaacc agctcccatg tgaactcaca gtgagagccc atttgctact gcggagaggg    57240
caccaggcat ctgctcccat gacccaaaca ctgcccacca ggccctacct ccaaccttgg    57300
ggtcatattt tattctgttc tatgctatgc tatgctatgc catgccatgc catgccatgc    57360
tattcctatt ctattatttg agacagaatc tcgctctgtt gcccaggctg gagtgcagtg    57420
gcatgatctt ggctcactgc aacctccacc tcccaggttc aagcgattct cctgcctcag    57480
cctcccgagt agctgggatt acaggcacac accaccacac ccgggtaatt tttgtatttt    57540
caatagagat ggggtttcac catgttggcc aggctggtct caaactcctg gcctcaagtg    57600
atccacttac ctcggcctcc caaagtgcca tgattacaga tgtgagtcac tgcgcccagt    57660
gagggtcaca tttccgttga gatttggagg ggcagacgtt ggagccatct gagccccctc    57720
gtcccgctct agcttctcct cccgtgtgcc ccgcggtgct ggtggcaggc ccttacgccg    57780
gttctggctg cacgctctgt tccagaagct ttcttccctg cttggttacc agaaaatcat    57840
cccatccatt acaaggacag ggtcccctta tctcccattc ccagggcagg acaccggggg    57900
cagggcaggt ggggaactga gcaagttctc tggggggcagg cgtggctatg gctccctctg    57960
ggtgggcgtc tggggagggg tggaggcagc cgtcagcgcc ctggcttgct cttcctccct    58020
ggccagagac tgtggccttg tgctgctccc gtgtgggctg cctgcacctc cagtgggttg    58080
tgctccctcc cctcccctcc cctcaagctc tgctgagcac cactgccttc cacagccccc    58140
actctcggga ggcgaggctc ctcgtggcca ttcctgtcct tggcacccac cccccacca    58200 acctggtaga gccttgggcg gggtctgtta ctccttgcat ggcgtagacc tccccacagt    58260
aggcacctga cacatacctc ctgggggggca ggcaggaggt gcgttgaggt ctcagccctg    58320
gcagtccctc ccctgcgtgg cataggcctc gccacagggt catcgagggt gggtggagac    58380
tgtactagac cactccccgc tggtcctaga aagggtccca tctgtctgct ctctgtttgg    58440
agtccagacc ttggttgctg tgccctgcat ggtgggctgg ggggcaccct ccagcctctc    58500
tgagtgcatg gcctctcctt gcagccatct gcctgcccaa ccagttccgg tgtgcgagcg    58560
gccagtgtgt cctcatcaaa cagcagtgcg actccttccc cgactgtatc gacggctccg    58620
acgagctcat gtgtggtgag ccagcttctg cacggggaa ggggcgtccg ggctgggttc    58680
ccccaggaac gtggagttta ggggaggaga cgtgcctttc cagcggggct gggggctgtg    58740
tgggagactc aggcggctgg gaggctcctg gcgggaggca gggaagcctt tcccagggca    58800
gcggccagga ggacagactg tgagctgtgg gctcggcggc tacagagtct gcctcagtgg    58860
```

```
gcggggctga tggtgtccag gtgcctgcag cacgcaccca cccacgggac cttgctgagc    58920
agcgtctgtc aggcagcaag attacccgag ggctgcagtg gtcctgttcc ctggcagctt    58980
actgtctggc tgaggaggag tgatgttcac atatgcacac atgtcatgtg cacacacatg    59040
tacatgacaa catcccacat gctcctcaaa tagcatgacc tgtacagtca cggatatagg    59100
gcctagggga taggaggcca agacagtcag ggaagacttt ccagaggcag tggctcctga    59160
aaggctgtct gattcaggca ggaagggagc tgagttcaga taggaagtag caatgagtca    59220
ttgtgtctgg ggacatggcc actccttcgc tgcagaggga cctgggctga gagctcctct    59280
cttatggctg cagtcgggag agaagtctgt tgggggagaa aggggcttc ctcaagggac    59340 tccctgtgcc ctttggcacc ttcgtgccag gtcaggcttg aggcctgaag gcagtggtgg    59400
gggccaccaa gggtcgcctc ctctgctggg caagttccca gtctgacggg cctgtgccgt    59460
gggccccagc tgtggggggcg ctgttgatgc gcagccaggc ctcgccgcca gagcccgcac    59520
gcttccattc cgctgacttc atcgacgccc tcaggatcgc tgggccggcc ctgtgggaga    59580
gtgaatgtgg cttttgccaa agttgagtct ggagcctgga aacttcccta tgggcagcct    59640
tgatagtgga gtggcccaag gagcccaccc agccgaccct gcccctcccg tggctggtgg    59700
gcggcaccag gggctgcctg gctttgctcg ttcaccaaca tcacccgggc tggccagggc    59760
gcgctcactt ctgccaccac cgagggccct gggcgaagga gtgaataccca ggctgccttg    59820 gcagggatgt gttgagggct gtggggagtc ggacagcggc gggggtcaga ggaggaggag    59880
ggtgcaccgt gcaggctgaa gggccacgtt accctgaggt tggccaggct ccccaggcct    59940
agcctcccag ctccccccact ttctccccac cctccaccag tggcaaagcc agccccttca    60000
gggcgcacgg tgtctgcccc caaggagggc ccattccgtt ggggttaatg ttggccacct    60060
ctttctgttt gtctctggca gaaatcacca agccgccctc agacgacagc ccggcccaca    60120
gcagtgccat cgggcccgtc attggcatca tcctctctct cttcgtcatg ggtggtgtct    60180
attttgtgtg ccagcgcgtg gtgtgccagc gctatgcggg ggccaacggg cccttcccgc    60240
acgagtatgt cagcgggacc ccgcacgtgc ccctcaattt catagccccg ggcggttccc    60300
agcatggccc cttcacaggt aaggagcctg agatatggaa tgatctggag gaggcaggag    60360
agtagtctgg gcagctttgg ggagtggagc agggatgtgc taccccaggc cctcttgcac    60420
atgtggcaga cattgctaat cgatcacagc attcagcctt tcccactgag cctgtgcttg    60480
gcatcagaat ccttcaacac agaggcctgc atggctgtag caacccaccc tttggcactg    60540
taggtgtgga gaaagctcct tggacttgac cttcatattc tagtaggaca tgtgctgtgt    60600
tgtccacaaa tcctcatgta ccctagaaat gaatgtgggg gcggctgggc tctctccaga    60660
gctgaaggaa tcactctgta ccatacagca gctttgtctt gagtgcagct gggatttgtg    60720
gctgagcagt tacaattcct acgtggccca ggcaccagga acgcaggctg tgtttgtaga    60780
tggctgggca gccgcaccgc agagctgcac catgctggtt tgtatcacat gggtgaccat    60840
ggtatgtcta agaaggtgga gtccctgtga ggtctgcagg tgcccccaca gctccaggcc    60900
accttgagga ttgcctctgc ctgcccagcc ctgagttccc tctcccctgt cctgtcccac    60960
tgtcacccca agccggcctc attgggagcc tgttggatgg cagggtatag atgtaacctg    61020
attctctctg gggagcgggg ttatctggct tctcaagagc tcctaggagc ccacagtggt    61080
ggcaccatca cagtcgcagc agccccagag aacgcggcc ctgtctgttc ctggcgtgct    61140
ctgtgctgcc ccgcctgggt tccctgcccc agtcgcagcc cccttggagg aggtaccatg    61200
tgtctcccgt ttcacagatg agccccgggg agctcactct agtagtggcc agagaggcct    61260
```

```
gcggctcagg gagcggggca catttccaac aggacacacc gccctggtct gagtctcgtg    61320
ggtagtggga gcagaggaga gcgccctatg tctgtggggc ggcttggctg agcctggaag    61380
ccacctgacc tcccccgtcc cttccctgcc aggcatcgca tgcggaaagt ccatgatgag    61440
ctccgtgagc ctgatggggg gccggggcgg ggtgcccctc tacgaccgga accacgtcac    61500 agggcctcg tccagcagct cgtccagcac gaaggccacg ctgtacccgc cggtgagggg    61560
cggggccggg gaggggcggg gcgggatggg gctgtgggcc cctcccaccg tcagtgctgg    61620
ccaccggagc cttcccgggt tcctgggggc tgtgccaccg cctctgaggc atgcttgctt    61680
tcttcccttt tcaaaccctt ctgcttcctt ctttaatgac attgttgatt gtggataatc    61740
tgaaaactac acaaaaatat aaagagccaa aatctcaccc aaatccacct cctagagtgg    61800
ctgttgggct ccgtcagcat ccaggcggcc gtctgtgttc cgcacggccc agcccatcga    61860
tagccgcctg caccaggcct gtctgccctc tgtgagcctc cccacagggt tccctccaca    61920
aacaccctgt tctcccaccc agggctggct gcttcctgga aaacagctgg atggttttgt    61980
gcatgacaga caaacacagg gtgattttcg tggctaaaat actccctgga gcttttggca    62040
gggtgagggg ctggctccag ctgagccacg ccttgagtga aatgactgtg aggagaataa    62100
actgccgctg ccctccagga tcactggggc tggctgggga aaccccccgt ttctgggagc    62160
acagtcccag gatgccaagg cgagcttggt gccgagatgt gaactcctga gtgtaaacag    62220
cgggggctga cttgacatgc tttgtatgct tttcatttgt tcctgcagct gtatgcccct    62280
aaggtgagtc cagcccccct ctgcttcctc tggggcctcg ccagtgagcc ccaccttgct    62340
ggggctggtt cctcctgccc ttctgggtat ccctcacatc tggggtcttg tcttcttgtt    62400
ttatttttct tttttttttg agacggagtt tcactttgt tgcccaggct tcagtgcaat    62460
ggtgtgatct ctaggctcac cgcaacctct gcctcccagg ttcaagcagt tctcctgcct    62520
cagcctccct agtagctggg attacaggca tgtgccacca cgcccagcta attttgtatt    62580
tttagtagag atggggtttc tccatgttgg tcaggctgat cttgaactcc ctacctcagg    62640
tgatccgccc accttggcct cccaaagtgc tgggattaca ggcgtgagcc accgcacctg    62700 gccttttct tttcttttct tttctttttt ctgagacagg gtctcgctct gtcacccagg    62760
ctggagtgca atggtgtcat catggctaac tgcagcctct accttctagg ctcaagcaat    62820
cctcccatct cagcccctaa gtagctagga ctgcacgcat gcatccccat gcccagctaa    62880
tatttacatt ttttgtagag atgaagtttc actatattgc ccaggctggt ctccaactcc    62940
tggactcgag cgatcctcct gcctcggcct ccccaggtgc tgggattaca ggcgtgagcc    63000
accgtgcctg gcctgggggta ttgtcttctt atggcacctg actgtggtgg gccctgggaa    63060
ggaagtagca gaagagggtt cttcttggtt tcctggacag taactgagtg ttctggaggc    63120
cccagggcct ggctttgttt agggacaaag ggaactggta accagaagcc gagagtttaa    63180
acacccactg cccttcttcc ctgctcctgc tgctgcaacc cagcttaacc agccaggagt    63240
gctaggaacc caagcagggc ccccgagcac acagcaggca gctcacgaat tctcttttcc    63300
tgttctccct tgggagctgg gaggatctta atcaggcaat aagagatggc actgagcagc    63360
cagctaattt tttaaatcac tttattgttt aaccatatga ctcacccact taaaaaaggg    63420
tacagttcag tgggttttag tgtattcaca gatgtgtgca accctcacca cagttaattt    63480
tagaacattt tcctgccct aaaagaaact ctgcatgaag ccagctgttt ttaaattagc    63540
aaagttattt tgcatccttt aaatatatgt tcatggtaca aaattcaaaa gatacagaag    63600
```

```
agtctgcagt ccaaagagac tccgccccca tgacgccaag caggactccc tgggaggcat    63660
ggcctcctgc agtgtgtttc ttctatgtcc ccccagggt catctgtaca tatgcaagca     63720
tacaagagcg tggactttgt tttccaagcc agaagataat tgtagattta tgtgcagttg    63780
tgagaaagag cacagaccca tttatcctct gcctggtttc ccccagtgct gcctgccatc    63840
ttgcatgact tccattccta tcataagcaa gacactgata acgattcttt caccttattc    63900
agattgacat aagtgttttt tgtttgttct tgagacaaac ttcctctgtc acccagtggg    63960
agtgcagtgg cacaatcaca gctcactgca gcctcaaact cctgggctca agcgattctc    64020
ctgcctcagt cccctcaagt agctcagatg gcaggtgtgc accatcatgc caggctaatt    64080 ttttaaatttt ttgtggaggt gaggcctcac taaatttcct gggctagtct tgaactcctg   64140
agctaaagtg atcctcctgc ctcagcctcc caaagtggta ggattacagg catgagccac    64200
tgcgcctggg ctgacatatg tgttttcgta agcccgaaag atagcatctg aagagtcaac    64260
attgagcctt gccttttgct gctaatgatg tataaaagct gctgttctga gcatttcgga    64320
ggctcccagc tgccgtgtgc accctgccta gagctctacc gtaacccatc tccgggagga    64380
ggtgctattg ttttcctcat tttgcaacaa ggaggctgaa gaactgagca tgaaccactg    64440
gcctgggtcg ttcggttggt aggcagtggg gccaggccat ccaactcaca accaccttct    64500
actctgcttc ccccgcaccc tgaagtttgt tctgtttga ggacagcc gtcacattct        64560 tggtggctga acagcactcc ttgtcaggtg tggctgggcc cccactggag ggcatcatgg    64620
tcctctctcc tgctgcggtt gaaccttggc tgtttcaacc actcctgcca agtggccctc    64680
tgaaagggac agtccatctt ttctcagcag agggccacac tggcaaaacg gtccctggca    64740
ccctttctct ccacctgtct aatatagagt aaaaatggta tcatgttaag atcttcattt    64800
atatttattt tatcatgaat gatgtaagca tcattttgtg tgtttaagaa cctttgggcc    64860
cagcgtgatg gcttgcagct gtaatctcag cactttagga ggctgagatg agcggatcac    64920
ttgaggccgg gagtttgaga ccagcctggc caacatggag aaaccccgtc tctagtaaaa    64980
atttaaaaat tagccgggta tggtgatccc agctacttgg gagtctgaag catgagaatt    65040
gcttgaacat gggaggcgga ggttgcagtg agccgagatc gcgccattgc actccagcct    65100
gggcgacaga gcgagactct gtctcacaaa aaaaaaaaaa aagaaaaga aagaaatta      65160 tcaatctcct cttttatggc atatatatat atatatatat atatatatat ttatttccct    65220
ttcttggtta tgttcataaa ggcctcccct gctctgatca taaaaacaa cttattttca     65280 cactctctct cttttttttt tgagacagag ttttgctcct gttgcccagg ctggagtgca    65340
gtggcgcaat ctcagctcac tgtaacctcc gcctcccggg ttggagtgat tctcctgcct    65400
taccttcccg agtagctggg attataggca tgcaccacca tgcctggcta atttttgtact  65460 tttagtagag acgggggttt ctccatgttg gtcaggctgg tctcgaactc gcgacctcag    65520
gtgatccacc cacctcggcc tcccaaagtg ctgggattac agacgtgagc caccatgccc    65580
agcccacact ctctttctta acgtcctcct cctttcgttt tacgttcaca tctttaattc    65640
ttctgggatt taattagatt tgatgagcaa ggtgggcatc cagcttgttt cttggctgat    65700
ggcttatggg tggcgtgaat tagtcggggt ctatcaggag gcagaaactc tatgagaatt    65760
tgaacagaga aagttccgtc tacaggctta ttaccaggga ctggaatagc agaaattgaa    65820
cagtgagatg tacagagaac tctaagaatg caggaatagg ccaggcatgg tggctcacac    65880
ctgtcatccc agcactttgg gagaccaagg cgggtggatc acctgaggtc aggagttcga    65940
gaccagcctg gccaacatag tgaaacccca tctctactaa aaatacaaaa aaattagctg    66000
```

```
ggtgtggtgg cgcatgcctg taatcccagc ttctcgggag tctgaggctg gagaatcact    66060
tgaacctggg aggcagaggt tgtagtgagc cgagatcatg ccattgtact ccagcctggg    66120
caacaagagc gagactcagt caaaacaaca acaacgcagg aatagcagat gagccgaggt    66180
ggggcctccc cagcccccac cccccacccc gcaccctggg ccgagatcca gtcctctttg    66240
aatagggcct gggcgtggtt cacgggacat ctgagacatt gccgaggcgc tgcactggtg    66300
gatcttgcca gaagtctgcc cagtgcagat ttgggcagaa tctcaaactg ccttgggatg    66360
taggagagaa accaggcctg gtcaagttca tgggaagagg tggaaacaga ccccataggc    66420
tggggcttgg gcagctgtag gaagccctct ctgctgcctc cctgcctgct ctctgctttg    66480
aagcatcttc cccagtgccc ccagtctcat gccctctcaa cgttgggtc aaatcctgag     66540 gaatacccag actggctctc tgggccaaag aggaccctct ccagaaagag cagggcccag    66600
tgcggcttcc taaagggcag gggaagggcc tggccactcc ccagaggcta ctcaccagcc    66660
atcaggatag ccccaggaag caggccttct cgagcccatt ttattacttt attttattat    66720
tttatttaat tttaaattta tttttgaga cagagtctca ctctgttgcc caggctggag     66780
tgcagtggtg cgatctcaac ccactgcagc ctctgcctcc agggttcaag ggattctccc    66840
acctcagcct cccaagtagc tgggattaca ggtgcccgcc accacacccg gctaattttc    66900 atattttag tagagacgag gtttcaccat gttggccagg ctggtctcga actcctgacc     66960
tcaagtgatc cgcccgcctc ggcctcccaa agtgctaggt caagcccatt ttaaagttga    67020
agaaactgag gctgaggtaa attccctccc cagggatcct gctgcagcca gaaggtggta   67080
aaacaggact tcacccgggt ctgtctggcg tgaaaggcag tgttcttgta ccaccctagg   67140
gggcctgaga gaactgagtc cctcgggcat aactgacagt tctgttccca ttattccgca   67200
ggggctcgga tctggctgta tgcttttccag gatggccttg gagacccaca taagccctac   67260 acccttggg aagctgcatg ttgggttggg gtgccgtcag tggcacttgt ggaaggtgca    67320
gacctgtgtg ggtgtgtggg cccagggccc ctggtccctt cctcccttg tagggctggt    67380 tgtgtgctgc ctggacctgg ggggcacgtt cacgtggtga atttgtctat ttactatccc   67440
cgctttgggg ctggtgccag cacaggccct tgtgaagggg gtgcctttgt ctggagtggg   67500 actgtgccc ctccctcagc gtggtgactt ctgtgtcagg gcttcagcag ggacgcagag    67560
cccctgagtg ttcggaacaa gggcgtcatt gcaggagtta gactgtgtgt gatggaggga   67620
ggaggggcag gaggaaaggt cagaaggaga gttcctggga aggtccctga ggagcctggt   67680
gaggtgctaa ctggtgtgga ggacactcag ggcctgtggg gacatctcct actgctgggg   67740
gccagccaca aagggaactg gccgaagtcc tgtccccgcc ttcacagccc agcatctggt   67800
cacaaggcag gtacttggaa gggcgcgggc acctgggcca aaagtgcctg ggttcccttt   67860
gcctttcact gagatgacct tcggggcagg tggctgctgc ctccctcct gtccccaggt    67920 tttgccaact ggccagagga aggggtcctg ggaagcaggg gggccagaag ccctctctgc   67980
aaggaaagcc cgaggggtgt gggaggaagg aaggaatgcc caggctggcg aggctctaag   68040
tcaccctggc ttggctctcc tcagatcctg aacccgccgc cctccccggc cacggacccc   68100
tccctgtaca acatggacat gttctactct tcaaacattc cggccactgc gagaccgtac   68160
aggtaggaca tcccctgcag ccctccatgg ccattgggtt cccgccagcc cgtggtggag   68220
gggcctaatc cccatgccac tgatgagggg aggtattctg ggtgctagtg ggcaggtgcc   68280
gggcccagcc ctgcctccct ctgctctgcc aaccacacta ggctgcctcc ccagacaagc   68340
```

```
tcagcgggca ctgcatgttg ggttcagaaa tcagcagaac tccacgttct gagctgctct    68400
tcaagttgct cctatggggg ttacttttaa gctgggaaat ggctgtggcg tcgaggggcc    68460 ggggcttgg  gctccaaact ctgactgtgt gtttgagtcc ggctgtggaa acctagccat    68520
tgagatgccc cctcttggtg gctctgtcct cttaggatgg gacaagtctg tgaaggctgc    68580
tgcagcaccc accgtagacc cctaatcgtg tgacgtcacc aggatggtcc gggctgctca    68640
cttgccacag tggcctgttt gagcccggga agccaacggg gctgctcagc tggacaccag    68700 cccccgagc  tgcccatgtt ggggtcacag gccccacctc cctggttggg gaggggcaac    68760
tgagagtgtg gagaggtggg acccaggtgt gctggtctcc gcaggggctg gatcagagcc    68820
tgggatgggc agggtgagcc tcctgacctt aacccagtg  gtgtcaggca acgtggccca    68880
cccgccagcc gcaccaggcc ccaccccgc  aggtgaaggg gtgggatagg ctgggcctgg    68940
gccaggacac ctctggacca cgcattcctc attgcttggg tccctggagc agcagggcct    69000
cccgagtgtg gtgccgcctg ccacctagtg gccatttcca cgaactccca ggcctggctg    69060
gggagccgga actgcagcct ccatttccac cccactccgg gtcgggccac ctccctgatg    69120
cctcagtatt atatcaaact gtcacagtct gtcccacagc cttacagacc actgtctcca    69180
gaatggtcac atccacactg gcagcccag  tctcgctagt tcctcgtccc acctcctgcc    69240
tttgctcatg cccgtcctgc tctgggccca ccgcggacac atcttccccc cgcccgccgt    69300
ctgacctcac agcagctggg ccccaagagg agtatcctgt cctgctgcac ttttctcaac    69360
acccggtgtt ggctgcacct tcccacccat tgcaggcccc tctgtgacag gacggggct    69420 cctaaacaca ccacagttcc gagtctgaac tcacacagtg ggatgcggcg tttctgggcc    69480
acagttgggt gcaggtagcc tctgggagga tgggaggtca ggagccatct tgcgagtcag    69540
gttgcttgaa ctcaggatgg aagtgttccg ggcccattgg ttgctgtatt agcctgttct    69600
cacgctgcta ataaagacat acccaagact gggtaattgt aaaggaaaga ggtttaacgg    69660
actcacagtt ccacctgcct ggggtggcct cacaatcatg gtagaagaca aggaggagca    69720
agtcacatct tacatggctt cagggaacag acagcatgag aaccaagcga aagggggtttc   69780 cccttgtaaa accatcaagt ctagtgagat ttattcacta ccacgagaac agtatggggg    69840
gaaccacccc catgattcaa tcatctccca ctgggtccct cccacagcac gtggaatta    69900 tgggagtaca attcaagatg agatttgggt ggggacacag ccaaacccta tcggttgcca    69960
acatttacag taacagtgtt aggtgaacag ttgtccagtc tcctgttttg tcggacactg    70020
tttctagcac cttccaggca gaatctcatg tatccttcac tttcgaaatg ggtactattt    70080
catccccact tttatcaatg agaaactaaa gctcgaagag gtcaagtaag ttcctggcca    70140
aggtcagcta gcaggctcta gaggcctcgt tctccttaga ggcagccttg ccagggccca    70200
ggcttggcag gctgcagggc aggtgcgggc atgcccatgg tagaggtggg accattgagg    70260
ctcagagagg gtaagtgatg agccctggcg acacagcggg gtgggtccag agtccggcct    70320
gcatcttctg gagctggcca gtggacaggc ctttcccgtt cacagccccg ggctgctgt    70380 gcccaccagg gcggatgtgc ctaccgaatc ccactcctct gtgtgtgtcc ctttcaggcc    70440
ctacatcatt cgaggaatgg cgccccgac  gacgccctgc agcaccgacg tgtgtgacag    70500
cgactacagc gccagccgct ggaaggccag caagtactac ctggatttga actcggactc    70560
agacccctat ccaccccac  ccacgcccca cagccagtac ctgtcggcgg aggacagctg    70620
cccgccctcg cccgccaccg agaggagcta cttccatctc ttcccgcccc ctccgtcccc    70680
ctgcacggac tcatcctgac ctcggccggg ccactctggc ttctctgtgc ccctgtaaat    70740
```

-continued

```
agttttaaat atgaacaaag aaaaaaatat attttatgat ttaaaaaata aatataattg    70800
ggattttaaa aacatgagaa atgtgaactg tgatggggtg ggcagggctg ggagaacttt    70860
gtacagtgga gaaatattta taaacttaat tttgtaaaac agaactgcca ttcttttgtg    70920
ccctgtgtgc atttgagttg tgtgtccccg tggagggaat gccgaccccc ggaccaccat    70980
gagagtcctc ctgcacccgg gcgtccctct gtccggctcc tgcagggaag ggctggggcc    71040
ttgggcagag gtggatatct cccctgggat gcatccctga gctgcaggcc gggccggctt    71100
tatgtgcgtg tggcctgtgc cgtcagaaag ggccctgggc ttcatcacgc tgttgctgtt    71160
cgtcttcctc agattcttag tcttttttttt tttttttttt ttttgagacg gagtctttct    71220
ctgtcatcca ggctggagtg cagtggtaca atctcagctc actgcaagct ccgactccca    71280
ggttcaagtg agtctcctgc ctcagcctcc cgagtagctg ggactacagg tgcgcgccac    71340
cacacccgcc cagctaattt ttgtattttt agtagagatg gggtttcacc atgttggcca    71400
ggatgatctc gatctcttga cctcgtgatc cgcccacctc ggcctcccaa agtgctggga    71460
ttataggcat gagccactgt acccagctga ctcttagtca cttttaagaa ggggactgtg    71520
ccttcatttt tcactgggcc ctgcagaata tatgcctggg ctctgggctc ttctgaacct    71580
gtgttggctt ccatctgacc tctctgtgcc agcccaaggc tgctgctctt cctgagggca    71640
aggagcccca tgactgcgtg ttgactcgct ggatggggct gctgagccca ctctgccaca    71700
ccacgtgccc ctggcaggga gggaatccct gggtcctcac aggaacagtc agcaagccac    71760
acctgacgcc tgctgtgggc ccatccctgc ggtgctggaa aagacagaca aggcctggtc    71820
actgcctctg cagggtcccc agtccgtgga aggagacagt aatctaggca ttttcggtgg    71880
ggaagctgag ctgttctcgt gtcctgaagg ccaggcggga acagccgtct tcagagggaa    71940
gggagaaaat gcacatcgca tcagtggaga agggcctgac ttccctcagc atggtggagg    72000
gaggtcagaa aacagtcaag cttgagtatt ctatagtgtc acctaaata                72049
```

<210> SEQ ID NO 10
<211> LENGTH: 8705
<212> TYPE: DNA
<213> ORGANISM: Homo sapiens

<400> SEQUENCE: 10

```
ggactcaggg gcagcaggga ggtacaccca tggttagtgg gcggaccata gggggtaatg      60
agagggtgaa tcgatggaac ctggggggaca caatcgaagt ggttccagag tcgggctgta    120
ctaattaaag agacggggca gtggacaggc attttcagtt gactgcccag ggagtgttct    180
gcccaacagg gaggatatgc gtacagaatc atactcgatc agcatgagtc caattcagac    240
cgtacatcag tggagatatg ggtcccccga tgactccgtg gaacactgat gtttgtgaca    300
ggggagtaca gcaccagcca tcagcaggcc agtaaatcat accggcctgc gaaattggac    360
tcagacccgg atccaccctg accgacgtcc caagccccca cccccaccc cccaccatgg    420 gccgagatcc agtcctcttt gaataggggc tggccgtggt tcacgggaca tctgagacat    480
tgccgaggcg ctgcattggt ggatcttgcc agaagtttgc ccagtgcaga tttgggcaga    540
atctcaaact gccttgggat gtaggagaga accaggcct ggtcaagttc atgggaagag    600
gtggaaacag accccatagg ctggggcttg ggcagctgta ggaagccctc tctgctgcct    660
ccctgcctgc tctctgcttt gaagcatctt ccccagtgcc cccagtctca tgccctctca    720
acgttggggt caaatcctga ggaatacccca gactggctct ctgggccaaa gaggacccctc    780
```

```
tccagaaaga gcagggccca gtgcggcttc ctaaagggca ggggaagggc ctggccactc    840
cccagaggct actcaccagc catcaggata gccccaggaa gcaggccttc tcgagcccat    900
tttattactt tattttatta ttttatttaa ttttaaattt attttttgag acagagtctc    960
actctgttgc ccaggctgga gtgcagtggt gcgatctcaa cccactgcag cctctgcctc   1020
cagggttcaa gggattctcc cacctcagcc tcccaagtag ctgggattac aggtgcccgc   1080
caccacaccc ggctaatttt catattttta gtagagatga ggtttcacca tgttggccag   1140
gctggtctcg aactcctgac ctcaagtgat ccgcccgcct cggcctccca aagtgctagg   1200
tcaagcccat tttaaagttg aagaaactga ggctgaggta aattccctcc ccagggatcc   1260
tgctgcagcc agaaggtggt aaaacaggac ttcacccggg tctgtctggc gtgaaaggca   1320
gtgttcttgt accaccctag ggggcctgag agaactgagt ccctcgggca taactgacag   1380
ttctgttccc attattccgc aggggctcgg atctggctgt atgcttttcca ggatggcctt   1440 ggagacccac ataagcccta cacccttggg aagctgcat gttgggttgg ggtgccgtca   1500
gtggcacttg tggaaggtgc agacctgtgt gggtgtgtgg gcccagggcc cctggtccct   1560 tcctccctttt gtagggctgg ttgtgtgctg cctggacctg gggggcacgt tcacgtggtg   1620
aatttgtcta tttactatcc ccgctttggg gctggtgcca gcacaggccc ttgtgaaggg   1680
ggtgcctttg tctggagtgg gactgtggcc cctccctcag cgtggtgact tctgtgtcag   1740
ggcttcagca gggacgcaga gccctgagt gttcggaaca agggcgtcat tgcaggagtt   1800
agactgtgtg tgatggaggg aggaggggca ggaggaaagg tcagaaggag agttcctggg   1860
aaggtccctg aggagcctgg tgaggtgcta actggtgtgg aggacactca gggcctgtgg   1920
ggacatctcc tactgctggg ggccagccac aaagggaact ggccgaagtc ctgtccccgc   1980
cttcacagcc cagcatctgg tcacaaggca ggtacttgga agggcgcggg cacctgggcc   2040
aaaagtgcct gggttccctt tgcctttcac tgagatgacc ttcggggcag gtggctgctg   2100
cctcccctcc tgtccccagg ttttgccaac tggccagagg aagggtcct gggaagcagg   2160 ggggccagaa gccctctctg caaggaaagc ccgaggggtg tgggaggaag aaggaatgc    2220 ccaggctggc gaggctctaa gtcaccctgg cttggctctc ctcagatcct gaacccgccg   2280
ccctccccgg ccacggaccc ctccctgtac aacatggaca tgttctactc ttcaaacatt   2340
ccggccactg cgagaccgta caggtaggac atcccctgca gccctccatg gccattgggt   2400
tcccgccagc ccgtggtgga gggggcctaat ccccatgcca ctgatgaggg gaggtattct   2460
gggtgctaat gggcaggtgc cgggcccagc cctgcctccc tctgctctgc caaccacact   2520
aggctgcctc cccagacaag ctcagcgggc actgcatgtt gggttcagaa atcagcagaa   2580
ctccacgttc tgagctgctc ttcaagttgc tcctatgggg gttacttta agctgggaaa   2640 tggctgtggc gtcgaggggc cgggggcttg ggctccagag tctgactgtg tgtttgagtc   2700
cggctgtgga aacctagcca ttgagatgcc ccctcttggt ggctctgtcc tcttaggatg   2760
ggacaagtct gtgaaggctg ctgcagcacc caccgtagac ccctaatcgt gtgacgtcac   2820
caggatggtc cgggctgctc acttgccaca gtggcctgtt tgagcccggg aagccaacgg   2880
ggctgctcag ctggacacca gcccccgag ctgcccatgt tgggtcaca ggccccacct   2940 ccctggtttgg ggaggggcaa ctgagagtgt ggagaggtgg acccaggtg tgctggtctc   3000 cgcagggggct ggatcagagc ctgggatggg cagggtgagc ctcctgacct ttaacccagt   3060
ggtgtcaggg aacgtggccc acccgccagc cgcaccaggc cccaccccg caggtgaagg   3120 ggtgggatag gctgggcctg ggccaggaca cctctggacc acgcattcct cattgcttgg   3180
```

-continued

```
gtccctggag cagcagggcc tcccgagtgt ggtgccgcct gccacctagt ggccatttcc    3240
acgaactccc aggcctggct ggggagccgg aactgcagcc tccatttcca ccccactccg    3300
ggtcgggcca cctccctgat gcctcagtat tatatcaaac tgtcacagtc tgtcccacag    3360
ccttacagac cactgtctcc agaatggtca catccacact gggcagccca gtctcgctag    3420
ttcctcgtcc cacctcctgc ctttgctcat gcccgtcctg ctctgggccc accgcggaca    3480
catcttcccc ccgcccgccg tctgacctca cagcagctgg gccccaagag gagtatcctg    3540
tcctgctgca cttttctcaa cacccggtgt tggctgcacc ttcccaccca ttgcaggccc    3600
ctctgtgaca ggacgggggc tcctaaacac accacagttc cgagtctgaa ctcacacagt    3660
gggatgcggc gtttctgggc cacagttggg tgcaggtagc ctctgggagg atgggaggtc    3720
aggagccatc ttgcgagtca ggttgcttga actcaggatg gaagtgttcc gggcccattg    3780
gttgctgtat tagcctgttc tcacgctgct aataaagaca tacccaagac tgggtaattg    3840
taaaggaaag aggtttaacg gactcacagt tccacctgcc tggggtggcc tcacaatcat    3900
ggtagaagac aaggaggagc aagtcacatc ttacatggct tcaggaaaca gacagcatga    3960
gaaccaagcg aaagggtttt cccccttgtaa aaccatcaag tctagtgaga tttattcact    4020
accacgagaa cagtatgggg ggaaccaccc ccatgattca atcatctccc actgggtccc    4080
tcccacagca cgtgggaatt atgggagtac aattcaagat gagatttggg tggggacaca    4140
gccaaacccct atcggttgcc aacatttaca gtaacagtgt taggtgaaca gttgtccagt    4200
ctcctgtttt gtcggacact gtttctagca ccttccaggc agaatctcat gtatccttca    4260
ctttcgaaat gggtactatt tcatccccac ttttatcaat gagaaactaa agctcgaaga    4320
ggtcaagtaa gttcctggcc aaggtcagct agcaggctct agaggcctcg ttctccttag    4380
aggcagcctt gccagggccc aggcttggca ggctgcaggg caggtgcggg catgcccatg    4440
gtagaggtgg gaccattgag gctcagagag ggtaagtgat gagccctggc gacacagcgg    4500
ggtgggtcca gagtccggcc tgcatcttct ggagctggcc agtggacagg cctttcccgt    4560
tcacagcccc ggggctgctg tgcccaccag ggcggatgtg cctaccgaat cccactcctc    4620
tgtgtgtgtc cctttcaggc cctacatcat tcgaggaatg gcgcccccga cgacgccctg    4680
cagcaccgac gtgtgtgaca gcgactacag cgccagccgc tggaaggcca gcaagtacta    4740
cctggatttg aactcggact cagaccccta tccacccccca cccacgcccc acagccagta    4800
cctgtcggcg gaggacagct gcccgccctc gcccgccacc gagaggagct acttccatct    4860
cttcccgccc cctccgtccc cctgcacgga tcatcctga cctcggccgg gccactctgg    4920
cttctctgtg cccctgtaaa tagttttaaa tatgaacaaa gaaaaaaata tattttatga    4980
tttaaaaat aaatataatt gggatttta aaacatgaga aatgtgaact gtgatggggt    5040
gggcagggct gggagaactt tgtacagtgg agaaatattt ataaacttaa ttttgtaaaa    5100
cagaactgcc attctttcgt gccctgtgtg catttgagtt gtgtgtcccc gtggagggaa    5160
tgccgacccc cggaccacca tgagagtcct cctgcacccg ggcgtccctc tgtccggctc    5220
ctgcagggaa gggctggggc cttgggcaga ggtggatatc tcccctggga tgcatccctg    5280
agctgcaggc cggccggct ttatgtgcgt gtggcctgtg ccgtcagaaa gggccctggg    5340
cttcatcacg ctgttgctgt tcgtcttcct cagattctta gtcttttttt tttttttttt    5400
ttttttgaga cggagtcttt ctctgtcatc caggctggag tgcagtggta caatctcagc    5460
tcactgcaag ctccgactcc caggttcaag tgagtctcct gcctcagcct cccgagtagc    5520
```

```
tgggactaca ggtgcgcgcc accacacccg cccagctaat ttttgtattt ttagtagaga   5580
tggggtttca ccatgttggc caggatgatc tcgatctctt gacctcgtga tccgcccacc   5640
tcggcctccc aaagtgctgg gattataggc atgagccact gtacccagct gactcttagt   5700 cactttttaag aagggactg tgccttcatt tttcactggg ccctgcagaa tatatgcctg   5760
ggctctgggc tcttctgaac ctgtgttggc ttccatctga cctctctgtg ccagcccaag   5820
gctgctgctc ttcctgaggg caaggagccc catgactgcg tgttgactcg ctggatgggg   5880
ctgctgagcc cactctgcca caccacgtgc cctggcagg gagggaatcc ctgggtcctc    5940
acaggaacag tcagcaagcc acacctgacg cctgctgtgg gcccatccct gcggtgctgg   6000
agaagacaga caaggcctgg tcactgcctc tgcagggtcc ccagtccgtg aaggagaca    6060 gtaatctagg cattttcggt ggggaagctg agctgttctc gtgtcctgaa ggccaggcgg   6120
gaacagccgt cttcagaggg aagggagaaa atgcacatcg catcagtgga aagggcctg    6180 acttccctca gcatggtgga gggaggtcag aaaacagtca agcttgttgc tgggtgacag   6240
tgcatttaat aatcaaaata taggctgggt acggtggctc atgcctgtaa tcccagcact   6300
ttgggaggct gaggcaggtg gatcacttga ggccaggagt ttgagaccgg cctggccaac   6360
atggcaaaac ctcaactact aaaatacaaa actagccgg gcgtggtggt gcacgcctgt    6420
aatcccagct acttgggagg ctgaggcagg agaattgctt gaacctggga ggcggaggct   6480
gcagtgagcc gagattgtgc cactgcactc cagcctgggc aacagagcaa gactctgtct   6540
caaaaaaaaa aaaaaaaaa gcaatacaaa atacaaatat cactttcact aaaagaaggg   6600
atggaagacc caaacaaac agaaacaac aaaatggcag gagtaagtcc ccacttatca    6660
ataataacat tgactgtaaa taggctaagc tctgcaatca aaagagtggg ccaggagcgg   6720
tggctcacgc ctgtaattcc aacgctttgg gaggctgagg cggatggatc atttgatgtc   6780
acgagtttta agaccagcct ggccaacaag gtgaaacccc atctgtacta aaaatacaaa   6840
aattagccag gcggtagtgg cacgcacctg taatcccagc tacttgtgag gctgaggcag   6900
gagaatcact ggaggctggg aagcggaggt tgctgtgagc caagatggag ccactgcact   6960
cccacctggg cgacagagtg agatcctgtc ttaagaaaaa aaagagtgga tgaatggatc   7020
aaaaaacaag acccaaccat ctcttgcata caagaaacac actttaccta taaaacaca   7080 ctaggccagg tgtggtggct cacacctgta atcccagccc tttgggaggc ctgactggca   7140
gatcacctga ggccaggagt ttcagaccag cttgaccgac atggcaaaac cccatctctc   7200
ctaaaaatac aaaaaaacaa aaaaagaaa aaggctggaa gtagtgatgt gtgcctgtag   7260
ccccagctac ttgggaggct gaggcaggag aattgcttga atccgggaag tggaggttgc   7320
agtgagccga gatggtgcca ctgcactcca gcctgggtga cagagcgaga ccctgtcata   7380
aaaaaaaaaa gaaagaaaa gaaaacgag aaaaacaaac acaaaattag tagaagaaaa    7440
gaaataataa agatcagaac aggccaggct catgggcaca gtggctcaac tcctacctgc   7500
tcaggagttt gagaccagtc tggccaacat ggcaaaaccc catctctcct aaaaatatga   7560
aaaaaaaaaa ataggctgga tgtggtgatg tgtgtgtgcc tgtagcccca gctacttggg   7620
aggctgaggt gggagaatca cttgagccca ggaagtggag gctgcagcga gtcatgaatg   7680
caccctgcac tctagctggg taactggagt gagattctgt ctcaaaaaag caagaccag    7740 agcagaaata aatgaaatgg aaatgaagga acaatgcaa aatgatacaa aaagttttt     7800 cgaaagata aacaaaatca acaaaccttt agccagatta agaaaaaag agagaagacc     7860 caaataaata aaatccgaga ttaaaaagga gacattacca ctgataccac agaaattcaa   7920
```

| aggatcatta gaggcaacta tgtgcaacta tatgctaatg aactggaaaa cctagaagaa | 7980 |
| ctgggtaaat ttctagacac atacaaccta tcaagattga accatgaaga aatccaaaac | 8040 |
| ctgaacaggc cgggcacggt ggcttacgcc tgtaatccca gcactttgga aggcctgaga | 8100 |
| tcaggagttc gagaccagcc tggccaacat ggtgaaaccc catctctact gaaaaaatat | 8160 |
| aaaaattagc cgggcgtggt ggcgggtgcc tctaatgtca gccactcggg aggctgaggc | 8220 |
| aggaaaatca cttgaacctg ggaggcatag gttgcagcga gccgaggttg caccactgca | 8280 |
| ctccagcctt ggcgacagag ccagactcca tctcaaaaaa attaaaataa caaaaacctg | 8340 |
| aacagaccaa taacaagtaa tgcgatgaaa actgtaataa aatgtttccc aacaaagaaa | 8400 |
| gcccaggaac aaatggcttc actgctgaat tttaccaaac attttttttt ttttgagacg | 8460 |
| gagtctcgct ctgtcgccca ggctggagtg cagtggtgta acctcggttc gctggtaact | 8520 |
| tatgcctctc aggctgcaag tgattttcct gcttcaggcc ccccgagtgg ctggaaatta | 8580 |
| gatggtactt gtcaaacaag gcctggctaa atttctatat ttccttcaag tagaagatgt | 8640 |
| gcttccaaca aaggttgggt tacggctggc ttctgaaaat cttggatttc aaggctcccc | 8700 |
| aaaag | 8705 |

<210> SEQ ID NO 11
<211> LENGTH: 66933
<212> TYPE: DNA
<213> ORGANISM: Homo sapiens

<400> SEQUENCE: 11

| tataatcaag cgcgttccgt ccagtccggt gggaagattt tcgatatgct tcgtgatctg | 60 |
| ctcaagaacg ttgatcttaa agggttcgag cctgatgtac gtattttgct taccaaatac | 120 |
| agcaatagta atggctctca gtccccgtgg atggaggagc aaattcggga tgcctgggga | 180 |
| agcatggttc taaaaaatgt tgtacgtgaa acggatgaag ttggtaaagg tcagatccgg | 240 |
| atgagaactg tttttgaaca ggccattgat caacgctctt caactggtgc ctggagaaat | 300 |
| gctcttttcta tttgggaacc tgtctgcaat gaaattttcg atcgtctgat taaaccacgc | 360 |
| tgggagatta gataatgaag cgtgcgcctg ttattccaaa acatacgctc aatactcaac | 420 |
| cggttgaaga tacttcgtta tcgacaccag ctgccccgat ggtggattcg ttaattgcgc | 480 |
| gcgtaggagt aatggctcgc ggtaatgcca ttactttgcc tgtatgtggt cgggatgtga | 540 |
| agtttactct tgaagtgctc cggggtgata gtgttgagaa gacctctcgg gtatggtcag | 600 |
| gtaatgaacg tgaccaggag ctgcttactg aggacgcact ggatgatctc atcccttctt | 660 |
| ttctactgac tggtcaacag acaccggcgt tcggtcgaag agtatctggt gtcatagaaa | 720 |
| ttgccgatgg gagtcgccgt cgtaaagctg ctgcacttac cgaaagtgat tatcgtgttc | 780 |
| tggttggcga gctggatgat gagcagatgg ctgcattatc cagattgggt aacgattatc | 840 |
| gcccaacaag tgcttatgaa cgtggtcagc gttatgcaag ccgattgcag aatgaatttg | 900 |
| ctggaaatat ttctgcgctg gctgatgcgg aaaatatttc acgtaagatt attacccgct | 960 |
| gtatcaacac cgccaaattg cctaaatcag ttgttgctct tttttctcac cccggtgaac | 1020 |
| tatctgcccg gtcaggtgat gcacttcaaa aagcctttac agataaagag gaattactta | 1080 |
| agcagcaggc atctaacctt catgagcaga aaaaagctgg ggtgatattt gaagctgaag | 1140 |
| aagttatcac tctttttaact tctgtgctta aacgtcatc tgcatcaaga actagtttaa | 1200 |
| gctcacgaca tcagtttgct cctggagcga cagtattgta taaggcgat aaaatggtgc | 1260 |

-continued

```
ttaacctgga caggtctcgt gttccaactg agtgtataga gaaaattgag gccattctta    1320
aggaacttga aaagccagca ccctgatgcg accacgtttt agtctacgtt tatctgtctt    1380
tacttaatgt cctttgttac aggccagaaa gcataactgg cctgaatatt ctctctgggc    1440
ccactgttcc acttgtatcg tcggtctgat aatcagactg ggaccacggt cccactcgta    1500
tcgtcggtct gattattagt ctgggaccac ggtcccactc gtatcgtcgg tctgattatt    1560
agtctgggac cacggtccca ctcgtatcgt cggtctgata atcagactgg gaccacggtc    1620
ccactcgtat cgtcggtctg attattagtc tgggaccatg gtcccactcg tatcgtcggt    1680
ctgattatta gtctgggacc acggtcccac tcgtatcgtc ggtctgatta ttagtctgga    1740
accacggtcc cactcgtatc gtcggtctga ttattagtct gggaccacgg tcccactcgt    1800
atcgtcggtc tgattattag tctgggacca cgatcccact cgtgttgtcg gtctgattat    1860
cggtctggga ccacggtccc acttgtattg tcgatcagac tatcagcgtg agactacgat    1920
tccatcaatg cctgtcaagg gcaagtattg acatgtcgtc gtaacctgta aacggagta    1980
acctcggtgt gcggttgtat gcctgctgtg gattgctgct gtgtcctgct tatccacaac    2040
attttgcgca cggttatgtg gacaaaatac ctggttaccc aggccgtgcc ggcacgttaa    2100
ccgggctgca tccgatgcaa gtgtgtcgct gtcgacgagc tcgcgagctc ggacatgagg    2160
ttgccccgta ttcagtgtcg ctgatttgta ttgtctgaag ttgttttac gttaagttga    2220
tgcagatcaa ttaatacgat acctgcgtca taattgatta tttgacgtgg tttgatggcc    2280
tccacgcacg ttgtgatatg tagatgataa tcattatcac tttacgggtc ctttccggtg    2340
atccgacagg ttacggggcg cgaccctcgc gggttttcgc tatttatgaa aattttccgg    2400
tttaaggcgt ttccgttctt cttcgtcata acttaatgtt tttatttaaa ataccctctg    2460
aaaagaaagg aaacgacagg tgctgaaagc gagcttttg gcctctgtcg tttcctttct    2520
ctgttttttgt ccgtggaatg aacaatggaa gtccgagctc atcgctaata acttcgtata    2580
gcatacatta tacgaagtta tattcgatgc ggccgcaagg ggttcgcgtc agcgggtgtt    2640
ggcgggtgtc ggggctggct taactatgcg gcatcagagc agattgtact gagagtgcac    2700
catatgcggt gtgaaatacc gcacagatgc gtaaggagaa ataccgcat caggcgccat    2760
tcgccattca ggctgcgcaa ctgttgggaa gggcgatcgg tgcgggcctc ttcgctatta    2820
cgccagctgg cgaaaggggg atgtgctgca aggcgattaa gttgggtaac gccagggttt    2880
tcccagtcac gacgttgtaa aacgacggcc agtgaattgt aatacgactc actatagggc    2940
gaattcgagc tcggtacccg gggatcctct agagtcgacc tgcaggcatg caagcttctc    3000
ttgtgccggt tgtacgctgt caggtcacac tggtgagtta ggcagggcac agatgcccag    3060
agcagaggga actttccttg gggattcaac acgtgcaagt cttagggct ggcaaatcct    3120
gccctcagct agagagggg cttttatttg agaccagaat cacctgagca tcctcctgtc    3180
cccagctgtg tccagcctgt ctgcagggac atcctgagag gaccaggctc tcccctcatc    3240
cacctgccta agtgccactc tgaaccctgt ccacctgtgc cgtggagggg cgtgacctca    3300
agctgctcag ccagcagcag gcttggccct gggggcagc agagacccag gtggctgtgg    3360
ggtgggtgct tcgtggcgtg gttctgaaac ttcgttggaa gtgtgtggac agtgccttgc    3420
ctgttctctg tgggaccta tttagaaacg aggtctgagt tactgggggt catcactgtg    3480
ttctgatggc ccagctgtgt ggaggccgcg gtgcagcccc atccaaggag ccagggccct    3540
gggtctagcc gtgaccagaa tgcatgcccc ggaggtgttt ctcatctcgc acctgtgttg    3600
cctggtgtgt caagtggtcg tgaaactctg tgttagctct tggtgttcct gaaagtgccc    3660
```

-continued

| | |
|---|---|
| ccgggtctca ggcctcagaa ccagggtttc ccttcatctc ggtggcctgg gagcatctgg | 3720 |
| gcagttgagc aaagagggcg attcacttga aggatgtgtc tggccctgcc taggagcccc | 3780 |
| ccggcacggt gctggggcct gaagctgccc tcggtggtg gagaggaggg agcgatgaag | 3840 |
| tggcgtcgag ctgggcagga agggtgagcc cctgcaaggt gggcatgctg ggacgctga | 3900 |
| gcagcatggc cagcagctgg gtctgcagcc tggtacccgg cgggacttgt ggttggggct | 3960 |
| ggtttgtggc caggagaggg gctggcagga gacaaggggg actgtgaggc agctcccacc | 4020 |
| cagcagctga agcccaatgg cctggctgtg tggctctcag ctgcgtgcat aacctctcag | 4080 |
| tgcttcagtt ctctcatttg taaaatgagg aaacaaacag tgccagcctc ccagaggtgt | 4140 |
| catgaggatg aacgagtgac catgtagcat gggctgggtg cgtgtcacct aacatcacca | 4200 |
| gcctttgcaa ggagagccct ggggcctgg ctgagtattt cccttgcccg cccacccca | 4260 |
| ggcctagact tgtgcctgct gcaggccctt gaccctgac cccattgcac ctgtctccac | 4320 |
| aggagccgag gaggtgctgc tgctggcccg gcggacggac ctacggagga tctcgctgga | 4380 |
| cacgccggac ttcaccgaca tcgtgctgca ggtggacgac atccggcacg ccattgccat | 4440 |
| cgactacgac ccgctagagg gctatgtcta ctggacagat gacgaggtgc gggccatccg | 4500 |
| cagggcgtac ctggacgggt ctggggcgca gacgctggtc aacaccgaga tcaacgaccc | 4560 |
| cgatggcatc gcggtcgact gggtggcccg aaacctctac tggaccgaca cgggcacgga | 4620 |
| ccgcatcgag gtgacgcgcc tcaacggcac ctcccgcaag atcctggtgt cggaggacct | 4680 |
| ggacgagccc cgagccatcg cactgcaccc cgtgatgggg taagacgggc gggggctggg | 4740 |
| gcctggagcc agggccaggc caagcacagg cgagagggag attgacctgg acctgtcatt | 4800 |
| ctgggacact gtcttgcatc agaacccgga ggagggcttg ttaaaacacc ggcagctggg | 4860 |
| cccccacccc agagcggtga ttcaggagct ccagggcggg gctgaagact tgggtttcta | 4920 |
| acaagcaccc cagtggtccg gtgctgctgc tgggtccatg cgtagaaagc cctggagacc | 4980 |
| tggagggagc cctttgttcc cctggcttca gtttcctcat ctgtagaatg gaacggtcca | 5040 |
| tctgggtgat ttccaggatg acagtagtga cagtaagggc agcctctgtg cactgacca | 5100 |
| cagtacaggc caggcctctt tttttcttt ttttttttg agatggagtc tcactctgtc | 5160 |
| gcccaggctg gagtgcagtg gtgtgatctc agctcactac aacctctgcc tcctgggctc | 5220 |
| aagtgattct cctgcctcag cctcctgagt agctgggatt acaggtgcct gccactgtgc | 5280 |
| ttggctaatg tttgtatttt tggtagagat ggggtttcac cgtcttggcc aggctggtcg | 5340 |
| caaactcctg acctcaggtg atccacctgc ctcagcctcc caaagtgctg ggattacagg | 5400 |
| catgagccac cacgcccggt caggccaggc ctcttttgaa cactttgcac accatgggtc | 5460 |
| ttttcatcca gggggtagg tacagttgta cagttgagga cactgaagcc cagagaggct | 5520 |
| cagggacttg cccagggtca cacagcagga tgtggcaggt gtgggctgg gcctggcagc | 5580 |
| gtggctccag cttttccagca tagaaatctg tgaaagcaga tagtttgtcg gtcggtaggg | 5640 |
| gagactttct gagacccgcc ccagcggctc agagggtagt agccagggc cttcctgggg | 5700 |
| gctcataacc cagaacactg aatgggaaaa ccctgatgga ggaggcgcag tggagctgtg | 5760 |
| ggtgccgatg ggaagtccca gaggagctgg gaggtcagta gcggtgctgc cctctgtgga | 5820 |
| gcacttagtg ggcaccaggt gtgtttccag gttcatggcc ctgggacctg aagctcagaa | 5880 |
| ggtgaagtaa cttgcccagg gcacccgtcg ggcagcggcg ggcagaggat ttgtgggctg | 5940 |
| tggagcctgt gctcgtggcc cagccctggg ggttgtgagt gtgctggccg gggagctttt | 6000 |

```
cctgcaagtg gactggtgtc taggagccag catgtcaggc agcaggcagc gggagtgcag   6060
caggcagcgg gagcacagca ggcagagggc ggggctcgag cagccatccg tggaccctgg   6120
ggcacggagg catgtgggag agggctgctc catggcagtg gctgaagggc tggttgtgc    6180 cccgaggagg gtggatgagg gtaagaagtg gggtccccag gggctttagc aagaggaggc   6240
ccaggaactg gttgccagct acagtgaagg gaacacggcc ctgaggtcag gagcttggtc   6300
aagtcactgt ctacatgggc ctcggtgtcc tcatctgtga aaaggaagg gatggggaag    6360 ctgactccaa ggcccctcct agccctggtt tcatgagtct gaggatccca gggacatggg   6420
cttggcagtc tgacctgtga ggtcgtgggg tccaggagg ggcaccgagc tggaagcggg    6480
aggcagaggg gctggccggc tgggtcagac acagctgaag cagaggctgt gacttggggc   6540
ctcagaacct tcacccctga gctgccaccc caggatctgg gttccctcct tggggggccc   6600
cagggaacaa gtcacctgtc ctttgcatag gggagccctt cagctatgtg cagaaggttc   6660
tgctctgccc cttcctccct ctaggtgctc agctcctcca gcccactagt cagatgtgag   6720
gctgccccag accctgggca gggtcatttc tgtccactga cctttgggat gggagatgag   6780
ctcttggccc ctgagagtcc aagggctggt gtggtgaaac ccgcacaggg tggaagtggg   6840
catccctgtc ccaggggagc ccccagggac tctggtcact gggcttgccg ctggcatgct   6900
cagtcctcca gcacttactg acaccagcat ctactgacac caacatttac aaacaccgac   6960
attgaccgac accgacattt accgacactg acatttacca acactgttta ccaacactga   7020
catctactga cactggcatc taccaacact gacatttacc gacactgaca tttaccaaca   7080
ctatttacca acactgacat ctactgacat tggcatctac caacaccaac atttaccgac   7140
accaacattt accaacactg aaatttaccg acaccgacat ttaccgacac cgtttaccaa   7200
caccgacgtt taccgacacc gacatttacc gacactgata tttaccaaca ctgacatcta   7260
ctgacgctgg catctactga caccgatgcc agcatctacc aacaccgaca tttaccaaca   7320 ctgacatta ctgacactga tatctactga cactggcatc tactgacacc aacatttacc    7380
aacaccagca tctaccaaca ccgacattta ccaacaccag catttaccaa caccgatgtt   7440
taccaacgcc gacgtttacc gacgccagca tctaccaaca ctgacattta ccgacaccga   7500
catttaccga cactgacatt tactgacact gacatctact gatactggca tctaccgaca   7560 ctgatatta ccaacgccag catctactga cactgatgtt taccaacacc gacatttacg    7620
agcaccgaca tttactgaca ccaatatta ctgacatcaa catttagcca tgtgatgggg    7680
gccggcttgg gggcaggcct tgctcttggc actggggatg ctgcagagac cagacagact   7740
catggggtca tggacttctg cttcttctcc agcctcatgt actggacaga ctggggagag   7800
aaccctaaaa tcgagtgtgc caacttggat gggcaggagc ggcgtgtgct ggtcaatgcc   7860
tccctcgggt ggcccaacgg cctggccctg gacctgcagg aggggaagct ctactgggga   7920
gacgccaaga cagacaagat cgaggtgagg ctcctgtgga catgtttgat ccaggaggcc   7980
aggcccagcc accccctgca gccagatgta cgtattggcg aggcaccgat gggtgcctgt   8040
gctctgctat ttgccacat ggaatgcttg agaaaatagt tacaatactt tctgacaaaa    8100
acgccttgag agggtagcgc tatacaacgt cctgtggtta cgtaagatgt tatcattcgg   8160
ccaggtgcct gtagacacag ctacttggag actgaggtgg gaggatcgct ggagtccaag   8220
agtttgaggc cagcccgggc aaaggggaca caggaatcct ctgcactgct tttgccactt   8280
actgtgagat ttaaattatt tcacaataca aaattaagac aaaaagttaa tcacatatcc   8340
actgccctgc ttaagacaga aaacatgggt gttgttgaag ccagaggcag ctgctggcct   8400
```

```
gagtttggtg attggttcct aagcagttga aggcagtttt gtttttccat agatgtctgt   8460
tctccctttg ctgggtgcag cctcgccctg ctgctgtggt cgggtttcag tggcctcgtc   8520
ccgtggacgc agcctcgccc tgccgctgtg gtcgggtttc agtggcctcg tcccgtggac   8580
gcagcctcgc cctgctgctg tggtcgggtt tcagtggcct cgtcccgtgg acgcagcctc   8640
gccctgccgc tgtggtcggg tttcagtggc tcgtcccgt ggacgcagcc tcgccctgcc   8700
gctgtggtcg ggtttcagtg gcctcgtccc atgggcgtgc tttggcagct ttttgctcac   8760
ctgtggagcc tctcttgagc ttttttgttt gttgtttgtt tttgtttgat tttgtttgat   8820
tgtttgtttt tgttgtcgtt gttgttgccc aggctggagt gcagtggcgc gatctcagct   8880
cactgaaacc tctgcctcct tgggttcatg ccattctcct gcctcagcct cccacatagc   8940
tgggattaca agtgcccgcc accacgcctg gctaaatttt gtattttag tagacagggg   9000
gtttcaccat gttggtcagg ctggtctgga actcctggtc tcacatgatc cacctgcctc   9060
ggcctcccaa agtgttggga ttacaggcgt gagccaccgc gcccagcctc tgttgagcat   9120
attttgaggt tctcttggtg ccagtgatat gtacatgtgt ccccatcgca ccatcgtcac   9180
ccattgaggt gacattggtg cctctcctcg gggtggatgc ctccctctgt ttccagcaac   9240
ttctgaagga ttttcctgag ctgcatcagt ccttgttgac gtcaccatcg gggtcacctt   9300
tgctctcctc agggctccca ggggaggccc gaatcaggca gcttgcaggg cagggcagga   9360
tggagaacac gagtgtgtgt ctgtgttgca ggatttcaga ccctgcttct gagcgggagg   9420
agtctcagca ccttcaggt ggggaaccca gggatggggg aggctgagtg gacgcccttc   9480
ccacgaaaac cctaggagct gcaggtgtgg ccatttcctg ctggagctcc ttgtaaatgt   9540
tttgttttg gcaaggccca tgtttgcggg ccgctgagga tgatttgcct tcacgcatcc   9600
ccgctacccg tgggagcagg tcagggactc gcgtgtctgt ggcacaccag gcctgtgaca   9660
ggcgttgttc catgtactgt ctcagcagtg gttttcttga acagggtct cgctcgctca   9720
cccaggcgag agtgcagtgg cgcaatcacg gctcgctgta gcctcaatct ccctgggctc   9780
aggtgatcct cctgcctcac cctctgagta gctgggacta cagacacata ccaccacacc   9840
cagctagttt ttgtgtattt tttgtggggg gagatggggt ttcgctgtgg tgcccaagct   9900
gatctcaaac tcctgaggca caagcgatcc acctgcctcg gcctcccaaa gtgctgggat   9960
gacaggcatc agccgtcaca cgcagctcaa tgattttatt gtggtaaaat aaacatagca  10020
caaaattgat gattttaacc attttaaagt gaacagttca ggctgggcgt ggtggcttat  10080
gcttgtaatc ccagtacttt gagaggctga ggtgggcaga tcacctgagg tcaggagttt  10140
gagaccagcc tggccaacat gatgaaatcc agtctctact aaaaatacaa aaattagccg  10200
ggcatggtgg caggtgcctg taatcccagc tactcgggag gctgaggcag gagaatcgct  10260
tgagcccggg aggtggaggt tgcagtgatc tgagatcatg ccactgcact ccaatctgtg  10320
tgacagagca agactctgtc ttgaaaaata aataaataaa aaaattttta aaagtgaac   10380
aattcagggc atttagtatg aggacaatgt ggtgcaggta tctctgctac tatctacttc  10440
tagaacactt tcttctgccc tgaaggaaac cccatgccca ccggcactca cgcccattct  10500
cccctctctc ccagcctctg tcaaccacta atctactttc tgtctctggg ggttcacttc  10560
ttctggacgt tttgtgtgac tggaatcctg caatatgtgg ccctgcgtg tggcttcttt  10620
ccatagcatt gtgttttcca gattcaccca cacattgtcg cacgttatca gaatctcatt  10680
cctgactggg tgcagtgggt taggcctgta atcctaacat tctgggaggc caaggcggga  10740
```

```
cgatcacttg aggcaggagt ttgagaccag cctggccagc ctagcaagac cccagctacc   10800
aaaaaatttt aaaagttaac tgaacgtggt ggtggtgggc acttgtggtt cccagctacc   10860
tgggaggctg aggtgggagg atcgcttaag cccaggaggt caaggctgca gtgagctatg   10920
atcgcaccac tgcactccag cctggacaac agagcaagac cctgtctgaa aaaaaaaaca   10980
aaaaaaaaag ttcctttctt tttgtggctg gatgacatcc cattgtatgg ccacagcaca   11040
ttttgtttgt ctgtttatcg ggtggtgggc agtggtttcc accttttgtc tcctgtgaat   11100
aatgctgctg tgaacatttg aattcaagtt tttgtttgaa cacctgttgt gaattatttg   11160
gatatatgtg taggggtagg attgctgagt cctatggtaa tgttaggttt gacttactga   11220
ggaaccatta aactgttttc aacagtggct gcgccgttct gcatcccac cggcagtgtg    11280 tgagggttct gactttacct cctcacaaac gcttcttttc catttaaaaa aatattcagc   11340
caggtgctct ggctcacgcc tgtaatccca gcactttggg aggccgtggc gggcggatca   11400
cctgaggtca ggagttcgag acgagcctgg ccaacatggt gtaacccat ctctaccaaa    11460 aatataaaaa ttagccgggt gtggcagcgg gcgcctgtaa tcccagctac ttgggaggct   11520
gaggcaggag aatcacttga acccgggagg cagaggttgc agtgagccaa gatcgcgcca   11580
ctacactcca gcctgggtga caagagtgaa actccatcta aaataaaaca aaaataaaaa   11640
taaataaaaa tttattaaaa cattcatcac agccagccta gtgggtgtcc catgtggctt   11700
tgcctcgcat ttccctgata actaggatgc tgagcgtctt gtcccaggct gccacacct    11760 cagcactttg agatacgtcg cacagtcccc atttgcgaac gagaaatgag gtttaggaa    11820 cagcagctgt gtcatgtcac acagcgagca ggggtctct gagccgtctg accccacagc    11880
cgaccaagct ccaatcctta ccgcctccta gtgttgtgga tgtagcccag ggtgctcca    11940 cattttcag atgagaacac cgaagctcaa aacaggagcg ttttgtccac attggataca    12000
cgatgtctgt ggtttggtcc tgaagtcact ttatatctca gtggtccaga ctggagtagg   12060 acaggggtt ctggggaatg gggaaggtgt ctcaggtgaa aggaaggaat tccagattct    12120
ccatactgtc cttgggaagt tagaagactc agagggtctg gcaaagtcag acaaagcaag   12180
agaaatgcag tcaggaggaa gcggagctgt ccaggaacag gggggtcgca ggagctcacc   12240
cccaggaact acacttgctg gggccttcgt gtcacaatga cgtgagcact gcgtgttgat   12300
tacccacttt tttttttttt ttgaggtgga gtctcgctct cttgcccagt ctggagtgca   12360
gtggcacgat ctcggctcac tgcaagctct gcctcccggg ttcatgccat tctcctgcct   12420
cagcctcccg cgtagctggg actacaggcg cctgccaccg cgccggcta atttttgtat    12480 ttttagtaga gatgggattt cactacatta gccaggatgg tctcgatctc ctgacctcat   12540
gatccgcccg tctcggcctc ccaaagtgct gggattacag gcgtgagcca ccgcgcccgg   12600
cccgatttcc cactttaaga atctgtctgt acatcctcaa agccctatac acagtgctgg   12660
gttgctatag ggaatatgag gcttacaggc catggtgctg gacacacaga agggacggag   12720
gtcaggaggt agaagggcgg agagagggaa caggcggagg tcacatcctt ggctttcaaa   12780
atgggccagg gagagacacc ctctgagcat ggtaggacag gaaagcaaga ttgaacaca    12840 ttgagagcaa ccgaggtggc tgggcgtggt ggcttacgcc tgtaatccca cactttgga    12900 aagctgaggt gggtggattg cttgaggcca ggagttcaag accagcctgg ccaacatggt   12960
gagaccccgt ctctactaaa tatacaaaaa ttagccaggc gtgatggtgc atacctgtaa   13020
tcccagctgc ttgggaggct gaggcaggag aattgcttaa acctgggagg cggaggttgc   13080
agtgagccga gatcccgcca ctgcactcca gcctgggcca cagagtgaga ctccatctca   13140
```

```
aaaaaaaaaa aaaaaaaga taaaaagacc aaccgaggaa ttgaagtggg ggggcgtcac    13200
agtagcagaa gggggatcgt ggagcaggcc accctgtggt catgcactgg aagctcatta    13260
cctgacgatt tggagctcat cactgggggc ctaaggagaa tagatactga aggatgagga    13320
gtgatggcgc ggggcacggg tgtctttggt ggccagaact tggggactgc tggggtgcct    13380
cactgcaggc cttctcagcg ccctttatat gcttacacag gctgtttcta agaggggggat   13440 acattgcata agcgttttca gactacctca tcatgggtcc ctttctttac cctctgtggc    13500
cctggtggcg cactctctgg gaaggtgcag gtggatgccc agacccgccc tgccatccac    13560
ctgcacgtcc agagctgact tagcctcgag attgctgctg gcacctcctg ccccgggaca    13620
cctcggatgt gcccgtggag atgctggctc tgtgttttct gctggagttt ggtgcgtctt    13680
ttcctcctgc aagtggccac cgctcttggg tatgtcctca ggcttctgcg agtcatggct    13740
gcttctcagg tccttgccca cgccaggag caaaccctcc tggcactttg ttcagggggtg    13800 gatgcgccag tgttcctgct gtggaccccc atctcacatg agggtcttgg gcctgcaggc    13860
tcgttcagga aacacccgct gagtacgcag tgtgtgccag ctgtgtccca ggcaatggcg    13920
gggacagtgg ctgctgctgg ggttgtggtg gcttctgggg actctgggga cagctgaggt    13980
gcaaggagcc acggctcctt gaggatgcag ttggactcca ggtggaaggg atggttgggg    14040
gaggtataaa tggggtcagg gaggagacac atttggaaca atgggaacat ttttaagatg    14100
ctatgtcggg aggcaacaag gtggccaacc caggtgctga ggagcccaca ccagccctgg    14160
acgtgttttg ccgctcacct ttgctgggga gtggtgggga agaggattcc gttccacgtg    14220
gtggtgtgcg cagctgggct gtgtggagct gggcgctagg aggaaggtgc tttctgcggg    14280
gctagccggg ctctgccttt gaacacaatc aggctccagg ttttcagcat ccagtgcatg    14340
agaggacttc acgggcagct gtggctgatc ccttgatgaa ttgggagaag aacaaaggtc    14400
tatgaaatga ggtttcatgt agatggcatt agagacgccc acaacagatt tacagagtgg    14460
agcggagacg gcggatgggt ctgggaggcc cctcctgctg gccttgactg tgacagctgt    14520
cctgggaatc agcttccagg ccgccccagc agcctgactg acacacacag gggttttagc    14580
cccatcctgc gaccagctgt tgccatcatc agtgacagct gggagtggcg gtggttccag    14640
ccctgggcac cctcccccacc tgctggggcc cacccagggc agtcctgaca cctacaggtt    14700
gcttggagcc gcatccgagt cctgccccac cacgtgtgaa gcccgagtgg tcgtgggctg    14760
aggtcccctg attgcatccc cacttcccctt ctgcttcaca tagctgcctc ttctcaccgt    14820
ttttccagcc tcctgggcta ggaattccag tgttgtgctg gctttgcccc aggacacctc    14880
cttagccctc ttcctgagtc tagagccccg ggggttggaa gttctggccc ctgggacacc    14940
tgcagccaca ctcagcttct cctgtgagcc tccagcatgt cccctcagga ccaagccctc    15000
acgttcttgc ctccccgccc acctgggctc agccagggga aggcctggct gggagcgtct    15060
cccctctgcc ctgcccttct cccctctacc ctgcccttct ctcctctgcc ccgccatggc    15120
ttttatatcc tgtgccacaa gacatggctg tgtgtgaaag tggcagggtc tggcatctct    15180
gtgggtctct gaggcccacg ctccagtgcc actcttccca cccgctggcc gtgccctcat    15240
gctggaggga cagcccagcc ctctcccgaa ccccagcccc atgtgcccag ctgccccgg     15300 ccctctcccc tggaagccgg ggtcactcca gccgtatgcc atggtgggga catcctgctt    15360
ccttggcctt ccaggggaagg tcctctttcc aaatggcgac acctggtccc tgcctggagg    15420
ctggaagctg tggcccttgt atgcccctcc agggtctgtg cgctcggttg gcccgagttc    15480
```

```
ccatcaccgt catcatcacc atcatcattg tcatttcgct tgtctgtgag ccggcctggt    15540
ctcccagagc agagaccctc tgaggtccag cctgagttgg ggtctccgtg ctgacccctg    15600
acggggactc aggacgtacc aggtctgggt caggagtgac ccccaaacct cgtgcccttt    15660
gacaggcacc cctgactttt gctaagtggg tggaggtgac atcacttaca gcgggagtga    15720
tgggacaggg tctgttggct gcactgtgct cccagggatc tggggagagg ctatatccct    15780
gggctttggc actgcagagc tgtgtgtgtt tgtgtgtgtg tgtgtgtgtg tgtgtgtgtg    15840
tgtgtgtgtg tgtgtgtgtg tttgcgtgcg cgcacatgtg tataagatct tttttttatta    15900 catgaagcaa gataactgtt gctgtttcct tttgggtttt gtgttcaaca gagtggggta    15960
cttcttccct cagacaacag aactctcccc tttaaacacg tgctgtcaga gggtgggtct    16020
tgggctcatg tctgtttgca cagccgagtc agaggaaaca cagggttctt cataaaaaca    16080
ctgcacagca ggcgactgtc cagagtcagc ctgcaggacg gcagcagccc tgcccctcag    16140
agcacagcta gggtgggctg ctttgggatc tcccgtcatt ccctcccagc tggcagccgg    16200
cggccggccc attccttggt gtgctggtca ggggggcgtg cgcctgctct gctcaccctg    16260
ggaatgggac agaagctggc agctcggaga ggacagggct ggacccttgg gtggcctctg    16320
gctggaccat ctcattgtcc tcagacacag cctctcgggt ctagtttcat ttcctgaaaa    16380
acaagtgcac agaactagag caggagtcga gagctacggc ccccgggcca gatccagccc    16440
tgccacctgt tttcacacca tgctcaagct gagtgggttt tacatttttt aattacttga    16500
aaaaaaaaaa gccaaaggag gtttcatgac ccatgaaaat tatatggaat tcaaaaaaaa    16560
aaaattatat ggaattcaaa tttcagtgtc cataaataat ttcttgagac agggtctcgc    16620
tctgtcaccc aggctggagt gcagtgctat ggcatggctc gctgtaccct tgacctccca    16680
ggctcaagcg atcctcctgt ctcagcctcc tgagtagctg ggactacggg tgtgtgccac    16740
caagcccggc taatttttttt ttaatttttag taaagacagg gtctttctat gttgcccagg    16800
cttttctgga actccatctt ggcctcccaa agtgctggga ttacaggctc gagccacgga    16860
gcccagcctg ttttttgtttt ttcactgata aagttttgcc gggtgtggta gtgtgtgcct    16920
ctagcgattt gggaggctga ggtgggagga tcgcttaagc ccaggagttt gaggctgggc    16980
tcaagtgatc aggaggtgaa ctatgatcat gtcattgcat tccagcctgg gtgacagagc    17040
aagaacctat ctcttaaaaa tatatatta aaaagtattg ggtgtggtgg ctcacgcctg    17100
tggtcccagc tacttaggca tctgaggtgg gaggatggct tgagcccagg agtttgaggt    17160
tgcagcgagc caagatcgtg tcactacact ctagcctggg tgacagagcc cagaccctgc    17220
ctctttaaaa aaaaaaacca aaaaacatgt attggaacac agccatgcct gttcagtcac    17280
gtgctctcca tgctgctttc tgctccagag acccttatgg cctgaaagct gaaaatattt    17340
tctatccttt acaaaaaagt ttgctgacct ctgtcctgga aaattcatct cccaagttct    17400
cttccggcac tggcgttcct gggtgtccta aatttggccc ctgttatttc tgaactctgt    17460
tttggctctg ttccctccca ggagccagga caggcacgtt ctctgcatct tgtcccctga    17520
cgcccagagg cttggctcgg ctcaggcatt cttggaaata tctggctcca ggaaaggcag    17580
aggcctcctg agtcagccca gagggaacct gccccaggtc tgggggaggc ctgacccagc    17640
agagtggctt tgccgatgg gttgggccgg tcaagatgtg ctgaaagttg tcctcagaag    17700
gccactttgg gattccttcc tccagtatta gagcaactga gagctgctca ttgcaagcct    17760
gatgttttcc cagttggccg ggtccaccgg gtgccctggg attctgggat ctgggtggaa    17820 agtaggggggc ttgggggagt gtcctggggtt ctggaatcca ggtggcaagt ggtgaggttc    17880
```

-continued

```
agggagtggc ttctgagcca ccatagggt ctctgtggga ggctctgccc atccaggaga    17940
ttccgcaggc cctgccggcc cagagccagc gtcttgcgct tgccgaggct acagccagcc    18000
ccagccgggt ggaacagccc gtcgcctcct ctcactttgt tttggggcca cctgggagtg    18060
tggagcaagg gtagagaggg aggaagtggc tgccggccgc tgcccagcac ccttgtttgc    18120
cttgggccct ctgtgggctc ctttttattg ctcttcaatg aagccaggga aatggacttc    18180
cttgcctcac ttcagttcaa catgtctgga agtttggtat aaaattaag aaagtgtgga    18240
aatagagcaa gaagagaaaa atctctccaa gagataatag tgacctctga gctgggcgcg    18300
gtggctcacg cctgtaaatc ccagtacttt gggaggctga ggcgggcaga tcacctgagg    18360
tcggagtttt gtgaccggcc tgaccaagat ggagaaaccc cgtctctact aaaaataaat    18420
aaataaataa ataaataaat acaaaattag ccaggcatgg tggcgcctgc ctataatccc    18480
agctaaggca ggagaatcgc ttgaacctgg gaggcaaagg ttgcagtgag ccaagatcac    18540
gccattgcac tctagtctgg gcaacaagag tgaaactccg tctcaaaaaa aataaataaa    18600
taaaaataaa aaatagtgac ctctggccag gtgtggcagc tcatacccgt aatcccagca    18660
ctttggaagg aaggccgaga tgggcagatt gctttagcac aggagtttga gaccagcctg    18720
gccaacatgg tggaaccca tctctacaaa aatagaataa aatttaagag gtaatagtga    18780
cctttggta gatcgaaacc tggattgctt tcttttcta aatgctgatt cttttctttg    18840
tggtgtttgt gttctgtgcc gatgtccctc ccccagccct gttattgtga gtggaagaag    18900
gggaaagggt tcgcccgcta ctgtgagccc ctcctctcac gctgggtgtc cttggagaag    18960
cctgcacttc ttcattgtac gccagggctg ggtccctccc tggagtggtt ctgtgctgct    19020
gggatggggc caaccctca gatgttttct gagtgtcaca cacaggtgtg tgcattcatg    19080
gcctttgcgt gtcttcctgt tgtggaggca aaaatgtgaa gaaccctaga tgatttttgg    19140
accagggctc catcacctgc tgttcattgc acaccggagc atccaggcat gggtggagag    19200
ctcagacttc caggcacggt cgcagggct ggtctaacca tgttcccgcc cgcctgctcg    19260
tcagaaccgc ctgttgggag ctgttatcat gataccatac ctgggccctg gctatccga    19320
ttctgactta attgctccag gttggggcca ggccgttgtt tgctgttttg ttgtttcttc    19380
tgtgacgtta gccactgggc taatctgagc ccctcagtta caggtggaga aactgagacc    19440
catgggggtg caaggacttg ccgaggaccc agagcccctt gggggcagag ctgaggcggg    19500
gcctggcttt gggtccccaga gcttccagtc cccttcccgc tctcctaaca gcttttttt    19560
ttgagacaag atctcaccct gtcacccagg ctggagtgca atggcatgat ctcggctcac    19620
tgcaatcttc gctagctgcg ttccagcgat tctcctgcct cagcctcccg agcagctggg    19680
attacaggtg tgtgccgcca tgcccagctc gttttttttt gtacttttag tagagatagg    19740
gtttcaccat gttggccagg ctgatctcga actcctgacc tcaaatgatc cgcctgcctc    19800
ggcctcccaa agtgctagga ttacaggctg ggatcacact gtgcctggcc ctagcagctt    19860
tgtcctgtgc catccaacaa cagatgaccg aagtctttgt ttcttaacat gcattccatc    19920
tgccttacag ttttgccacc tgcaaaacag aggacttgtc gcttttctgg taagctggaa    19980
atgtaatctg gtagcaggag gcctgtggaa gcttgccttt aatggccttg tgtctctttc    20040
atcctgtcct gagagccgga gaacttggat gttgcaccta actcaaccttt cctgttaaca    20100
tacagttctg caggctcatg gatcatcaga accacgtcct atctcacgcg gctgtatgct    20160
tccgttggtt caggtgtttt taccttgaca gtattttctc ctcggtggct tttgcggtgg    20220
```

```
ttgcttttaa tcagcattga ctcttcaaga aaaatattta gctgctacat ctcagaggag   20280
acagggtgga aagcatctga gacctgcagg ctcagactta gaaccagaag tgccctcaga   20340
gttcatccgg ccctgaccca gcgggaaatg agttcacaga gaagcgggag aactttgccc   20400
caggccctgc cgttgctcat aactgcccca ggtccttaca tttgctccag gtcctgcccc   20460
aggccctgca gttgctcata actgcccag gtccttatat ttgctccagg tcctgcccca   20520
ggtcctgcag ttgctctgtg tggtgggtgt gatctggagc cctccgccca ttgctgcacc   20580
tggggcaggc attgctaatt gatcccagga ctccttcctg cggagcacgc cctggttctc   20640
caggcagccg ctgcctgtca gcctgcagtg gttcgggaga ggacacctgc ttgcctggtc   20700
tgttccaaat cttgcttctc atcccagcac aggtagggg tgctatggga aagggatcct   20760
cagttggccc tgtcactgct ctatcagctg ggacgtggc atcctagtga aaacatcatg   20820
gccgggcgcg gtggctcacg cctggaatcc cagcactttg ggaggctgag gagggtggat   20880
cacttgaggt cagaagttcg agaccagcct ggtcaacatg gtgaaaccca tctctactaa   20940
aaatacaaaa attcgccagg tgtggtggcg ggtacctgta atccgagcta ctcgggaggc   21000
tgaggcagga gaatcgcttg aacctgggag gtggagcttg cagtgagccg agatcttgcc   21060
actgcactcc agcctgggca acagagtgag acgctgtctc aaaatctcaa acaaacaaac   21120
aaacaaaaaa caaacaaaca aagcgtcatt tatccagcac ccctgggaa ccatgctacc   21180 tggtgtttta tggtacctgg caaggtgcag gtgaagttgc tgctcttggg cattgaaccc   21240
gtcttgtttg gggcagctca ggccccaggc agggtccggg ttggctctcg ttggtgtggc   21300
cctggcccat ccagacctat atttctgccg tcctgcaggt gatcaatgtt gatgggacga   21360
agaggcggac cctcctggag gacaagctcc cgcacatttt cgggttcacg ctgctggggg   21420
acttcatcta ctggactgac tggcagcgcc gcagcatcga gcgggtgcac aaggtcaagg   21480
ccagccggga cgtcatcatt gaccagctgc ccgacctgat ggggctcaaa gctgtgaatg   21540
tggccaaggt cgtcggtgag tccggggggt cccaagccat ggctcagcca tgcagacttg   21600
catgaggagg aagtgacggg tccatgcctg gcataagtg ttgagctcag gtgccccgac   21660
ctggggaagg gcaggacagg aaaggtgaca gtatctggcc aaggacagat gggaagggac   21720
caagggagct gattagggag tggttatgga ctaggaatgt cggtaacaat ggttagaaag   21780
tgactaacat ttgttgagca cctgctgtgt gcccggccct ggccgggagc cttcgtgccc   21840
acagtgaccc cgtctgcaaa tgtagttcct tgccctactc gcactgggga gcaggacgca   21900
gagccgtgca tctcacaggt gccaagctca ggactccctc ctgggtctgc ctgggctggg   21960
ctgtgcttgt tgcccctgtg gcccacgcat gtgcacctc cacctgaaag ccaggatctt   22020
caggacgctc cccgaggagg tcgttgtctg gcacaatgat ttgtctcttc ctgaaaaggt   22080
gacagagtta cactggagag agcagcatcc aggtgcggca gggacaggcc tggggctcgc   22140
gggcagggac tctgtgtcct gccggggtcc cacactgcac ctgcttgtca gaggcactca   22200
gtcaatcttt gctgatgaag gatgagagga cagaggacgt gatgcttgct gctgcattgc   22260
ctgcagtcct gggtgagatg cccggggttga ctctgctgcc cgtcgggtgg atgtgatgtc   22320
agatccccgg cttaaaata cgagggagct gggaattgag ggagcaggtt ggggcagaaa   22380
gcacagcccc gtgaagcct ggagctgagg cagtgtgggc gacccctgga gcagtgagtg   22440
cttccttcat ggccttcatc gcaccctgca gtcctcatgt agggatgcc atccatgaat   22500 ttagttttcc cagcctcctt taaaaacgcg ttcatgctgg ggccggggca gtgcagtggc   22560
tcacatctga aatcccacca ctttgggagg ccgaggcggg tggatcatga ggtcaggaga   22620
```

```
tcgagaccat cctggctaac aaggtgaaac cccgtctcta ctaaaaatac aaaaaattag    22680
ccgggtgcgg tggcgggcgc ctgtagtccc agctactcgg gaggctgagg caggagaatg    22740
gcgtgaaccc gggaagcgga gcttgcagtg agccgagatt gcgccactgc agtccgcagt    22800
ccggcctggg cgacagagcg agactccgtc tcaaaaaaaa aaaaaaagt acaaaaaaaa    22860 aaaaattagt ctgggtgtgg tatcacgcgc ctataatctc actactcgag aggctgaggc    22920
ggagaattgc ttgaacccag gaggtagagg ttgtagtgag cccgtatcgt accactgccc    22980
tccacctggg caatagagcg agactctgtc tcaaaagaa aaaaaaaaaa agaacattta    23040
tgccaggtgt ggtggctcat gcctgaaatc ccagaacttt ggaagactga ggcaggagga    23100
tcacttgagc ccagaaattt gagagtgtct tccctgggca acatagagag acctcatctc    23160
taccagaaaa aaaaaaatta gcccggcatg gtggcatatc cctgtggtcc cagctactta    23220
gggggctgac gtggcaggat cacctgagtc tggaggcaga ggttgaagtg agctgagatc    23280
atgccactgc actccagcct gggtgacaga cagagaccct gtctcaaaaa aaaaaaaaaa    23340
aaaaagcatt tactatccac catggaaggt gagactgacc tgtgagtgat tgttcaaaga    23400
acaaaaaata aaccccagag ataagacaaa agggtgcctc catgggggtg tgatttaaag    23460
ctgagaaatt gggcttcttc cccctcccct ctcaccccgt ggtttgctaa aggagatggg    23520 aaaaggatt cttttttggg ctgaaatatt taacactaaa ttaaagccaa ttttaacagc    23580
actttggttg atgagtgaaa ttaacagact ggccaaaaat aaacgaacgg tctgtactat    23640
gtgaaaagga ggcagctttg gccatgctgg gccaatgtga gttttcaggg ttgctgggaa    23700
tgtctgtgaa tcggaggaag ggcctagctg ggactctcag gagccaaggc cctgaggggc    23760
aacttgcctg gtccctgccc tgaggcgttc actgctttct tcctgggcca gatcacaggc    23820
ccggaggctg gaccactggg ctggcactct tgccgagctg ctccctgact tcctgaccat    23880
gctcctttca gcagccttgc tgcactttag tttccttgaa tgaaaaatgg ggatgagaat    23940
agctcctacc tccaaggtga atggagtgag ttcggacagg tgactccctg ggaccagtgc    24000
ctggcgcctg acaaggtcca gtcagagccc gcactgctgt tactgatacc cttggctgta    24060 ccagggggaga acttggttgc cattgccagg tgttctccca ccaccccac tactgtccct    24120 gtttgatgtg tggcgggaat aaagctgtgc acattggagc ttttggcaca tcctggcttt    24180
caggtgaaag gtgcgtgtgt gtttgagggt ttagcctggc caacccagcc atgaggtcgg    24240
acctgacctg ggggtgagtc ctgagctcgg caccccctgag ctgtgtggct cacggcagca    24300
ttcattgtgt ggcttggccg cacccctttc cctgctgggc tgttgatgtt tagactggag    24360
cctctgtgtt cgcttccagg aaccaacccg tgtgcggaca ggaacggggg gtgcagccac    24420
ctgtgcttct tcacacccca cgcaacccgg tgtggctgcc ccatcggcct ggagctgctg    24480
agtgacatga agacctgcat cgtgcctgag gccttcttgg tcttcaccag cagagccgcc    24540
atccacagga tctccctcga gaccaataac aacgacgtgg ccatcccgct cacgggcgtc    24600
aaggaggcct cagccctgga ctttgatgtg tccaacaacc acatctactg gacagacgtc    24660
agcctgaagg tagcgtgggc cagaacgtgc acacaggcag cctttatggg aaaaccttgc    24720
ctctgttcct gcctcaaagg cttcagacac ttttcttaaa gcactatcgt atttattgta    24780
acgcagttca agctaatcaa atatgagcaa gcctatttaa aaaaaaaaaa gatgattata    24840
atgagcaagt ccggtagaca cacataaggg cttttgtgaa atgcttgtgt gaatgtgaaa    24900
tatttgttgt ccgttgagct tgacttcaga cacccaccc actcccttgt cggtgcccgt    24960
```

```
ttgctcagca gactctttct tcatttatag tgcaaatgta acatccagg acaaatacag    25020 gaagactttt tttttttttt tttgagacag agtcttactc tgttgcccag gctggagtac    25080
cgtagcgtga gctcagctca ctgcaacctc cgcctcccag gttcaagcga ttcttctgcc    25140
tcagcctcct gagtagctgg gactacagac atgcaccacc acacccagct aattttttt    25200 atatttttag tagagacagg gtttcatcat gttggccagg ctggtcttga actcctgacc    25260
tcaggtgatc tgcccgcctc ggcctcccaa agtgctgaga taacaggtgt gagccaccgt    25320
tcccggcata ggaaaacttt tgccttcta aagaagagtt tagcaaacta gtctgtgggc    25380
tggccttctg attctgtaaa gaaagtttga ttggtggctg ggtgcggtgg ctcacacctg    25440
taatcccatc actttgggag gccgacgtgg gcatatcacc tgatgtcggg acttcgagac    25500
cagcctcacc aacgtggaga aacccgtct ctactaaaaa tacaaaaaaa aaattaaccg    25560
ggcatggcgg cgcctgcctg taatcgcagc tactcaggag gctgaagcag gagaattgct    25620
tgaacctggg aggcggaggt tgtggtgagc tgagatggca ccattgcact ccagcctggg    25680
caacaaaagt gaaactccgt ctcagaaaaa aaaagtttg attggtgtaa ccaaagcgca    25740
tttgtttatg gattgtctgt ggcagctttt gttctgccga gatgagttgt gacagatctg    25800
tatgggctct aaagcctaaa acatgtgcca tccgccccttt acagaaaaa gtgtgctgac    25860 ctctgttcta aagtattgga caactacaat gtttgctcat ttattattct atgatttgtt    25920
ttctgctttt tgttgttgtt gttgttgttg agatagggtt tccctctgtc actcaggctg    25980
gagtgcagtg gtgtaatctc agctcactgc agcctcgacc tcctgggctc tagtgatcct    26040
ctcatctcag cctccctagt agctgggact acaggcacac accaccactc ctggctgatt    26100
tttttttttt tttttttttt ttgtggagac agggtttccg catgttgccc aggctggttt    26160
caaactccta ggctcaaaca cccacctcag cctcccaaag tgctgggatt acaggcgtga    26220
gccaccatgc ccagcctatt ctactgtttg tattacatag cttaaaaga ttttttatga    26280 cttaagtca caagggttct ttgtagaaaa aaatatatat ataggaaagt ataaaaagaa    26340
agtaaaaatt gtccataacc tctccagcca gagacgaccg ttgctgacac ctcagcatat    26400
tgcctttaag tctttttttct ctaagatagc atttctcttc atcacagtca tatgctacgc    26460
agaattctgt atcctgattt tttcacttga cattacaaca ggtatttgat ggcgctgtga    26520
caaactcttt ggcacaatct tttaaatgta tgaaatactc cactgcacag atgtttgctt    26580
ttaggcttaa ctgttctttt attttgcgtg tgctggttac agccgggcac agtggctcat    26640
gcctgtaatc acaacacttt gagagggtga ggcaggagga tcacttgagc ccagaagttt    26700
gagaccggcc tgggcaacat agtgagaccc catctctaca aaaactttt ttaataagtc    26760 gggcgtagtg gtgcatagct gtagtcccag ccaccaagga ggctgagttg ggaggattgc    26820
ttgagcccca ggaggttgat gctgcagtga cctgagatta ctccactgta ctccaacctg    26880
agcgacagag caagacttgt ctggggaaaa aaaaaaaaa aatatatata tatatatata    26940
tatatataca tatatacata cacgcacaca cacataatat aaaatatat atttataaat    27000 atataatata taatataaaa atatatattt ataaataaaa tttataaatt atatttataa    27060
gtaaatatat aatatataat ataaaaatat atattatata atatataata aaatatataa    27120
tataaaaata tatatttata aataatatat aatacatact tataagtata tatttaaaat    27180
atatgtaatg tatatttttt aatgtatgat atataaatata catttataaa tacacattta    27240
tattatttta tataaaatat atatataaatc tccaagttgc ttttttccaaa aaggtgtctt    27300 gctgcatttc aaacattcat ttaaaaactt gaatgctggt gatctggtcc agaatgtgtt    27360
```

-continued

```
cagtagctgc tgccagtggc caagcatctc gggagatgtc tacaaaacac gctggttctg    27420
gcctggcgtg gtggctcacg cctgtaatct cagcactttg ggaggctgag gcaggtggat    27480
caactgaggt ctggatttcg agaccagcct tgccagcttg gtgaaacccc atctctacta    27540
agaatacaaa aaaattagcc aggcgtggtg gcatgtgcct gtaatcccac ctacttggga    27600
ggctaaggct ggagaatcgc ttgaacccag ggggcagagg ttgcagtgag ccagatcgc     27660 accattgcac tccaggctgg gcaagaagag cgaaactccg tctcaaaaaa aaaaaaaaag    27720
atgctggttc ctaaaatgtg gccctttttcc tcctcacctg ctgccagacc atcagccgcg   27780
ccttcatgaa cgggagctcg gtggagcacg tggtggagtt tggccttgac taccccgagg    27840
gcatggccgt tgactggatg ggcaagaacc tctactgggc cgacactggg accaacagaa    27900
tcgaagtggc gcggctggac gggcagttcc ggcaagtcct cgtgtggagg gacttggaca    27960
acccgaggtc gctggccctg gatcccacca agggtaagt gtttgcctgt cccgtgcgtc     28020
cttgtgttca cctcgtatga gacagtgcgg gggtgccaac tgggcaaggt ggcaggctgt    28080
ccgtgtggcc ctcagtgatt agagctgtac tgatgtcatt agccttgatg gtggccagga    28140
ctggtagggc cctcagaggt catggagttc cttcgtggag cgggtgctga ggctgtatca    28200
ggcacagtgc tggctgcttt cacctgggcc gtctcaccga agtgtccatg gagcctgcgt    28260
agggtgggta tctgtgtcga ttttacagat gcagaaacag gctcagagaa accgagtgac    28320
ttccctaagg tcatataccc agttagagca gagctgggcc aggaagtgct gtctcaggct    28380
cctgaccagg tctccttgct ttgcactctt gccaaaacca tgatccagaa ctgactttga    28440
ggtccccgga cctcaggctc ctccgaaatg gcctcttgga ggctgctgag ccacagctta    28500
ggacccacct cgagaggcaa atgtgctttg agctgccagg cgtcctgggg gccctgcctt    28560
gggcacgggg ttcagacagg ccccagatgt gtgggcgtc tttctggact tgagttttct     28620
tttctgtgtg gtggacacag tgctcacccc ttaaagcacc tgtgatgtgt gcagcagccc    28680
aatccctgcc tgtcgcctgt tctgctaggg aaggaaggaa gacttcagga tggcaggaca    28740
acagaaagag gtccaggttt tagagcaagg gcaggtcaaa cttagaaaat ctggaatga    28800 ggatgtgcat ttcctcttct ggatctgcta aaagaagagg gaaggagggg ctgctggggg    28860
aggagcccag agccgagttt acatccggat cccgcaaggc ctcccctgcc ctgaggtctt    28920
gttttgtgat gtgcttgtgt ccatcctggt ttctgccgtg tccccaacat ccggccaagc    28980
ttaggtggat gttccagcac acactcaccc tgtctgtgca cctgttttg tgtccgtaag      29040 tgggtattta ctcaccttac gagtgagcca ctgtgggaat tcagggaggt ggcgcagtga    29100
ccacccctgg agggatatgt gtgtggcagg gtcgagggt ctcgccctt cctgcttcct      29160 gcgcgtggct ttctccagga cggggagggc tgagctgaag aggtggggac agttgcgtcc    29220
ccccgccacc cactgtcctg cggtgagagc agactcactg agcctgccct tctcccttgt    29280
gccttccagc tacatctact ggaccgagtg gggcggcaag ccgaggatcg tgcgggcctt    29340
catggacggg accaactgca tgacgctggt ggacaaggtg ggccgggcca acgacctcac    29400
cattgactac gctgaccagc gcctctactg gaccgacctg acaccaaca tgatcgagtc      29460 gtccaacatg ctgggtgagg gccgggctgg ggccttctgg tcatggaggg cggggcagcc    29520
gggcgttggc cactcccag cctcgccgca cgtaccctgt ggcctgcaag ttccccaacc      29580 tgcaggagc tgtggccaca cccacgactg cccagcagcc tcaccctctg ctgtgggagt     29640
tgtccccgtc cacccctggg tgcctttgct gcagttatgt cgggagaggc tctggtgaca    29700
```

```
gctgtttcct gtgcacctgc tgggcactag gtcccagcta atccctgtgc caggactcta   29760
atttcaccct aacacacatg gtggttttca ttgctgggga agctgaggcc tgagcacatg   29820
acttgcctta ggtcacatag ctggtgagtt caggatcccc cagagatacc agggccagca   29880
ctcgatcccc acccagccct gaaccccacc atgtgctggg attgtgctgg gagtgtccac   29940
acgcctggga ccccagggct ggtgctctca tctcctttttt ccagatcatg agaatgaggc   30000
tcagggaagt ttgaaaaaaa cctatcccaa gtcacacagc aacaggagca ggatttgaac   30060
ccagaaaagg ggaccgcaca ctctgttctg ctagagtagt tagctgtcct gggtgatatg   30120
gcaggtgaca ggggcaactg tgcttaacaa aggaaccccc atcccccctg ccaagttggg   30180
agactagaag gtcaggggca gaagctctga agggccaggt gcagtggctg acacctctaa   30240
tcccagcact ttgtgaggcc aaggcgggca gatgatttga gcccaggagt tcaagatcag   30300
cctgggtaat gtagtgagac gccatctcta caaaaaaatt ttttaaaaat tagctgggca   30360
tggtggttca tgcctgtagt ccaagctact tgggaggctc aggtgggagg attgcttgag   30420
cccaggaggt tgaggttgtg gtgagctgtg atcatgccac tgcactccag cctgggcaat   30480
agagtgagac cgtctccaaa aaaaaaaaaa gaagaagaaa aagaagctct gaggctccaa   30540
gtccccaggc acccctttggc ttgagggcag acaagggagg agagggtcac ctgggcagcc   30600 ctgactttttg tcccctggca aagggacctt cagtgacctt ggccctagga gagcctctga   30660
gcacgtcagc catgtcgaac cgctcaggaa gggcagcaag aatttggctt ctgacctctg   30720
cctctcctac tcgccatctg cactgggtgt ggttgtgccc attttacaga tgaggaggct   30780
ggggcatcga ccagctgaat gccttgtccc aggtactgcg taggcagagc tggcagttga   30840
accccgtgtc ctggttgtcg ctgggggtgg gctgcaccct gacttgtgag gccagtagca   30900
aggtttgcac gtgacttcgt gaccgtcacc cagctctgca gcacatcccg tgacccagct   30960
catccaggcc gcatgcaaac ctgttgccag gcgagaaacc agtcaccgca cagctgtggt   31020
tgcctgaaat gattaagctc attaatcacc ccggagtgag acagactca gatgaaaacc   31080 agcaaaagcc ctgaaactc atgtgaccct gccaatgagg gcggccatgt gcattgcagc   31140
ctggccgtca ctcctcggta cgtgttttgg acttaaacgc tccggatgtt tactgagtgc   31200
ttgattaata acatggaagg cctggtctca ttgctgtggg agtgaaggat gcacagccag   31260
gcctgacatg atgagaacaa gaacctggag tctcgctgcc tgggtggtaa tcctggccct   31320
gccacttagc aactgtgtga ctgtagccag gtcacttaat tttgctagat cctgcctgcg   31380
cttcagtgga tcttgctggt tttccaaggt ggccaaacac tttaaggcat tcatgtggtc   31440
gctaggctgc agggttgaac cctggctcac cccgcagggc gccgtgtgct ctgtggcctg   31500
gctgtgcctt tgctgacacc gtgcccgtgt gtgttcatgc aggtcaggag cgggtcgtga   31560
ttgccgacga tctcccgcac ccgttcggtc tgacgcagta cagcgattat atctactgga   31620
cagactggaa tctgcacagc attgagcggg ccgacaagac tagcggccgg aaccgcaccc   31680
tcatccaggg ccacctggac ttcgtgatgg acatcctggt gttccactcc tcccgccagg   31740
atggcctcaa tgactgtatg cacaacaacg ggcagtgtgg gcagctgtgc cttgccatcc   31800
ccggcggcca ccgctgcggc tgcgcctcac actacaccct ggaccccagc agccgcaact   31860
gcagccgtaa gtgcctcatg gtccccgca cctcactccc tcgttagatc aggctggttc   31920
tgggagctga cgctgaaagg agcttctcat ctggggttcc tgggtgtaca tagatggttg   31980
ggtaggttgt gcactgcaca agctgcatga tgctacctgg gggtccaggt ccaggctgga   32040
tggacttgtt gcttcatcag gacatagata aatggccaaa actcctcagc tggaaggtcc   32100
```

```
tgggcaggat ctttgggtgt gaaaaccagt cacaggggaa gggtgcttgc tcatactgcc    32160
agcacagtgc tgagtgcttt ccatagcgct cgtttactcc tcaagcctgg agggtgggga    32220
gtagcatggt cccatttcac gtacaaggaa cccgatgcac agagaggtgt ggcaacccat    32280
ccaaggccat acaactgggg tgggttgagc cggggttgac tgtggcaggc tggctcaaga    32340
gtccctgctc ctgaaccctt gccaggcagc ctggcatcag ctcggggaat ttttgccctg    32400
acccttggaa gcaagtgggc ctctttgttc tcatgtcagt gatgagaaga gtgactttcc    32460
tatggcccct ctggagtaca ggtgtttcct gttggcgggc tcttccccca tgacatcagc    32520
agcgagctgg ttatgattcc ctacgcagaa cttgatagtt tataaagctc tttgtcatcc    32580
aggccccgtt ggagtctcac gcagacctgg tcgcaggcgg ggctggtctt gcctgtccca    32640
gctgcatgga tggggaactt gaggcttgca aaggttaagg ggctgttcga ggcccaggct    32700
ggcaggagat gggcctgggc cagagtctgg gacttcccat gcctgggctg tctttggtcc    32760
tgttgctcac catccctccc tggggccatg accttagaga gccaaatgga ggtgcaggta    32820
acccacggca aggaggggtt gccatgactc agagtccccg tcctgtggcc ggcagtacct    32880
ggtgcaacga cttggatttc agaccagcca ctgtagcccg ctgacggtgc gctcgaagtg    32940
ccacagcttc tgaagccagg caggactcag gccaggagac tctgttagct gttgagaggg    33000
agaggccaac ggatgttctg gttctgctag agagctggtt cttcggatcc tggtaccagt    33060
gcactgagag gaggcccagc ttgattctgg ggctgccttg tggtggcatg tgctgctcac    33120
tgacaccctc gaggagtgtc ttctctcggg cttgttgact gtgcccggtt ttccgcagtt    33180
cactggtgca cacataggca catagcaaac cgcacacaca gtcgtgggta tgagtttcac    33240
tacattccac caccagtgtt cactaccatt acctgccttc cgtcttaagt gttcatcatt    33300
taaaaataaa tttattgggc tggacgcggt ggctcatgac tgttatccca gcactttggg    33360
aggctgaggc gggcagatca cctgaggtca ggagttcaag accagcctgg ccaatatggt    33420
gaaactccat ctctactaaa aatacaaaat tagctgggca tggtggggca tgcctataat    33480
cccagctact caggaggctg aggcaggaga atggcgtgaa cccgagaggc agagcttaca    33540
gtgagcccag atagcaccac tgcagtccag cgtgggcaac agtgcgagac tccatctcaa    33600
aaaaaaaata aataaataaa agaaaaataa atttatgatc tatttcaaaa ataacacatg    33660
tactttgaaa cagcagagac acatatgaca cggagaatga aattccccat agcgcacccc    33720
caagagacag ccctggtccc cccgtctttc ccgtggacct ccagcggggc agatgctgag    33780
ccgcctgttg tcgagtggcg tgctatcccg tcctccagct cctctgtggc ttacagacac    33840
ccacctgcag ccctgtcttt gcctcctcta gcgcccacca ccttcttgct gttcagccag    33900
aaatctgcca tcagtcggat gatcccggac gaccagcaca gcccggatct catcctgccc    33960
ctgcatggac tgaggaacgt caaagccatc gactatgacc cactgacaa gttcatctac    34020 tgggtggatg ggcgccagaa catcaagcga gccaaggacg acgggaccca ggcaggtgcc    34080
ctgtgggaag ggtgcgggt gtgcttccca aggcgctcct cttgctggtt tccaggctgc    34140
tgcccctgtc cttagcagag ggaggaaaca gaggatggct ctgggtgaat gatgacttgg    34200
gcttcgatta tgtagtcaca gggtatgacc ctgagatgcg tggaacccg agactgtgat    34260 tatatgtaga aactgggttt ccccgttgtt taagtagtca tggtgggtc agaccccaca    34320 ggacttttgt cttttcaaga aagaaaatgg tcgtgtgtca tgcagggta gttggtactg    34380 gttaatccag gtttatcctt tattttgtgg gaactgtaca gtcatttctg ctacaatgct    34440
```

-continued

```
gtatatgctc ttctgaaaga cacctatgca aaatcgcaca gtaaaaatga cacaactcat    34500
agggaaagcg gggccagggc acagccctca aaatctccat caatgacatg taagaaaaga    34560
gaggaacctg ggaaatagca aagtgccttt tgcacattaa atggttagct atatcccaca    34620
atactgtgca ttcgtaaacg ttaatgctgc aataaatacg gcacttcacc ttgggaagat    34680
ctggagttgg cttatgagtg tggaagggtg tagcgcatga gttttttgtga aacactggaa    34740 ggaggattgt gggaaatcaa atggaaagtt ctcaccccag gcgtggagaa gagtgggtca    34800
tggccccagc agtgagccca gggaggtcag agacggaggt gtgtgtgtgg gtgtgaccct    34860
gcgcagttcc ctgccggctg tagttttttg cattcgctta atgtttctcg tggaggaaat    34920
tgtgcatgag caaatgtgaa accgtgctgt gctcaaattg tcctaataca tcattgcatt    34980
ggaacagatt ggcttttttt tttttttttt tttttttttt tttttgagat ggagtctcac    35040
tctgtcacca gcctggagtg cagtggcatg atcttggctc actgcaacct tgcctccta    35100 tgttcaagtg attttcctgc ctcagcctcc tgagtaactg ggattacagg catgagccac    35160
cgcggccggc cagatttgca ttttttgaaac aactgctagg ctgggcgcgg tggctcacac    35220
ctgtaatccc agcactgtgg gaggccgagg caggtggatc acctgaggtc aggggttcga    35280
gaccagcctg gccaacatgg tgaaaccccg tctctactga atatacaaaa atcagctggg    35340
tgtggtggcg ggtgcctgta atcccagcta ctcaggaggc tgaggcagga gaattgcttg    35400
aacccaggag gcagaggttg cggtgagccg agatcacacc attgcactcc agcctgggca    35460
acaagagcaa aactccatct caaaaaataa aaaatagaaa acaagtgct gtagcggaag    35520 tgagcacttt gcggagtcag gcttgtgtgg cctgttccac aaatgatgtg ctcacggtgg    35580
cctcaggccc acctggagtc tgcagcatgg ggcacaacag gttcattagt gtagaattcc    35640
aggacaggcc tggctcctaa gcagccttct tttacaaaaa ctgcagagcc cgcctgtatc    35700
ctagcacttt gggaggccga agtgggtgga tcacgaggtc aggagttcaa gaccagcctg    35760
gccaacatgg tgaaacccca tctctactaa atatacgaaa attagctggg tgtggtggca    35820
cgcgcctgta gtcccagcta ctcgggaggc tgaggcagaa ttgcttgaac ctggaggtg    35880 gaggttgcag ggatctgaga ccatgtcatt gcactccagc ctgggcaaca gagcgagacg    35940
ccatctcaaa aaaaaaaaac ctacagagcc acacggcctc tttctccacc gagtgttggt    36000
gtgggagctt gtgttattgt ggtgaaatct tggtactttc ttgaggcaga gagaggctga    36060
gcgcctggag agactttcac atgggtcgcc atgtccgccg tcggtttcgc tgttgtgctc    36120
cccatctgaa ggctggtgcc gtccagacag gctggacgcc cctttccacc agatccttcc    36180
tcccgcagca gtttctagtt acgttgtact gtgaggtctg tgtccttggt tgatggcaaa    36240
agtcagccga attgaaattc agagccatgc ctggctccct ggagcttctc tcctgggcag    36300
ctgtgatcat tgcctctgct gtggtgtggg tggtggaaat ggattccttt catcttgctt    36360
gctacaggtg actgtcacgt ggagtccttt ggagagaggg acgtgttaat tgatggatgt    36420
ggctcccatg ctgagaaagc tcctgggcgt acattgcctt agagtttcat tggagctgcg    36480 ttctttatg tgtctgcta ggcagaagtg atgaagactt ggaagaaaac ccagaaggtt    36540
ttccacttaa tttggaaaat gtgcttttcc cctcctgtgt cttttgctaa ggtccagcct    36600
cctgcagcct cccgctctg tggactctgg ctttgattct ttattaggag tcccctgct    36660 cccccaaaag atggtgtcta aattatcatc caattggccg aggttttgtt ttctattaat    36720 tgttttatt ttttattgtg gtaaatttat ataacataaa atttgccatt ttaattgttt    36780
tgttattgtt gtttttgaga cagggtctca ccccagtgcc caggctggag tgcagtggtg    36840
```

-continued

```
cgatcatggc tcactgcagc ctcagcctcc agggctccag tgatcctctc acctcagcct    36900
ctctagtagc cgggactaca ggcatacact accacatctg gctgattttt tgtattttttt   36960 ttttattgta gagacccgct atgttgccca ggctggtctc aactcctgga ctcaagccat    37020
cctcccacct caccctccca aagtgctggg attacaggca tgagccacaa cacccagcca    37080
ttttaatttt ttttttttttt tttgagatgg agtctcactc tatcgcccag gctggagtgc   37140
agtggcgtgg tatcaactca ctgcaacctc tgcctcccag gttcaagcga ctctcctgcc    37200
tcagcctcct cccgagtagc tgggattaca ggtgcccatc actatgcctg gctaattttt    37260 gtattttttta gcagagacgg ggtttcacca tgttggccag gctggtcttg aactcctaac   37320
ctggtgatcc gcccgcctcg gcctcccaaa atgctgagat tacaggtgtg agccaccgtg    37380
cccggccttt ttttgttttt gagacagggt cttgccctgt cacccagact ggagtgcaat    37440
ggtgggctct tggctcactg cagcctccgc ctcccaggct caagttgtgc acctccacac    37500
ctggctaact gtattttatg tagagacaga tttcaccatg ttgcccaggc tgggcttgaa    37560
atggactcaa gcagtccacc cacctcagcc tcccaaagtg ctgagattac aggcgcgagc    37620
caccgcaccc agcccatttt acctattctg cagttgacag ttcagtggca ttcagtcagt    37680
tcacgaggta accatcactg ccattcatct ccagactact tcaccttctc ggcagatgtc    37740
cgaaactgtc cgcattgaac acactcctca tctccctctg acagccacca ttctactttg    37800
tatctctctc tgccttctct aggtacctca tgtaagtgga attataccaa tatttgccct    37860
tgtgtgactg gcttctttca tgtgacatgg tgtcctcaag gttcatctgt gttatagcct    37920
gtgtcagaat ttccttcctt aaagcctgaa taataacccg ttgtaaaggc tgggcgcggt    37980
ggctcacacc ctctaatccc agcattttgg gagtccgagg tgggcagatc acttgaggtc    38040
aggagtttga gaccagcctg gccaacatag tgaaaccctg gctctactaa aagtacaaaa    38100
ttagctgggt gtggtggcgc gcacctgtaa tcccagttac tcaggaggct gaggcaggag    38160
aatcgcttgt acccgggagg cagaggttgc agtgaaccaa gattgtgcct ctgcagtcca    38220
gcctgggtaa cagagtgaga cttcctgtct caaaaaaaaa aaaaatcatc ggatggatgg    38280
acggaccact tcttgttatt tatccatcca cgggtgctag gtttcttcca cctttggttg    38340
tcgtgaataa ggccactatg aacatttcct tccgtggtga aggttttgta ctagtgagga    38400
aaaggcgtgt ttgtggtgtt gcataggatt ctggtaagaa agtttgcact aaccataagt    38460
atttgtacta cattaaaatg aaagctcagg ggccgggcgc ggtggctcac gcctgtaatc    38520
ccagcacttt gggaggccag gcgggcgga tcatgaggtc aggagatcaa gaccatcctg    38580
gccaacatgg tgaaaccccg tctctactaa aaataccaaa aaactagcca ggtgtggtgg    38640
cgggcacctg tagtcccagc tacttgggag gctgaggcag gagaatggcg tgaacccggg    38700
aggcggagct tgcggtgagc cgagatcgct tcactgcact cgagcctggg caacagagca    38760
agactccgtc tcacgcaaaa ctctgtctca cgcaagactc cgtctcaaaa aaaaaagag    38820 ttcagggttt atgaaactgg ccagccgcgt aaagtttgct gtgttgtttt tgtgcccggg    38880
aggagtgtgg ccagggtgtc acgtcacaca gtacacgttt ctcagatggt ggttctccag    38940
actgctgtcc caaagtctgt ttttgcatct ggttcccaca gacccaccct ccacggtgag    39000
cctgattttg gccagggtag ctggaatctt gcttgtcttt cagcccggca gctgtaccag    39060
tccagggtcc acagctagtg cttttaggaa ggaatttgt tcagttggct ttgacacatg    39120 gcccctagg gtccacagct ctgtagtgat gtggatgttg ttatctacaa agacacatga    39180
```

-continued

```
tccttcgtgt ccagatgaaa gtgatgatgt ctttgcagct gcccagcaag gctgtgtgtg     39240
tgtgtgtgtg tgtgtgtgtg tgtgtgtgtg tggtgtgtgt gtggtgtgtg tgtgtgtatg     39300
ggggagggag gcacccttc catctggggg tgtgtgtgtg tggggtgtgt gtgtgtgtgt     39360
gcgcgtgtgt gtggtgtgtg gtgtgtgtgt gtgtatgggg gaggcaccct ttccatctgg     39420
gtccaagaga ctgggcctgg ggaagacgct tcttttatc tacttagaga ctttgtttta     39480
tttgtatttt tttgagacag ggtctcactc tgtcacccag gctggggtat ggtgatatga     39540
gcatagctca ctgcagcctc ggcctcccag gctgaagcga tcctcccacc tcagccttct     39600
gaatagctgg gactgtaggc gtgcgtcacc atactgagct attgttttt ttgtttggtt     39660 ggtttaattt tttttgatac agatggagtc ttgctatgtt gcccagacta gtctcaaact     39720
cctgaactca agtgattctc ccacctcagt ttcccgacat tctgggatca caggtgtgag     39780
ccactgctgt ctccctgttt tattaactgc tgaaagacct agataaagaa agtctgaaaa     39840
gacttactat cagagcacca tcctaagatg attccctctg actcaatgga gagggagggg     39900
agcttttcct tcaggcctgg gtggcaggag cccaggtgct ccaggcccca tttgccccag     39960
gccaaatcac tcgggaactt ggatgcagct gtctttcagg gtaacccaaa ggaaccagat     40020
ccccgcaggc agtaggcttc tgggctgtcc tctcctccta cgtcagctca gtaagagccc     40080
ttcgaaggga tgctgtgtcg gagccccaa aagcccaggc tcatccctga gatgcacagg     40140
gtgggctggg cttaggcagc gctcgagcat ctcctggacg gtgaccccag agagtgtgga     40200 gacgagagt ccttgagagt cactgagaga cgtggctgcc ctgccttccc aagagggct     40260 ctgagtcatt ccccacactc acctgcccct acccacccct acctggcccc cagcctcacc     40320
tacccccaca tctgtaccga tcccttacc cgcaccttcc ctaccacccc tcacctcccc     40380
tgtaccttca cctcccccac tcacccgccc ctgcacccct acctgtcccc cacccttcacc     40440 taacccccac cctcacctgc cctccctca cctggcctcc ttcgtgggg aagggggttg     40500 taagggcgg cccccaaact gtctgtcctg gtgccctgca gagaaaacag tacgtgaggg     40560
ccgcagtcca aaagcttgag tcctggaagg tggaggagac agggatgtgt tgggaagggc     40620
cccatggtct tggatccctt ctcgactgtc aatggggcct tcatgggagc gccagtctag     40680
tgatgcacag ctgggtgccc ggcgggtggc tgaggaggcc taaagtccga ggcggcaaga     40740
gctcttccag aggctgttgt cctaatcgct ctggcatact caggcgggca cgtagttagg     40800
agctgattgg agaggagaga cccccacacc aatactggga tttgactttc aggctaaact     40860
tgagaagtgt ggcctctgct gtcctgccag agctctccag ccagtgccca gggctctcca     40920
gccagtgccc gggggtctcc accagtgccc ggggtctcc gccagtgcca gggtctccg     40980 ccagtgccca ggggtctccg ccagtgctca ggagtcttgg tttctttgtc ttacagccct     41040
ttgttttgac ctctctgagc caaggccaaa acccagacag gcagcccac gacctcagca     41100 tcgacatcta cagccggaca ctgttctgga cgtgcgaggc caccaatacc atcaacgtcc     41160
acaggctgag cggggaagcc atggggtgg tgctgcgtgg ggaccgcgac aagcccaggg     41220
ccatcgtcgt caacgcggag cgagggtagg aggccaacgg gtgggtgggg gtgctgcccg     41280
tccaggcgtg cccgccgtgt cttatgccga atgccagcct tcacaggct ggggagactt     41340 tccacctggg gatccaatgg gtggctttcc agggtcccaa aagcaaacac aggttttca     41400 cagcccgtcc gggaaagcag aaagccccaa ggggctggaa ggggaaaggg ggagctctgc     41460
tgagaggtta caaggcagcg ctggccgacg ggagttgcag ttgataggtt ttgtatcatc     41520
cttgttaaac ttgaaccctg tgcagaaatc ccttccacgg catgggggct gcctgttgac     41580
```

```
tcgctcctgt tccaccacag ggagctcctg ggcttcttcc tcccagaggc ccccgacgct   41640
cccacctgtt ggtcgtcaga gcttctggtt ggtgggaagg cacccaggac cttgaggtct   41700
ccagagagaa aagccaggga aagagggaga ccgaaaccca tgtgacatga aactcaggct   41760
ccaaactgag cacgggaacg tttggggaca ggagcgcgat ggccttcctc agatagctgg   41820
ggggctggca tgaagacggg agctacagcc agcacaggtc ctgggccggg agcccagaga   41880
ttgagccctg actctgtcac ttactggcca cgtgaccttg gcgggtggc atagcctctt    41940 ggagactcag tttcctcatt ggtaggagtg acggccacag tggtgcgcc tctgcagcac     42000 acggggggct cggtgggcgg aagccccggg tctataaggc ggctgtgcag gagccagccg   42060
agctggtctc ccaacagcca gggctccggg gtccttagca gctgtggggg gcctgcacct   42120
gtttcccatg gctgctgtca gaaattacca gaagccaggt ggctgagagt aatggacact   42180
tgttctctca cagttcctga gggctgaagc ccgagatcga ggtgtgggca gggccctgcg   42240
ccctctgaag gctctgaggg aacctttggg cttctggtgg ctccaggcac cccttgactt   42300
gtggtcctgt cactccagtc tctctgtctg gctgcacatg gcgtggcctc ttctgtacca   42360
ttgaaggaca cttcagttgg atttaggcc taccctcacc cattgtggtc gtatcttgat    42420
ccttcatgac atttgtaaag accctgcttc caaataagct cacattctga ggttctgggg   42480
tgagcgggaa tttggagagc attgttcaac tagtatagaa tgtgacctgt cagcctcggg   42540
cagccctgag aggcaggggc tttccacagc ccagctgggt gccctgggct ccgtgctgtc   42600
cgaggagacg ccatccccac acccgtcctt cacccgccac cctcccgcag gtacctgtac   42660
ttcaccaaca tgcaggaccg ggcagccaag atcgaacgcg cagccctgga cggcaccgag   42720
cgcgaggtcc tcttcaccac cggcctcatc cgccctgtgg ccctggtggt agacaacaca   42780
ctgggcaagc tgttctgggt ggacgcggac ctgaagcgca ttgagagctg tgacctgtca   42840
ggtacgcgcc ccggggcctg ccctaaccgc agacacccgg ccttcattgt cagtaatggc   42900
agcagctgcc acattgtccg agacctgccg tgagcccagt gccgcgccag gggctttgtg   42960
tgtagcgtgt tttgtcctca cactgacagc tgtaggctgg ggttctgagt gagccccaca   43020
gggcagaggc agaaaatgag tctcagagag ggtgagcgag ctgcttgggg ccccacagca   43080
ggagatggag caggactgca gcctagcctc tgccccagc acctgcgcaa gaagctgctc    43140
tgctctggac tgtgttaggc tgcgagggct ggagagaaat gagagttggt gcttagagag   43200
ggggcgcagg tccccatggc ttttcctctt atgatgaggt agatgggtga agggaggggc   43260
catgcttgca ggggccagtg accgaggccc gccgttggaa ctgatggcct tcatcccgag   43320
cccagcccag gtgggagcag ggcttttccga ggcttgtct tgggtcggcc tgcttccagg    43380
gactctgctg cagctcccac ccctgtccaa agcatggaat cccccaggct ccctggcagt   43440
cctgtcaacc tctgtcctcc caagctgagt gtggggcaag ttctggaggt cagcactgct   43500 cagggggggcc cacgggctgc ttgcagggc caaccgcctg accctggagg acgccaacat     43560
cgtgcagcct ctgggcctga ccatccttgg caagcatctc tactggatcg accgccagca   43620
gcagatgatc gagcgtgtgg agaagaccac cggggacaag cggactcgca tccagggccg   43680
tgtcgcccac ctcactggca tccatgcagt ggaggaagtc agcctggagg agttctgtac   43740
gtgggggctg gcagtggggt gggcagggtg gcctctaaac ccgacccctg gaggaggctg   43800
gaggccagtg caagatcctg tgtggcctca gccaggcgt ggtctctgcc agatgccaac     43860
tgttgcccgc tggggttcag cgacatgtcc gaatgtcccg aggcctctga ggttgttttc   43920
```

```
ttttgccgca gaacaaatca ccacgaacag cgtttttaaga caacaccaac tcttttttt    43980
tttttttttt tgagtcagga tcttgctctg ttgcccaggc tggggtgccc tggtgcaaac    44040
acagttcact gcagcctcga cctctgggct taattaagtg aacaccttgc ctcagcctcc    44100
caggtagctg ggactacagg tgggcaccac cacacctggc taatttttt ttgtagagac     44160
gggtttccc catgttgccc aggctggtct gcaactcctg gcacaagct atctgcctgc      44220
tgtggcctcc caaagtgcta ggattatagg tgtgagccac tggcctgaca cacccacgg    44280
attgtctctc agttctgtaa ggcaaagtcc aggcacagcg tggctcacct gggttctctg   44340
ctcagggtct cacggggcca gaatcaaggt gtcaggaacg ctgggccctc agcggaggct   44400
ctgtggagaa attagcttcc ttgctcactc agcaggtagc agttgtggga tcgaggttct   44460
gttttctctc tggttattgg tcggggacca ctctcagctc ctagaggcca ccacaggtcc   44520
ttgccccgtg gccctctctg cctcagcagt gggggctccc tgcgtcagtc cctcccacac   44580
cttgagtctc tctgatttgc ttctaaaggg ccctgtgatt cggctcagcc acctttagat   44640
taggttagcc tccccttga tagactccaa gtcggctgat taataaccctt aatcacatct    44700
gcagaatccc ttctgccaca taaggtcatg acgccgtgct ggggactggg gtgggaaatt    44760
acgggtcat ttaggattct gcctgccact gccttgctgt gtcccagggc ttggggagg     44820
ggcctccaca gctgggacca cagtccttcc tcccctccat ggtaaccatc tgaggattac   44880
ttgagaccag cctgggcaac atggtgagaa cccatcccta caaaaatac aaacaaaaag    44940
ggaccaggct gggcttggtg gctcatgcct ataatcccag cactttggga gaccaaggtg   45000
ggctgatcac ttgaggttgg gagttcgaga ccagcctgcc caacatagtg aaatcccgtc   45060
tctactaaaa atacaaaaat tagctgggtg tggtggcagg cgcctgtatt cccagctact   45120
ggggaggctg aggtgggaga attacttgaa cctgggaggc ggaagttgca gtgagccaaa   45180
attacgccac tgcactccag cctaggcaat agagtgagac tccgtctcaa aaaaaaaaa   45240
gggccagggg tggtagtgac aaagagaccc tatcccaaaa aaaccgaaca ctgaatcctt   45300
gagactgagt aaggacactg tgaaattttt ctgggtgggg cagggaacag agcgtcttct   45360
gtcatttctt ccacctgggt gtggtcagct ctccctccaa gctgcctcct cttcttctca   45420
ttgtccgggt gttggacaca tttgttaac tggatagaat aacgcgagtt cccagggact   45480
tggtccattt gctatttat tttattttat tttatttat tttatttatt tatttattta     45540
tttatttatt tattgagatg gagtttcgtt tttgtcgccc aggctggagt gcagtggcgc   45600
gatctcggtt cactgcaacc tctgcctccc aggttcaagt gattctccta cctcagcctt   45660
ccaagtaact gggattacag gcacccacca ccataccagg ctaatttttt tgtattttta   45720
gtagagacgg gttttcgcca ttttgcccag gctggtcttc aactcctagc ctcaggtgat   45780
ccacgcacct cggcctccca aagtgctggg attacaggca tgagccacca cgcctggcac   45840
catttgctat tttaattccc atgtgtatta gtgtcccacg gctgctgtaa caaatgacca   45900
caaactggat ggcttaaagc aacagaaatg gattccccca atgtgctgga gaccagaagc   45960
ctgcgaccaa actgttggga gggctgtgct cctctgggg gctccaggga ggatctattt    46020
gttggcccctt ccagtgctgt gggtgccagc gttccacact tgtggatgcg ccgcctcaac   46080
ctctgcccat cttcatgtgt ccatctcctt tgtgtctgcg tctttacctc ttcttcttgt   46140
ctgtgttgcc tcttataagg acgtttgtca ttgggtttag gcccaccca aatcatccga    46200
gatgacctcg tcttgagatc cttaacctgc aaagaccctt tttccaaaaa aaggttatgc   46260
tcacagattc taggccttaa gacatgggtg tatctttctg gggggcacta tccaaccccct  46320
```

```
tatacaatga aagacgggaa gagggccagg tgtggtagtt cacgcctgta atctcagcac   46380
tttaggaagc tgaagcggga ggatcacttg agcccaggag tttacaagta gctaggcaac   46440
atgatgagac cccatttcta caaaaagtga aaaaaaaaa aaaaaaaaaa aagccaggtg   46500
tggtggctca cacctgtaat cccagcactt tgggaggctg aggcaggcag atcacgaggt   46560
caggagattg agaccatcct ggctaacacg gtgaaacccc gtctctacta aaaatacaaa   46620
aaattatggc cgggcgcagt ggctcccgcc tgtaatccca gcactttggg aggccgaggt   46680
gggtgaatta caaggtcaag agatcgagac catcttggct aacacggtga aaccccatca   46740
agatcacaag gtcaagagat ggagaccatc ctggctaaca cggtgaaacc ccgtctctac   46800
taaaaataca aaaaattagc cgggcatggt agcgggcgcc tgtagtccca gctgctcggg   46860
aggctgaggc aggagaatgg cgtgaacccg ggaggcggag cttgcggtga ccgagatcg   46920 ctccatgcca ctgcactcca gcctgggtga cagagtgaga ctccgtctca aaaaaaaaa   46980 aaaaaaaaa aaaaaagaa aattagccag gcacagtggc aggtgcctat tgtcccagct   47040
acttgggagg ctaaggcagg agaatggcat gaacccggga ggtggagttt gcagtgagcc   47100
gagatcatgc cactgcgctc cagcctgggc gatagagcaa gactctgtct caaaaaaaaa   47160
agccaggcat ggtggtgcat gcctgtagtc ccagctactc aagaggctga ggcaggaggg   47220
ttgttcgacc cacggagatc aaggctacag tgagccatga tcgcaccact gccctccagc   47280
ctgggtgaca gagtgtgacc ctgtctcaaa gtaagtaaat aggaggagag acaagtgggc   47340
agttcagact gatggtatgg gcacagtaga gactggtgca gacaggctgg cctgtgatgt   47400
caagcaactt ctgtaattgt ttccggcatc catttgtgtg tcaatttccg tgtcagtagg   47460
aagactctgt aggctgccaa gaggaataag tgggaggatc ctcccagaga ggccgggcct   47520
gcaggagggc cagttctcat gagttctcat ttggccccta ccctccaggc tgtggttctg   47580
aggtgggaga cagagcctga cctctgtttt tcttgttttg tctttgcagc agcccaccca   47640
tgtgcccgtg acaatggtgg ctgctcccac atctgtattg ccaagggtga tgggacacca   47700
cggtgctcat gcccagtcca cctcgtgctc ctgcagaacc tgctgacctg tggaggtagg   47760
tgtgacctag gtgctccttt ggggtgatgg acaggtacct gattctctgc ctgctaggct   47820
gctgcctggc atccttttaa aatcacagtc cctgtggcat ccagtttcca aagctgattg   47880
tgtcttcctt tgccctcctt tcttttctac tatgtgcatt cggtgctatg aattttcctc   47940
taagtactgc gtttcctgca tctcacaaat tttgttacat tttcattttc aggtagtttg   48000
aatattttta cacttctcct gagatgacat ctttggctca tgtgttattt agaagtgttg   48060
cttagtttct aaagagttgg ggcttttcca gctgtctctc tgcaactgat ttctaattta   48120
attctactgt agtctgagag cttattttat atgatttctg ttattttaaa tgtgttgggt   48180
gtggtgtttt tgttgttatt gttttttgtgt cttttttgttt tgttttgctt cgtttgtttt   48240 gttttttgaga cagtgtcttg ctctgtcact caggctggag tgcaatggcg cgatctcagc   48300
tcaccgcaac ctctgcctcc cgggttcaag tgatcctctt gcctcagcct cctgagtagc   48360
tgggattaca ggtgcacgcc accatacccca gctaattttt gtattttag tagagacggg   48420 gttttaccat gttggtcagg ctggtctcga actcctgacc tcgtgatccg cccacctcgg   48480
cctcccaaag tgctgggatt ataggcgtga gccactgtgc ctggccatta ggtgtgtttt   48540
atcacccagc atcatgcagt ttatcttggt gaatgttctg tgtactcttg aaagaatgt   48600 ggattctgct gttgttgggt ggagtgttcc agaaacatca attagatcca gttggttaat   48660
```

-continued

```
agtgctcatc aggttgtctc tatccttcct tcctgactgc ctgcttgagc tgtcagttat    48720
tgacaggggt gtggagtctc caactctaat ggtggatttg tttatttctc ctagtagttc    48780 tatcttttc tctccttcta cccttgatcc tcttctcccc ctagggcttc ctggtgttag    48840
tggtgggaga gtggggtagt gaagaacctg gactttaggg ccaaagaggc cagggttcaa    48900
atcctggctc tgtcacttcc cagttgagtg accctggctg gtgcctgaat ctctgtgagc    48960
ctccacttcc tcctctgtga aattgagagc acttacctgg caggctgtca tgggcatcaa    49020
gtaacagggc actccacctg gaccctgaca cgtgatgcac aggaatgcca gctgctatgc    49080
catgggtgtg gcagtagtaa taaagtgacc atctgtatcc tcaccacagt gaagcctgtc    49140
cagggctttc tctcctatgc ccccatgcct ccaggtggcc ttggatcctg ttggttctgt    49200
gctctgctca gcgacctttc tcccgtggga gttcctgggg gttcagcttc atcctacaga    49260
cagcagcaca cactggctgt gcacccttt tttttttttt tttttttttt tgagatggag    49320
tctcgctttt tcgcgcagg ctgaagtgca gtggtgtgat cttggctcac tgcaacctct    49380
acctcctggg ttcaagtgat tttcctgcct caccctccca gtagctggg attacaggct    49440 cccaccacca cgcccggcta atttttgtat tttcagtaga gatggtgttt caccatgttg    49500
gccaggatgg tcttgaactc ctgacctcag gtgatccgcc cacctcagcc tcccaaagtg    49560 caggattac aggcgtgagc caccacaccc ggagtgccgg ttgttttag cagtttgtct    49620 tgttcctgga gagactggct cctgcccagg agctcgggga gtagggccgc ggggtgctgc    49680
ctcacacctc gagtttggcc gtaagcagag gggacatttt gtgactgtcc ccctcctgag    49740
cttcccagca gcttttctcc aagttacagc ccaaaagctc aggtggattt gcaacccaac    49800
ggtgtctgtg cacctcccac tgatgcccga actgccctgg ccaagaaacg gggccgtcag    49860
aacgctgcac taactgcagc cttgggcctc catgccagag gccatgccct tccatccacc    49920
accccctggc ctgggccctg ggccctcctg gctcgggaac tccaggcccc ttcctcacgg    49980
ctcgagagac gtgtatttac cgcacaggtg cttgtcattc tcttgtggcc tcttctccag    50040
ggagatcaca gaaggacagg gcctcactga ggtctcggac atggacccctt tgatagtggc    50100 aggagccagg ctgggcaaga ggcggccaca gtcacctcag cagtgccatc accaccgcca    50160
ttcagccctt ccctgagccg ggcgcgcccc tggctctggc cccagtgtcc cagttacagc    50220
tcacaggagc ttgtggtgcc cagcggctgc ttctgattga gagtcgaggt cggaggcttt    50280 ggggaggctga gaggctgctc ggtttcacaa ctgctgaggg agacttgggc tccatctcag    50340
gtatgcccca tgtcgccctc aacctccagc caccggtcct ccgtgtcccc catggccagg    50400
cacggcttgc agacatctgt cgttggctcc tctcagccgt cgtgggctga ccctggcacg    50460
tcctcctgtg gctgagccca gtggggacag ctgcttcctt ttattaccct agaactctcg    50520
tctttgatca ggcccctcc cctatgccac acagtccctg tcactcgggt gagcccagta    50580
gtcatgggga aggcctgcgg gttccaaaca tccaaaggct tgcgtgcagc atgacagctt    50640
gaaaccgatg ttttttacct tgatcagatt tcagcttggc gggggctttg ctcagctttc    50700
agtgaggcct gggccgattt cccagcatcc cctcctgagg ccagcctctg tttcctgtga    50760
ttttctgcac aaagtgggag ggaggagtcc taggaaatgg ggggccacct cgaagcctag    50820
gcctcctctg gcttctctgt gccagtgccc ccacgctttg tgtctgtgtc cccagcccat    50880
gggactctgc tattccctga gtgctgccgc atgcccagcc cgcactgagg acgtggagcc    50940
ccgaggggca ggatgcctc catggtcaca cgtaggaagt ggcctccacc ctccgatgat    51000
cctctccctc ctcccttca gcgccctccc cgggggtgtc ctcagccctc ctgcctgtgc    51060
```

```
tttgtcccgt cttctgcagg cgcctgggac gtgctgacag gtcctctgcc ggctcctgcc    51120
ttgctatgcg cacgctggtc accacagagg cctggccctt cttctgtagc agtcccacac    51180
ccgcaacagg tgtggctgct gaccacctgc tttctgcccc tctggtcctg aggagggcgc    51240
agtgggcact caggcgtggc tgagcagatg tgtgttgccg ggaggaggaa ggactgctcc    51300
agtcagggct gaatttccca cccggagcat ttctgctgta tttggtgtag cgcctgctgc    51360
ttaaagctct gattcccagt tggcaccctt tcccttctgc attgaaaaac atacggatgc    51420
atgtcttctt gcagtgaatg tgtattctcc cagcctctct tctgggttgg ggctggaggt    51480
ggagcggcac acaggagccg cagcgatgga ggatgtgcgg gtgcagcacc ccgtacagca    51540
gggatgccaa acccgcgctg agtccctctc aacttctgct ttgaagccca gtcacgccat    51600
tgcctgggtt ttgctgggcg gggctgcgtg tgatgttctc ctctgtccct cccccagagc    51660
cgcccacctg ctccccggac cagtttgcat gtgccacagg ggagatcgac tgtatccccg    51720
gggcctggcg ctgtgacggc tttcccgagt gcgatgacca gagcgacgag gagggctgcc    51780
ccgtgtgctc cgccgcccag ttcccctgcg cgcggggtca gtgtgtggac ctgcgcctgc    51840
gctgcgacgg cgaggcagac tgtcaggacc gctcagacga ggcggactgt gacggtgagg    51900
ccctccccgt caaggctctg ccaagaccct ggccctgccc tccgggatac gagcttgggg    51960
ctgcctccgg cctcacagga gtagggctc tgaaaaccttt gcttgcagg gagattgcca    52020 agtctgtctt ttaggcccaa caaggaaaac tctgcagttc cacccatcct gtcccaccag    52080
gtagtgtggc ttgaaggcag actgtgaggg tctatctcac cttcctgcat taggtcagga    52140
gtttcacaga aacctgaggc acattcaggg gtgggctgca gaggtccatg gctcacaccc    52200
tggaaaatcc gccccaaaa acagtgctg tctccactga ccagtctgtg ggatagtgct    52260
taagcctgag tggtttctat caacatgtag aatcaggagg tataaagaga tttgctcagg    52320
catcctgggc cctctctgac cagcaggatc ttcctttaga tcttgacagt gaaacacatc    52380
tcttctgtgc cccctgtgag ttttctttca ttcattcatt cattcattca ttcattcatt    52440
cattcattcg agacagagtc ttgctctgtc acccaggctg gagtgccctg gtgtaatctc    52500
ggctcactgc aacctctgcc tccagggttc aatcgattct cctgcctcag cctcccgagt    52560
agctgggatg acaggtgcgc accaccatgc ctggctaatt tttgtatttt tagtagagac    52620 agggttttcac catgttggcc aggctggtct cgaactcctg acctcaggtg atccgcccgc    52680
ctcagcctcc caaagtgctg ggattacagg catgagccac cgcgcccggc ctgagttttc    52740
cttttatgaa ggacctgctt ggttggttgc ctgccacatg ttgtcagcac catgggccca    52800
ggactgctga ggagctgttg atgccctcgc tctcccagag ccaccggctc tgttagataa    52860
ttcacatgca gtctggccac tgtcctacgt cctcattcac aaagagcaga catttcgtag    52920
aagatgaggg cctgggagta acctccctgc atgttttttct ataaaggcat agtggttaag    52980
tccttccagc tcattgacca ttggagaatt ttatggaggc tgtagactag gggctggtaa    53040
actaagggcc cagggccaa atccagcctg ccacctactt ttgtaaataa agttttcttg    53100
gtgcacagcc atgcccattc attcatttgc acaatgtctg tggctgcttt catgccaaaa    53160
gcaagagaac tgagtggtta tgctggagac ctacggcctt caaagcccca gacctcacgt    53220
ctggcccttg acagacagag cttccccagc cctgctgcgc atcctggccc agcatgtgct    53280
gtgtgtgtga tttcagcttg caggagccgt ggttaggaat tgtccctgtg ttggtccatt    53340
ttgcattgct atgaaggagc acctgaggcc gggtagatta tgaaggaaag aggtctgtct    53400
```

```
ggctcatggt tctgtaggca gcaccagtat ggcacccgca tctgctcagc ttctagtgag    53460
gtctcaggaa gctttgactc atggtgaaag tcgaagcggg agcaggtgca tcacatggtg    53520
agagagggag caacggagag agagagagag cgcctctccc tcttgccctc accttgagag    53580
gagatgccag gctcctttaa gtaaccagct cccatgtgaa ctcacagtga gagcccattt    53640
gctactgcgg agagggcacc aggcatctgc tcccatgacc caaacactgc ccaccaggcc    53700
ctacctccaa ccttggggtc atattttatt ctgttctatg ctatgctatg ctatgccatg    53760
ccatgccatg ccatgctatt cctattctat tatttgagac agaatctcgc tctgttgccc    53820
aggctggagt gcagtggcat gatcttggct cactgcaacc tccacctccc aggttcaagc    53880
gattctcctg tatcagcctc ccgagtagct gggattacag gcacacacca ccacacccgg    53940 ctaattttg tattttcaat agagatgggg tttcaccatg ttggccaggc tggtctcaaa    54000
ctcctggcct caagtgatcc acctacctcg gcctcccaaa gtgccatgat tacagatgtg    54060
agtcactgcg cccagtgagg gtcacatttc cgttgagatt tggaggggca gacgttgag    54120 ccatctgagc cccctcgtcc cgctctagct tctcctcccg tgtgccccgc ggtgctggtg    54180
gcaggccctt acgccggttc tggctgcatg ctctgttcca gaagctttct tccctgcttg    54240
gttaccagaa aatcatccca tccattacaa ggacagggtc cccttatctc ccattcccag    54300
ggcaggacac cggggcagg gcaggtgggg aactgagcaa gttctctggg ggcaggcgtg    54360
gctatggctc cctctgggtg ggcgtctggg gaggggtgga ggcagccgtc agcgccctgg    54420
cttgctcttc ctccctggcc agagactgtg gccttgtgct gctcccgtgt gggctgcctg    54480
cacctccagt gggttgtgct ccctccctc ccctcccctc aagctctgct gagcaccact    54540
gccttccaca gccccactc tcgggaggcg aggctcctcg tggccattcc tgtccttggc    54600
acccaccccc ccaccaacct ggtagagcct tgggcggggt ctgttactcc ttgcatggcg    54660
tagacctccc cacagtaggc acctgacaca tacctcctgg ggggcaggca ggaggtgcgt    54720
tgaggtctca gccctggcag tccctcccct gcgtggcata ggcctcgcca cagggtcatc    54780
gagggtgggt ggagactgta ctagaccact ccccgctggt cctagaaagg gtcccatctg    54840
tctgctctct gtttggagtc cagaccttgg ttgctgtgcc ctgcatggtg ggctgggggg    54900
caccctccag cctctctgag tgcatggcct tccttgcag ccatctgcct gcccaaccag    54960
ttccggtgtg cgagcggcca gtgtgtcctc atcaaacagc agtgcgactc cttccccgac    55020
tgtatcgacg gctccgacga gctcatgtgt ggtgagccag cttctggcac ggggaagggg    55080
cgtccgggct gggttccccc aggaacgtgg agtttagggg aggagacgtg cctttccagc    55140
ggggctgggg gctgtgtggg agactcaggc ggctgggagg ctccttgcgg gaggcaggga    55200
agcctttccc agggcagcgg ccaggaggac agactgtgag ctgtgggctc ggcggctaca    55260
gagtctgcct cagtgggcgg ggctgatggt gtccaggtgc ctgcagcacg cacccaccca    55320
cgggaccttg ctgagcagcg tctgtcaggc agcaagatta cccgagggct gcagtggtcc    55380
tgttccctgg cagcttactg tctggctgag aggagtgat gttcacatat gcacacatgt    55440
catgtgcaca cacatgtaca tgacaacatc ccacatgctc ctcaaatagc atgacctgta    55500
cagtcacgga tatagggcct aggggatagg aggccaagac agtcaggaa gactttccag    55560 aggcagtggc tcctgaaagg ctgtctgatt caggcaggaa gggagctgag ttcagatagg    55620
aagtagcaat gagtcattgt gtctggggac atggccactc cttcgctgca gagggacctg    55680
ggctgagagc tcctctctta tggctgcagt cgggagagaa gtctgttggg gggagaaggg    55740
ggcttcctca agggactccc tgtgcccttt ggcaccttcg tgccaggtca ggcttgaggc    55800
```

```
ctgaaggcag tggtgggggc caccaagggt cgcctcctct gctgggcaag ttcccagtct    55860
gacgggcctg tgccgtgggc cccagctgtg ggggcgctgt tgatgcgcag ccaggcctcg    55920
ccgccagagc ccgcacgctt ccattccgct gacttcatcg acgccctcag gatcgctggg    55980
ccggccctgt gggagagtga atgtggcttt tgccaaagtt gagtctggag cctggaaact    56040
tccctatggg cagccttgat agtggagtgg cccaaggagc ccacccagcc gaccctgccc    56100
ctcccgtggc tggtgggcgg caccaggggc tgcctggctt tgctcgttca ccaacatcac    56160
ctgggctggc cagggcgcgc tcacttctgc caccaccgag ggccctgggc gaaggagtga    56220
ataccaggct gccttggcag ggatgtgttg agggctgtgg ggagtcggac agcggcgggg    56280
gtcagaggag gaggagggtg caccgtgcag gctgaagggc cacgttaccc tgaggttggc    56340
caggctcccc aggcctagcc tcccagctcc cccactttct ccccaccctc caccagtggc    56400
aaagccagcc ccttcagggc gcacggtgtc tgccccaag gagggcccat tccgttgggg    56460
ttaatgttgg ccacctcttt ctgtttgtct ctggcagaaa tcaccaagcc gccctcagac    56520
gacagcccgg cccacagcag tgccatcggg cccgtcattg gcatcatcct ctctctcttc    56580
gtcatgggtg gtgtctattt tgtgtgccag cgcgtggtgt gccagcgcta tgcgggggcc    56640
aacgggccct tcccgcacga gtatgtcagc gggaccccgc acgtgcccct caatttcata    56700
gccccgggcg gttcccagca tggccccttc acaggtaagg agcctgagat atggaatgat    56760
ctggaggagg caggagagta gtctgggcag ctttggggag tggagcaggg atgtgctacc    56820
ccaggccctc ttgcacatgt ggcagacatt gctaatcgat cacagcattc agcctttccc    56880
actgagcctg tgcttggcat cagaatcctt caacacagag gcctgcatgg ctgtagcaac    56940 ccacccttg gcactgtagg tgtggagaaa gctccttgga cttgaccttc atattctagt    57000
aggacatgtg ctgtgttgtc cacaaatcct catgtaccct agaaatgaat gtggggcgg    57060 ctgggctctc tccagagctg aaggaatcac tctgtaccat acagcagctt tgtcttgagt    57120
gcagctggga tttgtggctg agcagttaca attcctacgt ggcccaggca ccaggaacgc    57180
aggctgtgtt tgtagatggc tgggcagccg caccgcagag ctgcaccatg ctggtttgta    57240
tcacatgggt gaccatggta tgtctaagaa ggtggagtcc ctgtgaggtc tgcaggtgcc    57300
cccacagctc caggccacct tgaggattgc ctctgcctgc ccagccctga gttccctctc    57360
ccctgtcctg tcccactgtc accccaagcc ggcctcattg ggagcctgtt ggatggcagg    57420
gtatagatgt aacctgattc tctctgggga gcggggttat ctggcttctc aagagctcct    57480
aggagcccac agtggtggca ccatcacagt cgcagcagcc cccagagaac gcggccctgt    57540
ctgttcctgg cgtgctctgt gctgccccgc ctgggttccc tgccccagtc gcaggcccct    57600
tggaggaggt accatgtgtc tcccgttca cagatgagcc ccggggagct cactctagta    57660
gtggccagag aggcctgcgg ctcagggagc ggggcacatt tccaacagga cacaccgccc    57720
tggtctgagt ctcgtgggta gtgggagcag aggagagcgc cctatgtctg tggggcggct    57780
tggctgagcc tggaagccac ctgacctccc ccgtcccttc cctgccaggc atcgcatgcg    57840
gaaagtccat gatgagctcc gtgagcctga tggggggccg gggcggggtg ccctctacg    57900 accggaacca cgtcacaggg gcctcgtcca gcagctcgtc cagcacgaag gccacgctgt    57960
acccgccggt gaggggcggg gccggggagg ggcggggcgg gatgggctg tggcccctc    58020 ccaccgtcag tgctgccac cggaggcttc ccgggttcct gggggctgtg ccaccgcctc    58080
tgaggcatgc ttgctttctt ccctttcaa accccttctgc ttccttcttt aatgacattg    58140
```

```
ttgattgtgg ataatctgaa aactacacaa aaatataaag agccaaaatc tcacccaaat   58200
ccacctccta gagtggctgt tgggctccgt cagcatccag gcggccgtct gtgttccgca   58260
cggcccagcc catcgatagc cgcctgcacc aggcctgtct gccctctgtg agcctcccca   58320
cagggttccc tccacaaaca ccctgttctc ccacccaggc tggctgctt cctggaaaac    58380 agctggatgg ttttgtgcat gacagacaaa cacagggtga ttttcgtggc taaaatactc   58440
cctggagctt ttggcagggt gagggctgg ctccagctga gccacgcctt gagtgaaatg     58500
actgtgagga gaataaactg ccgctgccct ccaggatcac tggggctggc tggggagaac   58560
ccccgtttct gggagcacag tcccaggatg ccaaggcgag cttggtgccg agatgtgaac   58620
tcctgagtgt aaacagcggg ggctgacttg acatgctttg tatgcttttc atttgttcct   58680
gcagctgtat gccctaagg tgagtccagc cccttctgc ttcctctggg gcctcgccag      58740
tgagccccac cttgctgggg ctggttcctc ctgcccttct gggtatccct cacatctggg   58800
gtcttgtctt cttgttttct ttttcttttt ttttgagac ggagtttcac ttttgttgcc    58860
caggcttcag tgcaatggtg tgatctctag gctcaccgca acctctgcct cccaggttca   58920
agcagttccc ctgcctcagc ctccctagta gctgggatta caggcatgtg ccaccacgcc   58980
cagctaattt tgtattttta gtagagatgg ggtttctcca tgttggtcag gctgatcttg   59040
aactccctac ctcaggtgat ccgcccacct tggcctccca aagtgctggg attacaggcg   59100
tgagccaccg cacctggcct ttttctttc ttttcttttc tttttctga cagggtct       59160 cgctctgtca cccaggctgg agtgcaatgg tgtcatcatg gctaactgca gcctctacct   59220
tctaggctca agcaatcctc ccatctcagc ccctaagtag ctaggactgc acgcatgcat   59280
ccccatgccc agctaatatt tacatttttt gtagagatga gtttcacta tattgcccag    59340 gctggtctcc aactcctgga ctcgagcgat cctcctgcct cggcctcccc aggtgctggg   59400
attacaggcg tgagccaccg tgcctggcct ggggtattgt cttcttatgg cacctgactg   59460
tggtgggccc tgggaaggaa gtagcagaag agggttcttc ttggtttcct ggacagtaac   59520
tgagtgttct ggaggcccca gggcctggct ttgtttaggg acaaagggaa ctggtaacca   59580
gaagccgaga gtttaaacac ccactgccct tcttccctgc tcctgctgct gcaacccagc   59640
ttaaccagcc aggagtgcta ggaacccaag cagggccccc gagcacacag caggcagctc   59700
acgaattctc ttttcctgtt ctcccttggg agctgggagg atcttaatca ggcaataaga   59760
gatggcactg agcagccagc taatttttta aatcactta ttgtttaacc atatgactca    59820
cccacttaaa aagggtaca gttcagtggg ttttagtgta ttcacagatg tgtgcaaccc    59880
tcaccacagt taattttaga acatttcct gcccctaaaa gaaactctgc atgaagccag    59940 ctgttttaa attagcaaag ttattttgca tcctttaaat atatgttcat ggtacaaaat    60000
tcaaaagata cagaagagtc tgcagtccaa agagactccg ccccatgac gccaagcagg    60060 catccctggg aggcatggcc tcctgcagtg tgtttcttct atgtccccc aggggtcatc     60120 tgtacatatg caagcataca agagcgtgga ctttgttttc caagccagaa gataattgta   60180
gatttatgtg cagttgtgag aaagagcaca gacccattta tcctctgcct ggtttccccc   60240
agtgctgcct gccatcttgc atgacttcca ttcctatcat aagcaagaca ctgataacga   60300
ttctttcacc ttattcagat tgacataagt gttttttgtt tgttcttgag acaaacttcc   60360
tctgtcaccc agtgggagtg cagtggcaca atcacagctc actgcagcct caaactcctg   60420
ggctcaagcg attctcctgc ctcagtcccc tcaagtagct cagatggcag gtgtgcacca   60480
tcatgccagg ctaatttta aatttttgt ggaggtgagg cctcactaaa ttcctgggc     60540
```

```
tagtcttgaa ctcctgagct aaagtgatcc tcctgcctca gcctcccaaa gtggtaggat    60600
tacaggcatg agccactgcg cctgggctga catatgtgtt ttcgtaagcc cgaaagatag    60660
catctgaaga gtcaacattg agccttgcct tttgctgcta acgatgtata aaagctgctg    60720
ttctgagcat ttcggaggct cccagctgcc gtgtgcaccc tgcctagagc tctaccgtaa    60780
cccatctccg ggaggaggtg ctattgtttt cctcattttg caacaaggag gctgaagaac    60840
tgagcatgaa ccactggcct gggtcgttcg gttggtaggc agtggggcca ggccatccaa    60900
ctcacaacca ccttctactc tgcttccccc gcaccctgaa gtttgttctg ttttgaggac    60960
acagccgtca cattcttggt ggctgaacag cactccttgt caggcgtggc tgggccccca    61020
ctggagggca tcatggtcct ctctcctgct gcggttgaac cttggctgtt tcaaccactc    61080
ctgccaagtg gccctctgaa agggacagtc catctttct cagcagaggg ccacactggc    61140
aaaacggtcc ctggcaccct ttctctccac ctgtctaata tagagtaaaa atggtatcat    61200
gttaagatct tcatttatat ttattttatc atgaatgatg taagcatcat tttgtgtgtt    61260
taagaacctt tgggcccagc gtgatggctt gcagctgtaa tctcagcact ttaggaggct    61320
gagatgagcg gatcacttga ggccgggagt ttgagaccag cctggccaac atggagaaac    61380
cccgtctcta gtaaaaattt aaaaattagc cgggtatggt gatcccagct acttgggagt    61440
ctgaagcatg agaattgctt gaacatggga ggcggaggtt gcagtgagcc gagatcgcgc    61500
cattgcactc cagcctgggc gacagagcga gactctgtct caaaaaaaaa aaaaaaaag    61560 aaaagaaaag aaattatcaa tctcctcttt tatggcatat atatatatat atatatatat    61620
atatatatat atatatattt ttttttttg gttatgttca gaaaggcctt ccctgctctg    61680
atcataaaaa acaacttatt ttcacactct ctctcttttt tttttgagac agagttttgc    61740
tcctgttgcc caggctggag tgcagtggcg caatctcagc tcactgtaac ctccgcctcc    61800
cgggttggag tgattctcct gccttacctt cccgagtagc tgggattata ggcatgcacc    61860
accatgcctg gctaattttg tactttagt agagacgggg gtttctccat gttggtcagg    61920
ctggtctcga actcgcgacc tcaggtgatc cacccacctc ggcctcccaa agtgctggga    61980
ttacagacgt gagccaccat gcccagccca cactctcttt cttaacgtcc tcctcctttc    62040
gttttacgtt cacatcttta attcttctgg gatgtaatta gatttgatga gcaaggtggg    62100
catccagctt gtttcttggc tgatggctta tgggtggcgt gaattagtcg ggtctatca    62160 ggaggcagaa actctatgag aatttgaaca gagaaagttc cgtctacagg cttattacca    62220
gggactggaa tagcagaaat tgaacagtga gatgtacaga gaactctaag aatgcaggaa    62280
taggccaggc atggtggctc acacctgtca tcccagcact tgggagacc aaggcgggtg    62340 gatcacctga ggtcaggagt tcgagaccag cctggccaac atagtgaaac cccatctcta    62400
ctaaaaatac aaaaaatta gctgggtgtg gtggcgcatg cctgtaatcc cagctactcg    62460
ggaggctgag gcaggagaat cacttgaacc tgggaggcag aggttgcagt gagccgagat    62520
catgccactg tactccagcc tgggtggaag agcggaactc tgtctgaaaa aaaaaaaaaa    62580
aacaagaagt tcaacttgaa gggaaaaatg ccgtattgtc tttccctttg ttatgtcacc    62640
agggcacagt ccatcccagg ctggcgctga tccacgggct ggagaggggc tgccccagaa    62700
gaggacatgc caggaagggc ttggctggtg ttcaggagcc caggccaggt caggtcaaga    62760
ggtgttgagg ctggacggga gaggccagct aggggctcat gtaggatatg aggggtcggc    62820
ccatttcaac gtggaaactg agctcttctg cttctctttc ttcttcactg cattaagatt    62880
```

```
caataccgct tgggaagcag gtatttccct tcctataaag gatggttggg agcctgagtg    62940
ttgggagaaa gtgtagccgc tgagttacta acaactaggg ctgccgtcaa gcctatgggg    63000
aaagagagaa gaggacattt ggaaggagag agatcaagct gtggcaccct gggagaggac    63060
cacagaaaag aggccagtga gggggttccc cggtggcatc tgaaggtgtg gcccaaccag    63120
gaggtccaga ggctgccagc cgagtggccc aggagaggga acctcacagg ggctgagtgg    63180
gacccaagcc ctatccaccg tcctaaccac ccacatttct cgggaacaag acctcccaca    63240
gtggcctccc cggcagtgga aatagccaaa ctggcaacat ggactttctt caactgcccg    63300
ggcgatgctg cctcagtgcc ccagggcagg caggaagctc ccacacccat tctggaatga    63360
ggggttggag gaaggctgag ctgagcaaag gacccatctc tgctctggtt ggtggggagg    63420
gagcccatta tacaagagac ccctcagggc tcagtgaggg gtgacagaga cttggggagt    63480
agtggctgtc actgcagagg tgagagggtt tggagagaag gtacatgcct ttttggccac    63540
attgagtagc acctggtagc cagttagtaa cgtgtattgg ataaacaaaa gattaaacgg    63600
atgcaaaaaa aaatgttggc tttgcttctt tttacccaaa cctcagttcc ctcaagtaga    63660
ttctgggaac accccctacc tggctggact gttgtgaagt ttaaataagc caggttaact    63720
tcacctcctc ctttaagaca cagctcagac actgcctcct ccaagaagcc cctctggct    63780
tcctgtgtga atatgacggc cctctgggct ctagggtatc ttagaacaat gcttccttat    63840
ggctttggaa ccccgctgtc tcctggattg ggagcaaatg caggggagga gccacacctg    63900
actaatctct gggtctccca gcacataagt ggcataaggg cagggctgtg cccgcttcag    63960
gcacttactg aaggatgtac ttggcagagg gtaggcagcc ggcggatgag cccctcactc    64020
tccccagctg actgcgtggg cgggaaaggc gggttcagga gacccagcct ccctgggctg    64080
tcaccacctc tgcacatcca gccccattga tcaagggttc aattttttggg gtcctgttgg    64140
gaggccagga gactctctcc aggcacttct tccaggtctt tgtgttaggg tgtgtgtgtg    64200
tgtgtgtgtg tgtgtgtgtg tgtgttgttt gttttatttt atttatttat ttatttattt    64260
atttatttat ttatttattt tgagacgcag tctcgctctg ttgcccaggt tggagggtgg    64320
tggcatgatc tcggctcact gcaagctccg cctcccgggt tcacgccatt ctcctgcctc    64380
actcttcctg agtagccgga ttacaggcgc acgcaccatg cctggctaat tattttgttt    64440
ttttagtaga cagggtttt cgccacgttg cccaggctgg tcttgaatcc ctggcctcaa    64500
gcgatccgcc cgcctcagcc tcccaaagtg ctgggattac aggcgtgagc caccgtgccc    64560
gcccagccta ggggtacatg aaacttttt ttttttttt ttgagacaga gtttcactct    64620
gtcctcaggc tggagtgcag tggcgtgatc tcggcgtact gcaatctccg cctcccggtt    64680
caagcgattc tcctgcctca gcctcccgag tagctgggat tgcaggcacg cgccaccaca    64740
cccagctaat ttttgtattt ttagtagaga cgggctttca ccatgtggga caggatggtc    64800
tcgatctcct gacctcgtga tccgcccgcc tcagcctccg aaagtgctgg gattacaggc    64860
ctgagccacc gtgcccagcc atgatgtttt gatacaggca taacgtat aataatcaca    64920
tcagggtaaa tgatgtaacc atcacatcaa gcatttatcc tttgtgttac aaaaaaaaat    64980
ctaattatac tttcctactt attcttttt ttttttttt ttgagacgga gtctccctca    65040
gtcgcccagg ctggagtgca gtggcatgat ctcagttcac tgcaagctct gcctcctagc    65100
tctgcctcct gggttcatgc cattctcctg tctcagcctc gcgagtagct gggactacag    65160
gcgcctgcca ccgtgcccgg ctaatttttt ttttgtatt tttggtagag acagggtttc    65220
accgtgttag ccaggatggt ctcgatctcc tgacctcata atccgcccgt ctcggcctcc    65280
```

-continued

```
caaagtgctg ggattacagg catgagccac cgcccccagc ctatttattc ttaaatgtac   65340
aataaattat tgttgactcc agtcaccctg ctgtgctacc aaatacggat cttcttcatt   65400
ctatctaact gtatttctgt acctgttaac catctctcct ccacctcacc ccccaaaccc   65460
actacccttc tcagcctctg gtaaccatcc ttctactctc tatctctatg agttcaattg   65520
tattaatttt tagctccccg gccgggcacg gtggctcacg cctgtaatcc cagcacttca   65580
ggaggctgag gcaggtggat cacgaggtca ggagtttgag accagcctgg ccaacatggt   65640
ggaaccccat ctctactaaa aacacaaaaa ttagctgggc gtggtggtgg gcgcttgtag   65700
tcccagctac ttgggaggct gaggcaggag aatcgcttga aactgggagg cagaggttgc   65760
agtgagccaa gattgcgcca ctgcactcca gtctgggtga cagagtaaga ttccatcccg   65820
aaaaaaaaaa agtttagctc ccacaaataa gtgagaacac gtgaagtttc tctttctgtg   65880
cctcgcttgt ttcacttaac ataatgacct ccagttccat ccacgttgtt gctttgttat   65940
aaatgacagg atcttggtca ggcgcagtgg ctcatgcctg taatcccagc actttgggag   66000
gctgaggtgg actgatcatg aggtcaagag atcgagacca tcctggctaa cacagtgaaa   66060
ccccgtctct actaaaaata caagaaatta gccgggcgtg gtggtgggca cccatttccg   66120
ccccttctcg ggacgctgat gcacgacata ttacccatcc ccggaagact aatcctcccc   66180
cactctatat tgtacctctt cctttctcct ccacgcgatt ccccgagtaa cccgtcttcc   66240
ctccctcctc ggattacgct caccttttccg cttcaatcac gttgctccgt cccccttcccc   66300 attcgtacca ctcctcactt tcgtcttcct accccccacta tcccttttcg tcctctctat   66360
tccttactta ctcctccccc ttctcttcat acttcattcc ctccgctctt cccactcgcg   66420
ctcccacttt cacctagttg ccctcaccta cgttgccatc tcgcccccttc ttcagctctc   66480 ggcctctcac ccatctgtcc tctctcttac ctctctcctc atctcgctca gacatctctc   66540
tagactatcc ctcactttac cttctcagtc gtcttcttcc tatccttcgt tctccatgat   66600
cttcacgtcg ccatctcttt tcgccccttt catatgtctc tcttcatgtt ctcactatca   66660
ttctcatgat cactatcgtt ctcactactt atcactcccc tctttcttca tcaattcctc   66720
tccgtcattc tcgtctctct cttacaaccg ccttccttgt gctatctaac tcaaccatgc   66780
ctctcctact ctctctctat cgcccctcca tcgcttatgc atcctcttct attgcacacc   66840
cgcccctcca tcgcttatgc atcctcttct attgcacacc gcccctccat cgcttatgca   66900
tcctcttcta ttgcacatcc tcttctattg cac                                66933
```

<210> SEQ ID NO 12
<211> LENGTH: 21
<212> TYPE: DNA
<213> ORGANISM: Artificial Sequence
<220> FEATURE:
<223> OTHER INFORMATION: Artificial sequence is a primer.

<400> SEQUENCE: 12
ctgagcggaa ttcgtgagac c                                             21

<210> SEQ ID NO 13
<211> LENGTH: 23
<212> TYPE: DNA
<213> ORGANISM: Artificial Sequence
<220> FEATURE:
<223> OTHER INFORMATION: Artificial sequence is a primer.

<400> SEQUENCE: 13
ttggtctcac gtattccgct cga                                          23

<210> SEQ ID NO 14
<211> LENGTH: 20
<212> TYPE: DNA
<213> ORGANISM: Artificial Sequence
<220> FEATURE:
<223> OTHER INFORMATION: Artificial sequence is a primer.

<400> SEQUENCE: 14
ctcgagaatt ctggatcctc                                              20

<210> SEQ ID NO 15
<211> LENGTH: 22
<212> TYPE: DNA
<213> ORGANISM: Artificial Sequence
<220> FEATURE:
<223> OTHER INFORMATION: Artificial sequence is a primer.

<400> SEQUENCE: 15
ttgaggatcc agaattctcg ag                                           22

<210> SEQ ID NO 16
<211> LENGTH: 21
<212> TYPE: DNA
<213> ORGANISM: Artificial Sequence
<220> FEATURE:
<223> OTHER INFORMATION: Artificial sequence is a primer.

<400> SEQUENCE: 16
tgtatgcgaa ttcgctgcgc g                                            21

<210> SEQ ID NO 17
<211> LENGTH: 23
<212> TYPE: DNA
<213> ORGANISM: Artificial Sequence
<220> FEATURE:
<223> OTHER INFORMATION: Artificial sequence is a primer.

<400> SEQUENCE: 17
ttcgcgcagc gaattcgcat aca                                          23

<210> SEQ ID NO 18
<211> LENGTH: 21
<212> TYPE: DNA
<213> ORGANISM: Artificial Sequence
<220> FEATURE:
<223> OTHER INFORMATION: Artificial sequence is a primer.

<400> SEQUENCE: 18
gtccactgaa ttctcagtga g                                            21

<210> SEQ ID NO 19
<211> LENGTH: 23
<212> TYPE: DNA
<213> ORGANISM: Artificial Sequence
<220> FEATURE:
<223> OTHER INFORMATION: Artificial sequence is a primer.

<400> SEQUENCE: 19
ttgtcactga gaattcagtg gac                                          23

<210> SEQ ID NO 20
<211> LENGTH: 21
<212> TYPE: DNA
<213> ORGANISM: Artificial Sequence

```
<220> FEATURE:
<223> OTHER INFORMATION: Artificial sequence is a primer.

<400> SEQUENCE: 20
gaatccgaat tcctggtcag c                                         21

<210> SEQ ID NO 21
<211> LENGTH: 23
<212> TYPE: DNA
<213> ORGANISM: Artificial Sequence
<220> FEATURE:
<223> OTHER INFORMATION: Artificial sequence is a primer.

<400> SEQUENCE: 21
ttgctgacca ggaattcgga ttc                                       23

<210> SEQ ID NO 22
<211> LENGTH: 33
<212> TYPE: DNA
<213> ORGANISM: Artificial Sequence
<220> FEATURE:
<223> OTHER INFORMATION: Artificial sequence is a primer.

<400> SEQUENCE: 22
cuacuacuac uactgagcgg aattcgtgag acc                            33

<210> SEQ ID NO 23
<211> LENGTH: 32
<212> TYPE: DNA
<213> ORGANISM: Artificial Sequence
<220> FEATURE:
<223> OTHER INFORMATION: Artificial sequence is a primer.

<400> SEQUENCE: 23
cuacuacuac uactcgagaa ttctggatcc tc                             32

<210> SEQ ID NO 24
<211> LENGTH: 33
<212> TYPE: DNA
<213> ORGANISM: Artificial Sequence
<220> FEATURE:
<223> OTHER INFORMATION: Artificial sequence is a primer.

<400> SEQUENCE: 24
cuacuacuac uatgtatgcg aattcgctgc gcg                            33

<210> SEQ ID NO 25
<211> LENGTH: 33
<212> TYPE: DNA
<213> ORGANISM: Artificial Sequence
<220> FEATURE:
<223> OTHER INFORMATION: Artificial sequence is a primer.

<400> SEQUENCE: 25
cuacuacuac uagtccactg aattctcagt gag                            33

<210> SEQ ID NO 26
<211> LENGTH: 33
<212> TYPE: DNA
<213> ORGANISM: Artificial Sequence
<220> FEATURE:
<223> OTHER INFORMATION: Artificial sequence is a primer.

<400> SEQUENCE: 26
cuacuacuac uagaatccga attcctggtc agc                            33
```

<210> SEQ ID NO 27
<211> LENGTH: 45
<212> TYPE: DNA
<213> ORGANISM: Artificial Sequence
<220> FEATURE:
<223> OTHER INFORMATION: Artificial sequence is a primer.

<400> SEQUENCE: 27
aactggaaga attcgcggcc gcaggaattt tttttttttt ttttt        45

<210> SEQ ID NO 28
<211> LENGTH: 13
<212> TYPE: DNA
<213> ORGANISM: Artificial Sequence
<220> FEATURE:
<223> OTHER INFORMATION: Artificial sequence is a primer.

<400> SEQUENCE: 28
aattcggcac gag        13

<210> SEQ ID NO 29
<211> LENGTH: 9
<212> TYPE: DNA
<213> ORGANISM: Artificial Sequence
<220> FEATURE:
<223> OTHER INFORMATION: Artificial sequence is a primer.

<400> SEQUENCE: 29 ctcgtgccg        9

<210> SEQ ID NO 30
<211> LENGTH: 14
<212> TYPE: DNA
<213> ORGANISM: Artificial Sequence
<220> FEATURE:
<223> OTHER INFORMATION: Artificial sequence is a primer.

<400> SEQUENCE: 30
gtacgacggc cagt        14

<210> SEQ ID NO 31
<211> LENGTH: 16
<212> TYPE: DNA
<213> ORGANISM: Artificial Sequence
<220> FEATURE:
<223> OTHER INFORMATION: Artificial sequence is a primer.

<400> SEQUENCE: 31
aacagctatg accatg        16

<210> SEQ ID NO 32
<211> LENGTH: 18
<212> TYPE: DNA
<213> ORGANISM: Artificial Sequence
<220> FEATURE:
<223> OTHER INFORMATION: Artificial sequence is a primer.

<400> SEQUENCE: 32
ccaagttctg agaagtcc        18

<210> SEQ ID NO 33
<211> LENGTH: 20
<212> TYPE: DNA
<213> ORGANISM: Artificial Sequence
<220> FEATURE:
<223> OTHER INFORMATION: Artificial sequence is a primer.

```
<400> SEQUENCE: 33
aatacctgaa accatacctg                                              20

<210> SEQ ID NO 34
<211> LENGTH: 57
<212> TYPE: DNA
<213> ORGANISM: Artificial Sequence
<220> FEATURE:
<223> OTHER INFORMATION: Artificial sequence is a primer.

<400> SEQUENCE: 34
agctgctcgt agctgtctct ccctggatca cgggtacatg tactggacag actgggt    57

<210> SEQ ID NO 35
<211> LENGTH: 56
<212> TYPE: DNA
<213> ORGANISM: Artificial Sequence
<220> FEATURE:
<223> OTHER INFORMATION: Artificial sequence is a primer.

<400> SEQUENCE: 35
tgagacgccc ggattgagcg ggcagggata gcttattccc tgtgccgcat tacggc     56

<210> SEQ ID NO 36
<211> LENGTH: 27
<212> TYPE: DNA
<213> ORGANISM: Artificial Sequence
<220> FEATURE:
<223> OTHER INFORMATION: Artificial sequence is a primer.

<400> SEQUENCE: 36
agctgctcgt agctgtctct ccctgga                                      27

<210> SEQ ID NO 37
<211> LENGTH: 27
<212> TYPE: DNA
<213> ORGANISM: Artificial Sequence
<220> FEATURE:
<223> OTHER INFORMATION: Artificial sequence is a primer.

<400> SEQUENCE: 37
gccgtaatgc ggcacaggga ataagct                                      27

<210> SEQ ID NO 38
<211> LENGTH: 20
<212> TYPE: DNA
<213> ORGANISM: Artificial Sequence
<220> FEATURE:
<223> OTHER INFORMATION: Artificial sequence is a primer.

<400> SEQUENCE: 38
gagaggctat atccctgggc                                              20

<210> SEQ ID NO 39
<211> LENGTH: 20
<212> TYPE: DNA
<213> ORGANISM: Artificial Sequence
<220> FEATURE:
<223> OTHER INFORMATION: Artificial sequence is a primer.

<400> SEQUENCE: 39
acagcacgtg tttaaagggg                                              20

<210> SEQ ID NO 40
```

```
<211> LENGTH: 163
<212> TYPE: DNA
<213> ORGANISM: Homo sapiens

<400> SEQUENCE: 40
actaaagcgc cgccgccgcg ccatggagcc cgagtgagct cggcgcgggc ccgtccggcc      60
gccggacaac atggaggcag ctccgcccgg gccgccgtgg ccgctgctgc tgctgctgct     120
gctgctgctg cgctgtgcg gctgcccggc ccccgccgcg gcc                        163

<210> SEQ ID NO 41
<211> LENGTH: 419
<212> TYPE: DNA
<213> ORGANISM: Homo sapiens

<400> SEQUENCE: 41
gccccacagc ctcgccgctc ctgctatttg ccaaccgccg ggacgtacgg ctggtggacg      60
ccggcggagt caagctggag tccaccatcg tggtcagcgg cctggaggat gcggccgcag     120
tggacttcca gttttccaag ggagccgtgt actggacaga cgtgagcgag gaggccatca     180
agcagaccta cctgaaccag acgggggccg ccgtgcagaa cgtggtcatc tccggcctgg     240
tctctcccga cggcctcgcc tgcgactggg tgggcaagaa gctgtactgg acggactcag     300
agaccaaccg catcgaggtg gccaacctca atggcacatc ccggaaggtg ctcttctggc     360
aggaccttga ccagccgagg gccatcgcct ggaccccgc tcacgggtaa accctgctg      419

<210> SEQ ID NO 42
<211> LENGTH: 221
<212> TYPE: DNA
<213> ORGANISM: Homo sapiens

<400> SEQUENCE: 42
ccccgtcaca ggtacatgta ctggacagac tggggtgaga cgccccggat tgagcgggca      60
gggatggatg gcagcacccg gaagatcatt gtggactcgg acatttactg cccaatgga     120 ctgaccatcg acctggagga gcagaagctc tactgggctg acgccaagct cagcttcatc     180
caccgtgcca acctggacgg ctcgttccgg taggtaccca c                         221

<210> SEQ ID NO 43
<211> LENGTH: 221
<212> TYPE: DNA
<213> ORGANISM: Homo sapiens

<400> SEQUENCE: 43
tccctgactg caggcagaag gtggtggagg gcagcctgac gcacccttc gccctgacgc      60 tctccgggga cactctgtac tggacagact ggcagacccg ctccatccat gcctgcaaca     120
agcgcactgg ggggaagagg aaggagatcc tgagtgccct atactcaccc atggacatcc     180
aggtgctgag ccaggagcgg cagccttttt gtgagtgccg g                         221

<210> SEQ ID NO 44
<211> LENGTH: 156
<212> TYPE: DNA
<213> ORGANISM: Homo sapiens

<400> SEQUENCE: 44
tttctcagtc cacactcgct gtgaggagga caatggcggc tggtcccacc tgtgcctgct      60
gtccccaagc gagccttttt acacatgcgc ctgcccacg ggtgtgcaga tgcaggacaa     120
cggcaggacg tgtaaggcag gtgaggcggt gggacg                              156
```

<210> SEQ ID NO 45
<211> LENGTH: 416
<212> TYPE: DNA
<213> ORGANISM: Homo sapiens

<400> SEQUENCE: 45

```
ctccacagga gccgaggagg tgctgctgct ggcccggcgg acggacctac ggaggatctc      60
gctggacacg ccggacttca ccgacatcgt gctgcaggtg gacgacatcc ggcacgccat     120
tgccatcgac tacgacccgc tagagggcta tgtctactgg acagatgacg aggtgcgggc     180
catccgcagg gcgtacctgg acgggtctgg ggcgcagacg ctggtcaaca ccgagatcaa     240
cgaccccgat ggcatcgcgg tcgactgggg ggcccgaaac ctctactgga ccgacacggg     300
cacggaccgc atcgaggtga cgcgcctcaa cggcacctcc cgcaagatcc tggtgtcgga     360
ggacctggac gagccccgag ccatcgcact gcaccccgtg atggggtaag acgggc         416
```

<210> SEQ ID NO 46
<211> LENGTH: 198
<212> TYPE: DNA
<213> ORGANISM: Homo sapiens

<400> SEQUENCE: 46

```
ttcttctcca gcctcatgta ctggacagac tggggagaga accctaaaat cgagtgtgcc      60
aacttggatg ggcaggagcg gcgtgtgctg gtcaatgcct ccctcgggtg gcccaacggc     120
ctggccctgg acctgcagga ggggaagctc tactggggag acgccaagac agacaagatc     180
gaggtgaggc tcctgtgg                                                   198
```

<210> SEQ ID NO 47
<211> LENGTH: 244
<212> TYPE: DNA
<213> ORGANISM: Homo sapiens

<400> SEQUENCE: 47

```
ccgtcctgca ggtgatcaat gttgatggga cgaagaggcg gaccctcctg gaggacaagc      60
tcccgcacat tttcggggttc acgctgctgg gggacttcat ctactggact gactggcagc    120
gccgcagcat cgagcgggtg cacaaggtca aggccagccg ggacgtcatc attgaccagc    180
tgcccgacct gatgggctc aaagctgtga atgtggccaa ggtcgtcggt gagtccgggg     240
ggtc                                                                  244
```

<210> SEQ ID NO 48
<211> LENGTH: 313
<212> TYPE: DNA
<213> ORGANISM: Homo sapiens

<400> SEQUENCE: 48

```
gttcgcttcc aggaaccaac ccgtgtgcgg acaggaacgg ggggtgcagc cacctgtgct      60
tctgcacacc ccacgcaacc cggtgtggct gccccatcgg cctggagctg ctgagtgaca     120
tgaagacctg catcgtgcct gaggcctttt tggtcttcac cagcagagcc gccatccaca     180
ggatctccct cgagaccaat aacaacgacg tggccatccc gctcacgggc gtcaaggagg     240
cctcagccct ggactttgat gtgtccaaca accacatcta ctggacagac gtcagcctga     300
aggtagcgtg ggc                                                        313
```

<210> SEQ ID NO 49

<211> LENGTH: 255
<212> TYPE: DNA
<213> ORGANISM: Homo sapiens

<400> SEQUENCE: 49

| | | | | |
|---|---|---|---|---|
| cctgctgcca | gaccatcagc | cgcgccttca | tgaacgggag | ctcggtggag | cacgtggtgg | 60 |
| agtttggcct | tgactacccc | gagggcatgg | ccgttgactg | gatgggcaag | aacctctact | 120 |
| gggccgacac | tgggaccaac | agaatcgaag | tggcgcggct | ggacgggcag | ttccggcaag | 180 |
| tcctcgtgtg | gagggacttg | gacaacccga | ggtcgctggc | cctggatccc | accaaggggt | 240 |
| aagtgtttgc | ctgtc | | | | | 255 |

<210> SEQ ID NO 50
<211> LENGTH: 210
<212> TYPE: DNA
<213> ORGANISM: Homo sapiens

<400> SEQUENCE: 50

| | | | | | | |
|---|---|---|---|---|---|---|
| gtgccttcca | gctacatcta | ctggaccgag | tggggcggca | agccgaggat | cgtgcgggcc | 60 |
| ttcatggacg | ggaccaactg | catgacgctg | gtggacaagg | tgggccgggc | caacgacctc | 120 |
| accattgact | acgctgacca | gcgcctctac | tggaccgacc | tggacaccaa | catgatcgag | 180 |
| tcgtccaaca | tgctgggtga | gggccgggct | | | | 210 |

<210> SEQ ID NO 51
<211> LENGTH: 352
<212> TYPE: DNA
<213> ORGANISM: Homo sapiens

<400> SEQUENCE: 51

| | | | | | | |
|---|---|---|---|---|---|---|
| gtgttcatgc | aggtcaggag | cgggtcgtga | ttgccgacga | tctcccgcac | ccgttcggtc | 60 |
| tgacgcagta | cagcgattat | atctactgga | cagactggaa | tctgcacagc | attgagcggg | 120 |
| ccgacaagac | tagcggccgg | aaccgcaccc | tcatccaggg | ccacctggac | ttcgtgatgg | 180 |
| acatcctggt | gttccactcc | tcccgccagg | atggcctcaa | tgactgtatg | cacaacaacg | 240 |
| ggcagtgtgg | gcagctgtgc | cttgccatcc | ccggcgccca | ccgctgcggc | tgcgcctcac | 300 |
| actacaccct | ggaccccagc | agccgcaact | gcagccgtaa | gtgcctcatg | gt | 352 |

<210> SEQ ID NO 52
<211> LENGTH: 225
<212> TYPE: DNA
<213> ORGANISM: Homo sapiens

<400> SEQUENCE: 52

| | | | | | | |
|---|---|---|---|---|---|---|
| gcctcctcta | cgcccaccac | cttcttgctg | ttcagccaga | aatctgccat | cagtcggatg | 60 |
| atcccggacg | accagcacag | cccggatctc | atcctgcccc | tgcatggact | gaggaacgtc | 120 |
| aaagccatcg | actatgaccc | actggacaag | ttcatctact | gggtggatgg | cgccagaac | 180 |
| atcaagcgag | ccaaggacga | cgggacccag | gcaggtgccc | tgtgg | | 225 |

<210> SEQ ID NO 53
<211> LENGTH: 235
<212> TYPE: DNA
<213> ORGANISM: Homo sapiens

<400> SEQUENCE: 53

| | | | | | | |
|---|---|---|---|---|---|---|
| ctttgtctta | cagcccttttg | ttttgacctc | tctgagccaa | ggccaaaacc | cagacaggca | 60 |
| gccccacgac | ctcagcatcg | acatctacag | ccggacactg | ttctggacgt | gcgaggccac | 120 |

```
caataccatc aacgtccaca ggctgagcgg ggaagccatg ggggtggtgc tgcgtgggga      180
ccgcgacaag cccagggcca tcgtcgtcaa cgcggagcga gggtaggagg ccaac           235

<210> SEQ ID NO 54
<211> LENGTH: 218
<212> TYPE: DNA
<213> ORGANISM: Homo sapiens

<400> SEQUENCE: 54
ccaccctccc gcaggtacct gtacttcacc aacatgcagg accgggcagc caagatcgaa      60
cgcgcagccc tggacggcac cgagcgcgag gtcctcttca ccaccggcct catccgccct     120
gtggccctgg tggtggacaa cacactgggc aagctgttct gggtggacgc ggacctgaag     180
cgcattgaga gctgtgacct gtcaggtacg cgccccgg                             218

<210> SEQ ID NO 55
<211> LENGTH: 234
<212> TYPE: DNA
<213> ORGANISM: Homo sapiens

<400> SEQUENCE: 55
ggctgcttgc aggggccaac cgcctgaccc tggaggacgc caacatcgtg cagcctctgg      60
gcctgaccat ccttggcaag catctctact ggatcgaccg ccagcagcag atgatcgagc     120
gtgtggagaa gaccaccggg gacaagcgga ctcgcatcca gggccgtgtc gcccacctca     180
ctggcatcca tgcagtggag gaagtcagcc tggaggagtt ctgtacgtgg gggc           234

<210> SEQ ID NO 56
<211> LENGTH: 157
<212> TYPE: DNA
<213> ORGANISM: Homo sapiens

<400> SEQUENCE: 56
ttgtctttgc agcagcccac ccatgtgccc gtgacaatgg tggctgctcc cacatctgta      60
ttgccaaggg tgatgggaca ccacggtgct catgcccagt ccacctcgtg ctcctgcaga     120
acctgctgac ctgtggaggt aggtgtgacc taggtgc                             157

<210> SEQ ID NO 57
<211> LENGTH: 272
<212> TYPE: DNA
<213> ORGANISM: Homo sapiens

<400> SEQUENCE: 57
gttctcctct gtccctcccc cagagccgcc cacctgctcc ccggaccagt ttgcatgtgc      60
cacaggggag atcgactgta tccccggggc ctggcgctgt gacggctttc ccgagtgcga     120
tgaccagagc gacgaggagg gctgccccgt gtgctccgcc gcccagttcc cctgcgcgcg     180
gggtcagtgt gtggacctgc gcctgcgctg cgacggcgag gcagactgtc aggaccgctc     240
agacgaggtg gactgtgacg gtgaggccct cc                                  272

<210> SEQ ID NO 58
<211> LENGTH: 134
<212> TYPE: DNA
<213> ORGANISM: Homo sapiens

<400> SEQUENCE: 58
tctccttgca gccatctgcc tgcccaacca gttccggtgt gcgagcggcc agtgtgtcct      60
```

-continued

| | |
|---|---|
| catcaaacag cagtgcgact ccttccccga ctgtatcgac ggctccgacg agctcatgtg | 120 |
| tggtgagcca gctt | 134 |

<210> SEQ ID NO 59
<211> LENGTH: 274
<212> TYPE: DNA
<213> ORGANISM: Homo sapiens

<400> SEQUENCE: 59

| | |
|---|---|
| gtttgtctct ggcagaaatc accaagccgc cctcagacga cagcccggcc cacagcagtg | 60 |
| ccatcgggcc cgtcattggc atcatcctct ctctcttcgt catgggtggt gtctattttg | 120 |
| tgtgccagcg cgtggtgtgc cagcgctatg cgggggccaa cgggcccttc ccgcacgagt | 180 |
| atgtcagcgg gaccccgcac gtgccnctca atttcatagc cccgggcggt tcccagcatg | 240 |
| gccccttcac aggtaaggag cctgagatat ggaa | 274 |

<210> SEQ ID NO 60
<211> LENGTH: 164
<212> TYPE: DNA
<213> ORGANISM: Homo sapiens

<400> SEQUENCE: 60

| | |
|---|---|
| cttccctgcc aggcatcgca tgcggaaagt ccatgatgag ctccgtgagc ctgatggggg | 60 |
| gccggggcgg ggtgcccctc tacgaccgga accacgtcac aggggcctcg tccagcagct | 120 |
| cgtccagcac gaaggccacg ctgtacccgc cggtgagggg cggg | 164 |

<210> SEQ ID NO 61
<211> LENGTH: 130
<212> TYPE: DNA
<213> ORGANISM: Homo sapiens

<400> SEQUENCE: 61

| | |
|---|---|
| ttggctctcc tcagatcctg aacccgccgc cctccccggc cacggacccc tccctgtaca | 60 |
| acatggacat gttctactct tcaaacattc cggccactgc gagaccgtac aggtaggaca | 120 |
| tccccctgcag | 130 |

<210> SEQ ID NO 62
<211> LENGTH: 496
<212> TYPE: DNA
<213> ORGANISM: Homo sapiens

<400> SEQUENCE: 62

| | |
|---|---|
| tcaaacattc cggccactgc gagaccgtac aggccctaca tcattcgagg aatggcgccc | 60 |
| ccgacgacgc cctgcagcac cgacgtgtgt gacagcgact acagcgccag ccgctggaag | 120 |
| gccagcaagt actacctgga tttgaactcg gactcagacc cctatccacc cccacccacg | 180 |
| ccccacagcc agtacctgtc ggcggaggac agctgcccgc cctcgcccgc caccgagagg | 240 |
| agctacttcc atctcttccc gcccccctccg tccccctgca cggactcatc ctgacctcgg | 300 |
| ccgggccact ctggcttctc tgtgcccctg taaatagttt taaatatgaa caagaaaaa | 360 |
| aatatatttt atgatttaaa aaataaatat aattgggatt ttaaaaacat gagaaatgtg | 420 |
| aactgtgatg gggtgggcag ggctgggaga actttgtaca gtggagaaat atttataaac | 480 |
| ttaattttgt aaaaca | 496 |

<210> SEQ ID NO 63
<211> LENGTH: 22

```
<212> TYPE: DNA
<213> ORGANISM: Artificial Sequence
<220> FEATURE:
<223> OTHER INFORMATION: Artificial Sequence is a primer.

<400> SEQUENCE: 63
ttttgggtac acaattcagt cg                                              22

<210> SEQ ID NO 64
<211> LENGTH: 20
<212> TYPE: DNA
<213> ORGANISM: Artificial Sequence
<220> FEATURE:
<223> OTHER INFORMATION: Artificial Sequence is a primer.

<400> SEQUENCE: 64
aaaactgtgg gtgcttctgg                                                 20

<210> SEQ ID NO 65
<211> LENGTH: 21
<212> TYPE: DNA
<213> ORGANISM: Artificial Sequence
<220> FEATURE:
<223> OTHER INFORMATION: Artificial Sequence is a primer.

<400> SEQUENCE: 65
gtgattgagc caatcctgag a                                               21

<210> SEQ ID NO 66
<211> LENGTH: 21
<212> TYPE: DNA
<213> ORGANISM: Artificial Sequence
<220> FEATURE:
<223> OTHER INFORMATION: Artificial Sequence is a primer.

<400> SEQUENCE: 66
tgagccaaat aaacccttc t                                                21

<210> SEQ ID NO 67
<211> LENGTH: 20
<212> TYPE: DNA
<213> ORGANISM: Homo sapiens

<400> SEQUENCE: 67
ctggactacg tggccttctc                                                 20

<210> SEQ ID NO 68
<211> LENGTH: 19
<212> TYPE: DNA
<213> ORGANISM: Homo sapiens

<400> SEQUENCE: 68
ttcagaagca cttggctgg                                                  19

<210> SEQ ID NO 69
<211> LENGTH: 20
<212> TYPE: DNA
<213> ORGANISM: Homo sapiens

<400> SEQUENCE: 69
ctcagtgcca tgaagatgga                                                 20

<210> SEQ ID NO 70
<211> LENGTH: 21
<212> TYPE: DNA
```

```
<213> ORGANISM: Homo sapiens

<400> SEQUENCE: 70
caagatcact cgatctccag g                                      21

<210> SEQ ID NO 71
<211> LENGTH: 20
<212> TYPE: DNA
<213> ORGANISM: Homo sapiens

<400> SEQUENCE: 71
gtttcaggag actcagagtc                                        20

<210> SEQ ID NO 72
<211> LENGTH: 20
<212> TYPE: DNA
<213> ORGANISM: Homo sapiens

<400> SEQUENCE: 72
ttctgcaggt tgctgttgag                                        20

<210> SEQ ID NO 73
<211> LENGTH: 20
<212> TYPE: DNA
<213> ORGANISM: Homo sapiens

<400> SEQUENCE: 73
ttattgtgat ttcccgtggc                                        20

<210> SEQ ID NO 74
<211> LENGTH: 21
<212> TYPE: DNA
<213> ORGANISM: Homo sapiens

<400> SEQUENCE: 74
gccctctgtc ctgacttcag g                                      21

<210> SEQ ID NO 75
<211> LENGTH: 20
<212> TYPE: DNA
<213> ORGANISM: Homo sapiens

<400> SEQUENCE: 75
gagaaagaaa taagggggacc                                       20

<210> SEQ ID NO 76
<211> LENGTH: 20
<212> TYPE: DNA
<213> ORGANISM: Homo sapiens

<400> SEQUENCE: 76
tgctttgtaa agcactgaga                                        20

<210> SEQ ID NO 77
<211> LENGTH: 24
<212> TYPE: DNA
<213> ORGANISM: Homo sapiens

<400> SEQUENCE: 77
gaagtacggg cagttcagtg gcct                                   24

<210> SEQ ID NO 78
<211> LENGTH: 25
```

<212> TYPE: DNA
<213> ORGANISM: Homo sapiens

<400> SEQUENCE: 78
atacaccaag gtccatgttc cccgt                                    25

<210> SEQ ID NO 79
<211> LENGTH: 25
<212> TYPE: DNA
<213> ORGANISM: Homo sapiens

<400> SEQUENCE: 79
agcctgggcc acagcgtgag actac                                    25

<210> SEQ ID NO 80
<211> LENGTH: 25
<212> TYPE: DNA
<213> ORGANISM: Homo sapiens

<400> SEQUENCE: 80
tcccggagct tgcacacccg cttca                                    25

<210> SEQ ID NO 81
<211> LENGTH: 20
<212> TYPE: DNA
<213> ORGANISM: Homo sapiens

<400> SEQUENCE: 81
catgtgccca cctcattcat                                          20

<210> SEQ ID NO 82
<211> LENGTH: 20
<212> TYPE: DNA
<213> ORGANISM: Homo sapiens

<400> SEQUENCE: 82
caagattctg tagcttctgg                                          20

<210> SEQ ID NO 83
<211> LENGTH: 20
<212> TYPE: DNA
<213> ORGANISM: Homo sapiens

<400> SEQUENCE: 83
cagagaagtc aagggacttg                                          20

<210> SEQ ID NO 84
<211> LENGTH: 20
<212> TYPE: DNA
<213> ORGANISM: Homo sapiens

<400> SEQUENCE: 84
atcctctcac atcccacact                                          20

<210> SEQ ID NO 85
<211> LENGTH: 20
<212> TYPE: DNA
<213> ORGANISM: Homo sapiens

<400> SEQUENCE: 85
caaggctaaa agacgaaaaa                                          20

<210> SEQ ID NO 86

-continued

```
<211> LENGTH: 20
<212> TYPE: DNA
<213> ORGANISM: Homo sapiens

<400> SEQUENCE: 86
tcaggagcat ttcatctttt                                              20

<210> SEQ ID NO 87
<211> LENGTH: 19
<212> TYPE: DNA
<213> ORGANISM: Homo sapiens

<400> SEQUENCE: 87
aagtcgaggc tgcaaggag                                               19

<210> SEQ ID NO 88
<211> LENGTH: 20
<212> TYPE: DNA
<213> ORGANISM: Homo sapiens

<400> SEQUENCE: 88
gccctgtgtt cctttcagta                                              20

<210> SEQ ID NO 89
<211> LENGTH: 19
<212> TYPE: DNA
<213> ORGANISM: Homo sapiens

<400> SEQUENCE: 89
aaggtgtgag gatcactgg                                               19

<210> SEQ ID NO 90
<211> LENGTH: 17
<212> TYPE: DNA
<213> ORGANISM: Homo sapiens

<400> SEQUENCE: 90
agctcatggg ggctatt                                                 17

<210> SEQ ID NO 91
<211> LENGTH: 20
<212> TYPE: DNA
<213> ORGANISM: Homo sapiens

<400> SEQUENCE: 91
gcttctccga gtgtatcaac                                              20

<210> SEQ ID NO 92
<211> LENGTH: 20
<212> TYPE: DNA
<213> ORGANISM: Homo sapiens

<400> SEQUENCE: 92
atggcagagg acttagaaca                                              20

<210> SEQ ID NO 93
<211> LENGTH: 24
<212> TYPE: DNA
<213> ORGANISM: Homo sapiens

<400> SEQUENCE: 93
gatcagcgaa cttcctctcg gctc                                         24
```

```
<210> SEQ ID NO 94
<211> LENGTH: 24
<212> TYPE: DNA
<213> ORGANISM: Homo sapiens

<400> SEQUENCE: 94
tccacattga ggactgtggg aacg                                    24

<210> SEQ ID NO 95
<211> LENGTH: 20
<212> TYPE: DNA
<213> ORGANISM: Homo sapiens

<400> SEQUENCE: 95
gctaatcaca gtctaaccga                                         20

<210> SEQ ID NO 96
<211> LENGTH: 19
<212> TYPE: DNA
<213> ORGANISM: Homo sapiens

<400> SEQUENCE: 96
ttgcactgtc ttggatgca                                          19

<210> SEQ ID NO 97
<211> LENGTH: 25
<212> TYPE: DNA
<213> ORGANISM: Homo sapiens

<400> SEQUENCE: 97
gcacagctgt agtggggttc taggc                                   25

<210> SEQ ID NO 98
<211> LENGTH: 25
<212> TYPE: DNA
<213> ORGANISM: Homo sapiens

<400> SEQUENCE: 98
caggcgcaaa ggacatgcac acggc                                   25

<210> SEQ ID NO 99
<211> LENGTH: 25
<212> TYPE: DNA
<213> ORGANISM: Homo sapiens

<400> SEQUENCE: 99
caccgatgag tgcacgttca aggag                                   25

<210> SEQ ID NO 100
<211> LENGTH: 25
<212> TYPE: DNA
<213> ORGANISM: Homo sapiens

<400> SEQUENCE: 100
cagacagaga tgctccacgc catac                                   25

<210> SEQ ID NO 101
<211> LENGTH: 19
<212> TYPE: DNA
<213> ORGANISM: Homo sapiens

<400> SEQUENCE: 101
tttctgggtg tgtctgaat                                          19
```

```
<210> SEQ ID NO 102
<211> LENGTH: 20
<212> TYPE: DNA
<213> ORGANISM: Homo sapiens

<400> SEQUENCE: 102
acacagttgc tctaaagggt                                               20

<210> SEQ ID NO 103
<211> LENGTH: 20
<212> TYPE: DNA
<213> ORGANISM: Homo sapiens

<400> SEQUENCE: 103
catttgggaa atccagaaga                                               20

<210> SEQ ID NO 104
<211> LENGTH: 25
<212> TYPE: DNA
<213> ORGANISM: Homo sapiens

<400> SEQUENCE: 104
taggtgtctt attttttgtt gcttc                                         25

<210> SEQ ID NO 105
<211> LENGTH: 25
<212> TYPE: DNA
<213> ORGANISM: Homo sapiens

<400> SEQUENCE: 105
gacataccat gaacactata agagg                                         25

<210> SEQ ID NO 106
<211> LENGTH: 20
<212> TYPE: DNA
<213> ORGANISM: Homo sapiens

<400> SEQUENCE: 106
caacccatac cagggataag                                               20

<210> SEQ ID NO 107
<211> LENGTH: 21
<212> TYPE: DNA
<213> ORGANISM: Homo sapiens

<400> SEQUENCE: 107
gaacaagagg ggtaagttgg c                                             21

<210> SEQ ID NO 108
<211> LENGTH: 22
<212> TYPE: DNA
<213> ORGANISM: Homo sapiens

<400> SEQUENCE: 108
tgaggacaca gatactgatg gg                                            22

<210> SEQ ID NO 109
<211> LENGTH: 25
<212> TYPE: DNA
<213> ORGANISM: Homo sapiens

<400> SEQUENCE: 109
gaagtgttcc ctcttaaatt ctttg                                         25
```

<210> SEQ ID NO 110
<211> LENGTH: 25
<212> TYPE: DNA
<213> ORGANISM: Homo sapiens

<400> SEQUENCE: 110
gaactatatt gtagttagtg aggag                                  25

<210> SEQ ID NO 111
<211> LENGTH: 18
<212> TYPE: DNA
<213> ORGANISM: Homo sapiens

<400> SEQUENCE: 111
cctgtaaccc ccagtccc                                          18

<210> SEQ ID NO 112
<211> LENGTH: 22
<212> TYPE: DNA
<213> ORGANISM: Homo sapiens

<400> SEQUENCE: 112
tcttgcttcc taagtttctc gg                                     22

<210> SEQ ID NO 113
<211> LENGTH: 21
<212> TYPE: DNA
<213> ORGANISM: Homo sapiens

<400> SEQUENCE: 113
actccatcca cctcatcact g                                      21

<210> SEQ ID NO 114
<211> LENGTH: 20
<212> TYPE: DNA
<213> ORGANISM: Homo sapiens

<400> SEQUENCE: 114
tgctgtttgc ctcatctgac                                        20

<210> SEQ ID NO 115
<211> LENGTH: 20
<212> TYPE: DNA
<213> ORGANISM: Homo sapiens

<400> SEQUENCE: 115
gtggacaggc atagctgagg                                        20

<210> SEQ ID NO 116
<211> LENGTH: 21
<212> TYPE: DNA
<213> ORGANISM: Homo sapiens

<400> SEQUENCE: 116
tgttcactct tctgcctgca g                                      21

<210> SEQ ID NO 117
<211> LENGTH: 20
<212> TYPE: DNA
<213> ORGANISM: Homo sapiens

<400> SEQUENCE: 117

```
agctggactc tcacagaatg                                                 20

<210> SEQ ID NO 118
<211> LENGTH: 20
<212> TYPE: DNA
<213> ORGANISM: Homo sapiens

<400> SEQUENCE: 118
caagaggctg gtagaaggtg                                                 20

<210> SEQ ID NO 119
<211> LENGTH: 24
<212> TYPE: DNA
<213> ORGANISM: Homo sapiens

<400> SEQUENCE: 119
gactccagtc tgggcaataa aagc                                            24

<210> SEQ ID NO 120
<211> LENGTH: 22
<212> TYPE: DNA
<213> ORGANISM: Homo sapiens

<400> SEQUENCE: 120
ggtggcagca tgacctctaa ag                                              22

<210> SEQ ID NO 121
<211> LENGTH: 16
<212> TYPE: DNA
<213> ORGANISM: Homo sapiens

<400> SEQUENCE: 121
caggcccagt ctcttg                                                     16

<210> SEQ ID NO 122
<211> LENGTH: 18
<212> TYPE: DNA
<213> ORGANISM: Homo sapiens

<400> SEQUENCE: 122
cgtgtccaga tgaaagtg                                                   18

<210> SEQ ID NO 123
<211> LENGTH: 18
<212> TYPE: DNA
<213> ORGANISM: Homo sapiens

<400> SEQUENCE: 123
acctcacggt gtaatccc                                                   18

<210> SEQ ID NO 124
<211> LENGTH: 18
<212> TYPE: DNA
<213> ORGANISM: Homo sapiens

<400> SEQUENCE: 124
cttgaagccc atctttgc                                                   18

<210> SEQ ID NO 125
<211> LENGTH: 23
<212> TYPE: DNA
<213> ORGANISM: Homo sapiens

<400> SEQUENCE: 125
```

```
tatttgcaaa gcttgagact tct                                              23

<210> SEQ ID NO 126
<211> LENGTH: 20
<212> TYPE: DNA
<213> ORGANISM: Homo sapiens

<400> SEQUENCE: 126
aatcactgtg ctttgttgcc                                                  20

<210> SEQ ID NO 127
<211> LENGTH: 20
<212> TYPE: DNA
<213> ORGANISM: Homo sapiens

<400> SEQUENCE: 127
actttattgt cagcgtgggc                                                  20

<210> SEQ ID NO 128
<211> LENGTH: 18
<212> TYPE: DNA
<213> ORGANISM: Homo sapiens

<400> SEQUENCE: 128
actccctcga tggcttcc                                                    18

<210> SEQ ID NO 129
<211> LENGTH: 18
<212> TYPE: DNA
<213> ORGANISM: Homo sapiens

<400> SEQUENCE: 129
gagcagggga gagaaggc                                                    18

<210> SEQ ID NO 130
<211> LENGTH: 20
<212> TYPE: DNA
<213> ORGANISM: Homo sapiens

<400> SEQUENCE: 130
cccactggct tgttttattg                                                  20

<210> SEQ ID NO 131
<211> LENGTH: 25
<212> TYPE: DNA
<213> ORGANISM: Homo sapiens

<400> SEQUENCE: 131
agccacttta ttgttatttt gatgc                                            25

<210> SEQ ID NO 132
<211> LENGTH: 25
<212> TYPE: DNA
<213> ORGANISM: Homo sapiens

<400> SEQUENCE: 132
aagagtgaac aaaagcaaac atacc                                            25

<210> SEQ ID NO 133
<211> LENGTH: 18
<212> TYPE: DNA
<213> ORGANISM: Homo sapiens
```

```
<400> SEQUENCE: 133
gtggagtgtg ggattggg                                                    18

<210> SEQ ID NO 134
<211> LENGTH: 25
<212> TYPE: DNA
<213> ORGANISM: Homo sapiens

<400> SEQUENCE: 134
tactgttctt gataagtatg tcggc                                            25

<210> SEQ ID NO 135
<211> LENGTH: 25
<212> TYPE: DNA
<213> ORGANISM: Homo sapiens

<400> SEQUENCE: 135
atgcttttgc atgattctaa ttatt                                            25

<210> SEQ ID NO 136
<211> LENGTH: 21
<212> TYPE: DNA
<213> ORGANISM: Homo sapiens

<400> SEQUENCE: 136
tcccccaaaa gaatgtaaag g                                                21

<210> SEQ ID NO 137
<211> LENGTH: 20
<212> TYPE: DNA
<213> ORGANISM: Homo sapiens

<400> SEQUENCE: 137
ctggtcttcc ttgtgtgctg                                                  20

<210> SEQ ID NO 138
<211> LENGTH: 18
<212> TYPE: DNA
<213> ORGANISM: Homo sapiens

<400> SEQUENCE: 138
atcacccagg ccagggat                                                    18

<210> SEQ ID NO 139
<211> LENGTH: 24
<212> TYPE: DNA
<213> ORGANISM: Homo sapiens

<400> SEQUENCE: 139
tcagaagcag aactgttttt aaca                                             24

<210> SEQ ID NO 140
<211> LENGTH: 22
<212> TYPE: DNA
<213> ORGANISM: Homo sapiens

<400> SEQUENCE: 140
cctgcttgaa agttctagag cc                                               22

<210> SEQ ID NO 141
<211> LENGTH: 21
<212> TYPE: DNA
<213> ORGANISM: Homo sapiens
```

```
<400> SEQUENCE: 141
caagcccggg ttttattgaa a                                    21

<210> SEQ ID NO 142
<211> LENGTH: 18
<212> TYPE: DNA
<213> ORGANISM: Homo sapiens

<400> SEQUENCE: 142
gatgccagga ccatggac                                        18

<210> SEQ ID NO 143
<211> LENGTH: 24
<212> TYPE: DNA
<213> ORGANISM: Homo sapiens

<400> SEQUENCE: 143
gcatatagaa acaatttatt gccg                                 24

<210> SEQ ID NO 144
<211> LENGTH: 20
<212> TYPE: DNA
<213> ORGANISM: Homo sapiens

<400> SEQUENCE: 144
ctctgaagca gggaccagag                                      20

<210> SEQ ID NO 145
<211> LENGTH: 19
<212> TYPE: DNA
<213> ORGANISM: Homo sapiens

<400> SEQUENCE: 145
ctaccacacc acaccaggc                                       19

<210> SEQ ID NO 146
<211> LENGTH: 18
<212> TYPE: DNA
<213> ORGANISM: Homo sapiens

<400> SEQUENCE: 146
caagcgaaag ctgccttc                                        18

<210> SEQ ID NO 147
<211> LENGTH: 23
<212> TYPE: DNA
<213> ORGANISM: Homo sapiens

<400> SEQUENCE: 147
gttgtcttga cttcaggtct gtc                                  23

<210> SEQ ID NO 148
<211> LENGTH: 24
<212> TYPE: DNA
<213> ORGANISM: Homo sapiens

<400> SEQUENCE: 148
ttttccttca acaatcacta ctcc                                 24

<210> SEQ ID NO 149
<211> LENGTH: 20
<212> TYPE: DNA
```

```
<213> ORGANISM: Homo sapiens

<400> SEQUENCE: 149
gcgtggggat atagaggtca                                           20

<210> SEQ ID NO 150
<211> LENGTH: 20
<212> TYPE: DNA
<213> ORGANISM: Homo sapiens

<400> SEQUENCE: 150
tacgtggcca agaagctagg                                           20

<210> SEQ ID NO 151
<211> LENGTH: 24
<212> TYPE: DNA
<213> ORGANISM: Homo sapiens

<400> SEQUENCE: 151
taatatatcc ccagtctaag gcat                                      24

<210> SEQ ID NO 152
<211> LENGTH: 18
<212> TYPE: DNA
<213> ORGANISM: Homo sapiens

<400> SEQUENCE: 152
agcttgcaga tggagccc                                             18

<210> SEQ ID NO 153
<211> LENGTH: 25
<212> TYPE: DNA
<213> ORGANISM: Homo sapiens

<400> SEQUENCE: 153
tggttttaaa cctttaatga gaaaa                                     25

<210> SEQ ID NO 154
<211> LENGTH: 23
<212> TYPE: DNA
<213> ORGANISM: Homo sapiens

<400> SEQUENCE: 154
tgttgatcta taccctgttt ccg                                       23

<210> SEQ ID NO 155
<211> LENGTH: 25
<212> TYPE: DNA
<213> ORGANISM: Homo sapiens

<400> SEQUENCE: 155
aattatttaa aagagaggaa aggca                                     25

<210> SEQ ID NO 156
<211> LENGTH: 20
<212> TYPE: DNA
<213> ORGANISM: Homo sapiens

<400> SEQUENCE: 156
tggctgtgaa cttcctctga                                           20

<210> SEQ ID NO 157
<211> LENGTH: 25
```

```
<212> TYPE: DNA
<213> ORGANISM: Homo sapiens

<400> SEQUENCE: 157
ggttacagaa aaacatttga gagat                                   25

<210> SEQ ID NO 158
<211> LENGTH: 22
<212> TYPE: DNA
<213> ORGANISM: Homo sapiens

<400> SEQUENCE: 158
tgagctttag ttccttctc tg                                       22

<210> SEQ ID NO 159
<211> LENGTH: 23
<212> TYPE: DNA
<213> ORGANISM: Homo sapiens

<400> SEQUENCE: 159
ttgaaaaacc atttatttca ccg                                     23

<210> SEQ ID NO 160
<211> LENGTH: 18
<212> TYPE: DNA
<213> ORGANISM: Homo sapiens

<400> SEQUENCE: 160
tctgcggctg ttggattt                                           18

<210> SEQ ID NO 161
<211> LENGTH: 23
<212> TYPE: DNA
<213> ORGANISM: Homo sapiens

<400> SEQUENCE: 161
ttgaaaaacc atttatttca ccg                                     23

<210> SEQ ID NO 162
<211> LENGTH: 20
<212> TYPE: DNA
<213> ORGANISM: Homo sapiens

<400> SEQUENCE: 162
tgttctcttc tcccagcagg                                         20

<210> SEQ ID NO 163
<211> LENGTH: 23
<212> TYPE: DNA
<213> ORGANISM: Homo sapiens

<400> SEQUENCE: 163
ctttattgaa aacattgagt gca                                     23

<210> SEQ ID NO 164
<211> LENGTH: 20
<212> TYPE: DNA
<213> ORGANISM: Homo sapiens

<400> SEQUENCE: 164
ttgtcaaatt cccccaaaa                                          20

<210> SEQ ID NO 165
```

```
<211> LENGTH: 16
<212> TYPE: DNA
<213> ORGANISM: Homo sapiens
<220> FEATURE:
<221> NAME/KEY: misc_feature
<222> LOCATION: 12
<223> OTHER INFORMATION: n = A,T,C or G

<400> SEQUENCE: 165
aaaccacgac cnccaa                                                      16

<210> SEQ ID NO 166
<211> LENGTH: 20
<212> TYPE: DNA
<213> ORGANISM: Homo sapiens

<400> SEQUENCE: 166
ccctggaaag gtaagatgct                                                  20

<210> SEQ ID NO 167
<211> LENGTH: 23
<212> TYPE: DNA
<213> ORGANISM: Homo sapiens

<400> SEQUENCE: 167
cttttggtag agacaaggtc tca                                              23

<210> SEQ ID NO 168
<211> LENGTH: 25
<212> TYPE: DNA
<213> ORGANISM: Homo sapiens

<400> SEQUENCE: 168
tatctgtctg tagtgcttca aatgt                                            25

<210> SEQ ID NO 169
<211> LENGTH: 19
<212> TYPE: DNA
<213> ORGANISM: Homo sapiens

<400> SEQUENCE: 169
gacgaaggtg attcagggc                                                   19

<210> SEQ ID NO 170
<211> LENGTH: 19
<212> TYPE: DNA
<213> ORGANISM: Homo sapiens

<400> SEQUENCE: 170
actgaagaac tcttgtcct                                                   19

<210> SEQ ID NO 171
<211> LENGTH: 25
<212> TYPE: DNA
<213> ORGANISM: Homo sapiens

<400> SEQUENCE: 171
cagataaaag agtcactatg gctca                                            25

<210> SEQ ID NO 172
<211> LENGTH: 20
<212> TYPE: DNA
<213> ORGANISM: Homo sapiens

<400> SEQUENCE: 172
```
cacttctccc actttgtccc                                              20

<210> SEQ ID NO 173
<211> LENGTH: 25
<212> TYPE: DNA
<213> ORGANISM: Homo sapiens

<400> SEQUENCE: 173
ttattgataa gcattagtga acccc                                        25

<210> SEQ ID NO 174
<211> LENGTH: 20
<212> TYPE: DNA
<213> ORGANISM: Homo sapiens

<400> SEQUENCE: 174
tggcaagtta ggcacagtca                                              20

<210> SEQ ID NO 175
<211> LENGTH: 21
<212> TYPE: DNA
<213> ORGANISM: Homo sapiens

<400> SEQUENCE: 175
ctatgcccag agatgaacag g                                            21

<210> SEQ ID NO 176
<211> LENGTH: 20
<212> TYPE: DNA
<213> ORGANISM: Homo sapiens

<400> SEQUENCE: 176
tccactaagg gctatgtcgc                                              20

<210> SEQ ID NO 177
<211> LENGTH: 24
<212> TYPE: DNA
<213> ORGANISM: Homo sapiens

<400> SEQUENCE: 177
gccagcttta ttgagtaaac ttcc                                         24

<210> SEQ ID NO 178
<211> LENGTH: 22
<212> TYPE: DNA
<213> ORGANISM: Homo sapiens

<400> SEQUENCE: 178
cactggagac tacaagtggt gg                                           22

<210> SEQ ID NO 179
<211> LENGTH: 20
<212> TYPE: DNA
<213> ORGANISM: Homo sapiens

<400> SEQUENCE: 179
catcccaacc atcactcagt                                              20

<210> SEQ ID NO 180
<211> LENGTH: 22
<212> TYPE: DNA
<213> ORGANISM: Homo sapiens -continued

```
<400> SEQUENCE: 180
ggggactagc ttacagattt ga                                              22

<210> SEQ ID NO 181
<211> LENGTH: 23
<212> TYPE: DNA
<213> ORGANISM: Homo sapiens

<400> SEQUENCE: 181
agactacatt ttggaaccag tgg                                             23

<210> SEQ ID NO 182
<211> LENGTH: 23
<212> TYPE: DNA
<213> ORGANISM: Homo sapiens

<400> SEQUENCE: 182
tgaaaggata tttatagcct gga                                             23

<210> SEQ ID NO 183
<211> LENGTH: 20
<212> TYPE: DNA
<213> ORGANISM: Homo sapiens

<400> SEQUENCE: 183
gaaggttttg tccctcgatc                                                 20

<210> SEQ ID NO 184
<211> LENGTH: 20
<212> TYPE: DNA
<213> ORGANISM: Homo sapiens

<400> SEQUENCE: 184
tgagggttgg gaagatcata                                                 20

<210> SEQ ID NO 185
<211> LENGTH: 18
<212> TYPE: DNA
<213> ORGANISM: Homo sapiens

<400> SEQUENCE: 185
ccttcatagc cacacccg                                                   18

<210> SEQ ID NO 186
<211> LENGTH: 21
<212> TYPE: DNA
<213> ORGANISM: Homo sapiens

<400> SEQUENCE: 186
cagctaactg ttgacatgcc a                                               21

<210> SEQ ID NO 187
<211> LENGTH: 25
<212> TYPE: DNA
<213> ORGANISM: Homo sapiens

<400> SEQUENCE: 187
tctttactgt gcttacaact ttcct                                           25

<210> SEQ ID NO 188
<211> LENGTH: 20
<212> TYPE: DNA
<213> ORGANISM: Homo sapiens
```

```
<400> SEQUENCE: 188
caacagtgca gtcggtatcg                                               20

<210> SEQ ID NO 189
<211> LENGTH: 18
<212> TYPE: DNA
<213> ORGANISM: Homo sapiens

<400> SEQUENCE: 189
agatcagcaa gcagatag                                                 18

<210> SEQ ID NO 190
<211> LENGTH: 18
<212> TYPE: DNA
<213> ORGANISM: Homo sapiens

<400> SEQUENCE: 190
cattccacat ggatagac                                                 18

<210> SEQ ID NO 191
<211> LENGTH: 24
<212> TYPE: DNA
<213> ORGANISM: Homo sapiens

<400> SEQUENCE: 191 cataccatg aggtgtgcta cagg                                           24

<210> SEQ ID NO 192
<211> LENGTH: 21
<212> TYPE: DNA
<213> ORGANISM: Homo sapiens

<400> SEQUENCE: 192
gcattttctc atcatccttg c                                             21

<210> SEQ ID NO 193
<211> LENGTH: 20
<212> TYPE: DNA
<213> ORGANISM: Homo sapiens

<400> SEQUENCE: 193
ttacagccac caaggtttcc                                               20

<210> SEQ ID NO 194
<211> LENGTH: 20
<212> TYPE: DNA
<213> ORGANISM: Homo sapiens

<400> SEQUENCE: 194
aggtgtgtgt gccaggttga                                               20

<210> SEQ ID NO 195
<211> LENGTH: 25
<212> TYPE: DNA
<213> ORGANISM: Homo sapiens

<400> SEQUENCE: 195
cactgttatc tcattaactg tgagg                                         25

<210> SEQ ID NO 196
<211> LENGTH: 21
<212> TYPE: DNA
```

```
<213> ORGANISM: Homo sapiens

<400> SEQUENCE: 196
tttgattttg tgtctcccaa a                                              21

<210> SEQ ID NO 197
<211> LENGTH: 20
<212> TYPE: DNA
<213> ORGANISM: Homo sapiens

<400> SEQUENCE: 197
ccccactccc acttttattt                                                20

<210> SEQ ID NO 198
<211> LENGTH: 24
<212> TYPE: DNA
<213> ORGANISM: Homo sapiens

<400> SEQUENCE: 198
ccagtcacct ttactagtcc tttg                                           24

<210> SEQ ID NO 199
<211> LENGTH: 20
<212> TYPE: DNA
<213> ORGANISM: Homo sapiens

<400> SEQUENCE: 199
aggacacagc ctgcatctag                                                20

<210> SEQ ID NO 200
<211> LENGTH: 20
<212> TYPE: DNA
<213> ORGANISM: Homo sapiens

<400> SEQUENCE: 200
accaggcatt gcactaaaag                                                20

<210> SEQ ID NO 201
<211> LENGTH: 22
<212> TYPE: DNA
<213> ORGANISM: Homo sapiens

<400> SEQUENCE: 201
gatgggtcac actaacctgt ca                                             22

<210> SEQ ID NO 202
<211> LENGTH: 24
<212> TYPE: DNA
<213> ORGANISM: Homo sapiens

<400> SEQUENCE: 202
acatttatat ttggacatgc aacc                                           24

<210> SEQ ID NO 203
<211> LENGTH: 22
<212> TYPE: DNA
<213> ORGANISM: Homo sapiens

<400> SEQUENCE: 203
agcatcttta atgtgtcagg ca                                             22

<210> SEQ ID NO 204
<211> LENGTH: 18
```

```
<212> TYPE: DNA
<213> ORGANISM: Homo sapiens

<400> SEQUENCE: 204
atgtgctggg ctggaaag                                                 18

<210> SEQ ID NO 205
<211> LENGTH: 20
<212> TYPE: DNA
<213> ORGANISM: Homo sapiens

<400> SEQUENCE: 205
tcacattcaa aaatcggcaa                                               20

<210> SEQ ID NO 206
<211> LENGTH: 18
<212> TYPE: DNA
<213> ORGANISM: Homo sapiens

<400> SEQUENCE: 206
ctgcctgtgt ggtgtcgc                                                 18

<210> SEQ ID NO 207
<211> LENGTH: 25
<212> TYPE: DNA
<213> ORGANISM: Homo sapiens

<400> SEQUENCE: 207
tgttttattt ctcagtacaa agcca                                         25

<210> SEQ ID NO 208
<211> LENGTH: 19
<212> TYPE: DNA
<213> ORGANISM: Homo sapiens

<400> SEQUENCE: 208
gacctcctgt gacaccacg                                                19

<210> SEQ ID NO 209
<211> LENGTH: 25
<212> TYPE: DNA
<213> ORGANISM: Homo sapiens

<400> SEQUENCE: 209
ccaccaaatt atttatagtt ctgcg                                         25

<210> SEQ ID NO 210
<211> LENGTH: 23
<212> TYPE: DNA
<213> ORGANISM: Homo sapiens

<400> SEQUENCE: 210
gtaagattct ccactgttgc acc                                           23

<210> SEQ ID NO 211
<211> LENGTH: 20
<212> TYPE: DNA
<213> ORGANISM: Homo sapiens

<400> SEQUENCE: 211
cctataatgg gctggaccaa                                               20

<210> SEQ ID NO 212
```

```
<211> LENGTH: 21
<212> TYPE: DNA
<213> ORGANISM: Homo sapiens

<400> SEQUENCE: 212
actcctcatg tgaagtcacc g                                              21

<210> SEQ ID NO 213
<211> LENGTH: 20
<212> TYPE: DNA
<213> ORGANISM: Homo sapiens

<400> SEQUENCE: 213
cagtgtgcac gttttcattt                                                20

<210> SEQ ID NO 214
<211> LENGTH: 20
<212> TYPE: DNA
<213> ORGANISM: Homo sapiens

<400> SEQUENCE: 214
cagcatcttc agcacttacc                                                20

<210> SEQ ID NO 215
<211> LENGTH: 25
<212> TYPE: DNA
<213> ORGANISM: Homo sapiens

<400> SEQUENCE: 215
ctgcatttat tatgagaatc aacag                                          25

<210> SEQ ID NO 216
<211> LENGTH: 20
<212> TYPE: DNA
<213> ORGANISM: Homo sapiens

<400> SEQUENCE: 216
tgctgctggg agtcagagtc                                                20

<210> SEQ ID NO 217
<211> LENGTH: 23
<212> TYPE: DNA
<213> ORGANISM: Homo sapiens

<400> SEQUENCE: 217
cagggcactg agatacactt acc                                            23

<210> SEQ ID NO 218
<211> LENGTH: 21
<212> TYPE: DNA
<213> ORGANISM: Homo sapiens

<400> SEQUENCE: 218
aaggatcaag ccaggcattt g                                              21

<210> SEQ ID NO 219
<211> LENGTH: 20
<212> TYPE: DNA
<213> ORGANISM: Homo sapiens

<400> SEQUENCE: 219
acacatctct tctgtgcccc                                                20
```

-continued

```
<210> SEQ ID NO 220
<211> LENGTH: 18
<212> TYPE: DNA
<213> ORGANISM: Homo sapiens

<400> SEQUENCE: 220
tgaaccctgg aggcagag                                                   18

<210> SEQ ID NO 221
<211> LENGTH: 19
<212> TYPE: DNA
<213> ORGANISM: Homo sapiens

<400> SEQUENCE: 221
cattccccag tttgcagac                                                  19

<210> SEQ ID NO 222
<211> LENGTH: 19
<212> TYPE: DNA
<213> ORGANISM: Homo sapiens

<400> SEQUENCE: 222
gtgctgggat tacaggtgt                                                  19

<210> SEQ ID NO 223
<211> LENGTH: 20
<212> TYPE: DNA
<213> ORGANISM: Homo sapiens

<400> SEQUENCE: 223
gcagagaagt cctgttagcc                                                 20

<210> SEQ ID NO 224
<211> LENGTH: 20
<212> TYPE: DNA
<213> ORGANISM: Homo sapiens

<400> SEQUENCE: 224
ccatgctaga gaagcacaac                                                 20

<210> SEQ ID NO 225
<211> LENGTH: 20
<212> TYPE: DNA
<213> ORGANISM: Homo sapiens

<400> SEQUENCE: 225
agtgtggggc aggacctctg                                                 20

<210> SEQ ID NO 226
<211> LENGTH: 21
<212> TYPE: DNA
<213> ORGANISM: Homo sapiens

<400> SEQUENCE: 226
cagacagata gccctgggtt c                                               21

<210> SEQ ID NO 227
<211> LENGTH: 20
<212> TYPE: DNA
<213> ORGANISM: Homo sapiens

<400> SEQUENCE: 227
tccctcatcc ccttgtctgt                                                 20
```

```
<210> SEQ ID NO 228
<211> LENGTH: 19
<212> TYPE: DNA
<213> ORGANISM: Homo sapiens

<400> SEQUENCE: 228
agcccccctg gggataatc                                                    19

<210> SEQ ID NO 229
<211> LENGTH: 19
<212> TYPE: DNA
<213> ORGANISM: Homo sapiens

<400> SEQUENCE: 229
gatgcttacc taccacggc                                                    19

<210> SEQ ID NO 230
<211> LENGTH: 21
<212> TYPE: DNA
<213> ORGANISM: Homo sapiens

<400> SEQUENCE: 230
aggattccta tctgggctat g                                                 21

<210> SEQ ID NO 231
<211> LENGTH: 20
<212> TYPE: DNA
<213> ORGANISM: Homo sapiens

<400> SEQUENCE: 231
tggcagacca tgctccgcct                                                   20

<210> SEQ ID NO 232
<211> LENGTH: 20
<212> TYPE: DNA
<213> ORGANISM: Homo sapiens

<400> SEQUENCE: 232
gagaaggccg ggaggctctg                                                   20

<210> SEQ ID NO 233
<211> LENGTH: 25
<212> TYPE: DNA
<213> ORGANISM: Homo sapiens

<400> SEQUENCE: 233
ctccatcaca accagatttg aggct                                             25

<210> SEQ ID NO 234
<211> LENGTH: 22
<212> TYPE: DNA
<213> ORGANISM: Homo sapiens

<400> SEQUENCE: 234
gggtgtgagc tgctgctgaa gg                                                22

<210> SEQ ID NO 235
<211> LENGTH: 25
<212> TYPE: DNA
<213> ORGANISM: Homo sapiens

<400> SEQUENCE: 235
agtgggaaac ctcaggtagc tcccg                                             25
```

<210> SEQ ID NO 236
<211> LENGTH: 25
<212> TYPE: DNA
<213> ORGANISM: Homo sapiens

<400> SEQUENCE: 236
cagtttggct cagacatatg ggggc                                     25

<210> SEQ ID NO 237
<211> LENGTH: 20
<212> TYPE: DNA
<213> ORGANISM: Homo sapiens

<400> SEQUENCE: 237
cattagtagt gggggggacag                                          20

<210> SEQ ID NO 238
<211> LENGTH: 21
<212> TYPE: DNA
<213> ORGANISM: Homo sapiens

<400> SEQUENCE: 238
caaagcgaca gtgagttagg g                                         21

<210> SEQ ID NO 239
<211> LENGTH: 20
<212> TYPE: DNA
<213> ORGANISM: Homo sapiens

<400> SEQUENCE: 239
ggagtagacc atgattactg                                           20

<210> SEQ ID NO 240
<211> LENGTH: 19
<212> TYPE: DNA
<213> ORGANISM: Homo sapiens

<400> SEQUENCE: 240
catggtctat ttattctcg                                            19

<210> SEQ ID NO 241
<211> LENGTH: 22
<212> TYPE: DNA
<213> ORGANISM: Homo sapiens

<400> SEQUENCE: 241
cgccctggat cctcacacta ca                                        22

<210> SEQ ID NO 242
<211> LENGTH: 21
<212> TYPE: DNA
<213> ORGANISM: Homo sapiens

<400> SEQUENCE: 242
gggcatcagg ggatgggtag a                                         21

<210> SEQ ID NO 243
<211> LENGTH: 23
<212> TYPE: DNA
<213> ORGANISM: Homo sapiens

<400> SEQUENCE: 243

-continued gctcctatct gtgttttgaa tgg                                    23

<210> SEQ ID NO 244
<211> LENGTH: 22
<212> TYPE: DNA
<213> ORGANISM: Homo sapiens

<400> SEQUENCE: 244
ccgtggcata gataagtaaa cg                                     22

<210> SEQ ID NO 245
<211> LENGTH: 22
<212> TYPE: DNA
<213> ORGANISM: Homo sapiens

<400> SEQUENCE: 245
cttggagcgc tatgaggagg gc                                     22

<210> SEQ ID NO 246
<211> LENGTH: 23
<212> TYPE: DNA
<213> ORGANISM: Homo sapiens

<400> SEQUENCE: 246
atggcaactg accttccgtc ctg                                    23

<210> SEQ ID NO 247
<211> LENGTH: 16
<212> TYPE: DNA
<213> ORGANISM: Homo sapiens

<400> SEQUENCE: 247
ttggagtcac aggggc                                            16

<210> SEQ ID NO 248
<211> LENGTH: 17
<212> TYPE: DNA
<213> ORGANISM: Homo sapiens

<400> SEQUENCE: 248
cagcactatc cttgggg                                           17

<210> SEQ ID NO 249
<211> LENGTH: 21
<212> TYPE: DNA
<213> ORGANISM: Homo sapiens

<400> SEQUENCE: 249
aacaaagctg cttagcacct g                                      21

<210> SEQ ID NO 250
<211> LENGTH: 20
<212> TYPE: DNA
<213> ORGANISM: Homo sapiens

<400> SEQUENCE: 250
gatgaggacc aactggtgac                                        20

<210> SEQ ID NO 251
<211> LENGTH: 20
<212> TYPE: DNA
<213> ORGANISM: Homo sapiens

<400> SEQUENCE: 251

```
tttccaata atgtgacttc                                                20

<210> SEQ ID NO 252
<211> LENGTH: 20
<212> TYPE: DNA
<213> ORGANISM: Homo sapiens

<400> SEQUENCE: 252
caatcccaac cgtaacaggc                                               20

<210> SEQ ID NO 253
<211> LENGTH: 19
<212> TYPE: DNA
<213> ORGANISM: Homo sapiens

<400> SEQUENCE: 253
cttgatctcg cccaggaac                                                19

<210> SEQ ID NO 254
<211> LENGTH: 20
<212> TYPE: DNA
<213> ORGANISM: Homo sapiens

<400> SEQUENCE: 254
gctcgctgaa ggatgaagac                                               20

<210> SEQ ID NO 255
<211> LENGTH: 17
<212> TYPE: DNA
<213> ORGANISM: Homo sapiens

<400> SEQUENCE: 255
gaatcgcttg aacccag                                                  17

<210> SEQ ID NO 256
<211> LENGTH: 17
<212> TYPE: DNA
<213> ORGANISM: Homo sapiens

<400> SEQUENCE: 256
ccaggtggtc ttaacgg                                                  17

<210> SEQ ID NO 257
<211> LENGTH: 21
<212> TYPE: DNA
<213> ORGANISM: Homo sapiens
<220> FEATURE:
<221> NAME/KEY: misc_feature
<222> LOCATION: 8
<223> OTHER INFORMATION: n = A,T,C or G

<400> SEQUENCE: 257
gaacgttntt catgtaggcg t                                             21

<210> SEQ ID NO 258
<211> LENGTH: 16
<212> TYPE: DNA
<213> ORGANISM: Homo sapiens

<400> SEQUENCE: 258
taatggtcgc tgtccc                                                   16

<210> SEQ ID NO 259
```

```
<211> LENGTH: 22
<212> TYPE: DNA
<213> ORGANISM: Homo sapiens

<400> SEQUENCE: 259
agggaaaatg gtatgtgggg ag                                              22

<210> SEQ ID NO 260
<211> LENGTH: 18
<212> TYPE: DNA
<213> ORGANISM: Homo sapiens

<400> SEQUENCE: 260
gcagtgtgtg aaggcagg                                                   18

<210> SEQ ID NO 261
<211> LENGTH: 24
<212> TYPE: DNA
<213> ORGANISM: Homo sapiens

<400> SEQUENCE: 261
agtggacaaa atgaggaaaa cagg                                            24

<210> SEQ ID NO 262
<211> LENGTH: 23
<212> TYPE: DNA
<213> ORGANISM: Homo sapiens

<400> SEQUENCE: 262
ccaacacagt ttgctcacat gcc                                             23

<210> SEQ ID NO 263
<211> LENGTH: 20
<212> TYPE: DNA
<213> ORGANISM: Homo sapiens

<400> SEQUENCE: 263
tgacatcttt gcattatggc                                                 20

<210> SEQ ID NO 264
<211> LENGTH: 20
<212> TYPE: DNA
<213> ORGANISM: Homo sapiens

<400> SEQUENCE: 264
agttatccca cctgataccg                                                 20

<210> SEQ ID NO 265
<211> LENGTH: 20
<212> TYPE: DNA
<213> ORGANISM: Homo sapiens

<400> SEQUENCE: 265
agctcttgct tctcagtcca                                                 20

<210> SEQ ID NO 266
<211> LENGTH: 24
<212> TYPE: DNA
<213> ORGANISM: Homo sapiens

<400> SEQUENCE: 266
caaaagttgt ttctgtgttt gttc                                            24
```

```
<210> SEQ ID NO 267
<211> LENGTH: 22
<212> TYPE: DNA
<213> ORGANISM: Homo sapiens

<400> SEQUENCE: 267
gcctctcaaa gtagttggaa cc                                              22

<210> SEQ ID NO 268
<211> LENGTH: 23
<212> TYPE: DNA
<213> ORGANISM: Homo sapiens

<400> SEQUENCE: 268
tgtgtatcca tagtgcaaaa cag                                             23

<210> SEQ ID NO 269
<211> LENGTH: 19
<212> TYPE: DNA
<213> ORGANISM: Homo sapiens

<400> SEQUENCE: 269
ctcaaggcca ggcatcact                                                  19

<210> SEQ ID NO 270
<211> LENGTH: 19
<212> TYPE: DNA
<213> ORGANISM: Homo sapiens

<400> SEQUENCE: 270
ggactcttcc atgccagtg                                                  19

<210> SEQ ID NO 271
<211> LENGTH: 19
<212> TYPE: DNA
<213> ORGANISM: Homo sapiens

<400> SEQUENCE: 271
aatgatgatc tcaactctg                                                  19

<210> SEQ ID NO 272
<211> LENGTH: 19
<212> TYPE: DNA
<213> ORGANISM: Homo sapiens

<400> SEQUENCE: 272
actgaagaac tcttgtcct                                                  19

<210> SEQ ID NO 273
<211> LENGTH: 23
<212> TYPE: DNA
<213> ORGANISM: Homo sapiens

<400> SEQUENCE: 273
gacatctgtt agtctcataa ttc                                             23

<210> SEQ ID NO 274
<211> LENGTH: 18
<212> TYPE: DNA
<213> ORGANISM: Homo sapiens

<400> SEQUENCE: 274
ggtaacagtg tcttgctt                                                   18
```

```
<210> SEQ ID NO 275
<211> LENGTH: 21
<212> TYPE: DNA
<213> ORGANISM: Homo sapiens

<400> SEQUENCE: 275
ctatgtacaa aacaggaaga g                                        21

<210> SEQ ID NO 276
<211> LENGTH: 19
<212> TYPE: DNA
<213> ORGANISM: Homo sapiens

<400> SEQUENCE: 276
atcctagttt cctctcctt                                           19

<210> SEQ ID NO 277
<211> LENGTH: 23
<212> TYPE: DNA
<213> ORGANISM: Homo sapiens

<400> SEQUENCE: 277
gtaaatgaga aacagacaaa tga                                      23

<210> SEQ ID NO 278
<211> LENGTH: 23
<212> TYPE: DNA
<213> ORGANISM: Homo sapiens

<400> SEQUENCE: 278
ctattggatg tgatatgtta tgg                                      23

<210> SEQ ID NO 279
<211> LENGTH: 22
<212> TYPE: DNA
<213> ORGANISM: Homo sapiens

<400> SEQUENCE: 279
aagtagaaac aaaatgaggg ac                                       22

<210> SEQ ID NO 280
<211> LENGTH: 18
<212> TYPE: DNA
<213> ORGANISM: Homo sapiens

<400> SEQUENCE: 280
cctaccccaa ggtaacag                                            18

<210> SEQ ID NO 281
<211> LENGTH: 22
<212> TYPE: DNA
<213> ORGANISM: Homo sapiens

<400> SEQUENCE: 281
acttcctata aatggaggtg ag                                       22

<210> SEQ ID NO 282
<211> LENGTH: 18
<212> TYPE: DNA
<213> ORGANISM: Homo sapiens

<400> SEQUENCE: 282
gaggagcttc aagaggaa                                            18
```

<210> SEQ ID NO 283
<211> LENGTH: 23
<212> TYPE: DNA
<213> ORGANISM: Homo sapiens

<400> SEQUENCE: 283
catactccta gactcaagga atc                                              23

<210> SEQ ID NO 284
<211> LENGTH: 23
<212> TYPE: DNA
<213> ORGANISM: Homo sapiens

<400> SEQUENCE: 284
gaatgatgta catgaattct ttg                                              23

<210> SEQ ID NO 285
<211> LENGTH: 20
<212> TYPE: DNA
<213> ORGANISM: Homo sapiens

<400> SEQUENCE: 285
gtgttgagga gaaaagcact                                                  20

<210> SEQ ID NO 286
<211> LENGTH: 19
<212> TYPE: DNA
<213> ORGANISM: Homo sapiens

<400> SEQUENCE: 286
ctcccagtag tcacattcc                                                   19

<210> SEQ ID NO 287
<211> LENGTH: 23
<212> TYPE: DNA
<213> ORGANISM: Homo sapiens

<400> SEQUENCE: 287
caagttacaa ataacttaag ccg                                              23

<210> SEQ ID NO 288
<211> LENGTH: 23
<212> TYPE: DNA
<213> ORGANISM: Homo sapiens

<400> SEQUENCE: 288 caagaccota tctctacaaa aac                                              23

<210> SEQ ID NO 289
<211> LENGTH: 24
<212> TYPE: DNA
<213> ORGANISM: Homo sapiens

<400> SEQUENCE: 289
tttattagaa gtgactcttg gccc                                             24

<210> SEQ ID NO 290
<211> LENGTH: 20
<212> TYPE: DNA
<213> ORGANISM: Homo sapiens

<400> SEQUENCE: 290

```
gactacctgc cctcagcttg                                              20

<210> SEQ ID NO 291
<211> LENGTH: 20
<212> TYPE: DNA
<213> ORGANISM: Homo sapiens

<400> SEQUENCE: 291
ttctcatgta caaagcggtc                                              20

<210> SEQ ID NO 292
<211> LENGTH: 20
<212> TYPE: DNA
<213> ORGANISM: Homo sapiens

<400> SEQUENCE: 292
ccactggctt ctctcttttt                                              20

<210> SEQ ID NO 293
<211> LENGTH: 18
<212> TYPE: DNA
<213> ORGANISM: Homo sapiens

<400> SEQUENCE: 293
caccagaagg ttggggtg                                                18

<210> SEQ ID NO 294
<211> LENGTH: 21
<212> TYPE: DNA
<213> ORGANISM: Homo sapiens

<400> SEQUENCE: 294
actattacga catgaacgcg g                                            21

<210> SEQ ID NO 295
<211> LENGTH: 18
<212> TYPE: DNA
<213> ORGANISM: Homo sapiens

<400> SEQUENCE: 295
ctcatgctgg atgacccc                                                18

<210> SEQ ID NO 296
<211> LENGTH: 24
<212> TYPE: DNA
<213> ORGANISM: Homo sapiens

<400> SEQUENCE: 296
ttgcctttct tgaacttaa ttcc                                          24

<210> SEQ ID NO 297
<211> LENGTH: 19
<212> TYPE: DNA
<213> ORGANISM: Homo sapiens

<400> SEQUENCE: 297
tcacagcctt cagtcaggg                                               19

<210> SEQ ID NO 298
<211> LENGTH: 18
<212> TYPE: DNA
<213> ORGANISM: Homo sapiens

<400> SEQUENCE: 298
```

-continued acatgctgtg gcaccatg                              18

<210> SEQ ID NO 299
<211> LENGTH: 18
<212> TYPE: DNA
<213> ORGANISM: Homo sapiens

<400> SEQUENCE: 299
cctgagctac tgccacag                              18

<210> SEQ ID NO 300
<211> LENGTH: 20
<212> TYPE: DNA
<213> ORGANISM: Homo sapiens

<400> SEQUENCE: 300
ccctgacttg gacagtgtcc                            20

<210> SEQ ID NO 301
<211> LENGTH: 18
<212> TYPE: DNA
<213> ORGANISM: Homo sapiens

<400> SEQUENCE: 301
tcagagtcac tcctgccc                              18

<210> SEQ ID NO 302
<211> LENGTH: 22
<212> TYPE: DNA
<213> ORGANISM: Homo sapiens

<400> SEQUENCE: 302
caaattcaag ctcatccaga cc                         22

<210> SEQ ID NO 303
<211> LENGTH: 18
<212> TYPE: DNA
<213> ORGANISM: Homo sapiens

<400> SEQUENCE: 303
cggcatttca tccaggac                              18

<210> SEQ ID NO 304
<211> LENGTH: 20
<212> TYPE: DNA
<213> ORGANISM: Homo sapiens

<400> SEQUENCE: 304
ggtgtaggag gtgcgacaat                            20

<210> SEQ ID NO 305
<211> LENGTH: 20
<212> TYPE: DNA
<213> ORGANISM: Homo sapiens

<400> SEQUENCE: 305
ttccatttat tgagcacctg                            20

<210> SEQ ID NO 306
<211> LENGTH: 20
<212> TYPE: DNA
<213> ORGANISM: Homo sapiens

```
<400> SEQUENCE: 306
cttaagccac tgtgttttgg                                               20

<210> SEQ ID NO 307
<211> LENGTH: 20
<212> TYPE: DNA
<213> ORGANISM: Homo sapiens

<400> SEQUENCE: 307
cctcctacac ctgcaaaagc                                               20

<210> SEQ ID NO 308
<211> LENGTH: 19
<212> TYPE: DNA
<213> ORGANISM: Homo sapiens

<400> SEQUENCE: 308
tggaagaacc ccagaggac                                                19

<210> SEQ ID NO 309
<211> LENGTH: 23
<212> TYPE: DNA
<213> ORGANISM: Homo sapiens

<400> SEQUENCE: 309
aaagcacaaa agtaacagca aca                                           23

<210> SEQ ID NO 310
<211> LENGTH: 20
<212> TYPE: DNA
<213> ORGANISM: Homo sapiens

<400> SEQUENCE: 310
gtgtgtgggc cacaatattg                                               20

<210> SEQ ID NO 311
<211> LENGTH: 20
<212> TYPE: DNA
<213> ORGANISM: Homo sapiens

<400> SEQUENCE: 311
agagcacctt tcctcagcac                                               20

<210> SEQ ID NO 312
<211> LENGTH: 20
<212> TYPE: DNA
<213> ORGANISM: Homo sapiens

<400> SEQUENCE: 312
agaatctcat cacaggggcg                                               20

<210> SEQ ID NO 313
<211> LENGTH: 25
<212> TYPE: DNA
<213> ORGANISM: Homo sapiens

<400> SEQUENCE: 313
aaaaaggaca gtgtctaaaa tttga                                         25

<210> SEQ ID NO 314
<211> LENGTH: 25
<212> TYPE: DNA
<213> ORGANISM: Homo sapiens
```

<400> SEQUENCE: 314
aattgttttt gtttgttttt tgagt  25

<210> SEQ ID NO 315
<211> LENGTH: 22
<212> TYPE: DNA
<213> ORGANISM: Homo sapiens

<400> SEQUENCE: 315
gatttaggga gtacaagtgc gg  22

<210> SEQ ID NO 316
<211> LENGTH: 25
<212> TYPE: DNA
<213> ORGANISM: Homo sapiens

<400> SEQUENCE: 316
ggggacaaat tatactttat tcagg  25

<210> SEQ ID NO 317
<211> LENGTH: 22
<212> TYPE: DNA
<213> ORGANISM: Homo sapiens

<400> SEQUENCE: 317
ccatcatcat attggtgtga cc  22

<210> SEQ ID NO 318
<211> LENGTH: 18
<212> TYPE: DNA
<213> ORGANISM: Homo sapiens

<400> SEQUENCE: 318
tggctgccca agaagaag  18

<210> SEQ ID NO 319
<211> LENGTH: 24
<212> TYPE: DNA
<213> ORGANISM: Homo sapiens

<400> SEQUENCE: 319
ttaagatgcc attaaactca tgac  24

<210> SEQ ID NO 320
<211> LENGTH: 20
<212> TYPE: DNA
<213> ORGANISM: Homo sapiens

<400> SEQUENCE: 320
ccaaggagat gaccaagtgg  20

<210> SEQ ID NO 321
<211> LENGTH: 22
<212> TYPE: DNA
<213> ORGANISM: Homo sapiens

<400> SEQUENCE: 321
ccatctcttt tatcagggtt gg  22

<210> SEQ ID NO 322
<211> LENGTH: 24
<212> TYPE: DNA

```
<213> ORGANISM: Homo sapiens

<400> SEQUENCE: 322
ctctgtgcaa gtaagcatct taca                                    24

<210> SEQ ID NO 323
<211> LENGTH: 20
<212> TYPE: DNA
<213> ORGANISM: Homo sapiens

<400> SEQUENCE: 323
cgactgtgta ttttccacag                                         20

<210> SEQ ID NO 324
<211> LENGTH: 20
<212> TYPE: DNA
<213> ORGANISM: Homo sapiens

<400> SEQUENCE: 324
agaagcccat atcaatgcac                                         20

<210> SEQ ID NO 325
<211> LENGTH: 23
<212> TYPE: DNA
<213> ORGANISM: Homo sapiens

<400> SEQUENCE: 325
agcttaaagt aggacaacca tgg                                     23

<210> SEQ ID NO 326
<211> LENGTH: 20
<212> TYPE: DNA
<213> ORGANISM: Homo sapiens

<400> SEQUENCE: 326
ggatgcttca ctccagaaag                                         20

<210> SEQ ID NO 327
<211> LENGTH: 21
<212> TYPE: DNA
<213> ORGANISM: Homo sapiens

<400> SEQUENCE: 327
tgttgtttat ttccacctgc c                                       21

<210> SEQ ID NO 328
<211> LENGTH: 18
<212> TYPE: DNA
<213> ORGANISM: Homo sapiens

<400> SEQUENCE: 328
agagtggctg caggccag                                           18

<210> SEQ ID NO 329
<211> LENGTH: 25
<212> TYPE: DNA
<213> ORGANISM: Homo sapiens

<400> SEQUENCE: 329
tttttttttt tacacgaatt tgagg                                   25

<210> SEQ ID NO 330
<211> LENGTH: 23
```

```
<212> TYPE: DNA
<213> ORGANISM: Homo sapiens

<400> SEQUENCE: 330
tgaggaagta aaacaggtc atc                                        23

<210> SEQ ID NO 331
<211> LENGTH: 23
<212> TYPE: DNA
<213> ORGANISM: Homo sapiens

<400> SEQUENCE: 331
atgaaatctt aagcagaatc cca                                       23

<210> SEQ ID NO 332
<211> LENGTH: 20
<212> TYPE: DNA
<213> ORGANISM: Homo sapiens

<400> SEQUENCE: 332
cacagagtcc cagggtctgt                                           20

<210> SEQ ID NO 333
<211> LENGTH: 25
<212> TYPE: DNA
<213> ORGANISM: Homo sapiens

<400> SEQUENCE: 333
aaaggccttt atttatctct ctctg                                     25

<210> SEQ ID NO 334
<211> LENGTH: 18
<212> TYPE: DNA
<213> ORGANISM: Homo sapiens

<400> SEQUENCE: 334
gcctcagagc tggtgggt                                             18

<210> SEQ ID NO 335
<211> LENGTH: 25
<212> TYPE: DNA
<213> ORGANISM: Homo sapiens

<400> SEQUENCE: 335
gcttctaagt cttagagtca gctgg                                     25

<210> SEQ ID NO 336
<211> LENGTH: 19
<212> TYPE: DNA
<213> ORGANISM: Homo sapiens

<400> SEQUENCE: 336
agcccacagt cagcctacc                                            19

<210> SEQ ID NO 337
<211> LENGTH: 20
<212> TYPE: DNA
<213> ORGANISM: Homo sapiens

<400> SEQUENCE: 337
ttggttaaat gatgcccaga                                           20

<210> SEQ ID NO 338
```

```
<211> LENGTH: 18
<212> TYPE: DNA
<213> ORGANISM: Homo sapiens

<400> SEQUENCE: 338
tggtcccact cacatccc                                                       18

<210> SEQ ID NO 339
<211> LENGTH: 19
<212> TYPE: DNA
<213> ORGANISM: Homo sapiens

<400> SEQUENCE: 339
acacagcatg cagggagag                                                      19

<210> SEQ ID NO 340
<211> LENGTH: 19
<212> TYPE: DNA
<213> ORGANISM: Homo sapiens

<400> SEQUENCE: 340
atccctggtg cttaggtgg                                                      19

<210> SEQ ID NO 341
<211> LENGTH: 21
<212> TYPE: DNA
<213> ORGANISM: Homo sapiens

<400> SEQUENCE: 341
gatggaagta gctcctctcg g                                                   21

<210> SEQ ID NO 342
<211> LENGTH: 21
<212> TYPE: DNA
<213> ORGANISM: Homo sapiens

<400> SEQUENCE: 342
ggaaggccag caagtactac c                                                   21

<210> SEQ ID NO 343
<211> LENGTH: 18
<212> TYPE: DNA
<213> ORGANISM: Homo sapiens

<400> SEQUENCE: 343
ccggtgcttg gaaagatg                                                       18

<210> SEQ ID NO 344
<211> LENGTH: 20
<212> TYPE: DNA
<213> ORGANISM: Homo sapiens

<400> SEQUENCE: 344
gaagtgtctc tgttggggga                                                     20

<210> SEQ ID NO 345
<211> LENGTH: 22
<212> TYPE: DNA
<213> ORGANISM: Homo sapiens

<400> SEQUENCE: 345
ttacaggcat gagtcactac gc                                                  22
```

```
<210> SEQ ID NO 346
<211> LENGTH: 21
<212> TYPE: DNA
<213> ORGANISM: Homo sapiens

<400> SEQUENCE: 346
accactctca cagcccttac a                                              21

<210> SEQ ID NO 347
<211> LENGTH: 18
<212> TYPE: DNA
<213> ORGANISM: Homo sapiens

<400> SEQUENCE: 347
ccctccctcc acacacac                                                  18

<210> SEQ ID NO 348
<211> LENGTH: 20
<212> TYPE: DNA
<213> ORGANISM: Homo sapiens

<400> SEQUENCE: 348
gctcactgaa ctttcagggc                                                20

<210> SEQ ID NO 349
<211> LENGTH: 20
<212> TYPE: DNA
<213> ORGANISM: Homo sapiens

<400> SEQUENCE: 349
agatacgggc aaaacactgg                                                20

<210> SEQ ID NO 350
<211> LENGTH: 21
<212> TYPE: DNA
<213> ORGANISM: Homo sapiens

<400> SEQUENCE: 350
gttgaatata gagcagggcc c                                              21

<210> SEQ ID NO 351
<211> LENGTH: 20
<212> TYPE: DNA
<213> ORGANISM: Homo sapiens

<400> SEQUENCE: 351
ttctgaggtc agggctgtct                                                20

<210> SEQ ID NO 352
<211> LENGTH: 21
<212> TYPE: DNA
<213> ORGANISM: Homo sapiens

<400> SEQUENCE: 352
agcttggaaa atctcgtgtc a                                              21

<210> SEQ ID NO 353
<211> LENGTH: 18
<212> TYPE: DNA
<213> ORGANISM: Homo sapiens

<400> SEQUENCE: 353
actcagtccc tcccaccc                                                  18
```

```
<210> SEQ ID NO 354
<211> LENGTH: 20
<212> TYPE: DNA
<213> ORGANISM: Homo sapiens

<400> SEQUENCE: 354
tcctctcact ccttcccaga                                              20

<210> SEQ ID NO 355
<211> LENGTH: 19
<212> TYPE: DNA
<213> ORGANISM: Homo sapiens

<400> SEQUENCE: 355
gtgatcacgg ctcaacctg                                               19

<210> SEQ ID NO 356
<211> LENGTH: 18
<212> TYPE: DNA
<213> ORGANISM: Homo sapiens

<400> SEQUENCE: 356
tggaggactg cttgagcc                                                18

<210> SEQ ID NO 357
<211> LENGTH: 19
<212> TYPE: DNA
<213> ORGANISM: Homo sapiens

<400> SEQUENCE: 357
ctgcagctgc ctcagtttc                                               19

<210> SEQ ID NO 358
<211> LENGTH: 20
<212> TYPE: DNA
<213> ORGANISM: Homo sapiens

<400> SEQUENCE: 358
tcaaaagtgc tggtgacagc                                              20

<210> SEQ ID NO 359
<211> LENGTH: 20
<212> TYPE: DNA
<213> ORGANISM: Homo sapiens

<400> SEQUENCE: 359
atttccagag ccagctcaaa                                              20

<210> SEQ ID NO 360
<211> LENGTH: 25
<212> TYPE: DNA
<213> ORGANISM: Homo sapiens

<400> SEQUENCE: 360
ctttaatgtt gtgatgacac aaagc                                        25

<210> SEQ ID NO 361
<211> LENGTH: 20
<212> TYPE: DNA
<213> ORGANISM: Homo sapiens

<400> SEQUENCE: 361
gatcatgcac tgttgaccac                                              20
```

<210> SEQ ID NO 362
<211> LENGTH: 25
<212> TYPE: DNA
<213> ORGANISM: Homo sapiens

<400> SEQUENCE: 362
tacatttgaa acatttaaaa cctga                                    25

<210> SEQ ID NO 363
<211> LENGTH: 24
<212> TYPE: DNA
<213> ORGANISM: Homo sapiens

<400> SEQUENCE: 363
aactgagctg taaccagact ggga                                     24

<210> SEQ ID NO 364
<211> LENGTH: 22
<212> TYPE: DNA
<213> ORGANISM: Homo sapiens

<400> SEQUENCE: 364
tggaacagtc tggtcctgat gg                                       22

<210> SEQ ID NO 365
<211> LENGTH: 25
<212> TYPE: DNA
<213> ORGANISM: Homo sapiens

<400> SEQUENCE: 365
ttatcccttt attgtttctc ctttg                                    25

<210> SEQ ID NO 366
<211> LENGTH: 24
<212> TYPE: DNA
<213> ORGANISM: Homo sapiens

<400> SEQUENCE: 366
tggtcacctg tatttattgc tagg                                     24

<210> SEQ ID NO 367
<211> LENGTH: 22
<212> TYPE: DNA
<213> ORGANISM: Homo sapiens

<400> SEQUENCE: 367
tcttcaaagc ctctgcagta cc                                       22

<210> SEQ ID NO 368
<211> LENGTH: 22
<212> TYPE: DNA
<213> ORGANISM: Homo sapiens

<400> SEQUENCE: 368
ctcatctcca acctgtctaa cc                                       22

<210> SEQ ID NO 369
<211> LENGTH: 24
<212> TYPE: DNA
<213> ORGANISM: Homo sapiens

<400> SEQUENCE: 369

| | |
|---|---|
| gtggctgcag ctaatgtaag acac | 24 |

<210> SEQ ID NO 370
<211> LENGTH: 24
<212> TYPE: DNA
<213> ORGANISM: Homo sapiens

<400> SEQUENCE: 370

| | |
|---|---|
| cagcagagac aatggcgtaa gtcc | 24 |

<210> SEQ ID NO 371
<211> LENGTH: 20
<212> TYPE: DNA
<213> ORGANISM: Homo sapiens

<400> SEQUENCE: 371

| | |
|---|---|
| ctgattgaga accagaacag | 20 |

<210> SEQ ID NO 372
<211> LENGTH: 20
<212> TYPE: DNA
<213> ORGANISM: Homo sapiens

<400> SEQUENCE: 372

| | |
|---|---|
| taaagcccta taacctctcc | 20 |

<210> SEQ ID NO 373
<211> LENGTH: 20
<212> TYPE: DNA
<213> ORGANISM: Homo sapiens

<400> SEQUENCE: 373

| | |
|---|---|
| tagtaaggga ccttcaccag | 20 |

<210> SEQ ID NO 374
<211> LENGTH: 20
<212> TYPE: DNA
<213> ORGANISM: Homo sapiens

<400> SEQUENCE: 374

| | |
|---|---|
| agatgtttgg tatgacttgg | 20 |

<210> SEQ ID NO 375
<211> LENGTH: 20
<212> TYPE: DNA
<213> ORGANISM: Homo sapiens

<400> SEQUENCE: 375

| | |
|---|---|
| gatgattaaa ctctcctggc | 20 |

<210> SEQ ID NO 376
<211> LENGTH: 20
<212> TYPE: DNA
<213> ORGANISM: Homo sapiens

<400> SEQUENCE: 376

| | |
|---|---|
| gagacagcta agcactcatg | 20 |

<210> SEQ ID NO 377
<211> LENGTH: 19
<212> TYPE: DNA
<213> ORGANISM: Homo sapiens

<400> SEQUENCE: 377

```
gaggtggtgg gcacctgta                                              19

<210> SEQ ID NO 378
<211> LENGTH: 20
<212> TYPE: DNA
<213> ORGANISM: Homo sapiens

<400> SEQUENCE: 378
agaggggagg aacacacctt                                             20

<210> SEQ ID NO 379
<211> LENGTH: 20
<212> TYPE: DNA
<213> ORGANISM: Homo sapiens

<400> SEQUENCE: 379
gaccagagtc tgcccagaag                                             20

<210> SEQ ID NO 380
<211> LENGTH: 19
<212> TYPE: DNA
<213> ORGANISM: Homo sapiens

<400> SEQUENCE: 380
tccccagctc tatcccaac                                              19

<210> SEQ ID NO 381
<211> LENGTH: 20
<212> TYPE: DNA
<213> ORGANISM: Homo sapiens

<400> SEQUENCE: 381
ggagggatgg acaagtctga                                             20

<210> SEQ ID NO 382
<211> LENGTH: 20
<212> TYPE: DNA
<213> ORGANISM: Homo sapiens

<400> SEQUENCE: 382
gtccagctcg ctgactatcc                                             20

<210> SEQ ID NO 383
<211> LENGTH: 20
<212> TYPE: DNA
<213> ORGANISM: Homo sapiens

<400> SEQUENCE: 383
tcaaaacaca gtcatctcca                                             20

<210> SEQ ID NO 384
<211> LENGTH: 20
<212> TYPE: DNA
<213> ORGANISM: Homo sapiens

<400> SEQUENCE: 384
gcaaaggctt taccatattg                                             20

<210> SEQ ID NO 385
<211> LENGTH: 16
<212> TYPE: DNA
<213> ORGANISM: Homo sapiens
```

```
<400> SEQUENCE: 385
gctcagcacc cccatt                                                    16

<210> SEQ ID NO 386
<211> LENGTH: 16
<212> TYPE: DNA
<213> ORGANISM: Homo sapiens

<400> SEQUENCE: 386
tccctgctcg ggaaac                                                    16

<210> SEQ ID NO 387
<211> LENGTH: 20
<212> TYPE: DNA
<213> ORGANISM: Homo sapiens

<400> SEQUENCE: 387
gttctccaga gagacagcac                                                20

<210> SEQ ID NO 388
<211> LENGTH: 19
<212> TYPE: DNA
<213> ORGANISM: Homo sapiens

<400> SEQUENCE: 388
gagagcaaca ctattgccc                                                 19

<210> SEQ ID NO 389
<211> LENGTH: 21
<212> TYPE: DNA
<213> ORGANISM: Homo sapiens

<400> SEQUENCE: 389
tatagacttc agccctgctg c                                              21

<210> SEQ ID NO 390
<211> LENGTH: 20
<212> TYPE: DNA
<213> ORGANISM: Homo sapiens

<400> SEQUENCE: 390
cctctgtagg atgcagttgg                                                20

<210> SEQ ID NO 391
<211> LENGTH: 20
<212> TYPE: DNA
<213> ORGANISM: Homo sapiens

<400> SEQUENCE: 391
ttgctacgca ctcctctact                                                20

<210> SEQ ID NO 392
<211> LENGTH: 20
<212> TYPE: DNA
<213> ORGANISM: Homo sapiens

<400> SEQUENCE: 392
gtgaaggcag gaaatgtgac                                                20

<210> SEQ ID NO 393
<211> LENGTH: 20
<212> TYPE: DNA
<213> ORGANISM: Homo sapiens
```

```
<400> SEQUENCE: 393
atcctagacc agaggagccc                                              20

<210> SEQ ID NO 394
<211> LENGTH: 20
<212> TYPE: DNA
<213> ORGANISM: Homo sapiens

<400> SEQUENCE: 394 ctcccctgg tccagttatt                                               20

<210> SEQ ID NO 395
<211> LENGTH: 20
<212> TYPE: DNA
<213> ORGANISM: Homo sapiens

<400> SEQUENCE: 395
aactttcatt tgccaaggga                                              20

<210> SEQ ID NO 396
<211> LENGTH: 20
<212> TYPE: DNA
<213> ORGANISM: Homo sapiens

<400> SEQUENCE: 396
agcagatctg ctcttgcgat                                              20

<210> SEQ ID NO 397
<211> LENGTH: 20
<212> TYPE: DNA
<213> ORGANISM: Homo sapiens

<400> SEQUENCE: 397
acagttgtca tcggtaggca                                              20

<210> SEQ ID NO 398
<211> LENGTH: 22
<212> TYPE: DNA
<213> ORGANISM: Homo sapiens

<400> SEQUENCE: 398
aaaagtatga atgggatgga gc                                           22

<210> SEQ ID NO 399
<211> LENGTH: 20
<212> TYPE: DNA
<213> ORGANISM: Homo sapiens

<400> SEQUENCE: 399
gtgcaggtgg cgtttatttt                                              20

<210> SEQ ID NO 400
<211> LENGTH: 21
<212> TYPE: DNA
<213> ORGANISM: Homo sapiens

<400> SEQUENCE: 400
ccctatatct ccgtgtgctc c                                            21

<210> SEQ ID NO 401
<211> LENGTH: 21
<212> TYPE: DNA
```

```
<213> ORGANISM: Homo sapiens

<400> SEQUENCE: 401
gctctagtgg gaaacctcag g                                              21

<210> SEQ ID NO 402
<211> LENGTH: 20
<212> TYPE: DNA
<213> ORGANISM: Homo sapiens

<400> SEQUENCE: 402
gaattccagg ctcttgcttg                                                20

<210> SEQ ID NO 403
<211> LENGTH: 20
<212> TYPE: DNA
<213> ORGANISM: Homo sapiens

<400> SEQUENCE: 403
ggtttggtct caaaggcaaa                                                20

<210> SEQ ID NO 404
<211> LENGTH: 20
<212> TYPE: DNA
<213> ORGANISM: Homo sapiens

<400> SEQUENCE: 404
ccagtacatg gtggtcacca                                                20

<210> SEQ ID NO 405
<211> LENGTH: 20
<212> TYPE: DNA
<213> ORGANISM: Homo sapiens

<400> SEQUENCE: 405
gctgccttgg aatttctgtt                                                20

<210> SEQ ID NO 406
<211> LENGTH: 18
<212> TYPE: DNA
<213> ORGANISM: Homo sapiens

<400> SEQUENCE: 406
gtgctgtggt ggggaaag                                                  18

<210> SEQ ID NO 407
<211> LENGTH: 20
<212> TYPE: DNA
<213> ORGANISM: Homo sapiens

<400> SEQUENCE: 407
attcaagctc atccagaccc                                                20

<210> SEQ ID NO 408
<211> LENGTH: 20
<212> TYPE: DNA
<213> ORGANISM: Homo sapiens

<400> SEQUENCE: 408
ggactggccc tttgaaactc                                                20

<210> SEQ ID NO 409
<211> LENGTH: 22
```

```
<212> TYPE: DNA
<213> ORGANISM: Homo sapiens

<400> SEQUENCE: 409
atattgaccg tgcacaaata cg                                        22

<210> SEQ ID NO 410
<211> LENGTH: 21
<212> TYPE: DNA
<213> ORGANISM: Homo sapiens

<400> SEQUENCE: 410
agacctggga aaagtggaga a                                         21

<210> SEQ ID NO 411
<211> LENGTH: 20
<212> TYPE: DNA
<213> ORGANISM: Homo sapiens

<400> SEQUENCE: 411
attggcagtg gaaaatgctt                                           20

<210> SEQ ID NO 412
<211> LENGTH: 25
<212> TYPE: DNA
<213> ORGANISM: Homo sapiens

<400> SEQUENCE: 412
ttaatctttt gtcaacttcc tgatt                                     25

<210> SEQ ID NO 413
<211> LENGTH: 23
<212> TYPE: DNA
<213> ORGANISM: Homo sapiens

<400> SEQUENCE: 413
tctgtcctcc tttcaccgga agc                                       23

<210> SEQ ID NO 414
<211> LENGTH: 29
<212> TYPE: DNA
<213> ORGANISM: Homo sapiens

<400> SEQUENCE: 414
ggataaagaa actccgctct gctggtaga                                 29

<210> SEQ ID NO 415
<211> LENGTH: 25
<212> TYPE: DNA
<213> ORGANISM: Homo sapiens

<400> SEQUENCE: 415
tcagggcctg tgttgccgca ctctg                                     25

<210> SEQ ID NO 416
<211> LENGTH: 25
<212> TYPE: DNA
<213> ORGANISM: Homo sapiens

<400> SEQUENCE: 416
agcgatgtaa agggtaccag tgccg                                     25

<210> SEQ ID NO 417
```

```
<211> LENGTH: 18
<212> TYPE: DNA
<213> ORGANISM: Homo sapiens

<400> SEQUENCE: 417
aggcatgcaa gcttctta                                                 18

<210> SEQ ID NO 418
<211> LENGTH: 18
<212> TYPE: DNA
<213> ORGANISM: Homo sapiens

<400> SEQUENCE: 418
ccgggaggag acatctat                                                 18

<210> SEQ ID NO 419
<211> LENGTH: 19
<212> TYPE: DNA
<213> ORGANISM: Homo sapiens

<400> SEQUENCE: 419
tggtaagcac agaaaatgc                                                19

<210> SEQ ID NO 420
<211> LENGTH: 18
<212> TYPE: DNA
<213> ORGANISM: Homo sapiens

<400> SEQUENCE: 420
aatggatggg ggattatt                                                 18

<210> SEQ ID NO 421
<211> LENGTH: 18
<212> TYPE: DNA
<213> ORGANISM: Homo sapiens

<400> SEQUENCE: 421
ctggacgtta tgtctgcc                                                 18

<210> SEQ ID NO 422
<211> LENGTH: 18
<212> TYPE: DNA
<213> ORGANISM: Homo sapiens

<400> SEQUENCE: 422
agaggcccag tcacagat                                                 18

<210> SEQ ID NO 423
<211> LENGTH: 19
<212> TYPE: DNA
<213> ORGANISM: Homo sapiens

<400> SEQUENCE: 423
atcactctga actgccact                                                19

<210> SEQ ID NO 424
<211> LENGTH: 20
<212> TYPE: DNA
<213> ORGANISM: Homo sapiens

<400> SEQUENCE: 424
cccttctgtt tttctgtttt                                               20
```

-continued

```
<210> SEQ ID NO 425
<211> LENGTH: 18
<212> TYPE: DNA
<213> ORGANISM: Homo sapiens

<400> SEQUENCE: 425
caagctttga aggaagag                                                     18

<210> SEQ ID NO 426
<211> LENGTH: 19
<212> TYPE: DNA
<213> ORGANISM: Homo sapiens

<400> SEQUENCE: 426
taggacgtta agtgaggac                                                    19

<210> SEQ ID NO 427
<211> LENGTH: 18
<212> TYPE: DNA
<213> ORGANISM: Homo sapiens

<400> SEQUENCE: 427
gctctgcagt gggtaaaa                                                     18

<210> SEQ ID NO 428
<211> LENGTH: 18
<212> TYPE: DNA
<213> ORGANISM: Homo sapiens

<400> SEQUENCE: 428
actctccaag actgtgcg                                                     18

<210> SEQ ID NO 429
<211> LENGTH: 18
<212> TYPE: DNA
<213> ORGANISM: Homo sapiens

<400> SEQUENCE: 429
ccctttctga ggcaagat                                                     18

<210> SEQ ID NO 430
<211> LENGTH: 18
<212> TYPE: DNA
<213> ORGANISM: Homo sapiens

<400> SEQUENCE: 430
gaccacctgg gagagaac                                                     18

<210> SEQ ID NO 431
<211> LENGTH: 18
<212> TYPE: DNA
<213> ORGANISM: Homo sapiens

<400> SEQUENCE: 431
cgctatgagt cccatctg                                                     18

<210> SEQ ID NO 432
<211> LENGTH: 18
<212> TYPE: DNA
<213> ORGANISM: Homo sapiens

<400> SEQUENCE: 432
gatcagctgc aatgaagg                                                     18
```

```
<210> SEQ ID NO 433
<211> LENGTH: 18
<212> TYPE: DNA
<213> ORGANISM: Homo sapiens

<400> SEQUENCE: 433
ttgagtacac ggggtgac                                                 18

<210> SEQ ID NO 434
<211> LENGTH: 18
<212> TYPE: DNA
<213> ORGANISM: Homo sapiens

<400> SEQUENCE: 434
cgcaggactg aaagatga                                                 18

<210> SEQ ID NO 435
<211> LENGTH: 18
<212> TYPE: DNA
<213> ORGANISM: Homo sapiens

<400> SEQUENCE: 435
acctgtctcc tctcctgg                                                 18

<210> SEQ ID NO 436
<211> LENGTH: 18
<212> TYPE: DNA
<213> ORGANISM: Homo sapiens

<400> SEQUENCE: 436
tgcttttctt ctgtggga                                                 18

<210> SEQ ID NO 437
<211> LENGTH: 18
<212> TYPE: DNA
<213> ORGANISM: Homo sapiens

<400> SEQUENCE: 437
atgaccagca agcattgt                                                 18

<210> SEQ ID NO 438
<211> LENGTH: 18
<212> TYPE: DNA
<213> ORGANISM: Homo sapiens

<400> SEQUENCE: 438
gtactgggat tacaggcg                                                 18

<210> SEQ ID NO 439
<211> LENGTH: 18
<212> TYPE: DNA
<213> ORGANISM: Homo sapiens

<400> SEQUENCE: 439
gcagaaggtc ctttggat                                                 18

<210> SEQ ID NO 440
<211> LENGTH: 18
<212> TYPE: DNA
<213> ORGANISM: Homo sapiens

<400> SEQUENCE: 440
tttgcaggat tcatgctt                                                 18
```

<210> SEQ ID NO 441
<211> LENGTH: 19
<212> TYPE: DNA
<213> ORGANISM: Homo sapiens

<400> SEQUENCE: 441
cgacattctt ttctggagg                                          19

<210> SEQ ID NO 442
<211> LENGTH: 19
<212> TYPE: DNA
<213> ORGANISM: Homo sapiens

<400> SEQUENCE: 442
acctttgcat gttggtttt                                          19

<210> SEQ ID NO 443
<211> LENGTH: 18
<212> TYPE: DNA
<213> ORGANISM: Homo sapiens

<400> SEQUENCE: 443 gcactttcc ttccttcc                                            18

<210> SEQ ID NO 444
<211> LENGTH: 18
<212> TYPE: DNA
<213> ORGANISM: Homo sapiens

<400> SEQUENCE: 444
tgctttgctt tcttctgg                                           18

<210> SEQ ID NO 445
<211> LENGTH: 19
<212> TYPE: DNA
<213> ORGANISM: Homo sapiens

<400> SEQUENCE: 445
acagctccag agagaagga                                          19

<210> SEQ ID NO 446
<211> LENGTH: 19
<212> TYPE: DNA
<213> ORGANISM: Homo sapiens

<400> SEQUENCE: 446
gcagtcactt gaaaccaga                                          19

<210> SEQ ID NO 447
<211> LENGTH: 18
<212> TYPE: DNA
<213> ORGANISM: Homo sapiens

<400> SEQUENCE: 447
aggcatcaag ctttcctt                                           18

<210> SEQ ID NO 448
<211> LENGTH: 18
<212> TYPE: DNA
<213> ORGANISM: Homo sapiens

<400> SEQUENCE: 448

```
ggtttagaga accgagcc                                                18
```

<210> SEQ ID NO 449
<211> LENGTH: 18
<212> TYPE: DNA
<213> ORGANISM: Homo sapiens

<400> SEQUENCE: 449

```
gtggtgctgc aagttacc                                                18
```

<210> SEQ ID NO 450
<211> LENGTH: 18
<212> TYPE: DNA
<213> ORGANISM: Homo sapiens

<400> SEQUENCE: 450

```
ggaatccctt tctttcca                                                18
```

<210> SEQ ID NO 451
<211> LENGTH: 18
<212> TYPE: DNA
<213> ORGANISM: Homo sapiens

<400> SEQUENCE: 451

```
gaccatttgt tacgcagc                                                18
```

<210> SEQ ID NO 452
<211> LENGTH: 19
<212> TYPE: DNA
<213> ORGANISM: Homo sapiens

<400> SEQUENCE: 452

```
gatgggtgtg aatgaacaa                                               19
```

<210> SEQ ID NO 453
<211> LENGTH: 19
<212> TYPE: DNA
<213> ORGANISM: Homo sapiens

<400> SEQUENCE: 453

```
ctcaagcttc tgttcatgc                                               19
```

<210> SEQ ID NO 454
<211> LENGTH: 18
<212> TYPE: DNA
<213> ORGANISM: Homo sapiens

<400> SEQUENCE: 454

```
gctgtgagtg tcttggct                                                18
```

<210> SEQ ID NO 455
<211> LENGTH: 18
<212> TYPE: DNA
<213> ORGANISM: Homo sapiens

<400> SEQUENCE: 455

```
tacagaaaac cgcagctc                                                18
```

<210> SEQ ID NO 456
<211> LENGTH: 18
<212> TYPE: DNA
<213> ORGANISM: Homo sapiens

<400> SEQUENCE: 456

-continued gccaccaaag gaaagatt 18

<210> SEQ ID NO 457
<211> LENGTH: 18
<212> TYPE: DNA
<213> ORGANISM: Homo sapiens

<400> SEQUENCE: 457
aaaaggaggg aatcatgg 18

<210> SEQ ID NO 458
<211> LENGTH: 18
<212> TYPE: DNA
<213> ORGANISM: Homo sapiens

<400> SEQUENCE: 458
tcacttagca ggaggcag 18

<210> SEQ ID NO 459
<211> LENGTH: 18
<212> TYPE: DNA
<213> ORGANISM: Homo sapiens

<400> SEQUENCE: 459
ctgagcatcc gatgagac 18

<210> SEQ ID NO 460
<211> LENGTH: 18
<212> TYPE: DNA
<213> ORGANISM: Homo sapiens

<400> SEQUENCE: 460
gtgcaaaatg agcagctt 18

<210> SEQ ID NO 461
<211> LENGTH: 18
<212> TYPE: DNA
<213> ORGANISM: Homo sapiens

<400> SEQUENCE: 461
tctaacccct tactgggc 18

<210> SEQ ID NO 462
<211> LENGTH: 18
<212> TYPE: DNA
<213> ORGANISM: Homo sapiens

<400> SEQUENCE: 462
tcctcaaact gggaatga 18

<210> SEQ ID NO 463
<211> LENGTH: 18
<212> TYPE: DNA
<213> ORGANISM: Homo sapiens

<400> SEQUENCE: 463
tttacacagg accaggga 18

<210> SEQ ID NO 464
<211> LENGTH: 18
<212> TYPE: DNA
<213> ORGANISM: Homo sapiens

```
<400> SEQUENCE: 464
atctccccca ctcagaag                                                 18

<210> SEQ ID NO 465
<211> LENGTH: 18
<212> TYPE: DNA
<213> ORGANISM: Homo sapiens

<400> SEQUENCE: 465
gtccacgggc tttattct                                                 18

<210> SEQ ID NO 466
<211> LENGTH: 22
<212> TYPE: DNA
<213> ORGANISM: Homo sapiens

<400> SEQUENCE: 466
tgagcataaa tttcattagc tg                                            22

<210> SEQ ID NO 467
<211> LENGTH: 20
<212> TYPE: DNA
<213> ORGANISM: Homo sapiens

<400> SEQUENCE: 467
ggaagagcaa aataaatcca                                               20

<210> SEQ ID NO 468
<211> LENGTH: 19
<212> TYPE: DNA
<213> ORGANISM: Homo sapiens

<400> SEQUENCE: 468
ggtgcacaga attgttcat                                                19

<210> SEQ ID NO 469
<211> LENGTH: 18
<212> TYPE: DNA
<213> ORGANISM: Homo sapiens

<400> SEQUENCE: 469
agcacgctta tttcatgg                                                 18

<210> SEQ ID NO 470
<211> LENGTH: 18
<212> TYPE: DNA
<213> ORGANISM: Homo sapiens

<400> SEQUENCE: 470
gtaacaccag cagggaca                                                 18

<210> SEQ ID NO 471
<211> LENGTH: 18
<212> TYPE: DNA
<213> ORGANISM: Homo sapiens

<400> SEQUENCE: 471
tcctgctgca ttatggat                                                 18

<210> SEQ ID NO 472
<211> LENGTH: 18
<212> TYPE: DNA
<213> ORGANISM: Homo sapiens
```

```
<400> SEQUENCE: 472
gggggtgaga agtaggaa                                          18

<210> SEQ ID NO 473
<211> LENGTH: 18
<212> TYPE: DNA
<213> ORGANISM: Homo sapiens

<400> SEQUENCE: 473
atggggatta aatacggg                                          18

<210> SEQ ID NO 474
<211> LENGTH: 18
<212> TYPE: DNA
<213> ORGANISM: Homo sapiens

<400> SEQUENCE: 474
agctagcatt gggctctt                                          18

<210> SEQ ID NO 475
<211> LENGTH: 18
<212> TYPE: DNA
<213> ORGANISM: Homo sapiens

<400> SEQUENCE: 475
ctgaggagaa gaggctgg                                          18

<210> SEQ ID NO 476
<211> LENGTH: 18
<212> TYPE: DNA
<213> ORGANISM: Homo sapiens

<400> SEQUENCE: 476
cgccttacaa ggcaagta                                          18

<210> SEQ ID NO 477
<211> LENGTH: 18
<212> TYPE: DNA
<213> ORGANISM: Homo sapiens

<400> SEQUENCE: 477
aggatgcttg ctagggtt                                          18

<210> SEQ ID NO 478
<211> LENGTH: 18
<212> TYPE: DNA
<213> ORGANISM: Homo sapiens

<400> SEQUENCE: 478
cacaagtgtc tggaaggc                                          18

<210> SEQ ID NO 479
<211> LENGTH: 18
<212> TYPE: DNA
<213> ORGANISM: Homo sapiens

<400> SEQUENCE: 479
ggtctcagga gcccttta                                          18

<210> SEQ ID NO 480
<211> LENGTH: 21
<212> TYPE: DNA
```

-continued

<213> ORGANISM: Homo sapiens

<400> SEQUENCE: 480
acatgccact cttctcacta a                                       21

<210> SEQ ID NO 481
<211> LENGTH: 18
<212> TYPE: DNA
<213> ORGANISM: Homo sapiens

<400> SEQUENCE: 481
acttaaccaa ggatgggg                                           18

<210> SEQ ID NO 482
<211> LENGTH: 18
<212> TYPE: DNA
<213> ORGANISM: Homo sapiens

<400> SEQUENCE: 482
caacccacga gcataaga                                           18

<210> SEQ ID NO 483
<211> LENGTH: 18
<212> TYPE: DNA
<213> ORGANISM: Homo sapiens

<400> SEQUENCE: 483
taggctctgc actcttgg                                           18

<210> SEQ ID NO 484
<211> LENGTH: 18
<212> TYPE: DNA
<213> ORGANISM: Homo sapiens

<400> SEQUENCE: 484
acccacggag tctctctc                                           18

<210> SEQ ID NO 485
<211> LENGTH: 18
<212> TYPE: DNA
<213> ORGANISM: Homo sapiens

<400> SEQUENCE: 485
taaaggcggt gaagtgag                                           18

<210> SEQ ID NO 486
<211> LENGTH: 18
<212> TYPE: DNA
<213> ORGANISM: Homo sapiens

<400> SEQUENCE: 486
ctaccgctct cctaggct                                           18

<210> SEQ ID NO 487
<211> LENGTH: 18
<212> TYPE: DNA
<213> ORGANISM: Homo sapiens

<400> SEQUENCE: 487
tggggccaga taattctt                                           18

<210> SEQ ID NO 488
<211> LENGTH: 18

```
<212> TYPE: DNA
<213> ORGANISM: Homo sapiens

<400> SEQUENCE: 488
ctggtgtttg gtggtgtt                                                 18

<210> SEQ ID NO 489
<211> LENGTH: 18
<212> TYPE: DNA
<213> ORGANISM: Homo sapiens

<400> SEQUENCE: 489
aaggaagagg tcaccagg                                                 18

<210> SEQ ID NO 490
<211> LENGTH: 18
<212> TYPE: DNA
<213> ORGANISM: Homo sapiens

<400> SEQUENCE: 490
cacaaattcc atttccca                                                 18

<210> SEQ ID NO 491
<211> LENGTH: 21
<212> TYPE: DNA
<213> ORGANISM: Homo sapiens

<400> SEQUENCE: 491
tcaataggtg atccaacatt t                                             21

<210> SEQ ID NO 492
<211> LENGTH: 18
<212> TYPE: DNA
<213> ORGANISM: Homo sapiens

<400> SEQUENCE: 492
aaagtcccac aaagggtc                                                 18

<210> SEQ ID NO 493
<211> LENGTH: 18
<212> TYPE: DNA
<213> ORGANISM: Homo sapiens

<400> SEQUENCE: 493
gggtaggggg atctttttt                                                18

<210> SEQ ID NO 494
<211> LENGTH: 18
<212> TYPE: DNA
<213> ORGANISM: Homo sapiens

<400> SEQUENCE: 494
tgtggaacat tcattggc                                                 18

<210> SEQ ID NO 495
<211> LENGTH: 18
<212> TYPE: DNA
<213> ORGANISM: Homo sapiens

<400> SEQUENCE: 495
gtcctgggaa agatggaa                                                 18

<210> SEQ ID NO 496
```

```
<211> LENGTH: 18
<212> TYPE: DNA
<213> ORGANISM: Homo sapiens

<400> SEQUENCE: 496
tcaaagcgtc tcccataa                                                   18

<210> SEQ ID NO 497
<211> LENGTH: 18
<212> TYPE: DNA
<213> ORGANISM: Homo sapiens

<400> SEQUENCE: 497
tctttcgctg tacttggc                                                   18

<210> SEQ ID NO 498
<211> LENGTH: 18
<212> TYPE: DNA
<213> ORGANISM: Homo sapiens

<400> SEQUENCE: 498
tgggaggtca gagtgatg                                                   18

<210> SEQ ID NO 499
<211> LENGTH: 19
<212> TYPE: DNA
<213> ORGANISM: Homo sapiens

<400> SEQUENCE: 499
ggacagtgta tgtgttggg                                                  19

<210> SEQ ID NO 500
<211> LENGTH: 18
<212> TYPE: DNA
<213> ORGANISM: Homo sapiens

<400> SEQUENCE: 500
aggcagctgt ttttgtga                                                   18

<210> SEQ ID NO 501
<211> LENGTH: 18
<212> TYPE: DNA
<213> ORGANISM: Homo sapiens

<400> SEQUENCE: 501
cttcttgagt cccgtgtg                                                   18

<210> SEQ ID NO 502
<211> LENGTH: 19
<212> TYPE: DNA
<213> ORGANISM: Homo sapiens

<400> SEQUENCE: 502
caaccgagaa tcctctagc                                                  19

<210> SEQ ID NO 503
<211> LENGTH: 18
<212> TYPE: DNA
<213> ORGANISM: Homo sapiens

<400> SEQUENCE: 503
gctgggagag aatcacaa                                                   18
```

```
<210> SEQ ID NO 504
<211> LENGTH: 18
<212> TYPE: DNA
<213> ORGANISM: Homo sapiens

<400> SEQUENCE: 504
gctttgcaga agagacca                                                 18

<210> SEQ ID NO 505
<211> LENGTH: 18
<212> TYPE: DNA
<213> ORGANISM: Homo sapiens

<400> SEQUENCE: 505
acgctgtcag gtcacact                                                 18

<210> SEQ ID NO 506
<211> LENGTH: 18
<212> TYPE: DNA
<213> ORGANISM: Homo sapiens

<400> SEQUENCE: 506
ggaggatgct caggtgat                                                 18

<210> SEQ ID NO 507
<211> LENGTH: 18
<212> TYPE: DNA
<213> ORGANISM: Homo sapiens

<400> SEQUENCE: 507
tagggggatc tttttcca                                                 18

<210> SEQ ID NO 508
<211> LENGTH: 18
<212> TYPE: DNA
<213> ORGANISM: Homo sapiens

<400> SEQUENCE: 508
gagcaatttg aaaagcca                                                 18

<210> SEQ ID NO 509
<211> LENGTH: 18
<212> TYPE: DNA
<213> ORGANISM: Homo sapiens

<400> SEQUENCE: 509
atggtccagc tcctctgt                                                 18

<210> SEQ ID NO 510
<211> LENGTH: 18
<212> TYPE: DNA
<213> ORGANISM: Homo sapiens

<400> SEQUENCE: 510
atagagcacc ccatctcc                                                 18

<210> SEQ ID NO 511
<211> LENGTH: 18
<212> TYPE: DNA
<213> ORGANISM: Homo sapiens

<400> SEQUENCE: 511
aacattgctg ttagccca                                                 18
```

```
<210> SEQ ID NO 512
<211> LENGTH: 18
<212> TYPE: DNA
<213> ORGANISM: Homo sapiens

<400> SEQUENCE: 512
gcaatcgaaa cagcattc                                                 18

<210> SEQ ID NO 513
<211> LENGTH: 18
<212> TYPE: DNA
<213> ORGANISM: Homo sapiens

<400> SEQUENCE: 513
atgagttggc agctgaag                                                 18

<210> SEQ ID NO 514
<211> LENGTH: 18
<212> TYPE: DNA
<213> ORGANISM: Homo sapiens

<400> SEQUENCE: 514
aatgaaggtc ttgcctcc                                                 18

<210> SEQ ID NO 515
<211> LENGTH: 20
<212> TYPE: DNA
<213> ORGANISM: Homo sapiens

<400> SEQUENCE: 515
gaggagaaga tccacaagcg                                               20

<210> SEQ ID NO 516
<211> LENGTH: 20
<212> TYPE: DNA
<213> ORGANISM: Homo sapiens

<400> SEQUENCE: 516
tctctggggc atactgaacc                                               20

<210> SEQ ID NO 517
<211> LENGTH: 18
<212> TYPE: DNA
<213> ORGANISM: Homo sapiens

<400> SEQUENCE: 517
ctgagctttt ggcactgt                                                 18

<210> SEQ ID NO 518
<211> LENGTH: 18
<212> TYPE: DNA
<213> ORGANISM: Homo sapiens

<400> SEQUENCE: 518
ctgctaggtg acagcagg                                                 18

<210> SEQ ID NO 519
<211> LENGTH: 20
<212> TYPE: DNA
<213> ORGANISM: Homo sapiens

<400> SEQUENCE: 519
tgtatgagtc tggagggtgt                                               20
```

```
<210> SEQ ID NO 520
<211> LENGTH: 18
<212> TYPE: DNA
<213> ORGANISM: Homo sapiens

<400> SEQUENCE: 520
acacctggct gaggaaat                                                 18

<210> SEQ ID NO 521
<211> LENGTH: 18
<212> TYPE: DNA
<213> ORGANISM: Homo sapiens

<400> SEQUENCE: 521
gcaggggacg tgataata                                                 18

<210> SEQ ID NO 522
<211> LENGTH: 18
<212> TYPE: DNA
<213> ORGANISM: Homo sapiens

<400> SEQUENCE: 522
ttttgcttcc taccatgc                                                 18

<210> SEQ ID NO 523
<211> LENGTH: 18
<212> TYPE: DNA
<213> ORGANISM: Homo sapiens

<400> SEQUENCE: 523
aaaattgtga gcacctcc                                                 18

<210> SEQ ID NO 524
<211> LENGTH: 23
<212> TYPE: DNA
<213> ORGANISM: Homo sapiens

<400> SEQUENCE: 524
tttatattta aagtggcttt gtt                                           23

<210> SEQ ID NO 525
<211> LENGTH: 18
<212> TYPE: DNA
<213> ORGANISM: Homo sapiens

<400> SEQUENCE: 525
gtgcaaagcc cacagtat                                                 18

<210> SEQ ID NO 526
<211> LENGTH: 18
<212> TYPE: DNA
<213> ORGANISM: Homo sapiens

<400> SEQUENCE: 526
aggaaaatgc aagagcag                                                 18

<210> SEQ ID NO 527
<211> LENGTH: 20
<212> TYPE: DNA
<213> ORGANISM: Homo sapiens

<400> SEQUENCE: 527
```

```
ccactgaatt gcatactttg                                              20

<210> SEQ ID NO 528
<211> LENGTH: 18
<212> TYPE: DNA
<213> ORGANISM: Homo sapiens

<400> SEQUENCE: 528
tctgggtcca gtctgcta                                                18

<210> SEQ ID NO 529
<211> LENGTH: 18
<212> TYPE: DNA
<213> ORGANISM: Homo sapiens

<400> SEQUENCE: 529
agattttggg gagtcagg                                                18

<210> SEQ ID NO 530
<211> LENGTH: 17
<212> TYPE: DNA
<213> ORGANISM: Homo sapiens

<400> SEQUENCE: 530
gcgctcaagc aattctc                                                 17

<210> SEQ ID NO 531
<211> LENGTH: 18
<212> TYPE: DNA
<213> ORGANISM: Homo sapiens

<400> SEQUENCE: 531
caagccccaa agtagtca                                                18

<210> SEQ ID NO 532
<211> LENGTH: 18
<212> TYPE: DNA
<213> ORGANISM: Homo sapiens

<400> SEQUENCE: 532
gaatcatcca atccacga                                                18

<210> SEQ ID NO 533
<211> LENGTH: 18
<212> TYPE: DNA
<213> ORGANISM: Homo sapiens

<400> SEQUENCE: 533
agcctccagg tgactacc                                                18

<210> SEQ ID NO 534
<211> LENGTH: 18
<212> TYPE: DNA
<213> ORGANISM: Homo sapiens

<400> SEQUENCE: 534
gaaggacatg gtcagcag                                                18

<210> SEQ ID NO 535
<211> LENGTH: 18
<212> TYPE: DNA
<213> ORGANISM: Homo sapiens

<400> SEQUENCE: 535
```

```
atgctttcag cattttcg                                        18

<210> SEQ ID NO 536
<211> LENGTH: 18
<212> TYPE: DNA
<213> ORGANISM: Homo sapiens

<400> SEQUENCE: 536
tgatccgtgg tagggtta                                        18

<210> SEQ ID NO 537
<211> LENGTH: 18
<212> TYPE: DNA
<213> ORGANISM: Homo sapiens

<400> SEQUENCE: 537
gtcggattgg tttcacaa                                        18

<210> SEQ ID NO 538
<211> LENGTH: 19
<212> TYPE: DNA
<213> ORGANISM: Homo sapiens

<400> SEQUENCE: 538
ttttatggga atttcagcc                                       19

<210> SEQ ID NO 539
<211> LENGTH: 21
<212> TYPE: DNA
<213> ORGANISM: Homo sapiens

<400> SEQUENCE: 539
tttggaaaag aacagaaatg t                                    21

<210> SEQ ID NO 540
<211> LENGTH: 19
<212> TYPE: DNA
<213> ORGANISM: Homo sapiens

<400> SEQUENCE: 540
ggctagtctt tcctgaacc                                       19

<210> SEQ ID NO 541
<211> LENGTH: 18
<212> TYPE: DNA
<213> ORGANISM: Homo sapiens

<400> SEQUENCE: 541
ccttaatgcc cctgattc                                        18

<210> SEQ ID NO 542
<211> LENGTH: 18
<212> TYPE: DNA
<213> ORGANISM: Homo sapiens

<400> SEQUENCE: 542
gcgtttacaa gctgagga                                        18

<210> SEQ ID NO 543
<211> LENGTH: 18
<212> TYPE: DNA
<213> ORGANISM: Homo sapiens
```

-continued

```
<400> SEQUENCE: 543
tcaagcttgc tttctcaa                                                 18

<210> SEQ ID NO 544
<211> LENGTH: 18
<212> TYPE: DNA
<213> ORGANISM: Homo sapiens

<400> SEQUENCE: 544
gtagcccagc aagtgtct                                                 18

<210> SEQ ID NO 545
<211> LENGTH: 18
<212> TYPE: DNA
<213> ORGANISM: Homo sapiens

<400> SEQUENCE: 545
cctggctgga gataggat                                                 18

<210> SEQ ID NO 546
<211> LENGTH: 18
<212> TYPE: DNA
<213> ORGANISM: Homo sapiens

<400> SEQUENCE: 546
cttcccctct gcctatgt                                                 18

<210> SEQ ID NO 547
<211> LENGTH: 18
<212> TYPE: DNA
<213> ORGANISM: Homo sapiens

<400> SEQUENCE: 547
ggcacgtact tcctacca                                                 18

<210> SEQ ID NO 548
<211> LENGTH: 18
<212> TYPE: DNA
<213> ORGANISM: Homo sapiens

<400> SEQUENCE: 548
ggtgcttctt acaggcaa                                                 18

<210> SEQ ID NO 549
<211> LENGTH: 16
<212> TYPE: DNA
<213> ORGANISM: Homo sapiens

<400> SEQUENCE: 549
acccaggctg gtgtgt                                                   16

<210> SEQ ID NO 550
<211> LENGTH: 23
<212> TYPE: DNA
<213> ORGANISM: Homo sapiens

<400> SEQUENCE: 550
actgagttaa ttatcactcc cct                                           23

<210> SEQ ID NO 551
<211> LENGTH: 18
<212> TYPE: DNA
<213> ORGANISM: Homo sapiens
```

```
<400> SEQUENCE: 551 gatgcattt gcttcacc                                          18

<210> SEQ ID NO 552
<211> LENGTH: 21
<212> TYPE: DNA
<213> ORGANISM: Homo sapiens

<400> SEQUENCE: 552 tctgcttta gagctgttag c                                      21

<210> SEQ ID NO 553
<211> LENGTH: 19
<212> TYPE: DNA
<213> ORGANISM: Homo sapiens

<400> SEQUENCE: 553
tcaagcttca aagagcaga                                        19

<210> SEQ ID NO 554
<211> LENGTH: 18
<212> TYPE: DNA
<213> ORGANISM: Homo sapiens

<400> SEQUENCE: 554
ggagtacatc ccaggacc                                         18

<210> SEQ ID NO 555
<211> LENGTH: 19
<212> TYPE: DNA
<213> ORGANISM: Homo sapiens

<400> SEQUENCE: 555
tggtgctttt aaatccaga                                        19

<210> SEQ ID NO 556
<211> LENGTH: 21
<212> TYPE: DNA
<213> ORGANISM: Homo sapiens

<400> SEQUENCE: 556
ctcccttact tacttgcatt g                                     21

<210> SEQ ID NO 557
<211> LENGTH: 18
<212> TYPE: DNA
<213> ORGANISM: Homo sapiens

<400> SEQUENCE: 557
tcttctccca gggaatct                                         18

<210> SEQ ID NO 558
<211> LENGTH: 18
<212> TYPE: DNA
<213> ORGANISM: Homo sapiens

<400> SEQUENCE: 558
tttatgtccc ctgagcac                                         18

<210> SEQ ID NO 559
<211> LENGTH: 19
<212> TYPE: DNA
```

```
<213> ORGANISM: Homo sapiens

<400> SEQUENCE: 559
tccctggcta tcttgaatc                                          19

<210> SEQ ID NO 560
<211> LENGTH: 16
<212> TYPE: DNA
<213> ORGANISM: Homo sapiens

<400> SEQUENCE: 560
cttgactggg tccacg                                             16

<210> SEQ ID NO 561
<211> LENGTH: 20
<212> TYPE: DNA
<213> ORGANISM: Homo sapiens

<400> SEQUENCE: 561
cgagacgcca gtagatacca                                         20

<210> SEQ ID NO 562
<211> LENGTH: 20
<212> TYPE: DNA
<213> ORGANISM: Homo sapiens

<400> SEQUENCE: 562
catcctccat gcctttcagt                                         20

<210> SEQ ID NO 563
<211> LENGTH: 20
<212> TYPE: DNA
<213> ORGANISM: Homo sapiens

<400> SEQUENCE: 563
agttccagag aacgagacgc                                         20

<210> SEQ ID NO 564
<211> LENGTH: 20
<212> TYPE: DNA
<213> ORGANISM: Homo sapiens

<400> SEQUENCE: 564
cttgtcatcc tccatgcctt                                         20

<210> SEQ ID NO 565
<211> LENGTH: 20
<212> TYPE: DNA
<213> ORGANISM: Homo sapiens

<400> SEQUENCE: 565
gagcgtgaga ggttgaggag                                         20

<210> SEQ ID NO 566
<211> LENGTH: 20
<212> TYPE: DNA
<213> ORGANISM: Homo sapiens

<400> SEQUENCE: 566
aaacaaactc cagacgcacc                                         20

<210> SEQ ID NO 567
<211> LENGTH: 24
```

```
<212> TYPE: DNA
<213> ORGANISM: Homo sapiens

<400> SEQUENCE: 567
ctgaaccact acctgtatga cctg                                      24

<210> SEQ ID NO 568
<211> LENGTH: 25
<212> TYPE: DNA
<213> ORGANISM: Homo sapiens

<400> SEQUENCE: 568
ctaactactt actcctacag ggccc                                     25

<210> SEQ ID NO 569
<211> LENGTH: 23
<212> TYPE: DNA
<213> ORGANISM: Homo sapiens

<400> SEQUENCE: 569
gaagcatttc aatactttaa ctg                                       23

<210> SEQ ID NO 570
<211> LENGTH: 20
<212> TYPE: DNA
<213> ORGANISM: Homo sapiens

<400> SEQUENCE: 570
ccactccagt gcacccaatc                                           20

<210> SEQ ID NO 571
<211> LENGTH: 20
<212> TYPE: DNA
<213> ORGANISM: Homo sapiens

<400> SEQUENCE: 571
cttctcctgg ccactctgac                                           20

<210> SEQ ID NO 572
<211> LENGTH: 21
<212> TYPE: DNA
<213> ORGANISM: Homo sapiens

<400> SEQUENCE: 572
ggtttacctt tgaatcccag c                                         21

<210> SEQ ID NO 573
<211> LENGTH: 22
<212> TYPE: DNA
<213> ORGANISM: Homo sapiens

<400> SEQUENCE: 573
tgaggatgaa tgagcacata gg                                        22

<210> SEQ ID NO 574
<211> LENGTH: 21
<212> TYPE: DNA
<213> ORGANISM: Homo sapiens

<400> SEQUENCE: 574
tttgtggtcc attgagtagg c                                         21

<210> SEQ ID NO 575
```

-continued

```
<211> LENGTH: 20
<212> TYPE: DNA
<213> ORGANISM: Homo sapiens

<400> SEQUENCE: 575 agggaagga atgtgcttgg                                              20

<210> SEQ ID NO 576
<211> LENGTH: 20
<212> TYPE: DNA
<213> ORGANISM: Homo sapiens

<400> SEQUENCE: 576
ttcggctgag cgggcagtgt                                             20

<210> SEQ ID NO 577
<211> LENGTH: 26
<212> TYPE: DNA
<213> ORGANISM: Homo sapiens

<400> SEQUENCE: 577
attgaaggtc ctccaaaaga atgctg                                      26

<210> SEQ ID NO 578
<211> LENGTH: 30
<212> TYPE: DNA
<213> ORGANISM: Homo sapiens

<400> SEQUENCE: 578
agaacgtcaa catatctttt tgggggacac                                  30

<210> SEQ ID NO 579
<211> LENGTH: 22
<212> TYPE: DNA
<213> ORGANISM: Homo sapiens

<400> SEQUENCE: 579
ttgtatttga ggactttgct cg                                          22

<210> SEQ ID NO 580
<211> LENGTH: 20
<212> TYPE: DNA
<213> ORGANISM: Homo sapiens

<400> SEQUENCE: 580
cggtaccatc ctcctcttcc                                             20

<210> SEQ ID NO 581
<211> LENGTH: 20
<212> TYPE: DNA
<213> ORGANISM: Homo sapiens

<400> SEQUENCE: 581
tttttgcctc atctatgccc                                             20

<210> SEQ ID NO 582
<211> LENGTH: 20
<212> TYPE: DNA
<213> ORGANISM: Homo sapiens

<400> SEQUENCE: 582
gggtgacaga gcaagactcc                                             20
```

```
<210> SEQ ID NO 583
<211> LENGTH: 18
<212> TYPE: DNA
<213> ORGANISM: Homo sapiens

<400> SEQUENCE: 583
ttgctcaagt tctcctgg                                                 18

<210> SEQ ID NO 584
<211> LENGTH: 18
<212> TYPE: DNA
<213> ORGANISM: Homo sapiens

<400> SEQUENCE: 584
accttgtttt gagggggag                                                18

<210> SEQ ID NO 585
<211> LENGTH: 18
<212> TYPE: DNA
<213> ORGANISM: Homo sapiens

<400> SEQUENCE: 585
cttggctatt tggacagc                                                 18

<210> SEQ ID NO 586
<211> LENGTH: 18
<212> TYPE: DNA
<213> ORGANISM: Homo sapiens

<400> SEQUENCE: 586
gggcatttac tcacttgc                                                 18

<210> SEQ ID NO 587
<211> LENGTH: 19
<212> TYPE: DNA
<213> ORGANISM: Homo sapiens

<400> SEQUENCE: 587
cttgtgtcag ttgtcaggg                                                19

<210> SEQ ID NO 588
<211> LENGTH: 19
<212> TYPE: DNA
<213> ORGANISM: Homo sapiens

<400> SEQUENCE: 588
tggaattgtt gtgtcttgg                                                19

<210> SEQ ID NO 589
<211> LENGTH: 18
<212> TYPE: DNA
<213> ORGANISM: Homo sapiens

<400> SEQUENCE: 589
ccagttccac tggatgtt                                                 18

<210> SEQ ID NO 590
<211> LENGTH: 18
<212> TYPE: DNA
<213> ORGANISM: Homo sapiens

<400> SEQUENCE: 590
atgggctgtg tttctcaa                                                 18
```

```
<210> SEQ ID NO 591
<211> LENGTH: 18
<212> TYPE: DNA
<213> ORGANISM: Homo sapiens

<400> SEQUENCE: 591
ctgcctatcc ctggactt                                                    18

<210> SEQ ID NO 592
<211> LENGTH: 18
<212> TYPE: DNA
<213> ORGANISM: Homo sapiens

<400> SEQUENCE: 592
agtttgtccc tagtgccc                                                    18

<210> SEQ ID NO 593
<211> LENGTH: 19
<212> TYPE: DNA
<213> ORGANISM: Homo sapiens

<400> SEQUENCE: 593
caacacgtct gacatccat                                                   19

<210> SEQ ID NO 594
<211> LENGTH: 16
<212> TYPE: DNA
<213> ORGANISM: Homo sapiens

<400> SEQUENCE: 594
ggatagtgca caccca                                                      16

<210> SEQ ID NO 595
<211> LENGTH: 22
<212> TYPE: DNA
<213> ORGANISM: Homo sapiens

<400> SEQUENCE: 595
tgggtggtac tattgttccc at                                               22

<210> SEQ ID NO 596
<211> LENGTH: 20
<212> TYPE: DNA
<213> ORGANISM: Homo sapiens

<400> SEQUENCE: 596
agttccagcc cccttaccag                                                  20

<210> SEQ ID NO 597
<211> LENGTH: 20
<212> TYPE: DNA
<213> ORGANISM: Homo sapiens

<400> SEQUENCE: 597
ggccactatc atccctgtgt                                                  20

<210> SEQ ID NO 598
<211> LENGTH: 20
<212> TYPE: DNA
<213> ORGANISM: Homo sapiens

<400> SEQUENCE: 598
tttcacatgg gaagaacacg                                                  20
```

```
<210> SEQ ID NO 599
<211> LENGTH: 20
<212> TYPE: DNA
<213> ORGANISM: Homo sapiens

<400> SEQUENCE: 599
acagtgacac tagggacggg                                              20

<210> SEQ ID NO 600
<211> LENGTH: 20
<212> TYPE: DNA
<213> ORGANISM: Homo sapiens

<400> SEQUENCE: 600
tgccaggatg gagataacaa                                              20

<210> SEQ ID NO 601
<211> LENGTH: 20
<212> TYPE: DNA
<213> ORGANISM: Homo sapiens

<400> SEQUENCE: 601
cctgtggcac acatatcacc                                              20

<210> SEQ ID NO 602
<211> LENGTH: 20
<212> TYPE: DNA
<213> ORGANISM: Homo sapiens

<400> SEQUENCE: 602
acaaccaaga atggagccac                                              20

<210> SEQ ID NO 603
<211> LENGTH: 20
<212> TYPE: DNA
<213> ORGANISM: Homo sapiens

<400> SEQUENCE: 603
tgctgtgtaa caagtcccca                                              20

<210> SEQ ID NO 604
<211> LENGTH: 20
<212> TYPE: DNA
<213> ORGANISM: Homo sapiens

<400> SEQUENCE: 604
tgaacggagg acctaccaag                                              20

<210> SEQ ID NO 605
<211> LENGTH: 20
<212> TYPE: DNA
<213> ORGANISM: Homo sapiens

<400> SEQUENCE: 605
gcagggtccg actcactaag                                              20

<210> SEQ ID NO 606
<211> LENGTH: 20
<212> TYPE: DNA
<213> ORGANISM: Homo sapiens

<400> SEQUENCE: 606
```

```
gctgtgagtt cccttacgc                                                    20

<210> SEQ ID NO 607
<211> LENGTH: 20
<212> TYPE: DNA
<213> ORGANISM: Homo sapiens

<400> SEQUENCE: 607
acagtgggga caaagacagg                                                   20

<210> SEQ ID NO 608
<211> LENGTH: 20
<212> TYPE: DNA
<213> ORGANISM: Homo sapiens

<400> SEQUENCE: 608
tacagggcac ctcccagtag                                                   20

<210> SEQ ID NO 609
<211> LENGTH: 21
<212> TYPE: DNA
<213> ORGANISM: Homo sapiens

<400> SEQUENCE: 609
tcttctgtta aggtttcccc c                                                 21

<210> SEQ ID NO 610
<211> LENGTH: 20
<212> TYPE: DNA
<213> ORGANISM: Homo sapiens

<400> SEQUENCE: 610
tgtctcaaac ctccctctgc                                                   20

<210> SEQ ID NO 611
<211> LENGTH: 20
<212> TYPE: DNA
<213> ORGANISM: Homo sapiens

<400> SEQUENCE: 611
aacatatttc ctccccagcc                                                   20

<210> SEQ ID NO 612
<211> LENGTH: 19
<212> TYPE: DNA
<213> ORGANISM: Homo sapiens

<400> SEQUENCE: 612
cagtcccagc caatgagaa                                                    19

<210> SEQ ID NO 613
<211> LENGTH: 20
<212> TYPE: DNA
<213> ORGANISM: Homo sapiens

<400> SEQUENCE: 613
ctcctctgca tgggagaatc                                                   20

<210> SEQ ID NO 614
<211> LENGTH: 20
<212> TYPE: DNA
<213> ORGANISM: Homo sapiens

<400> SEQUENCE: 614
```

-continued agacctggga ccagtctgtg  20

<210> SEQ ID NO 615
<211> LENGTH: 20
<212> TYPE: DNA
<213> ORGANISM: Homo sapiens

<400> SEQUENCE: 615
gggagacgac gtcacaagat  20

<210> SEQ ID NO 616
<211> LENGTH: 20
<212> TYPE: DNA
<213> ORGANISM: Homo sapiens

<400> SEQUENCE: 616
tgatgttggg aagatggtga  20

<210> SEQ ID NO 617
<211> LENGTH: 20
<212> TYPE: DNA
<213> ORGANISM: Homo sapiens

<400> SEQUENCE: 617
caggcatctt ctatgtgcca  20

<210> SEQ ID NO 618
<211> LENGTH: 20
<212> TYPE: DNA
<213> ORGANISM: Homo sapiens

<400> SEQUENCE: 618
gggaggcaca agttctttca  20

<210> SEQ ID NO 619
<211> LENGTH: 20
<212> TYPE: DNA
<213> ORGANISM: Homo sapiens

<400> SEQUENCE: 619
acttcgtggc actgagtgtg  20

<210> SEQ ID NO 620
<211> LENGTH: 20
<212> TYPE: DNA
<213> ORGANISM: Homo sapiens

<400> SEQUENCE: 620
cctttcttac ggatgaggca  20

<210> SEQ ID NO 621
<211> LENGTH: 20
<212> TYPE: DNA
<213> ORGANISM: Homo sapiens

<400> SEQUENCE: 621
ggctgctgag ctcttctgat  20

<210> SEQ ID NO 622
<211> LENGTH: 20
<212> TYPE: DNA
<213> ORGANISM: Homo sapiens

```
<400> SEQUENCE: 622
tgggtctctc tgcctgactt                                              20

<210> SEQ ID NO 623
<211> LENGTH: 20
<212> TYPE: DNA
<213> ORGANISM: Homo sapiens

<400> SEQUENCE: 623
tcacctactt ccagcttccg                                              20

<210> SEQ ID NO 624
<211> LENGTH: 20
<212> TYPE: DNA
<213> ORGANISM: Homo sapiens

<400> SEQUENCE: 624
agacctggga ccagtctgtg                                              20

<210> SEQ ID NO 625
<211> LENGTH: 20
<212> TYPE: DNA
<213> ORGANISM: Homo sapiens

<400> SEQUENCE: 625
ctcctctgca tgggagaatc                                              20

<210> SEQ ID NO 626
<211> LENGTH: 20
<212> TYPE: DNA
<213> ORGANISM: Homo sapiens

<400> SEQUENCE: 626
aattcaggag acctgggacc                                              20

<210> SEQ ID NO 627
<211> LENGTH: 15
<212> TYPE: DNA
<213> ORGANISM: Artificial Sequence
<220> FEATURE:
<223> OTHER INFORMATION: Artificial Sequence is a BstXI-linker adapter.

<400> SEQUENCE: 627
gtcttcacca cgggg                                                   15

<210> SEQ ID NO 628
<211> LENGTH: 11
<212> TYPE: DNA
<213> ORGANISM: Artificial Sequence
<220> FEATURE:
<223> OTHER INFORMATION: Artificial Sequence is a BstXI-linker adapter.

<400> SEQUENCE: 628
gtggtgaaga c                                                       11

<210> SEQ ID NO 629
<211> LENGTH: 18
<212> TYPE: DNA
<213> ORGANISM: Artificial Sequence
<220> FEATURE:
<223> OTHER INFORMATION: Artificial Sequence is a primer.

<400> SEQUENCE: 629
ccaagttctg agaagtcc                                                18
```

<210> SEQ ID NO 630
<211> LENGTH: 17
<212> TYPE: DNA
<213> ORGANISM: Artificial Sequence
<220> FEATURE:
<223> OTHER INFORMATION: Artificial Sequence is a primer.

<400> SEQUENCE: 630
aatacctgaa accatac                                                17

<210> SEQ ID NO 631
<211> LENGTH: 17
<212> TYPE: DNA
<213> ORGANISM: Artificial Sequence
<220> FEATURE:
<223> OTHER INFORMATION: Artificial Sequence is an allele specific
      oligonucleotide.

<400> SEQUENCE: 631
agactggggt gagacgc                                                17

<210> SEQ ID NO 632
<211> LENGTH: 19
<212> TYPE: DNA
<213> ORGANISM: Artificial Sequence
<220> FEATURE:
<223> OTHER INFORMATION: Artificial Sequence is an allele specific
      oligonucleotide.

<400> SEQUENCE: 632
cagactgggt tgagacgcc                                              19

<210> SEQ ID NO 633
<211> LENGTH: 24
<212> TYPE: DNA
<213> ORGANISM: Artificial Sequence
<220> FEATURE:
<223> OTHER INFORMATION: Artificial Sequence is a primer.

<400> SEQUENCE: 633
cccgtgtgct ccgccgccca gttc                                        24

<210> SEQ ID NO 634
<211> LENGTH: 25
<212> TYPE: DNA
<213> ORGANISM: Artificial Sequence
<220> FEATURE:
<223> OTHER INFORMATION: Artificial Sequence is a primer.

<400> SEQUENCE: 634
ggctcacgga gctcatcatg gactt                                       25

<210> SEQ ID NO 635
<211> LENGTH: 502
<212> TYPE: DNA
<213> ORGANISM: Artificial Sequence
<220> FEATURE:
<223> OTHER INFORMATION: Artificial Sequence is a primer.

<400> SEQUENCE: 635
cccgtgtgct ccgccgccca gttcccctgc gcgcggggtc agtgtgtgga cctgcgcctg     60
cgctgcgacg gcgaggcaga ctgtcaggac cgctcagacg aggtggactg tgacgccatc    120
tgcctgccca accagttccg gtgtgcgagc ggccagtgtg tcctcatcaa acagcagtgc    180

```
gactccttcc ccgactgtat cgacggctcc gacgagctca tgtgtgaaat caccaagccg        240
ccctcagacg acagcccggc ccacagcagt gccatcgggc ccgtcattgg catcatcctc        300
tctctcttcg tcatgggtgg tgtctatttt gtgtgccagc gcgtggtgtg ccagcgctat        360 gcggggcca acgggccctt cccgcacgag tatgtcagcg ggaccccgca cgtgcccctc         420
aatttcatag ccccgggcgg ttcccagcat ggccccttca caggcatcgc atgcggaaag        480
tccatgatga gctccgtgag cc                                                 502

<210> SEQ ID NO 636
<211> LENGTH: 21
<212> TYPE: DNA
<213> ORGANISM: Artificial Sequence
<220> FEATURE:
<223> OTHER INFORMATION: Artificial Sequence is a primer.

<400> SEQUENCE: 636
agcgaggcca ccatccacag g                                                   21

<210> SEQ ID NO 637
<211> LENGTH: 21
<212> TYPE: DNA
<213> ORGANISM: Artificial Sequence
<220> FEATURE:
<223> OTHER INFORMATION: Artificial Sequence is a primer.

<400> SEQUENCE: 637
tcgctggtcg gcataatcaa t                                                   21

<210> SEQ ID NO 638
<211> LENGTH: 501
<212> TYPE: DNA
<213> ORGANISM: Artificial Sequence
<220> FEATURE:
<223> OTHER INFORMATION: Artificial Sequence is a primer.

<400> SEQUENCE: 638
agcagagcca ccatccacag gatctccctg gagactaaca caacgatgt ggctatccca         60 ctcacgggtg tcaaagaggc ctctgcactg gactttgatg tgtccaacaa tcacatctac       120
tggactgatg ttagcctcaa gacgatcagc cgagccttca tgaatgggag ctcagtggag       180
cacgtgattg agtttggcct cgactaccct gaaggaatgg ctgtggactg gatgggcaag       240
aacctctatt gggcggacac agggaccaac aggattgagg tggcccggct ggatgggcag       300
ttccggcagg tgcttgtgtg gagagacctt gacaacccca ggtctctggc tctggatcct       360
actaaaggct acatctactg gactgagtgg ggtggcaagc caaggattgt gcgggccttc       420
atggatggga ccaattgtat gacactggta gacaaggtgg gccgggccaa cgacctcacc       480
attgattatg ccgaccagcg a                                                  501

<210> SEQ ID NO 639
<211> LENGTH: 26
<212> TYPE: RNA
<213> ORGANISM: Artificial Sequence
<220> FEATURE:
<223> OTHER INFORMATION: Artificial Sequence is a Zmax1 oligonucleotide.

<400> SEQUENCE: 639
raguacagcu ucuugccaac ccaguc                                              26

<210> SEQ ID NO 640
<211> LENGTH: 26
```

-continued

```
<212> TYPE: RNA
<213> ORGANISM: Artificial Sequence
<220> FEATURE:
<223> OTHER INFORMATION: Artificial Sequence is a Zmax1 oligonucleotide.

<400> SEQUENCE: 640
ruccuccagg ucgaugguca gcccau                                          26

<210> SEQ ID NO 641
<211> LENGTH: 26
<212> TYPE: RNA
<213> ORGANISM: Artificial Sequence
<220> FEATURE:
<223> OTHER INFORMATION: Artificial Sequence is a Zmax1 oligonucleotide.

<400> SEQUENCE: 641
rgucugaguc cgaguucaaa uccagg                                          26
```

HIGH BONE MASS GENE OF 11Q13.3

RELATED APPLICATIONS

This application is a continuation-in-part of application No. 09/229,319, filed Jan. 13, 1999, which claims benefit of U.S. Provisional Application No. 60/071,449, filed Jan. 13, 1998, and U.S. Provisional Application No. 60/105,511, filed Oct. 23, 1998, all of which are herein incorporated by reference in their entirety.

FIELD OF THE INVENTION

The present invention relates generally to the field of genetics, genomics and molecular biology. More particularly, the invention relates to methods and materials used to isolate, detect and sequence a high bone mass gene and corresponding wild-type gene, and mutants thereof. The present invention also relates to the high bone mass gene, the corresponding wild-type gene, and mutants thereof. The genes identified in the present invention are implicated in the ontology and physiology of bone development. The invention also provides nucleic acids, proteins, cloning vectors, expression vectors, transformed hosts, methods of developing pharmaceutical compositions, methods of identifying molecules involved in bone development, and methods of diagnosing and treating diseases involved in bone development. In preferred embodiments, the present invention is directed to methods for treating, diagnosing, preventing and screening for normal and abnormal conditions of bone, including metabolic bone diseases such as osteoporosis.

BACKGROUND OF THE INVENTION

Two of the most common types of osteoporosis are postmenopausal and senile osteoporosis. Osteoporosis affects men as well as women, and, taken with other abnormalities of bone, presents an ever-increasing health risk for an aging population. The most common type of osteoporosis is that associated with menopause. Most women lose between 20–60% of the bone mass in the trabecular compartment of the bone within 3–6 years after the cessation of menses. This rapid loss is generally associated with an increase of bone resorption and formation. However, the resorptive cycle is more dominant and the result is a net loss of bone mass. Osteoporosis is a common and serious disease among postmenopausal women. There are an estimated 25 million women in the United States alone who are afflicted with this disease. The results of osteoporosis are both personally harmful, and also account for a large economic loss due to its chronicity and the need for extensive and long-term support (hospitalization and nursing home care) from the disease sequelae. This is especially true in more elderly patients. Additionally, while osteoporosis is generally not thought of as a life-threatening condition, a 20–30% mortality rate is related to hip fractures in elderly women. A large percentage of this mortality rate can be directly associated with postmenopausal osteoporosis.

The most vulnerable tissue in the bone to the effects of postmenopausal osteoporosis is the trabecular bone. This tissue is often referred to as spongy bone and is particularly concentrated near the ends of the bone near the joints and in the vertebrae of the spine. The trabecular tissue is characterized by small structures which inter-connect with each other as well as the more solid and dense cortical tissue which makes up the outer surface and central shaft of the bone. This criss-cross network of trabeculae gives lateral support to the outer cortical structure and is critical to the biomechanical strength of the overall structure. In postmenopausal osteoporosis, it is primarily the net resorption and loss of the trabeculae which lead to the failure and fracture of the bone. In light of the loss of the trabeculae in postmenopausal women, it is not surprising that the most common fractures are those associated with bones which are highly dependent on trabecular support, e.g., the vertebrae, the neck of the femur, and the forearm. Indeed, hip fracture, Colle's fractures, and vertebral crush fractures are indicative of postmenopausal osteoporosis.

One of the earliest generally accepted methods for treatment of postmenopausal osteoporosis was estrogen replacement therapy. Although this therapy frequently is successful, patient compliance is low, primarily due to the undesirable side-effects of chronic estrogen treatment. Frequently cited side-effects of estrogen replacement therapy include reinitiation of menses, bloating, depression, and fear of breast or uterine cancer. In order to limit the known threat of uterine cancer in those women who have not undergone a hysterectomy, a protocol of estrogen and progestin cyclic therapy is often employed. This protocol is similar to that which is used in birth control regimens, and often is not tolerated by women because of the side-effects characteristic of progestin. More recently, certain antiestrogens, originally developed for the treatment of breast cancer, have been shown in experimental models of postmenopausal osteoporosis to be efficacious. Among these agents is raloxifene (See, U.S. Pat. No. 5,393,763, and Black et al, J. Clin. Invest., 93:63–69 (1994)). In addition, tamoxifene, a widely used clinical agent for the treatment of breast cancer, has been shown to increase bone mineral density in post menopausal women suffering from breast cancer (Love et al, N. Engl. J. Med., 326:852–856 (1992)).

Another therapy for the treatment of postmenopausal osteoporosis is the use of calcitonin. Calcitonin is a naturally occurring peptide which inhibits bone resorption and has been approved for this use in many countries (Overgaard et al, Br. Med. J., 305:556–561 (1992)). The use of calcitonin has been somewhat limited, however. Its effects are very modest in increasing bone mineral density and the treatment is very expensive. Another therapy for the treatment of postmenopausal osteoporosis is the use of bis-phosphonates. These compounds were originally developed for use in Paget's disease and malignant hypercalcemia. They have been shown to inhibit bone resorption. Alendronate, one compound of this class, has been approved for the treatment of postmenopausal osteoporosis. These agents may be helpful in the treatment of osteoporosis, but these agents also have potential liabilities which include osteomalacia, extremely long half-life in bone (greater than 2 years), and possible "frozen bone syndrome," e.g., the cessation of normal bone remodeling.

Senile osteoporosis is similar to postmenopausal osteoporosis in that it is marked by the loss of bone mineral density and resulting increase in fracture rate, morbidity, and associated mortality. Generally, it occurs in later life, i.e., after 70 years of age. Historically, senile osteoporosis has been more common in females, but with the advent of a more elderly male population, this disease is becoming a major factor in the health of both sexes. It is not clear what, if any, role hormones such as testosterone or estrogen have in this disease, and its etiology remains obscure. Treatment of this disease has not been very satisfactory. Hormone therapy, estrogen in women and testosterone in men, has shown equivocal results; calcitonin and bis-phosphonates may be of some utility.

The peak mass of the skeleton at maturity is largely under genetic control. Twin studies have shown that the variance in bone mass between adult monozygotic twins is smaller than between dizygotic twins (Slemenda et al, *J. Bone Miner. Res.*, 6:561–567 (1991); Young et al, *J. Bone Miner. Res.*, 6:561–567 (1995); Pocock et al, *J. Clin. Invest.*, 80:706–710 (1987); Kelly et al, *J. Bone Miner. Res.*, 8:11–17 (1993)), and it has been estimated that up to 60% or more of the variance in skeletal mass is inherited (Krall et al, *J. Bone Miner. Res.*, 10:S367 (1993)). Peak skeletal mass is the most powerful determinant of bone mass in elderly years (Hui et al, *Ann. Int. Med.*, 111:355–361 (1989)), even though the rate of age-related bone loss in adult and later life is also a strong determinant (Hui et al, *Osteoporosis Int.*, 1:30–34 (1995)). Since bone mass is the principal measurable determinant of fracture risk, the inherited peak skeletal mass achieved at maturity is an important determinant of an individual's risk of fracture later in life. Thus, study of the genetic basis of bone mass is of considerable interest in the etiology of fractures due to osteoporosis.

Recently, a strong interest in the genetic control of peak bone mass has developed in the field of osteoporosis. The interest has focused mainly on candidate genes with suitable polymorphisms to test for association with variation in bone mass within the normal range, or has focused on examination of genes and gene loci associated with low bone mass in the range found in patients with osteoporosis. The vitamin D receptor locus (VDR) (Morrison et al, *Nature*, 367:284–287 (1994)), PTH gene (Howard et al, *J. Clin. Endocrinol. Metab.*, 80:2800–2805 (1995); Johnson et al, *J. Bone Miner. Res.*, 8:11–17 (1995); Gong et al, *J. Bone Miner. Res.*, 10:S462 (1995)) and the estrogen receptor gene (Hosoi et al, *J. Bone Miner. Res.*, 10:S170 (1995); Morrison et al, *Nature*, 367:284–287 (1994)) have figured most prominently in this work. These studies are difficult because bone mass (the phenotype) is a continuous, quantitative, polygenic trait, and is confounded by environmental factors such as nutrition, co-morbid disease, age, physical activity, and other factors. Also, this type of study design requires large numbers of subjects. In particular, the results of VDR studies to date have been confusing and contradictory (Garnero et al, *J. Bone Miner. Res.*, 10:1283–1288 (1995); Eisman et al, *J. Bone. Miner. Res.*, 10:1289–1293 (1995); Peacock, *J. Bone Miner. Res.*, 10:1294–1297 (1995)). Furthermore, the work thus far has not shed much light on the mechanism(s) whereby the genetic influences might exert their effect on bone mass.

While it is well known that peak bone mass is largely determined by genetic rather than environmental factors, studies to determine the gene loci (and ultimately the genes) linked to variation in bone mass are difficult and expensive. Study designs which utilize the power of linkage analysis, e.g., sib-pair or extended family, are generally more informative than simple association studies, although the latter do have value. However, genetic linkage studies involving bone mass are hampered by two major problems. The first problem is the phenotype, as discussed briefly above. Bone mass is a continuous, quantitative trait, and establishing a discrete phenotype is difficult. Each anatomical site for measurement may be influenced by several genes, many of which may be different from site to site. The second problem is the age component of the phenotype. By the time an individual can be identified as having low bone mass, there is a high probability that their parents or other members of prior generations will be deceased and therefore unavailable for study, and younger generations may not have even reached peak bone mass, making their phenotyping uncertain for genetic analysis.

Regardless, linkage analysis can be used to find the location of a gene causing a hereditary "disorder" and does not require any knowledge of the biochemical nature of the disorder, i.e., a mutated protein that is believed to cause the disorder does not need to be known. Traditional approaches depend on assumptions concerning the disease process that might implicate a known protein as a candidate to be evaluated. The genetic localization approach using linkage analysis can be used to first find the general chromosomal region in which the defective gene is located and then to gradually reduce the size of the region in order to determine the location of the specific mutated gene as precisely as possible. After the gene itself is discovered within the candidate region, the messenger RNA and the protein are identified and, along with the DNA, are checked for mutations.

The genetic localization approach has practical implications since the location of the disease can be used for prenatal diagnosis even before the altered gene that causes the disease is found. Linkage analysis can enable families, even many of those that do not have a sick child, to know whether they are carriers of a disease gene and to evaluate the condition of an unborn child through molecular diagnosis. The transmission of a disease within families, then, can be used to find the defective gene. As used herein, reference to "high bone mass" (HBM) is analogous to reference to a disease state, although from a practical standpoint high bone mass can actually help a subject avoid the disease known as osteoporosis.

Linkage analysis is possible because of the nature of inheritance of chromosomes from parents to offspring. During meiosis, the two parental homologues pair to guide their proper separation to daughter cells. While they are lined up and paired, the two homologues exchange pieces of the chromosomes, in an event called "crossing over" or "recombination."The resulting chromosomes are chimeric, that is, they contain parts that originate from both parental homologues. The closer together two sequences are on the chromosome, the less likely that a recombination event will occur between them, and the more closely linked they are. In a linkage analysis experiment, two positions on the chromosomes are followed from one generation to the next to determine the frequency of recombination between them. In a study of an inherited disease, one of the chromosomal positions is marked by the disease gene or its normal counterpart, i.e., the inheritance of the chromosomal region can be determined by examining whether the individual displays symptoms of the disorder or not. The other position is marked by a DNA sequence that shows natural variation in the population such that the two homologues can be distinguished based on the copy of the "marker" sequence that they possess. In every family, the inheritance of the genetic marker sequence is compared to the inheritance of the disease state. If, within a family carrying an autosomal dominant disorder such as high bone mass, every affected individual carries the same form of the marker and all the unaffected individuals carry at least one different form of the marker, there is a great probability that the disease gene and the marker are located close to each other. In this way, chromosomes may be systematically checked with known markers and compared to the disease state. The data obtained from the different families is combined, and analyzed together by a computer using statistical methods. The result is information indicating the probability of linkage between the genetic marker and the disease allowing different distances between them. A positive result can mean that the disease is very close to the marker, while a negative result indicates that it is far away on that chromosome, or on an entirely different chromosome.

Linkage analysis is performed by typing all members of the affected family at a given marker locus and evaluating the co-inheritance of a particular disease state with the marker probe, thereby determining how often the two of them are co-inherited. The recombination frequency can be used as a measure of the genetic distance between two gene loci. A recombination frequency of 1% is equivalent to 1 map unit, or 1 centiMorgan (cM), which is roughly equivalent to 1,000 kb of DNA. This relationship holds up to frequencies of about 20% or 20 cM.

The entire human genome is 3,300 cM long. In order to find an unknown disease gene within 5–10 cM of a marker locus, the whole human genome can be searched with roughly 330 informative marker loci spaced at approximately 10 cM intervals (Botstein et al, *Am. J. Hum. Genet.*, 32:314–331 (1980)). The reliability of linkage results is established by using a number of statistical methods. The method most commonly used for the analysis of linkage in humans is the LOD score method (Morton, *Prog. Clin. Biol. Res.*, 147:245–265 (1984), Morton et al, *Am. J. Hum. Genet.*, 38:868–883 (1986)) which was incorporated into the computer program LIPED by Ott, *Am. J. Hum. Genet.*, 28:528–529 (1976). LOD scores are the logarithm of the ratio of the likelihood that two loci are linked at a given distance to that they are not linked (>50 cM apart). The advantage of using logarithmic values is that they can be summed among families with the same disease. This becomes necessary given the relatively small size of human families.

By convention, a total LOD score greater than +3.0 (that is, odds of linkage at the specified recombination frequency being 1000 times greater than odds of no linkage) is considered to be significant evidence for linkage at that particular recombination frequency. A total LOD score of less than −2.0 (that is, odds of no linkage being 100 times greater than odds of linkage at the specified frequency) is considered to be strong evidence that the two loci under consideration are not linked at that particular recombination frequency. Until recently, most linkage analyses have been performed on the basis of two-point data, which is the relationship between the disorder under consideration and a particular genetic marker. However, as a result of the rapid advances in mapping the human genome over the last few years, and concomitant improvements in computer methodology, it has become feasible to carry out linkage analyses using multi-point data. Multi-point analysis provide a simultaneous analysis of linkage between the disease and several linked genetic markers, when the recombination distance among the markers is known.

Multi-point analysis is advantageous for two reasons. First, the informativeness of the pedigree is usually increased. Each pedigree has a certain amount of potential information, dependent on the number of parents heterozygous for the marker loci and the number of affected individuals in the family. However, few markers are sufficiently polymorphic as to be informative in all those individuals. If multiple markers are considered simultaneously, then the probability of an individual being heterozygous for at least one of the markers is greatly increased. Second, an indication of the position of the disease gene among the markers may be determined. This allows identification of flanking markers, and thus eventually allows isolation of a small region in which the disease gene resides. Lathrop et al, *Proc. Natl. Acad. Sci. USA*, 81:3443–3446 (1984) have written the most widely used computer package, LINKAGE, for multi-point analysis.

There is a need in the art for identifying the gene associated with a high bone mass phenotype. The present invention is directed to this, as well as other, important ends.

SUMMARY OF THE INVENTION

The present invention describes the Zmax1 gene and the HBM gene on chromosome 11q13.3 by genetic linkage and mutation analysis. The use of additional genetic markers linked to the genes has aided this discovery. By using linkage analysis and mutation analysis, persons predisposed to HBM may be readily identified. Cloning methods using Bacterial Artificial Chromosomes have enabled the inventors to focus on the chromosome region of 11q13.3 and to accelerate the sequencing of the autosomal dominant gene. In addition, the invention identifies the Zmax1 gene and the HBM gene, and identifies the guanine-to-thymine polymorphism mutation at position 582 in the Zmax1 gene that produces the HBM gene and the HBM phenotype.

The present invention identifies the Zmax1 gene and the HBM gene, which can be used to determine if people are predisposed to HBM and, therefore, not susceptible to diseases characterized by reduced bone density, including, for example, osteoporosis, or are predisposed and susceptible to diseases characterized by abnormally high bone density, such as, for example, osteoporosis. Older individuals carrying the HBM gene express the HBM protein, and, therefore, do not develop osteoporosis. In other words, the HBM gene is a suppressor of osteoporosis. This in vivo observation is a strong evidence that treatment of normal individuals with the HBM gene or protein, or fragments thereof, will ameliorate osteoporosis.

Moreover, such treatment will be indicated in the treatment of bone lesions, particularly bone fractures, for bone remodeling in the healing of such lesions. For example, persons predisposed to or suffering from stress fractures (i.e., the accumulation of stress-induced microfractures, eventually resulting in a true fracture through the bone cortex) may be identified and/or treated by means of the invention. Moreover, the methods and compositions of the invention will be of use in the treatment of secondary osteoporosis, where the course of therapy involves bone remodeling, such as endocrine conditions accompanying corticosteroid administration, hyperthyroidism, hypogonadism, hematologic malignancies, malabsorption and alcoholism, as well as disorders associated with vitamin D and/or phosphate metabolism, such as osteomalacia and rickets, and diseases characterized by abnormal or disordered bone remodeling, such as Paget's disease, and in neoplasms of bone, which may be benign or malignant.

In various embodiments, the present invention is directed to nucleic acids, proteins, vectors, and transformed hosts of HBM and Zmax1.

Additionally, the present invention is directed to applications of the above embodiments of the invention including, for example, gene therapy, pharmaceutical development, and diagnostic assays for bone development disorders. In preferred embodiments, the present invention is directed to methods for treating, diagnosing, preventing and screening for osteoporosis.

These and other aspects of the present invention are described in more detail below.

BRIEF DESCRIPTION OF THE FIGURES

FIGS. 2A–2B depicts the BAC/STS content physical map of the HBM region in 11q13.3. STS markers derived from genes, ESTs, microsatellites, random sequences, and BAC endsequences are denoted above the long horizontal line. For markers that are present in GDB the same nomenclature has been used. Locus names (D11S####) are listed in parentheses after the primary name if available. STSs derived from BAC endsequences are listed with the BAC name first followed by L or R for the left and right end of the clone, respectively. The two large arrows indicate the genetic markers that define the HBM critical region. The horizontal lines below the STSs indicate BAC clones identified by PCR-based screening of a nine-fold coverage BAC library. Open circles indicate that the marker did not amplify the corresponding BAC library address during library screening. Clone names use the following convention: B for BAC, the plate, row and column address, followed by -H indicating the HBM project (i.e., B36F16-H).

FIGS. 3A–3F show the genomic structure of Zmax1 with flanking intron sequences. Translation is initiated by the underlined "ATG" in exon 1. The site of the polymorphism in the HBM gene is in exon 3 and is represented by the underlined "G," whereby this nucleotide is a "T" in the HBM gene. The 3' untranslated region of the mRNA is underlined within exon 23 (exon 1, SEQ ID NO:40; exon 2, SEQ ID NO:41; exon 3, SEQ ID NO:42; exon 4, SEQ ID NO:43; exon 5, SEQ ID NO:44; exon 6, SEQ ID NO:45; exon 7, SEQ ID NO:46; exon 8, SEQ ID NO:47; exon 9, SEQ ID NO:48; exon 10, SEQ ID NO:49; exon 11, SEQ ID NO:50; exon 12, SEQ ID NO:51; exon 13, SEQ ID NO:52; exon 14, SEQ ID NO:53; exon 15, SEQ ID NO:54; exon 16, SEQ ID NO:55; exon 17, SEQ ID NO:56; exon 18, SEQ ID NO:57; exon 19, SEQ ID NO:58; exon 20, SEQ ID NO:59; exon 21, SEQ ID NO:60; exon 22, SEQ ID NO:61; and exon 23; SEQ ID NO:62).

FIG. 4 also shows the site of the glycine to valine change that occurs in the HBM protein. The signal peptide is located at amino acids 1–22, the extracellular domain is located at amino acids 23–1385, the transmembrane segment is located at amino acids 1386–1413, and the cytoplasmic domain is located at amino acids 1414–1615.

FIGS. 6A–6J show the nucleotide and amino acid sequences of the wild-type gene, Zmax1. The location for the base pair substitution at nucleotide 582, a guanine to thymine, is underlined. This allelic variant is the HBM gene. The HBM gene encodes for a protein with an amino acid substitution of glycine to valine at position 171. The 5' untranslated region (UTR) boundaries bases 1 to 70, and the 3' UTR boundaries bases 4916–5120.

FIGS. 7A and 7B are northern blot analyses showing the expression of Zmax1 in various tissues.

DETAILED DESCRIPTION OF THE INVENTION

Figure 1:
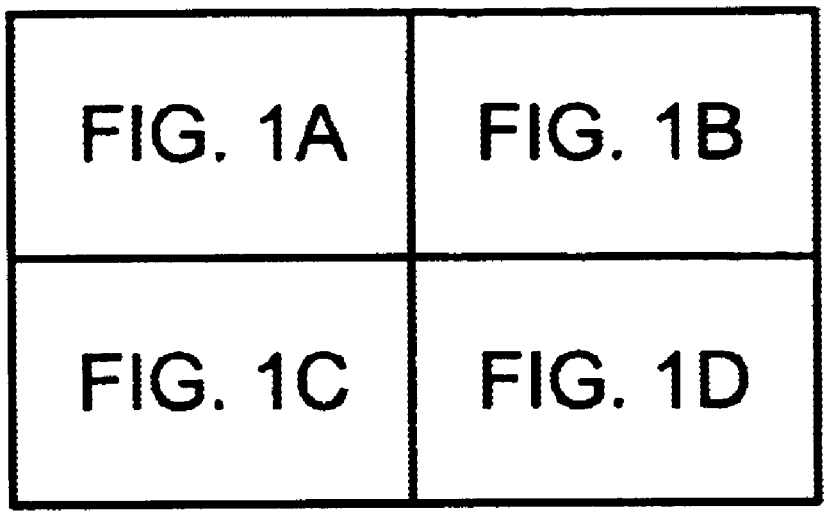
FIGS. 1A–1D shows the pedigree of the individuals used in the genetic linkage studies. Under each individual is an ID number, the z-score for spinal BMD, and the allele calls for the critical markers on chromosome 11. Solid symbols represent "affected" individuals. Symbols containing "N" are "unaffected" individuals. DNA from 37 individuals was genotyped. Question marks denote unknown genotypes or individuals who were not genotyped.
Figure 1A:
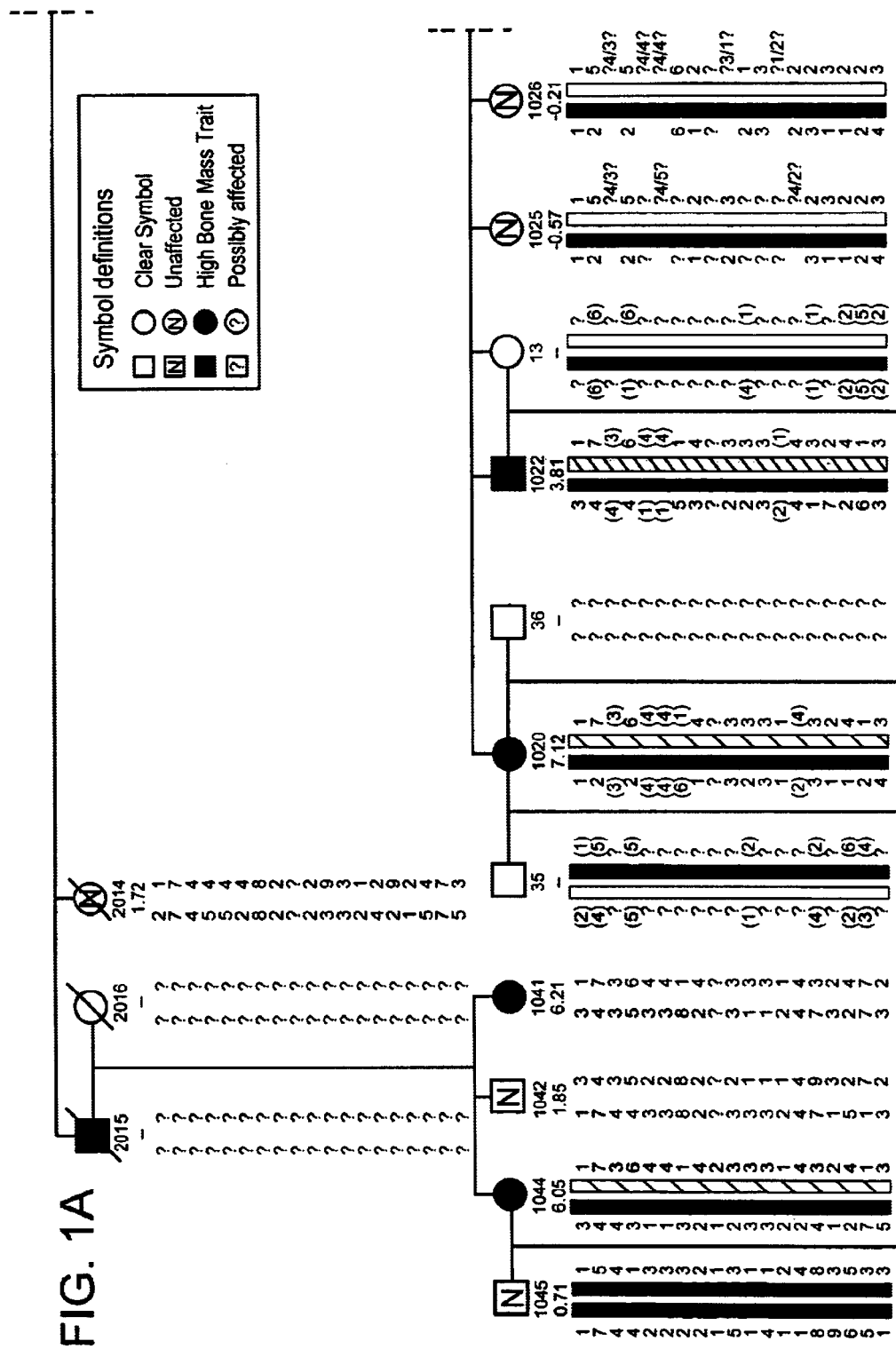
Figure 1B:
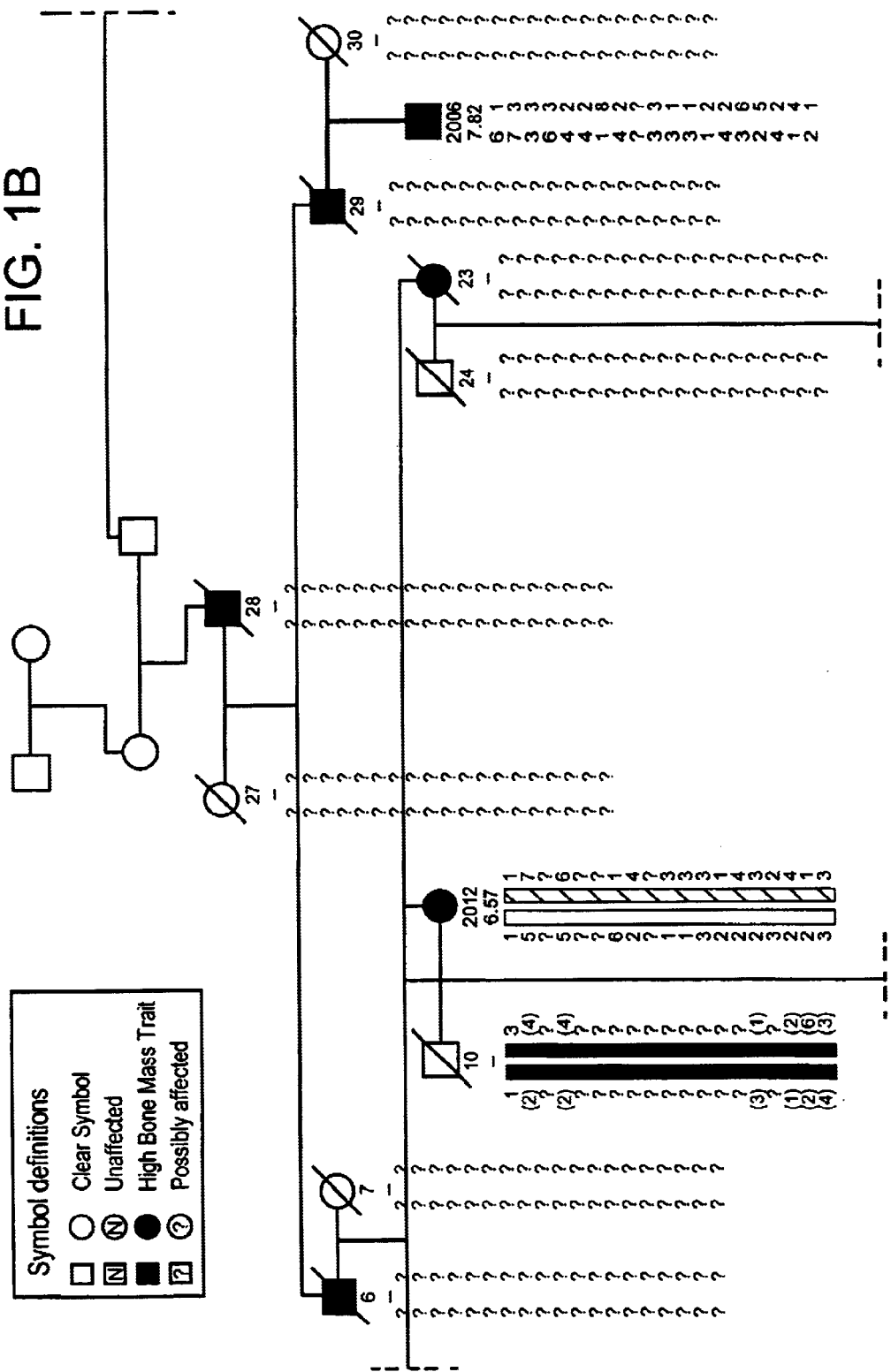
Figure 1C:
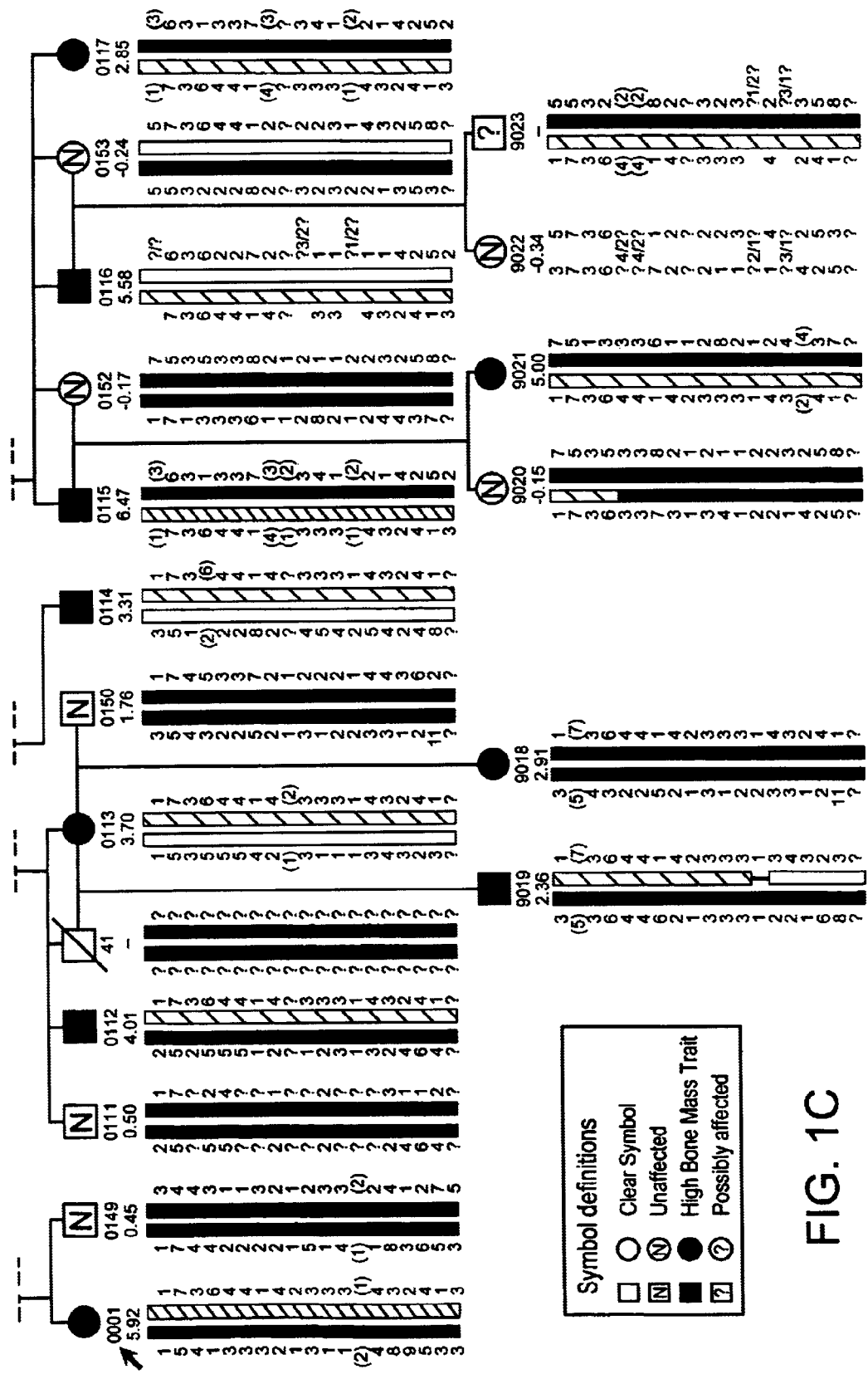
Figure 1D:
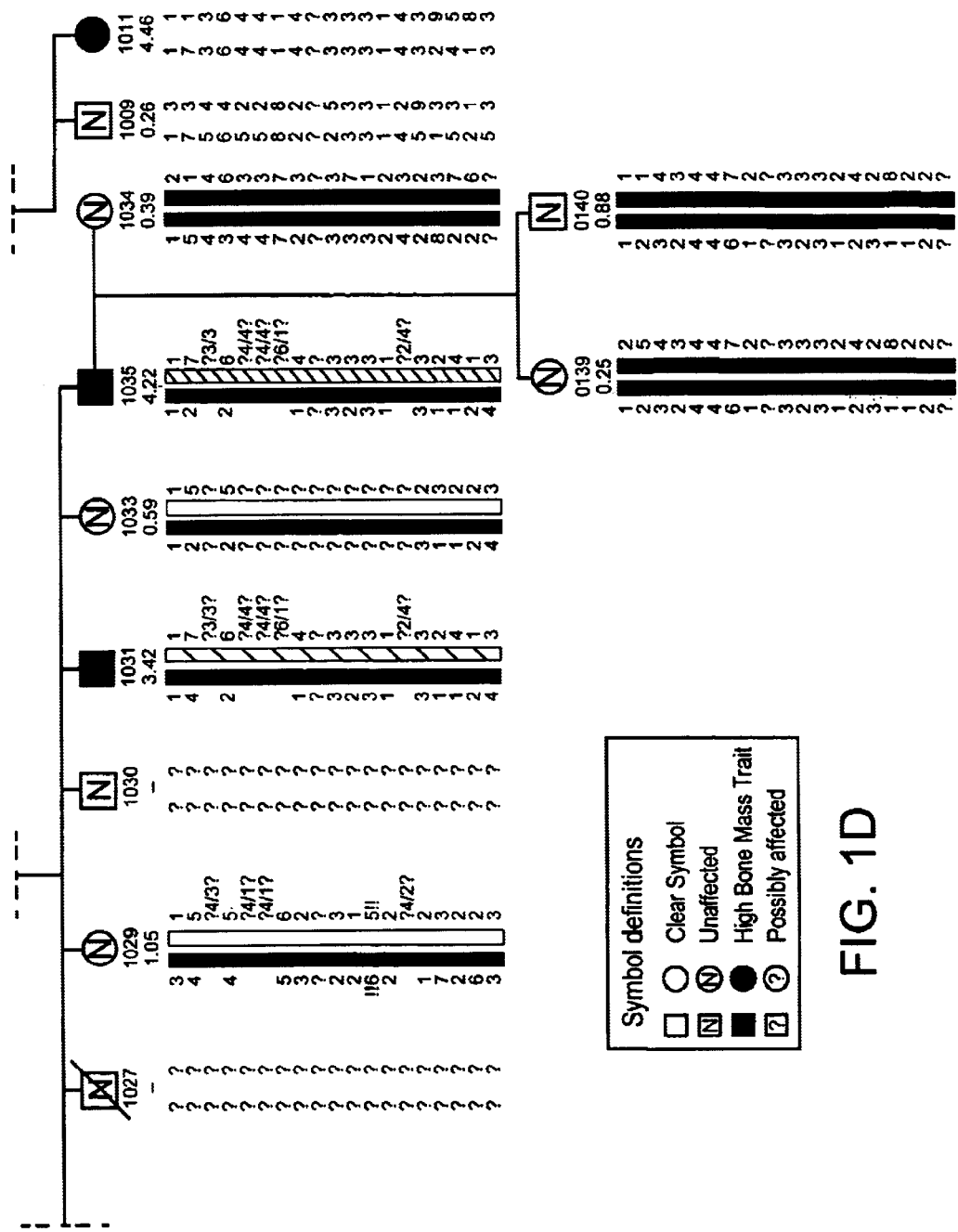
Figure 4:
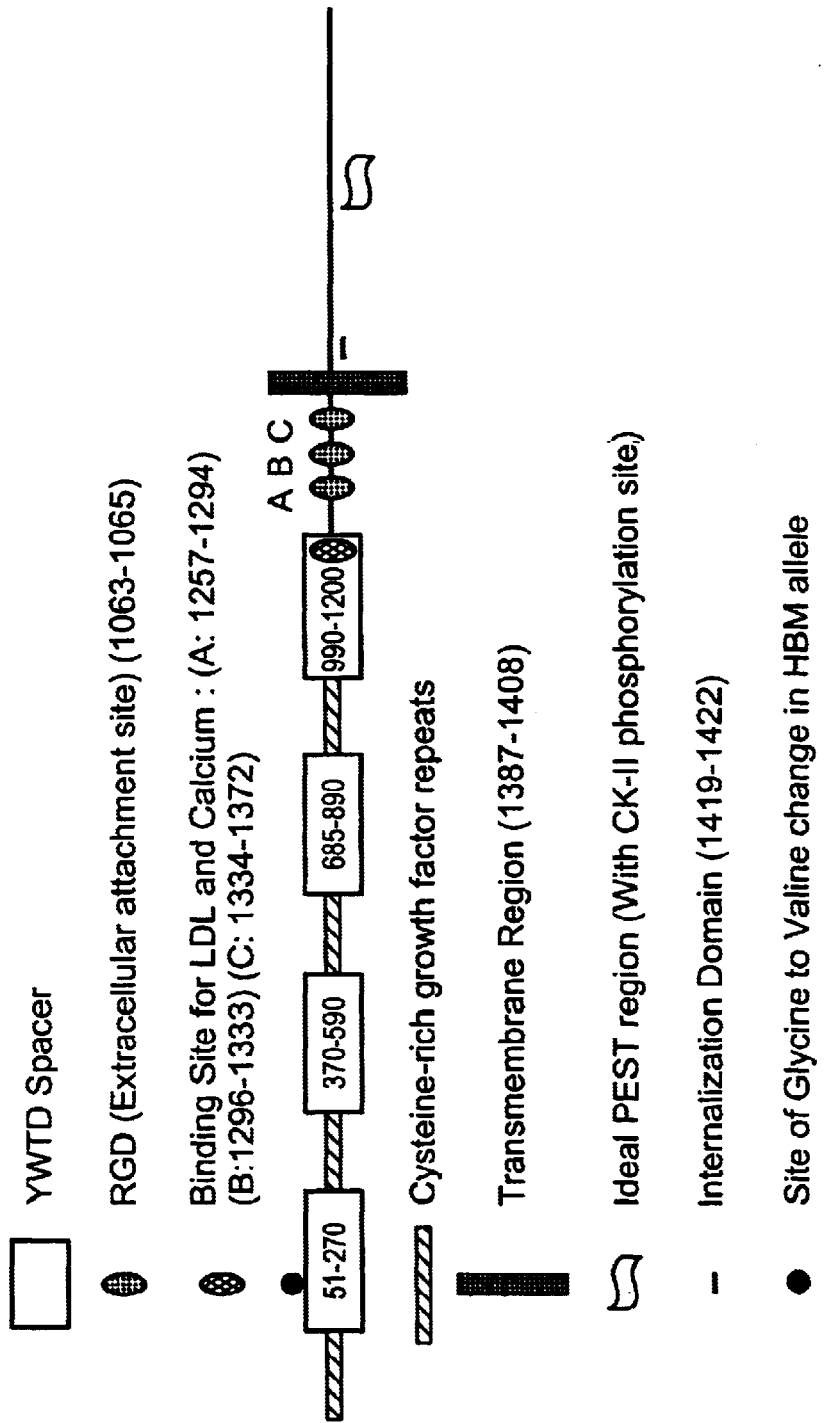
FIG. 4 shows the domain organization of Zmax1, including the YWTD spacers, the extracellular attachment site, the binding site for LDL and calcium, the cysteine-rich growth factor repeats, the transmembrane region, the ideal PEST region with the CK-II phosphorylation site and the internalization domain.

To aid in the understanding of the specification and claims, the following definitions are provided.

"Gene" refers to a DNA sequence that encodes through its template or messenger RNA a sequence of amino acids characteristic of a specific peptide. The term "gene" includes intervening, non-coding regions, as well as regulatory regions, and can include 5' and 3' ends.

"Gene sequence" refers to a DNA molecule, including both a DNA molecule which contains a non-transcribed or non-translated sequence. The term is also intended to include any combination of gene(s), gene fragment(s), non-transcribed sequence(s) or non-translated sequence(s) which are present on the same DNA molecule.

The sequences of the present invention may be derived from a variety of sources including DNA, cDNA, synthetic DNA, synthetic RNA or combinations thereof. Such sequences may comprise genomic DNA which may or may not include naturally occurring introns. Moreover, such genomic DNA may be obtained in association with promoter regions or poly (A) sequences. The sequences, genomic DNA or cDNA may be obtained in any of several ways. Genomic DNA can be extracted and purified from suitable cells by means well known in the art. Alternatively, mRNA can be isolated from a cell and used to produce cDNA by reverse transcription or other means.

"cDNA" refers to complementary or copy DNA produced from an RNA template by the action of RNA-dependent DNA polymerase (reverse transcriptase). Thus, a "cDNA clone" means a duplex DNA sequence complementary to an RNA molecule of interest, carried in a cloning vector or PCR amplified. This term includes genes from which the intervening sequences have been removed.

"Recombinant DNA" means a molecule that has been recombined by in vitro splicing cDNA or a genomic DNA sequence.

"Cloning" refers to the use of in vitro recombination techniques to insert a particular gene or other DNA sequence into a vector molecule. In order to successfully clone a desired gene, it is necessary to use methods for generating DNA fragments, for joining the fragments to vector molecules, for introducing the composite DNA molecule into a host cell in which it can replicate, and for selecting the clone having the target gene from amongst the recipient host cells.

"cDNA library" refers to a collection of recombinant DNA molecules containing cDNA inserts which together comprise the entire genome of an organism. Such a cDNA library can be prepared by methods known to one skilled in the art and described by, for example, Cowell and Austin, "cDNA Library Protocols," Methods in Molecular Biology (1997). Generally, RNA is first isolated from the cells of an organism from whose genome it is desired to clone a particular gene.

"Cloning vehicle" refers to a plasmid or phage DNA or other DNA sequence which is able to replicate in a host cell. The cloning vehicle is characterized by one or more endonuclease recognition sites at which such DNA sequences may be cut in a determinable fashion without loss of an essential biological function of the DNA, which may contain a marker suitable for use in the identification of transformed cells.

"Expression control sequence" refers to a sequence of nucleotides that control or regulate expression of structural genes when operably linked to those genes. These include, for example, the lac systems, the trp system, major operator and promoter regions of the phage lambda, the control region of fd coat protein and other sequences known to control the expression of genes in prokaryotic or eukaryotic cells. Expression control sequences will vary depending on whether the vector is designed to express the operably linked gene in a prokaryotic or eukaryotic host, and may contain transcriptional elements such as enhancer elements, termination sequences, tissue-specificity elements and/or translational initiation and termination sites.

"Expression vehicle" refers to a vehicle or vector similar to a cloning vehicle but which is capable of expressing a gene which has been cloned into it, after transformation into a host. The cloned gene is usually placed under the control of (i.e., operably linked to) an expression control sequence.

"Operator" refers to a DNA sequence capable of interacting with the specific repressor, thereby controlling the transcription of adjacent gene(s).

"Promoter" refers to a DNA sequence that can be recognized by an RNA polymerase. The presence of such a sequence permits the RNA polymerase to bind and initiate transcription of operably linked gene sequences.

"Promoter region" is intended to include the promoter as well as other gene sequences which may be necessary for the initiation of transcription. The presence of a promoter region is sufficient to cause the expression of an operably linked gene sequence.

"Operably linked" means that the promoter controls the initiation of expression of the gene. A promoter is operably linked to a sequence of proximal DNA if upon introduction into a host cell the promoter determines the transcription of the proximal DNA sequence(s) into one or more species of RNA. A promoter is operably linked to a DNA sequence if the promoter is capable of initiating transcription of that DNA sequence.

"Prokaryote" refers to all organisms without a true nucleus, including bacteria.

"Eukaryote" refers to organisms and cells that have a true nucleus, including mammalian cells.

"Host" includes prokaryotes and eukaryotes, such as yeast and filamentous fungi, as well as plant and animal cells. The term includes an organism or cell that is the recipient of a replicable expression vehicle.

"Fragment" of a gene refers to any variant of the gene that possesses the biological activity of that gene.

"Variant" refers to a gene that is substantially similar in structure and biological activity or immunological characteristics to either the entire gene or to a fragment of the gene. Provided that the two genes possess a similar activity, they are considered variant as that term is used herein even if the sequence of amino acid residues is not identical.

"Amplification of nucleic acids" refers to methods such as polymerase chain reaction (PCR), ligation amplification (or ligase chain reaction, LCR) and amplification methods based on the use of Q-beta replicase. These methods are well known in the art and described, for example, in U.S. Pat. Nos. 4,683,195 and 4,683,202. Reagents and hardware for conducting PCR are commercially available. Primers useful for amplifying sequences from the HBM region are preferably complementary to, and hybridize specifically to sequences in the HBM region or in regions that flank a target region therein. HBM sequences generated by amplification may be sequenced directly. Alternatively, the amplified sequence(s) may be cloned prior to sequence analysis.

"Antibodies" may refer to polyclonal and/or monoclonal antibodies and fragments thereof, and immunologic binding equivalents thereof, that can bind to the HBM proteins and fragments thereof or to nucleic acid sequences from the HBM region, particularly from the HBM locus or a portion thereof. The term antibody is used both to refer to a homogeneous molecular entity, or a mixture such as a serum product made up of a plurality of different molecular entities. Proteins may be prepared synthetically in a protein synthesizer and coupled to a carrier molecule and injected over several months into rabbits. Rabbit sera is tested for immunoreactivity to the HBM protein or fragment. Monoclonal antibodies may be made by injecting mice with the proteins, or fragments thereof. Monoclonal antibodies will be screened by ELISA and tested for specific immunoreactivity with HBM protein or fragments thereof. Harlow et al, *Antibodies: A Laboratory Manual*, Cold Spring Harbor Laboratory, Cold Spring Harbor, N.Y. (1988). These antibodies will be useful in assays as well as pharmaceuticals.

"HBM" refers to high bone mass.

"HBM protein" refers to a protein that is identical to a Zmax1 protein except that it contains an alteration of glycine 171 to valine. An HBM protein is defined for any organism that encodes a Zmax1 true homologue. For example, a mouse HBM protein refers to the mouse Zmax1 protein having the glycine 170 to valine substitution.

"HBM gene" refers to the genomic DNA sequence found in individuals showing the HBM characteristic or phenotype, where the sequence encodes the protein indicated by SEQ ID NO: 4. The HBM gene and the Zmax1 gene are allelic. The protein encoded by the HBM gene has the property of causing elevated bone mass, while the protein encoded by the Zmax1 gene does not. The HBM gene and the Zmax1 gene differ in that the HBM gene has a thymine at position 582, while the Zmax1 gene has a guanine at position 582. The HBM gene comprises the nucleic acid sequence shown as SEQ ID NO: 2. The HBM gene may also be referred to as an "HBM polymorphism."

"Normal," "wild-type," "unaffected" and "Zmax1" all refer to the genomic DNA sequence that encodes the protein indicated by SEQ ID NO: 3. The Zmax1 gene has a guanine at position 582. The Zmax1 gene comprises the nucleic acid sequence shown as SEQ ID NO: 1. "Normal," "wild-type," "unaffected" and "Zmax1" also refer to allelic variants of the genomic sequence that encodes proteins that do not contribute to elevated bone mass. The Zmax1 gene is common in the human population, while the HBM gene is rare.

"5YWT+EGF" refers to a repeat unit found in the Zmax1 protein, consisting of five YWT repeats followed by an EGF repeat.

"Bone development" generally refers to any process involved in the change of bone over time, including, for example, normal development, changes that occur during disease states, and changes that occur during aging. "Bone development disorder" particularly refers to any disorders in bone development including, for example, changes that occur during disease states and changes that occur during aging. Bone development may be progressive or cyclical in nature. Aspects of bone that may change during development include, for example, mineralization, formation of specific anatomical features, and relative or absolute numbers of various cell types.

"Bone modulation" or "modulation of bone formation" refers to the ability to affect any of the physiological processes involved in bone remodeling, as will be appreciated by one skilled in the art, including, for example, bone resorption and appositional bone growth, by, inter alia, osteoclastic and osteoblastic activity, and may comprise some or all of bone formation and development as used herein.

"Normal bone density" refers to a bone density within two standard deviations of a Z score of 0.

A "Zmax1 system" refers to a purified protein, cell extract, cell, animal, human or any other composition of matter in which Zmax1 is present in a normal or mutant form.

A "surrogate marker" refers to a diagnostic indication, symptom, sign or other feature that can be observed in a cell, tissue, human or animal that is correlated with the HBM gene or elevated bone mass or both, but that is easier to measure than bone density. The general concept of a surrogate marker is well accepted in diagnostic medicine.

The present invention encompasses the Zmax1 gene and Zmax1 protein in the forms indicated by SEQ ID NOS: 1 and 3, respectively, and other closely related variants, as well as the adjacent chromosomal regions of Zmax1 necessary for its accurate expression. In a preferred embodiment, the present invention is directed to at least 15 contiguous nucleotides of the nucleic acid sequence of SEQ ID NO: 1.

The present invention also encompasses the HBM gene and HBM protein in the forms indicated by SEQ ID NOS: 2 and 4, respectively, and other closely related variants, as well as the adjacent chromosomal regions of the HBM gene necessary for its accurate expression. In a preferred embodiment, the present invention is directed to at least 15 contiguous nucleotides of the nucleic acid sequence of SEQ ID NO: 2. More preferably, the present invention is directed to at least 15 contiguous nucleotides of the nucleic acid sequence of SEQ ID NO: 2, wherein one of the 15 contiguous nucleotides is the thymine at nucleotide 582.

The invention also relates to the nucleotide sequence of the Zmax1 gene region, as well as the nucleotide sequence of the HBM gene region. More particularly, a preferred embodiment are the BAC clones containing segments of the Zmax1 gene region B200E21-H and B527D12-H. A preferred embodiment is the nucleotide sequence of the BAC clones consisting of SEQ ID NOS: 5–12.

The invention also concerns the use of the nucleotide sequence to identify DNA probes for the Zmax1 gene and the HBM gene, PCR primers to amplify the Zmax1 gene and the HBM gene, nucleotide polymorphisms in the Zmax1 gene and the HBM gene, and regulatory elements of the Zmax1 gene and the HBM gene.

This invention describes the further localization of the chromosomal location of the Zmax1 gene and HBM gene on chromosome 11q13.3 between genetic markers D11S987 and SNP_CONTIG033-6, as well as the DNA sequences of the Zmax1 gene and the HBM gene. The chromosomal location was refined by the addition of more genetic markers to the mapping panel used to map the gene, and by the extension of the pedigree to include more individuals. The pedigree extension was critical because the new individuals that have been genotyped harbor critical recombination events that narrow the region. To identify genes in the region on 11q13.3, a set of BAC clones containing this chromosomal region was identified. The BAC clones served as a template for genomic DNA sequencing, and also as a reagent for identifying coding sequences by direct cDNA selection. Genomic sequencing and direct cDNA selection were used to characterize more than 1.5 million base pairs of DNA from 11q13.3. The Zmax1 gene was identified within this region and the HBM gene was then discovered after mutational analysis of affected and unaffected individuals.

When a gene has been genetically localized to a specific chromosomal region, the genes in this region can be characterized at the molecular level by a series of steps that include: cloning of the entire region of DNA in a set of overlapping clones (physical mapping), characterization of genes encoded by these clones by a combination of direct cDNA selection, exon trapping and DNA sequencing (gene identification), and identification of mutations in these genes by comparative DNA sequencing of affected and unaffected members of the HBM kindred (mutation analysis).

Physical mapping is accomplished by screening libraries of human DNA cloned in vectors that are propagated in *E. coli* or *S. cereviseae* using PCR assays designed to amplify unique molecular landmarks in the chromosomal region of interest. To generate a physical map of the HBM candidate region, a library of human DNA cloned in Bacterial Artificial Chromosomes (BACs) was screened with a set of Sequence Tagged Site (STS) markers that had been previously mapped to chromosome 11q12-q13 by the efforts of the Human Genome Project.

STSs are unique molecular landmarks in the human genome that can be assayed by PCR. Through the combined efforts of the Human Genome Project, the location of thousands of STSs on the twenty-two autosomes and two sex chromosomes has been determined. For a positional cloning effort, the physical map is tied to the genetic map because the markers used for genetic mapping can also be used as STSs for physical mapping. By screening a BAC library with a combination of STSs derived from genetic markers, genes, and random DNA fragments, a physical map comprised of overlapping clones representing all of the DNA in a chromosomal region of interest can be assembled.

BACs are cloning vectors for large (80 kilobase to 200 kilobase) segments of human or other DNA that are propagated in *E. coli*. To construct a physical map using BACs, a library of BAC clones is screened so that individual clones harboring the DNA sequence corresponding to a given STS or set of STSs are identified. Throughout most of the human genome, the STS markers are spaced approximately 20 to 50 kilobases apart, so that an individual BAC clone typically contains at least two STS markers. In addition, the BAC libraries that were screened contain enough cloned DNA to cover the human genome six times over. Therefore, an individual STS typically identifies more than one BAC clone. By screening a six-fold coverage BAC library with a series of STS markers spaced approximately 50 kilobases apart, a physical map consisting of a series of overlapping BAC clones, i.e. BAC contigs, can be assembled for any region of the human genome. This map is closely tied to the genetic map because many of the STS markers used to prepare the physical map are also genetic markers.

When constructing a physical map, it often happens that there are gaps in the STS map of the genome that result in the inability to identify BAC clones that are overlapping in a given location. Typically, the physical map is first constructed from a set of STSs that have been identified through the publicly available literature and World Wide Web resources. The initial map consists of several separate BAC contigs that are separated by gaps of unknown molecular distance. To identify BAC clones that fill these gaps, it is necessary to develop new STS markers from the ends of the clones on either side of the gap. This is done by sequencing the terminal 200 to 300 base pairs of the BACs flanking the gap, and developing a PCR assay to amplify a sequence of 100 or more base pairs. If the terminal sequences are demonstrated to be unique within the human genome, then the new STS can be used to screen the BAC library to identify additional BACs that contain the DNA from the gap in the physical map. To assemble a BAC contig that covers a region the size of the HBM candidate region (2,000,000 or more base pairs), it is often necessary to develop new STS markers from the ends of several clones.

After building a BAC contig, this set of overlapping clones serves as a template for identifying the genes encoded in the chromosomal region. Gene identification can be accomplished by many methods. Three methods are commonly used: (1) a set of BACs selected from the BAC contig to represent the entire chromosomal region can be sequenced, and computational methods can be used to identify all of the genes, (2) the BACs from the BAC contig can be used as a reagent to clone cDNAs corresponding to the genes encoded in the region by a method termed direct cDNA selection, or (3) the BACs from the BAC contig can be used to identify coding sequences by selecting for specific DNA sequence motifs in a procedure called exon trapping. The present invention includes genes identified by the first two methods.

To sequence the entire BAC contig representing the HBM candidate region, a set of BACs was chosen for subcloning into plasmid vectors and subsequent DNA sequencing of these subclones. Since the DNA cloned in the BACs represents genomic DNA, this sequencing is referred to as genomic sequencing to distinguish it from cDNA sequencing. To initiate the genomic sequencing for a chromosomal region of interest, several non-overlapping BAC clones are chosen. DNA for each BAC clone is prepared, and the clones are sheared into random small fragments which are subsequently cloned into standard plasmid vectors such as pUC18. The plasmid clones are then grown to propagate the smaller fragments, and these are the templates for sequencing. To ensure adequate coverage and sequence quality for the BAC DNA sequence, sufficient plasmid clones are sequenced to yield six-fold coverage of the BAC clone. For example, if the BAC is 100 kilobases long, then phagemids are sequenced to yield 600 kilobases of sequence. Since the BAC DNA was randomly sheared prior to cloning in the phagemid vector, the 600 kilobases of raw DNA sequence can be assembled by computational methods into overlapping DNA sequences termed sequence contigs. For the purposes of initial gene identification by computational methods, six-fold coverage of each BAC is sufficient to yield ten to twenty sequence contigs of 1000 base pairs to 20,000 base pairs.

The sequencing strategy employed in this invention was to initially sequence "seed" BACs from the BAC contig in the HBM candidate region. The sequence of the "seed" BACs was then used to identify minimally overlapping BACs from the contig, and these were subsequently sequenced. In this manner, the entire candidate region was sequenced, with several small sequence gaps left in each BAC. This sequence served as the template for computational gene identification. One method for computational gene identification is to compare the sequence of BAC contig to publicly available databases of cDNA and genomic sequences, e.g. unigene, dbEST, genbank. These comparisons are typically done using the BLAST family of computer algorithms and programs (Altschul et al, *J. Mol. Biol.*, 215:403–410 (1990)). The BAC sequence can also be translated into protein sequence, and the protein sequence can be used to search publicly available protein databases, using a version of BLAST designed to analyze protein sequences (Altschul et al, *Nucl. Acids Res.*, 25:3389–3402 (1997)). Another method is to use computer algorithms such as MZEF (Zhang, *Proc. Natl. Acad. Sci.*, 94:565–568 (1997)) and GRAIL (Uberbacher et al, *Methods Enzymol.*, 266:259–281 (1996)), which predict the location of exons in the sequence based on the presence of specific DNA sequence motifs that are common to all exons, as well as the presence of codon usage typical of human protein encoding sequences.

In addition to identifying genes by computational methods, genes were also identified by direct cDNA selection (Del Mastro et al, *Genome Res.* 5(2):185–194 (1995)). In direct cDNA selection, cDNA pools from tissues of interest are prepared, and the BACs from the candidate region are used in a liquid hybridization assay to capture the cDNAs which base pair to coding regions in the BAC. In the methods described herein, the cDNA pools were created from several different tissues by random priming the first strand cDNA from polyA RNA, synthesizing the second strand cDNA by standard methods, and adding linkers to the ends of the cDNA fragments. The linkers are used to amplify the cDNA pools. The BAC clones are used as a template for in vitro DNA synthesis to create a biotin labelled copy of the BAC DNA. The biotin labelled copy of the BAC DNA is then denatured and incubated with an excess of the PCR amplified, linkered cDNA pools which have also been denatured. The BAC DNA and cDNA are allowed to anneal in solution, and heteroduplexes between the BAC and the cDNA are isolated using streptavidin coated magnetic beads. The cDNAs that are captured by the BAC are then amplified using primers complimentary to the linker sequences, and the hybridization/selection process is repeated for a second round. After two rounds of direct cDNA selection, the cDNA fragments are cloned, and a library of these direct selected fragments is created.

The cDNA clones isolated by direct selection are analyzed by two methods. Since a pool of BACs from the HBM candidate region is used to provide the genomic DNA sequence, the cDNAs must be mapped to individual BACs. This is accomplished by arraying the BACs in microtiter dishes, and replicating their DNA in high density grids. Individual cDNA clones are then hybridized to the grid to confirm that they have sequence identity to an individual BAC from the set used for direct selection, and to determine the specific identity of that BAC. cDNA clones that are confirmed to correspond to individual BACs are sequenced. To determine whether the cDNA clones isolated by direct selection share sequence identity or similarity to previously identified genes, the DNA and protein coding sequences are compared to publicly available databases using the BLAST family of programs.

The combination of genomic DNA sequence and cDNA sequence provided by BAC sequencing and by direct cDNA selection yields an initial list of putative genes in the region. The genes in the region were all candidates for the HBM locus. To further characterize each gene, Northern blots were performed to determine the size of the transcript corresponding to each gene, and to determine which putative exons were transcribed together to make an individual gene. For Northern blot analysis of each gene, probes were prepared from direct selected cDNA clones or by PCR amplifying specific fragments from genomic DNA or from the BAC encoding the putative gene of interest. The Northern blots gave information on the size of the transcript and the tissues in which it was expressed. For transcripts which were not highly expressed, it was sometimes necessary to perform a reverse transcription PCR assay using RNA from the tissues of interest as a template for the reaction.

Gene identification by computational methods and by direct cDNA selection provides unique information about the genes in a region of a chromosome. When genes are identified, then it is possible to examine different individuals for mutations in each gene.

I. Phenotyping Using DXA Measurements

Spinal bone mineral content (BMC) and bone mineral density (BMD) measurements performed at Creighton University (Omaha, Nebraska) were made by DXA using a Norland Instruments densitometer (Norland XR2600 Densitometer, Dual Energy X-ray Absorptiometry, DXA). Spinal BMC and BMD at other locations used the machinery available. There are estimated to be 800 DXA machines currently operating in the U.S. Most larger cities have offices or imaging centers which have DXA capabilities, usually a Lunar or Hologic machine. Each location that provided spine BMC and BMD data included copies of the printouts from their machines to provide verification that the regions of interest for measurement of BMD have been chosen appropriately. Complete clinical histories and skeletal radiographs were obtained.

The HBM phenotype is defined by the following criteria: very high spinal BMD; a clinical history devoid of any known high bone mass syndrome; and skeletal radiographs showing a normal shape of the appendicular skeleton.

II. Genotyping of Microsatellite Markers

To narrow the genetic interval to a region smaller than that originally reported by Johnson et al, *Am. J. Hum. Genet.*, 60:1326–1332 (1997), additional microsatellite markers on chromosome 11q12-13 were typed. The new markers included: D11S4191, D11S1883, D11S1785, D11S4113, D11S4136, D11S4139, (Dib, et al, *Nature*, 380:152–154 (1996), FGF3 (Polymeropolous, et al, *Nucl. Acid Res.*, 18:7468 (1990)), as well as GTC_HBM_Marker_1, GTC_HBM_Marker_2, GTC_HBM_Marker_3, GTC_HBM_Marker_4, GTC_HBM_Marker_5, GTC_HBM_Marker_6, and GTC_HBM_Marker_7 (See FIG. 2).

Blood (20 ml) was drawn into lavender cap (EDTA containing) tubes by a certified phlebotomist. The blood was stored refrigerated until DNA extraction. DNA has been extracted from blood stored for up to 7 days in the refrigerator without reduction in the quality or quantity of yield. For those subjects that have blood drawn at distant sites, a shipping protocol was successfully used on more than a dozen occasions. Blood samples were shipped by overnight express in a styrofoam container with freezer packs to provide cooling. Lavender cap tubes were placed on individual plastic shipping tubes and then into "zip-lock" biohazard bags. When the samples arrived the next day, they were immediately processed to extract DNA.

The DNA extraction procedure used a kit purchased from Gentra Systems, Inc. (Minneapolis, Minn.). Briefly, the procedure involved adding 3 volumes of a red blood cell lysis buffer to the whole blood. After incubations for 10 minutes at room temperature, the solution was centrifuged in a Beckman tabletop centrifuge at 2,000×g for 10 minutes. The white blood cell pellet was resuspended in Cell Lysis Buffer. Once the pellet was completely resuspended and free of cell clumps, the solution was digested with RNase A for 15 minutes at 37° C. Proteins were precipitated by addition of the provided Protein Precipitation Solution and removed by centrifugation. The DNA was precipitated out of the supernatant by addition of isopropanol. This method was simple and fast, requiring only 1–2 hours, and allowed for the processing of dozens of samples simultaneously. The yield of DNA was routinely >8 mg for a 20 ml sample of whole blood and had a MW of >50 kb. DNA was archived by storing coded 50 $\mu$g aliquots at −80° C. as an ethanol precipitate.

DNA was genotyped using one fluorescently labeled oligonucleotide primer and one unlabeled oligonucleotide primer. Labeled and unlabeled oligonucleotides were obtained from Integrated DNA Technologies, Inc. (Coralville, Iowa). All other reagents for microsatellite genotyping were purchased from Perkin Elmer-Applied Biosystems, Inc. ("PE-ABI") (Norwalk, Conn.). Individual PCR reactions were performed for each marker, as described by PE-ABI using AmpliTaq DNA Polymerase. The reactions were added to 3.5 $\mu$l of loading buffer containing deionized formamide, blue dextran and TAMRA 350 size standards (PE-ABI). After heating at 95° C. for 5 minutes to denature the DNA, the samples were loaded and electrophoresed as described in the operator's manual for the Model 377 DNA Sequencer (PE-ABI, Foster City, Calif.). After gel electrophoresis, the data was analyzed using PE-ABI GENESCAN™ and GENOTYPER™ software. First, within the GENESCAN™ software, the lane tracking was manually optimized prior to the first step of analysis. After the gel lane data was extracted, the standard curve profiles of each lane were examined and verified for linearity and size calling. Lanes, which had problems with either of these parameters, were re-tracked and verified. Once all lanes were tracked and the size standards were correctly identified, the data were imported into GENOTYPER™ for allele identification To expedite allele calling (binning), the program Linkage Designer from the Internet web-site of Dr. Guy Van Camp (http://alt.www.uia.ac.be/u/dnalab/ld.html) was used. This program greatly facilitates the importing of data generated by GENOTYPER™ into the pedigree drawing program Cyrillic (Version 2.0, Cherwell Scientific Publishing Limited, Oxford, Great Britain) and subsequent linkage analysis using the program LINKAGE (Lathrop et al, *Am. J. Hum. Genet.*, 37:482–498 (1985)).

III. Linkage Analysis

FIG. 1 demonstrates the pedigree of the individuals used in the genetic linkage studies for this invention. Specifically, two-point linkage analysis was performed using the MLINK and LINKMAP components of the program LINKAGE (Lathrop et al, *Am. J. Hum. Genet.*, 37:482–498 (1985)). Pedigree/marker data was exported from Cyrillic as a pre-file into the Makeped program and converted into a suitable ped-file for linkage analysis.

The original linkage analysis was performed using three models: (i) an autosomal dominant, fully penetrant model, (ii) an autosomal dominant model with reduced penetrance, and (iii) a quantitative trait model. The HBM locus was mapped to chromosome 11q12-13 by analyzing DNA for linked markers from 22 members of a large, extended kindred. A highly automated technology was used with a panel of 345 fluorescent markers which spanned the 22 autosomes at a spacing interval ranging from 6–22 cM. Only markers from this region of chromosome 11 showed evidence of linkage (LOD score ~3.0). The highest LOD score (5.74) obtained by two-point and multipoint analysis was D11S987 (map position 55 in FIG. 2). The 95% confidence interval placed the HBM locus between markers D11S905 and D11S937 (map position 41–71 in FIG. 2). Haplotype analysis also places the Zmax1 gene in this same region. Further descriptions of the markers D11S987, D11S905, and D11S937 can be found in Gyapay et al, *Nature Genetics*, Vol. 7, (1994).

In this invention, the inventors report the narrowing of the HBM interval to the region between markers D11S987 and GTC_HBM_Marker_5. These two markers lie between the delimiting markers from the original analysis (D11S11S905 and D11S937) and are approximately 3 cM from one another. The narrowing of the interval was accomplished using genotypic data from the markers D11S4191, D11S1883, D11S1785, D11S4113, D11S4136, D11S4139, (Dib et al, *Nature*, 380:152–154(1996)), FGF3 (Polymeropolous et al, *Nucl. Acid Res.*, 18:7468 (1990)) (information about the genetic markers can be found at the internet site of the Genome Database, http://gdbwww.gdb.org/), as well as the markers GTC_HBM_Marker_1, GTC_HBM_Marker_2, GTC_HBM_Marker_3, GTC_HBM_Marker_4, GTC_HBM_Marker_5, GTC_HBM_Marker_6, and GTC_HBM_Marker_7.

As shown in FIG. 1, haplotype analysis with the above genetic markers identifies recombination events (crossovers) in individuals 9019 and 9020 that significantly refine the interval of chromosome 11 to which the Zmax1 gene is localized. Individual 9019 is an HBM-affected individual that inherits a portion of chromosome 11 from the maternal chromosome with the HBM gene, and a portion from the chromosome 11 homologue. The portion inherited from the HBM gene-carrying chromosome includes markers D11S935, D11S1313, GTC_HBM_Marker_4, D11S987, D11S1296, GTC_HBM_Marker_6, GTC_HBM_Marker_2, D11S970, GTC_HBM_Marker_3, D11S4113, GTC_HBM_Marker_1, GTC_HBM_Marker_7 and GTC_HBM_Marker_5. The portion from D11S4136 and continuing in the telomeric direction is derived from the non-HBM chromosome. This data places the Zmax1 gene in a location centromeric to the marker GTC_HBM_Marker_5. Individual 9020 is an unaffected individual who also exhibits a critical recombination event. This individual inherits a recombinant paternal chromosome 11 that includes markers D11S935, D11S1313, GTC_HBM_Marker_4, D11S987, D11 S1296 and GTC_HBM_Marker_6 from her father's (individual 0115) chromosome 11 homologue that carries the HBM gene, and markers GTC_HBM_Marker_2, D11S970, GTC_HBM_Marker_3, GTC_HBM_Marker_1, GTC_HBM_Marker_7, GTC_HBM_Marker_5, D11S4136, D11S4139, D11S1314, and D11S937 from her father's chromosome 11 that does not carry the HBM gene. Marker D11S4113 is uninformative due to its homozygous nature in individual 0115. This recombination event places the centromeric boundary of the HBM region between markers D11S1296 and D11S987.

Two-point linkage analysis was also used to confirm the location of the Zmax1 gene on chromosome 11. The linkage results for two point linkage analysis under a model of full penetrance are presented in Table 1 below. This table lists the genetic markers in the first column and the recombination fractions across the top of the table. Each cell of the column shows the LOD score for an individual marker tested for linkage to the Zmax1 gene at the recombination fraction shown in the first row. For example, the peak LOD score of 7.66 occurs at marker D11S970, which is within the interval defined by haplotype analysis.

TABLE 1

| Marker | 0.0 | 0.05 | 0.1 | 0.15 | 0.2 | 0.25 | 0.3 | 0.35 | 0.4 |
|---|---|---|---|---|---|---|---|---|---|
| D11S935 | - infinity | 0.39 | 0.49 | 0.47 | 0.41 | 0.33 | 0.25 | 0.17 | 0.10 |
| D11S1313 | - infinity | 2.64 | 2.86 | 2.80 | 2.59 | 2.30 | 1.93 | 1.49 | 1.00 |
| D11S987 | - infinity | 5.49 | 5.18 | 4.70 | 4.13 | 3.49 | 2.79 | 2.03 | 1.26 |
| D11S4113 | 4.35 | 3.99 | 3.62 | 3.24 | 2.83 | 2.40 | 1.94 | 1.46 | 0.97 |
| D11S1337 | 2.29 | 2.06 | 1.81 | 1.55 | 1.27 | 0.99 | 0.70 | 0.42 | 0.18 |
| D11S970 | 7.66 | 6.99 | 6.29 | 5.56 | 4.79 | 3.99 | 3.15 | 2.30 | 1.44 |
| D11S4136 | 6.34 | 5.79 | 5.22 | 4.61 | 3.98 | 3.30 | 2.59 | 1.85 | 1.11 |
| D11S4139 | 6.80 | 6.28 | 5.73 | 5.13 | 4.50 | 3.84 | 3.13 | 2.38 | 1.59 |
| FGF3 | 0.59 | 3.23 | 3.15 | 2.91 | 2.61 | 2.25 | 1.84 | 1.40 | 0.92 |
| D11S1314 | 6.96 | 6.49 | 5.94 | 5.34 | 4.69 | 4.01 | 3.27 | 2.49 | 1.67 |
| D11S937 | -infinity | 4.98 | 4.86 | 4.52 | 4.06 | 3.51 | 2.88 | 2.20 | 1.47 |

A single nucleotide polymorphism (SNP) further defines the HBM region. This SNP is termed SNP_Contig033-6 and is located 25 kb centromeric to the genetic marker GTC_HBM_Marker_5. This SNP is telomeric to the genetic marker GTC_HBM_Marker_7. SNP_Contig033-6 is present in HBM-affected individual 0113. However, the HBM-affected individual 9019, who is the son of 0113, does not carry this SNP. Therefore, this indicates that the crossover is centromeric to this SNP. The primer sequence for the genetic markers GTC_HBM_Marker_5 and GTC_HBM_Marker_7 is shown in Table 2 below.

TABLE 2

| Marker | Primer (Forward) | Primer (Reverse) |
|---|---|---|
| GTC_HBM_Marker_5 | TTTTGGGTACACAATTCAGTCG (SEQ. ID. NO.:63) | AAAACTGTGGGTGCTTCTGG (SEQ. ID. NO.:64) |
| GTC_HBM_Marker_7 | GTGATTGAGCCAATCCTGAGA (SEQ. ID. NO.:65) | TGAGCCAAATAAACCCCTTCT (SEQ. ID. NO.:66) |

The kindred described have several features of great interest, the most important being that their bones, while very dense, have an absolutely normal shape. The outer dimensions of the skeletons of the HBM-affected individuals are normal, and, while medullary cavities are present, there is no interference with hematopoiesis. The HBM-affected members seem to be resistant to fracture, and there are no neurologic symptoms, and no symptoms of impairment of any organ or system function in the members examined. HBM-affected members of the kindred live to advanced age without undue illness or disability. Furthermore, the HBM phenotype matches no other bone disorders such as osteoporosis, osteoporosis pseudoglioma, Engelmann's disease, Ribbing's disease, hyperphosphatasemia, Van Buchem's disease, melorheostosis, osteopetrosis, pycnodysostosis, sclerostenosis, osteopoikilosis, acromegaly, Paget's disease, fibrous dysplasia, tubular stenosis, osteogenesis imperfecta, hypoparathyroidism, pseudohypoparathyroidism, pseudopseudohypoparathyroidism, primary and secondary hyperparathyroidism and associated syndromes, hypercalciuria, medullary carcinoma of the thyroid gland, osteomalacia and other diseases. Clearly, the HBM locus in this family has a very powerful and substantial role in regulating bone density, and its identification is an important step in understanding the pathway(s) that regulate bone density and the pathogenesis of diseases such as osteoporosis.

In addition, older individuals carrying the HBM gene, and therefore expression of the HBM protein, do not show loss of bone mass characteristic of normal individuals. In other words, the HBM gene is a suppressor of osteoporosis. In essence, individuals carrying the HBM gene are dosed with the HBM protein, and, as a result, do not develop osteoporosis. This in vivo observation is strong evidence that treatment of normal individuals with the HBM gene or protein, or a fragment thereof, will ameliorate osteoporosis.

IV. Physical Mapping

To provide reagents for the cloning and characterization of the HBM locus, the genetic mapping data described above were used to construct a physical map of the region containing Zmax1 on chromosome 11q13.3. The physical map consists of an ordered set of molecular landmarks, and a set of BAC clones that contain the Zmax1 gene region from chromosome 11q13.3.

Various publicly available mapping resources were utilized to identify existing STS markers (Olson et al, *Science*, 245:1434–1435 (1989)) in the HBM region. Resources included the GDB, the Whitehead Institute Genome Center, dbSTS and dbEST (NCBI), 11 db, the University of Texas Southwestern GESTEC, the Stanford Human Genome Center, and several literature references (Courseaux et al, *Genomics*, 40:13–23 (1997), Courseaux et al, *Genomics*, 37:354–365 (1996), Guru et al, *Genomics*, 42:436–445 (1997), Hosoda et al, *Genes Cells*, 2:345–357 (1997), James et al, *Nat. Genet.*, 8:70–76 (1994), Kitamura et al, *DNA Research*, 4:281–289 (1997), Lemmens et al, *Genomics*, 44:94–100 (1997), Smith et al, *Genome Res.*, 7:835–842 (1997)). Maps were integrated manually to identify markers mapping to the region containing Zmax1.

Primers for existing STSs were obtained from the GDB or literature references are listed in Table 3 below. Thus, Table 3 shows the STS markers used to prepare the physical map of the Zmax1 gene region.

TABLE 3

HBM STS Table

| STS Name | Locus Name | Type | GDB Access. # | Size (kb) | Forward Primer | Reverse Primer | Gene Name |
|---|---|---|---|---|---|---|---|
| ACTN3 | | Gene | GDB:197568 | 0.164 | CTGGACTACGTGGCCTTCTC CACTTGGCTGG (SEQ. ID NO.: 67) | TTCAGAAG- CACTTGGCTGG (SEQ. ID NO.: 68) | Actinin, alpha 3 - skeletal muscle |
| PC-B/PC-Y | | Gene | GDB:197884 | 0.125 | CTCAGTGCCATGAAGATGGA CACTCGATCTCAGG (SEQ. ID NO.: 69) | CAAGAT- CACTCGATCTCAGG (SEQ. ID NO.: 70) | Pyruvate Carboxylaye |
| | D11S2161E | Gene | | 0.322 | GTTTCAGGAGACTCAGAGTC GTTGCTGTTGAG (SEQ. ID NO.: 71) | TTCTGCAG- GTTGCTGTTGAG (SEQ. ID NO.: 72) | Adenosine Receptor (A2) Gene |
| ADRBK1 | | Gene | GDB:4590179 | 0.117 | TTATTGTGATTTCCCGTGGC GTCCTGACTTCAGG (SEQ. ID NO.: 73) | GCCCTCT- GTCCTGACTTCAGG (SEQ. ID NO.: 74) | Beta-adrenergic receptor kinase |
| PSANK3 | | GENE | | 0.259 | GAGAAAGAAATAAGGGACC TAAAGCACTGAGA (SEQ. ID NO.: 75) | TGCTTTG- TAAAGCACTGAGA (SEQ. ID NO.: 76) | sim. to Human endogenous retrovirus mRNA long terminal repeat |
| PP1(1/2)/PP1(2/2) | | Gene | GDB:197566 | 0.208 | GAAGTACGGCAGTTCAGTGGCCT CACCAAGGTCCATGTTCCCGT (SEQ. ID NO.: 77) | ATA- CACCAAGGTCCATGTTCCCGT (SEQ. ID NO.: 78) | Protein phosphatase 1, catalytic subunit, alpha isoform |
| GSTP1.PCR1 | | Gene | GDB:270066 | 0.19 | AGCCTGGGCCACAGCGTGAGACTACGT TCCCGGAGCTTGCACACCCGCTTCACA (SEQ. ID NO.: 79) | (SEQ. ID NO.: 80) | Glutathione S-transferase pi |
| NDUFV1 | | Gene | | 0.521 | CATGTGCCCACCTCATTCAT CAAGATTCT- GTAGCTTCTGG (SEQ. ID NO.: 81) | GTAGCTTCTGG (SEQ. ID NO.: 82) | NADH dehydrogenase (ubiquinone) flavoprotein 1 (51kD) |
| PSANK2 | | GENE | | 0.157 | CAGAGAAGTCAAGGGACTTG CACATCCCACACT (SEQ. ID NO.: 83) | ATCCTCT- CACATCCCACACT (SEQ. ID NO.: 84) | Aldehyde Dehydrogenase 8 (ALDH8) |
| PSANK1 | | EST | | 0.3 | CAAGGCTAAAAGACGAAAAA TCAGGAG- CATTTCATCTTTT (SEQ. ID NO.: 85) | GCCCTGTGT- CATTTCATCTTTT (SEQ. ID NO.: 86) | Human ribosomal protein L37 (PSANK1) pseudogene. |
| UT5620 | D11S1917 | MSAT | GDB:314521 | 0.211 | AAGTCGAGGCTGCAAGGAG TCCTTTCAGTA (SEQ. ID NO.: 87) | GCCCTGTGT- TCCTTTCAGTA (SEQ. ID NO.: 88) | |
| AFM289ya9 | D11S1337 | MSAT | GDB:199805 | 0.287 | AAGGTGTGAGGATCACTGG CATGGGGGCTATT (SEQ. ID NO.: 89) | AGCT- CATGGGGGCTATT (SEQ. ID NO.: 90) | |
| GALN | | Gene | | 0.322 | GCTTCTCCGAGTGTATCAAC GAGGACTTAGAACA (SEQ. ID NO.: 91) | ATGGCA- GAGGACTTAGAACA (SEQ. ID NO.: 92) | Preprogalanin (GAL1) |
| pMS51 | D11S97 | VNTR | GDB:177850 | | GATCAGGGAACTTCCTCTCGGCTC CATTGAGGACTGTGGAAACG (SEQ. ID NO.: 93) | TCCA- CATTGAGGACTGTGGAAACG (SEQ. ID NO.: 94) | |
| BCL1(1)/BCL1(2) | | Gene | | 0.205 | GCTAATCACAGTCTAACCGA GTCTTGGATGCA (SEQ. ID NO.: 95) | TTGCACT- GTCTTGGATGCA (SEQ. ID NO.: 96) | B-cell CLL/lymphoma 1 - Cyclin D1 (PRAD1 gene) |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| CCND1 | | Gene | GDB:4590141 | 0.248 | GCACAGCTGTAGTGGGTTCTAGGC GCGCAAAGGACATGCACACGGC (SEQ. ID NO.: 97) | GCAGAGCATGCACACGGC (SEQ. ID NO.: 98) | Cyclin D1 |
| FGF4 | | Gene | GDB:4590113 | 0.549 | CACCGATGAGTGCACGTTCAAGGAG CAGACAGAGATGCTCCACGCCATA (SEQ. ID NO.: 99) | (SEQ. ID NO.: 100) | Fibroblast growth factor 4 |
| FGF3.PCR1 | | Gene | GDB:188627 | 0.161 | TTTCTGGGTGTGTCTGAAT ACACAGT-TGCTCTAAAGGGT (SEQ. ID NO.: 101) | (SEQ. ID NO.: 102) | Fibroblast growth factor 3 |
| AFM164ZF12 | D11S913 | MSAT | GDB:188151 | 0.22 | CATTTGGGAAATCCAGAAGA TAGGT-GTCTTATTTTTGTTGCTTC (SEQ. ID NO.: 103) | (SEQ. ID NO.: 104) | |
| AFMA19OYD5 | | MSAT | GDB:1222329 | 0.275 | GACATACCATGAAACACTATAAGAGG CAACCCATACCAGGGATAAG (SEQ. ID NO.: 105) | (SEQ. ID NO.: 106) | |
| SMGC-15295 | D11S4689 | STS | GDB:740600 | 0.147 | GAACAAGAGGGGTAAGTTGGC TGAGGA-CACAGATACTGATGGG (SEQ. ID NO.: 107) | (SEQ. ID NO.: 108) | |
| SHGC-3084 | D11S4540 | STS | GDB:740102 | 0.167 | GAAGTGTTCCCTCTTAAATTCTTTG GAAC-TATATTGTAGTTAGTGAGGAG (SEQ. ID NO.: 109) | (SEQ. ID NO.: 110) | |
| SHGC-14407 | D11S4664 | STS | GDB:740516 | 0.158 | CCTGTAACCCCCAGTCCC TCTTGCTTC-CTAAGTTTCTCGG (SEQ. ID NO.: 111) | (SEQ. ID NO.: 112) | |
| SHGC-10946 | D11S4327 | Gene | GDB:674522 | 0.311 | ACTCCATCCACCTCATCACTG TGCT-GTTTGCCTCATCTGAC (SEQ. ID NO.: 113) | (SEQ. ID NO.: 114) | Choline Kinase |
| S515 | D11S703 | STS | GDB:196290 | 0.166 | GTGGACAGGCATAGCTGAGG TGT-TCACTCTTCTGCCTGCAG (SEQ. ID NO.: 115) | (SEQ. ID NO.: 116) | |
| AFM147XD10 | D11S1889 | MSAT | GDB:307895 | 0.183 | AGCTGGACTCTCACAGAATG CAAGAG-GCTGGTAGAAGGTG (SEQ. ID NO.: 117) | (SEQ. ID NO.: 118) | |
| AFMA131YE5 | D11S987 | MSAT | GDB:195002 | 0.082 | GACTCCAGTCTGGGCAATAAAAGC GGTG-GCAGCATGACCTCTAAAG (SEQ. ID NO.: 119) | (SEQ. ID NO.: 120) | |
| AFMb358xa9 | D11S4178 | MSAT | GDB:611922 | 0.237 | CAGGCCCAGTCTCTTG CGTGTCCAGAT-GAAAGTG (SEQ. ID NO.: 121) | (SEQ. ID NO.: 122) | |
| AFMa272yb5 | D11S4113 | MSAT | GDB:608115 | 0.218 | ACCTTACGGTGTAATCCC CTTGAAGC-CCATCTTTGC (SEQ. ID NO.: 123) | (SEQ. ID NO.: 124) | |
| WI-17803 | | EST | GDB:4581644 | 0.15 | TATTTGCAAAGCTTGAGACTTCT AAT-CACGTGCTTTGTTGCC (SEQ. ID NO.: 125) | (SEQ. ID NO.: 126) | |
| SGC31923 | | EST | GDB:4578606 | 0.126 | ACTTTATTGTCAGCGTGGGC ACTCCCTC-GATGGCTTCC (SEQ. ID NO.: 127) | (SEQ. ID NO.: 128) | |
| WI-7741 | D11S4364 | GENE | GDB:677652 | 0.324 | GAGCACGGGAGAGAAGGC CCCAACTG-GCTTGTTTTATTG | | Transformation-sensitive protein IEF SSP 3521 |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| SGC35223 | | EST | GDB:4582598 | 0.13 | AGCCACTTTATTGTTATTTTGATGC (SEQ. ID NO: 129) | (SEQ. ID NO: 130) | ZNF162 - splicing factor 1 |
| WI-16754 | | EST | GDB:4578377 | 0.15 | AAGAGTGAACAAAAGCAAACATACC (SEQ. ID NO: 131) | (SEQ. ID NO: 132) | |
| WI-6315 | D11S4418 | EST | GDB:678804 | 0.224 | GTGGAGTGTGGGATTGGG TACTGTTCT-TGATAAGTATGTCGGC (SEQ. ID NO: 333) | (SEQ. ID NO: 134) | |
| WI-16915 | | EST | GDB:4584055 | 0.125 | ATGCTTTTGCATGATTCTAATTATT TCCCCAAAAGAAATGTAAAGG (SEQ. ID NO: 135) | (SEQ. ID NO: 136) | |
| SGC30608 | | EST | GDB:4583346 | 0.128 | CTGGTCTTCCTTGTGTGCTG ATCACCCAG-GCCAGGGAT (SEQ. ID NO: 137) | (SEQ. ID NO: 138) | Mitogen inducible gene (MIG-2) |
| WI-17663 | | EST | GDB:4583346 | 0.126 | TCAGAAGCAGAACTGTTTTAACA CCT-GCTTGAAAGTTCTAGAGCC (SEQ. ID NO: 139) | (SEQ. ID NO: 140) | |
| WI-6383 | | Gene | GDB:1222237 | 0.199 | CAAGCCGGTTTTTATTGAAA GATGCCAG-GACCATGGAC (SEQ. ID NO: 141) | (SEQ. ID NO: 142) | |
| SGC31567 | | Gene | GDB:4578432 | 0.207 | GCATATAGAAACAATTTATTGCCG CTCT-GAAGCAGGGACCAGAG (SEQ. ID NO: 343) | (SEQ. ID NO: 144) | Human tat interactive protein (TIP60) |
| SGC30658 | | EST | GDB:4584037 | 0.15 | CTACCACACCACCAGGC CAAGC-GAAAGCTGCCTTC (SEQ. ID NO: 145) | (SEQ. ID NO: 146) | Calcium activated neutral protease large subunit, muCANP, calpain |
| SGC34590 | | EST | GDB:4582382 | 0.13 | GTTGTCTTGACTTCAGGTCTGTC TTTTC-CTTCAACAATCACTACTCC (SEQ. ID NO: 147) | (SEQ. ID NO: 148) | |
| SGC33927 | | EST | GDB:1222235 | 0.15 | GCGTGGGATATAGAGGTCA TACGTGGC-CAAGAAGCTAG (SEQ. ID NO: 149) | (SEQ. ID NO: 150) | |
| WI-8671 | | EST | GDB:1222257 | 0.124 | TAATATATCCCCAGTCTAAGGCAT AGCT-TGCAGATGGAGCCC (SEQ. ID NO: 151) | (SEQ. ID NO: 152) | |
| WI-12334 | | EST | GDB:4581874 | 0.127 | TGGTTTTAAACCTTTAATGAGAAAA TGT-TGATCTATACCCTGTTTCCG (SEQ. ID NO: 153) | (SEQ. ID NO: 154) | |
| WI-18402 | | EST | GDB:4584947 | 0.113 | AATTATTTAAAAGAGAGGAAAGGCA TGGCTGTGAACTTCCTCTGA (SEQ. ID NO: 155) | (SEQ. ID NO: 156) | |
| WI-28671 | | EST | GDB:4576606 | 0.131 | GGTTACAGAAAAACATTTGAGAGAT TGAGCTTTAGTTCCCTTCTCTG (SEQ. ID NO: 157) | (SEQ. ID NO: 158) | |
| WI-12856 | | EST | GDB:4576606 | 1.209 | TTGAAAACCATTTATTTCACCG TCTGCG-GCTGTTGGATTT (SEQ. ID NO: 159) | (SEQ. ID NO: 160) | H1ark |
| | | EST | | | TTGAAAACCATTTATTTCACCG TGT-TCTCTTCTCCCAGCAGG (SEQ. ID NO: 161) | (SEQ. ID NO: 162) | H1ark |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| SGC33767 | | EST | GDB:4581116 | 0.15 | CTTTATTGAAAACATTGAGTTGCATTGT-CAAATTCCCCCAAAA (SEQ. ID NO.: 163) | (SEQ. ID NO.: 164) | |
| AFM343YB5 | | MSAT | GDB:1222332 | 0.181 | AAACCGACCNCCAA CCCTGGAAAGG-TAAGATGCT (SEQ. ID NO.: 165) | (SEQ. ID NO.: 166) | |
| SGC33744 | | EST | GDB:4575826 | 0.15 | CTTTTGGTAGAGACAAGGTCTCA TATCT-GTCTGTAGTGCTTCAAATGT (SEQ. ID NO.: 167) | (SEQ. ID NO.: 168) | |
| SGC32272 | | EST | GDB:4581592 | 0.135 | GACGAAGGTGATTCAGGGC ACTGAA-GAACTCTTGTCCT (SEQ. ID NO.: 169) | (SEQ. ID NO.: 170) | |
| SGC34148 | | EST | GDB:4583084 | 0.1 | CAGATAAAAGAGTCACTATGGCTCA CACTTCTCCCACTTTGTCCC (SEQ. ID NO.: 171) | (SEQ. ID NO.: 172) | |
| WI-18546 | | EST | GDB:4574598 | 0.133 | TTATTGATAAGCATTAGTGAACCCC TGGCAAGTTAGGCACAGTCA (SEQ. ID NO.: 173) | (SEQ. ID NO.: 174) | Human 1.1 kb mRNA upregulated in retinoic acid treated HL-60 neutrophilic cells |
| SGC31103 | | EST | GDB:4567265 | 0.1 | CTATGCCCAGAGATGAACAGG TCCAC-TAAGGGCTATGTGC (SEQ. ID NO.: 175) | (SEQ. ID NO.: 176) | |
| SGC30028 | | Gene | GDB:4580505 | 0.128 | GCCAGCTTTATTGAGTAAACTTCC CACTG-GAGACTACAAGTGGTGG (SEQ. ID NO.: 177) | (SEQ. ID NO.: 178) | Human pyruvate carboxylase precursor |
| WI-2875 | D11S4407 | STS | GDB:678546 | 0.125 | CATCCCAACCATCACTCAGT GGGGAC-TAGCTTACAGATTTGA (SEQ. ID NO.: 179) | (SEQ. ID NO.: 180) | |
| SGC36985 | | Gene | GDB:4577182 | 0.223 | AGACTACATTTTGGAACCAGTGG (SEQ. ID NO.: 181) | (SEQ. ID NO.: 182) | LAR-interacting protein 1b |
| GCT16807 | D11S4270 | STS | GDB:626245 | 0.137 | GAAGGTTTTGTCCCTCGATC TGAGGGT-TGGGAAGATCATA (SEQ. ID NO.: 183) | (SEQ. ID NO.: 184) | |
| WI-6504 | D11S3974 | EST | GDB:588142 | 0.174 | CCTTCATAGCCACACCCG CAGCTAACTGT-TGACATGCCA (SEQ. ID NO.: 185) | (SEQ. ID NO.: 186) | |
| SGC31049 | | EST | GDB:4580093 | 0.15 | TCTTTACTGTGCTTACAACTTTCCT CAA-CAGTGCAGTCGGTATCG (SEQ. ID NO.: 387) | (SEQ. ID NO.: 188) | |
| TIGR-A002J17 | | EST | GDB:1222193 | 0.199 | AGATCAGCAAGCAGATAG CATTCCA-CATGGATAGAC (SEQ. ID NO.: 189) | (SEQ. ID NO.: 190) | NDUFV1 |
| WI-5996 | D11S2382 | EST | GDB:458683 | 0.1 | CATACCTATGAGGTGTGCTACAGG GCATTTTCTCCATCATCCTTGC (SEQ. ID NO.: 191) | (SEQ. ID NO.: 192) | amplaxin (EMS1) |
| WI-16987 | | EST | GDB:4575848 | 0.15 | TTACAGCCACCAAGGTTTCC AGGTGTGT-GTGCCAGGTTGA (SEQ. ID NO.: 193) | (SEQ. ID NO.: 194) | Nuclear mitotic apparatus protein 1. NUMA |
| SGC31912 | | EST | GDB:4567868 | 0.101 | CACTGTTATCTCATTAACTGTGAGG TTTGATTTTGTCTCCCAAA | | |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| WI-13500 | | EST | GDB:4577893 | 0.15 | CCCCACTCCCACTTTTATTT CCACTCAC-CTTTACTAGTCCTTTG (SEQ. ID NO: 195) | (SEQ. ID NO: 196) | |
| CHLC.GAATT1B01.P79 33 | D11S971 | MSAT | GDB:684255 | 0.103 | AGGACACAGCCTGCATCTAG ACCAG-GCATTGCACTAAAAG (SEQ. ID NO: 197) | (SEQ. ID NO: 198) | |
| SGC35519 | | Gene | GDB:4577180 | 0.134 | GATGGGTCACACTAACCTGTCA ACATT-TATATTTGGACATGCAACC (SEQ. ID NO: 199) | (SEQ. ID NO: 200) | LAR-interacting protein 1a mRNA |
| WI-11974 | | EST | GDB:1222255 | 0.108 | AGCATCTTTAATGTGTCAGGCA ATGT-GCTGGGCTGGAAAG (SEQ. ID NO: 201) | (SEQ. ID NO: 202) | Carnitine palmitoyl transferase I |
| WI-15244 | | Gene | GDB:4574740 | 0.308 | TCACATTCAAAAATCGGCAA CTGCCTGT-GTGGTGTCGC (SEQ. ID NO: 203) | (SEQ. ID NO: 204) | Beta-adrenergic receptor kinase 1. ADRB3 |
| WI-17496 | | EST | GDB:4583336 | 0.133 | TGTTTTATTTCTCAGTACAAAGCCA GAC-CTCCTGTGACACCACG (SEQ. ID NO: 205) | (SEQ. ID NO: 206) | |
| WI-9359 | D11S4383 | EST | GDB:678144 | 0.111 | CCACCAAATTATTTATAGTTCTGCG GTAA-GATTCTCCACTGTTGCACC (SEQ. ID NO: 207) | (SEQ. ID NO: 208) | FGF4 |
| WI-4232 | | STS | GDB:1222250 | 0.175 | CCTATAATGGGCTGGACCAA ACTCCTCAT-GTGAAGTCACCG (SEQ. ID NO: 209) | (SEQ. ID NO: 210) | |
| SHGC-4167 | | EST | GDB:4566789 | 0.161 | CAGTGTGCACGTTTTCATTT CAGCATCT-TCAGCACTTACC (SEQ. ID NO: 211) | (SEQ. ID NO: 212) | Human DNA helicase gen (SMBP2) |
| WI-14303 | | EST | GDB:4576938 | 0.15 | CTGCATTTATTATGAGAATCAACAG TGCT-GCTGGGAGTCAGAGTC (SEQ. ID NO: 213) | (SEQ. ID NO: 214) | |
| WI-16597 | | EST | GDB:4585666 | 0.13 | CAGGGCACTGAGATACACTTACC AAG-GATCAAGCAGGCATTTG (SEQ. ID NO: 215) | (SEQ. ID NO: 216) | |
| RC29S1CATTFOR/RC2 9S1CATTREV | D11S970 | MSAT | GDB:191084 | 0.15 | ACACATCTCTTCTGTGCCCC TGAACCCTG-GAGGCAGAG (SEQ. ID NO: 217) | (SEQ. ID NO: 218) | |
| UT979 | D11S1296 | MSAT | GDB:198525 | 0.362 | CATTCCCCAGTTTGCAGAC GTGCTGGGAT-TACAGGTGT (SEQ. ID NO: 219) | (SEQ. ID NO: 220) | |
| 1281/1282 | D11S1959E | EST | GDB:335216 | 0.07 | GCAGAGAAGTCCTGTTAGCC CCATGCTA-GAGAAGCACAAC (SEQ. ID NO: 221) | (SEQ. ID NO: 222) | |
| D11S468 | D11S468 | STS | | 0.096 | AGTGTTGGGCAGGACCTCTG CAGACA-GATAGCCCTGGGTTC (SEQ. ID NO: 223) | (SEQ. ID NO: 224) | |
| D11S668 | D11S668 | STS | GDB:179349 | 0.143 | TCCCCTCATCCCCTTGTCTGT AGC-CCCCTGGGGATAATC (SEQ. ID NO: 225) | (SEQ. ID NO: 226) | |
| | | | | | (SEQ. ID NO: 227) | (SEQ. ID NO: 228) | |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| RH18048 | | Gene | GDB:4572853 | 0.188 | GATGCTTACCTACCACGGC CTATCTGGGCTATG (SEQ. ID NO.: 229) | GAGGATTC- AGGATTC- | Aldehyde dehydrogenase (ALDH8) |
| IGHMBP2 | | Gene | GDB:4590087 | 0.699 | TGGCAGACCATGCTCCGCCT GAGAAGGC- CGGGAGGCTCTG (SEQ. ID NO.: 231) | Human DNA helicase gen (SMBP2) (SEQ. ID NO.: 230) | |
| NUMA | | Gene | GDB:4590244 | 0.277 | CTCCATCACAACCAGATTTGAGGCT GGGTGTGAGCTGCTGCTGAAGG (SEQ. ID NO.: 233) | Nuclear mitotic apparatus protein 1, NUMA (SEQ. ID NO.: 232) | |
| KRN1 | | Gene | GDB:4590232 | 0.228 | AGTGGGAAACCTCAGGTAGCTCCCGA CAGTTTGGCTCAGACATATGGGGGCA (SEQ. ID NO.: 235) | High sulphur keratin, KRN (SEQ. ID NO.: 234) | |
| Cda1ff06 | D11S2302E | EST | GDB:445887 | 0.091 | CATTAAGTAGTGCGGGGACAG CAAAGC- GACAGTTGAGTTGGGG (SEQ. ID NO.: 237) | (SEQ. ID NO.: 236) | |
| RH10753 | | Gene | GDB:4563588 | 0.194 | GGAGTAGACCATGATTACTG CATGGTC- TATTTATTCTCG (SEQ. ID NO.: 239) | protein phosphatase 2A, PP2A (SEQ. ID NO.: 238) | |
| EMS1 | | Gene | GDB:459016 | 0.84 | CGCCCTGGATCCTCACACTACA GGGCAT- CAGGGGATGGGTAGA (SEQ. ID NO.: 241) | Amplaxin (SEQ. ID NO.: 240) | |
| SHGC-11098 | DXS9736 | Gene | GDB:737674 | 0.137 | GCTCCTATCTGTGTTTTGAAATGG CCGTG- GCATAAGATAAGTAAACG (SEQ. ID NO.: 243) | (SEQ. ID NO.: 242) | |
| INPPL1 | | Gene | GDB:4590093 | 0.382 | CTTGGAGCGCTATGAGGAGGGC ATG- GCAACTGACCTTCCGTCCTG (SEQ. ID NO.: 245) | Androgen Receptor (SEQ. ID NO.: 244) | |
| RH18051 | | EST | GDB:4572859 | 0.195 | TTGGAGTCACAGGGGC CAGCACTATCCT- TGGGG (SEQ. ID NO.: 247) | 51C protein, inositol polyphosphate phosphatase- like 1 (SEQ. ID NO.: 246) | |
| Cda1ce11 | D11S2297E | EST | GDB:445869 | 0.1 | AACAAAGCTGCTTAGGCACCTG GATGAG- GACCAACTGGTGAC (SEQ. ID NO.: 249) | NOF1 (SEQ. ID NO.: 248) | |
| 1249/1250 | D11S1957E | EST | GDB:335210 | 0.247 | TTTTCCAATAATGTGACTTC CAATC- CCAACCGTAACAGGC (SEQ. ID NO.: 251) | (SEQ. ID NO.: 250) | |
| NDUFV1 | D11S2245E | EST | GDB:445695 | 0.158 | CTTGATCTCGCCCAGGAAC GCTCGCT- GAAGGATGAAGAC (SEQ. ID NO.: 253) | NDUFV1 (SEQ. ID NO.: 252) | |
| AFM032zg5 | D11S4136 | MSAT | GDB:609546 | 0.19 | GAATCGCTTGAACCCAG CCAGGTGGTCT- TAACGG (SEQ. ID NO.: 255) | (SEQ. ID NO.: 254) | |
| AFMa059xg9 | D11S4196 | MSAT | GDB:614025 | 0.2 | GAACGTTNTTCATGTAGGCGT TAATG- GTCGCTGTCCC (SEQ. ID NO.: 257) | (SEQ. ID NO.: 256) | |
| Cda17c12 | D11S2288E | EST | GDB:445842 | 0.158 | AGGGAAAATGGTATGTGGGGAG GCAGT- GTGTGAAGGCAGG (SEQ. ID NO.: 259) | (SEQ. ID NO.: 258) | |
| SHGC-1364 | D11S951E | EST | GDB:4562765 | 0.137 | AGTGGACAAAATGAGGAAAACAGG CCAACACAGTTTGCTCACATGCC | (SEQ. ID NO.: 260) | |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| RH17410 | | EST | GDB:4571587 | 0.126 | (SEQ. ID NO: 261) | TGACATCTTTGCATTATGGC AGTTATC-CCACCTGATACCG (SEQ. ID NO.: 262) | |
| RH17414 | | EST | GDB:4571595 | 0.121 | (SEQ. ID NO: 263) | AGCTCTTGCTTCTCAGTCCA CAAAAGT-TGTTTCGTGTTTGTTC (SEQ. ID NO.: 264) | |
| RH17770 | | EST | GDB:4572301 | 0.267 | (SEQ. ID NO: 265) | GCCTCTCAAAGTAGTTGGAACC TGTG-TATCCATAGTTGGAAAACAG (SEQ. ID NO.: 266) | |
| SEA | | EST | GDB:4590169 | 0.13 | (SEQ. ID NO: 267) | CTCAAGGCCAGGCATCACT GGACTCTTC-CATGCCAGTG (SEQ. ID NO.: 268) | S13 avian erythroblastosis oncogene homolog |
| RH10689 | | EST | GDB:4563460 | 0.107 | (SEQ. ID NO: 269) | AATGATGATCTCAACTCTG ACTGAA-GAACTCTTGTCCT (SEQ. ID NO.: 270) | |
| TIGR-A006P20 | | EST | GDB:4587692 | 0.236 | (SEQ. ID NO: 271) | GACATCTGTTAGTCTCATAATTC GGTAA-CAGTGTCTTGCTT (SEQ. ID NO.: 272) | |
| TIGR-A007D15 | | Gene | GDB:4588398 | 0.24 | (SEQ. ID NO: 273) | CTATGTACAAAACAGGAAGAG ATC-CTAGTTTCCTCTCCTT (SEQ. ID NO.: 274) | Menin gene (MEN1) |
| TIGR-A008B14 | | EST | GDB:4588882 | 0.141 | (SEQ. ID NO: 275) | GTAAATGAGAAACAGACAAATGA CTAT-TGGATGTGATATGTTATGG (SEQ. ID NO.: 276) | |
| TIGR-A008K11 | | EST | GDB:4589094 | 0.203 | (SEQ. ID NO: 277) | AAGTAGAAACAAAATGAGGGAC CCTAC-CCCAAGGTAACAG (SEQ. ID NO.: 278) | |
| TIGR-A008P15 | | EST | GDB:4589662 | 0.182 | (SEQ. ID NO: 279) | ACTTCCTATAAATGGAGGTGAG GAG-GAGCTTCAAGAGGAA (SEQ. ID NO.: 280) | |
| TIGR-A008T11 | | EST | GDB:4589278 | 0.338 | (SEQ. ID NO: 281) | CATACTCCTAGACTCAAGGAATC GAAT-GATGTACATGAATTCTTTG (SEQ. ID NO.: 282) | |
| TIGR-A008U40 | | EST | GDB:4589364 | 0.107 | (SEQ. ID NO: 283) | GTGTTGAGGAGAAAAGCACT CTCCCAG-TAGTCACAITCC (SEQ. ID NO.: 284) | |
| TIGR-A008X45 | | EST | GDB:4589838 | 0.242 | (SEQ. ID NO: 285) | CAAGTTACAAATAACTTAAGCCG CAA-GACCCTATCTCTACAAAAAC (SEQ. ID NO.: 286) | |
| SHGC-11839 | D11S4611 | Gene | GDB:740339 | 0.151 | (SEQ. ID NO: 287) | TTTATTAGAAGTGACTCTTTGGCCC GAC-TACCTGCCCTCAGCTTG (SEQ. ID NO.: 288) | Folate receptor 2 (FBP2) |
| NIB1242 | D11S4929E | EST | GDB:3888276 | 0.149 | (SEQ. ID NO: 289) | TTCTCATGTACAAAGCGGTC CCACTGGCT-cGMP-stimulated 3',5'-cyclic nucleotide TCTCTCTTTTT (SEQ. ID NO.: 290) | phosphodiesterase PDE2A3 (PDE2A) |
| SHGC-13599 | D22S1553 | Gene | GDB:737558 | 0.147 | (SEQ. ID NO: 291) | CACCAGAAGGTTGGGGTG ACTATTACGA- Macrophage Migration Inhibitory factor CATGAACGCGG (SEQ. ID NO.: 292) | |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| SHGC-11867 | D11S4331 | Gene | GDB:674684 | 0.14 | CTCATGCTGGATGACCCC TTGCCTTTCT-TGAAACTTAATTCC (SEQ. ID NO.: 295) | (SEQ. ID NO: 296) | P2U Purinoceptor |
| SHGC-15349 | D12S2124 | EST | GDB:740819 | 0.141 | TCACAGCCTTCAGTCAGGG ACATGCT-GTGGCACCATG (SEQ. ID NO.: 297) | (SEQ. ID NO.: 298) | |
| 8da84a05 | D11S2235E | EST | GDB:445662 | 0.095 | CCTGAGCTACTGCCACAG CCCTGACTTG-GACAGTGTCC (SEQ. ID NO.: 299) | (SEQ. ID NO.: 300) | |
| Bda99d07 | D11S2238E | EST | GDB:445674 | 0.09 | TCAGAGTCACTCCTGCCC CAAAT-TCAAGCTCATCCAGACC (SEQ. ID NO.: 301) | (SEQ. ID NO.: 302) | |
| folr1 | | Gene | GDB:197840 | 0.3 | CGGCATTTCATCCAGGAC GGTGTAGGAG-GTGCGACAAT (SEQ. ID NO.: 303) | (SEQ. ID NO.: 304) | Folate receptor2 (FBP2) |
| N1B1738 | D11S4284 | EST | GDB:626260 | 0.173 | TTCCATTTATTGAGCACCTG CTTAAGC-CACTGTGTTTTGG (SEQ. ID NO.: 305) | (SEQ. ID NO.: 306) | |
| WI-7351 | D11S4433 | Gene | GDB:679143 | 0.324 | CCTCCTACACCTGCAAAAGC TGGAA-GAACCCCAGAGGAC (SEQ. ID NO.: 307) | (SEQ. ID NO.: 318) | Folate receptor3 (FBP3) |
| WI-14325 | | EST | GDB:4578507 | 0.132 | AAAGCACAAAAGTAACAGCAACA GTGT-GTGGGCCACAATATTG (SEQ. ID NO.: 309) | (SEQ. ID NO.: 310) | |
| WI-15192 | | EST | GDB:4575806 | 0.15 | AGAGCACCTTTCCTCAGCAC AGAATCT-CATCACAGGGGCG (SEQ. ID NO.: 311) | (SEQ. ID NO.: 312) | |
| WI-17872 | | EST | GDB:4577492 | 0.141 | AAAAAGGACAGTGTCTAAAATTTGA AAT-TGTTTTTGTTTGTTTTTGAGT (SEQ. ID NO.: 313) | (SEQ. ID NO.: 314) | |
| SHGC-30732 | | EST | GDB:4567830 | 0.105 | GATTTAGGGAGTACAAGTGCGG GGGGA-CAAATTATACTTTATTCAGG (SEQ. ID NO.: 315) | (SEQ. ID NO.: 316) | |
| stSG4288 | | EST | GDB:4566057 | 0.123 | CCATCATCATATTGGTGTGACC TGGCTGC-CCAAGAAGAAG (SEQ. ID NO.: 317) | (SEQ. ID NO.: 318) | |
| WI-13814 | | EST | GDB:4579290 | 0.15 | TTAAGATGCCATTAAACTCATGAC CCAAG-(DRES9 GAGATGACCAAGTGG (SEQ. ID NO.: 319) | (SEQ. ID NO.: 320) | |
| WI-14122 | | Gene | GDB:4576114 | 0.126 | CCATCTCTTTTATCAGGGTTGG CTCTGTG- Human VEGF related factor isoform VRF186 CAAGTAAGCATCTTACA (SEQ. ID NO.: 321) | (SEQ. ID NO.: 322) | precursor (VRF) |
| 2729/2730 | D11S4057 | EST | GDB:596509 | 0.118 | CGACTGTGTATTTTCCACAG AGAAGC-CCATATCAATGCAC (SEQ. ID NO.: 323) | (SEQ. ID NO.: 324) | |
| SHGC-31329 | | EST | GDB:4567386 | 0.15 | AGCTTAAAGTAGGACAACCATGG GGAT-GCTTCACTCCAGAAAG (SEQ. ID NO.: 325) | (SEQ. ID NO.: 326) | |
| SGC33858 | | EST | GDB:4578600 | 0.127 | TGTTGTTTATTTCCACCTGCC AGAGTG-GCTGCAGGCCAG | | |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| WI-12191 | | EST | GDB:1222208 | 0.15 | (SEQ. ID NO: 327) | (SEQ. ID NO: 328) | |
| WI-13701 | | EST | GDB:4574692 | 0.15 | TTTTTTTTTTACACGAATTTGAGG (SEQ. ID NO: 329) | TGAGGAAGTAAAACAGGTCATC (SEQ. ID NO: 330) | |
| WI-14069 | | EST | GDB:4584373 | 0.15 | ATGAAATCTAAGCAGAATCCCA (SEQ. ID NO: 331) | CACAGAGTCCCAGGGTCTGT (SEQ. ID NO: 332) | |
| WI-14272 | | EST | GDB:4578525 | 0.125 | AAAGGCCTTTATTTATCTCTCTCTG (SEQ. ID NO: 333) | GCCTCAGAGCTGGTGGGT (SEQ. ID NO: 334) | |
| WI-17347 | | EST | GDB:4578523 | 0.127 | GCTTCTAAGTCTTAGAGTCAGCTGG (SEQ. ID NO: 335) | AGCCCACAGTCAGCCTACC (SEQ. ID NO: 336) | |
| stSG1561 | | EST | GDB:4564415 | 0.215 | TTGGTTAAATGATGCCCAGA (SEQ. ID NO: 337) | TGGTCCCACTCACATCCC (SEQ. ID NO: 338) | |
| stSG1938 | | EST | GDB:4564568 | 0.137 | ACACAGCATGCAGGGAGAG (SEQ. ID NO: 339) | ATCCCTGGTGCTTAGGTGG (SEQ. ID NO: 340) | |
| stSG2759 | | EST | GDB:4565137 | 0.141 | GATGGAAGTAGCTCCTCTCGG (SEQ. ID NO: 341) | GGAAGGCCAGCAAGTACTACC (SEQ. ID NO: 342) | |
| RH97 | | EST | GDB:4559690 | 0.17 | CCGGTTGCTTGGAAAGATG (SEQ. ID NO: 343) | GAAGTGTCTCGTTGGGGGA (SEQ. ID NO: 344) | |
| stSG4794 | | EST | GDB:4573113 | 0.141 | TTACAGGCATGAGTCACTACGC (SEQ. ID NO: 345) | ACCACTCTCACAGCCCTTACA (SEQ. ID NO: 346) | |
| stSG4957 | | EST | GDB:4569051 | 0.171 | CCCTCCCTCCACACAC (SEQ. ID NO: 347) | GCTCACTGAACTTTCAGGGC (SEQ. ID NO: 348) | |
| stSG4974 | | EST | GDB:4569063 | 0.166 | AGATACGGGCAAAACACTGG (SEQ. ID NO: 349) | GTTGAATATAGAGCAGGGCCC (SEQ. ID NO: 350) | |
| stSG8144 | | EST | GDB:4573137 | 0.17 | TTCTGAGGTCAGGGCTGTCT (SEQ. ID NO: 351) | AGCTTGGAAAATCTCGTGTCA (SEQ. ID NO: 352) | |
| stSG9275 | | EST | GDB:4569999 | 0.19 | ACTCAGTTCCCTCCCACCC (SEQ. ID NO: 353) | TCCTCTCACTCCTTCCCAGA (SEQ. ID NO: 354) | |
| SHGC-10667 | D11S4583 | Gene | GDB:740246 | 0.277 | GTGATCACGGCTCAACCTG (SEQ. ID NO: 355) | TGGAGGACTGCTTGAGCC (SEQ. ID NO: 356) | |
| SHGC-11930 | | Gene | GDB:1231223 | 0.21 | CTGCAGCTGCCTCAGTTTC (SEQ. ID NO: 357) | TCAAAAGTGCTGGTGACAGC (SEQ. ID NO: 358) | Human protein kinase (MLK-3) |
| | | | | | ATTTCCAGAGCCAGCTCAAA (SEQ. ID NO: 359) | CTTTAATTGT-TGTTGATGACACAAAGC (SEQ. ID NO: 360) | FGF3 |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| SHGC-32786 | | EST | GDB:4567878 | 0.125 | GATCATGCACTGTTGACCAC TACATTTGAAACATTTAAAACCTGA (SEQ. ID NO.: 361) | GATCATGCACTGTTGACCAC TACATTTGAAACATTTAAAACCTGA (SEQ. ID NO.: 362) | |
| FKBP2 | | Gene | | 0.064 | AACTGAGCTGTAACCAGACTGGGA TGGAACAGTCTGGTCCTGATGG (SEQ. ID NO.: 363) | (SEQ. ID NO.: 364) | FK506-Binding Protein Precursor (FKBP-13) |
| WI-13116 | | EST | GDB:4585099 | 0.202 | TTATCCCTTTATTGTTTCTCCTTTG TGGT- CACCTGTATTTATTGCTAGG (SEQ. ID NO.: 365) | (SEQ. ID NO.: 366) | |
| MDU1 | | Gene | GDB:4590064 | 0.859 | TCTTCAAAGCCTCTGCAGTACC CTCATCTCCAACCTGTCTAACC (SEQ. ID NO.: 367) | (SEQ. ID NO.: 368) | 4F2 CellL-Surface Antigen Heavy Chain (4F2HC) |
| S453 | D11S579 | STS | GDR:196276 | 0.108 | GTGGCTGCAGCTAATGTAAGACAC CAG- CAGAGACAATGGCGTAAGTCC (SEQ. ID NO.: 369) | (SEQ. ID NO.: 370) | |
| STS1-cSRL-112e11 | D11S3866 | STS | GDB:547681 | 0.135 | CTGATTGAGAACCAGAACAG TAAAGC- CCTATAACCTCTCC (SEQ. ID NO.: 371) | (SEQ. ID NO.: 372) | |
| STS1-cSRL-44a3 | D11S3830 | STS | GTC:547609 | 0.118 | TAGTAAGGGACCTTCACCAG AGAT- GTTTGGTATGACTTGG (SEQ. ID NO.: 373) | (SEQ. ID NO.: 374) | |
| STS1-cSRL-31b12 | D11S2439 | STS | GDB:459728 | 0.123 | GATGATTAAACTCCTCTGGC GAGA- CAGCTAAGCACTCATG (SEQ. ID NO.: 375) | (SEQ. ID NO.: 376) | |
| cSRL-4f9 | D11S1137 | STS | GDB:197824 | 0.196 | GAGGTGGTGGGCACCTGTA AGAGGG- GAGGAACACACCTT (SEQ. ID NO.: 377) | (SEQ. ID NO.: 378) | Folate receptor2 (FBP2) |
| SHGC-10323 | D11S4351 | Gene | GDB:676135 | 0.141 | GACCAGAGTCTGCCCAGAAG TCCCCAGCTCTATCCCAAC (SEQ. ID NO.: 379) | (SEQ. ID NO.: 380) | Collagen binding protein 2. colligin-2 gene (CBP2) |
| WI-9219 | | Gene | GDB:678379 | 0.1 | GGAGGGATGGACAAGTCTGA GTC- CAGCTCGCTGACTATCC (SEQ. ID NO.: 381) | (SEQ. ID NO.: 382) | Retinal outer segment membrane protein 1, ROM1 |
| GTC_ZNF | | Gene | | 0.172 | TCAAAAACACAGTCATCTCCA GCAAAG- GCTTTACCATATTG (SEQ. ID NO.: 383) | (SEQ. ID NO.: 384) | ZNF126 |
| AFMa152yh1 | D11S4087 | MSAT | GDB:603797 | 0.158 | GCTCAGCACCCCCATT TCCCTGCTCGG- GAAAC (SEQ. ID NO.: 385) | (SEQ. ID NO.: 386) | |
| AFMb331zh5 | D11S4162 | MSAT | GDB:613241 | 0.263 | GTTCTCCAGAGAGACAGGAC GAGAG- CAACACTATTGCCC (SEQ. ID NO.: 387) | (SEQ. ID NO.: 388) | |
| AFMb038yb9 | D11S4139 | MSAT | GDB:609621 | 0.151 | TATAGACTTCAGCCCTGCTGC CCTCTG- TAGGATGCAGTTGG (SEQ. ID NO.: 389) | (SEQ. ID NO.: 390) | |
| AFM212xe3 | D11S1314 | MSAT | GDB:199292 | 0.209 | TTGCTACGCACTCCTCTACT GTGAAG- GCAGGAAATGTGAC (SEQ. ID NO.: 391) | (SEQ. ID NO.: 392) | |
| WI-18813 | | EST | | 0.13 | ATCCTAGACCAGAGGAGCCC CTC- CCCCTGGTCCAGTTATT | | Serine/threonine kinase |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| WI-19549 | | EST | | 0.252 | (SEQ. ID NO: 393) AACTTTCATTTGCCAAGGGA GCTCTTGCGAT (SEQ. ID NO: 395) | (SEQ. ID NO: 394) AGCAGATCT- (SEQ. ID NO: 396) | |
| WI-20154 | | EST | | 0.25 | ACAGTTGTCATCGGTAGGCA GAATGGGATGGAGC (SEQ. ID NO: 397) | AAAAGTAT- (SEQ. ID NO: 398) | |
| WI-22393 | | EST | GDB:4583084 | 0.142 | GTGCAGGTGGCGTTTATTTT CCCTATATCTCCGTGTGCTCC (SEQ. ID NO: 399) | (SEQ. ID NO: 400) | DRES9 |
| WI-7587 | | EST | GDB:1223732 | 0.274 | GCTCTAGTGGGAAACCTCAGG GAATTC- CAGGCTCTTGCTTG (SEQ. ID NO: 401) | (SEQ. ID NO: 402) | Ultra high-sulphur keratin protein (KRN1) |
| EST455579 | | EST | | 0.273 | GGTTTGGTCTCAAAGGCAAA CCAGTA- CATGGTGGTCACCA (SEQ. ID NO: 403) | (SEQ. ID NO: 404) | |
| WI-21134 | | EST | | 0.293 | GCTGCCTTGGAATTTCTGTT GTGCTGTG- GTGGGAAAG (SEQ. ID NO: 405) | (SEQ. ID NO: 406) | Fas-associating death domain-containing protein, FADD |
| WI-21698 | | EST | | 0.25 | ATTCAAGCTCATCCAGACCC GGACTGGC- CCTTTGAAACTC (SEQ. ID NO: 407) | (SEQ. ID NO: 408) | |
| SHGC-7373 | D11S4567 | STS | GDB:740192 | 0.225 | ATATTGACCGTGCACAAATACG AGAC- CTGGGAAAAGTGGAGAA (SEQ. ID NO: 409) | (SEQ. ID NO: 410) | |
| SHGC-36533 | | STS | | 0.125 | ATTGGCAGTGGAAAATGCTT TTAATCTTTTGTCAACTTCCTGATT (SEQ. ID NO: 411) | (SEQ. ID NO: 412) | |
| ARIX | | Gene | | 0.242 | tctgtcctcttcaccgaagc ggataaagaaactccgctct- gctggta (SEQ. ID NO: 413) ga (SEQ. ID NO: 414) | | Arix homeodomain protein, neuroendocrine specific, tx factor |
| CLCI.PCR | | Gene | GDB:626613 | | TCAGGGCCTGTGTTGCCGCACTCTG AGC- GATGTAAAGGGTACCAGTGCCGAG (SEQ. ID NO: 415) G (SEQ. ID NO: 416) | | Chloride channel current inducer ICLN gene |
| B188N21-HL | | STS | | | AGGCATGCAAGCTTCTTA CCGGGAG- GAGACATCTAT (SEQ. ID NO: 417) | (SEQ. ID NO: 418) | |
| B234C17-HR | | STS | | | TGGTAAGCACAGAAAATGC AATG- GATGGGGATTATT (SEQ. ID NO: 419) | (SEQ. ID NO: 420) | |
| B225G10-HR | | STS | | | CTGGACGTTATGTCTGCC AGAGGC- CCAGTCACAGAT (SEQ. ID NO: 421) | (SEQ. ID NO: 422) | |
| B8247F23-HR | | STS | | | ATCACTCTGAACTGCCACT CCCTTCT- GTTTTTCTGTTTT (SEQ. ID NO: 423) | (SEQ. ID NO: 424) | |
| B337H24-HL | | STS | | | CAAGCTTTGAAGGAAGAG TAGGACGT- TAAGTAGGAC | | |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| B337L5-HL | | STS | | | GCTCTGCAGTGGGTAAAA GACTGTGCG (SEQ. ID NO.: 425) | ACTCTCCAA- (SEQ. ID NO.: 426) | |
| B382N10-HR | | STS | | | CCCTTTCTGAGGCAAGAT GAGAGAAC (SEQ. ID NO.: 427) | GACCACCTGG- (SEQ. ID NO.: 428) | |
| B12I1-HR | | STS | | | CGCTATGAGTCCCATCTG CAATGAAGG (SEQ. ID NO.: 429) | GATCAGCTG- (SEQ. ID NO.: 430) | |
| B180D17-HR | | STS | | | TTGAGTACACGGGGTGAC GAAAGATGA (SEQ. ID NO.: 431) | CGCAGGACT- (SEQ. ID NO.: 432) | |
| B236E6-HR | | STS | | | ACCTGTCTCCTCCTCCTGG TCTGTGGGA (SEQ. ID NO.: 433) | TGCTTTTCT- (SEQ. ID NO.: 434) | |
| B278E22-NR | | STS | | | ATGACCAGCAAGCATTGT TACAGGCG (SEQ. ID NO.: 435) | GTACTGGGAT- (SEQ. ID NO.: 436) | |
| B312F21-HR | | STS | | | GCAGAAGGTCCTTTGGAT TCATGCTT (SEQ. ID NO.: 437) | TTTGCAGGAT- (SEQ. ID NO.: 438) | |
| B337H24-HR | | STS | | | CGACATTCTTTTCTGGAGG GTTGGTTTT (SEQ. ID NO.: 439) | ACCTTTGCAT- (SEQ. ID NO.: 440) | |
| B358H9-HR | | STS | | | GCACTTTTCCTTCTTCTCC TGCTTTTGCTTTCTTCTGG (SEQ. IP NO.: 441) | (SEQ. ID NO.: 442) | |
| B148N18-HL | | STS | | | ACAGCTCCAGAGAGAAGGA CACTTGAAACCAGA (SEQ. ID NO.: 443) | GCAGT- (SEQ. ID NO.: 444) | |
| B172N12-HL | | STS | | | AGGCATCAAGCTTTCCTT GAGAACCGAGCC (SEQ. ID NO.: 445) | GGTTTA- (SEQ. ID NO.: 446) | |
| B172N12-HR | | STS | | | GTGGTTGCTGCAAGTTACC CCTTTCTTTCCA (SEQ. ID NO.: 447) | GGAATC- (SEQ. ID NO.: 448) | |
| B215J11-HR | | STS | | | GACCATTTGTTACGCAGC GAATGAACAA (SEQ. ID NO.: 449) | GATGGGTGT- (SEQ. ID NO.: 450) | |
| B223E5-HR | | STS | | | CTCAAGCTTCTGTTCATGC GTCTTGGCT (SEQ. ID NO.: 451) | GCTGTGAGT- (SEQ. ID NO.: 452) | |
| B312B3-HR | | STS | | | TACAGAAAACCGCAGCTC CAAAGGAAAGATT (SEQ. ID NO.: 453) | GCCAC- (SEQ. ID NO.: 454) | |
| B328G19-HL | | STS | | | AAAAGGAGGGAATCATGG CAGGAGGCAG (SEQ. ID NO.: 455) | TCACTTAG- (SEQ. ID NO.: 456) (SEQ. ID NO.: 457) (SEQ. ID NO.: 458) | |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| B328G19-HR | | STS | | | CTGAGCATCCGATGAGAC GAGCAGCTT (SEQ. ID NO: 459) | GTGCAAAAT (SEQ. ID NO: 460) | |
| 8329I10-HL | | STS | | | CAAACTGGGAATGA (SEQ. ID NO: 461) | TCTAACCCCTTACTGGGCTCCT (SEQ. ID NO: 462) | |
| D329I10-HR | | STS | | | CCCCACTCAGAAG (SEQ. ID NO: 463) | TTTACACAGGACCAGGGA ATCTC- (SEQ. ID NO: 464) | |
| B368G19-HL | | STS | | | AAATTTCATTAGCTG (SEQ. ID NO: 465) | GTCCACGGGCTTTATTCT TGAGCAT- (SEQ. ID NO: 466) | |
| B368G19-HR | | STS | | | GAATTGTTCAT (SEQ. ID NO: 467) | GGAAGAGCAAAATAAATCCA GGTGCACA- (SEQ. ID NO: 468) | |
| B36F16-HL | | STS | | | CAGGGACA (SEQ. ID NO: 469) | AGCACGCTTATTTCATGG GTAACACCAG- (SEQ. ID NO: 470) | |
| B250K11-HR | | STS | | | GAGAAGTAGGAA (SEQ. ID NO: 471) | TCCTGCTGCATTATGGAT GGGGGT- (SEQ. ID NO: 472) | |
| B338D17-HR | | STS | | | TGGGCTCTT (SEQ. ID NO: 473) | ATGGGGATTAAATACGGG AGCTAGCAT- (SEQ. ID NO: 474) | |
| 8268I23-HL | | STS | | | CAAGGCAAGTA (SEQ. ID NO: 475) | CTGAGGAGAAAGAGGCTGG CGCCTTA- (SEQ. ID NO: 476) | |
| B268I23-HR | | STS | | | GTCTGAAGGC (SEQ. ID NO: 477) | AGGATGCTTGCTAGGGTT CACAAGT- (SEQ. ID NO: 478) | |
| B371E15-HR | | STS | | | CACTCTTCTCACTAA (SEQ. ID NO: 479) | GGTCTCAGGAGCCCTTTA ACATGC- (SEQ. ID NO: 480) | |
| B312F21-HL | | STS | | | GAGCATAAGA (SEQ. ID NO: 481) | ACTTAACCAAGGATGGGG CAACCCAC- (SEQ. ID NO: 482) | |
| B338D17-HL | | STS | | | GAGTTCTCTCTC (SEQ. ID NO: 483) | TAGGCTCTGCACTCTTGG ACCCACG- (SEQ. ID NO: 484) | |
| B369H19-HL | | STS | | | CGCTCTCCTAGGCT (SEQ. ID NO: 485) | TAAAGGCGGTGAAGTGAG CTAC- (SEQ. ID NO: 486) | |
| B369H19-HR | | STS | | | GTGGTTGTT (SEQ. ID NO: 487) | TGGGGCCAGATAATTCTT CTGGTGTTTG- (SEQ. ID NO: 488) | |
| B444M11-HR | | STS | | | CATTTCCCA (SEQ. ID NO: 489) | AAGGAAGAGGTCACCAGG CACAAATTC- (SEQ. ID NO: 490) | |
| B269L23-HL | | STS | | | TCAATAGGTGATCCAACATTT AAAGTC- CCACAAAGGGTC | | |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| B250K11-HL | | STS | | | (SEQ. ID NO.: 491) | (SEQ. ID NO.: 492) GGGTAGGGGGATCTTTTT TGTGGAACAT-TCATTGGC | |
| B269L23-HR | | STS | | | (SEQ. ID NO.: 493) GTCCTGGGAAAGATGGAA | (SEQ. ID NO.: 494) TCAAAGCGTCTCCCATAA | |
| B364H4-HL | | STS | | | (SEQ. ID NO.: 495) TCTTTCGCTGTACTTGGC TGGGAGGTCA-GAGTGATG | (SEQ. ID NO.: 496) | |
| B364H4-HR | | STS | | | (SEQ. ID NO.: 497) GGACAGTGTATGTGTTGGG AGGCAGCT-GTTTTTGTCA | (SEQ. ID NO.: 498) | |
| B473O3-HR | | STS | | | (SEQ. ID NO.: 499) CTTCTTGAGTCCCGTGTG CAAC-CGAGAATCCTCTAGC | (SEQ. ID NO.: 500) | |
| B180D17-HL | | STS | | | (SEQ. ID NO.: 501) GCTGGGAGAGAATCACAA GCTTTGCA-GAAGAGACCA | (SEQ. ID NO.: 502) | |
| B200E21-HL | | STS | | | (SEQ. ID NO.: 503) ACGCTGTCAGGTCACACT GGAGGATGCT-CAGGTGAT | (SEQ. ID NO.: 504) | |
| B200E21-HR | | STS | | | (SEQ. ID NO.: 505) TAGGGGGATCTTTTTCCA GAG-CAATTTGAAAAGCCA | (SEQ. ID NO.: 506) | |
| B14L15-HR | | STS | | | (SEQ. ID NO.: 507) ATGGTCCAGCTCCTCTGT ATAGAGCAC-CCCATCTCC | (SEQ. ID NO.: 508) | |
| B442P6-HR | | STS | | | (SEQ. ID NO.: 509) AACATTGCTGTTAGCCCA GCAATCGAAA-CAGCATTC | (SEQ. ID NO.: 510) | |
| B188N21-NR | | STS | | | (SEQ. ID NO.: 511) ATGAGTTGGCAGCTGAAG AATGAAG-GTCTTGCCTCC | (SEQ. ID NO.: 512) | |
| GTC-ARRB1 | | Gene | | 0.067 | (SEQ. ID NO.: 513) GAGGAGAAGATCCACAAGCG TCTCTGGGGCATACTGAACC | (SEQ. ID NO.: 514) | Beta-arrestin-1 |
| B508A5-HL | | STS | | | (SEQ. ID NO.: 515) CTGAGCTTTTGGCACTGT CTGCTAGGT-GACAGCAGG | (SEQ. ID NO.: 516) | |
| B36F16-HR | | STS | | | (SEQ. ID NO.: 517) TGTATGAGTCTGGAGGGTGT ACACCTG-GCTGAGGAAAT | (SEQ. ID NO.: 518) | |
| B117N18-HL | | STS | | | (SEQ. ID NO.: 519) GCAGGGACGTGATAATA TTTTGCTTC-CTAACCATGC | (SEQ. ID NO.: 520) | |
| B14L15-HL | | STS | | | (SEQ. ID NO.: 521) AAAATTGTGAGCACCTCC TTTATATT-TAAAGTGGCTTTGTT | (SEQ. ID NO.: 522) | |
| | | | | | (SEQ. ID NO.: 523) | (SEQ. ID NO.: 524) | |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| B21K22-HL | | STS | | | GTGCAAAGCCCACAGTAT AGGAAAATG-CAAGAGCAG (SEQ. ID NO.: 525) | | |
| B21K22-HR | | STS | | | CCACTGAATTGCATACTTTG TCTGGGTC-CAGTCTGCTA (SEQ. ID NO.: 527) | | |
| B223ES-HL | | STS | | | AGATTTTGGGGAGTCAGG GCGCTCAAG-CAATTCTC (SEQ. ID NO.: 529) | | |
| B278E22-HL | | STS | | | CAAGCCCCAAAGTAGTCA GAATCATC-CAATCCACGA (SEQ. ID NO.: 531) | | |
| B444M11-HL | | STS | | | AGCCTCCAGGTGACTACC GAAGGACATG-GTCAGCAG (SEQ. ID NO.: 533) | | |
| B543O19-HR | | STS | | | ATGCTTTCAGCATTTTCG TGATCCGTGG-TAGGGTTA (SEQ. ID NO.: 535) | | |
| B117N18-HR | | STS | | | GTCGGATTGGTTTCACAA TTTTATGG-GAATTTCAGCC (SEQ. ID NO.: 537) | | |
| B543019-HL | | STS | | | TTTGAAAAGAACAGAAATGT GGCTAGTCTTTCCTGAACC (SEQ. ID NO.: 539) | | |
| B442P6-HL | | STS | | | CCTTAAATGCCCCTGATTC GCGTTTA-CAAGCTGAAGA (SEQ. ID NO.: 541) | | |
| B367H4-HR | | STS | | | TCAAGCTTGCTTTCTCAA GTAGCCCAG-CAAGTGTCT (SEQ. ID NO.: 543) | | |
| B250E21 HR | | STS | | | CCTGGCTGGAGATAGGAT CTTCCCCTCT-GCCTATGT (SEQ. ID NO.: 545) | | |
| B250E21-HL | | STS | | | GGCACGTACTTCCTACCA GGTGCTTCTTA-CAGGCAA (SEQ. ID NO.: 547) | | |
| B248C16-HR | | STS | | | ACCCAGGCTGGTGTGT ACTGAGTTAAT-TATCACTCCCCT (SEQ. ID NO.: 549) | | |
| 8248C16-HL | | STS | | | GATTGCATTTTGCTTCACC TCTGCTTTTA-GAGCTGTTAGC (SEQ. ID NO.: 551) | | |
| B160D8-HR | | STS | | | TCAAGCTTCAAAGAGCAGA GGAGTA-CATCCCAGGACC (SEQ. ID NO.: 553) | | |
| B539L7-HR | | STS | | | TGGTTGCTTTTAAATCCAGA CTCCCTTACT-TACTTGCATTG (SEQ. ID NO.: 555) | | |
| B473O3-HL | | STS | | | TCTCTCCCAGGGAATCT TTTATGTC-CCCTGAGCAC | | |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| AFMa190xd9 | D11S4095 | STS | GDB:606064 | 0.193 | (SEQ. ID NO.: 557) | TCCCTGGCTATCTTGAATC CTTGACTGGGTCCACG (SEQ. ID NO.: 558) | |
| ARRB1 (2) | | STS | | | CGAGACGCCAGTAGATACCA CATGCCTTTCAGT (SEQ. ID NO.: 559) | CATCCTC- CATCCTC-CATCCTCCATGCCTT (SEQ. ID NO.: 560) | |
| ARRB1 (1) | | STS | | | AGTTCCAGAGAAACGAGACGC CATCCTCCATGCCTT (SEQ. ID NO.: 561) | CTTGT- (SEQ. ID NO.: 562) | |
| P102F3S | | STS | GDB:6054145 | | GAGCGTGAGAGGTTGAGGAG CAAACTCCAGACGCACC (SEQ. ID NO.: 563) | AAA- (SEQ. ID NO.: 564) | |
| N172A | | STS | GDB:6054146 | 0.208 | CTGAACCACTACCTGTATGACCTG TACTTACTCCTACAGGGCCC (SEQ. ID NO.: 565) | CTAAC- (SEQ. ID NO.: 566) | |
| N60A | | STS | GDB:6054147 | 0.23 | GAAGCAATTCAATACTTTAACTG CAGTGCACCCAATC (SEQ. ID NO.: 567) | CCACTC- (SEQ. ID NO.: 568) | |
| cCI11-44A | | STS | GDB:6054148 | 0.239 | CTTCTCCTGGCCACTCTGAC CTTTGAATCCCAGC (SEQ. ID NO.: 569) | GGTTTAC- (SEQ. ID NO.: 570) | |
| CN1677-2A | | STS | GDB:6054149 | 0.271 | TGAGGATGAATGAGCACATAGG GTCCATTGAGTAGGC (SEQ. ID NO.: 571) | TTTGTG- (SEQ. ID NO.: 572) | |
| cCI11-524B | | STS | GDB:6054150 | 0.221 | AGGGGAAGGAATGTGCTTGG GAGCGGGCAGTGT (SEQ. ID NO.: 573) | TTCGGCT- (SEQ. ID NO.: 574) | |
| P117F3T | | STS | GDB:6054151 | 0.168 | ATTGAAGGTCCTCCAAAAGAATGCTG- CAGC AGAACGTCAA- CATATCTTTTGGGGGACAC (SEQ. ID NO.: 575) | (SEQ. ID NO.: 576) | |
| ARRB1 (3) | | Gene | | | TTGTATTTGAGGACTTTGCTCG CATCCTCCTCCTCC (SEQ. ID NO.: 577) | CGGTAC- (SEQ. ID NO.: 578) | |
| B215J11-HL | | STS | | 0.122 | TTTTTGCCTCATCTATGCCC GAGCAAGACTCC (SEQ. ID NO.: 579) | GGGTGACA- (SEQ. ID NO.: 580) | |
| B317G1-HR | | STS | | | TTGCTCAAGTTCTCCCTGG TGTTTTGAGGGGAG (SEQ. ID NO.: 581) | ACCT- (SEQ. ID NO.: 582) | |
| B317G1-HL | | STS | | | CTTGGCTATTTGGACAGC CACTTGC (SEQ. ID NO.: 583) | GGGCATTTACT- (SEQ. ID NO.: 584) | |
| B292J18-HR | | STS | | | CTTGTGTCAGTTGTCAGGG TGTGTCTTGG (SEQ. ID NO.: 585) | TGGAATTGT- (SEQ. ID NO.: 586) | |
| B10A18-HL | | STS | | | CCAGTTCCACTGGATGTT GTTTCTCAA (SEQ. ID NO.: 587) | ATGGGCTGT- (SEQ. ID NO.: 588) | |
| | | | | | (SEQ. ID NO.: 589) | (SEQ. ID NO.: 590) | |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| B10A18-HR | | STS | | | CTGCCTATCCCTGGACTT AGTTTGTC-CCTAGTGCCC (SEQ. ID NO: 591) | (SEQ. ID NO: 592) | |
| B527D12-HL | | STS | | | CAACACGTCTGACATCCAT GGATAGTG-CACACCCA (SEQ. ID NO: 593) | (SEQ. ID NO: 594) | |
| B372J11-HR | | STS | | | TGGGTTGGTACTATTGTTCCCAT AGTTC-CAGCCCCCTTACCAG (SEQ. ID NO: 595) | (SEQ. ID NO: 596) | |
| B372J11-HL | | STS | | | GGCCACTATCATCCCTGTGT TTTCA-CATGGAAGAACACG (SEQ. ID NO: 597) | (SEQ. ID NO: 598) | |
| B37E17-HR(GS) | | STS | | | ACAGTGACACTAGGGACGGG TGCCAG-GATGGAGATAACAA (SEQ. ID NO: 599) | (SEQ. ID NO: 600) | |
| B37E17-HL(GS) | | STS | | | CCTGTGGCACACATATCACC ACAACCAA-GAATGGAGCCAC (SEQ. ID NO: 601) | (SEQ. ID NO: 602) | |
| B34F22-HR(GS) | | STS | | | TGCTGTGTAACAAGTCCCCA TGAACG-GAGGACCTACCAAG (SEQ. ID NO: 603) | (SEQ. ID NO: 604) | |
| B34F22-HL(GS) | | STS | | | GCAGGGTCCGACTCACTAAG GCTGT-GAGTTCCCTTTACGC (SEQ. ID NO: 605) | (SEQ. ID NO: 606) | |
| B648P22-HR1 | | STS | | | ACAGTGGGGACAAAGACAGG TACAGGGCACCTCCCAGTAG (SEQ. ID NO: 607) | (SEQ. ID NO: 608) | |
| B82A4-HR2 | | STS | | | TCTTCTGTTAAGGTTTCCCCC TGTCT-CAAACCTCCCTCTGC (SEQ. ID NO: 609) | (SEQ. ID NO: 610) | |
| B648P22-HL | | STS | | | AACATATTTCCTCCCCAGCC CAGTC-CCAGCCAATGAGAAC (SEQ. ID NO: 611) | (SEQ. ID NO: 612) | |
| B82L11-HL (GS) | | STS | | | CTCCTCTGCATGGGAGAATC AGACCTGG-GACCAGTCTGTG (SEQ. ID NO: 613) | (SEQ. ID NO: 614) | |
| B86I13-HL (GS) | | STS | | | GGGAGACGACGTCACAAGAT TGATGT-TGGGAAGAATGGTGA (SEQ. ID NO: 615) | (SEQ. ID NO: 616) | |
| 144A24-HL | | STS | | | CAGGCATCTTCTATGTGCCA GGGAGGCA-CAAGTTCTTTCA (SEQ. ID NO: 617) | (SEQ. ID NO: 618) | |
| B82L11-HR (GS) | | STS | | | ACTTCGTGGCACTGAGTGTG CCTTTCT-TACGGATGAGGCA (SEQ. ID NO: 619) | (SEQ. ID NO: 620) | |
| B86I13-HR (GS) | | STS | | | GGCTGCTGAGCTCTTCTGAT TGGGTCTCTCTGCCTGACTT (SEQ. ID NO: 621) | (SEQ. ID NO: 622) | |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| B82L11-HL2 (GS) | | STS | | | TCACCTACTTCCAGCTTCCG AGACCTGG-GACCAGTCTGTG (SEQ. ID NO.: 623) | (SEQ. ID NO.: 824) | |
| B82L11-HL3 (GS) | | STS | | | CTCCTCTGCATGGGAGAATC AATTCAG-GAGACCTGGGACC (SEQ. ID NO.: 625) | (SEQ. ID NO.: 626) | |

Novel STSs were developed either from publicly available genomic sequence or from sequence-derived BAC insert ends. Primers were chosen using a script which automatically performs vector and repetitive sequence masking using Cross_match (P. Green, U. of Washington) and subsequent primer picking using Primer3 (Rozen, Skaletsky (1996, 1997). Primer3 is available at www.genome.wi.mit.edu/genome_software/other/primer3.html.

Polymerase chain reaction (PCR) conditions for each primer pair were initially optimized with respect to $MgCl_2$ concentration. The standard buffer was 10 mM Tris-HCl (pH 8.3), 50 mM KCl, $MgCl_2$, 0.2 mM each dNTP, 0.2 µM each primer, 2.7 ng/µl human DNA, 0.25 units of AmpliTaq (Perkin Elmer) and $MgCl_2$ concentrations of 1.0 mM, 1.5 mM, 2.0 mM or 2.4 mM. Cycling conditions included an initial denaturation at 94° C. for 2 minutes followed by 40 cycles at 94° C. for 15 seconds, 55° C. for 25 seconds, and 72° C. for 25 seconds followed by a final extension at 72° C. for 3 minutes. Depending on the results from the initial round of optimization the conditions were further optimized if necessary. Variables included increasing the annealing temperature to 58° C. or 60° C., increasing the cycle number to 42 and the annealing and extension times to 30 seconds, and using AmpliTaqGold (Perkin Elmer).

BAC clones (Kim et al, *Genomics*, 32:213–218 (1996), Shizuya et al, *Proc. Natl. Acad. Sci. USA*, 89:8794–8797 (1992)) containing STS markers of interest were obtained by PCR-based screening of DNA pools from a total human BAC library purchased from Research Genetics. DNA pools derived from library plates 1–596 were used corresponding to nine genomic equivalents of human DNA. The initial screening process involved PCR reactions of individual markers against superpools, i.e., a mixture of DNA derived from all BAC clones from eight 384-well library plates. For each positive superpool, plate (8), row (16) and column (24) pools were screened to identify a unique library address. PCR products were electrophoresed in 2% agarose gels (Sigma) containing 0.5 µg/ml ethidium bromide in 1×TBE at 150 volts for 45 min. The electrophoresis units used were the Model A3-1 systems from Owl Scientific Products. Typically, gels contained 10 tiers of lanes with 50 wells/tier. Molecular weight markers (100 bp ladder, Life Technologies, Bethesda, Md.) were loaded at both ends of the gel. Images of the gels were captured with a Kodak DC40 CCD camera and processed with Kodak 1D software. The gel data were exported as tab elimited text files; names of the files included information about the library screened, the gel image files and the marker screened. These data were automatically imported using a customized Perl script into Filemaker™ PRO (Claris Corp.) databases for data storage and analysis. In cases where incomplete or ambiguous clone address information was obtained, additional experiments were performed to recover a unique, complete library address.

Recovery of clonal BAC cultures from the library involved streaking out a sample from the library well onto LB agar (Maniatis et al, *Molecular Cloning: A Laboratory Manual.*, Cold Spring Harbor Laboratory, Cold Spring Harbor, N.Y. (1982)) containing 12.5 µg/ml chloramphenicol (Sigma). Two individual colonies and a portion of the initial streak quadrant were tested with appropriate STS markers by colony PCR for verification. Positive clones were stored in LB broth containing 12.5 µg/ml chloramphenicol and 15% glycerol at −70° C.

Several different types of DNA preparation methods were used for isolation of BAC DNA. The manual alkaline lysis miniprep protocol listed below (Maniatis et al, *Molecular Cloning: A Laboratory Manual*, Cold Spring Harbor Laboratory, Cold Spring Harbor, N.Y. (1982)) was successfully used for most applications, i.e., restriction mapping, CHEF gel analysis, FISH mapping, but was not successfully reproducible in endsequencing. The Autogen and Qiagen protocols were used specifically for BAC DNA preparation for endsequencing purposes.

Bacteria were grown in 15 ml Terrific Broth containing 12.5 µg/ml chloramphenicol in a 50 ml conical tube at 37° C. for 20 hrs with shaking at 300 rpm. The cultures were centrifuged in a Sorvall RT 6000 D at 3000 rpm (~1800 g) at 4° C. for 15 min. The supernatant was then aspirated as completely as possible. In some cases cell pellets were frozen at −20° C. at this step for up to 2 weeks. The pellet was then vortexed to homogenize he cells and minimize clumping. 250 µl of P1 solution (50 mM glucose, 15 mM Tris-HCl, pH 8, 10 mM EDTA, and 100 µg/ml RNase A) was added and the mixture pipetted up and down to mix. The mixture was then transferred to a 2 ml Eppendorf tube. 350 µl of P2 solution (0.2 N NaOH, 1% SDS) was then added, the mixture mixed gently and incubated for 5 min. at room temperature. 350 µl of P3 solution (3M KOAc, pH 5.5) was added and the mixture mixed gently until a white precipitate formed. The solution was incubated on ice for 5 min. and then centrifuged at 4° C. in a microfuge for 10 min. The supernatant was transferred carefully (avoiding the white precipitate) to a fresh 2 ml Eppendorf tube, and 0.9 ml of isopropanol was added, the solution mixed and left on ice for 5 min. The samples were centrifuged for 10 min., and the supernatant removed carefully. Pellets were washed in 70% ethanol and air dried for 5 min. Pellets were resuspended in 200 µl of TE8 (10 mM Tris-HCl, pH 8.0, 1.0 mM EDTA), and RNase A (Boehringer Mannheim) added to 100 µg/ml. Samples were incubated at 37° C. for 30 min., then precipitated by addition of $C_2H_3O_2Na.3H_2O$ to 0.5 M and 2 volumes of ethanol. Samples were centrifuged for 10 min., and the pellets washed with 70% ethanol followed by air drying and dissolving in 50 µl TE8. Typical yields for this DNA prep were 3–5 µg/15 ml bacterial culture. Ten to 15 µl were used for HindIII restriction analysis; 5 µl was used for NotI digestion and clone insert sizing by CHEF gel electrophoresis.

BACs were inoculated into 15 ml of 2×LB Broth containing 12.5 µg/ml chloramphenicol in a 50 ml conical tube. 4 tubes were inoculated for each clone. Cultures were grown overnight (~16 hr) at 37° C. with vigorous shaking (>300 rpm). Standard conditions for BAC DNA isolation were followed as recommended by the Autogen 740 manufacturer. 3 ml samples of culture were placed into Autogen tubes for a total of 60 ml or 20 tubes per clone. Samples were dissolved finally in 100 µl TE8 with 15 seconds of shaking as part of the Autogen protocol. After the Autogen protocol was finished DNA solutions were transferred from each individual tube and pooled into a 2 ml Eppendorf tube. Tubes with large amounts of debris (carry over from the pelleting debris step) were avoided. The tubes were then rinsed with 0.5 ml of TE8 successively and this solution added to the pooled material. DNA solutions were stored at 4° C.; clumping tended to occur upon freezing at −20° C. This DNA was either used directly for restriction mapping, CHEF gel analysis or FISH mapping or was further purified as described below for use in endsequencing reactions.

The volume of DNA solutions was adjusted to 2 ml with TE8, samples were then mixed gently and heated at 65° C. for 10 min. The DNA solutions were then centrifuged at 4° C. for 5 min. and the supernatants transferred to a 15 ml conical tube. The NaCl concentration was then adjusted to 0.75 M (~0.3 ml of 5 M NaCl to the 2 ml sample). The total volume was then adjusted to 6 ml with Qiagen column equilibration buffer (Buffer QBT). The supernatant containing the DNA was then applied to the column and allowed to enter by gravity flow. Columns were washed twice with 10 ml of Qiagen Buffer QC. Bound DNA was then eluted with four separate 1 ml aliquots of Buffer QF kept at 65° C. DNA was precipitated with 0.7 volumes of isopropanol (~2.8 ml). Each sample was then transferred to 4 individual 2.2 ml Eppendorf tubes and incubated at room temperature for 2 hr or overnight. Samples were centrifuged in a microfuge for 10 min. at 4° C. The supernatant was removed carefully and 1 ml of 70% ethanol was added. Samples were centrifuged again and because the DNA pellets were often loose at this stage, the supernatant removed carefully. Samples were centrifuged again to concentrate remaining liquid which was removed with a micropipet tip. DNA pellets were then dried in a desiccator for 10 min. 20 $\mu$l of sterile distilled and deionized $H_2O$ was added to each tube which was then placed at 4° C. overnight. The four 20 $\mu$l samples for each clone were pooled and the tubes rinsed with another 20 $\mu$l of sterile distilled and deionized $H_2O$ for a final volume of 100 $\mu$l. Samples were then heated at 65° C. for 5 min. and then mixed gently. Typical yields were 2–5 $\mu$g/60 ml culture as assessed by NotI digestion and comparison with uncut lambda DNA.

3 ml of LB Broth containing 12.5 $\mu$g/ml of chloramphenicol was dispensed into autoclaved Autogen tubes. A single tube was used for each clone. For inoculation, glycerol stocks were removed from −70° C. storage and placed on dry ice. A small portion of the glycerol stock was removed from the original tube with a sterile toothpick and transferred into the Autogen tube; the toothpick was left in the Autogen tube for at least two minutes before discarding. After inoculation the tubes were covered with tape making sure the seal was tight. When all samples were inoculated, the tube units were transferred into an Autogen rack holder and placed into a rotary shaker at 37° C. for 16–17 hours at 250 rpm. Following growth, standard conditions for BAC DNA preparation, as defined by the manufacturer, were used to program the Autogen. Samples were not dissolved in TE8 as part of the program and DNA pellets were left dry. When the program was complete, the tubes were removed from the output tray and 30 $\mu$l of sterile distilled and deionized $H_2O$ was added directly to the bottom of the tube. The tubes were then gently shaken for 2–5 seconds and then covered with parafilm and incubated at room temperature for 1–3 hours. DNA samples were then transferred to an Eppendorf tube and used either directly for sequencing or stored at 4° C. for later use.

V. BAC Clone Characterization for Physical Mapping

DNA samples prepared either by manual alkaline lysis or the Autogen protocol were digested with HindIII for analysis of restriction fragment sizes. This data were used to compare the extent of overlap among clones. Typically 1–2 $\mu$g were used for each reaction. Reaction mixtures included: 1×Buffer 2 (New England Biolabs), 0.1 mg/ml bovine serum albumin (New England Biolabs), 50 $\mu$g/ml RNase A (Boehringer Mannheim), and 20 units of HindIII (New England Biolabs) in a final volume of 25 $\mu$l. Digestions were incubated at 37° C. for 4–6 hours. BAC DNA was also digested with NotI for estimation of insert size by CHEF gel analysis (see below). Reaction conditions were identical to those for HindIII except that 20 units of NotI were used. Six $\mu$l of 6×Ficoll loading buffer containing bromphenol blue and xylene cyanol was added prior to electrophoresis.

HindIII digests were analyzed on 0.6% agarose (Seakem, FMC Bioproducts) in 1×TBE containing 0.5 $\mu$g/ml ethidium bromide. Gels (20 cm×25 cm) were electrophoresed in a Model A4 electrophoresis unit (Owl Scientific) at 50 volts for 20–24 hrs. Molecular weight size markers included undigested lambda DNA, HindIII digested lambda DNA, and HaeIII digested_X 74 DNA. Molecular weight markers were heated at 65° C. for 2 min. prior to loading the gel. Images were captured with a Kodak DC40 CCD camera and analyzed with Kodak 1D software.

NotI digests were analyzed on a CHEF DRII (BioRad) electrophoresis unit according to the manufacturer's recommendations. Briefly, 1% agarose gels (BioRad pulsed field grade) were prepared in 0.5×TBE, equilibrated for 30 minutes in the electrophoresis unit at 14° C., and electrophoresed at 6 volts/cm for 14 hrs with circulation. Switching times were ramped from 10 sec to 20 sec. Gels were stained after electrophoresis in 0.5 $\mu$g/ml ethidium bromide. Molecular weight markers included undigested lambda DNA, HindIII digested lambda DNA, lambda ladder PFG ladder, and low range PFG marker (all from New England Biolabs).

BAC DNA prepared either by the manual alkaline lysis or Autogen protocols were labeled for FISH analysis using a Bioprime labeling kit (BioRad) according to the manufacturer's recommendation with minor modifications. Approximately 200 ng of DNA was used for each 50 $\mu$l reaction. 3 $\mu$l were analyzed on a 2% agarose gel to determine the extent of labeling. Reactions were purified using a Sephadex G50 spin column prior to in situ hybridization. Metaphase FISH was performed as described (Ma et al, *Cytogenet. Cell Genet.*, 74:266–271 (1996)).

VI. BAC Endsequencing

The sequencing of BAC insert ends utilized DNA prepared by either of the two methods described above. The DYEnamic energy transfer primers and Dynamic Direct cycle sequencing kits from Amersham were used for sequencing reactions. Ready made sequencing mix including the M13-40 forward sequencing primer was used (Catalog #US79730) for the T7 BAC vector terminus; ready made sequencing mix (Catalog #US79530) was mixed with the M13-28 reverse sequencing primer (Catalog #US79339) for the SP6 BAC vector terminus. The sequencing reaction mixes included one of the four fluorescently labeled dye-primers, one of the four dideoxy termination mixes, dNTPs, reaction buffer, and Thermosequenase. For each BAC DNA sample, 3 $\mu$l of the BAC DNA sample was aliquoted to 4 PCR strip tubes. 2 $\mu$l of one of the four dye primer/termination mix combinations was then added to each of the four tubes. The tubes were then sealed and centrifuged briefly prior to PCR. Thermocycling conditions involved a 1 minute denaturation at 95° C., 15 second annealing at 45° C., and extension for 1 minute at 70° C. for 35 total After cycling the plates were centrifuged briefly to collect all the liquid to the bottom of the tubes. 5 $\mu$l of sterile distilled and deionized $H_2O$ was then added into each tube, the plates sealed and centrifuged briefly again. The four samples for each BAC were then pooled together. DNA was then precipitated by adding 1.5 $\mu$l of 7.5 M $NH_4OAc$ and 100 $\mu$l of −20° C. 100% ethanol to each tube. Samples were mixed by pipetting up and down once. The plates were then sealed and incubated on ice for 10 minutes. Plates were centrifuged in a table top Haraeus centrifuge at 4000 rpm (3,290 g) for 30 minutes at 4° C. to recover the DNA. The supernatant was removed and excess liquid blotted onto paper towels. Pellets were washed by adding 100 $\mu$l of −20° C. 70% ethanol into each tube and recentrifuging at 4000 rpm (3,290 g) for 10 minutes at 4° C. The supernatant was removed and excess liquid again removed by blotting on a paper towel. Remaining traces of liquid were removed by placing the plates upside down over a paper towel and centrifuging only until the centrifuge reached 800 rpm. Samples were then air dried at room temperature for 30 min. Tubes were capped and stored dry at −20° C. until electrophoresis. Immediately prior to electrophoresis the DNA was dissolved in 1.5 µl of Amersham loading dye. Plates were then sealed and centrifuged at 2000 rpm (825 g). The plates were then vortexed on a plate shaker for 1–2 minutes. Samples were then recentrifuged at 2000 rpm (825 g) briefly. Samples were then heated at 65° C. for 2 min. and immediately placed on ice. Standard gel electrophoresis was performed on ABI 377 fluorescent sequencers according to the manufacturer's recommendation.

VII. Sub-cloning and Sequencing of HBM BAC DNA

The physical map of the Zmax1 gene region provides a set of BAC clones that contain within them the Zmax1 gene and the HBM gene. DNA sequencing of several of the BACs from the region has been completed. The DNA sequence data is a unique reagent that includes data that one skilled in the art can use to identify the Zmax1 gene and the HBM gene, or to prepare probes to identify the gene(s), or to identify DNA sequence polymorphisms that identify the gene(s).

BAC DNA was isolated according to one of two protocols, either a Qiagen purification of BAC DNA (Qiagen, Inc. as described in the product literature) or a manual purification which is a modification of the standard alkaline lysis/Cesium Chloride preparation of plasmid DNA (see e.g., Ausubel et al, *Current Protocols in Molecular Biology*, John Wiley & Sons (1997)). Briefly for the manual protocol, cells were pelleted, resuspended in GTE (50 mM glucose, 25 mM Tris-Cl (pH 8), 10 mM EDTA) and lysozyme (50 mg/ml solution), followed by NaOH/SDS (1% SDS/0.2N NaOH) and then an ice-cold solution of 3M KOAc (pH 4.5–4.8). RnaseA was added to the filtered supernatant, followed by Proteinase K and 20% SDS. The DNA was then precipitated with isopropanol, dried and resuspended in TE (10 mM Tris, 1 mM EDTA (pH 8.0)). The BAC DNA was further purified by Cesium Chloride density gradient centrifugation (Ausubel et al, *Current Protocols in Molecular Biology*, John Wiley & Sons (1997)).

Following isolation, the BAC DNA was sheared hydrodynamically using an HPLC (Hengen, *Trends in Biochem. Sci.*, 22:273–274 (1997)) to an insert size of 2000–3000 bp. After shearing, the DNA was concentrated and separated on a standard 1% agarose gel. A single fraction, corresponding to the approximate size, was excised from the gel and purified by electroelution (Sambrook et al, *Molecular Cloning: A Laboratory Manual*, Cold Spring Harbor Laboratory, Cold Spring, N.Y. (1989)).

The purified DNA fragments were then blunt-ended using T4 DNA polymerase. The blunt-ended DNA was then ligated to unique BstXI-linker adapters (SEQ. ID. NOS.: 627–628) (5' GTCTTCACCACGGGG and 5' GTGGTGAAGAC in 100–1000 fold molar excess). These linkers were complimentary to the BstXI-cut pMPX vectors (constructed by the inventors), while the overhang was not self-complimentary. Therefore, the linkers would not concatemerize nor would the cut-vector religate itself easily. The linker-adapted inserts were separated from the unincorporated linkers on a 1% agarose gel and purified using GeneClean (BIO 101, Inc.). The linker-adapted insert was then ligated to a modified pBlueScript vector to construct a "shotgun" subclone library. The vector contained an out-of-frame lacZ gene at the cloning site which became in-frame in the event that an adapter-dimer is cloned, allowing these to be avoided by their blue-color.

All subsequent steps were based on sequencing by ABI377 automated DNA sequencing methods. Only major modifications to the protocols are highlighted. Briefly, the library was then transformed into DH5α competent cells (Life Technologies, Bethesda, Md., DH5α transformation protocol). It was assessed by plating onto antibiotic plates containing ampicillin and IPTG/Xgal. The plates were incubated overnight at 37° C. Successful transformants were then used for plating of clones and picking for sequencing. The cultures were grown overnight at 37° C. DNA was purified using a silica bead DNA preparation (Ng et al, *Nucl. Acids Res.*, 24:5045–5047 (1996)) method. In this manner, 25 µg of DNA was obtained per clone.

These purified DNA samples were then sequenced using ABI dye-terminator chemistry. The ABI dye terminator sequence reads were run on ABI377 machines and the data was directly transferred to UNIX machines following lane tracking of the gels. All reads were assembled using PHRAP (P. Green, Abstracts of DOE Human Genome Program Contractor-Grantee Workshop V, January 1996, p. 157) with default parameters and quality scores. The initial assembly was done at 6-fold coverage and yielded an average of 8–15 contigs. Following the initial assembly, missing mates (sequences from clones that only gave one strand reads) were identified and sequenced with ABI technology to allow the identification of additional overlapping contigs. Primers for walking were selected using a Genome Therapeutics program Pick_primer near the ends of the clones to facilitate gap closure. These walks were sequenced using the selected clones and primers. Data were reassembled with PHRAP into sequence contigs.

VIII. Gene Identification by Computational Methods

Following assembly of the BAC sequences into contigs, the contigs were subjected to computational analyses to identify coding regions and regions bearing DNA sequence similarity to known genes. This protocol included the following steps.

1. Degap the contigs: the sequence contigs often contain symbols (denoted by a period symbol) that represent locations where the individual ABI sequence reads have insertions or deletions. Prior to automated computational analysis of the contigs, the periods were removed. The original data was maintained for future reference.

2. BAC vector sequences were "masked" within the sequence by using the program cross match (Phil Green, http:\\chimera.biotech.washington.edu\UWGC). Since the shotgun libraries construction detailed above leaves some BAC vector in the shotgun libraries, this program was used to compare the sequence of the BAC contigs to the BAC vector and to mask any vector sequence prior to subsequent steps. Masked sequences were marked by an "X" in the sequence files, and remained inert during subsequent analyses.

3. *E. coli* sequences contaminating the BAC sequences were masked by comparing the BAC contigs to the entire *E. coli* DNA sequence.

4. Repetitive elements known to be common in the human genome were masked using cross match. In this implementation of crossmatch, the BAC sequence was compared to a database of human repetitive elements (Jerzy Jerka, Genetic Information Research Institute, Palo Alto, Calif.). The masked repeats were marked by X and remained inert during subsequent analyses.

5. The location of exons within the sequence was predicted using the MZEF computer program (Zhang, *Proc. Natl. Acad. Sci.*, 94:565–568 (1997)).

6. The sequence was compared to the publicly available unigene database (National Center for Biotechnology Information, National Library of Medicine, 38A, 8N905, 8600 Rockville Pike, Bethesda, Md. 20894; www.ncbi.nlm.nih.gov) using the blastn2 algorithm (Altschul et al, *Nucl. Acids Res.*, 25:3389–3402 (1997)). The parameters for this search were: E=0.05, v=50, B=50 (where E is the expected probability score cutoff, V is the number of database entries returned in the reporting of the results, and B is the number of sequence alignments returned in the reporting of the results (Altschul et al, *J. Mol. Biol.*, 215:403–410 (1990)).

7. The sequence was translated into protein for all six reading frames, and the protein sequences were compared to a non-redundant protein database compiled from Genpept Swissprot PIR (National Center for Biotechnology Information, National Library of Medicine, 38A, 8N905, 8600 Rockville Pike, Bethesda, Md. 20894; www.ncbi.nlm.nih.gov). The parameters for this search were E=0.05, V=50, B=50, where E, V, and B are defined as above.

8. The BAC DNA sequence was compared to the database of the cDNA clones derived from direct selection experiments (described below) using blastn2 (Altschul et al, *Nucl. Acids. Res.*, 25:3389–3402 (1997)). The parameters for this search were E=0.05, V=250, B=250, where E, V, and B are defined as above.

9. The BAC sequence was compared to the sequences of all other BACs from the HBM region on chromosome 11q12-13 using blastn2 (Altschul et al, *Nucl. Acids. Res.*, 25:3389–3402 (1997)). The parameters for this search were E=0.05, V=50, B=50, where E, V, and B are defined as above.

10. The BAC sequence was compared to the sequences derived from the ends of BACs from the HBM region on chromosome 11q12-13 using blastn2 (Altschul et al, *Nucl. Acids. Res.*, 25:3389–3402 (1997)). The parameters for this search were E=0.05, V=50, B=50, where E, V, and B are defined as above.

11. The BAC sequence was compared to the Genbank database (National Center for Biotechnology Information, National Library of Medicine, 38A, 8N905, 8600 Rockville Pike, Bethesda, Md. 20894; www.ncbi.nlm.nih.gov) using blastn2 (Altschul et al, *Nucl. Acids. Res.*, 25:3389–3402 (1997)). The parameters for this search were E=0.05, V=50, B=50, where E, V, and B are defined as above.

12. The BAC sequence was compared to the STS division of Genbank database (National Center for Biotechnology Information, National Library of Medicine, 38A, 8N905, 8600 Rockville Pike, Bethesda, Md. 20894; www.ncbi.nlm.nih.gov) using blastn2 (Altschul et al, 1997). The parameters for this search were E=0.05, V=50, B=50, where E, V, and B are defined as above.

13. The BAC sequence was compared to the Expressed Sequence (EST) Tag Genbank database (National Center for Biotechnology Information, National Library of Medicine, 38A, 8N905, 8600 Rockville Pike, Bethesda, Md. 20894; www.ncbi.nlm.nih.gov) using blastn2 (Altschul et al, *Nucl. Acids. Res.*, 25:3389–3402 (1997)). The parameters for this search were E=0.05, V=250, B=250, where E, V, and B are defined as above.

X. Gene Identification by Direct cDNA Selection

Primary linkered cDNA pools were prepared from bone marrow, calvarial bone, emoral bone, kidney, skeletal muscle, testis and total brain. Poly (A)+RNA was prepared from calvarial and femoral bone tissue (Chomczynski et al, *Anal. Biochem.*, 162:156–159 (1987); D'Alessio et al, *Focus*, 9:1–4 (1987)) and the remainder of the mRNA was purchased from Clontech (Palo Alto, Calif.). In order to generate oligo(dT) and random primed cDNA pools from the same tissue, 2.5 µg mRNA was mixed with oligo(dT) primer in one reaction and 2.5 µg mRNA was mixed with random hexamers in another reaction, and both were converted to first and second strand cDNA according to manufacturers recommendations (Life Technologies, Bethesda, Md.). Paired phosphorylated cDNA linkers (see sequence below) were annealed together by mixing in a 1:1 ratio (10 µg each) incubated at 65° C. for five minutes and allowed to cool to room temperature.

Paired linkers oligo1/2
 OLIGO 1: 5' CTG AGC GGA ATT CGT GAG ACC3' (SEQ ID NO:12)
 OLIGO 2: 5' TTG GTC TCA CGT ATT CCG CTC GA3' (SEQ ID NO:13)
Paired linkers oligo3/4
 OLIGO 3: 5' CTC GAG AAT TCT GGA TCC TC3' (SEQ ID NO:14)
 OLIGO 4: 5' TTG AGG ATC CAG AAT TCT CGA G3' (SEQ ID NO:15)
Paired linkers oligo5/6
 OLIGO 5: 5' TGT ATG CGA ATT CGC TGC GCG3' (SEQ ID NO:16)
 OLIGO 6: 5' TTC GCG CAG CGA ATT CGC ATA CA3' (SEQ ID NO:17)
Paired linkers oligo7/8
 OLIGO 7: 5' GTC CAC TGA ATT CTC AGT GAG3' (SEQ ID NO:18)
 OLIGO 8: 5' TTG TCA CTG AGA ATT CAG TGG AC3' (SEQ ID NO:19)
Paired linkers oligo11/12
 OLIGO 11: 5' GAA TCC GAA TTC CTG GTC AGC3' (SEQ ID NO:20)
 OLIGO 12: 5' TTG CTG ACC AGG AAT TCG GAT TC3' (SEQ ID NO:21)

Linkers were ligated to all oligo(dT) and random primed cDNA pools (see below) according to manufacturers instructions (Life Technologies, Bethesda, Md.).

Oligo 1/2 was ligated to oligo(dT) and random primed cDNA pools prepared from bone marrow. Oligo 3/4 was ligated to oligo(dT) and random primed cDNA pools prepared from calvarial bone. Oligo 5/6 was ligated to oligo (dT) and random primed cDNA pools prepared from brain and skeletal muscle. Oligo 7/8 was ligated to oligo(dT) and random primed cDNA pools prepared from kidney. Oligo 11/12 was ligated to oligo(dT) and random primed cDNA pools prepared from femoral bone.

The cDNA pools were evaluated for length distribution by PCR amplification using 1 µl of a 1:1, 1:10, and 1:100 dilution of the ligation reaction, respectively. PCR reactions were performed in a Perkin Elmer 9600, each 25 µl volume reaction contained 1 µl of DNA, 10 mM Tris-HCl (pH 8.3), 50 mM KCl, 1.5 mM MgCl2, 0.001% gelatin, 200 mM each dNTPs, 10 μM primer and 1 unit Taq DNA polymerase (Perkin Elmer) and was amplified under the following conditions: 30 seconds at 94° C., 30 seconds at 60° C. and 2 minutes at 72° C. for 30 cycles. The length distribution of the amplified cDNA pools were evaluated by electrophoresis on a 1% agarose gel. The PCR reaction that gave the best representation of the random primed and oligo(dT) primed cDNA pools was scaled up so that ~2–3 μg of each cDNA pool was produced. The starting cDNA for the direct selection reaction comprised of 0.5 μg of random primed cDNAs mixed with 0.5 μg of oligo(dT) primed cDNAs.

The DNA from the 54 BACs that were used in the direct cDNA selection procedure was isolated using Nucleobond AX columns as described by the manufacturer (The Nest Group, Inc.).

The BACs were pooled in equimolar amounts and 1 μg of the isolated genomic DNA was labelled with biotin 16-UTP by nick translation in accordance with the manufacturers instructions (Boehringer Mannheim). The incorporation of the biotin was monitored by methods that could be practiced by one skilled in the art (Del Mastro and Lovett, *Methods in Molecular Biology*, Humana Press Inc., NJ (1996)).

Direct cDNA selection was performed using methods that could be practiced by one skilled in the art (Del Mastro and Lovett, *Methods in Molecular Biology*, Humana Press Inc., NJ (1996)). Briefly, the cDNA pools were multiplexed in two separate reactions: In one reaction cDNA pools from bone marrow, calvarial bone, brain and testis were mixed, and in the other cDNA pools from skeletal muscle, kidney and femoral bone were mixed. Suppression of the repeats, yeast sequences and plasmid in the cDNA pools was performed to a Cot of 20. 100 ng of biotinylated BAC DNA was mixed with the suppressed cDNAs and hybridized in solution to a Cot of 200. The biotinylated DNA and the cognate cDNAs was captured on streptavidin-coated paramagnetic beads. The beads were washed and the primary selected cDNAs were eluted. These cDNAs were PCR amplified and a second round of direct selection was performed. The product of the second round of direct selection is referred to as the secondary selected material. A Galanin cDNA clone, previously shown to map to 11q12-13 (Evans, *Genomics*, 18:473–477 (1993)), was used to monitor enrichment during the two rounds of selection.

The secondary selected material from bone marrow, calvarial bone, femoral bone, kidney, skeletal muscle, testis and total brain was PCR amplified using modified primers of oligos 1, 3, 5, 7 and 11, shown below, and cloned into the UDG vector pAMP10 (Life Technologies, Bethesda, Md.), in accordance with the manufacturer's recommendations. Modified primer sequences:

Oligo1-CUA: 5' CUA CUA CUA CUA CTG AGC GGA ATT CGT GAG ACC3' (SEQ ID NO:22)

Oligo3-CUA: 5' CUA CUA CUA CUA CTC GAG AAT TCT GGA TCC TC3' (SEQ ID NO:23)

Oligo5-CUA: 5' CUA CUA CUA CUA TGT ATG CGA ATT CGC TGC GCG3' (SEQ ID NO:24)

Oligo7-CUA: 5' CUA CUA CUA CUA GTC CAC TGA ATT CTC AGT GAG3' (SEQ ID NO:25)

Oligo11-CUA: 5' CUA CUA CUA CUA GAA TCC GAA TTC CTG GTC AGC3' (SEQ ID NO:26)

The cloned secondary selected material, from each tissue source, was transformed into MAX Efficiency DH5a Competent Cells (Life Technologies, Bethesda, Md.) as recommended by the manufacturer. 384 colonies were picked from each transformed source and arrayed into four 96 well microtiter plates.

All secondarily selected cDNA clones were sequenced using M13 dye primer terminator cycle sequencing kit (Applied Biosystems), and the data collected by the ABI 377 automated fluorescence sequencer (Applied Biosystems).

All sequences were analyzed using the BLASTN, BLASTX and FASTA programs (Altschul et al, *J. Mol. Biol.*, 215:403–410 (1990), Altschul et al, *Nucl. Acids. Res.*, 25:3389–3402 (1997)). The cDNA sequences were compared to a database containing sequences derived from human repeats, mitochondrial DNA, ribosomal RNA, *E. coli* DNA to remove background clones from the dataset using the program cross_match. A further round of comparison was also performed using the program BLASTN2 against known genes (Genbank) and the BAC sequences from the HBM region. Those cDNAs that were >90% homologous to these sequences were filed according to the result and the data stored in a database for further analysis. cDNA sequences that were identified but did not have significant similarity to the BAC sequences from the HBM region or were eliminated by cross_match were hybridized to nylon membranes which contained the BACs from the HBM region, to ascertain whether they hybridized to the target.

Hybridization analysis was used to map the cDNA clones to the BAC target that selected them. The BACs that were identified from the HBM region were arrayed and grown into a 96 well microtiter plate. LB agar containing 25 μg/ml kanamycin was poured into 96 well microtiter plate lids. Once the agar had solidified, pre-cut Hybond N+ nylon membranes (Amersham) were laid on top of the agar and the BACs were stamped onto the membranes in duplicate using a hand held 96 well replica plater (V&P Scientific, Inc.). The plates were incubated overnight at 37° C. The membranes were processed according to the manufacturers recommendations.

The cDNAs that needed to be mapped by hybridization were PCR amplified using the relevant primer (oligos 1, 3, 5, 7 and 11) that would amplify that clone. For this PCR amplification, the primers were modified to contain a Tinkered digoxigenin molecule at the 5' of the oligonucleotide. The PCR amplification was performed under the same conditions as described in Preparation of cDNA Pools (above). The PCR products were evaluated for quality and quantity by electrophoresis on a 1% agarose gel by loading 5 μl of the PCR reaction. The nylon membranes containing the stamped BACs were individually pre-hybridized in 50 ml conical tubes containing 10 ml of hybridization solution (5×SSPE, 0.5×Blotto, 2.5% SDS and 1 mM EDTA (pH 8.0)). The 50 ml conical tubes were placed in a rotisserie oven (Robbins Scientific) for 2 hours at 65° C. 25 ng of each cDNA probe was denatured and added into individual 50 ml conical tubes containing the nylon membrane and hybridization solution. The hybridization was performed overnight at 65° C. The filters were washed for 20 minutes at 65° C. in each of the following solutions: 3×SSPE, 0.1% SDS; 1×SSPE, 0.1% SDS and 0.1×SSPE, 0.1% SDS.

The membranes were removed from the 50 ml conical tubes and placed in a dish. Acetate sheets were placed between each membrane to prevent them from sticking to each other. The incubation of the membranes with the Anti-DIG-AP and CDP-Star was performed according to manufacturers recommendations (Boehringer Mannheim). The membranes were wrapped in Saran wrap and exposed to Kodak Bio-Max X-ray film for 1 hour.

X. cDNA Cloning and Expression Analysis

To characterize the expression of the genes identified by direct cDNA selection and genomic DNA sequencing in comparison to the publicly available databases, a series of experiments were performed to further characterize the genes in the HBM region. First, oligonucleotide primers were designed for use in the polymerase chain reaction (PCR) so that portions of a cDNA, EST, or genomic DNA could be amplified from a pool of DNA molecules (a cDNA library) or RNA population (RT-PCR and RACE). The PCR primers were used in a reaction containing genomic DNA to verify that they generated a product of the size predicted based on the genomic (BAC) sequence. A number of cDNA libraries were then examined for the presence of the specific cDNA or EST. The presence of a fragment of a transcription unit in a particular cDNA library indicates a high probability that additional portions of the same transcription unit will be present as well.

A critical piece of data that is required when characterizing novel genes is the length, in nucleotides, of the processed transcript or messenger RNA (mRNA). One skilled in the art primarily determines the length of an mRNA by Northern blot hybridization (Sambrook et al, Molecular Cloning: A Laboratory Manual, Cold Spring Harbor Laboratory, Cold Spring Harbor N.Y. (1989)). Groups of ESTs and direct-selected cDNA clones that displayed significant sequence similarity to sequenced BACs in the critical region were grouped for convenience into approximately 30 kilobase units. Within each 30 kilobase unit there were from one up to fifty ESTs and direct-selected cDNA clones which comprised one or more independent transcription units. One or more ESTs or direct-selected cDNAs were used as hybridization probes to determine the length of the mRNA in a variety of tissues, using commercially available reagents (Multiple Tissue Northern blot; Clontech, Palo Alto, Calif.) under conditions recommended by the manufacturer.

Directionally cloned cDNA libraries from femoral bone, and calvarial bone tissue were constructed by methods familiar to one skilled in the art (for example, Soares in *Automated DNA Sequencing and Analysis*, Adams, Fields and Venter, Eds., Academic Press, NY, pages 110–114 (1994)). Bones were initially broken into fragments with a hammer, and the small pieces were frozen in liquid nitrogen and reduced to a powder in a tissue pulverizer (Spectrum Laboratory Products). RNA was extracted from the powdered bone by homogenizing the powdered bone with a standard Acid Guanidinium Thiocyanate-Phenol-Chloroform extraction buffer (e.g. Chomczynski and Sacchi, *Anal. Biochem.*, 162:156–159 (1987)) using a polytron homogenizer (Brinkman Instruments). Additionally, human brain and lung total RNA was purchased from Clontech. PolyA RNA was isolated from total RNA using dynabeads-dT according to the manufacturer's recommendations (Dynal, Inc.).

First strand cDNA synthesis was initiated using an oligonucleotide primer with the sequence: 5'-AACTGGAAGAATTC GCGCCGCAGGAATTTTTTTTTTTTTTTTTTT-3' (SEQ ID NO:27). This primer introduces a NotI restriction site (underlined) at the 3' end of the cDNA. First and second strand synthesis were performed using the "one-tube" cDNA synthesis kit as described by the anufacturer (Life Technologies, Bethesda, Md.). Double stranded cDNAs were treated with T4 polynucleotide kinase to ensure that the ends of the molecules were blunt (Soares in *Automated DNA Sequencing and Analysis*, Adams, Fields and Venter, Eds., Academic Press, NY, pages 110–114 (1994)), and the blunt ended cDNAs were then size selected by a Biogel column (Huynh et al in *DNA Cloning*, Vol. 1, Glover, Ed., IRL Press, Oxford, pages 49–78 (1985)) or with a size-sep 400 sepharose column (Pharmacia, catalog #27-5105-01). Only cDNAs of 400 base pairs or longer were used in subsequent steps. EcoRI adapters (sequence: 5' OH-AATTCGGCACGAG-OH 3' (SEQ ID NO:28), and 5' p-CTCGTGCCG-OH 3' (SEQ ID NO:29)) were then ligated to the double stranded cDNAs by methods familiar to one skilled in the art (Soares, 1994). The EcoRI adapters were then removed from the 3' end of the cDNA by digestion with NotI (Soares, 1994). The cDNA was then ligated into the plasmid vector pBluescript II KS+ (Stratagene, La Jolla, Calif.), and the ligated material was transformed into *E. coli* host DH10B or DH 12S by electroporation methods familiar to one skilled in the art (Soares, 1994). After growth overnight at 37° C., DNA was recovered from the *E. coli* colonies after scraping the plates by processing as directed for the Mega-prep kit (Qiagen, Chatsworth, Calif.). The quality of the cDNA libraries was estimated by counting a portion of the total numbers of primary transformants and determining the average insert size and the percentage of plasmids with no cDNA insert. Additional cDNA libraries (human total brain, heart, kidney, leukocyte, and fetal brain) were purchased from Life Technologies, Bethesda, Md.

cDNA libraries, both oligo (dT) and random hexamer ($N_6$) primed, were used for isolating cDNA clones transcribed within the HBM region: human bone, human brain, human kidney and human skeletal muscle (all cDNA libraries were made by the inventors, except for skeletal muscle (dT) and kidney (dT) cDNA libraries). Four 10×10 arrays of each of the 10 cDNA libraries were prepared as follows: the cDNA libraries were titered to $2.5 \times 10^6$ using primary transformants. The appropriate volume of frozen stock was used to inoculate 2 L of LB/ampicillin (100 mg/ml). This inoculated liquid culture was aliquotted into 400 tubes of 4 ml each. Each tube contained approximately 5000 cfu. The tubes were incubated at 30° C. overnight with gentle agitation. The cultures were grown to an OD of 0.7–0.9. Frozen stocks were prepared for each of the cultures by aliquotting 100 µl of culture and 300 µl of 80% glycerol. Stocks were frozen in a dry ice/ethanol bath and stored at −70° C. The remaining culture was DNA prepared using the Qiagen (Chatsworth, Calif.) spin miniprep kit according to the manufacturer's instructions. The DNAs from the 400 cultures were pooled to make 80 column and row pools. The cDNA libraries were determined to contain HBM cDNA clones of interest by PCR. Markers were designed to amplify putative exons. Once a standard PCR optimization was performed and specific cDNA libraries were determined to contain cDNA clones of interest, the markers were used to screen the arrayed library. Positive addresses indicating the presence of cDNA clones were confirmed by a second PCR using the same markers.

Once a cDNA library was identified as likely to contain cDNA clones corresponding to a specific transcript of interest from the HBM region, it was manipulated to isolate the clone or clones containing cDNA inserts identical to the EST or direct-selected cDNA of interest. This was accomplished by a modification of the standard "colony screening" method (Sambrook et al, *Molecular Cloning: A Laboratory Manual*, Cold Spring Harbor Laboratory, Cold Spring Harbor N.Y. (1989)). Specifically, twenty 150 mm LB+ampicillin agar plates were spread with 20,000 colony forming units (cfu) of cDNA library and the colonies allowed to grow overnight at 37° C. Colonies were transferred to nylon filters (Hybond from Amersham, or equivalent) and duplicates prepared by pressing two filters together essentially as described (Sambrook et al, *Molecular Cloning: A Laboratory Manual*, Cold Spring Harbor Laboratory, Cold Spring Harbor N.Y. (1989)). The "master" plate was then incubated an additional 6–8 hours to allow the colonies to grow back. The DNA from the bacterial colonies was then affixed to the nylon filters by treating the filters sequentially with denaturing solution (0.5 N NaOH, 1.5 M NaCl) for two minutes, neutralization solution (0.5 M Tris-Cl pH 8.0, 1.5 M NaCl) for two minutes (twice). The bacterial colonies were removed from the filters by washing in a solution of 2×SSC/ 0.1% SDS for one minute while rubbing with tissue paper. The filters were air dried and baked under vacuum at 80° C. for 1–2 hours.

A cDNA hybridization probe was prepared by random hexamer labeling (Fineberg and Vogelstein, *Anal. Biochem.*, 132:6–13 (1983)) or by including gene-specific primers and no random hexamers in the reaction (for small fragments). Specific activity was calculated and was >5×10$^8$ cpm/10$^8$ μg of cDNA. The colony membranes were then prewashed in 10 mM Tris-Cl pH 8.0, 1 M NaCl, 1 mM EDTA, 0.1% SDS for 30 minutes at 55° C. Following the prewash, the filters were prehybridized in >2 ml/filter of 6×SSC, 50% deionized formamide, 2% SDS, 5×Denhardt's solution, and 100 mg/ml denatured salmon sperm DNA, at 42° C. for 30 minutes. The filters were then transferred to hybridization solution (6×SSC, 2% SDS, 5×Denhardt's, 100 mg/ml denatured salmon sperm DNA) containing denatured α$^{32}$P-dCTP-labelled cDNA probe and incubated at 42° C. for 16–18 hours.

After the 16–18 hour incubation, the filters were washed under constant agitation in 2×SSC, 2% SDS at room temperature for 20 minutes, followed by two washes at 65° C. for 15 minutes each. A second wash was performed in 0.5×SSC, 0.5% SDS for 15 minutes at 65° C. Filters were then wrapped in plastic wrap and exposed to radiographic film for several hours to overnight. After film development, individual colonies on plates were aligned with the autoradiograph so that they could be picked into a 1 ml solution of LB Broth containing ampicillin. After shaking at 37° C. for 1–2 hours, aliquots of the solution were plated on 150 mm plates for secondary screening. Secondary screening was identical to primary screening (above) except that it was performed on plates containing ~250 colonies so that individual colonies could be clearly identified for picking.

After colony screening with radiolabeled probes yielded cDNA clones, the clones were characterized by restriction endonuclease cleavage, PCR, and direct sequencing to confirm the sequence identity between the original probe and the isolated clone. To obtain the full-length cDNA, the novel sequence from the end of the clone identified was used to probe the library again. This process was repeated until the length of the cDNA cloned matches that estimated to be full-length by the northern blot analysis.

RT-PCR was used as another method to isolate full length clones. The cDNA was synthesized and amplified using a "Superscript One Step RT-PCR" kit (Life Technologies, Gaithersburg, Md.). The procedure involved adding 1.5 μg of RNA to the following: 25 μl of reaction mix provided which is a proprietary buffer mix with MgSO$_4$ and dNTP's, 1 μl sense primer (10 μM) and 1 μl anti-sense primer (10 μM), 1 μl reverse transcriptase and Taq DNA polymerase mix provided and autoclaved water to a total reaction mix of 50 μl. The reaction was then placed in a thermocycler for 1 cycle at 50° C. for 15 to 30 minutes, then 94° C. for 15 seconds, 55–60° C. for 30 seconds and 68–72° C. for 1 minute per kilobase of anticipated product and finally 1 cycle of 72° C. for 5–10 minutes. The sample was analyzed on an agarose gel. The product was excised from the gel and purified from the gel (GeneClean, Bio 101). The purified product was cloned in pCTNR (General Contractor DNA Cloning System, 5 Prime-3 Prime, Inc.) and sequenced to verify that the clone was specific to the gene of interest.

Rapid Amplification of cDNA ends (RACE) was performed following the manufacturer's instructions using a Marathon cDNA Amplification Kit (Clontech, Palo Alto, Calif.) as a method for cloning the 5' and 3' ends of candidate genes. cDNA pools were prepared from total RNA by performing first strand synthesis, where a sample of total RNA sample was mixed with a modified oligo (dT) primer, heated to 70° C., cooled on ice and followed by the addition of: 5×first strand buffer, 10 mM dNTP mix, and AMV Reverse Transcriptase (20 U/μl). The tube was incubated at 42° C. for one hour and then the reaction tube was placed on ice. For second strand synthesis, the following components were added directly to the reaction tube: 5×second strand buffer, 10 mM dNTP mix, sterile water, 20×second strand enzyme cocktail and the reaction tube was incubated at 16° C. for 1.5 hours. T4 DNA Polymerase was added to the reaction tube and incubated at 16° C. for 45 minutes. The second-strand synthesis was terminated with the addition of an EDTA/Glycogen mix. The sample was subjected to a phenol/chloroform extraction and an ammonium acetate precipitation. The cDNA pools were checked for quality by analyzing on an agarose gel for size distribution. Marathon cDNA adapters (Clontech) were then ligated onto the cDNA ends. The specific adapters contained priming sites that allowed for amplification of either 5' or 3' ends, depending on the orientation of the gene specific primer (GSP) that was chosen. An aliquot of the double stranded cDNA was added to the following reagents: 10 μM Marathon cDNA adapter, 5×DNA ligation buffer, T4 DNA ligase. The reaction was incubated at 16° C. overnight. The reaction was heat inactivated to terminate the reaction. PCR was performed by the addition of the following to the diluted double stranded cDNA pool: 10×cDNA PCR reaction buffer, 10 μM dNTP mix, 10 μM GSP, 10 μM API primer (kit), 50×Advantage cDNA Polymerase Mix. Thermal Cycling conditions were 94° C. for 30 seconds, 5 cycles of 94° C. for 5 seconds, 72° C. for 4 minutes, 5 cycles of 94° C. for 5 seconds, 70° C. for 4 minutes, 23 cycles of 94° C. for 5 seconds, 68° C. for 4 minutes. After the first round of PCR was performed using the GSP to extend to the end of the adapter to create the adapter primer binding site, exponential amplification of the specific cDNA of interest was observed. Usually a second nested PCR is performed to confirm the specific cDNA. The RACE product was analyzed on an agarose gel and then excised and purified from the gel (GeneClean, BIO 101). The RACE product was then cloned into pCTNR (General Contractor DNA Cloning System, 5'-3', Inc.) and the DNA sequence determined to verify that the clone is specific to the gene of interest.

XI. Mutation Analysis

Comparative genes were identified using the above procedures and the exons from each gene were subjected to mutation detection analysis. Comparative DNA sequencing was used to identify polymorphisms in HBM candidate genes from chromosome 11q12-13. DNA sequences for candidate genes were amplified from patient lymphoblastoid cell lines.

The inventors developed a method based on analysis of direct DNA sequencing of PCR products amplified from candidate regions to search for the causative polymorphism. The procedure consisted of three stages that used different subsets of HBM family to find segregating polymorphisms and a population panel to assess the frequency of the polymorphisms. The family resources result from a single founder leading to the assumption that all affected individuals will share the same causative polymorphism.

Candidate regions were first screened in a subset of the HBM family consisting of the proband, daughter, and her mother, father and brother. Monochromosomal reference sequences were produced concurrently and used for comparison. The mother and daughter carried the HBM polymorphism in this nuclear family, providing the ability to monitor polymorphism transmission. The net result is that two HBM chromosomes and six non-HBM chromosomes were screened. This allowed exclusion of numerous frequent alleles. Only alleles exclusively present in the affected individuals passed to the next level of analysis.

Polymorphisms that segregated exclusively with the HBM phenotype in this original family were then re-examined in an extended portion of the HBM pedigree consisting of two additional nuclear families. These families consisted of five HBM and three unaffected individuals. The HBM individuals in this group included the two critical crossover individuals, providing the centromeric and telomeric boundaries of the critical region. Tracking the heredity of polymorphisms between these individuals and their affected parents allowed for further refining of the critical region. This group brought the total of HBM chromosomes screened to seven and the total of non-HBM chromosomes to seventeen.

When a given polymorphism continued to segregate exclusively with the HBM phenotype in the extended group, a population panel was then examined. This panel of 84 persons consisted of 42 individuals known to have normal bone mineral density and 42 individuals known to be unrelated but with untyped bone mineral density. Normal bone mineral density is within two standard deviations of BMD Z score 0. The second group was from the widely used CEPH panel of individuals. Any segregating polymorphisms found to be rare in this population were subsequently examined on the entire HBM pedigree and a larger population.

Polymerase chain reaction (PCR) was used to generate sequencing templates from the HBM family's DNA and monochromosomal controls. Enzymatic amplification of genes within the HBM region on 11q12-13 was accomplished using the PCR with oligonucleotides flanking each exon as well as the putative 5' regulatory elements of each gene. The primers were chosen to amplify each exon as well as 15 or more base pairs within each intron on either side of the splice. All PCR primers were made as chimeras to facilitate dye primer sequencing. The M13-21F (5'-GTA A CGA CGG CCA GT-3') (SEQ ID NO:30) and −28REV (5'-AAC AGC TAT GAC CAT G-3') (SEQ ID NO:31) primer binding sites were built on to the 5' end of each forward and reverse PCR primer, respectively, during synthesis. 150 ng of genomic DNA was used in a 50 μl PCR with 2UAmpliTaq, 500 nM primer and 125 μM dNTP. Buffer and cycling conditions were specific to each primer set. TaqStart antibody (Clontech) was used for hot start PCR to minimize primer dimer formation. 10% of the product was examined on an agarose gel. The appropriate samples were diluted 1:25 with deionized water before sequencing.

Each PCR product was sequenced according to the standard Energy Transfer primer (Amersham) protocol. All reactions took place in 96 well trays. 4 separate reactions, one each for A, C, G and T were performed for each template. Each reaction included 2 μl of the sequencing reaction mix and 3 μl of diluted template. The plates were then heat sealed with foil tape and placed in a thermal cycler and cycled according to the manufacturer's recommendation. After cycling, the 4 reactions were pooled. 3 μl of the pooled product was transferred to a new 96 well plate and 1 μl of the manufacturer's loading dye was added to each well. All 96 well pipetting procedures occurred on a Hydra 96 pipetting station (Robbins Scientific, USA). 1 μl of pooled material was directly loaded onto a 48 lane gel running on an ABI 377 DNA sequencer for a 10 hour, 2.4 kV run.

Polyphred (University of Washington) was used to assemble sequence sets for viewing with Consed (University of Washington). Sequences were assembled in groups representing all relevant family members and controls for a specified target region. This was done separately for each of the three stages. Forward and reverse reads were included for each individual along with reads from the monochromosomal templates and a color annotated reference sequence. Polyphred indicated potential polymorphic sites with a purple flag. Two readers independently viewed each assembly and assessed the validity of the purple-flagged sites.

A total of 23 exons present in the mature mRNA and several other portions of the primary transcript were evaluated for heterozygosity in the nuclear family of two HBM-affected and two unaffected individuals. 25 SNPs were identified, as shown in the table below.

TABLE 4

Single Nucleotide Polymorphisms in the Zmax1 Gene and Environs

| Exon Name | Location | Base Change |
| --- | --- | --- |
| b200e21-h_Contig1_1.nt | 69169 (309G) | C/A |
| b200e21-h_Contig4_12.nt | 27402 (309G) | A/G |
| b200e21-h_Contig4_13.nt | 27841 (309G) | T/C |
| b200e21-h_Contig4_16.nt | 35600 (309G) | A/G |
| b200e21-h_Contig4_21.nt | 45619 (309G) | G/A |
| b200e21-h_Contig4_22.nt-a | 46018 (309G) | T/G |
| b200e21-h_Contig4_22.nt-b | 46093 (309G) | T/G |
| b200e21-h_Contig4_22.nt-c | 46190 (309G) | A/G |
| b200e21-h_Contig4_24.nt-a | 50993 (309G) | T/C |
| b200e21-h_Contig4_24.nt-b | 51124 (309G) | C/T |
| b200e21-h_Contig4_25.nt | 55461 (309G) | C/T |
| b200e21-h_Contig4_33.nt-a | 63645 (309G) | C/A |
| b200e21-h_Contig4_33.nt-b | 63646 (309G) | A/C |
| b200e21-h_Contig4_61.nt | 24809 (309G) | T/G |
| b200e21-h_Contig4_62.nt | 27837 (309G) | T/C |
| b200e21-h_Contig4_63.nt-a | 31485 (309G) | C/T |
| b200e21-h_Contig4_63.nt-b | 31683 (309G) | A/G |
| b200e21-h_Contig4_9.nt | 24808 (309G) | T/G |
| b527d12-h_Contig030g_1.nt-a | 31340 (308G) | T/C |
| b527d12-h_Contig030g_1.nt-b | 32538 (308G) | A/G |
| b527d12-h_Contig080C_2.nt | 13224 (308G) | A/G |
| b527d12-h_Contig087C_1.nt | 21119 (308G) | C/A |
| b527d12-h_Contig087C_4.nt | 30497 (308G) | G/A |
| b527d12-h_Contig088C_4.nt | 24811 (309G) | A/C |
| b527d12-h_Contig089_1HP.nt | 68280 (309G) | G/A |

In addition to the polymorphisms presented in Table 4, two additional polymorphisms can also be present in SEQ ID NO:2. These is a change at position 2002 of SEQ ID NO:2. Either a guanine or an adenine can appear at this position. This polymorphism is silent and is not associated with any change in the amino acid sequence. The second change is at position 4059 of SEQ ID NO:2 corresponding in a cytosine (C) to thymine (T) change. This polymorphism results in a corresponding amino acid change from a valine (V) to an alanine (A). Other polymorphisms were found in the candidate gene exons and adjacent intron sequences. Any one or combination of the polymorphisms listed in Table 4 or the two discussed above could also have a minor effect on bone mass when present in SEQ ID NO:2.

The present invention encompasses the nucleic acid sequences having the nucleic acid sequence of SEQ ID NO: 1 with the above-identified point mutations.

Figure 5:
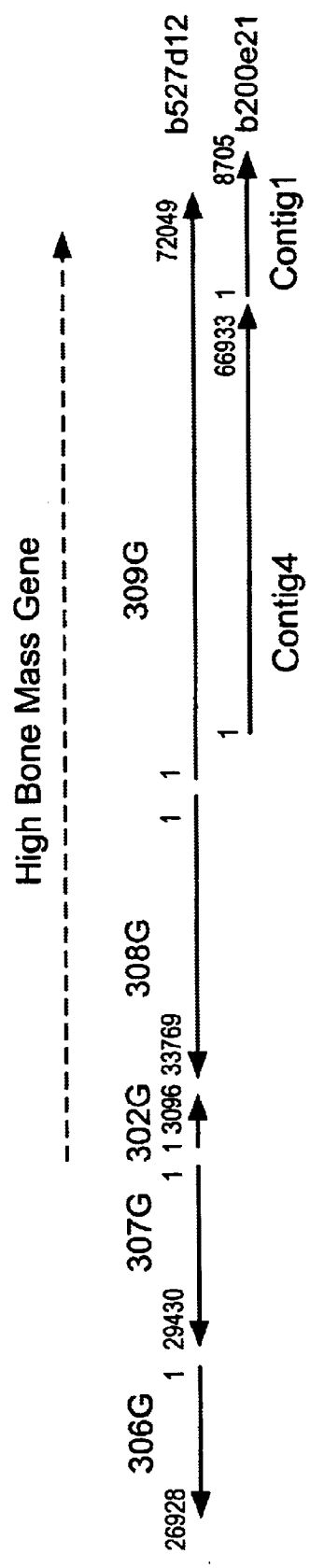
FIG. 5 is a schematic illustration of the BAC contigs B527D12 and B200E21 in relation to the HBM gene.
Figure 8:
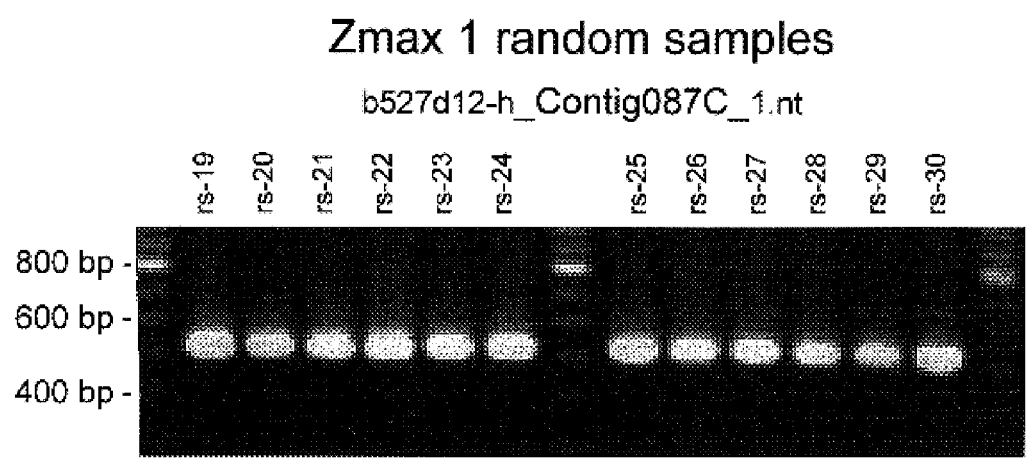
FIG. 8 shows a PCR product analysis.

Preferably, the present invention encompasses the nucleic acid of SEQ ID NO: 2. Specifically, a base-pair substitution changing G to T at position 582 in the coding sequence of Zmax1 (the HBM gene) was identified as heterozygous in all HBM individuals, and not found in the unaffected individuals (i.e., b527d12-h_Contig087C_1.nt). FIG. 5 shows the order of the contigs in B527D12. The direction of transcription for the HBM gene is from left to right. The sequence of contig308G of B527D12 is the reverse complement of the coding region to the HBM gene. Therefore, the relative polymorphism in contig 308G shown in Table 4 as a base change substitution of C to A is the complement to the G to T substitution in the HBM gene. This mutation causes a substitution of glycine 171 with valine (G171V).

The HBM polymorphism was confirmed by examining the DNA sequence of different groups of individuals. In all members of the HBM pedigree (38 individuals), the HBM polymorphism was observed in the heterozygous form in affected (i.e., elevated bone mass) individuals only (N=18). In unaffected relatives (N=20) (BMDZ<2.0) the HBM polymorphism was never observed. To determine whether this gene was ever observed in individuals outside of the HBM pedigree, 297 phenotyped individuals were characterized at the site of the HBM gene. None were heterozygous at the site of the HBM polymorphism. In an unphenotyped control group, 1 of 42 individuals was observed to be heterozygous at position 582. Since this individual is deceased, their bone mineral density could not be obtained. Taken together, these data prove that the polymorphism observed in the kindred displaying the high bone mass phenotype is strongly correlated with the G®T polymorphism at position 582 of Zmax1. Taken together, these results establish that the HBM polymorphism genetically segregates with the HBM phenotype, and that both the HBM polymorphism and phenotype are rare in the general population.

XII. Allele Specific Oligonucleotide (ASO) Analysis

The amplicon containing the HBMI polymorphism was PCR amplified using primers specific for the exon of interest. The appropriate population of individuals was PCR amplified in 96 well microtiter plates as follows. PCR reactions (20 µL) containing 1×Promega PCR buffer (Cat. #M1883 containing 1.5 mM MgCl$_2$), 100 mM dNTP, 200 nM PCR primers (SEQ. ID. NO.: 629–630) (1863F: CCAAGTTCTGAGAAGTCC and 1864R: AATACCTGAAACCATACCTG), 1 U Amplitaq, and 20 ng of genomic DNA were prepared and amplified under the following PCR conditions: 94° C., 1 minute, (94° C., 30 sec.; 58° C., 30 sec.; 72° C., 1 min.)×35 cycles), 72° C., 5', 4° C., hold. Loading dye was then added and 10 µl of the products was electrophoresed on 1.5% agarose gels containing 1 µg/ml ethidium bromide at 100–150 V for 5–10 minutes. Gels were treated 20 minutes in denaturing solution (1.5 M NaCl, 0.5 N NaOH), and rinsed briefly with water. Gels were then neutralized in 1 M Tris-HCl, pH 7.5, 1.5 M NaCl, for 20 minutes and rinsed with water. Gels were soaked in 10×SSC for 20 minutes and blotted onto nylon transfer membrane (Hybond N+-Amersham) in 10×SSC overnight. Filters were the rinsed in 6×SSC for 10 minutes and UV crosslinked.

The allele specific oligonucleotides (ASO) were designed with the polymorphism approximately in the middle. Oligonucleotides were phosphate free at the 5' end and were purchased from Gibco BRL. Sequences of the oligonucleotides are (SEQ. ID. NOS.: 631–632):

2326 Zmax1.ASO.g: AGACTGGGGTGAGACGC

2327 Zmax1.ASO.t: CAGACTGGGTTGAGACGCC The polymorphic nucleotides are underlined. To label the oligos, 1.5 µl of 1 µg/µl ASO oligo (2326.Zmax1.ASO.g or 2327.Zmax1.ASO.t), 11 µl ddH$_2$O, 2 µl 10×kinase forward buffer, 5 µl γ-$^{32}$P-ATP (6000 Ci/mMole), and 1 µl T4 polynucleotide kinase (10 U/µl) were mixed, and the reaction incubated at 37° C. for 30–60 minutes. Reactions were then placed at 95° C. for 2 minutes and 30 ml H$_2$O was added. The probes were purified using a G25 microspin column (Pharmacia).

Blots were prehybridized in 10 ml 5×SSPE, 5×Denhardt's, 2% SDS, and 100 µg/ml, denatured, sonicated salmon sperm DNA at 40° C. for 2 hr. The entire reaction mix of kinased oligo was then added to 10 ml fresh hybridization buffer (5×SSPE, 5×Denhardts, 2% SDS) and hybridized at 40° C. for at least 4 hours to overnight.

All washes done in 5×SSPE, 0.1% SDS. The first wash was at 45° C. for 15 minutes; the solution was then changed and the filters washed 50° C. for 15 minutes. Filters were then exposed to Kodak biomax film with 2 intensifying screens at −70° C. for 15 minutes to 1 hr. If necessary the filters were washed at 55° C. for 15 minutes and exposed to film again. Filters were stripped by washing in boiling 0.1×SSC, 0.1% SDS for 10 minutes at least 3 times.

Figure 9:
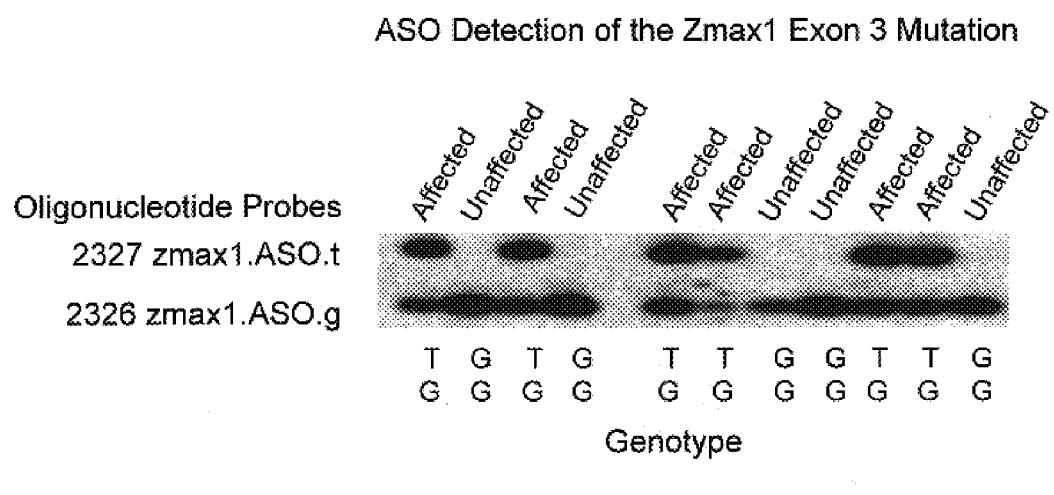
FIG. 9 shows allele specific oligonucleotide detection of the Zmax1 exon 3 mutation.

The two films that best captured the allele specific assay with the 2 ASOs were converted into digital images by scanning them into Adobe PhotoShop. These images were overlaid against each other in Graphic Converter and then scored and stored in FileMaker Pro 4.0 (see FIG. 9).

XIII. Cellular Localization of Zmax1

A. Gene Expression in Rat Tibia by Non Isotopic In Situ Hybridization

In situ hybridization was conducted by Pathology Associates International (PAI), Frederick, Md. This study was undertaken to determine the specific cell types that express the Zmax1 gene in rat bone with particular emphasis on areas of bone growth and remodeling. Zmax1 probes used in this study were generated from both human (HuZmax1) and mouse (MsZmax1) cDNAs, which share an 87% sequence identity. The homology of human and mouse Zmax1 with rat Zmax1 is unknown.

For example, gene expression by non-isotopic in situ hybridization was performed as follows, but other methods would be known to the skilled artisan. Tibias were collected from two 6 to 8 week old female Sprague Dawley rats euthanized by carbon dioxide asphyxiation. Distal ends were removed and proximal tibias were snap frozen in OCT embedding medium with liquid nitrogen immediately following death. Tissues were stored in a −80° C. freezer.

Probes for amplifying PCR products from cDNA were prepared as follows. The primers to amplify PCR products from a cDNA clone were chosen using published sequences of both human LRP5 (Genbank Accession No. ABO17498) and mouse LRP5 (Genbank Accession No. AF064984). In order to minimize cross reactivity with other genes in the LDL receptor family, the PCR products were derived from an intracellular portion of the protein coding region. PCR was performed in a 50 µl reaction volume using cDNA clone as template. PCR reactions contained 1.5 mM MgCl$_2$, 1 unit Amplitaq, 200 µM dNTPs and 2 µM each primer. PCR cycling conditions were 94° C. for 1 min., followed by 35 cycles of 94° C. for 30 seconds, 55° C. for 30 seconds, 72° C. for 30 seconds; followed by a 5 minute extension at 72° C. The reactions were then run on a 1.5% agarose Tris-Acetate gel. DNA was eluted from the agarose, ethanol precipitated and resuspended in 10 mM Tris, pH 8.0. Gel purified PCR products were prepared for both mouse and human cDNAs and supplied to Pathology Associates International for in situ hybridizations.

The sequence of the human and mouse PCR primers and products were as follows:

Human Zmax1 sense primer (HBM1253) (SEQ. ID. NO.: 633)

CCCGTGTGCTCCGCCGCCCAGTTC

Human Zmax1 antisense primer (HBM1465) (SEQ. ID. NO.: 634)

GGCTCACGGAGCTCATCATGGACTT

Human Zmax1 PCR product (SEQ. ID. NO.: 635)

CCCGTGTGCTCCGCCGCCCAGTTCCCCTGCGCGCGGGGTCAGTGTGTGGACCTGC

GCCTGCGCTGCGACGGCGAGGCAGACTGTCAGGACCGCTCAGACGAGGTGGACT

GTGACGCCATCTGCCTGCCCAACCAGTTCCGGTGTGCGAGCGGCCAGTGTGTCCT

CATCAAACAGCAGTGCGACTCCTTCCCCGACTGTATCGACGGCTCCGACGAGCTC

ATGTGTGAAATCACCAAGCCGCCCTCAGACGACAGCCCGGCCCACAGCAGTGCC

ATCGGGCCCGTCATTGGCATCATCCTCTCTCTCTTCGTCATGGGTGGTGTCTATTT

TGTGTGCCAGCGCGTGGTGTGCCAGCGCTATGCGGGGGCCAACGGGCCCTTCCC

GCACGAGTATGTCAGCGGGACCCCGCACGTGCCCCTCAATTTCATAGCCCCGGG

CGGTTCCCAGCATGGCCCCTTCACAGGCATCGCATGCGGAAAGTCCATGATGAG

CTCCGTGAGCC

Mouse Zmax1 Sense primer (HBM1655) (SEQ. ID. NO.: 636)

AGCGAGGCCACCATCCACAGG

Mouse zmax1 antisense primer (HBM1656) (SEQ. ID. NO.: 637)

TCGCTGGTCGGCATAATCAAT

Mouse Zmax1 PCR product (SEQ. ID. NO.: 638)

AGCAGAGCCACCATCCACAGGATCTCCCTGGAGACTAACAACAACGATGTGGCT

ATCCCACTCACGGGTGTCAAAGAGGCCTCTGCACTGGACTTTGATGTGTCCAACA

ATCACATCTACTGGACTGATGTTAGCCTCAAGACGATCAGCCGAGCCTTCATGAA

TGGGAGCTCAGTGGAGCACGTGATTGAGTTTGGCCTCGACTACCCTGAAGGAAT

GGCTGTGGACTGGATGGGCAAGAACCTCTATTGGGCGGACACAGGGACCAACAG

GATTGAGGTGGCCCGGCTGGATGGGCAGTTCCGGCAGGTGCTTGTGTGGAGAGA

CCTTGACAACCCCAGGTCTCTGCCTCTGGATCCTACTAAAGGCTACATCTACTGG

ACTGAGTGGGGTGGCAAGCCAAGGATTGTGCGGGCCTTCATGGATGGGACCAAT

TGTATGACACTGGTAGACAAGGTGGGCCGGGCCAACGACCTCACCATTGATTAT

GCCGACCAGCGA

Riboprobes were synthesized as follows. The PCR products were reamplified with chimeric primers designed to incorporate either a T3 promoter upstream, or a T7 promoter downstream of the reamplification products. The resulting PCR products were used as template to synthesize digoxigenin-labeled riboprobes by in vitro transcription (IVT). Antisense and sense riboprobes were synthesized using T7 and T3 RNA polymerases, respectively, in the presence of digoxigenin-11-UTP (Boehringer-Mannheim) using a MAXIscript IVT kit (Ambion) according to the manufacturer. The DNA was then degraded with Dnase-1, and unincorporated digoxigenin was removed by ultrafiltration. Riboprobe integrity was assessed by electrophoresis through a denaturing polyacrylamide gel. Molecular size was compared with the electrophoretic mobility of a 100–1000 base pair (bp) RNA ladder (Ambion). Probe yield and labeling was evaluated by blot immunochemistry. Riboprobes were stored in 5 $\mu$l aliquots at −80° C.

The in situ hybridization was performed as follows. Frozen rat bone was cut into 5 $\mu$M sections on a Jung CM3000 cryostat (Leica) and mounted on adhesive slides (Instrumedics). Sections were kept in the cryostat at −20° C. until all the slides were prepared in order to prevent mRNA degradation prior to post-fixation for 15 minutes in 4% paraformaldehyde. Following post-fixation, sections were incubated with 1 ng/$\mu$l of either antisense or sense riboprobe in Pathology Associates International (PAI) customized hybridization buffer for approximately 40 hours at 58° C. Following hybridization, slides were subjected to a series of post-hybridization stringency washes to reduce nonspecific probe binding. Hybridization was visualized by immunohistochemistry with an anti-digoxigenin antibody (FAB fragment) conjugated to alkaline phosphatase. Nitroblue tetrazolium chloride/bromochloroindolyl phosphate (Boehringer-Mannheim), a precipitating alkaline phosphatase substrate, was used as the chromogen to stain hybridizing cells purple to nearly black, depending on the degree of staining. Tissue sections were counter-stained with nuclear fast red. Assay controls included omission of the probe, omission of probe and anti-digoxigenin antibody.

Specific cell types were assessed for demonstration of hybridization with antisense probes by visualizing a purple to black cytoplasmic and/or peri-nuclear staining indicating a positive hybridization signal for mRNA. Each cell type was compared to the replicate sections, which were hybridized with the respective sense probe. Results were considered positive if staining was observed with the antisense probe and no staining or weak background with the sense probe.

Figure 10A:
FIGS. 10A and 10B show the cellular localization of mouse Zmax1 by in situ hybridization at 100×magnification using sense and antisense probes.
Figure 10B:
Figure 11A:
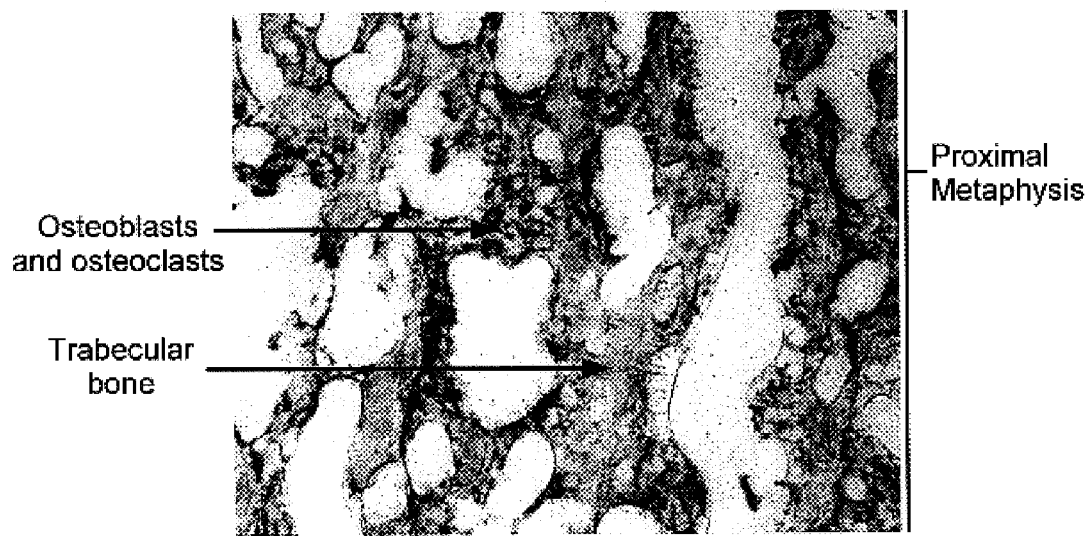
FIGS. 11A and 11B show the cellular localization of mouse Zmax1 by in situ hybridization at 400×magnification using sense and antisense probes.
Figure 11B:
Figure 12A:
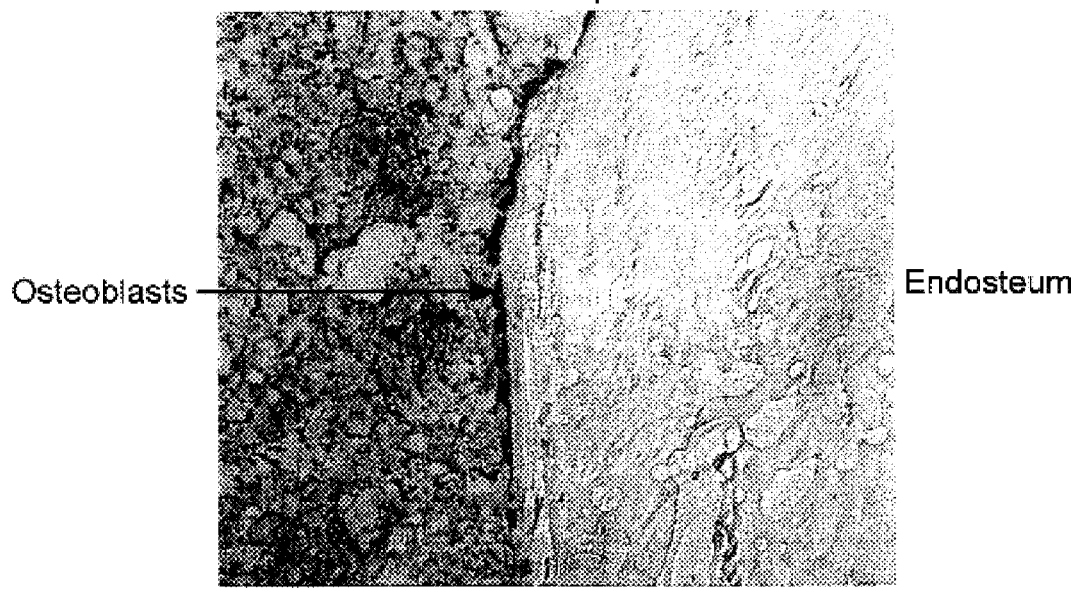
FIGS. 12A and 12B show the cellular localization of mouse Zmax1 by in situ hybridization of osteoblasts in the endosteum at 400×magnification using sense and antisense probes.
Figure 12B:

The cellular localization of the hybridization signal for each of the study probes is summarized in Table 5. Hybridization for Zmax1 was primarily detected in areas of bone involved in remodeling, including the endosteum and trabecular bone within the metaphysis. Hybridization in selected bone lining cells of the periosteum and epiphysis were also observed. Positive signal was also noted in chondrocytes within the growth plate, particularly in the proliferating chondrocytes. See FIGS. 10, 11 and 12 for representative photomicrographs of in situ hybridization results.

TABLE 5

Summary of Zmax1 in situ hybridization in rat tibia

| PROBE | SITE | ISH SIGNAL |
|---|---|---|
| Hu Zmax1 | Epiphysis | |
| | Osteoblasts | + |
| | Osteoclasts | |
| | Growth Plate | |
| | resting chondrocytes | − |
| | proligferating chondrocytes | + |
| | hypertrophic chondrocytes | − |
| | Metaphysis | |
| | osteoblasts | + |
| | osteoclasts | + |
| | Diaphysis | − |
| | Endosteum | |
| | osteoblasts | + |
| | osteoclasts | + |
| | Periosteum | − |
| Ms7max1 | Epiphysis | |
| | Osteoblasts | + |
| | Osteoclasts | − |
| | Growth Plate | |
| | resting chondrocytes | − |
| | proligferating chondrocytes | + |
| | hypertrophic chondrocytes | + |
| | Metaphysis | |
| | osteoblasts | + |
| | osteoclasts | + |
| | Diaphysis | − |
| | Endosteum | |
| | osteoblasts | + |
| | osteoclasts | + |
| | Periosteum | + |

Legend: "+" = hybridization signal detected "−" = no hybridization signal detected
"ISH" - In situ hybridization These studies confirm the positional expression of Zmax1 in cells involved in bone remodeling and bone formation. Zmax1 expression in the zone of proliferation and in the osteoblasts and osteoclasts of the proximal metaphysis, suggests that the Zmax1 gene is involved in the process of bone growth and mineralization. The activity and differentiation of osteoblasts and osteoclasts are closely coordinated during development as bone is formed and during growth as well as in adult life as bone undergoes continuous remodeling. The formation of internal bone structures and bone remodeling result from the coupling of bone resorption by activated osteoclasts with subsequent deposition of new material by osteoblasts. Zmax1 is related to the LDL receptor gene, and thus may be a receptor involved in mechanosensation and subsequent signaling in the process of bone remodeling. Therefore, changes in the level of expression of this gene could impact on the rate of remodeling and degree of mineralization of bone.

XIV. Antisense

Antisense oligonucleotides are short synthetic nucleic acids that contain complementary base sequences to a targeted RNA. Hybridization of the RNA in living cells with the antisense oligonucleotide interferes with RNA function and ultimately blocks protein expression. Therefore, any gene for which the partial sequence is known can be targeted by an antisense oligonucleotide.

Antisense technology is becoming a widely used research tool and will play an increasingly important role in the validation and elucidation of therapeutic targets identified by genomic sequencing efforts.

Antisense technology was developed to inhibit gene expression by utilizing an oligonucleotide complementary to the mRNA that encodes the target gene. There are several possible mechanisms for the inhibitory effects of antisense oligonucleotides. Among them, degradation of mRNA by RNase H is considered to be the major mechanism of inhibition of protein function. This technique was originally used to elucidate the function of a target gene, but may also have therapeutic applications, provided it is designed carefully and properly.

An example of materials and methods for preparing antisense oligonucleotides can be performed as follows. Preliminary studies have been undertaken in collaboration with Sequiter (Natick, Mass.) using the antisense technology in the osteoblast-like murine cell line, MC3T3. These cells can be triggered to develop along the bone differentiation sequence. An initial proliferation period is characterized by minimal expression of differentiation markers and initial synthesis of collagenous extracellular matrix. Collagen matrix synthesis is required for subsequent induction of differentiation markers. Once the matrix synthesis begins, osteoblast marker genes are activated in a clear temporal sequence: alkaline phosphatase is induced at early times while bone sialoprotien and osteocalcin appear later in the differentiation process. This temporal sequence of gene expression is useful in monitoring the maturation and mineralization process. Matrix mineralization, which does not begin until several days after maturation has started, involves deposition of mineral on and within collagen fibrils deep within the matrix near the cell layer-culture plate interface. The collagen fibril-associated mineral formed by cultured osteoblasts resembles that found in woven bone in vivo and therefore is used frequently as a study reagent.

MC3T3 cells were transfected with antisense oligonucleotides for the first week of the differentiation, according to the manufacturer's specifications (U.S. Pat. No. 5,849,902).

The oligonucleotides designed for Zmax1 are given below (SEQ. ID. NOS.: 639–641):

10875: AGUACAGCUUCUUGCCAACCCAGUC
10876: UCCUCCAGGUCGAUGGUCAGCCCAU
10877: GUCUGAGUCCGAGUUCAAAUCCAGG

Figure 13:
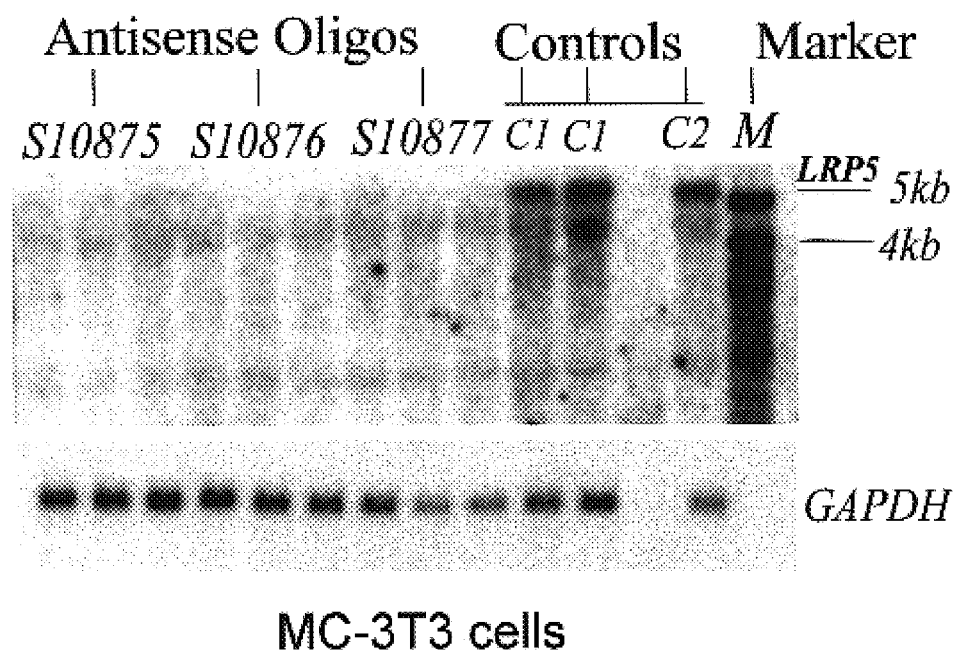
FIG. 13 shows antisense inhibition of Zmax1 expression in MC-3T3 cells.

FIG. 13 shows the results of antisense inhibition of Zmax1 in MC3T3 cells. The three oligonucleotides shown above were transfected into MC3T3 and RNA was isolated according to standard procedures. Northern analysis clearly shows markedly lower steady state levels of the Zmax1 transcript while the control gene GAPDH remained unchanged. Thus, antisense technology using the primers described above allows for the study of the role of Zmax1 expression on bone biology.

The protein encoded by Zmax1 is related to the Low Density Lipoprotein receptor (LDL receptor). See, Goldstein et al, *Ann. Rev. Cell Biology*, 1:1–39 (1985); Brown et al, *Science*, 232:34–47 (1986). The LDL receptor is responsible for uptake of low density lipoprotein, a lipid-protein aggregate that includes cholesterol. Individuals with a defect in the LDL receptor are deficient in cholesterol removal and tend to develop artherosclerosis. In addition, cells with a defective LDL receptor show increased production of cholesterol, in part because of altered feedback regulation of cholesterol synthetic enzymes and in part because of increased transcription of the genes for these enzymes. In some cell types, cholesterol is a precursor for the formation of steroid hormones.

Thus, the LDL receptor may, directly or indirectly, function as a signal transduction protein and may regulate gene expression. Because Zmax1 is related to the LDL receptor, this protein may also be involved in signaling between cells in a way that affects bone remodeling.

The glycine 171 amino acid is likely to be important for the function of Zmax1 because this amino acid is also found in the mouse homologue of Zmax1. The closely related LRP6 protein also contains glycine at the corresponding position (Brown et al, *Biochemical and Biophysical Research Comm.*, 248:879–888 (1988)). Amino acids that are important in a protein's structure or function tend to be conserved between species, because natural selection prevents mutations with altered amino acids at important positions from arising.

In addition, the extracellular domain of Zmax1 contains four repeats consisting of five YWT motifs followed by an EFG motif. This 5YWT+EGF repeat is likely to form a distinct folded protein domain, as this repeat is also found in the LDL receptor and other LDL receptor-related proteins. The first three 5YWT+EGF repeats are very similar in their structure, while the fourth is highly divergent. Glycine 171 occurs in the central YWT motif of the first 5YWT+EGF repeat in Zmax1. The other two similar 5YWT+EGF repeats of Zmax1 also contain glycine at the corresponding position, as does the 5YWT+EGF repeat in the LDL receptor protein. However, only 17.6% of the amino acids are identical among the first three 5YWT+EGF repeats in Zmax1 and the single repeat in the LDL receptor. These observations indicate that glycine 171 is essential to the function of this repeat, and mutation of glycine 171 causes a functional alteration of Zmax1. The cDNA and peptide sequences are shown in FIGS. 6A–6J. The critical base at nucleotide position 582 is indicated in bold and is underlined.

Northern blot analysis (FIGS. 7A–B) reveals that Zmax1 is expressed in human bone tissue as well as numerous other tissues. A multiple-tissue Northern blot (Clontech, Palo Alto, Calif.) was probed with exons from Zmax1. As shown in FIG. 7A, the 5.5 kb Zmax1 transcript was highly expressed in heart, kidney, lung, liver and pancreas and is expressed at lower levels in skeletal muscle and brain. A second northern blot, shown in FIG. 7B, confirmed the transcript size at 5.5 kb, and indicated that Zmax1 is expressed in bone, bone marrow, calvaria and human osteoblastic cell lines.

Taken together, these results indicate that the HBM polymorphism in the Zmax1 gene is responsible for the HBM phenotype, and that the Zmax1 gene is important in bone development. In addition, because mutation of Zmax1 can alter bone mineralization and development, it is likely that molecules that bind to Zmax1 may usefully alter bone development. Such molecules may include, for example, small molecules, proteins, RNA aptamers, peptide aptamers, and the like.

XV. Preparation of Nucleic Acids, Vectors, Transformations and Host Cells

Large amounts of the nucleic acids of the present invention may be produced by replication in a suitable host cell. Natural or synthetic nucleic acid fragments coding for a desired fragment will be incorporated into recombinant nucleic acid constructs, usually DNA constructs, capable of introduction into and replication in a prokaryotic or eukaryotic cell. Usually the nucleic acid constructs will be suitable for replication in a unicellular host, such as yeast or bacteria, but may also be intended for introduction to (with and without integration within the genome) cultured mammalian or plant or other eukaryotic cell lines. The purification of nucleic acids produced by the methods of the present invention is described, for example, in Sambrook et al, *Molecular Cloning. A Laboratory Manual*, 2nd Ed. (Cold Spring Harbor Laboratory, Cold Spring Harbor, N.Y. (1989) or Ausubel et al, *Current Protocols in Molecular Biology*, J. Wiley and Sons, NY (1992).

The nucleic acids of the present invention may also be produced by chemical synthesis, e.g., by the phosphoramidite method described by Beaucage et al, *Tetra. Letts.*, 22:1859–1862 (1981) or the triester method according to Matteucci, et al, *J. Am. Chem. Soc.*, 103:3185 (1981), and may be performed on commercial, automated oligonucleotide synthesizers. A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

Nucleic acid constructs prepared for introduction into a prokaryotic or eukaryotic host may comprise a replication system recognized by the host, including the intended nucleic acid fragment encoding the desired protein, and will preferably also include transcription and translational initiation regulatory sequences operably linked to the protein encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals may also be included where appropriate, whether from a native HBM or Zmax1 protein or from other receptors or from secreted proteins of the same or related species, which allow the protein to cross and/or lodge in cell membranes, and thus attain its functional topology, or be secreted from the cell. Such vectors may be prepared by means of standard recombinant techniques well known in the art and discussed, for example, in Sambrook et al, *Molecular Cloning. A Laboratory Manual*, 2nd Ed. (Cold Spring Harbor Laboratory, Cold Spring Harbor, N.Y. (1989) or Ausubel et al, *Current Protocols in Molecular Biology*, J. Wiley and Sons, NY (1992).

An appropriate promoter and other necessary vector sequences will be selected so as to be functional in the host, and may include, when appropriate, those naturally associated with Zmax1 or HBM genes. Examples of workable combinations of cell lines and expression vectors are described in Sambrook et al, *Molecular Cloning. A Laboratory Manual*, 2nd Ed. (Cold Spring Harbor Laboratory, Cold Spring Harbor, N.Y. (1989) or Ausubel et al, *Current Protocols in Molecular Biology*, J. Wiley and Sons, NY (1992). Many useful vectors are known in the art and may be obtained from such vendors as Stratagene, New England BioLabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in EP 73,675A. Appropriate non-native mammalian promoters might include the early and late promoters from SV40 (Fiers et al, *Nature*, 273:113 (1978)) or promoters derived from murine Moloney leukemia virus, mouse tumor virus, avian sarcoma viruses, adenovirus II, bovine papilloma virus or polyoma. In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, Cold Spring Harbor, N.Y. (1983).

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc.; b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see, Kubo et al, *FEBS Letts*. 241:119 (1988)), or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. See generally, Sambrook et al., 1989 and Ausubel et al., 1992. The introduction of the nucleic acids into the host cell by any method known in the art, including those described above, will be referred to herein as "transformation." The cells into which have been introduced nucleic acids described above are meant to also include the progeny of such cells.

Large quantities of the nucleic acids and proteins of the present invention may be prepared by expressing the Zmax1 or HBM nucleic acids or portions thereof in vectors or other expression vehicles in compatible prokaryotic or eukaryotic host cells. The most commonly used prokaryotic hosts are strains of *Escherichia coli*, although other prokaryotes, such as *Bacillus subtilis* or Pseudomonas may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan (eds.), *Cell Culture. Methods in Enzymology*, volume 58, Academic Press, Inc., Harcourt Brace Jovanovich, NY, (1979)). Examples of commonly used mammalian host cell lines are VERO and HeLa cells, Chinese hamster ovary (CHO) cells, and WI38, BHK, and COS cell lines, although it will be appreciated by the skilled practitioner that other cell lines may be appropriate, e.g., to provide higher expression desirable glycosylation patterns, or other features.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the nucleic acids of the present invention will be useful not only for the production of the nucleic acids and proteins of the present invention, but also, for example, in studying the characteristics of Zmax1 or HBM proteins.

Antisense nucleic acid sequences are useful in preventing or diminishing the expression of Zmax1 or HBM, as will be appreciated by one skilled in the art. For example, nucleic acid vectors containing all or a portion of the Zmax1 or HBM gene or other sequences from the Zmax1 or HBM region may be placed under the control of a promoter in an antisense orientation and introduced into a cell. Expression of such an antisense construct within a cell will interfere with Zmax1 or HBM transcription and/or translation and/or replication.

The probes and primers based on the Zmax1 and HBM gene sequences disclosed herein are used to identify homologous Zmax1 and HBM gene sequences and proteins in other species. These Zmax1 and HBM gene sequences and proteins are used in the diagnostic/prognostic, therapeutic and drug screening methods described herein for the species from which they have been isolated.

XVI. Protein Expression and Purification

Expression and purification of the HBM protein of the invention can be performed essentially as outlined below. To facilitate the cloning, expression and purification of membrane and secreted protein from the HBM gene, a gene expression system, such as the pET System (Novagen), for cloning and expression of recombinant proteins in *E. coli* was selected. Also, a DNA sequence encoding a peptide tag, the His-Tap, was fused to the 3' end of DNA sequences of interest to facilitate purification of the recombinant protein products. The 3' end was selected for fusion to avoid alteration of any 5' terminal signal sequence.

Nucleic acids chosen, for example, from the nucleic acids set forth in SEQ ID NOS: 1, 3 and 5–12 for cloning HBM were prepared by polymerase chain reaction (PCR). Synthetic oligonucleotide primers specific for the 5' and 3' ends of the HBM nucleotide sequence were designed and purchased from Life Technologies (Gaithersburg, Md.). All forward primers (specific for the 5' end of the sequence) were designed to include an NcoI cloning site at the 5' terminus. These primers were designed to permit initiation of protein translation at the methionine residue encoded within the NcoI site followed by a valine residue and the protein encoded by the HBM DNA sequence. All reverse primers (specific for the 3' end of the sequence) included an EcoRI site at the 5' terminus to permit cloning of the HBM sequence into the reading frame of the pET-28b. The pET-28b vector provided a sequence encoding an additional 20 carboxyl-terminal amino acids including six histidine residues (at the C-terminus), which comprised the histidine affinity tag.

Genomic DNA prepared from the HBM gene was used as the source of template DNA for PCR amplification (Ausubel et al, *Current Protocols in Molecular Biology*, John Wiley & Sons (1994)). To amplify a DNA sequence containing the HBM nucleotide sequence, genomic DNA (50 ng) was introduced into a reaction vial containing 2 mM $MgCl_2$, 1 µM synthetic oligonucleotide primers (forward and reverse primers) complementary to and flanking a defined HBM, 0.2 mM of each of deoxynucleotide triphosphate, dATP, dGTP, dCTP, dTTP and 2.5 units of heat stable DNA polymerase (Amplitaq, Roche Molecular Systems, Inc., Branchburg, N.J.) in a final volume of 100 microliters.

Upon completion of thermal cycling reactions, each sample of amplified DNA was purified using the Qiaquick Spin PCR purification kit (Qiagen, Gaithersburg, Md.). All amplified DNA samples were subjected to digestion with the restriction endonucleases, e.g., NcoI and EcoRI (New England BioLabs, Beverly, Mass.) (Ausubel et al, *Current Protocols in Molecular Biology*, John Wiley & Sons, Inc. (1994)). DNA samples were then subjected to electrophoresis on 1.0% NuSeive (FMC BioProducts, Rockland, Me.) agarose gels. DNA was visualized by exposure to ethidium bromide and long wave UV irradiation. DNA contained in slices isolated from the agarose gel was purified using the Bio 101 GeneClean Kit protocol (Bio 101, Vista, Calif.).

The pET-28b vector was prepared for cloning by digestion with restriction endonucleases, e.g., NcoI and EcoRI (New England BioLabs, Beverly, Mass.) (Ausubel et al, *Current Protocols in Molecular Biology*, John Wiley & Sons, Inc. (1994)). The pET-28a vector, which encodes the histidine affinity tag that can be fused to the 5' end of an inserted gene, was prepared by digestion with appropriate restriction endonucleases.

Following digestion, DNA inserts were cloned (Ausubel et al, *Current Protocols in Molecular Biology*, John Wiley & Sons, Inc. (1994)) into the previously digested pET-28b expression vector. Products of the ligation reaction were then used to transform the BL21 strain of *E. coli* (Ausubel et al, *Current Protocols in Molecular Biology*, John Wiley & Sons, Inc. (1994)) as described below.

Competent bacteria, *E. coli* strain BL21 or *E. coli* strain BL21 (DE3), were transformed with recombinant pET expression plasmids carrying the cloned HBM sequence according to standard methods (Ausubel et al, *Current Protocols in Molecular Biology*, John Wiley & Sons, Inc. (1994)). Briefly, 1 µl of ligation reaction was mixed with 50 µl of electrocompetent cells and subjected to a high voltage pulse, after which samples were incubated in 0.45 ml SOC medium (0.5% yeast extract, 2.0% tryptone, 10 mM NaCl, 2.5 mM KCl, 10 mM $MgCl_2$, 10 mM $MgSO_4$ and 20 mM glucose) at 37° C. with shaking for 1 hour. Samples were then spread on LB agar plates containing 25 µg/ml kanamycin sulfate for growth overnight. Transformed colonies of BL21 were then picked and analyzed to evaluate cloned inserts, as described below.

Individual BL21 clones transformed with recombinant pET-28b HBM nucleotide sequences were analyzed by PCR amplification of the cloned inserts using the same forward and reverse primers specific for the HBM sequences that were used in the original PCR amplification cloning reactions. Successful amplification verifies the integration of the HBM sequence in the expression vector (Ausubel et al, *Current Protocols in Molecular Biology*, John Wiley & Sons, Inc. (1994)).

Individual clones of recombinant pET-28b vectors carrying properly cloned HBM nucleotide sequences were picked and incubated in 5 ml of LB broth plus 25 µg/ml kanamycin sulfate overnight. The following day plasmid DNA was isolated and purified using the Qiagen plasmid purification protocol (Qiagen Inc., Chatsworth, Calif.).

The pET vector can be propagated in any *E. coli* K-12 strain, e.g., HMS174, HB101, JM109, DH5 and the like, for purposes of cloning or plasmid preparation. Hosts for expression include *E. coli* strains containing a chromosomal copy of the gene for T7 RNA polymerase. These hosts were lysogens of bacteriophage DE3, a lambda derivative that carries the lacI gene, the lacUV5 promoter and the gene for T7 RNA polymerase. T7 RNA polymerase was induced by addition of isopropyl-β-D-thiogalactoside (IPTG), and the T7 RNA polymerase transcribes any target plasmid containing a functional T7 promoter, such as pET-28b, carrying its gene of interest. Strains include, for example, BL21(DE3) (Studier et al, *Meth. Enzymol.*, 185:60–89 (1990)).

To express the recombinant HBM sequence, 50 ng of plasmid DNA are isolated as described above to transform competent BL21(DE3) bacteria as described above (provided by Novagen as part of the pET expression kit). The lacZ gene (β-galactosidase) is expressed in the pET-System as described for the HBM recombinant constructions. Transformed cells were cultured in SOC medium for 1 hour, and the culture was then plated on LB plates containing 25 µg/ml kanamycin sulfate. The following day, the bacterial colonies were pooled and grown in LB medium containing kanamycin sulfate (25 µg/ml) to an optical density at 600 nM of 0.5 to 1.0 O.D. units, at which point 1 mM IPTG was added to the culture for 3 hours to induce gene expression of the HBM recombinant DNA constructions.

After induction of gene expression with IPTG, bacteria were collected by centrifugation in a Sorvall RC-3B centrifuge at 3500×g for 15 minutes at 4° C. Pellets were resuspended in 50 ml of cold mM Tris-HCl, pH 8.0, 0.1 M NaCl and 0.1 mM EDTA (STE buffer). Cells were then centrifuged at 2000×g for 20 minutes at 4° C. Wet pellets were weighed and frozen at −80° C. until ready for protein purification.

A variety of methodologies known in the art can be used to purify the isolated proteins (Coligan et al, *Current Protocols in Protein Science*, John Wiley & Sons (1995)). For example, the frozen cells can be thawed, resuspended in buffer and ruptured by several passages through a small volume microfluidizer (Model M-110S, Microfluidics International Corp., Newton, Mass.). The resultant homogenate is centrifuged to yield a clear supernatant (crude extract) and, following filtration, the crude extract is fractioned over columns. Fractions are monitored by absorbance at $OD_{280}$ nm and peak fractions may be analyzed by SDS-PAGE.

The concentrations of purified protein preparations are quantified spectrophotometrically using absorbance coefficients calculated from amino acid content (Perkins, *Eur. J. Biochem.*, 157:169–180 (1986)). Protein concentrations are also measured by the method of Bradford, *Anal. Biochem.*, 72:248–254 (1976) and Lowry et al, *J. Biol. Chem.*, 193:265–275 (1951) using bovine serum albumin as a standard.

SDS-polyacrylamide gels of various concentrations were purchased from BioRad (Hercules, Calif.), and stained with Coomassie blue. Molecular weight markers may include rabbit skeletal muscle myosin (200 kDa), *E. coli* β-galactosidase (116 kDa), rabbit muscle phosphorylase B (97.4 kDa), bovine serum albumin (66.2 kDa), ovalbumin (45 kDa), bovine carbonic anyhdrase (31 kDa), soybean trypsin inhibitor (21.5 kDa), egg white lysozyme (14.4 kDa) and bovine aprotinin (6.5 kDa).

Once a sufficient quantity of the desired protein has been obtained, it may be used for various purposes. A typical use is the production of antibodies specific for binding. These antibodies may be either polyclonal or monoclonal, and may be produced by in vitro or in vivo techniques well known in the art. Monoclonal antibodies to epitopes of any of the peptides identified and isolated as described can be prepared from murine hybridomas (Kohler, *Nature*, 256:495 (1975)). In summary, a mouse is inoculated with a few micrograms of HBM protein over a period of two weeks. The mouse is then sacrificed. The cells that produce antibodies are then removed from the mouse's spleen. The spleen cells are then fused with polyethylene glycol with mouse myeloma cells. The successfully fused cells are diluted in a microtiter plate and growth of the culture is continued. The amount of antibody per well is measured by immunoassay methods such as ELISA (Engvall, *Meth. Enzymol.*, 70:419 (1980)). Clones producing antibody can be expanded and further propagated to produce HBM antibodies. Other suitable techniques involve in vitro exposure of lymphocytes to the antigenic polypeptides, or alternatively, to selection of libraries of antibodies in phage or similar vectors. See Huse et al, *Science*, 246:1275–1281 (1989). For additional information on antibody production see Davis et al, *Basic Methods in Molecular Biology*, Elsevier, N.Y., Section 21-2 (1989).

XVII. Methods of Use: Gene Therapy

In recent years, significant technological advances have been made in the area of gene therapy for both genetic and acquired diseases. (Kay et al, *Proc. Natl. Acad. Sci. USA*, 94:12744–12746 (1997)) Gene therapy can be defined as the deliberate transfer of DNA for therapeutic purposes. Improvement in gene transfer methods has allowed for development of gene therapy protocols for the treatment of diverse types of diseases. Gene therapy has also taken advantage of recent advances in the identification of new therapeutic genes, improvement in both viral and nonviral gene delivery systems, better understanding of gene regulation, and improvement in cell isolation and transplantation.

The preceding experiments identify the HBM gene as a dominant mutation conferring elevated bone mass. The fact that this mutation is dominant indicates that expression of the HBM protein causes elevated bone mass. Older individuals carrying the HBM gene, and, therefore expressing the HBM protein, do not suffer from osteoporosis. These individuals are equivalent to individuals being treated with the HBM protein. These observations are a strong experimental indication that therapeutic treatment with the HBM protein prevents osteoporosis. The bone mass elevating activity of the HBM gene is termed "HBM function."

Therefore, according to the present invention, a method is also provided of supplying HBM function to mesenchymal stem cells (Onyia et al, *J. Bone Miner. Res.*, 13:20–30 (1998); Ko et al, *Cancer Res.*, 56:4614–4619 (1996)). Supplying such a function provides protection against osteoporosis. The HBM gene or a part of the gene may be introduced into the cell in a vector such that the gene remains extrachromosomal. In such a situation, the gene will be expressed by the cell from the extrachromosomal location.

Vectors for introduction of genes both for recombination and for extrachromosomal maintenance are known in the art, and any suitable vector may be used. Methods for introducing DNA into cells such as electroporation, calcium phosphate co-precipitation, and viral transduction are known in the art, and the choice of method is within the competence of one skilled in the art (Robbins, Ed., *Gene Therapy Protocols*, Human Press, NJ (1997)). cells transformed with the HBM gene can be used as model systems to study osteoporosis and drug treatments that promote bone growth.

As generally discussed above, the HBM gene or fragment, where applicable, may be used in gene therapy methods in order to increase the amount of the expression products of such genes in mesenchymal stem cells. It may be useful also to increase the level of expression of a given HBM protein, or a fragment thereof, even in those cells in which the wild type gene is expressed normally. Gene therapy would be carried out according to generally accepted methods as described by, for example, Friedman, *Therapy for Genetic Diseases*, Friedman, Ed., Oxford University Press, pages 105–121 (1991).

A virus or plasmid vector containing a copy of the HBM gene linked to expression control elements and capable of replicating inside mesenchymal stem cells, is prepared. Suitable vectors are known and described, for example, in U.S. Pat. No. 5,252,479 and WO 93/07282, the disclosures of which are incorporated by reference herein in their entirety. The vector is then injected into the patient, either locally into the bone marrow or systemically (in order to reach any mesenchymal stem cells located at other sites, i.e., in the blood). If the transfected gene is not permanently incorporated into the genome of each of the targeted cells, the treatment may have to be repeated periodically.

Gene transfer systems known in the art may be useful in the practice of the gene therapy methods of the present invention. These include viral and non-viral transfer methods. A number of viruses have been used as gene transfer vectors, including polyoma, i.e., SV40 (Madzak et al, *J. Gen. Virol.*, 73:1533–1536 (1992)), adenovirus (Berkner, *Curr. Top. Microbiol. Immunol.*, 158:39–61 (1992); Berkner et al, *Bio Techniques*, 6:616–629 (1988); Gorziglia et al, *J. Virol.*, 66:4407–4412 (1992); Quantin et al, *Proc. Natl. Acad. Sci. USA*, 89:2581–2584 (1992); Rosenfeld et al, *Cell*, 68:143–155 (1992); Wilkinson et al, *Nucl. Acids Res.*, 20:2233–2239 (1992); Stratford-Perricaudet et al, *Hum. Gene Ther.*, 1:241–256 (1990)), vaccinia virus (Mackett et al, *Biotechnology*, 24:495–499 (1992)), adeno-associated virus (Muzyczka, *Curr. Top. Microbiol. Immunol.*, 158:91–123 (1992); Ohi et al, *Gene*, 89:279–282 (1990)), herpes viruses including HSV and EBV (Margolskee, *Curr. Top. Microbiol. Immunol.*, 158:67–90 (1992); Johnson et al, *J. Virol.*, 66:2952–2965 (1992); Fink et al, *Hum. Gene Ther.*, 3:11–19 (1992); Breakfield et al, *Mol. Neurobiol.*, 1:337–371 (1987); Fresse et al, *Biochem. Pharmacol.*, 40:2189–2199 (1990)), and retroviruses of avian (Brandyopadhyay et al, *Mol. Cell Biol.*, 4:749–754 (1984); Petropouplos et al, *J. Virol.*, 66:3391–3397 (1992)), murine (Miller, *Curr. Top. Microbiol. Immunol.*, 158:1–24 (1992); Miller et al, *Mol. Cell Biol.*, 5:431–437 (1985); Sorge et al, *Mol. Cell Biol.*, 4:1730–1737 (1984); Mann et al, *J. Virol.*, 54:401–407 (1985)), and human origin (Page et al, *J. Virol.*, 64:5370–5276 (1990); Buchschalcher et al, *J. Virol.*, 66:2731–2739 (1992)). Most human gene therapy protocols have been based on disabled murine retroviruses.

Non-viral gene transfer methods known in the art include chemical techniques such as calcium phosphate coprecipitation (Graham et al, *Virology*, 52:456–467 (1973); Pellicer et al, *Science*, 209:1414–1422 (1980)), mechanical techniques, for example microinjection (Anderson et al, *Proc. Natl. Acad. Sci. USA*, 77:5399–5403 (1980); Gordon et al, *Proc. Natl. Acad. Sci. USA*, 77:7380–7384 (1980); Brinster et al, *Cell*, 27:223–231 (1981); Constantini et al, *Nature*, 294:92–94 (1981)), membrane fusion-mediated transfer via liposomes (Felgner et al, *Proc. Natl. Acad. Sci. USA*, 84:7413–7417 (1987); Wang et al, *Biochemistry*, 28:9508–9514 (1989); Kaneda et al, *J. Biol. Chem.*, 264:12126–12129 (1989); Stewart et al, *Hum. Gene Ther.*, 3:267–275 (1992); Nabel et al, *Science*, 249:1285–1288 (1990); Lim et al, *Circulation*, 83:2007–2011 (1992)), and direct DNA uptake and receptor-mediated DNA transfer (Wolff et al, *Science*, 247:1465–1468 (1990); Wu et al, *BioTechniques*, 11:474–485 (1991); Zenke et al, *Proc. Natl. Acad. Sci. USA*, 87:3655–3659 (1990); Wu et al, *J. Biol. Chem.*, 264:16985–16987 (1989); Wolff et al, *BioTechniques*, 11:474–485 (1991); Wagneret al, 1990; Wagner et al, *Proc. Natl. Acad. Sci. USA*, 88:4255–4259 (1991); Cotten et al, *Proc. Natl. Acad. Sci. USA*, 87:4033–4037 (1990); Curiel et al, *Proc. Natl. Acad. Sci. USA*, 88:8850–8854 (1991); Curiel et al, *Hum. Gene Ther.*, 3:147–154 (1991)). Viral-mediated gene transfer can be combined with direct in vivo vectors to the mesenchymal stem cells and not into the surrounding cells (Romano et al, *In Vivo*, 12(1):59–67 (1998); Gonez et al, *Hum. Mol. Genetics*, 7(12):1913–9 (1998)). Alternatively, the retroviral vector producer cell line can be injected into the bone marrow (Culver et al, *Science*, 256:1550–1552 (1992)). Injection of producer cells would then provide a continuous source of vector particles. This technique has been approved for use in humans with inoperable brain tumors.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged.

Liposome/DNA complexes have been shown to be capable of mediating direct in vivo gene transfer. While in standard liposome preparations the gene transfer process is non-specific, localized in vivo uptake and expression have been reported in tumor deposits, for example, following direct in situ administration (Nabel, *Hum. Gene Ther.*, 3:399–410 (1992)).

XVIII. Methods of Use: Transformed Hosts, Development of Pharmaceuticals and Research Tools Cells and animals that carry the HBM gene can be used as model systems to study and test for substances that have potential as therapeutic agents (Onyia et al, *J. Bone Miner. Res.*, 13:20–30 (1998); Broder et al, *Bone*, 21:225–235 (1997)). The cells are typically cultured mesenchymal stem cells. These may be isolated from individuals with somatic or germline HBM genes. Alternatively, the cell line can be engineered to carry the HBM gene, as described above. After a test substance is applied to the cells, the transformed phenotype of the cell is determined. Any trait of transformed cells can be assessed, including formation of bone matrix in culture (Broder et al, *Bone*, 21:225–235 (1997)), mechanical properties (Kizer et al, *Proc. Natl. Acad. Sci. USA*, 94:1013–1018 (1997)), and response to application of putative therapeutic agents.

Animals for testing therapeutic agents can be selected after treatment of germline cells or zygotes. Such treatments include insertion of the Zmax1 gene, as well as insertion of the HBM gene and disrupted homologous genes. Alternatively, the inserted Zmax1 gene(s) and/or HBM gene(s) of the animals may be disrupted by insertion or deletion mutation of other genetic alterations using conventional techniques, such as those described by, for example, Capechi, *Science*, 244:1288 (1989); Valancuis et al, *Mol. Cell Biol.*, 11:1402 (1991); Hasty et al, *Nature*, 350:243 (1991); Shinkai et al, *Cell*, 68:855 (1992); Mombaerts et al, *Cell*, 68:869 (1992); Philpott et al, *Science*, 256:1448 (1992); Snouwaert et al, *Science*, 257:1083 (1992); Donehower et al, *Nature*, 356:215 (1992). After test substances have been administered to the animals, the growth of bone must be assessed. If the test substance enhances the growth of bone, then the test substance is a candidate therapeutic agent. These animal models provide an extremely important vehicle for potential therapeutic products.

Individuals carrying the HBM gene have elevated bone mass. The HBM gene causes this phenotype by altering the activities, levels, expression patterns, and modification states of other molecules involved in bone development. Using a variety of established techniques, it is possible to identify molecules, preferably proteins or mRNAs, whose activities, levels, expression patterns, and modification states are different between systems containing the Zmax1 gene and systems containing the HBM gene. Such systems can be, for example, cell-free extracts, cells, tissues or living organisms, such as mice or humans. For a mutant form of Zmax1, a complete deletion of Zmax1, mutations lacking the extracellular or intracellular portion of the protein, or any other mutation in the Zmax1 gene may be used. It is also possible to use expression of antisense Zmax1 RNA or oligonucleotides to inhibit production of the Zmax1 protein. For a mutant form of HBM, a complete deletion of HBM, mutations lacking the extracellular or intracellular portion of the HBM protein, or any other mutation in the HBM gene may be used. It is also possible to use expression of antisense HBM RNA or oligonucleotides to inhibit production of the HBM protein.

Molecules identified by comparison of Zmax1 systems and HBM systems can be used as surrogate markers in pharmaceutical development or in diagnosis of human or animal bone disease. Alternatively, such molecules may be used in treatment of bone disease. See, Schena et al, *Science*, 270:467–470 (1995).

For example, a transgenic mouse carrying the HBM gene in the mouse homologue is constructed. A mouse of the genotype HBM/+ is viable, healthy and has elevated bone mass. To identify surrogate markers for elevated bone mass, HBM/+ (i.e., heterozygous) and isogenic +/+ (i.e., wild-type) mice are sacrificed. Bone tissue mRNA is extracted from each animal, and a "gene chip" corresponding to mRNAs expressed in the +/+ individual is constructed. mRNA from different tissues is isolated from animals of each genotype, reverse-transcribed, fluorescently labeled, and then hybridized to gene fragments affixed to a solid support. The ratio of fluorescent intensity between the two populations is indicative of the relative abundance of the specific mRNAs in the +/+ and HBM/+ animals. Genes encoding mRNAs over- and under-expressed relative to the wild-type control are candidates for genes coordinately regulated by the HBM gene.

One standard procedure for identification of new proteins that are part of the same signaling cascade as an already-discovered protein is as follows. Cells are treated with radioactive phosphorous, and the already-discovered protein is manipulated to be more ore less active. The phosphorylation state of other proteins in the cell is then monitored by polyacrylamide gel electrophoresis and autoradiography, or similar techniques. Levels of activity of the known protein may be manipulated by many methods, including, for example, comparing wild-type mutant proteins using specific inhibitors such as drugs or antibodies, simply adding or not adding a known extracellular protein, or using antisense inhibition of the expression of the known protein (Tamura et al, *Science*, 280(5369):1614–7 (1998); Meng, *EMBO J.*, 17(15):4391–403 (1998); Cooper et al, *Cell*, 1:263–73 (1982)).

In another example, proteins with different levels of phosphorylation are identified in TE85 osteosarcoma cells expressing either a sense or antisense cDNA for Zmax1. TE85 cells normally express high levels of Zmax1 (Dong et al, *Biochem. & Biophys. Res. Comm.*, 251:784–790 (1998)). Cells containing the sense construct express even higher levels of Zmax1, while cells expressing the antisense construct express lower levels. Cells are grown in the presence of $^{32}$P, harvested, lysed, and the lysates run on SDS polyacrylamide gels to separate proteins, and the gels subjected to autoradiography (Ausubel et al, *Current Protocols in Molecular Biology*, John Wiley & Sons (1997)). Bands that differ in intensity between the sense and antisense cell lines represent phosphoproteins whose phosphorylation state or absolute level varies in response to levels of Zmax1. As an alternative to the $^{32}$P-labeling, unlabeled proteins may be separated by SDS-PAGE and subjected to immunoblotting, using the commercially available anti-phosphotyrosine antibody as a probe (Thomas et al, *Nature*, 376(6537):267–71 (1995)). As an alternative to the expression of antisense RNA, transfection with chemically modified antisense oligonucleotides can be used (Woolf et al, *Nucleic Acids Res.*, 18(7): 1763–9 (1990)).

Many bone disorders, such as osteoporosis, have a slow onset and a slow response to treatment. It is therefore useful to develop surrogate markers for bone development and mineralization. Such markers can be useful in developing treatments for bone disorders, and for diagnosing patients who may be at risk for later development of bone disorders. Examples of preferred markers are N- and C-terminal telopeptide markers described, for example, in U.S. Pat. Nos. 5,455,179, 5,641,837 and 5,652,112, the disclosures of which are incorporated by reference herein in their entirety. In the area of HIV disease, CD4 counts and viral load are useful surrogate markers for disease progression (Vlahov et al, *JAMA*, 279(1):35–40 (1998)). There is a need for analogous surrogate markers in the area of bone disease.

A surrogate marker can be any characteristic that is easily tested and relatively insensitive to non-specific influences. For example, a surrogate marker can be a molecule such as a protein or mRNA in a tissue or in blood serum. Alternatively, a surrogate marker may be a diagnostic sign such as sensitivity to pain, a reflex response or the like.

In yet another example, surrogate markers for elevated bone mass are identified using a pedigree of humans carrying the HBM gene. Blood samples are withdrawn from three individuals that carry the HBM gene, and from three closely related individuals that do not. Proteins in the serum from these individuals are electrophoresed on a two dimensional gel system, in which one dimension separates proteins by size, and another dimension separates proteins by isoelectric point (Epstein et al, *Electrophoresis*, 17(11):1655–70 (1996)). Spots corresponding to proteins are identified. A few spots are expected to be present in different amounts or in slightly different positions for the HBM individuals compared to their normal relatives. These spots correspond to proteins that are candidate surrogate markers. The identities of the proteins are determined by microsequencing, and antibodies to the proteins can be produced by standard methods for use in diagnostic testing procedures. Diagnostic assays for HBM proteins or other candidate surrogate markers include using antibodies described in this invention and a reporter molecule to detect HBM in human body fluids, membranes, bones, cells, tissues or extracts thereof. The antibodies can be labeled by joining them covalently or noncovalently with a substance that provides a detectable signal. In many scientific and patent literature, a variety of reporter molecules or labels are described including radionuclides, enzymes, fluorescent, chemi-luminescent or chromogenic agents (U.S. Pat. Nos. 3,817,837; 3,850,752; 3,939,350; 3,996,345; 4,277,437; 4,275,149; and 4,366, 241).

Using these antibodies, the levels of candidate surrogate markers are measured in normal individuals and in patients suffering from a bone disorder, such as osteoporosis, osteoporosis pseudoglioma, Engelmann's disease, Ribbing's disease, hyperphosphatasemia, Van Buchem's disease, melorheostosis, osteopetrosis, pychodysostosis, sclerosteosis, osteopoikilosis, acromegaly, Paget's disease, fibrous dysplasia, tubular stenosis, osteogenesis imperfecta, hypoparathyroidism, pseudohypoparathyroidism, pseudopseudohypoparathyroidism, primary and secondary hyperparathyroidism and associated syndromes, hypercalciuria, medullary carcinoma of the thyroid gland, osteomalacia and other diseases. Techniques for measuring levels of protein in serum in a clinical setting using antibodies are well established. A protein that is consistently present in higher or lower levels in individuals carrying a particular disease or type of disease is a useful surrogate marker.

A surrogate marker can be used in diagnosis of a bone disorder. For example, consider a child that present to a physician with a high frequency of bone fracture. The underlying cause may be child abuse, inappropriate behavior by the child, or a bone disorder. To rapidly test for a bone disorder, the levels of the surrogate marker protein are measured using the antibody described above.

Levels of modification states of surrogate markers can be measured as indicators of the likely effectiveness of a drug that is being developed. It is especially convenient to use surrogate markers in creating treatments for bone disorders, because alterations in bone development or mineralization may require a long time to be observed. For example, a set of bone mRNAs, termed the "HBM-inducible mRNA set" is found to be overexpressed in HBM/+ mice as compared to +/+ mice, as described above. Expression of this set can be used as a surrogate marker. Specifically, if treatment of +/+ mice with a compound results in overexpression of the HBM-inducible mRNA set, then that compound is considered a promising candidate for further development.

This invention is particularly useful for screening compounds by using the Zmax1 or HBM protein or binding fragment thereof in any of a variety of drug screening techniques.

The Zmax1 or HBM protein or fragment employed in such a test may either be free in solution, affixed to a solid support, or borne on a cell surface. One method of drug screening utilizes eukaryotic or prokaryotic host cells which are stably transformed with recombinant nucleic acids expressing the protein or fragment, preferably in competitive binding assays. Such cells, either in viable or fixed form, can be used for standard binding assays. One may measure, for example, for the formation of complexes between a Zmax1 or HBM protein or fragment and the agent being tested, or examine the degree to which the formation of a complex between a Zmax1 or HBM protein or fragment and a known ligand is interfered with by the agent being tested.

Thus, the present invention provides methods of screening for drugs comprising contacting such an agent with a Zmax1 or HBM protein or fragment thereof and assaying (i) for the presence of a complex between the agent and the Zmax1 or HBM protein or fragment, or (ii) for the presence of a complex between the Zmax1 or HBM protein or fragment and a ligand, by methods well known in the art. In such competitive binding assays the Zmax1 or HBM protein or fragment is typically labeled. Free Zmax1 or HBM protein or fragment is separated from that present in a protein:protein complex, and the amount of free (i.e., uncomplexed) label is a measure of the binding of the agent being tested to Zmax1 or HBM or its interference with Zmax1 or HBM: ligand binding, respectively.

Another technique for drug screening provides high throughput screening for compounds having suitable binding affinity to the Zmax1 or HBM proteins and is described in detail in WO 84/03564. Briefly stated, large numbers of different small peptide test compounds are synthesized on a solid substrate, such as plastic pins or some other surface. The peptide test compounds are reacted with Zmax1 or HBM proteins and washed. Bound Zmax1 or HBM protein is then detected by methods well known in the art. Purified Zmax1or HBM can be coated directly onto plates for use in the aforementioned drug screening techniques. However, non-neutralizing antibodies to the protein can be used to capture antibodies to immobilize the Zmax1 or HBM protein on the solid phase.

This invention also contemplates the use of competitive drug screening assays in which neutralizing antibodies capable of specifically binding the Zmax1 or HBM protein compete with a test compound for binding to the Zmax1 or HBM protein or fragments thereof. In this manner, the antibodies can be used to detect the presence of any peptide that shares one or more antigenic determinants of the Zmax1 or HBM protein.

A further technique for drug screening involves the use of host eukaryotic cell lines or cells (such as described above) that have a nonfunctional Zmax1 or HBM gene. These host cell lines or cells are defective at the Zmax1 or HBM protein level. The host cell lines or cells are grown in the presence of drug compound. The rate of growth of the host cells is measured to determine if the compound is capable of regulating the growth of Zmax1 or HBM defective cells.

The goal of rational drug design is to produce structural analogs of biologically active proteins of interest or of small molecules with which they interact (e.g., agonists, antagonists, inhibitors) in order to fashion drugs which are, for example, more active or stable forms of the protein, or which, e.g., enhance or interfere with the function of a protein in vivo. See, e.g., Hodgson, Bio/Technology, 9:19–21 (1991). In one approach, one first determines the three-dimensional structure of a protein of interest (e.g., Zmax1 or HBM protein) or, for example, of the Zmax1- or HBM-receptor or ligand complex, by x-ray crystallography, by computer modeling or most typically, by a combination of approaches. Less often, useful information regarding the structure of a protein may be gained by modeling based on the structure of homologous proteins. An example of rational drug design is the development of HIV protease inhibitors (Erickson et al, Science, 249:527–533 (1990)). In addition, peptides (e.g., Zmax1 or HBM protein) are analyzed by an alanine scan (Wells, Methods in Enzymol., 202:390–411 (1991)). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

Thus, one may design drugs which have, e.g., improved Zmax1 or HBM protein activity or stability or which act as inhibitors, agonists, antagonists, etc. of Zmax1 or HBM protein activity. By virtue of the availability of cloned Zmax1 or HBM sequences, sufficient amounts of the Zmax1 or HBM protein may be made available to perform such analytical studies as x-ray crystallography. In addition, the knowledge of the Zmax1 or HBM protein sequence provided herein will guide those employing computer modeling techniques in place of, or in addition to x-ray crystallography.

XIX. Methods of Use: Avian and Mammalian Animal Husbandry

The Zmax1 DNA and Zmax1 protein and/or the HBM DNA and HBM protein can be used for vertebrate and preferably human therapeutic agents and for avian and mammalian veterinary agents, including for livestock breeding. Birds, including, for example, chickens, roosters, hens, turkeys, ostriches, ducks, pheasants and quails, can benefit from the identification of the gene and pathway for high bone mass. In many examples cited in literature (for example, McCoy et al, Res. Vet. Sci., 60(2):185–186 (1996)), weakened bones due to husbandry conditions cause cage layer fatigue, osteoporosis and high mortality rates. Additional therapeutic agents to treat osteoporosis or other bone disorders in birds can have considerable beneficial effects on avian welfare and the economic conditions of the livestock industry, including, for example, meat and egg production.

XX. Methods of Use: Diagnostic Assays Using Zmax1-specific Oligonucleotides for Detection of Genetic Alterations Affecting Bone Development In cases where an alteration or disease of bone development is suspected to involve an alteration of the Zmax1 gene or the HBM gene, specific oligonucleotides may be constructed and used to assess the level of Zmax1 mRNA or HBM mRNA, respectively, in bone tissue or in another tissue that affects bone development.

For example, to test whether a person has the HBM gene, which affects bone density, polymerase chain reaction can be used. Two oligonucleotides are synthesized by standard methods or are obtained from a commercial supplier of custom-made oligonucleotides. The length and base composition are determined by standard criteria using the Oligo 4.0 primer Picking program (Wojchich Rychlik, 1992). One of the oligonucleotides is designed so that it will hybridize only to HBM DNA under the PCR conditions used. The other oligonucleotide is designed to hybridize a segment of Zmax1 genomic DNA such that amplification of DNA using these oligonucleotide primers produces a conveniently identified DNA fragment. For example, the pair of primers CCAAGTTCTGAGAAGTCC (SEQ ID NO:32) and AATACCTGAAACCA TACCTG (SEQ ID NO:33) will amplify a 530 base pair DNA fragment from a DNA sample when the following conditions are used: step 1 at 95° C. for 120 seconds; step 2 at 95° C. for 30 seconds; step 3 at 58° C. for 30 seconds; step 4 at 72° C. for 120 seconds; where steps 2–4 are repeated 35 times. Tissue samples may be obtained from hair follicles, whole blood, or the buccal cavity.

The fragment generated by the above procedure is sequenced by standard techniques. Individuals heterozygous for the HBM gene will show an equal amount of G and T at the second position in the codon for glycine 171. Normal or homozygous wild-type individuals will show only G at this position.

Other amplification techniques besides PCR may be used as alternatives, such as ligation-mediated PCR or techniques involving Q-beta replicase (Cahill et al, *Clin. Chem.*, 37(9) :1482–5 (1991)). For example, the oligonucleotides AGCT-GCTCGTAGCT G TCTCTCCCTGGATCACGGGTACAT-GTACTGGACAGACTGGGT (SEQ ID NO:34) and TGAGACGCCCGGATTGAGCGGGCAGG-GATAGCTTATTCCCTGT GCCGCATTACGGC (SEQ ID NO:35) can be hybridized to a denatured human DNA sample, treated with a DNA ligase, and then subjected to PCR amplification using the primer oligonucleotides AGCT-GCTCGTAG CTGTCTCTCCCTGGA (SEQ ID NO:36) and GCCGTAATGCGGCACAGGGAATAAGCT (SEQ ID NO:37). In the first two oligonucleotides, the outer 27 bases are random sequence corresponding to primer binding sites, and the inner 30 bases correspond to sequences in the Zmax1 gene. The T at the end of the first oligonucleotide corresponds to the HBM gene. The first two oligonucleotides are ligated only when hybridized to human DNA carrying the HBM gene, which results in the formation of an amplifiable 114 bp DNA fragment.

Products of amplification can be detected by agarose gel electrophoresis, quantitative hybridization, or equivalent techniques for nucleic acid detection known to one skilled in the art of molecular biology (Sambrook et al, *Molecular Cloning: A Laboratory Manual*, Cold Spring Harbor Laboratory, Cold Spring, N.Y. (1989)).

Other alterations in the Zmax1 gene or the HBM gene may be diagnosed by the same type of amplification-detection procedures, by using oligonucleotides designed to identify those alterations. These procedures can be used in animals as well as humans to identify alterations in Zmax1 or HBM that affect bone development.

Expression of Zmax1 or HBM in bone tissue may be accomplished by fusing the cDNA of Zmax1 or HBM, respectively, to a bone-specific promoter in the context of a vector for genetically engineering vertebrate cells. DNA constructs are introduced into cells by packaging the DNA into virus capsids, by the use of cationic liposomes, electroporation, or by calcium phosphate transfection. Transfected cells, preferably osteoblasts, may be studied in culture or may be introduced into bone tissue in animals by direct injection into bone or by intravenous injection of osteoblasts, followed by incorporation into bone tissue (Ko et al, *Cancer Research*, 56(20):4614–9 (1996)). For example, the osteocalcin promoter, which is specifically active in osteoblasts, may be used to direct transcription of the Zmax1 gene or the HBM gene. Any of several vectors and transfection methods may be used, such as retroviral vectors, adenovirus vectors, or vectors that are maintained after transfection using cationic liposomes, or other methods and vectors described herein.

Alteration of the level of functional Zmax1 protein or HBM protein affects the level of bone mineralization. By manipulating levels of functional Zmax1 protein or HBM protein, it is possible to affect bone development and to increase or decrease levels of bone mineralization. For example, it may be useful to increase bone mineralization in patients with osteoporosis. Alternatively, it may be useful to decrease bone mineralization in patients with osteopetrosis or Paget's disease. Alteration of Zmax1 levels or HBM levels can also be used as a research tool. Specifically, it is possible to identify proteins, mRNA and other molecules whose level or modification status is altered in response to changes in functional levels of Zmax1 or HBM. The pathology and pathogenesis of bone disorders is known and described, for example, in Rubin and Farber (Eds.), *Pathology*, 2nd Ed., S.B. Lippincott Co., Philadelphia, Pa. (1994).

A variety of techniques can be used to alter the levels of functional Zmax1 or HBM. For example, intravenous or intraosseous injection of the extracellular portion of Zmax1 or mutations thereof, or HBM or mutations thereof, will alter the level of Zmax1 activity or HBM activity, respectively, in the body of the treated human, animal or bird. Truncated versions of the Zmax1 protein or HBM protein can also be injected to alter the levels of functional Zmax1 protein or HBM protein, respectively. Certain forms of Zmax1 or HBM enhance the activity of endogenous protein, while other forms are inhibitory.

In a preferred embodiment, the HBM protein is used to treat osteoporosis. In a further preferred embodiment, the extracellular portion of the HBM protein is used. This HBM protein may be optionally modified by the addition of a moiety that causes the protein to adhere to the surface of cells. The protein is prepared in a pharmaceutically acceptable solution and is administered by injection or another method that achieves acceptable pharmacokinetics and distribution.

In a second embodiment of this method, Zmax1 or HBM levels are increased or decreased by gene therapy techniques. To increase Zmax1 or HBM levels, osteoblasts or another useful cell type are genetically engineered to express high levels of Zmax1 or HBM as described above. Alternatively, to decrease Zmax1 or HBM levels, antisense constructs that specifically reduce the level of translatable Zmax1 or HBM mRNA can be used. In general, a tissue-nonspecific promoter may be used, such as the CMV promoter or another commercially available promoter found in expression vectors (Wu et al, *Toxicol. Appl. Pharmacol.*, 141(1):330–9 (1996)). In a preferred embodiment, a Zmax1 cDNA or its antisense is transcribed by a bone-specific promoter, such as the osteocalcin or another promoter, to achieve specific expression in bone tissue. In this way, if a Zmax1-expressing DNA construct or HBM-expressing construct is introduced into non-bone tissue, it will not be expressed.

In a third embodiment of this method, antibodies against Zmax1 or HBM are used to inhibit its function. Such antibodies are identified herein.

In a fourth embodiment of this method, drugs that inhibit Zmax1 function or HBM function are used. Such drugs are described herein and optimized according to techniques of medicinal chemistry well known to one skilled in the art of pharmaceutical development.

Zmax1 and HBM interact with several proteins, such as ApoE. Molecules that inhibit the interaction between Zmax1 or HBM and ApoE or another binding partner are expected to alter bone development and mineralization. Such inhibitors may be useful as drugs in the treatment of osteoporosis, osteopetrosis, or other diseases of bone mineralization. Such inhibitors may be low molecular weight compounds, proteins or other types of molecules. See, Kim et al, *J. Biochem.* (Tokyo), 124(6):1072–1076 (1998).

Inhibitors of the interaction between Zmax1 or HBM and interacting proteins may be isolated by standard drug-screening techniques. For example, Zmax1 protein, (or a fragment thereof) or HBM protein (or a fragment thereof) can be immobilized on a solid support such as the base of microtiter well. A second protein or protein fragment, such as ApoE is derivatized to aid in detection, for example with fluorescein. Iodine, or biotin, then added to the Zmax1 or HBM in the presence of candidate compounds that may specifically inhibit this protein-protein domain of Zmax1 or HBM, respectively, and thus avoid problems associated with its transmembrane segment. Drug screens of this type are well known to one skilled in the art of pharmaceutical development.

Because Zmax1 and HBM are involved in bone development, proteins that bind to Zmax1 and HBM are also expected to be involved in bone development. Such binding proteins can be identified by standard methods, such as co-immunoprecipitation, co-fractionation, or the two-hybrid screen (Ausubel et al, *Current Protocols in Molecular Biology*, John Wiley & Sons (1997)). For example, to identify Zmax1-interacting proteins or HBM-interacting proteins using the two-hybrid system, the extracellular domain of Zmax1 or HBM is fused to LexA and expressed for the yeast vector pEG202 (the "bait") and expressed in the yeast strain EGY48. The yeast strain is transformed with a "prey" library in the appropriate vector, which encodes a galactose-inducible transcription-activation sequence fused to candidate interacting proteins. The techniques for initially selecting and subsequently verifying interacting proteins by this method are well known to one skilled in the art of molecular biology (Ausubel et al, *Current Protocols in Molecular Biology*, John Wiley & Sons (1997)).

In a preferred embodiment, proteins that interact with HBM, but not Zmax1, are identified using a variation of the above procedure (Xu et al, *Proc. Natl. Acad. Sci. USA*, 94(23):12473–8 (Nov. 1997)). This variation of the two-hybrid system uses two baits, and Zmax1 and HBM are each fused to LexA and TetR, respectively. Alternatively, proteins that interact with the HBM but not Zmax1 are also isolated. These procedures are well known to one skilled in the art of molecular biology, and are a simple variation of standard two-hybrid procedures.

As an alternative method of isolating Zmax1 or HBM interacting proteins, a biochemical approach is used. The Zmax1 protein or a fragment thereof, such as the extracellular domain, or the HBM protein or a fragment thereof, such as the extracellular domain, is chemically coupled to Sepharose beads. The Zmax1- or HBM-coupled beads are poured into a column. An extract of proteins, such as serum proteins, proteins in the supernatant of a bone biopsy, or intracellular proteins from gently lysed TE85 osteoblastic cells, is added to the column. Non-specifically bound proteins are eluted, the column is washed several times with a low-salt buffer, and then tightly binding proteins are eluted with a high-salt buffer. These are candidate proteins that bind to Zmax1 or HBM, and can be tested for specific binding by standard tests and control experiments. Sepharose beads used for coupling proteins and the methods for performing the coupling are commercially available (Sigma), and the procedures described here are well known to one skilled in the art of protein biochemistry.

As a variation of the above procedure, proteins that are eluted by high salt from the Zmax1- or HBM-Sepharose column are then added to an HBM-Zmax1-sepharose column. Proteins that flow through without sticking are proteins that bind to Zmax1 but not to HBM. Alternatively, proteins that bind to the HBM protein and not to the Zmax1 protein can be isolated by reversing the order in which the columns are used.

XXI. Method of Use: Transformation-associated Recombination (TAR) Cloning

Essential for the identification of novel allelic variants of Zmax1 is the ability to examine the sequence of both copies of the gene in an individual. To accomplish this, two "hooks," or regions of significant similarity, are identified within the genomic sequence such that they flank the portion of DNA that is to be cloned. Most preferably, the first of these hooks is derived from sequences 5' to the first exon of interest and the second is derived from sequences 3' to the last exon of interest. These two "hooks" are cloned into a bacterial/yeast shuttle vector such as that described by Larionov et al, *Proc. Natl. Acad. Sci. USA*, 94:7384–7387 (1997). Other similar vector systems may also be used. To recover the entire genomic copy of the Zmax1 gene, the plasmid containing the two "hooks" is linearized with a restriction endonuclease or is produced by another method such as PCR. This linear DNA fragment is introduced into yeast cells along with human genomic DNA. Typically, the yeast *Saccharomyces cerevisiae* is used as a host cell, although Larionov et al (in press) have reported using chicken host cells as well. During and after the process of transformation, the endogenous host cell converts the linear plasmid to a circle by a recombination event whereby the region of the human genomic DNA homologous to the "hooks" is inserted into the plasmid. This plasmid can be recovered and analyzed by methods well known to one skilled in the art. Obviously, the specificity for this reaction requires the host cell machinery to recognize sequences similar to the "hooks" present in the linear fragment. However, 100% sequence identity is not required, as shown by Kouprina et al, *Genomics*, 53(1):21–28 (October 1998), where the author describes using degenerate repeated sequences common in the human genome to recover fragments of human DNA from a rodent/human hybrid cell line.

In another example, only one "hook" is required, as described by Larionov et al, *Proc. Natl. Acad. Sci. USA*, 95(8):4469–74 (April 1998). For this type of experiment, termed "radial TAR cloning," the other region of sequence similarity to drive the recombination is derived from a repeated sequence from the genome. In this way, regions of DNA adjacent to the Zmax1 gene coding region can be recovered and examined for alterations that may affect function.

XXII. Methods of Use: Genomic Screening

The use of polymorphic genetic markers linked to the HBM gene or to Zmax1 is very useful in predicting susceptibility to osteoporosis or other bone diseases. Koller et al, *Amer. J. Bone Min. Res.*, 13:1903–1908 (1998) have demonstrated that the use of polymorphic genetic markers is useful for linkage analysis. Similarly, the identification of polymorphic genetic markers within the high bone mass gene will allow the identification of specific allelic variants that are in linkage disequilibrium with other genetic lesions that affect bone development. Using the DNA sequence from the BACs, a dinucleotide CAn repeat was identified and two unique PCR primers that will amplify the genomic DNA containing this repeat were designed, as shown below:

B200E21C16_L: GAGAGGCTATATCCCTGGGC (SEQ ID NO:38)

B200E21C16_R: ACAGCACGTGTTTAAAGGGG (SEQ ID NO:39)

and used in the genetic mapping study.

This method has been used successfully by others skilled in the art (e.g., Sheffield et al, *Genet.*, 4:1837–1844 (1995); LeBlanc-Straceski et al, *Genomics*, 19:341–9 (1994); Chen et al, *Genomics*, 25:1–8 (1995)). Use of these reagents with populations or individuals will predict their risk for osteoporosis. Similarly, single nucleotide polymorphisms (SNPs), such as those shown in Table 4 above, can be used as well to predict risk for developing bone diseases or resistance to osteoporosis in the case of the HBM gene.

XXIII. Methods of Use: Modulators of Tissue Calcification

The calcification of tissues in the human body is well documented. Towler et al, *J. Biol. Chem.*, 273:30427–34 (1998) demonstrated that several proteins known to regulate calcification of the developing skull in a model system are expressed in calcified aorta. The expression of Msx2, a gene transcribed in osteoprogenitor cells, in calcified vascular tissue indicates that genes which are important in bone development are involved in calcification of other tissues. Treatment with HBM protein, agonists or antagonists is likely to ameliorate calcification (such as the vasculature, dentin and bone of the skull visera) due to its demonstrated effect on bone mineral density. In experimental systems where tissue calcification is demonstrated, the overexpression or repression of Zmax1 activity permits the identification of molecules that are directly regulated by the Zmax1 gene. These genes are potential targets for therapeutics aimed at modulating tissue calcification. For example, an animal, such as the LDLR –/–, mouse is fed a high fat diet and is observed to demonstrate expression of markers of tissue calcification, including Zmax1. These animals are then treated with antibodies to Zmax1 or HBM protein, antisense oligonucleotides directed against Zmax1 or HBM cDNA, or with compounds known to bind the Zmax1 or HBM protein or its binding partner or ligand. RNA or proteins are extracted from the vascular tissue and the relative expression levels of the genes expressed in the tissue are determined by methods well known in the art. Genes that are regulated in the tissue are potential therapeutic targets for pharmaceutical development as modulators of tissue calcification.

The nucleic acids, proteins, peptides, amino acids, small molecules or other pharmaceutically useful compounds of the present invention that are to be given to an individual may be administered in the form of a composition with a pharmaceutically acceptable carrier, excipient or diluent, which are well known in the art. The individual may be a mammal or a bird, preferably a human, a rat, a mouse or bird. Such compositions may be administered to an individual in a pharmaceutically effective amount. The amount administered will vary depending on the condition being treated and the patient being treated. The compositions may be administered alone or in combination with other treatments.

EXAMPLES

The present invention is described by reference to the following Examples, which are offered by way of illustration and are not intended to limit the invention in any manner. Standard techniques well known in the art or the techniques specifically described below were utilized.

Example 1

The propositus was referred by her physicians to the Creighton Osteoporosis Center for evaluation of what appeared to be unusually dense bones. She was 18 years old and came to medical attention two years previous because of back pain, which was precipitated by an auto accident in which the car in which she was riding as a passenger was struck from behind. Her only injury was soft tissue injury to her lower back that was manifested by pain and muscle tenderness. There was no evidence of fracture or subluxation on radiographs. The pain lasted for two years, although she was able to attend school full time. By the time she was seen in the Center, the pain was nearly resolved and she was back to her usual activities as a high school student. Physical exam revealed a normal healthy young woman standing 66 inches and weighing 128 pounds. Radiographs of the entire skeleton revealed dense looking bones with thick cortices. All bones of the skeleton were involved. Most importantly, the shapes of all the bones were entirely normal. The spinal BMC was 94.48 grams in L1–4, and the spinal BMD was 1.667 gm/cm$^2$ in L1–4. BMD was 5.62 standard deviations (SD) above peak skeletal mass for women. These were measured by DXA using a Hologic 2000~. Her mother was then scanned and a lumbar spinal BMC of 58.05 grams and BMD of 1.500 gm/cm$^2$ were found. Her mother's values place her 4.12 SD above peak mass and 4.98 SD above her peers. Her mother was 51 years old, stood 65 inches and weighed 140 pounds. Her mother was in excellent health with no history of musculoskeletal or other symptoms. Her father's lumbar BMC was 75.33 grams and his BMD was 1.118 gm/cm$^2$. These values place him 0.25 SD above peak bone mass for males. He was in good health, stood 72 inches tall, and weighed 187 pounds.

These clinical data suggested that the propositus inherited a trait from her mother, which resulted in very high bone mass, but an otherwise normal skeleton, and attention was focused on the maternal kindred. In U.S. Pat. No. 5,691,153, twenty-two of these members had measurement of bone mass by DXA. In one case, the maternal grandfather of the propositus, was deceased, however, medical records, antemortem skeletal radiographs and a gall bladder specimen embedded in paraffin for DNA genotyping were obtained. His radiographs showed obvious extreme density of all of the bones available for examination including the femur and the spine, and he was included among the affected members. In this invention, the pedigree has been expanded to include 37 informative individuals. These additions are a significant improvement over the original kinship (Johnson et al, *Am. J. Hum. Genet.*, 60:1326–1332 (1997)) because, among the fourteen individuals added since the original study, two individuals harbor key crossovers. X-linkage is ruled out by the presence of male-to-male transmission from individual 12 to 14 and 15.

Example 2

The present invention describes DNA sequences derived from two BAC clones from the HBM gene region, as evident in Table 6 below, which is an assembly of these clones. Clone b200e21-h (ATCC No. 98628; SEQ ID NOS: 10–11) was deposited at the American Type Culture Collection (ATCC), 10801 University Blvd., Manassas, Va. 20110-2209 U.S.A., on Dec. 30, 1997. Clone b527d12-h (ATCC No. 98907; SEQ ID NOS: 5–9) was deposited at the American Type Culture Collection (ATCC), 10801 University Blvd., Manassas, Va. 20110-2209 U.S.A., on Oct. 2, 1998. These sequences are unique reagents that can be used by one skilled in the art to identify DNA probes for the Zmax1 gene, PCR primers to amplify the gene, nucleotide polymorphisms in the Zmax1 gene, or regulatory elements of the Zmax1 gene.

TABLE 6

| Contig | ATCC No. | SEQ ID NO. | Length (base pairs) |
|---|---|---|---|
| b527d12-h_contig302G | 98907 | 5 | 3096 |
| b527d12-h_contig306G | 98907 | 6 | 26928 |
| b527d12-h_contig307G | 98907 | 7 | 29430 |
| b527d12-h_contig308G | 98907 | 8 | 33769 |
| b527d12-h_contig309G | 98907 | 9 | 72049 |
| b200e21-h_contig1 | 98628 | 10 | 8705 |
| b200e21-h_contig4 | 98628 | 11 | 66933 |

The disclosure of each of the patents, patent applications and publications cited in the specification is hereby incorporated by reference herein in its entirety.

Although the invention has been set forth in detail, one skilled in the art will recognize that numerous changes and modifications can be made, and that such changes and modifications may be made without departing from the spirit and scope of the invention.

What is claimed is:

1. An isolated nucleic acid comprising the nucleic acid of SEQ ID NO: 2.

2. The isolated nucleic acid of claim 1, wherein the nucleic acid is a ribonucleic acid counterpart of SEQ ID NO: 2.

3. An isolated nucleic acid encoding the amino acid of SEQ ID NO:4.

4. A replicative cloning vector comprising the nucleic acid of claim 1 and a replicon operative in an isolated host cell.

5. An isolated host cell transformed with the replicative cloning vector of claim 4.

6. An expression vector comprising the nucleic acid of claim 1 operably linked to a transcription regulatory region.

7. An isolated host cell transformed with the expression vector of claim 6.

8. A method for in vitro expression of a HBM protein in host cells comprising:

constructing an expression vector comprising a promoter that directs expression operably linked to the nucleic acid of claim 1;

transfecting said host cells with said expression vector; and expressing the HBM protein in said host cells under conditions suitable for cell growth.

9. An isolated nucleic acid comprising at least 15 contiguous nucleotides of SEQ ID NO:2, wherein said 15 contiguous nucleotides comprise position 582 of SEQ ID NO:2, and wherein said position 582 is a mutation associated with the HBM phenotype.

10. The isolated nucleic acid of claim 9, wherein said isolated nucleic acid is a ribonucleic acid counterpart of SEQ ID NO:2.

11. An isolated nucleic acid comprising at least 15 contiguous nucleotides of SEQ ID NO:2, wherein said 15 contiguous nucleotides comprise position 582 of SEQ ID NO:2, and wherein said position 582 is a mutation associated with a HBM phenotype, and which encodes for an amino acid sequence including a valine corresponding to a valine at position 171 of SEQ ID NO:4.

12. The isolated nucleic acid of claim 11, wherein said isolated nucleic acid is a ribonucleic acid counterpart of SEQ ID NO:2.

13. An isolated ribonucleic acid comprising at least 15 contiguous nucleotides of the nucleic acid of SEQ ID NO:2, wherein one of the at least 15 contiguous nucleotides comprise position 582 of SEQ ID NO:2.

14. A replicative cloning vector comprising the nucleic acid of claim 9 and a replicon operative in a host cell.

15. An isolated host cell transformed with the replicative cloning vector of claim 14.

16. An expression vector comprising the nucleic acid of claim 9 operably linked to a transcription regulatory region.

17. An isolated host cell transformed with the expression vector of claim 16.

18. An isolated nucleic acid encoding the extracellular domain of the amino acid sequence of SEQ ID NO 4.

19. The method of expressing the HBM protein of claim 8, wherein said host cells are eukaryotic cells.

20. The method of expressing the HBM protein of claim 19, wherein said eukaryotic cells are bone cells selected from the group consisting of mesenchymal stem cells, osteoclasts, osteoblasts, and chondrocytes.

21. The method of claim 20, wherein the promoter that directs expression in said bone cells is an osteocalcin promoter, a bone sialoprotein promoter or an AML-3 promoter.

22. The method of expressing the HBM protein of claim 8, wherein said host cells are prokaryotic cells.

23. The isolated nucleic acid of claim 9, wherein said position 582 is not a guanine.

24. The isolated nucleic acid of claim 9, wherein said position 582 is a thymine.

* * * * *